United States Patent
Deng et al.

(10) Patent No.: US 12,312,353 B2
(45) Date of Patent: *May 27, 2025

(54) PIPERIDINYL-METHYL-PURINEAMINES AS NSD2 INHIBITORS AND ANTI-CANCER AGENTS

(71) Applicant: Novartis AG, Basel (CH)

(72) Inventors: Haibing Deng, Shanghai (CN); Jinbiao Liu, Shanghai (CN); Counde Oyang, Sunnyvale, CA (US); Ce Wang, Shanghai (CN); Qitao Xiao, Shanghai (CN); Guoliang Xun, Jiangsu (CN); Haiqiang Zeng, Shanghai (CN)

(73) Assignee: NOVARTIS AG, Basel (CH)

( * ) Notice: Subject to any disclaimer, the term of this patent is extended or adjusted under 35 U.S.C. 154(b) by 344 days.

This patent is subject to a terminal disclaimer.

(21) Appl. No.: 17/739,855

(22) Filed: May 9, 2022

(65) Prior Publication Data

US 2023/0002388 A1    Jan. 5, 2023

Related U.S. Application Data

(63) Continuation of application No. 17/327,226, filed on May 21, 2021, now Pat. No. 11,420,970, which is a continuation of application No. PCT/IB2020/057602, filed on Aug. 12, 2020.

(30) Foreign Application Priority Data

Aug. 14, 2019   (WO) ................ PCT/CN2019/100542

(51) Int. Cl.
C07D 473/34    (2006.01)

(52) U.S. Cl.
CPC ................ C07D 473/34 (2013.01)

(58) Field of Classification Search
CPC ..... A61K 31/52; C07D 471/04; C07D 473/34
USPC ........................... 514/263.22, 263.4; 544/277
See application file for complete search history.

(56) References Cited

U.S. PATENT DOCUMENTS

| | | | | |
|---|---|---|---|---|
| 11,420,970 | B1 * | 8/2022 | Deng | C07D 519/00 |
| 2006/0052403 | A1 | 3/2006 | Isobe et al. | |
| 2014/0128389 | A1 | 5/2014 | Halcomb et al. | |
| 2024/0002385 | A1 | 1/2024 | Connolly et al. | |
| 2024/0352017 | A1 | 10/2024 | Connolly et al. | |

FOREIGN PATENT DOCUMENTS

| | | |
|---|---|---|
| CN | 1512992 A | 7/2004 |
| CN | 1684966 A | 10/2005 |
| CN | 1688580 A | 10/2005 |
| CN | 101679433 A | 3/2010 |
| CN | 102666541 A | 9/2012 |
| CN | 108853110 A | 11/2018 |
| CN | 109223794 A | 1/2019 |
| JP | 2004137157 A | 5/2004 |
| JP | 2013508373 A | 3/2013 |
| WO | WO-2002085905 A1 | 10/2002 |
| WO | WO-2005123697 A1 | 12/2005 |
| WO | WO-2008114817 A1 | 9/2008 |
| WO | WO-2011049825 A1 | 4/2011 |
| WO | WO-2013139882 A1 | 9/2013 |
| WO | WO-2019196918 A1 | 10/2019 |
| WO | WO-2021026803 A1 | 2/2021 |
| WO | WO-2021028854 A1 | 2/2021 |
| WO | WO-2023225141 A1 | 11/2023 |
| WO | WO-2023225144 A1 | 11/2023 |
| WO | WO-2023225150 A1 | 11/2023 |
| WO | WO-2023225154 A1 | 11/2023 |

OTHER PUBLICATIONS

Tisi, D. et al., "Structure of the Epigenetic Oncogene MMSET and Inhibition by N-Alkyl Sinefungin Derivatives," *ACS Chemical Biology*, vol. 11, No. 11, pp. 3093-3105 (2016).
International Search Report and Written Opinion for International Application No. PCT/CN2019/100542, dated Apr. 24, 2020 (13 pages).
International Search Report and Written Opinion for International Application No. PCT/IB2020/057602, dated Sep. 9, 2020 (8 pages).
Brusova, Chemistry, Moscow State University, (4 pages). Retrieved from the internet on Feb. 10, 2023 from: http://www.chem.msu.su/rus/teaching/brusova/4.html.
Berge, S. M. et al. "Pharmaceutical Salts," *J. Pharmaceutical Sciences*, 1977, vol. 66, No. 1, p. 1-19.
Zhang, L. et al. "Recent advances in nuclear receptor-binding SET domain 2 (NSD2) inhibitors: An update and perspectives," *Eur. J. Med. Chem.*, 2023, 250, 115232.
Caira, M. R. "Crystalline Polymorphism of Organic Compounds." In: Design of Organic Solids. *Topics in Current Chemistry*, ed. E. Weber, Springer, Berlin, 1998, vol. 198, p. 163-208.

(Continued)

*Primary Examiner* — Kahsay Habte
(74) *Attorney, Agent, or Firm* — Dechert LLP

(57) ABSTRACT

The present invention provides a compound of Formula (I):

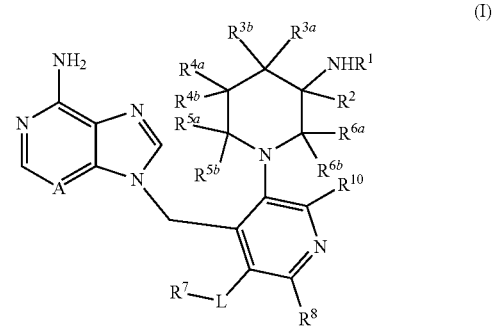

or an enantiomer, an enantiomeric mixture, or a pharmaceutically acceptable salt thereof; wherein the variables are as defined herein. The present invention further provides pharmaceutical compositions comprising such compounds; and methods of using such compounds for treating a disease or condition mediated by nuclear SET domain-containing protein 2 (NSD2).

20 Claims, No Drawings

(56) References Cited

OTHER PUBLICATIONS

International Search Report and Written Opinion for International Application No. PCT/US2023/022643 (8 pages).
International Search Report and Written Opinion for International Application No. PCT/US2023/022646 (7 pages).
International Search Report and Written Opinion for International Application No. PCT/US2023/022656 (9 pages).
International Search Report and Written Opinion for International Application No. PCT/US2023/022665 (8 pages).

* cited by examiner

PIPERIDINYL-METHYL-PURINEAMINES AS NSD2 INHIBITORS AND ANTI-CANCER AGENTS

CROSS-REFERENCE TO RELATED APPLICATIONS

This application is a continuation of U.S. patent application Ser. No. 17/327,226, filed May 21, 2021, now U.S. Pat. No. 11,420,970, which is a continuation of international (PCT) patent application no. PCT/IB2020/057602, filed Aug. 12, 2020, which claims the benefit of and priority to PCT/CN2019/100542, filed Aug. 14, 2019; the contents of these applications are incorporated by reference herein in their entirety.

FIELD OF THE INVENTION

The present invention relates to compounds, compositions and methods for inhibiting the nuclear SET domain-containing protein 2 (NSD2).

BACKGROUND OF THE INVENTION

The nuclear receptor-binding SET domain protein 2 (NSD2), also known as Wolf-Hirschhorn syndrome candidate 1 (WHSC1) or multiple myeloma SET domain (MM-SET) is an epigenetic modifier, and is believed to have a driving role in oncogenesis. Both NSD2 overexpression and point mutations that increase its catalytic activity are associated with several human cancers. (Coussens et al., J. Biol. Chem. 293, 13750-13654 (2018).

NSD2 is dysregulated by the t(4;14)(p16.3;q32.3) translocation in approximately 15% of multiple myeloma (MM) cases. Increased expression of NSD2 in t(4;14)+MM cell lines is associated with increased levels of H3K36me2 and reciprocally decreased levels of H3K27me3. Such correlation suggests a causal relationship between NSD2 histone methyltransferase (HMT) activity and the MM oncogene.

High expression of the NSD2 protein has been demonstrated in different human cancer types, including bladder, brain, gastrointestinal, lung, liver, ovary, skin, uterus, breast, prostate and glioblastoma. (Coussens et al., supra; Ezponda et al., Oncogene 32:2882-2890 (2013)). Notably, NSD2 is among the most frequently mutated genes in pediatric cancer genomes. The NSD2 SET domain variant, E1099K, was identified in both acute lymphoblastic leukemia tumors and cell lines with increased H3K36me2 that lack the t(4;14) translocation. Sequence results of >1000 pediatric cancer genomes, representing 21 different cancers, revealed the E1099K variant in 14% of t(12;21) ETV6-RUNX1 containing acute lymphoblastic leukemia (ALL). NSD2 is also among the most frequently mutated genes found in mantle cell lymphoma tumors, where both E1099K and T1 150A variants are observed. The E1099K variant has also been reported in chronic lymphocytic leukemia (CLL), lung and stomach cancers. (Coussens et al., supra). In general, NSD2 upregulation is associated with aggressive tumor behavior and poor prognosis. (Ezponda et al., supra).

NSD2 is a promising target for cancer therapy, and there remains a need for selective inhibitors of NSD2.

SUMMARY OF THE INVENTION

The present invention provides novel compounds that inhibit NSD2; and compositions and methods for treating or preventing a disease or condition mediated by NSD2.

In one aspect, the invention provides a compound of Formula (I):

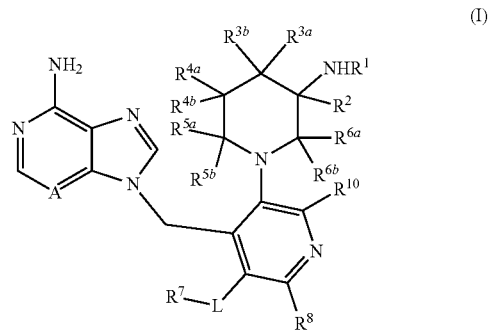

or an enantiomer, an enantiomeric mixture, or a pharmaceutically acceptable salt thereof; wherein:
A is N or $CR^9$ wherein $R^9$ is hydrogen or halo;
L is a bond or $C_{1-4}$ alkylene;
$R^1$ is H; or
$R^1$ and $R^2$ together with NH forms a 5-8 membered heterocyclyl containing 1-2 heteroatoms selected from N, O and S as ring members; wherein said 5-8 membered heterocyclyl is unsubstituted or substituted by an oxo substituent;
$R^2$ is selected from the group consisting of:
(i) hydrogen, —$C_{1-6}$ alkyl, -halo$C_{1-6}$ alkyl, -hydroxy$C_{1-6}$ alkylene, -hydroxyhalo$C_{1-6}$ alkylene, —$C_{1-6}$alkoxy$C_{1-6}$alkylene, -halo$C_{1-6}$ alkoxy$C_{1-6}$ alkylene or —$C_{3-8}$ cycloalkoxy($C_{1-6}$ alkyl);
(ii) cyano; -cyano$C_{1-6}$ alkylene; —$C_{1-6}$ alkylthio$C_{1-6}$alkyl; —$C_{2-6}$ alkenyl; -halo$C_{2-6}$ alkenyl; —$C_{2-6}$ alkynyl; —$C_{1-4}$ alkylSO$C_{1-4}$alkyl; —$C_{1-4}$ alkyISO$_2C_{1-4}$alkyl; —$SO_2R_8$ or —$C(C_{1-4}$ alkyl)=N—$O(C_{1-4}$ alkyl);
(iii) —$C_{1-4}$alkylcarbonyl; —$(CR^aR^b)_p$—$C(=O)$—$OR^{10}$; or —$C(=O)$—$(CR^aR^b)_q R^{11}$—; wherein $R^{11}$ is $C_{3-7}$ cycloalkyl, 5-6 membered heterocyclyl or 5-6 membered heteroaryl, each of which is independently unsubstituted or substituted with $C_{1-6}$ alkyl or $C_{1-6}$ alkoxy;
(iv) —$(CR^aR^b)_r$—$C(=O)$—$NR^{12}R^{13}$ wherein $R^{12}$ is hydrogen or $C_{1-6}$ alkyl; $R^{13}$ is hydrogen, —$C_{1-6}$ alkyl or a 5-6 membered heterocyclic ring; or $R^{12}$ and $R^{13}$ together form a 5-6 membered heterocyclic ring; wherein said 5-6 membered heterocyclic ring is unsubstituted or substituted with $C_{1-4}$ alkyl;
(v) 5-6 membered heterocyclyl$C_{0-6}$alkyl or 5-6 membered heterocyclyl(halo$C_{1-4}$ alkyl) wherein each said heterocyclyl radical is unsubstituted or substituted by oxo; and
(vi) 5-9 membered heteroaryl$C_{0-6}$alkyl or 5-9 membered heteroaryl(halo$C_{1-4}$alkyl), wherein each said heteroaryl radical is unsubstituted or substituted by —$C_{1-4}$ alkyl, -halo$C_{1-4}$ alkyl, -hydroxy$C_{1-4}$ alkylene, —$C_{1-4}$ alkoxy, -halo$C_{1-4}$ alkoxy, halo, hydroxy, cyano, oxido, -aminocarbonyl$C_{0-6}$alkyl, —$C_{1-4}$alkylaminocarbonyl$C_{0-6}$ alkyl, -di$C_{1-4}$alkylaminocarbonyl$C_{0-6}$alkyl or —$C_{3-7}$ cycloalkyl;
$R^{3a}$, $R^{3b}$, $R^{4a}$, $R^{4b}$, $R^{5a}$, $R^{5b}$, $R^{6a}$ and $R^{6b}$ are independently hydrogen, halo, cyano, hydroxyl, —$C_{1-6}$ alkyl, -halo$C_{1-6}$ alkyl, -hydroxy$C_{1-6}$ alkylene, —$C_{1-6}$ alkoxy, —$C_{1-6}$alkoxy$C_{1-6}$alkylene, -halo$C_{1-6}$ alkoxy$C_{1-6}$ alkylene, -hydroxyhalo$C_{1-6}$ alkylene, aryl, —$C(=O)$—$OR^{14}$ or —$(CR^aR^b)_s$—$C(=O)$—$NR^{15}R^{16}$; or $R^{3a}$ and $R^{3b}$, $R^{4a}$ and $R^{4b}$, $R^{5a}$ and $R^{5b}$ or $R^{6a}$ and $R^{6b}$ forms an oxo substituent;

$R^7$ is H, —$C_{1-4}$ alkoxy, halo or $C_{1-4}$ alkyl; or 3-8 membered heterocyclyl, which is unsubstituted or substituted by halo;

$R^8$ is $C_{3-8}$ cycloalkyl($C_{0-6}$alkyl); 4-6 membered heterocyclyl$C_{0-6}$alkyl comprising 1-3 heteroatoms selected from N, O and S; aryl or 5-9 membered heteroaryl$C_{0-6}$alkyl comprising 1-3 heteroatoms selected from N, O and S; wherein $R^8$ is unsubstituted or substituted by 1-3 $R^{17}$;

$R^{17}$ is halo, hydroxy, cyano, —$C_{1-6}$ alkyl, -halo$C_{1-6}$ alkyl, —$C_{1-6}$ alkoxy, -halo$C_{1-6}$ alkoxy, —$NR^aC(\!=\!O)CR^c\!=\!C(R^c)_2$ or —$(CR^aR^b)_r$—$NR^a$—$C(\!=\!O)$—$R^{18}$;

$R^a$, $R^b$, $R^c$, $R^{10}$, $R^{14}$, $R^{15}$ and $R^{16}$ are independently hydrogen or —$C_{1-4}$ alkyl;

$R^{18}$ is —$C_{1-4}$ alkyl or —$C_{1-4}$ haloalkyl; and p, q, r, s and t are independently 0-4.

In another aspect, the invention provides a pharmaceutical composition comprising a therapeutically effective amount of a compound of Formula (I) or sub-formulae thereof, or a pharmaceutically acceptable salt thereof; and one or more pharmaceutically acceptable carriers.

In yet another aspect, the invention provides a combination, in particular a pharmaceutical combination, comprising a therapeutically effective amount of a compound of Formula (I) or sub-formulae thereof, or a pharmaceutically acceptable salt thereof; and one or more therapeutically active agent(s).

The compounds of the invention, alone or in combination with one or more therapeutically active agent(s), can be used for treating or preventing a disease or condition mediated by NSD2; and more particularly wherein the disease or condition is characterized by overexpression or undesired upregulation of NSD2.

DETAILED DESCRIPTION OF THE INVENTION

The present invention provides compositions and methods for treating or preventing a disease or condition mediated by NSD2.

Definitions

For purposes of interpreting this specification, the following definitions will apply and whenever appropriate, terms used in the singular will also include the plural and vice versa.

As used herein, the term "—$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-4}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

As used herein, the term "—$C_{2-6}$alkenyl" refers to a straight or branched hydrocarbon chain radical group consisting solely of carbon and hydrogen atoms, containing at least one double bond, having from two to six carbon atoms, which is attached to the rest of the molecule by a single bond. The term "$C_{2-4}$alkenyl" is to be construed accordingly. Examples of $C_{2-6}$alkenyl include, but are not limited to, ethenyl, prop-1-enyl, but-1-enyl, pent-1-enyl, pent-4-enyl and penta-1,4-dienyl.

As used herein, the term "—$C_{2-6}$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_{2-4}$alkynyl" is to be construed accordingly. Examples of $C_{2-6}$alkynyl include, but are not limited to, ethynyl, prop-1-ynyl, but-1-ynyl, pent-1-ynyl, pent-4-ynyl and penta-1,4-diynyl.

As used herein, the term "—$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy.

As used herein, the term "—$C_{1-6}$alkoxy$C_{1-6}$alkylene" refers to a radical of the formula —$R_a$—O—$R_a$ where each $R_a$ is independently a $C_{1-6}$alkyl radical as defined above. The oxygen atom may be bonded to any carbon atom in either alkyl radical. Examples of $C_{1-6}$alkoxy $C_{1-6}$alkyl include, but are not limited to, methoxy-methyl, methoxy-ethyl, ethoxy-ethyl, 1-ethoxy-propyl and 2-methoxy-butyl.

As used herein, the term "—$C_{1-4}$alkylcarbonyl" refers to a radical of the formula —$C(\!=\!O)$—$R_a$ where $R_a$ is a $C_{1-4}$alkyl radical as defined above.

As used herein, the term "—$C_{1-4}$alkylthio$C_{1-4}$alkyl" refers to a radical of the formula
—$R_a$—S—$R_a$ where each $R_a$ is independently a $C_{1-4}$ alkyl radical as defined above.

As used herein, the term "-hydroxy$C_{1-6}$alkylene" refers to a $C_{1-6}$alkyl radical as defined above, wherein one of the hydrogen atoms of the $C_{1-6}$alkyl radical is replaced by OH. Examples of hydroxy$C_{1-6}$alkyl include, but are not limited to, ethan-1-olyl, 2-methylpropan-1-olyl, hydroxy-methyl, 2-hydroxy-ethyl, 2-hydroxy-propyl, 3-hydroxy-propyl and 5-hydroxy-pentyl.

As used herein, the term "-aminocarbonyl$C_{0-6}$alkyl" refers to a radical of the formula
—$R_a$—$C(\!=\!O)$—$NH_2$ wherein $R_a$ is a single bond or a $C_{1-6}$alkyl radical as defined above.

As used herein, the term "—$C_{1-4}$alkylaminocarbonyl$C_{0-6}$alkyl" refers to a radical of the formula
—$R_{a1}$—$C(\!=\!O)$—NH—$R_{a2}$ where $R_{a1}$ is a single bond or a $C_{1-6}$ alkyl radical as defined above; and $R_{a2}$ is a $C_{1-6}$alkyl radical as defined above.

As used herein, the term "-di$C_{1-4}$alkylaminocarbonyl$C_{0-6}$alkyl" refers to a radical of the formula —$R_{a1}$—$C(\!=\!O)$—$N(R_{a2})$—$R_{a2}$ where $R_{a1}$ is a single bond or a $C_{1-6}$alkyl radical as defined above; and each $R_{a2}$ is a $C_{1-4}$alkyl radical as defined above, and may be the same or different.

As used herein, the term "—$C_{3-8}$cycloalkyl$C_{0-6}$alkyl" refers to a stable monocyclic saturated hydrocarbon radical consisting solely of carbon and hydrogen atoms, having from three to eight carbon atoms, and which is attached to the rest of the molecule by a single bond (i.e., $C_{3-8}$cycloalkyl) or by a $C_{1-6}$alkyl radical as defined above. The terms "$C_{3-7}$cycloalkyl" and "$C_{3-7}$ cycloalkyl$C_{0-4}$alkyl" are to be construed accordingly. Examples of $C_{3-8}$cycloalkyl$C_{0-6}$alkyl include, but are not limited to, cyclopropyl, cyclopropylmethyl, cyclobutyl, cyclobutyl-ethyl, cyclopentyl, cyclopentyl-propyl, cyclohexyl, cycloheptyl and cyclooctyl.

As used herein, the term "—$C_{3-8}$cycloalkoxy$C_{1-6}$alkyl" refers to a radical of the formula —$R_a$—O—$R_b$ wherein $R_a$ is independently a $C_{1-6}$alkyl radical as defined above and $R_b$ is a $C_{3-8}$cycloalkyl as defined above. Examples of $C_{3-8}$cycloalkoxy$C_{1-6}$alkyl include but are not limited to cyclopropoxymethyl and cyclobutoxymethyl.

"Halo" refers to bromo, chloro, fluoro or iodo.

As used herein, the term "-haloC$_{1-6}$alkyl" refers to a C$_{1-6}$alkyl radical, as defined above, substituted by one or more halo radicals, as defined above. Examples of haloC$_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl. The term "haloC$_{1-4}$alkyl" is to be construed accordingly.

As used herein, the term "-haloC$_{1-6}$alkoxyC$_{1-4}$alkylene" refers to a radical of the formula —R$_{a1}$—O—R$_{a2}$ wherein R$_{a1}$ is a C$_{1-6}$alkyl radical as defined above; and R$_{a2}$ is a haloC$_{1-6}$alkyl as defined above. Examples of haloC$_{1-6}$alkoxyC$_{1-4}$alkyl include but are not limited to (difluoromethoxyl)methyl, (2,2,2-trifluoroethoxy)methyl and (2,2-difluoroethoxy)methyl.

As used herein, the term "-hydroxylhaloC$_{1-6}$alkylene" refers to a haloC$_{1-6}$alkyl radical, as defined above, substituted by one or more hydroxyl radicals. Examples of hydroxylhaloC$_{1-6}$alkyl include but are not limited to, 2,2-difluoroethan-1-olyl; 2-fluoroethan-1-olyl; and 2,2,2-trifluoroethan-1-olyl.

As used herein, the term "-cyanoC$_{1-6}$ alkylene" refers to a radical of the formula —R$_a$—CN, where R$_a$ is a C$_{1-4}$alkyl radical as defined above.

As used herein, the term "-haloC$_{2-6}$alkenyl" refers to a C$_{2-6}$alkenyl radical, as defined above, substituted by one or more halo radicals, as defined above.

As used herein, the term "heterocyclyl" or "heterocyclic" refers to a stable 4-7 membered non-aromatic monocyclic ring radical comprising 1, 2, or 3, heteroatoms individually selected from nitrogen, oxygen and sulfur. The heterocyclyl radical may be bonded via a carbon atom or heteroatom. The term "5-6 membered heterocyclyl" is to be construed accordingly. Examples of heterocyclyl include, but are not limited to, azetidinyl, oxetanyl, pyrrolinyl, pyrrolidyl, tetrahydrofuryl, tetrahydrothienyl, piperidyl, piperazinyl, tetrahydropyranyl or morpholinyl or perhydroazepinyl.

As used herein, the term "heterocyclylC$_{0-6}$alkyl" refers to a heterocyclic ring as defined above which is attached to the rest of the molecule by a single bond or by a C$_{1-6}$alkyl radical as defined above.

As used herein, the term "heteroaryl" refers to a 5-9 membered aromatic monocyclic or fused ring radical comprising 1, 2, 3 or 4 heteroatoms individually selected from nitrogen, oxygen and sulfur. The heteroaryl radical may be bonded via a carbon atom or heteroatom. The term "5-6 membered heteroaryl" is to be construed accordingly. Examples of 5-6 membered monocyclic heteroaryls include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl. Examples of fused heteroaryls include but are not limited to 9-membered heteroaryls such as benzofuranyl; 2,3-dihydrobenzofuranyl, 1,3-dihydroisobenzofuranyl; benzo[d][1,3]dioxol-5-yl; imidazo[1,2-a]pyridinyl; pyrazolo[1,5-a]pyridinyl; 1H-indazolyl; and 1H-benzo[d]-imidazolyl.

As used herein, the term "heteroarylC$_{0-6}$alkyl" refers to a heteroaryl ring as defined above which is attached to the rest of the molecule by a single bond or by a C$_{1-6}$alkyl radical as defined above.

As used herein, the term "heteroaryl(haloC$_{1-4}$alkyl)" refers to a heteroaryl ring as defined above which is attached to the rest of the molecule by a haloC$_{1-4}$alkyl as defined above. An illustrative example of an heteroaryl(haloC$_{1-4}$alkyl) is fluoro(pyridin-2-yl)methyl.

"IC$_{50}$", as used herein, refers to the molar concentration of an inhibitor or modulator that produces 50% inhibition.

"Protected derivatives", as used herein, refers to derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, p-methoxyethoxymethyl ether, p-methoxybenzyl, methylthiomethyl ether, pivaloyl, silyl ether, carbobenzyloxy, benzyl, tert-butoxycarbonyl, p-methoxyphenyl, 9-fluorenylmethyloxycarbonyl, acetals, ketals, acylals, dithianes, methyl esters, benzyl esters, tert-butyl esters, and silyl esters. A comprehensive list of suitable protecting groups can be found in T. W. Greene, *Protecting Groups in Organic Synthesis*, 3rd edition, John Wiley & Sons, Inc. 1999.

The term "disease or condition mediated by nuclear SET domain-containing protein 2 (NSD2)" refers to a disease or condition that is directly or indirectly regulated by NSD2.

As used herein, the term "subject" refers to mammals, primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

As used herein, the term "anti-cancer agent" or antineoplastic agent, refers to a therapeutic agent that is useful for treating or controlling the growth of cancerous cells.

As used herein, the term "anti-inflammatory agent" refers to a therapeutic agent that reduces inflammation (redness, swelling and/or pain) in the body. Anti-inflammatory agents block certain substances in the body that cause inflammation.

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, 22$^{nd}$ Ed. Pharmaceutical Press, 2013, pp. 1049-1070).

As used herein, the term "a," "an," "the" and similar terms used in the context of the present invention (especially in the context of the claims) are to be construed to cover both the singular and plural unless otherwise indicated herein or clearly contradicted by the context.

Description of Preferred Embodiments

The present invention provides novel compounds that inhibit NSD2; and compositions and methods for treating or preventing a condition mediated by NSD2.

Various enumerated embodiments of the invention are described herein. Features specified in each embodiment may be combined with other specified features to provide further embodiments of the present invention.

Embodiment 1. A compound of Formula (I), or an enantiomer, an enantiomeric mixture, or a pharmaceutically acceptable salt thereof; as described above.

Embodiment 2. A compound of Formula (I) according to Embodiment 1, or an enantiomer, an enantiomeric mixture, or a pharmaceutically acceptable salt thereof; wherein A is N.

Embodiment 3. A compound of Formula (I) according to Embodiment 1 or 2, or an enantiomer, an enantiomeric mixture, or a pharmaceutically acceptable salt thereof; wherein
$R^{3a}$ is hydrogen or halo; and $R^{3b}$ is hydrogen, halo, -hydroxyl, —$C_{1-6}$ alkoxy or cyano; or
$R^{4a}$ is hydrogen or halo; and $R^{4b}$ is hydrogen, halo, —$C_{1-6}$alkoxyC$_{1-6}$alkylene, —$C_{1-6}$ alkyl or -haloC$_{1-6}$ alkyl; or
$R^{5a}$ is hydrogen and $R^{5b}$ is hydrogen or —$C_{1-6}$ alkyl; or $R^{5a}$ and $R^{5b}$ together form an oxo substituent.

Embodiment 4. A compound of Formula (I) according to any one of Embodiments 1-3, or an enantiomer, an enantiomeric mixture, or a pharmaceutically acceptable salt thereof; wherein
$R^{6a}$ is hydrogen or halo;
$R^{6b}$ is hydrogen, -haloC$_{1-6}$ alkoxyC$_{1-6}$ alkylene, -hydroxyC$_{1-6}$ alkylene, -hydroxyhaloC$_{1-6}$ alkylene, carboxyl, phenyl or —(CR$^a$R$^b$)$_t$—C(O)—NR$^{15}$R$^{16}$;
$R^a$, $R^b$, $R^{15}$ and $R^{16}$ are independently hydrogen or —$C_{1-4}$ alkyl; and
t is 0-1; or
$R^{6a}$ and $R^{6b}$ together form an oxo substituent.

Embodiment 5. A compound of Formula (I) according to any one of Embodiments 1-4, or an enantiomer, an enantiomeric mixture, or a pharmaceutically acceptable salt thereof; wherein $R^7$ is H, —$C_{1-4}$ alkoxy or halo.

Embodiment 6. A compound of Formula (I) according to any one of Embodiments 1-5, or an enantiomer, an enantiomeric mixture, or a pharmaceutically acceptable salt thereof; wherein $R^1$, $R^{3a}$, $R^{3b}$, $R^{4a}$, $R^{4b}$, $R^{5a}$, $R^{5b}$, $R^{6a}$, $R^{6b}$ and $R^7$ are hydrogen.

Embodiment 7. A compound of Formula (I) according to Embodiment 1, wherein said compound is a compound of Formula (II):

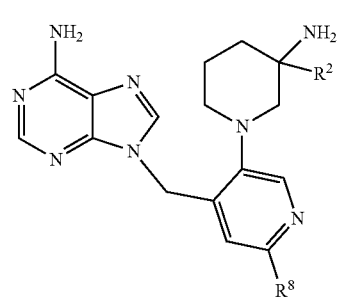

or an enantiomer, an enantiomeric mixture, or a pharmaceutically acceptable salt thereof.

Embodiment 8. A compound of Formula (II) according to Embodiment 7, wherein said compound is a compound of Formula (IIA):

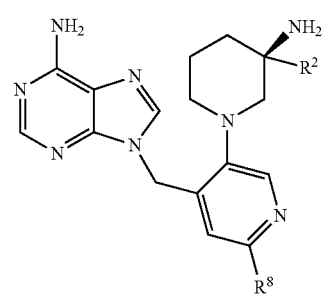

or an enantiomer, an enantiomeric mixture, or a pharmaceutically acceptable salt thereof.

Embodiment 9. A compound according to any one of Embodiments 1-8, or an enantiomer, an enantiomeric mixture, or a pharmaceutically acceptable salt thereof, wherein $R^2$ is hydrogen, —$C_{1-6}$ alkyl, -haloC$_{1-6}$ alkyl, -hydroxyC$_{1-6}$ alkylene, -hydroxyhaloC$_{1-6}$ alkylene, —$C_{1-6}$alkoxyC$_{1-6}$ alkylene, -haloC$_{1-6}$ alkoxyC$_{1-6}$ alkylene or —$C_{3-8}$ cycloalkoxy(C$_{1-6}$ alkyl).

Embodiment 10. A compound according to any one of Embodiments 1-8 or an enantiomer, an enantiomeric mixture, or a pharmaceutically acceptable salt thereof; wherein $R^2$ is —$C_{1-4}$ alkylcarbonyl;
—(CR$^a$R$^b$)$_p$—C(O)—OR$^{10}$ wherein R$^{10}$ is hydrogen or —$C_{1-4}$ alkyl;
—C(O)—(CR$^a$R$^b$)$_q$—R$^{11}$ wherein R$^{11}$ is C$_{3-6}$ cycloalkyl, 5-6 membered heterocyclyl or 5-6 membered heteroaryl, each of which is independently unsubstituted or substituted with —$C_{1-6}$ alkyl or —$C_{1-6}$ alkoxy; or
—(CR$^a$R$^b$)$_r$—C(O)—NR$^{12}$R$^{13}$; wherein
$R^{12}$ is hydrogen or —$C_{1-6}$ alkyl;
$R^{13}$ is hydrogen, —$C_{1-6}$ alkyl or a 5-6 membered heterocyclic ring; or
$R^{12}$ and $R^{13}$ together form a 5-6 membered heterocyclic ring; wherein said 5-6 membered heterocyclic ring is unsubstituted or substituted with —$C_{1-4}$ alkyl; and
$R^a$, $R^b$ and $R^{11}$ are independently hydrogen or —$C_{1-4}$ alkyl; and
p, q and r are independently 0-2.

Embodiment 11. A compound according to any one of Embodiments 1-8 or an enantiomer, an enantiomeric mixture, or a pharmaceutically acceptable salt thereof; wherein $R^2$ is selected from the group:

pyridin-2-yl, (pyridin-2-yl)methyl or (pyridin-2-yl)ethyl, wherein said pyridin-2-yl is independently unsubstituted or substituted with 1-2 —$C_{1-4}$ alkyl, —$C_{1-4}$ haloalkyl, hydroxyl, -hydroxy$C_{1-4}$ alkylene, cyano, —$C_{1-4}$ alkoxy, —$C_{1-6}$ alkoxy$C_{1-6}$alkylene, -halo$C_{1-4}$ alkoxy, halo or —$C_{3-7}$ cycloalkyl;

thiazol-4-yl, thiazol-2-ylmethyl, oxazol-2-yl, oxazol-2-ylmethyl, pyridazin-3-yl, pyridazin-3-ylmethyl, pyrazin-2-yl, pyrazin-2-ylmethyl, pyrimidin-4-yl, pyrimidin-4-ylmethyl, each of which is independently unsubstituted or substituted with —$C_{1-4}$ alkyl or halo;

1H-pyrazol-3-yl, (1H-pyrazol-3-yl)methyl, 1-methyl-1H-pyrazol-4-yl, (1,2,3-triazol-4-yl), isoxazol-3-yl, each of which is independently unsubstituted or substituted with —$C_{1-4}$ alkyl, halo or —$C_{3-7}$ cycloalkyl;

1,4-dioxan-2-yl;

pyridin-2(1H)-onyl; and pyridin-1-oxide-2-yl.

Embodiment 12. A compound according to any one of Embodiment 1-11 or an enantiomer, an enantiomeric mixture, or a pharmaceutically acceptable salt thereof; wherein $R^8$ is cyclopropyl; cyclobutyl; cyclohexyl or azetidinyl.

Embodiment 13. A compound according to any one of Embodiment 1-11 or an enantiomer, an enantiomeric mixture, or a pharmaceutically acceptable salt thereof; wherein $R^8$ is 2,3-dihydrobenzofuran-5-yl; 1,3-dihydroisobenzofuran-5-yl; benzo[d][1,3]dioxol-5-yl; imidazo[1,2-a]pyridin-6-yl or pyrazolo[1,5-a]pyridine-6-yl.

Embodiment 14. A compound according to any one of Embodiment 1-13 or an enantiomer, an enantiomeric mixture, or a pharmaceutically acceptable salt thereof; wherein $R^8$ is pyridyl, unsubstituted or substituted with 1-2 halo, —$C_{1-6}$ alkyl or —$C_{1-6}$ alkoxy; 1H-indazol-5-yl unsubstituted or substituted with 1-2 halo or —$C_{1-6}$ alkyl; or 1H-benzo[d]-imidazol-6-yl unsubstituted or substituted with —$C_{1-6}$ alkyl.

Embodiment 15. A compound according to any one of Embodiment 1-13 or an enantiomer, an enantiomeric mixture, or a pharmaceutically acceptable salt thereof; wherein $R^8$ is phenyl substituted with 1-3 $R^{17}$;

$R^{17}$ is halo, hydroxy, cyano, —$C_{1-6}$ alkyl, -halo$C_{1-6}$ alkyl, —$C_{1-6}$ alkoxy, -halo$C_{1-6}$ alkoxy, —$NR^dC(O)CR^d$=$C(R^d)_2$ or —$(CR^aR^b)_t$—$NR^d$—$C(O)$—$R^{18}$;

$R^a$, $R^b$ and $R^d$ are independently hydrogen or —$C_{1-4}$ alkyl;

$R^{18}$ is —$C_{1-4}$ haloalkyl; and t is 0-1.

Embodiment 16. A compound according to any one of Embodiment 1-13 or an enantiomer, an enantiomeric mixture, or a pharmaceutically acceptable salt thereof; wherein $R^8$ is phenyl substituted with 1-3 $R^{17}$; and $R^{17}$ is halo, hydroxy, —$C_{1-6}$ alkyl, -halo$C_{1-6}$ alkyl, —$C_{1-6}$ alkoxy or -halo$C_{1-6}$ alkoxy.

Embodiment 17. A compound of Formula (II)

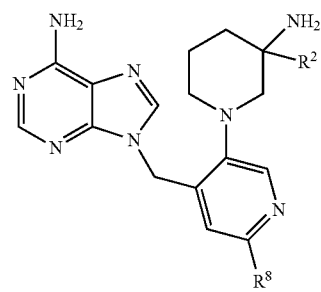

(II)

or an enantiomer, an enantiomeric mixture, or a pharmaceutically acceptable salt thereof;
wherein:
$R^2$ is hydrogen, —$C_{1-6}$ alkyl, -halo$C_{1-6}$ alkyl, -hydroxy$C_{1-6}$ alkylene, -hydroxyhalo$C_{1-6}$ alkylene, —$C_{1-6}$alkoxy$C_{1-6}$alkylene, -halo$C_{1-6}$ alkoxy$C_{1-6}$ alkylene or —$C_{3-8}$ cycloalkoxy($C_{1-6}$ alkyl);
$R^8$ is phenyl substituted with 1-3 $R^{17}$; and
$R^{17}$ is halo, hydroxy, —$C_{1-6}$ alkyl, -halo$C_{1-6}$ alkyl, —$C_{1-6}$ alkoxy or -halo$C_{1-6}$ alkoxy.

Embodiment 18. A compound of Formula (II) according to Embodiment 17, wherein said compound is a compound of Formula (IIA):

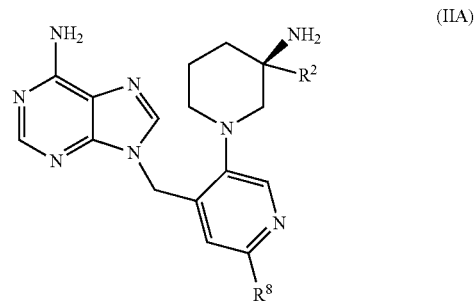

(IIA)

or an enantiomer, an enantiomeric mixture, or a pharmaceutically acceptable salt thereof.

Embodiment 19. A compound according to any one of Embodiments 1-18 or an enantiomer, an enantiomeric mixture, or a pharmaceutically acceptable salt thereof; wherein $R^2$ is hydrogen; 2,2-difluoroethyl; 2-methyl-propan-1-olyl; ethan-1-olyl; 2,2-difluoroethan-1-olyl; 2-fluoroethan-1-olyl; 2,2,2-trifluoroethan-1-olyl; difluoromethoxyl; or 2,2,2-trifluoroethoxyl.

Embodiment 20. A compound according to any one of Embodiments 1-18 or an enantiomer, an enantiomeric mixture, or a pharmaceutically acceptable salt thereof; wherein $R^2$ is

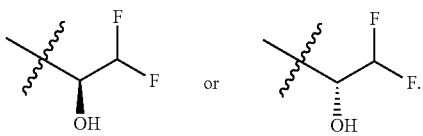 [SMILES: *[C@H](O)C(F)F ; *[C@@H](O)C(F)F]

Embodiment 21. A compound according to any one of Embodiments 1-20, wherein said compound is a compound from Table 2; or an enantiomer, an enantiomeric mixture, or a pharmaceutically acceptable salt thereof.

Embodiment 22. The compound according to Embodiment 21, wherein said compound is selected from the group consisting of:

1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol;

1-(3-amino-1-(4-((6-amino-9H-purin-9-yl)methyl)-6-(2-(difluoromethyl)-4-fluorophenyl)pyridin-3-yl)piperidin-3-yl)-2,2-difluoroethan-1-ol;

1-(3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol;

1-(3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol;

1-(3-amino-1-(4-((6-amino-9H-purin-9-yl)methyl)-6-(3,5-difluoro-4-methoxyphenyl)pyridin-3-yl)piperidin-3-yl)-2,2-difluoroethan-1-ol;

1-(3-amino-1-(4-((6-amino-9H-purin-9-yl)methyl)-6-(4-methoxy-2-(trifluoromethyl)phenyl)pyridin-3-yl)piperidin-3-yl)-2,2-difluoroethan-1-ol;

1-(3-amino-1-(4-((6-amino-9H-purin-9-yl)methyl)-6-(2-chloro-4-methoxyphenyl)pyridin-3-yl)piperidin-3-yl)-2,2-difluoroethan-1-ol;

1-(3-amino-1-(4-((6-amino-9H-purin-9-yl)methyl)-6-(2-(difluoromethyl)-4,5-difluorophenyl)pyridin-3-yl)piperidin-3-yl)-2,2-difluoroethan-1-ol;

1-(3-amino-1-(4-((6-amino-9H-purin-9-yl)methyl)-6-(2,3,4-trifluorophenyl)pyridin-3-yl)piperidin-3-yl)-2,2-difluoroethan-1-ol;

1-(3-amino-1-(4-((6-amino-9H-purin-9-yl)methyl)-6-(4-fluoro-2-methoxyphenyl)pyridin-3-yl)piperidin-3-yl)-2,2-difluoroethan-1-ol; and 1-(3-amino-1-(4-((6-amino-9H-purin-9-yl)methyl)-6'-chloro-5'-fluoro-[2,2'-bipyridin]-5-yl)piperidin-3-yl)-2,2-difluoroethan-1-ol;

or an enantiomer, an enantiomeric mixture, or a pharmaceutically acceptable salt thereof.

Embodiment 23. The compound according to Embodiment 22, wherein said compound is in the (R) configuration, (S) configuration, or a mixture thereof.

Embodiment 24. The compound according to Embodiment 1, wherein said compound is (R)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol, or a pharmaceutically acceptable salt thereof.

Embodiment 25. The compound according to Embodiment 1, wherein said compound is (R)-1-((R)-3-amino-1-(4-((6-amino-9H-purin-9-yl)methyl)-6-(2-(difluoromethyl)-4-fluorophenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2-(difluoromethyl)-4-fluorophenyl)pyridin-3-yl)piperidin-3-yl)-2,2-difluoroethan-1-ol, or a pharmaceutically acceptable salt thereof.

Embodiment 26. The compound according to Embodiment 1, wherein said compound is (R)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol, or a pharmaceutically acceptable salt thereof.

Embodiment 27. The compound according to Embodiment 1, wherein said compound is (R)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol, or a pharmaceutically acceptable salt thereof.

Embodiment 28. The compound according to Embodiment 1, wherein said compound is (R)-1-((R)-3-amino-1-(4-((6-amino-9H-purin-9-yl)methyl)-6-(3,5-difluoro-4-methoxyphenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(3,5-difluoro-4-methoxyphenyl)pyridin-3-yl)piperidin-3-yl)-2,2-difluoroethan-1-ol, or a pharmaceutically acceptable salt thereof.

Embodiment 29. The compound according to Embodiment 1, wherein said compound is (R)-1-((R)-3-amino-1-(4-((6-amino-9H-purin-9-yl)methyl)-6-(4-methoxy-2-(trifluoromethyl)phenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(4-methoxy-2-(trifluoromethyl)phenyl)pyridin-3-yl)piperidin-3-yl)-2,2-difluoroethan-1-ol, or a pharmaceutically acceptable salt thereof.

Embodiment 30. The compound according to Embodiment 1, wherein said compound is (R)-1-((R)-3-amino-1-(4-((6-amino-9H-purin-9-yl)methyl)-6-(2-chloro-4-methoxyphenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2-chloro-4-methoxyphenyl)pyridin-3-yl)piperidin-3-yl)-2,2-difluoroethan-1-ol, or a pharmaceutically acceptable salt thereof.

Embodiment 31. The compound according to Embodiment 1, wherein said compound is (R)-1-((R)-3-amino-1-(4-((6-amino-9H-purin-9-yl)methyl)-6-(2-(difluoromethyl)-4,5-difluorophenyl)pyridin-3-yl)piperidin-3-yl)-2,2-difluoroethan-1-ol, or a pharmaceutically acceptable salt thereof. Alternatively, the compound is (S)-1-((R)-3-amino-1-(4-((6-amino-9H-purin-9-yl)methyl)-6-(2-(difluoromethyl)-4,5-difluorophenyl)pyridin-3-yl)piperidin-3-yl)-2,2-difluoroethan-1-ol, or a pharmaceutically acceptable salt thereof.

Embodiment 32. The compound according to Embodiment 1, wherein said compound is (R)-1-((R)-3-amino-1-(4-((6-amino-9H-purin-9-yl)methyl)-6-(2,3,4-trifluorophenyl)pyridin-3-yl)piperidin-3-yl)-2,2-difluoroethan-1-ol, or a pharmaceutically acceptable salt thereof.

Alternatively, the compound is (S)-1-((R)-3-amino-1-(4-((6-amino-9H-purin-9-yl)methyl)-6-(2,3,4-trifluorophenyl)pyridin-3-yl)piperidin-3-yl)-2,2-difluoroethan-1-ol, or a pharmaceutically acceptable salt thereof.

Embodiment 33. The compound according to Embodiment 1, wherein said compound is (R)-1-((R)-3-amino-1-(4-((6-amino-9H-purin-9-yl)methyl)-6-(4-fluoro-2-methoxyphenyl)pyridin-3-yl)piperidin-3-yl)-2,2-difluoroethan-1-ol, or a pharmaceutically acceptable salt thereof.

Alternatively, the compound is (S)-1-((R)-3-amino-1-(4-((6-amino-9H-purin-9-yl)methyl)-6-(4-fluoro-2-methoxyphenyl)pyridin-3-yl)piperidin-3-yl)-2,2-difluoroethan-1-ol, or a pharmaceutically acceptable salt thereof.

Embodiment 34. The compound according to Embodiment 1, wherein said compound is (R)-1-((R)-3-amino-1-(4-((6-amino-9H-purin-9-yl)methyl)-6'-chloro-5'-fluoro-[2,2'-bipyridin]-5-yl)piperidin-3-yl)-2,2-difluoroethan-1-ol, or a pharmaceutically acceptable salt thereof.

Alternatively, the compound is (S)-1-((R)-3-amino-1-(4-((6-amino-9H-purin-9-yl)methyl)-6'-chloro-5'-fluoro-[2,2'-bipyridin]-5-yl)piperidin-3-yl)-2,2-difluoroethan-1-ol, or a pharmaceutically acceptable salt thereof.

Embodiment 35. A pharmaceutical composition comprising a compound according to any one of Embodiments 1-34 and one or more pharmaceutically acceptable carrier.

Embodiment 36. A combination comprising a compound according to any one of Embodiments 1-34 and one or more additional therapeutically active agent.

Embodiment 37. The combination according to Embodiment 36, wherein said one or more additional therapeutically active agent is an anti-cancer agent, an analgesic, an anti-inflammatory agent, or a combination thereof.

Embodiment 38. A compound according to any one of Embodiments 1-34 and optionally in combination with a second therapeutic agent, for use in treating a disease or condition mediated by nuclear SET domain-containing protein 2 (NSD)2.

Embodiment 39. The compound according to Embodiment 38, wherein said second therapeutic agent is an anti-cancer agent, an analgesic, an anti-inflammatory agent or a combination thereof.

Embodiment 40. Use of a compound according to any one of Embodiments 1-34 and optionally in combination with a second therapeutic agent, in the manufacture of a medicament for a disease or condition mediated by NSD2.

Embodiment 41. A method for treating a disease or condition mediated by nuclear SET domain-containing protein 2 (NSD2), comprising administering to a subject in need thereof, a therapeutically effective amount of a compound according to any one of Embodiments 1-34 and optionally in combination with a second therapeutic agent; thereby treating said disease or condition mediated by NSD2.

Embodiment 42. A method for treating a disease or condition that benefit from or is treatable by inhibition of nuclear SET domain-containing protein 2 (NSD2), comprising administering to a subject in need thereof, a therapeutically effective amount of a compound according to any one of Embodiments 1-34 and optionally in combination with a second therapeutic agent; thereby treating said disease or condition that benefit from or is treatable by inhibition by NSD2.

Embodiment 43. The method according to Embodiment 41 or 42, wherein said disease or condition mediated by NSD2, or said disease or condition that benefit from or is treatable by inhibition of NSD2, is breast cancer, cervical cancer, skin cancer (particularly squamous cell carcinoma), ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia (particularly acute lymphoblastic leukemia), non-Hodgkin's lymphoma (particularly mantle cell lymphoma), or pulmonary arterial hypertension.

Embodiment 44. The method according to Embodiment 41 or 42, wherein said disease or condition mediated by NSD2, or said disease or condition that benefit from or is treatable by inhibition of NSD2, is lung cancer.

Embodiment 45. The method according to Embodiment 44, wherein said lung cancer is small cell or non-small cell lung cancer.

Embodiment 46. The method according to Embodiment 41 or 42, wherein said disease or condition mediated by NSD2, or said disease or condition that benefit from or is treatable by inhibition of NSD2, is leukemia.

Embodiment 47. The method according to Embodiment 46, wherein said leukemia is acute lymphoblastic leukemia (ALL), acute myeloid leukemia (AML), chronic myeloid leukemia (CML) or chronic myelomonocytic leukemia (CMML).

Embodiment 48. The method according to Embodiment 41 or 42, wherein said disease or condition mediated by NSD2, or said disease or condition that benefit from or is treatable by inhibition of NSD2, is skin cancer.

Embodiment 49. The method according to Embodiment 48, wherein said skin cancer is melanoma, basal cell carcinoma or squamous cell carcinoma.

Embodiment 50. The method according to Embodiment 41 or 42, wherein said disease or condition mediated by NSD2, or said disease or condition that benefit from or is treatable by inhibition of NSD2, is lymphoma.

Embodiment 51. The method according to Embodiment 50, wherein said lymphoma is Hodgkin's lymphoma or non-Hodgkin's lymphoma.

Embodiment 52. The method according to Embodiment 50, wherein said lymphoma is mantle cell lymphoma or diffuse large B cell lymphoma.

Embodiment 53. The method according to Embodiment 41 or 42, wherein said disease or condition mediated by NSD2, or said disease or condition that benefit from or is treatable by inhibition of NSD2, is myeloma.

Embodiment 54. A method according to any one of Embodiment 41-53, wherein said compound is administered orally.

Unless specified otherwise, the term "compounds of the present invention" or "compound of the present invention" refers to compounds of Formula (I) subformulae thereof, and exemplified compounds, and salts thereof, as well as all stereoisomers (including diastereoisomers and enantiomers), rotamers, tautomers and isotopically labeled compounds (including deuterium substitutions), as well as inherently formed moieties.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. Substituents at atoms with unsaturated double bonds may, if possible, be present in cis-(Z)— or trans-(E)-form. If the compound contains a disubstituted cycloalkyl, the cycloalkyl substituent may have a cis- or trans-configuration.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of compounds of the present invention or of intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds of the present invention or racemic intermediates can also be resolved by chiral chromatography, e.g., high pressure liquid chromatography (HPLC) using a chiral adsorbent.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of Formula (I) or sub-formulae thereof. The concentration of deuterium, may be defined by the isotopic enrichment factor. The term "isotopic enrichment factor" as used herein means the ratio between the isotopic abundance and the natural abundance of a specified isotope. If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of Formula (I) or sub-formulae thereof can generally be prepared by conventional techniques known to those skilled in the art or by processes analogous to those described in the accompanying examples using an appropriate isotopically-labeled reagents in place of the non-labeled reagent previously employed.

The compounds of the present invention are either obtained in the free form, as a salt thereof. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of the present invention in acetate, ascorbate, adipate, aspartate, benzoate, besylate, bromide/hydrobromide, bicarbonate/carbonate, bisulfate/sulfate, camphorsulfonate, caprate, chloride/hydrochloride, chlorotheophyllinate, citrate, ethanedisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate, trifenatate, trifluoroacetate or xinafoate salt form.

Processes for Making Compounds of the Invention

All methods described herein can be performed in any suitable order, unless otherwise indicated or otherwise clearly contradicted by context.

Compounds of Formula (I) can be prepared as generally illustrated in Scheme 1, wherein $R^1$, $R^2$, $R^3$, . . . are as defined above. As depicted in Scheme 1, Boc protected 3-CN or 3-CO$_2$Et piperidine undergoes $S_N2$ or $S_NAr$ reaction in the presence of strong bases (e.g. NaHMDS) and an electrophile containing $R_2$ to generate compound 2 or 2' with quaternary center, which was further hydrolyzed to corresponding carboxylic acid 3 or primary amide 3' either in basic conditions (e.g. LiOH) or oxidative hydrolysis conditions (e.g. H$_2$O$_2$, NaOH). Acid 3 or amide 3' further undergoes Curtius or Hofmann rearrangement to generate protected quaternary amine 4. After selective Boc de-protection, piperidine 5 reacts with fluorinated pyridine 6 in the presence of organic bases (e.g. DIPEA) under heat to yield coupling product 7. Ester 7 is further reduced to benzylic alcohol 8 by mild reducing agent (e.g. NaBH$_4$, LiCl), which undergoes Mistunobu reaction with Boc protected adenine Intermediate B to provide compound 9. After deprotection under acidic or hydrogenation conditions, chiral target molecule 10 is yielded followed by SFC separation.

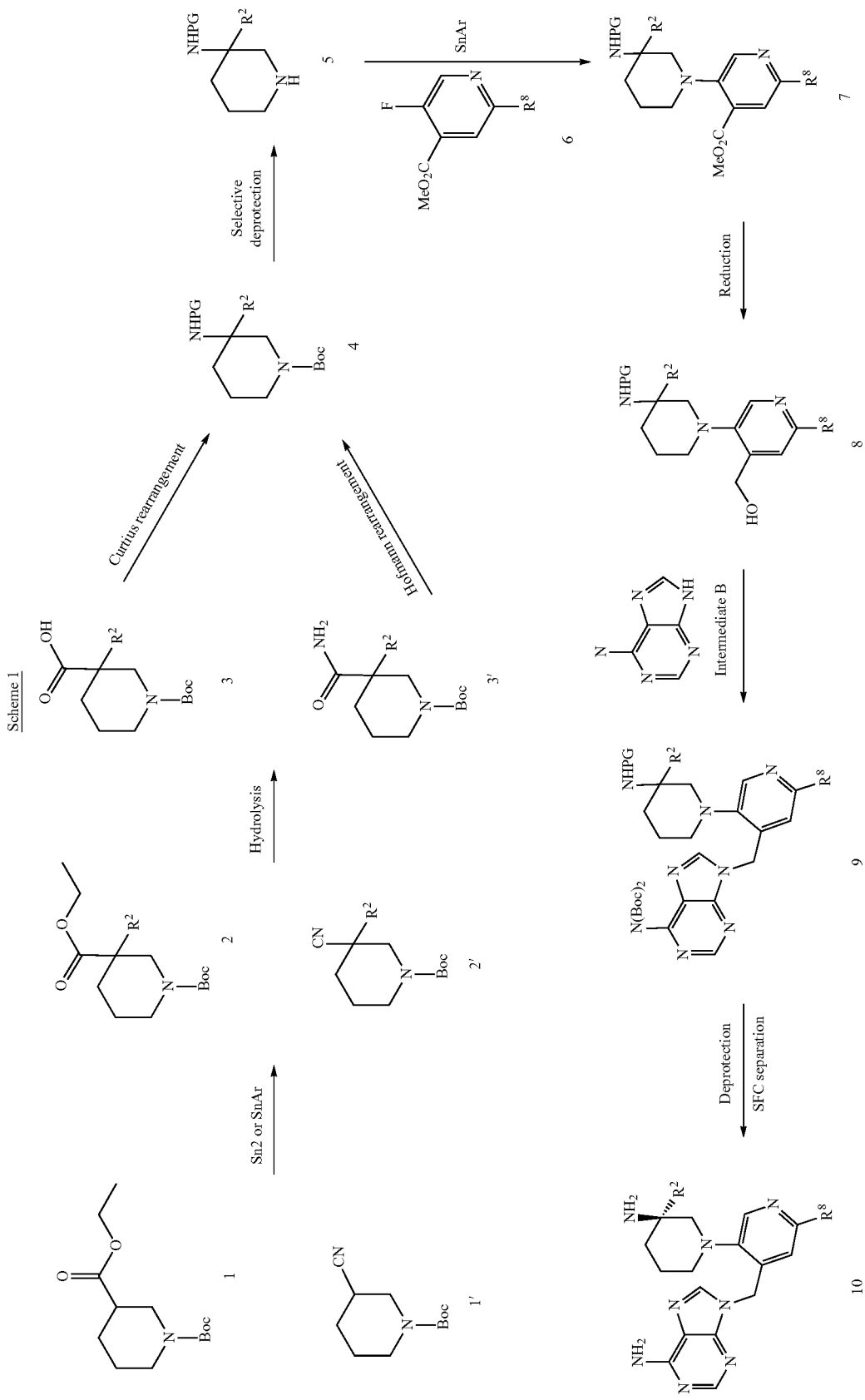

The invention further includes any variant of the present processes; for example, wherein an intermediate product obtainable at any stage thereof is used as starting material and the remaining steps are carried out; wherein starting materials are formed in situ under the reaction conditions; or wherein the reaction components are used in the form of their salts or optically pure material. Compounds of the invention and intermediates can also be converted into each other according to methods generally known to those skilled in the art.

Pharmacology and Utility

In one aspect, the invention provides compounds of Formula (I) or subformulae thereof, or a pharmaceutically acceptable salt thereof, that are useful for therapy; particularly, for treating or preventing a disease or condition that is mediated by NSD2.

In another aspect, the invention provides the use of a compound of Formula (I) or subformulae thereof, or a pharmaceutically acceptable salt thereof, for treating a disease or condition that benefit from or is treatable by inhibition of NSD2; and for the manufacture of a medicament for treating a disease or condition that is treatable by inhibition of NSD2.

Examples of diseases or conditions that are mediated by NDS2, or that benefit from or are treatable by inhibition of NSD2, include but is not limited to breast cancer, cervical cancer, skin cancer (particularly skin squamous cell carcinoma), ovarian cancer, gastric cancer, prostate cancer, pancreatic cancer, lung cancer, hepatocellular carcinoma, head and neck cancer, peripheral nerve sheath tumor, osteosarcoma, multiple myeloma, neuroblastoma, leukemia (particularly acute lymphoblastic leukemia), non-Hodgkin's lymphoma (particularly mantle cell lymphoma), and pulmonary arterial hypertension.

Pharmaceutical Compositions, Dosage and Administration

In another aspect, the present invention provides a pharmaceutical composition comprising a compound of the present invention, or a pharmaceutically acceptable salt thereof, and a pharmaceutically acceptable carrier.

In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethylene glycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and e) absorbents, colorants, flavors and sweeteners.

In another aspect, the compounds of the present invention are combined with other therapeutic agents, such as other anti-cancer agents, anti-allergic agents, anti-nausea agents (or anti-emetics), pain relievers, cytoprotective agents, and combinations thereof.

In one embodiment, the other therapeutic agent is an anti-cancer agent or chemo-therapeutic agent. Examples of anti-cancer agents considered for use in combination therapies of the invention include but are not limited erlotinib, bortezomib, fulvestrant, sunitinib, imatinib mesylate, letrozole, finasunate, platins such as oxaliplatin, carboplatin, and cisplatin, finasunate, fluorouracil, rapamycin, leucovorin, lapatinib, lonafamib, sorafenib, gefitinib, camptothecin, topotecan, bryostatin, adezelesin, anthracyclin, carzelesin, bizelesin, dolastatin, auristatins, duocarmycin, eleutherobin, taxols such as paclitaxel or docetaxel, cyclophosphamide, doxorubicin, vincristine, prednisone or prednisolone, other alkylating agents such as mechlorethamine, chlorambucil, and ifosfamide, antimetabolites such as azathioprine or mercaptopurine, other microtubule inhibitors (vinca alkaloids like vincristine, vinblastine, vinorelbine and vindesine, as well as taxanes), podophyllotoxins (etoposide, teniposide, etoposide phosphate, and epipodophyllotoxins), topoisomerase inhibitors, other cytotoxins such as actinomycin, daunorubicin, valrubicin, idarubicin, edrecolomab, epirubicin, bleomycin, plicamycin, mitomycin, as well as other anticancer antibodies (cetuximab, bevacizumab, ibritumomab, abagovomab, adecatumumab, afutuzumab, alacizumab, alemtuzumab, anatumomab, apolizumab, bavituximab, belimumab, bivatuzumab mertansine, blinatumomab, brentuximab vedotin, cantuzumab mertansine, catumazomab, cetuximab, citatuzumab bogatox, cixutumumab, clivatuzumab tetraxetan, conatumumab, dacetuzumab, daclizumab, detumomab, ecromeximab, edrecolomab, elotuzumab, epratuzumab, ertumaxomab, etaracizumab, farletuzumab, figitumumab, fresolimumab, galiximab, gembatumumab vedotin, gemtuzumab, ibritumomab tiuxetan, inotuzumab ozogamicin, intetumumab, ipilimumab, iratumumab, labetuzumab, lexatumumab, lintuzumab, lucatumumab, lumilisimab, mapatumumab, matuzumab, milatuzumab, mitumomab, nacolomab tafenatox, naptumomab estafenatox, necitumumab, nimotuzumab, ofatumumab, olaratumab, oportuzumab monatox, oregovomab, panitumumab, pemtumomab, pertuzumab, pintumomab, pritumumab, ramucirumab, rilotumumab, robatumumab, rituximab, sibrotuzumab, tacatuzumab tetraxetan, taplitumomab paptox, tenatumomab, ticilimumab, tigatuzumab, tositumomab or $^{131}$I-tositumomab, trastuzumab, tremelimumab, tuocotuzumab celmoleukin, veltuzumab, visilizumab, volocixumab, votumumab, zalutumumab, zanolimumab, IGN-101, MDX-010, ABX-EGR, EMD72000, lor-t1, MDX-220, MRA, H-11 scFv, huJ591, TriGem, TriAb, R3, MT-201, G-250, ACA-125, Onyvax-105, CD:-960, CeaVac, BrevaRexAR54, IMC-1C11, GlioMab-H, ING-1, anti-LCG MAbs, MT-103, KSB-303, Therex, KW2871, anti-HMI.24, Anti-PTHrP, 2C4 antibody, SGN-30, TRAIL-RI MAb, Prostate Cancer antibody, H22xKi-r, ABX-Mai, Imuteran, Monopharm-C), and antibody-drug conjugates comprising any of the above agents (especially auristatins MMAE and MMAF, maytansinoids like DM-1, calicheamycins, or various cytotoxins).

In another embodiment, the compounds of the invention are combined with another therapeutic agent selected from anastrozole (ARIMIDEX®), bicalutamide (CASODEX®), bleomycin sulfate (BLENOXANE®), busulfan (MYLERAN®), busulfan injection (BUSULFEX®), capecitabine (XELODA®), N4-pentoxycarbonyl-5-deoxy-5-fluorocytidine, carboplatin (PARAPLATIN®), carmustine (BiCNU®), chlorambucil (LEUKERAN®), cisplatin (PLATINOL®), cladribine (LEUSTATIN®), cyclophosphamide (CYTOXAN® or NEOSAR®), cytarabine, cytosine arabinoside (CYTOSAR-U®), cytarabine liposome injection (DEPOCYT®), dacarbazine (DTIC-Dome®), dactinomycin (actinomycin D, COSMEGAN®), daunorubicin hydrochloride (CERUBIDINE®), daunorubicin citrate liposome injection (DAUNOXOME®), dexamethasone, docetaxel (TAXOTERE®), doxorubicin hydrochloride (ADRIAMYCIN®, RUBEX®), etoposide (VEPESID®), fludarabine phosphate (FLUDARA®), 5-fluorouracil (ADRUCIL®, EFUDEX®), flutamide (EULEXIN®), tezacitibine, gemcitabine (difluorodeoxycitidine), hydroxyurea (HYDREA®), idarubicin (IDAMYCIN®), ifosfamide (IFEX®), irinotecan (CAMPTOSAR®), L-asparaginase (ELSPAR®), leucovorin calcium, melphalan (ALKERAN®), 6-mercaptopurine (PURINETHOL®), methotrexate (FOLEX®), mitoxantrone (NOVANTRONE®), gemtuzumab ozogamicin (MYLOTARG™), paclitaxel (TAXOL®), nab-paclitaxel (ABRAXANE*), phoenix (Yttrium90/MX-DTPA), pentostatin, polifeprosan 20 with carmustine implant (GLIADEL®), tamoxifen citrate (NOLVADEX®), teniposide (VUMON®), 6-thioguanine, thiotepa, tirapazamine (TIRAZONE®), topotecan hydrochloride for injection (HYCAMPTIN®), vinblastine (VELBAN®), vincristine (ONCOVIN®), and vinorelbine (NAVELBINE®).

In another embodiment, the compounds of the present invention are combined with another therapeutic agent capable of inhibiting BRAF, MEK, CDK4/6, SHP-2, HDAC, EGFR, MET, mTOR, PI3K or AKT, or a combination thereof. In a particular embodiment, the compounds of the present invention are combined with another therapeutic agent selected from vemurafinib, debrafinib, LGX818, trametinib, MEK162, LEE011, PD-0332991, panobinostat, verinostat, romidepsin, cetuximab, gefitinib, erlotinib, lapatinib, panitumumab, vandetanib, INC280, everolimus, simolimus, BMK120, BYL719 or CLR457, or a combination thereof.

In another embodiment, the therapeutic agent for use with the compounds of the present invention is selected based on the disease or condition that is being treated. For example, in the treatment of melanoma, the other therapeutic agent may be selected from aldesleukin (e.g., PROLEUKIN®), dabrafenib (e.g., TAFINLAR®), dacarbazine, recombinant interferon alfa-2b (e.g., INTRON® A), ipilimumab, trametinib (e.g., MEKINIST®), peginterferon alfa-2b (e.g., PEGINTRON®, SYLATRON™), vemurafenib (e.g., ZELBORAF®)), and ipilimumab (e.g., YERVOY®).

For the treatment of ovarian cancer, the other therapeutic agent may be selected from doxorubicin hydrochloride (Adriamycin®), carboplatin (PARAPLATIN®), cyclophosphamide (CYTOXAN®, NEOSAR®), cisplatin (PLATINOL®, PLATINOL-AQ®), doxorubicin hydrochloride liposome (DOXIL®, DOX-SL®, EVACET®, LIPODOX®), gemcitabine hydrochloride (GEMZAR®), topotecan hydrochloride (HYCAMTIN®), and paclitaxel (TAXOL®).

For the treatment of thyroid cancer, the other therapeutic agent may be selected from doxorubicin hydrochloride (Adriamycin®), cabozantinib-S-malate (COMETRIQ®), and vandetanib (CAPRELSA®).

For the treatment of colon cancer, the other therapeutic may be selected from fluorouracil (e.g., ADRUCIL®, EFUDEX®, FLUOROPLEX®), bevacizumab (AVASTIN®), irinotecan hydrochloride (CAMPTOSTAR®), capecitabine (XELODA®), cetuximab (ERBITUX®), oxaliplatin (ELOXATIN®), leucovorin calcium (WELLCOVORIN®), regorafenib (STIVARGA®), panitumumab (VECTIBIX®), and ziv-aflibercept (ZALTRAP®).

For the treatment of lung cancer, the other therapeutic may be selected from methotrexate, methotrexate LPF (e.g., FOLEX®, FOLEX PFS®, Abitrexate®, MEXATE®, MEXATE-AQ®), paclitaxel (TAXOL®), paclitaxel albumin-stabilized nanoparticle formulation (ABRAXANE®), afatinib dimaleate (GILOTRIF®), pemetrexed disodium (ALIMTA®), bevacizumab (AVASTIN®), carboplatin (PARAPLATIN®), cisplatin (PLATINOL®, PLATINOL-AQ®), crizotinib (XALKORI®), erlotinib hydrochloride (TARCEVA®), gefitinib (IRESSA®) and gemcitabine hydrochloride (GEMZAR®).

For the treatment of pancreatic cancer, the other therapeutic agent may be selected from fluorouracil (ADRUCIL®), EFUDEX®, FLUOROPLEX®), erlotinib hydrochloride (TARCEVA®), gemcitabine hydrochloride (GEMZAR®), and mitomycin or mitomycin C (MITOZYTREX™, MUTAMYCIN®).

For the treatment of cervical cancer, the other therapeutic agent may be selected from bleomycin (BLENOXANE®), cisplatin (PLATINOL®, PLATINOL-AQ®) and topotecan hydrochloride (HYCAMTIN®).

For the treatment of head and neck cancer, the other therapeutic agent may be selected from methotrexate, methotrexate LPF (e.g., FOLEX®, FOLEX PFS®, Abitrexate@, MEXATE@, MEXATE-AQ®), fluorouracil (ADRUCIL®, EFUDEX®, FLUOROPLEX®), bleomycin (BLENOXANE®), cetuximab (ERBITUX®), cisplatin (PLATINOL®, PLATINOL-AQ®) and docetaxel (TAXOTERE®).

For the treatment of leukemia, including chronic myelomonocytic leukemia (CMML), the other therapeutic agent can be selected from bosutinib (BOSULIF®), cyclophosphamide (CYTOXAN®, NEOSAR®), cytarabine (CYTOSAR-U@, TARABINE PFS®), dasatinib (SPRYCEL®), imatinib mesylate (GLEEVEC®), ponatinib (ICLUSIG®), nilotinib (TASIGNA®) and omacetaxine mepesuccinate (SYNRIBO®).

In another aspect, the present invention provides pharmaceutical compositions comprising at least one compound of the present invention (e.g., a compound of Formula (I) or a sub-formulae thereof) or a pharmaceutically acceptable salt thereof, together with a pharmaceutically acceptable carrier suitable for administration to a human or animal subject, either alone or together with other anti-cancer agents.

In combination therapies, compositions will either be formulated together as a combination therapeutic, or as separate compositions. The compound of the invention and the other therapeutic agent may be manufactured and/or formulated by the same or different manufacturers. The structure of therapeutic agents identified by code numbers, generic or trade names may be taken from the actual edition of the standard compendium "The Merck Index" or from databases, e.g. Patents International (e.g. IMS World Publications). The other therapeutic agents, which can be used in combination with a compound of the present invention, can be prepared and administered as described in the art, such as in the documents cited above.

Optionally, the pharmaceutical composition may comprise a pharmaceutically acceptable carrier, as described above. The pharmaceutical composition or combination of the present invention can be in unit dosage of about 0.5-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease. The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution.

In another aspect, the present invention provides methods of treating human or animal subjects suffering from a cellular proliferative disease, such as cancer, comprising administering to the subject a therapeutically effective amount of a compound of the present invention or a pharmaceutically acceptable salt thereof, either alone or in combination with other anti-cancer agents. In combination therapy, the compound of the present invention and other anti-cancer agent(s) may be administered either simultaneously, concurrently or sequentially with no specific time limits, wherein such administration provides therapeutically effective levels of the two compounds in the body of the patient. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

In one embodiment, the compound of the present invention and the other anti-cancer agent(s) is generally administered sequentially in any order by infusion or orally. The dosing regimen may vary depending upon the stage of the disease, physical fitness of the patient, safety profiles of the individual drugs, and tolerance of the individual drugs, as well as other criteria well-known to the attending physician and medical practitioner(s) administering the combination. The compound of the present invention and other anti-cancer agent(s) may be administered within minutes of each other, hours, days, or even weeks apart depending upon the particular cycle being used for treatment. In addition, the cycle could include administration of one drug more often than the other during the treatment cycle and at different doses per administration of the drug.

In yet another aspect, compounds of the present invention may be combined with other anti-cancer agents, anti-allergic agents, anti-nausea agents (or anti-emetics), pain relievers, cytoprotective agents, and combinations thereof.

In some instances, patients may experience allergic reactions to the compounds of the present invention and/or other anti-cancer agent(s) during or after administration. Therefore, anti-allergic agents may be administered to minimize the risk of an allergic reaction. Suitable anti-allergic agents include corticosteroids, such as dexamethasone (e.g., DECADRON®), beclomethasone (e.g., BECLOVENT®), hydrocortisone (also known as cortisone, hydrocortisone sodium succinate, hydrocortisone sodium phosphate; e.g., ALA-CORT®, hydrocortisone phosphate, Solu-CORTEF®, HYDROCORT Acetate® and LANACORT®), prednisolone (e.g., DELTA-Cortel®, ORAPRED®, PEDIAPRED® and PRELONE®), prednisone (e.g., DELTASONE®, LIQUID RED®, METICORTEN® and ORASONE®), methylprednisolone (also known as 6-methylprednisolone, methylprednisolone acetate, methylprednisolone sodium succinate; e.g., DURALONE®, MEDRALONE®, MEDROL®, M-PREDNISOL® and SOLU-MEDROL®); antihistamines, such as diphenhydramine (e.g., BENADRYL®), hydroxyzine, and cyproheptadine; and bronchodilators, such as the beta-adrenergic receptor agonists, albuterol (e.g., PROVENTIL®), and terbutaline (BRETHINE®).

In other instances, patients may experience nausea during and after administration of the compound of the present invention and/or other anti-cancer agent(s). Therefore, anti-emetics may be administered in preventing nausea (upper stomach) and vomiting. Suitable anti-emetics include aprepitant (EMEND®), ondansetron (ZOFRAN®), granisetron HCl (KYTRIL®), lorazepam (ATIVAN®. dexamethasone (DECADRON®), prochlorperazine (COMPAZINE®), casopitant (REZONIC® and Zunrisa®), and combinations thereof.

In yet other instances, medication to alleviate the pain experienced during the treatment period is prescribed to make the patient more comfortable. Common over-the-counter analgesics, such TYLENOL®, are often used. Opioid analgesic drugs such as hydrocodone/paracetamol or hydrocodone/acetaminophen (e.g., VICODIN®), morphine (e.g., ASTRAMORPH® or AVINZA®), oxycodone (e.g., OXYCONTIN® or PERCOCET®), oxymorphone hydrochloride (OPANA®), and fentanyl (e.g., DURAGESIC®) are also useful for moderate or severe pain.

Furthermore, cytoprotective agents (such as neuroprotectants, free-radical scavengers, cardioprotectors, anthracycline extravasation neutralizers, nutrients and the like) may be used as an adjunct therapy to protect normal cells from treatment toxicity and to limit organ toxicities. Suitable cytoprotective agents include amifostine (ETHYOL®), glutamine, dimesna (TAVOCEPT®), mesna (MESNEX®), dexrazoxane (ZINECARD® or TOTECT®), xaliproden (XAPRILA®), and leucovorin (also known as calcium leucovorin, citrovorum factor and folinic acid).

In yet another aspect, a compound of the present invention may be used in combination with known therapeutic processes, for example, with the administration of hormones or in radiation therapy. In certain instances, a compound of the present invention may be used as a radiosensitizer, especially for the treatment of tumors which exhibit poor sensitivity to radiotherapy.

In yet another aspect, the present invention provides kits comprising one or more compounds of the present invention and another therapeutic agent as described above. Representative kits include (a) compound of Formula (I) or sub-formulae thereof or a pharmaceutically acceptable salt thereof; and (b) at least one other therapeutic agent e.g., as indicated above; whereby such kit may further comprise a package insert or other labeling including directions for administration. The kits of the invention may be used for administering different dosage forms, for example, oral and parenteral; for administering two or more separate pharmaceutical compositions at different dosage intervals; or for titrating the separate compositions against one another;

wherein at least one pharmaceutical composition comprises a compound a Formula (I) or sub-formulae thereof.

EXAMPLES

Temperatures are given in degrees Celsius. The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Unless otherwise specified, starting materials are generally available from commercial sources.

The Examples herein merely illuminate the invention and does not limit the scope of the invention otherwise claimed. Further, the compounds of the present invention can be produced by organic synthesis methods known to one of ordinary skill in the art as shown in the following examples. Where desired, conventional protecting groups are used to protect reactive functional groups in accordance with standard practice, for example, see T. W. Greene and P. G. M. Wuts in "Protecting Groups in Organic Synthesis", John Wiley and Sons, 1991.

Abbreviations

Abbreviations as used herein, are defined as follows: "1×" for once, "2×" for twice, "3×" for thrice, "00" for degrees Celsius, "aq" for aqueous, "FCC" for flash column chromatography, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" or "hrs" for hour or hours, "RT" for room temperature, "ON" for overnight, "atm" for atmosphere, "psi" for pounds per square inch, "conc." for concentrate, "sat" or "sat'd" for saturated, "MW" for molecular weight, "mw" or "pwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" or "LC-MS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "b" for delta, "s" for singlet, "d" for doublet, "t" for triplet, "q" for quartet, "m" for multiplet, "br" for broad, "Hz" for hertz, "ee" for "enantiomeric excess" and "a", "p", "R", "r", "S", "s", "E", and "Z" are stereochemical designations familiar to one skilled in the art.

The following abbreviations used herein below have the corresponding meanings:

Δ heat
AIBN azobisisobutyronitrile
AcOH acetic acid
Bn Benzyl
Boc tert-butyloxycarbonyl
Boc$_2$O di-tert butyl dicarbonate
B(OMe)$_3$ trimethyl borate
BSA bovine serum albumin
Cbz benzyloxycarbonyl
CbzCl benzyl chloroformate
CDCl$_3$ chloroform-d
CD$_3$OD methanol-d$_4$
dd doublet of doublets
DAST diethylaminosulfur trifluoride
DCM dichloromethane
DEAD Diethyl azodicarboxylate
DIAD diisopropyl azodicarboxylate
DIPEA N,N-diisopropylethylamine
DMAP 4-dimethylaminopyridine
DMEM Dulbecco Modified Eagle Medium
DMF dimethylformamide
DMP Dess-Martin periodinane
DMSO dimethylsulfoxide
DPPA diphenylphosphoryl azide
EA ethyl alcohol
EtOAc ethyl acetate
EtOH ethanol
FBS fetal bovine serum
HATU Hexafluorophosphate Azabenzotriazole Tetramethyl Uronium)
KHMDS potassium bis(trimethylsilyl)amide
LiHMDS lithium bis(trimethylsilyl)amide
MeOH methanol
MgSO$_4$ magnesium sulfate
MHz megahertz
min minutes
m/z mass to charge ratio
NaHCO$_3$ sodium bicarbonate
Na$_2$SO$_4$ sodium sulfate
NBS N-bromosuccinimide
NH$_4$Cl ammonium chloride
PBu$_3$ tributylphosphine
Pd(dppf)Cl$_2$ [1,1'-Bis(diphenylphosphino)ferrocene]dichloropalladium (II)
PE petroleum ether
PhI(OAc)$_2$ (diacetoxyiodo)benzene
ppm parts per million
rac racemic
SFC Supercritical fluid chromatography
TBAF tetra-n-butylammonium fluoride
TEA triethylamine
TFA trifluoroacetic acid
THF tetrahydrofuran
TMSI trimethylsilyl iodide
UV ultraviolet High performance liquid chromatography (HPLC) was performed using an Agilent 1260 HPLC System (Santa Clara, CA). The analytical column was reversed phase Phenomenex Kinetex C18-2.6 µm, 4.6×50 mm. A gradient elution was used (flow rate 2.0 mL/min), starting with 5% methanol/95% water and progressing to 95% methanol/5% water over a period of 10 minutes. All solvents contained 0.1% formic acid (FA). Compounds were detected by ultraviolet light (UV) absorption at 214, 254 and 300 nm. HPLC solvents were purchased from Sigma Aldrich (St. Louis, MO).

Mass spectrometric analysis was performed on an Agilent System (Agilent 1260 HPLC and an Agilent 6130 mass spectrometer detector; Column: Phenomenex Kinetex 2.6 um C18, column size 4.6×50 mm; column temperature 40° C.; gradient: 5 95% methanol in water with 0.1% FA over a 2 min period; flow rate 2.0 mL/min (or Polar gradient 5-50% over 2.0 min, or Non-Polar gradient 50-95% over 2.0 min);

Mass Spectrometer molecular weight scan range 100 1000; or 100-1500; capillary voltage 4000 V. All masses were reported as those of the protonated parent ions, unless otherwise indicated.

Nuclear magnetic resonance (NMR) analysis was performed using a Bruker 400 MHz NMR. The spectral reference was either TMS or the known chemical shift of the solvent.

Chiral Preparative HPLC Methods Employed in Purification of Examples

SFC chiral screening was carried out on a Thar Instruments Investigator system. The Thar Investigator system consists of:

ALIAS autosampler
Thar Fluid Delivery Module (0 to 10 mL/min)
Thar SFC 10 position column oven
Waters 2998 PDA
Thar Automated Back Pressure Regulator All of the Thar components are part of the SuperPure Discovery Series line. The system flowed at 3.0 mL/min and kept at 38° C. The system back pressure was set to 100 bar. Each sample was screened through a battery of ten 5 µm columns:

5 µm 4.6×150 mm ChiralPak AD
5 µm 4.6×150 mm ChiralCel OD
5 µm 4.6×150 mm ChiralCel OJ
5 µm 4.6×150 mm ChiralPak AS
5 µm 4.6×250 mm ChiralPak AY
5 µm 4.6×250 mm ChiralCel OZ
5 µm 4.6×150 mm ChiralPak IC
5 µm 4.6×150 mm ChiralPak IG
5 µm 4.6×250 mm Regis Whelk-01
5 µm 4.6×250 mm ChromegaChiral CC4

The system ran a gradient from 5% co-solvent to 50% co-solvent in 9 minutes followed by a 10 minutes hold at 50% co-solvent, a switch back to 5% co-solvent and a 0.5 minute hold at initial condition. In between each gradient there was a 4 minute equilibration method that flows 5% co-solvent through the next column to be screened. The typical solvents screened were, MeOH, EtOH, IPA, MeOH+ 0.5% $NH_3$, EtOH+0.5% $NH_3$, IPA+0.1% $NH_3$. Once separation was detected using one of the gradient methods, an isocratic method can be developed, and if necessary, scaled up for separation on the Thar Prep 80 system.

Intermediates

Intermediate A: Methyl 2-(3,4-difluorophenyl)-5-fluoroisonicotinate

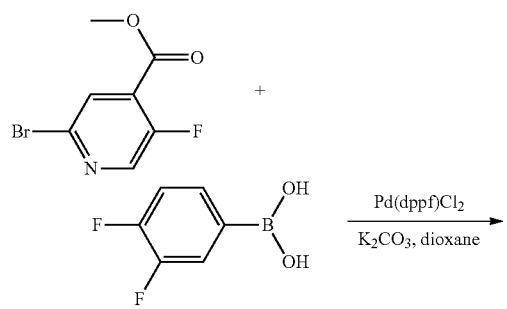

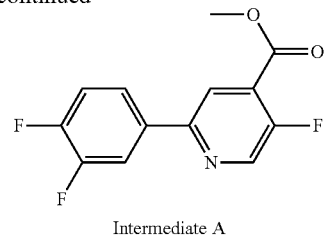

Intermediate A

A mixture of compound methyl 2-bromo-5-fluoroisonicotinate (110 g, 470.04 mmol, 1.0 eq.), (3,4-difluorophenyl) boronic acid (111.34 g, 705.06 mmol, 1.5 eq), Pd(dppf)Cl$_2$ (8.60 g, 11.75 mmol, 0.025 eq) and potassium carbonate (129.92 g, 940.08 mmol, 2.0 eq) in 1,4-dioxane (1. Pd(dppf) Cl$_2$ 1 L) was heated to 100° C. for 16 hours under N$_2$. The mixture was diluted with H$_2$O (500 mL) and EtOAc (1.3 L) and stirred for 15 mins. The organic layer was separated, washed with brine (500 mL), dried over Na$_2$SO$_4$ and concentrated, the residue purified by combi-flash (5%-50% EtOAc in PE) and trituration (PE:EA=50/1, 100 mL) to afford methyl 2-(3,4-difluorophenyl)-5-fluoroisonicotinate (Intermediate A). $^1$H NMR (CDCl$_3$ 400 MHz): δ 8.56 (d, J=2.0 Hz, 1H), 8.05 (d, J=5.6 Hz, 1H), 7.79 (ddd, J=2.4, 8.4, 10.8 Hz, 1H), 7.64 (td, J=2.8, 8.8 Hz, 1H), 7.26-7.11 (m, 1H), 3.94 (s, 3H).

Intermediate B

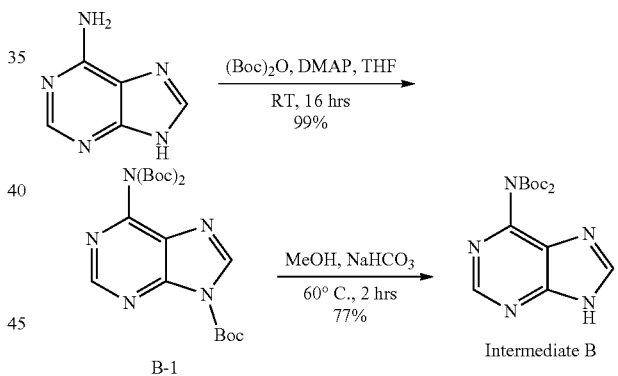

To a solution of compound 9H-purin-6-amine (15 g, 111 mmol) in THF (500 mL) were added di-tert butyl dicarbonate (Boc$_2$O) (96.91 g, 444 mmol) and DMAP (1.36 g, 11.1 mmol). The resulting mixture was stirred at RT for 16 h. The THF was removed in vacuo. The residue was partitioned between EtOAc (400 mL) and HCl solution (1.0 M in H$_2$O) (200 mL). The organic layer was dried over Na$_2$SO$_4$ and concentrated to give tert-butyl 6-(bis(tert-butoxycarbonyl) amino)-9H-purine-9-carboxylate (Intermediate B-1).

To a solution of tert-butyl 6-(bis(tert-butoxycarbonyl) amino)-9H-purine-9-carboxylate (Intermediate B-1) (48 g, 110 mmol) in MeOH (500 mL) was added sat·NaHCO$_3$ solution (250 mL). The resulting mixture was heated at 60° C. for 2 h. The MeOH was removed in vacuo. The residue was extracted with a solution of MeOH:DCM (1:10) (300 mL*7 times). The combined organic layers were washed with H$_2$O (150 mL), dried over Na$_2$SO$_4$ and concentrated. The residue was washed with a solution of EtOAc:PE (1:10) (100 mL) and filtered. The filter cake was dried in vacuo to get give Intermediate B. $^1$H NMR (400 MHz, DMSO-$d_6$) δ 8.70 (s, 1H), 8.48 (s, 1H), 1.36 (s, 18H). LC-MS: [M+H)]$^+$ =336.2.

Intermediate C: Methyl 5-fluoro-2-(3-fluorophenyl)isonicotinate

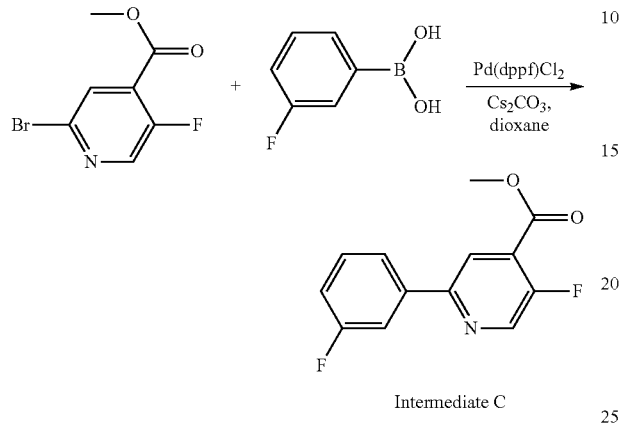

Intermediate C

Methyl 5-fluoro-2-(3-fluorophenyl)isonicotinate (Intermediate C) was prepared by using a procedure similar to that of Intermediate A. $^1$H-NMR (400 MHz, CDCl$_3$) δ 8.66 (s, 1H), 8.18 (d, J=6.4 Hz, 1H), 7.76-7.72 (m, 2H), 7.48-7.42 (m, 1H), 7.15-7.11 (m, 1H), 4.01 (s, 3H).

Intermediate D: Methyl 5-fluoro-2-(3-fluoro-4-methoxyphenyl)isonicotinate

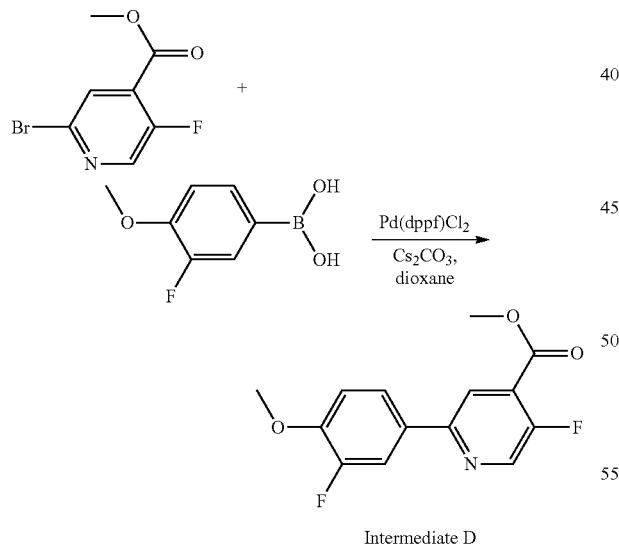

Intermediate D

A suspension of methyl 2-bromo-5-fluoroisonicotinate (1.0 g, 4.27 mmol), (3-fluoro-4-methoxyphenyl)boronic acid (1.089 g, 6.41 mmol), Cs$_2$CO$_3$ (2.78 g, 8.55 mmol) and PdCl$_2$(dppf) CH$_2$Cl$_2$ adduct (0.349 g, 0.427 mmol) in dioxane (10 mL) was stirred at 100° C. under Ar for 2 hr. Then the mixture was diluted with water, extracted with EtOAc, the organic layer was dried over Na$_2$SO$_4$, filtered and concentrated in vacuum. The residue was purified by CombiFlash (PE/EA, EA: 20-40% for 50 mins) to afford methyl 5-fluoro-2-(3-fluoro-4-methoxyphenyl)isonicotinate (Intermediate D). $^1$H NMR (400 MHz, DMSO-$d_6$) δ 8.79 (t, 1H), 8.24 (t, 1H), 7.95-7.87 (m, 2H), 7.27 (t, 3H), 3.92 (d, 6H). LC-MS: [M+H]$^+$=279.9.

Intermediate F-2: 2-(2-(difluoromethyl)-4-fluorophenyl)-4,4,5,5-tetramethyl-1,3,2-dioxaborolane

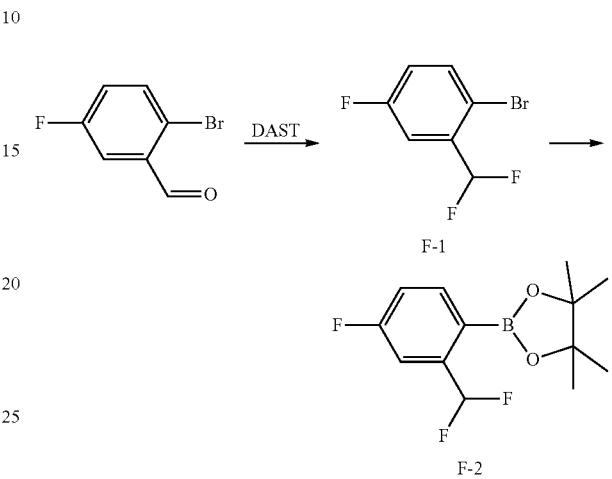

To a solution of 2-bromo-5-fluorobenzaldehyde (8 g, 39.4 mmol) in DCM (30 mL), was added DAST (10.41 mL, 79 mmol) at 0° C., then the mixture was stirred at rt for 18 hr under N$_2$. The reaction mixture was washed with water, the organic layer was dried over Na$_2$SO$_4$, filtered and concentrated in vacuum. The residue was purified by CombiFlash (elution gradient: 0% to 10% EtOAc in n-hexane in 30 mins) to afford 1-bromo-2-(difluoromethyl)-4-fluorobenzene (Intermediate F-1). LC-MS: [M+H]$^+$=225.0, 227.0.

A suspension of 1-bromo-2-(difluoromethyl)-4-fluorobenzene (Intermediate F-1) (2.2 g, 9.78 mmol), 4,4,4',4', 5,5,5',5'-octamethyl-2,2'-bi(1,3,2-dioxaborolane (2.98 g, 11.73 mmol) and KOAc (1.919 g, 19.56 mmol) and PdCl$_2$ (dppf)·CH$_2$Cl$_2$ (0.798 g, 0.978 mmol) adduct in dioxane (30 mL) was stirred at 110° C. for 3 hr under N$_2$ atmosphere. The mixture was diluted with water, extracted with EtOAc, the organic layer was dried over Na$_2$SO$_4$, filtered and concentrated in vacuum. The residue was purified by CombiFlash (elution gradient: 0% to 10% EtOAc in PE in 30 mins) to afford 2-(2-(difluoromethyl)-4-fluorophenyl)-4,4,5,5-tetramethyl-1,3,2-dioxaborolane (Intermediate F-2) as a colorless syrup. LC-MS: [M+H]$^+$=272.3.

Intermediate L-2: 2-(2-(difluoromethyl)-4,5-difluorophenyl)-4,4,5,5-tetramethyl-1,3,2-dioxaborolane

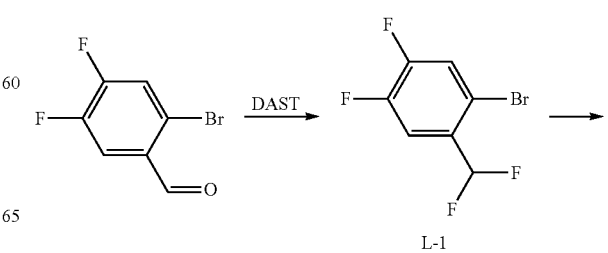

-continued

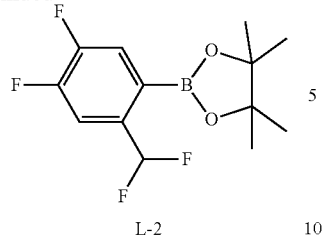

L-2

1-bromo-2-(difluoromethyl)-4,5-difluorobenzene (Intermediate L-1) and 2-(2-(difluoromethyl)-4,5-difluorophenyl)-4,4,5,5-tetramethyl-1,3,2-dioxaborolane (Intermediate L-2) were prepared following procedures analogous to the preparation of Intermediates F-1 and F-2, respectively.

Intermediate L-1: $^1$H NMR (CDCl$_3$, 400 MHz): δ 7.54-7.45 (m, 2H), 6.97-6.70 (t, J1=54.8 Hz, J2=109.6 Hz, 1H).

Intermediate L-2: $^1$H NMR (CDCl$_3$, 400 MHz): δ 7.75-7.66 (m, 1H), 7.57-7.50 (m, 1H), 7.47-7.14 (m, 1H), 1.36 (s, 12H).

Intermediate O-1:
6-Bromo-2-chloro-3-fluoropyridine

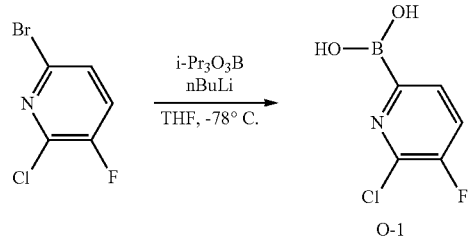

O-1

To a solution of 6-bromo-2-chloro-3-fluoropyridine (3.0 g, 0.014 mol, 1.0 eq.) and i-Pr$_3$O$_3$B (4.0 g, 0.021 mol, 1.5 eq.) in anhydrous THF (30 mL) was added n-BuLi (9 mL, 0.021 mol, 2.5M sol., 1.5 eq.) dropwise at −78° C. The resulting mixture was stirred at −78° C. for 1 hour and warmed to 20° C. for another 1 hour. The reaction was quenched with saturated NH$_4$Cl (50 mL), acidified with conc. HCl to PH=4, stirred for 1 hour at 20° C. Extracted with ethyl acetate (50 mL*3). The combined organic layer was dried over Na$_2$SO$_4$, concentrated in vacuo to afford 6-bromo-2-chloro-3-fluoropyridine (Intermediate O-1). LC-MS: [M+H]$^+$=176.0.

Intermediates E-O were prepared following procedures analogous to the preparation of Intermediate A, from the reaction of methyl 2-bromo-5-fluoroisonicotinate and corresponding boronic acid or ester.

| Intermediate | Boronic acid/ester | LC-MS and/or $^1$H NMR |
|---|---|---|
| E | | $^1$H NMR (400 MHz, CDCl$_3$) δ ppm 8.70 (s, 1H), 8.31-8.29 (d, J = 5.6 Hz, 1H), 7.79-7.90 (m, 1H), 7.11-7.02 (m, 1H), 4.03 (s, 3H). LC-MS: [M + H]$^+$ = 286.1. |
| F | | LC-MS: [M + H]$^+$ = 300.1 |
| G | | LC-MS: [M + H]$^+$ = 298.1.1 |

| Intermediate | Boronic acid/ester | LC-MS and/or ¹H NMR |
|---|---|---|
| H | (methyl 2-(2-(difluoromethyl)-4-methoxyphenyl)-5-fluoroisonicotinate) / (2-(2-(difluoromethyl)-4-methoxyphenyl)-4,4,5,5-tetramethyl-1,3,2-dioxaborolane) | LC-MS: [M + H]⁺ = 312.1 |
| I | (methyl 2-(3,5-difluoro-4-methoxyphenyl)-5-fluoroisonicotinate) / (2-(3,5-difluoro-4-methoxyphenyl)-4,4,5,5-tetramethyl-1,3,2-dioxaborolane) | LC-MS: [M + H]⁺ = 298.1 |
| J | (methyl 5-fluoro-2-(4-methoxy-2-(trifluoromethyl)phenyl)isonicotinate) / (4-methoxy-2-(trifluoromethyl)phenylboronic acid) | LC-MS: [M + H]⁺ = 330.1 |
| K | (methyl 2-(2-chloro-4-methoxyphenyl)-5-fluoroisonicotinate) / (2-chloro-4-methoxyphenylboronic acid) | LC-MS: [M + H]⁺ = 296.1 |
| L | (methyl 2-(2-(difluoromethyl)-4,5-difluorophenyl)-5-fluoroisonicotinate) / (L-2) (2-(2-(difluoromethyl)-4,5-difluorophenyl)-4,4,5,5-tetramethyl-1,3,2-dioxaborolane) | ¹H NMR (CDCl₃, 400 MHz): δ 8.69-8.68 (d, J = 1.6 Hz, 1H), 7.97-7.95 (d, J = 6.4 Hz, 1H), 7.68-7.63 (m, 1H), 7.47-7.37 (m, 1H), 7.21-7.97 (m, 1H), 4.02 (s, 3H). LC-MS: [M + H]⁺ = 318.2. |
| M | (methyl 5-fluoro-2-(2,3,4-trifluorophenyl)isonicotinate) / (2,3,4-trifluorophenylboronic acid) | LC-MS: [M + H]⁺ = 286.2. |
| N | (methyl 5-fluoro-2-(4-fluoro-2-methoxyphenyl)isonicotinate) / (4-fluoro-2-methoxyphenylboronic acid) | ¹H NMR (400 MHz, DMSO-d₆) δ 8.84 (d, J = 2.1 Hz, 1H), 8.24 (d, J = 5.9 Hz, 1H), 7.80 (dd, J = 8.7, 7.1 Hz, 1H), 7.12 (dd, J = 11.5, 2.5 Hz, 1H), 6.93 (td, J = 8.4, 2.5 Hz, 1H), 3.93 (s, 3H), 3.89 (s, 3H). LC-MS: [M + H]⁺ = 280.0. |

| Intermediate | Boronic acid/ester | LC-MS and/or $^1$H NMR |
|---|---|---|
| 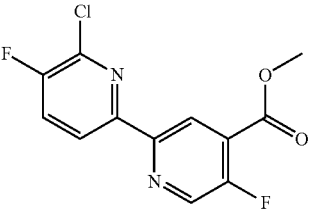 [SMILES: COC(=O)c1cc(-c2ccc(F)c(Cl)n2)ncc1F] | 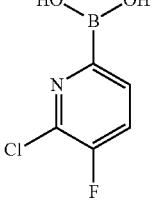 (O-1) | $^1$H NMR (400 MHz, DMSO-d6) δ = 8.79 (d, J = 5.9 Hz, 1H), 8.61 (d, J = 1.8 Hz, 1H), 8.34 (dd, J = 3.5, 8.4 Hz, 1H), 7.63-7.57 (m, 1H), 4.03 (s, 3H). LC-MS: [M + H]$^+$ = 285.1 |

Intermediate 1-1: 5-Fluoro-2-(3-fluoro-4-methoxyphenyl)isonicotinaldehyde

Intermediate 22-7: tert-Butyl (3-(cyclopropoxymethyl)piperidin-3-yl)carbamate

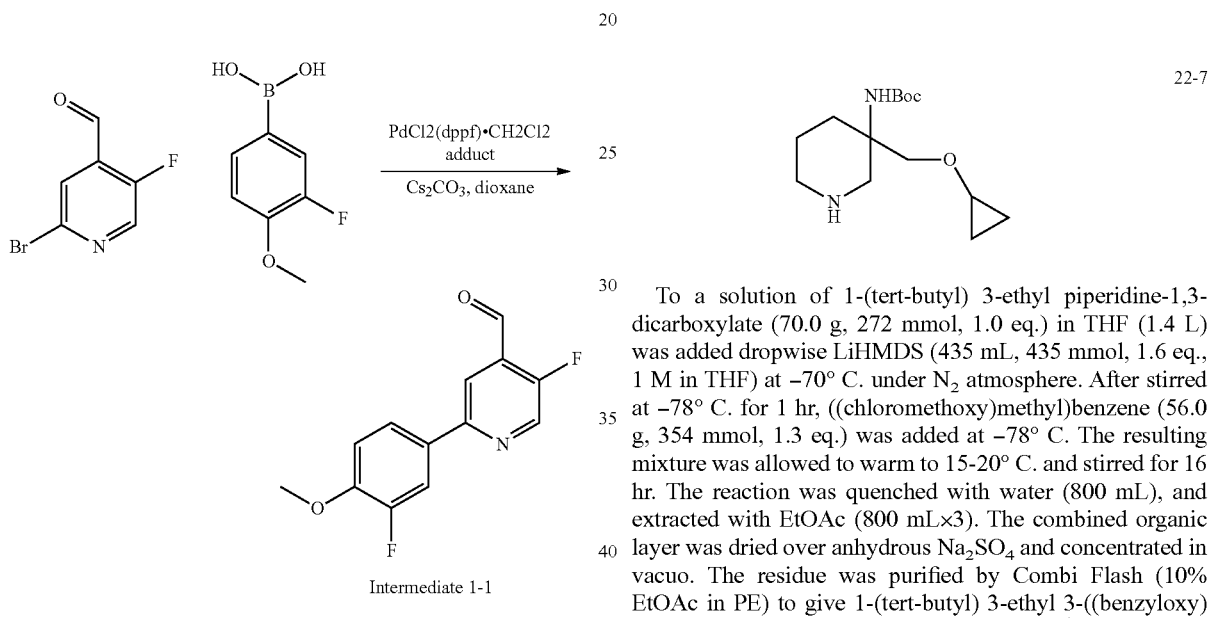

Intermediate 1-1

A suspension of 2-bromo-5-fluoroisonicotinaldehyde (8 g, 27.5 mmol), (3-fluoro-4-methoxyphenyl)boronic acid (4.67 g, 27.5 mmol), PdCl$_2$(dppf)·CH$_2$Cl$_2$ adduct (1.121 g, 1.373 mmol) and cesium carbonate (13.42 g, 41.2 mmol) in dioxane (50 mL) was stirred at 10000 for 3 hr under nitrogen atmosphere. The reaction mixture was filtered and the filtrate was concentrated in vacuum to afford a black residue. The residue was redissolved in DCM (60 mL), washed with water (20 mL), brine (20 mL), dried over anhydrous magnesium sulfate, filtered and concentrated in vacuum. The residue was purified by silica gel column chromatography (EtOAc in hexane and DCM, EtOAc/DCM/Hexane=8/20/100) to give 5-fluoro-2-(3-fluoro-4-methoxyphenyl)isonicotinaldehyde (Intermediate 1-1). $^1$H NMR (400 MHz, CDCl$_3$) δ 10.51 (d, J=2.1 Hz, 1H), 8.77 (d, J=1.9 Hz, 1H), 8.07 (dd, J=5.3, 2.1 Hz, 1H), 7.85 (dd, J=12.5, 2.4 Hz, 1H), 7.78 (d, J=8.6 Hz, 1H), 7.11 (td, J=8.6, 2.2 Hz, 1H), 4.01 (d, J=2.2 Hz, 3H). LC-MS: [M+H]$^+$=249.9.

To a solution of 1-(tert-butyl) 3-ethyl piperidine-1,3-dicarboxylate (70.0 g, 272 mmol, 1.0 eq.) in THF (1.4 L) was added dropwise LiHMDS (435 mL, 435 mmol, 1.6 eq., 1 M in THF) at −70° C. under N$_2$ atmosphere. After stirred at −78° C. for 1 hr, ((chloromethoxy)methyl)benzene (56.0 g, 354 mmol, 1.3 eq.) was added at −78° C. The resulting mixture was allowed to warm to 15-20° C. and stirred for 16 hr. The reaction was quenched with water (800 mL), and extracted with EtOAc (800 mL×3). The combined organic layer was dried over anhydrous Na$_2$SO$_4$ and concentrated in vacuo. The residue was purified by Combi Flash (10% EtOAc in PE) to give 1-(tert-butyl) 3-ethyl 3-((benzyloxy)methyl)piperidine-1,3-dicarboxylate (22-1). $^1$H NMR (400 MHz, CDCl$_3$) δ ppm 7.20-7.40 (5H, m), 4.50 (2H, q, J=12.8 Hz), 4.10-4.20 (2H, m), 3.65-3.85 (2H, m), 3.45-3.60 (2H, m), 3.30-3.45 (2H, m), 1.90-2.10 (1H, m), 1.65-1.75 (1H, m), 1.50-1.60 (2H, m), 1.45 (9H, s), 1.20-1.30 (3H, m). LC-MS: [M+H−100]$^+$=278.1.

A mixture of 1-(tert-butyl) 3-ethyl 3-((benzyloxy)methyl) piperidine-1,3-dicarboxylate (22-1) (50.0 g, 132 mmol, 1.0 eq.) and Pd/C (5.00 g, 10% wet) in dioxane/2N HCl (1 L, v/v=1/1) was stirred under H$_2$ balloon at 20° C. for 16 hr. Then the mixture was filtered and the filtrate was concentrated in vacuo. The pH of the residue was adjusted to 8-9 with NaHCO$_3$ aqueous.

Then THF (500 mL) and CbzCl (45.0 g, 265 mmol, 2.0 eq.) were added. The resulting mixture was stirred at 5-10° C. for 24 hr. The mixture was extracted with EtOAc (500 mL×3). The combined organic layers were dried over anhydrous Na$_2$SO$_4$ and concentrated in vacuo. The residue was purified by Combi Flash (30% EtOAc in PE) to give 1-benzyl 3-ethyl 3-(hydroxymethyl)piperidine-1,3-dicarboxylate (22-2). $^1$H NMR (400 MHz, CDCl$_3$) δ ppm 7.30-7.40 (5H, m), 5.05-5.20 (2H, s), 4.05-4.20 (2H, m), 2.60-4.05 (7H, m), 1.55-1.95 (4H, m), 1.15-1.30 (3H, m).

To a solution of 1-benzyl 3-ethyl 3-(hydroxymethyl) piperidine-1,3-dicarboxylate (22-2) (31.0 g, 96.5 mmol, 1.0 eq.) and Py (15.3 g, 193 mmol, 2.0 eq.) in DCM (300 mL) was added dropwise Tf₂O (57.0 g, 193 mmol, 2.0 eq.) at −70° C. under N₂. Then the mixture was allowed to warm to 10-15° C., and stirred for 1 hr. The reaction was quenched with water (500 mL), and extracted with DCM (500 mL×2). The combined organic layer was washed with water (500 mL×3), dried over anhydrous Na₂SO₄ and concentrated in vacuo. The residue was purified by Combi Flash (10% EtOAc in PE) to give 1-benzyl 3-ethyl 3-((((trifluoromethyl) sulfonyl)oxy) methyl)piperidine-1,3-dicarboxylate (22-3). ¹H NMR (400 MHz, CDCl₃) δ ppm 7.30-7.45 (5H, m), 5.05-5.25 (2H, s), 4.45-4.75 (2H, m), 4.05-4.25 (2H, m), 3.60-3.85 (2H, m), 3.20-3.40 (3H, m), 1.95-2.10 (1H, m), 1.75-1.90 (1H, m), 1.60-1.75 (2H, m), 1.15-1.30 (3H, m).

To a solution of compound cyclopropanol (3.20 g, 55.1 mmol, 1.0 eq.) in THF (100 mL) was added NaH (60% in mineral oil, 2.70 g, 66.1 mmol, 1.2 eq.) at 0° C. After stirred at 10-15° C. for 30 min, a solution of 1-benzyl 3-ethyl 3-((((trifluoromethyl)sulfonyl)oxy)methyl)piperidine-1,3-dicarboxylate (22-3) (27.0 g, 60.6 mmol, 1.1 eq) in THF (100 mL) was added at 0° C. The resulting mixture was stirred at 10-15° C. for 3 hr. The reaction was quenched with water (500 mL), and extracted with EtOAc (500 mL×2). The combined organic layers were washed with water (500 mL×3), dried over anhydrous Na₂SO₄ and concentrated in vacuo. The residue was purified by Combi Flash (20% EtOAc in PE) to 1-benzyl 3-ethyl 3-(cyclopropoxymethyl) piperidine-1,3-dicarboxylate (22-4). ¹H NMR (400 MHz, CDCl₃) δ ppm 7.25-7.45 (5H, m), 5.05-5.25 (2H, s), 4.05-4.20 (2H, m), 3.86 (1H, d, J=13.2 Hz), 3.30-3.60 (5H, m), 3.10-3.25 (1H, m), 1.90-2.05 (1H, m), 1.50-1.70 (3H, m), 1.95 (3H, t, J=6.8 Hz), 0.30-0.55 (4H, m).

A mixture of 1-benzyl 3-ethyl 3-(cyclopropoxymethyl) piperidine-1,3-dicarboxylate (22-4) (10.0 g, 27.6 mmol, 1.0 eq.) and LiOH·H₂O (11.6 g, 276 mmol, 10.0 eq.) in MeOH/ THF/H₂O (120 mL, v/v/v=1/1/1) was stirred at 20° C. for 16 hr. Then the mixture was concentrated in vacuo to remove THF and MeOH. The residue was diluted with water (300 mL), and extracted with EtOAc (200 mL). The pH of the aqueous layer was adjusted to 5 by 1N HCl, then the aqueous layer was extracted with EtOAc (300 mL×3). The combined organic layers were dried over anhydrous Na₂SO₄ and concentrated in vacuo to give 1-((benzyloxy)carbonyl)-3-(cyclopropoxymethyl)piperidine-3-carboxylic acid (22-5). ¹H NMR (400 MHz, CDCl₃) δ ppm 7.25-7.45 (5H, m), 5.14 (2H, s), 3.79 (1H, d, J=13.6 Hz), 3.15-3.65 (6H, m), 1.90-2.00 (1H, m), 1.50-1.80 (3H, m), 0.30-0.60 (4H, m).

A solution of 1-((benzyloxy)carbonyl)-3-(cyclopropoxymethyl)piperidine-3-carboxylic acid (22-5) (6.00 g, 18 mmol, 1.0 eq) DPPA (5.50 g, 19.8 mmol, 1.1 eq) and Et₃N (3.60 g, 36 mmol, 2.0 eq.) in toluene (100 mL) was stirred at 80° C. under N₂ for 2 hr. Then the reaction was concentrated in vacuo. The residue was dissolved in THF (100 mL). Then KOH (3.03 g, 54 mmol, 3.0 eq) and water (10 mL) were added. The mixture was stirred at 15-20° C. for 4 hr. Then Boc₂O (5.90 g, 27 mmol, 1.5 eq) and K₂CO₃ (10.0 g, 72 mmol, 4.0 eq) were added. The resulting mixture was stirred at 15-20° C. for 16 hr. The mixture was extracted with EtOAc (200 mL×3). The combined organic layers were dried over anhydrous Na₂SO₄ and concentrated in vacuo. The residue was purified by Combi Flash (15% EtOAc in PE) to give benzyl 3-((tert-butoxycarbonyl)amino)-3-(cyclopropoxymethyl)piperidine-1-carboxylate (22-6). H NMR (400 MHz, CDCl₃) δ ppm 7.25-7.45 (5H, m), 5.05-5.25 (2H, m), 4.40-4.80 (1H, brs), 3.50-4.05 (4H, m), 3.00-3.35 (3H, m), 2.15-2.55 (1H, m), 1.60-1.75 (1H, m), 1.35-1.55 (11H, m), 0.30-0.60 (4H, m).

A mixture of benzyl 3-((tert-butoxycarbonyl)amino)-3-(cyclopropoxymethyl)piperidine-1-carboxylate (22-6) (4.90 g, 12.1 mmol) and Pd/C (500 mg, 10% wet) in MeOH (100 mL) was stirred under H₂ balloon at 15-20° C. for 1 hr. Then the Pd/C was filtered off and the filtrate was concentrated in vacuo to give tert-butyl (3-(cyclopropoxymethyl)piperidin-3-yl)carbamate (Intermediate 22-7). ¹H NMR (400 MHz, CDCl₃) δ ppm 4.82 (1H, brs), 3.80 (1H, d, J=10.0 Hz), 3.53 (1H, d, J=9.6 Hz), 3.20-3.30 (1H, m), 3.01 (1H, d, J=12.4 Hz), 2.85-2.95 (1H, m), 2.55-2.65 (2H, m), 2.05-2.20 (1H, brs), 1.30-1.70 (13H, m), 0.35-0.60 (4H, m).

Intermediate 47-6: tert-Butyl (3-(2,2-difluoroethyl)piperidin-3-yl)carbamate

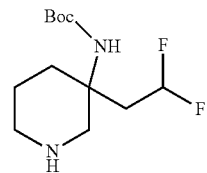

47-6

To a solution of 1-benzyl 3-methyl piperidine-1,3-dicarboxylate (5 g, 18.03 mmol) in THF (70 mL) was added 1M LHMDS in THF (19.83 mL, 19.83 mmol) dropwise at −78° C. in 30 min. The mixture was stirred at −78° C. for another 30 min. Then 1,1-difluoro-2-iodoethane (6.92 g, 36.1 mmol) was added. The mixture was stirred at −78° C. for another 2 hr. Then the temperature was allowed to increase to RT slowly, and the mixture was allowed to stir at RT for overnight. The reaction was quenched by addition of water (10 mL). The most THF was removed under reduced pressure. The residue was extracted with ethyl acetate (30 mL*2), the combined organic phase washed with water (20 mL), brine (20 mL), dried over anhydrous magnesium sulfate, filtered and concentrated. The crude product was purified by flash chromatography (elution gradient: 5% to 20% EtOAc in hexane in 40 mins) to afford 1-benzyl 3-methyl 3-(2,2-difluoroethyl)piperidine-1,3-dicarboxylate (47-1). LC-MS: [M+H]⁺=341.9.

To a solution of 1-benzyl 3-methyl 3-(2,2-difluoroethyl) piperidine-1,3-dicarboxylate (47-1) (6 g, 17.58 mmol) in methanol (50 mL) was added lithium hydroxide (4.21 g, 176 mmol) in water (30 mL). The mixture was stirred at RT overnight and the solvent was removed. The residue was diluted with water (20 mL), then the mixture was washed with ethyl acetate (5 mL), and the aqueous layer was acidified by HCl to PH=3. Then the mixture was extracted with DCM (20 mL*3). The combined organic layer was dried over anhydrous magnesium sulfate, filtered and concentrated in vacuo to afford crude 1-((benzyloxy)carbonyl)-3-(2,2-difluoroethyl)piperidine-3-carboxylic acid (47-2). LC-MS: [M+H]⁺=328.1.

To a solution of 1-((benzyloxy)carbonyl)-3-(2,2-difluoroethyl)piperidine-3-carboxylic acid (47-2) (5 g, 15.28 mmol) in Toluene (70 mL) was added TEA (4.26 mL, 30.6 mmol) and DPPA (3.70 mL, 16.80 mmol). The mixture was stirred at 100° C. under nitrogen protection for 2 hr. The mixture was diluted with ethyl acetate (60 mL), washed with water (20 mL), brine (60 mL). The organic phase was dried over anhydrous magnesium sulfate, filtered and concentrated to give crude benzyl 3-(2,2-difluoroethyl)-3-isocyanatopiperidine-1-carboxylate (47-3). LC-MS: [M+H]⁺=325.1.

To a solution of benzyl 3-(2,2-difluoroethyl)-3-isocyanatopiperidine-1-carboxylate (47-3) (5.7 g, 12.30 mmol) in 1,4-dioxane (25 mL) was added 6M HCl (25 mL, 150 mmol). The mixture was stirred at 45° C. for 30 hr. The mixture was cooled to rt and diluted with 20 ml of water. Then it was washed with ethyl acetate (5 mL). The aqueous phase was basified with sodium hydroxide to adjust the pH value to 9. Then the mixture was extracted with DCM (30 mL*3). The organic layer was combined and dried over anhydrous magnesium sulfate, filtered and concentrated to afford crude benzyl 3-amino-3-(2,2-difluoroethyl)piperidine-1-carboxylate (47-4). LC-MS: [M+H]+=299.2.

To a solution of benzyl 3-amino-3-(2,2-difluoroethyl)piperidine-1-carboxylate (intermediate 47-4) (4 g, 13.41 mmol) in DCM (50 mL) was added Boc-anhydride (4.67 mL, 20.11 mmol) and DIPEA (7.03 mL, 40.2 mmol) at RT under $N_2$ atmosphere. The mixture was stirred at 40° C. for 20 h. The mixture was cooled to RT and diluted with DCM (30 mL), washed with water (20 mL), brine (20 mL), dried over anhydrous magnesium sulfate, filtered and concentrated in vacuo to afford the crude product. The crude product was purified by flash chromatography (elution gradient: 5% to 20% EtOAc in hexane in 30 mins) to afford benzyl 3-((tert-butoxycarbonyl)amino)-3-(2,2-difluoroethyl)piperidine-1-carboxylate (47-5). LC-MS: [M+H]$^+$=399.0.

To a solution of benzyl 3-((tert-butoxycarbonyl)amino)-3-(2,2-difluoroethyl)piperidine-1-carboxylate (47-5) (4 g, 10.04 mmol) in methanol (50 mL) was added 10% Pd(OH)$_2$ on carbon, wet (1.410 g, 0.502 mmol), the mixture was stirred at rt for 3 hr under a hydrogen balloon. The reaction mixture was filtered and concentrated to afford the crude tert-butyl (3-(2,2-difluoroethyl)piperidin-3-yl)carbamate (Intermediate 47-6). LC-MS: [M+H]$^+$=265.0.

Intermediate 78-5: Methyl tert-butyl 3-(methylcarbamoyl)piperidin-3-ylcarbamate

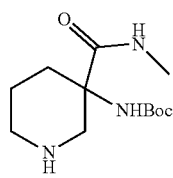

78-5

To a solution of $(NH_4)_2CO_3$ (2.13 g, 22 mmol) in $H_2O$ (8 mL) was added another solution of 1-benzylpiperidin-3-one (500 mg, 2 mmol) in EtOH (8 mL). Then trimethylsilyl cyanide (TMSCN) (0.74 mL, 5.5 mmol) was added to the mixture dropwise at RT. The resulting mixture was stirred at 70° C. for 16 h. The EtOH was removed in vacuo. The resulting mixture was extracted with EtOAc (20 mL*3). The organic layer was washed with $H_2O$ (20 mL), brine (20 mL), dried over $Na_2SO_4$ and concentrated in vacuo. The residue obtained was recrystallized from EtOAc:PE (1:5) to give 7-benzyl-1,3,7-triazaspiro[4.5]decane-2,4-dione (78-1). $^1$H NMR (400 MHz, CD$_3$OD) δ 7.46-7.17 (m, 5H), 3.54 (dd, J=29.8, 13.2 Hz, 2H), 2.90 (d, J=10.8 Hz, 1H), 2.69 (d, J=11.2 Hz, 1H), 2.32 (d, J=11.2 Hz, 1H), 2.08 (t, J=10.6 Hz, 1H), 1.88-1.59 (m, 4H). LC-MS (UV 214): (M+H)$^+$=260.1

A mixture of 7-benzyl-1,3,7-triazaspiro[4.5]decane-2,4-dione (78-1) (1 g, 3.86 mmol) in 10 M of 2.0 M KOH aqueous solution was heated at 120° C. for 16 h. The mixture was cooled to RT. Con. HCl solution (12.0 M in $H_2O$) was added to the mixture to adjust pH=4-5. The $H_2O$ was removed in vacuo. The residue was washed with a solution of MeOH:DCM (10%, 30 mL) and filtered. The filtrate was dried over $Na_2SO_4$ and concentrated to give crude 3-amino-1-benzylpiperidine-3-carboxylic acid (78-2). LC-MS [M+H]$^+$=235.3.

A mixture of 3-amino-1-benzylpiperidine-3-carboxylic acid (78-2) (5.7 g, 24.33 mmol), $K_2CO_3$ (13.45 g, 97.31 mmol), Boc$_2$O (8.2 mL, 36.49 mmol), THF (100 mL) and $H_2O$ (100 mL) was stirred at RT for 16 h. The reaction mixture was extracted with EtOAc, the combined organic phase was washed with water, brine, dried over anhydrous sodium sulfate, concentrated to give a residue. The residue was purified by combi-flash (silica gel, KMnO$_4$, NH$_3$·H$_2$O: MeOH:DCM, 20:100:1000) to give 1-benzyl-3-(tert-butoxycarbonylamino)piperidine-3-carboxylic acid (78-3). LC-MS: [M+H]$^+$=335.3.

To a solution of 1-benzyl-3-(tert-butoxycarbonylamino) piperidine-3-carboxylic acid (78-3) (670 mg, 2.00 mmol), HATU (1.5 g, 4.00 mmol) and DIPEA (778 mg, 6.00 mmol) in DCM (20 mL), was added CH$_3$NH$_2$ (35% in MeOH, 2 mL). The mixture was stirred at RT for 1 h. The reaction mixture was diluted with water, extracted with EtOAc, the combined organic phase was washed with sat. aq. NaHCO$_3$ (20 mL), brine (20 mL), dried over anhydrous sodium sulfate, concentrated to give a residue. The residue was purified by flash chromatography (elution gradient: 10% to 50% EtOAc in PE in 30 mins) to afford tert-butyl 1-benzyl-3-(methylcarbamoyl)piperidin-3-ylcarbamate (78-4). LC-MS: [M+H]$^+$=348.3.

To a solution of tert-butyl 1-benzyl-3-(methylcarbamoyl) piperidin-3-ylcarbamate (78-4) (290 mg, 0.836 mmol) in EtOH (10 mL) was added Pd(OH)$_2$ (87 mg). The resulting mixture was stirred at RT for 4 h under H$_2$ atmosphere. The mixture was filtered and the filtrate was concentrated to give crude methyl tert-butyl 3-(methylcarbamoyl)piperidin-3-ylcarbamate (Intermediate 78-5). $^1$H NMR (400 MHz, DMSO-d$_6$) δ 7.87 (s, 1H), 7.29 (s, 1H), 3.62-3.59 (m, 1H), 3.04-2.87 (m, 3H), 2.61-2.60 (m, 3H), 1.83-1.76 (m, 3H), 1.53-1.51 (m, 1H), 1.38 (s, 9H), 1.27-1.25 (m, 1H). LC-MS (UV 214): [M+H]$^+$=258.4.

Intermediate 89-6: Methyl (3-(2,3-dimethylbutanoyl)piperidin-3-yl)carbamate

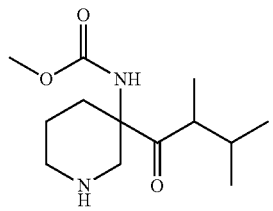

89-6

To a solution of tert-butyl 3-cyanopiperidine-1-carboxylate (10 g, 47.6 mmol, 1.0 eq.) in dry THF (100 mL) was added 1 M LiHMDS (71.4 mL, 71.4 mmol, 1.5 eq) dropwise at −78° C. under nitrogen. The mixture was stirred at −78° C. for 40 min. Then 3-methylbutanal (6.1 g, 71.4 mmol, 1.5 eq.) was added in one portion at −78° C. Then the mixture was stirred at RT for 4 hours. The mixture was quenched with water (200 mL), extracted with EA (100 mL*2), washed with brine (200 mL), dried over anhydrous sodium sulfate, filtered, concentrated. The residue was purified by flash chromatography (PE/EA=92/8 to 90/10 to 70/30) to give tert-butyl 3-cyano-3-(1-hydroxy-3-methylbutyl)piperidine-1-carboxylate (89-1). ¹H NMR (400 MHz, CD₃OD) δ ppm 4.57 (d, J=13.6 Hz, 0.5H), 4.24-3.93 (m, 1.5H), 3.56 (dd, J=1.6, 10.8 Hz, 0.5H), 3.52-3.42 (m, 0.5H), 3.09-2.56 (m, 2H), 2.22-2.09 (m, 0.5H), 2.01-1.82 (m, 1.5H), 1.78-1.53 (m, 4H), 1.48 (s, 9H), 1.41-1.29 (m, 1H), 0.99 (dd, J=1.6, 6.8 Hz, 3H), 0.95-0.89 (m, 3H). LC-MS: [M+H]⁺=297.2 To a solution of tert-butyl 3-cyano-3-(1-hydroxy-3-methylbutyl)piperidine-1-carboxylate (89-1) (5.5 g, 18.5 mmol, 1.0 eq.) in CH₂Cl₂ (100 mL) was added DMP (11.8 g, 27.8 mmol, 1.5 eq.).

The mixture was stirred at RT for 30 min. The mixture was diluted with H₂O (100 mL) and extracted with CH₂Cl₂ (100 mL*2). The organic layers were washed with brine (200 mL), dried over sodium sulfate, filtered, concentrated and purified by combi-flash (PE/EA=80/20) to afford tert-butyl 3-cyano-3-(3-methylbutanoyl)piperidine-1-carboxylate (89-2). ¹H NMR (400 MHz, CDCl₃) δ ppm 4.59-3.90 (m, 2H), 3.22-2.92 (m, 1H), 2.87-2.58 (m, 3H), 2.29-2.03 (m, 2H), 1.98-1.69 (m, 3H), 1.50 (s, 9H), 1.03-0.89 (m, 6H). LC-MS: [M+H]⁺=295.1.

To a solution of tert-butyl 3-cyano-3-(3-methylbutanoyl) piperidine-1-carboxylate (89-2) (3.3 g, 11.2 mmol, 1.0 eq.) in THF (40 mL) was added LiHMDS (12.3 mL, 12.3 mmol, 1.1 eq. 1M in THF) dropwise at −78° C. under N₂. The mixture was stirred at −78° C. for 20 min. Then MeI (1.8 g, 12.3 mmol, 1.1 eq.) was added to the mixture. The mixture was stirred at RT for another 4 hours. The reaction was quenched with H₂O (40 mL) and extracted with EtOAc (40 mL*2). The organic layers were combined and washed with brine (100 mL), dried over sodium sulfate, filtered, concentrated and purified by combi-flash (5% EtOAc in hexane) to give tert-butyl 3-cyano-3-(2,3-dimethylbutanoyl)piperidine-1-carboxylate (89-3). ¹H NMR (400 MHz, CD₃OD) δ ppm 4.50-4.02 (m, 2H), 3.23-2.64 (m, 3H), 2.27-1.72 (m, 5H), 1.49 (s, 9H), 1.16-1.06 (m, 3H), 1.01-0.88 (m, 6H). LC-MS: [M+H]⁺=310.2.

To a mixture of tert-butyl 3-cyano-3-(2,3-dimethylbutanoyl)piperidine-1-carboxylate (89-3) (3.3 g, 11 mmol, 1.0 eq.) in MeOH (40 mL) was added NaOH (21 mL, 21 mmol, 1 M/L) and H₂O₂ (17 ml, 30% aq. solution). The mixture was stirred at RT for 16 hours. The mixture was quenched with saturated aqueous Na₂SO₃ (100 mL), extracted with EtOAc (100 mL*2). The combined organic layers were washed with brine (150 mL), dried over anhydrous Na₂SO₄, filtered and concentrated in vacuo. The residue was purified by silica gel column chromatography (15%-30% EtOAc in PE) to give tert-butyl 3-carbamoyl-3-(2,3-dimethylbutanoyl)piperidine-1-carboxylate (89-4). ¹H NMR (400 MHz, CDCl₃) δ ppm 7.15 (brs, 1H), 5.35 (brs, 1H), 4.78-2.28 (m, 5H), 1.94-1.57 (m, 5H), 1.47 (s, 9H), 1.00 (dd, J=7.2, 20.0 Hz, 3H), 0.90-0.80 (m, 6H). LC-MS: [M+H]⁺=327.0.

To a solution of tert-butyl 3-carbamoyl-3-(2,3-dimethylbutanoyl)piperidine-1-carboxylate (89-4) (1.37 g, 4.2 mmol, 1.0 eq.) in MeOH (30 mL) was added PhI(OAc)₂ (1.6 g, 5.04 mmol, 1.2 eq.) and KOH (589 mg, 10.5 mmol, 2.5 eq.). The mixture was stirred at 0° C. for 15 minutes. The mixture was stirred at RT for another 2 hours. The mixture was diluted with H₂O (40 mL), extracted with EtOAc (40 mL*2). The combined organic layers were washed with brine (40 mL), dried over anhydrous Na₂SO₄, filtered and concentrated in vacuo. The residue was purified by silica gel column chromatography (20% EtOAc in PE) to give tert-butyl 3-(2,3-dimethylbutanoyl)-3-((methoxycarbonyl) amino)piperidine-1-carboxylate (89-5). ¹H NMR (400 MHz, CD₃OD): δ 4.74-4.42 (m, 1H), 4.14-3.91 (m, 1H), 3.80-3.48 (m, 3H), 3.29-3.12 (m, 1H), 2.96-2.64 (m, 2H), 1.98-1.50 (m, 5H), 1.43 (s, 9H), 1.01-0.85 (m, 9H). LC-MS: [M+H]⁺=357.1.

To a solution of tert-butyl 3-(2,3-dimethylbutanoyl)-3-((methoxycarbonyl)amino)piperidine-1-carboxylate (89-5) (500 mg, 1.40 mmol, 1.0 eq.) in DCM (10 mL) was added TFA (10 mL) at RT. The mixture was stirred at RT for 30 minutes. The mixture was concentrated in vacuo and diluted with H₂O (15 mL), basified by NH₃·H₂O to pH=11, extracted with CHCl₃/i-PrOH (3:1, 20 mL*3). The combined organic layers were washed with brine (30 mL), dried over anhydrous Na₂SO₄, filtered and concentrated to give methyl (3-(2,3-dimethylbutanoyl)piperidin-3-yl)carbamate (Intermediate 89-6). ¹H NMR (400 MHz, CD₃OD) δ ppm 3.63 (s, 3H), 3.27-3.20 (m, 1H), 3.07-2.95 (m, 1H), 2.92-2.81 (m, 2H), 2.66-2.55 (m, 1H), 2.10-2.00 (m, 1H), 1.94-1.76 (m, 2H), 1.72-1.57 (m, 1H), 1.54-1.44 (m, 1H), 1.00-0.95 (m, 3H), 0.91-0.74 (m, 6H). LC-MS: [M+H]⁺=257.1.

Intermediate 113-5: tert-Butyl (3-(2,2-difluoro-1-hydroxyethyl)piperidin-3-yl)carbamate

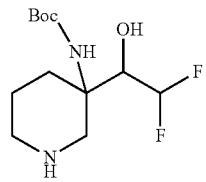

To a solution of 1-benzyl 3-ethyl 3-((tert-butoxycarbonyl) amino)piperidine-1,3-dicarboxylate (5.0 g, 12.30 mmol) in THF (80 mL) and methanol (80 mL), was added lithium chloride (10.43 g, 246 mmol) and sodium tetrahydroborate (9.31 g, 246 mmol) at rt under N₂ atmosphere, the reaction mixture was stirred at RT for 18 hours under N₂ atmosphere. The reaction mixture was diluted with water, extracted with EtOAc (50 mL*3), the combined organic phase was washed with water (50 mL), brine (50 mL), dried over anhydrous sodium sulfate, concentrated to give a crude product. The crude product was purified by flash chromatography (elution gradient: 10% to 50% EtOAc in PE in 30 mins) to give benzyl 3-((tert-butoxycarbonyl)amino)-3-(hydroxymethyl) piperidine-1-carboxylate (113-1). LC-MS: [M+H]⁺=365.2.

To a solution of benzyl 3-((tert-butoxycarbonyl)amino)-3-(hydroxymethyl)piperidine-1-carboxylate (113-1) (6.2 g, 17.01 mmol) in DCM (50 mL) was added Dess-Martin Periodinane (14.43 g, 34.0 mmol) at 0° C. under N₂ atmosphere, the reaction mixture was stirred at RT for 2 h under N₂ atmosphere. The reaction mixture was diluted with 30 ml of sat. NaHCO₃ aqueous solution, extracted with DCM (40 mL*3), the combined organic phase was washed with water (50 mL), brine (50 mL), dried over anhydrous sodium sulfate, concentrated to give a crude product. The crude product was purified by flash chromatography (elution gradient: 10% to 40% EtOAc in PE in 30 mins) to afford benzyl 3-((tert-butoxycarbonyl)amino)-3-formylpiperidine-1-carboxylate (113-2). LC-MS: [M+H]⁺=362.1.

To a solution of benzyl 3-((tert-butoxycarbonyl)amino)-3-formylpiperidine-1-carboxylate (113-2) (3 g, 8.28 mmol) and (difluoro(phenylsulfonyl)methyl)trimethylsilane (4.38 g, 16.56 mmol) in anhydrous THF (50 mL) was added a solution of TBAT (0.447 g, 0.828 mmol) in 15 mL anhydrous THF dropwise at −78° C. under N$_2$ atmosphere. After addition, the reaction mixture was slowly warmed to rt and stirred at rt for 18 h under N$_2$ atmosphere. And then TBAF (10.76 mL, 10.76 mmol) was added and the reaction mixture was stirred at rt for another 30 min. The reaction mixture was diluted sat. NaCl solution, extracted with EtOAc (50 mL*3), the combined organic phase was washed with water (40 mL), brine (40 mL), dried over anhydrous sodium sulfate, and concentrated to give a crude product. The crude product was purified by flash chromatography (elution gradient: 10% to 50% EtOAc in hexane in 40 mins) to afford benzyl 3-((tert-butoxycarbonyl)amino)-3-(2,2-difluoro-1-hydroxy-2-(phenylsulfonyl)ethyl) piperidine-1-carboxylate (113-3). LC-MS: [M+H]$^+$=555.2.

To a solution of benzyl 3-((tert-butoxycarbonyl)amino)-3-(2,2-difluoro-1-hydroxy-2-(phenylsulfonyl)ethyl) piperidine-1-carboxylate (113-3) (2.4 g, 4.33 mmol) in DMF (50 mL), was added 40 mL of HOAc/NaOAc (1:1) buffer solution (4 mol/L). Magnesium turning (1.578 g, 64.9 mmol) were added in portions. The reaction mixture was stirred at room temperature for 4 h. The reaction was quenched with water and extracted with EtOAc (30 mL*3). The combined organic layers were washed with water (30 mL), brine (30 mL), dried over anhydrous Na$_2$SO$_4$, filtered and concentrated to give a residue. The residue was purified by flash chromatography (elution gradient: 0% to 40% EtOAc in PE in 40 mins) to afford benzyl 3-((tert-butoxycarbonyl)amino)-3-(2,2-difluoro-1-hydroxyethyl)piperidine-1-carboxylate (113-4). LC-MS: [M+H]$^+$=415.2.

To a solution of benzyl 3-((tert-butoxycarbonyl)amino)-3-(2,2-difluoro-1-hydroxyethyl)piperidine-1-carboxylate (113-4) (1.0 g, 2.413 mmol) in MeOH (50 mL) was added Pd(OH)$_2$ (0.068 g, 0.483 mmol) at RT, the reaction mixture was stirred at RT for 0.5 h under H$_2$ atmosphere. The reaction mixture was filtered and concentrated to give tert-butyl (3-(2,2-difluoro-1-hydroxyethyl)piperidin-3-yl)carbamate (Intermediate 113-5). LC-MS: [M+H]+=281.

Intermediate 156-2: 1-(3-amino-1-(4-(hydroxymethyl)-6-(2,4,5-trifluorophenyl)pyridin-3-yl)piperidin-3-yl)-2,2-difluoroethan-1-ol

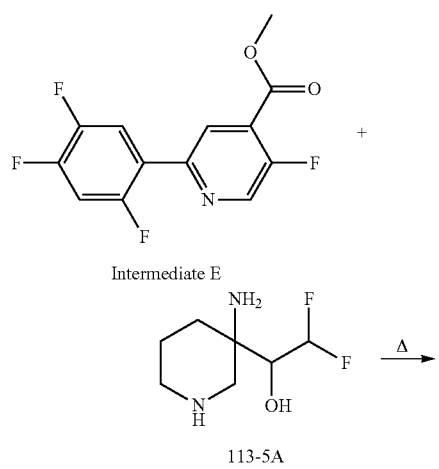

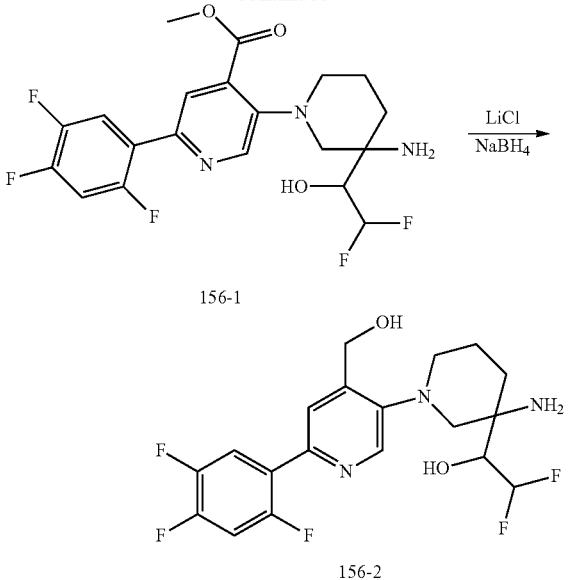

To a mixture of methyl 5-fluoro-2-(2,4,5-trifluorophenyl) isonicotinate (Intermediate E) (2.5 g, 8.77 mmol) and 1-(3-aminopiperidin-3-yl)-2,2-difluoroethan-1-ol (Intermediate 113-5A) (3.58 g, 8.77 mmol) in DMSO (40 ml) was added DIPEA (40 ml, 229 mmol). The mixture was heated to 100° C. for 3 hrs. The mixture was cooled to room temperature and was treated with EtOAc (50 ml) and H$_2$O (50 ml). The layers were separated and the aqueous layer was extracted with EtOAc (50 ml*3). The combined organic layers were washed with brine, dried over Na$_2$SO$_4$ and filtered. The filtrate was concentrated. The residue was purified, eluting with EtOAc in n-hexane (0 to 50%) to give methyl 5-(3-amino-3-(2,2-difluoro-1-hydroxyethyl)piperidin-1-yl)-2-(2,4,5-trifluorophenyl)isonicotinate (Intermediate 156-1). $^1$H NMR (400 MHz, CDCl$_3$) δ 8.52 (s, 1H), 8.09-7.98 (m, 1H), 7.92 (ddd, J=11.3, 9.1, 7.2 Hz, 1H), 7.04 (td, J=10.2, 6.4 Hz, 1H), 5.92 (td, J=55.2, 3.5 Hz, 1H), 3.98 (s, 3H), 3.65 (td, J=12.9, 3.5 Hz, 1H), 3.36-3.21 (m, 2H), 3.11 (d, J=11.8 Hz, 1H), 2.99 (ddd, J=12.2, 10.2, 3.2 Hz, 1H), 2.02 (tdd, J=15.2, 9.7, 4.6 Hz, 1H), 1.88-1.65 (m, 3H). LC-MS: [M+H]$^+$= 446.1.

To a mixture of methyl 5-(3-amino-3-(2,2-difluoro-1-hydroxyethyl)piperidin-1-yl)-2-(2,4,5-trifluorophenyl) isonicotinate (Intermediate 156-1) (3.2 g, 7.18 mmol) and LiCl (6.09 g, 144 mmol) in MeOH (100 ml) and THF (100 ml) was added NaBH$_4$ (5.44 g, 144 mmol) at 0° C. the mixture was stirred at room temperature for 4 hrs. LC-MS indicated most of sm was consumed. The mixture was quenched with H$_2$O (50 ml) and was extracted with EtOAc (50 ml*4). The combined organic layers were washed with brine, dried over Na$_2$SO$_4$ and filtered. The filtrate was concentrated. The filtrate was concentrated and purified, eluting with MeOH in DCM (0 to 10%) to give 1-(3-amino-1-(4-(hydroxymethyl)-6-(2,4,5-trifluorophenyl)pyridin-3-yl)piperidin-3-yl)-2,2-difluoroethan-1-ol (Intermediate 156-2). $^1$H NMR (400 MHz, CDCl$_3$) δ 8.47 (s, 1H), 7.89 (ddd, J=11.2, 9.1, 7.2 Hz, 1H), 7.81 (d, J=2.0 Hz, 1H), 7.04 (td, J=10.2, 6.5 Hz, 1H), 5.92 (td, J=55.2, 3.6 Hz, 1H), 5.12-4.62 (m, 2H), 3.68 (td, J=12.5, 3.6 Hz, 1H), 3.09 (dd, J=25.6, 10.6 Hz, 3H), 2.97-2.89 (m, 1H), 2.09-1.72 (m, 4H). LC-MS: [M+H]$^+$=418.2, 419.1.

Intermediate 158-3: tert-butyl (tert-butoxycarbonyl)(9-((5-(3-((tert-butoxycarbonyl)amino)-3-(2,2-difluoro-1-hydroxyethyl)piperidin-1-yl)-2-(2-(difluoromethyl)-4-fluorophenyl)pyridin-4-yl)methyl)-9H-purin-6-yl)carbamate

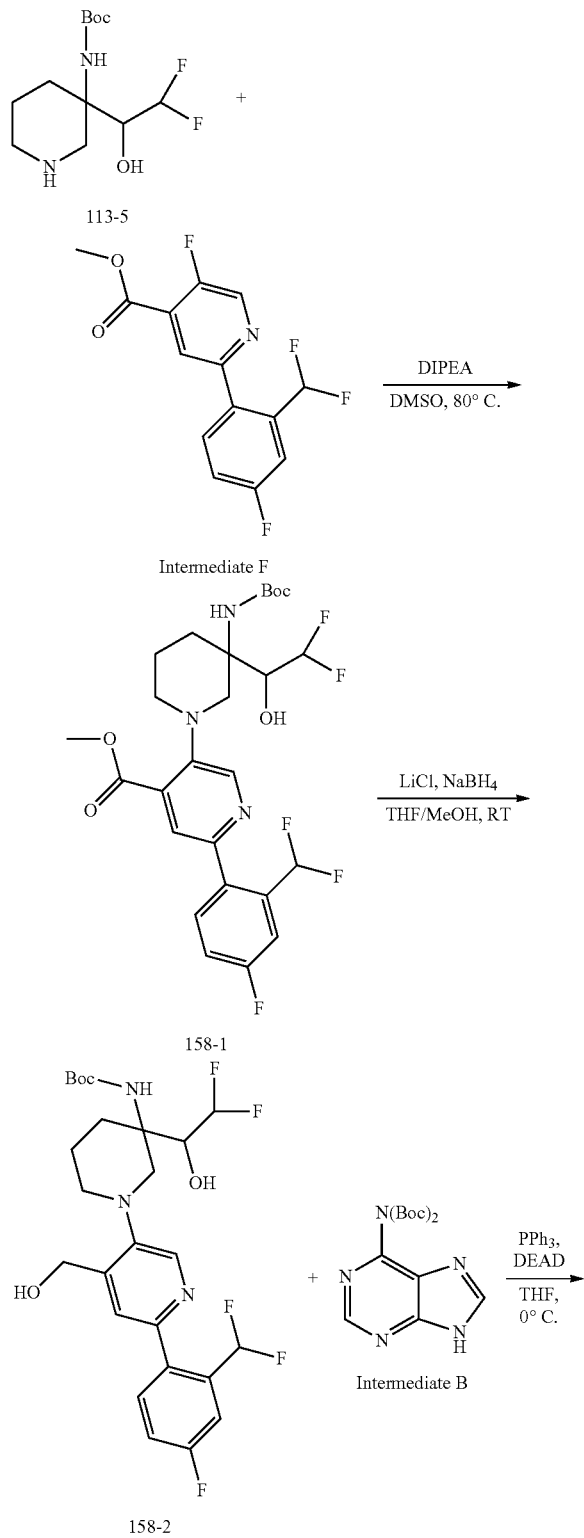

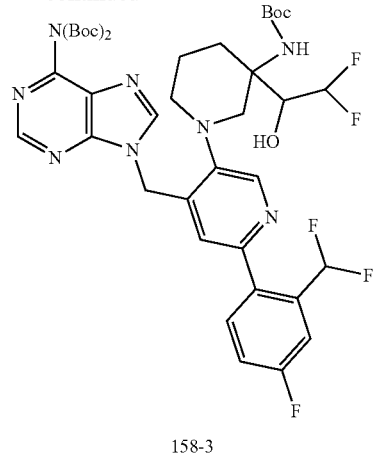

To a solution of tert-butyl (3-(2,2-difluoro-1-hydroxyethyl)piperidin-3-yl)carbamate (Intermediate 113-5) (1.828 g, 4.48 mmol) and methyl 2-(2-(difluoromethyl)-4-fluorophenyl)-5-fluoroisonicotinate (Intermediate F) (1.34 g, 4.48 mmol in DMSO (15 mL) was added DIPEA (15.64 mL, 90 mmol) at RT, the reaction mixture was stirred at 80° C. for 8 hr under N₂ atmosphere. The reaction mixture was diluted with water (40 mL), extracted with EtOAc (30 mL*3). The combined organic layers were washed with water (20 mL*3), brine (20 mL), dried over anhydrous Na₂SO₄, filtered and concentrated to give a residue. The residue was purified by flash chromatography (elution gradient: 0% to 10% MeOH in DCM in 40 mins) to afford methyl 5-(3-((tert-butoxycarbonyl)amino)-3-(2,2-difluoro-1-hydroxyethyl)piperidin-1-yl)-2-(2-(difluoromethyl)-4-fluorophenyl)isonicotinate (Intermediate 158-1). LC-MS: [M+H]⁺=460.1.

To a solution of methyl 5-(3-((tert-butoxycarbonyl)amino)-3-(2,2-difluoro-1-hydroxyethyl)piperidin-1-yl)-2-(2-(difluoromethyl)-4-fluorophenyl)isonicotinate (Intermediate 158-1) (1.5 g, 3.27 mmol) in THF (30 mL) and MeOH (30 mL), was added NaBH₄ (2.471 g, 65.3 mmol) and LiCl (2.77 g, 65.3 mmol). The reaction mixture was stirred at 20° C. for 2 hr under N₂ atmosphere. The reaction mixture was diluted with 30 ml of water, extracted with EtOAc (20 mL*3). The combined organic layers were washed with water (20 mL), brine (20 mL), concentrated to give a crude product. The crude product was purified by flash chromatography (elution gradient: 0% to 10% MeOH DCM in 30 mins) to afford tert-butyl (3-(2,2-difluoro-1-hydroxyethyl)-1-(6-(2-(difluoromethyl)-4-fluorophenyl)-4-(hydroxymethyl)pyridin-3-yl)piperidin-3-yl)carbamate (Intermediate 158-2). LC-MS: [M+H]⁺=432.

To a solution of tert-butyl (3-(2,2-difluoro-1-hydroxyethyl)-1-(6-(2-(difluoromethyl)-4-fluorophenyl)-4-(hydroxymethyl)pyridin-3-yl)piperidin-3-yl)carbamate (Intermediate 158-2) (500 mg, 1.159 mmol), Intermediate B (389 mg, 1.159 mmol) and PPh₃ (912 mg, 3.48 mmol) in THF (50 mL), was added DEAD (0.550 mL, 3.48 mmol), the reaction mixture was stirred at 0° C. for 30 min under N₂ atmosphere. The reaction mixture was diluted with 20 ml of water, extracted with EtOAc (20 mL*3). The combined organic layers were washed with water (20 mL), brine (20 mL), concentrated to give a crude product. The crude product was purified by flash chromatography (elution gradient: 0% to 10% MeOH in DCM in 30 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(2-(difluororomethyl)-4-fluorophenyl)pyridin-4-yl)methyl)-9H-purin-6-yl)carbamate (Intermediate 158-3). LC-MS: [M+H]⁺= 749.

Intermediate 160-3: tert-butyl (tert-butoxycarbonyl)(9-((5-(3-((tert-butoxycarbonyl)amino)-3-(2,2-difluoro-1-hydroxyethyl)piperidin-1-yl)-2-(2,5-difluoro-4-methoxyphenyl)pyridin-4-yl)methyl)-9H-purin-6-yl)carbamate

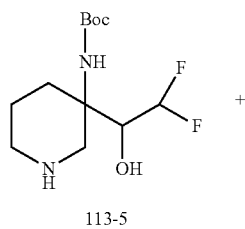

113-5

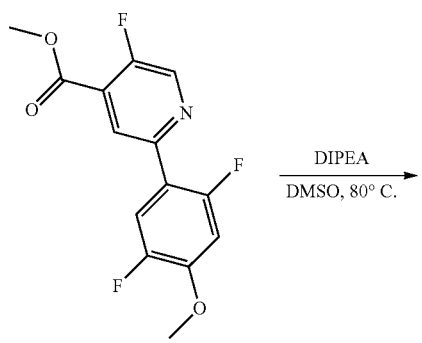

Intermediate G

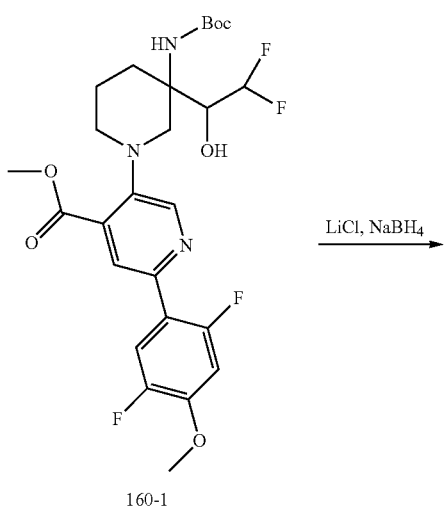

160-1

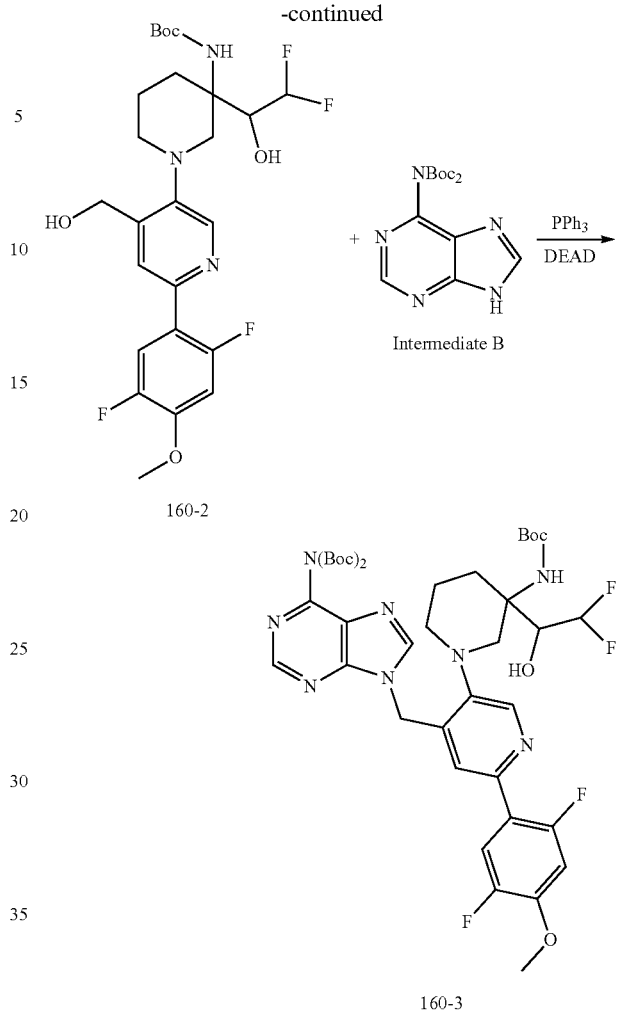

To a solution of methyl 2-(2,5-difluoro-4-methoxyphenyl)-5-fluoroisonicotinate (Intermediate G) (2.0 g, 6.73 mmol) and tert-butyl (3-(2,2-difluoro-1-hydroxyethyl)piperidin-3-yl)carbamate (Intermediate 113-5) (2.263 g, 8.07 mmol) in DMSO (10 mL) was added DIPEA (23.50 mL, 135 mmol) under N₂ atmosphere, and the reaction mixture was stirred at 120° C. for 6 hrs. The reaction mixture was diluted with water, extracted with EtOAc, the combined organic phase was washed with water, brine, dried over Na₂SO₄, concentrated to give a crude product. The crude product was purified by flash chromatography (elution gradient: 10% to 50% EtOAc in n-hexane in 30 mins) to afford methyl 5-(3-((tert-butoxycarbonyl)amino)-3-(2,2-difluoro-1-hydroxyethyl)piperidin-1-yl)-2-(2-(difluoromethyl)-4-fluorophenyl)isonicotinate (Intermediate 160-1). LC-MS: [M+H]+=558.1.

To a solution of methyl 5-(3-((tert-butoxycarbonyl)amino)-3-(2,2-difluoro-1-hydroxyethyl)piperidin-1-yl)-2-(2-(difluoromethyl)-4-fluorophenyl)isonicotinate (Intermediate 160-1) (1.9 g, 3.41 mmol) in THF (30 mL) and methanol (30 mL) was added LiCl (0.068 g, 3.41 mmol) and NaBH₄ (0.068 g, 3.41 mmol) at 0° C. The reaction mixture was stirred at rt for 2 hours under N₂. The reaction mixture was diluted with water, extracted with EtOAc, the combined organic phase was washed with water, brine, dried over sodium sulfate, concentrated to give a crude product. The crude product was purified by flash chromatography (elution gradient: 10% to 60% EtOAc in n-hexane in 40 mins) to afford tert-butyl (3-(2,2-difluoro-1-hydroxyethyl)-1-(6-(2,5-difluoro-4-methoxyphenyl)-4-(hydroxymethyl) pyridin-3-yl)piperidin-3-yl)carbamate (Intermediate 160-2). LC-MS: [M+H]+=530.2.

To a solution of tert-butyl (3-(2,2-difluoro-1-hydroxyethyl)-1-(6-(2,5-difluoro-4-methoxyphenyl)-4-(hydroxymethyl)pyridin-3-yl)piperidin-3-yl)carbamate (Intermediate 160-2) (1.2 g, 2.3 mmol), Intermediate B (0.76 g, 2.3 mmol) and PPh₃ (1.783 g, 6.80 mmol) in THF (20 mL) was added DEAD (1.1 mL, 6.8 mmol) dropwise at 0° C. under N₂ atmosphere, the reaction mixture was stirred at 0° C. for 0.5 hr under N₂ atmosphere. The reaction mixture was quenched with water and extracted with EtOAc, the combined organic phase was washed with water, brine, dried over Na₂SO₄, concentrated to give a crude product. The crude product was purified by flash chromatography (elution gradient: 10% to 50% EtOAc in n-hexane in 50 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(2,5-difluoro-4-methoxyphenyl)pyridin-4-yl)methyl)-9H-purin-6-yl)carbamate (Intermediate 160-3). LC-MS: [M+H]+=847.3.

The following intermediates were prepared following procedures analogous to the preparation of tert-butyl (3-(2,2-difluoro-1-hydroxyethyl)-1-(6-(2,5-difluoro-4-methoxyphenyl)-4-(hydroxymethyl) pyridin-3-yl)piperidin-3-yl)carbamate (Intermediate 160-2), from reacting the corresponding fluoroisonicotinate with 1-(3-aminopiperidin-3-yl)-2,2-difluoroethan-1-ol (Intermediate 113-5A) (Intermediate Nos. 162-2, 164-2 and 166-2) or tert-butyl (3-(2,2-difluoro-1-hydroxyethyl)piperidin-3-yl)carbamate (Intermediate 113-5) (Intermediate Nos. 168-2, 170-2, 172-2).

| Intermediate No. | | LC-MS |
|---|---|---|
| 162-2 | [structure] (Intermediate H) | [M + H]+ = 444.2, 445.2 |
| 164-2 | [structure] (Intermediate I) | [M + H]+ = 430.1 |
| 166-2 | [structure] (Intermediate J) | [M + H]+ = 462.1 |
| 168-2 | [structure] (Intermediate K) | [M + H]+ = 528.2 |

| Intermediate No. | | | LC-MS |
|---|---|---|---|
| 170-2 | 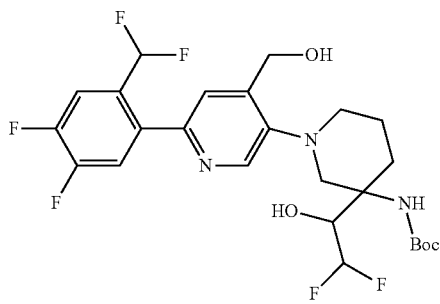 [SMILES: CC(C)(C)OC(=O)NC1(C(O)C(F)F)CCCN(c2cnc(-c3cc(F)c(F)cc3C(F)F)cc2CO)C1] | 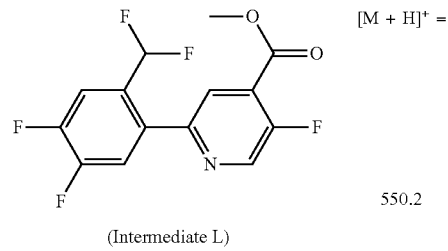(Intermediate L) | [M + H]⁺ = 550.2 |
| 172-2 | 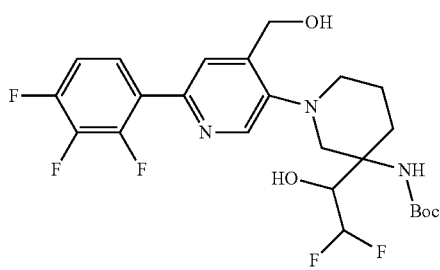 [SMILES: CC(C)(C)OC(=O)NC1(C(O)C(F)F)CCCN(c2cnc(-c3ccc(F)c(F)c3F)cc2CO)C1] | 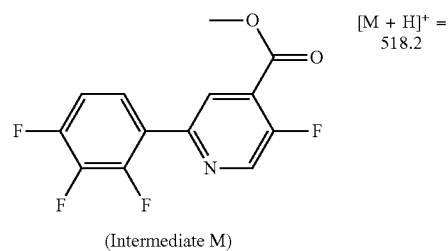(Intermediate M) | [M + H]⁺ = 518.2 |
| 174-2 | 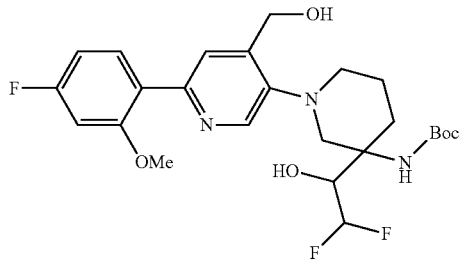 [SMILES: COc1cc(F)ccc1-c1cc(CO)c(N2CCCC(NC(=O)OC(C)(C)C)(C(O)C(F)F)C2)cn1] | 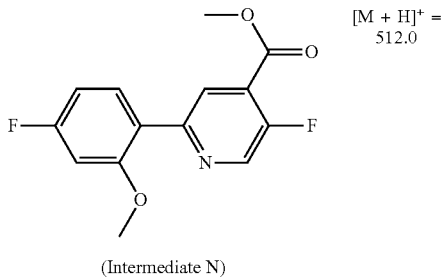(Intermediate N) | [M + H]⁺ = 512.0 |
| 175-2 | 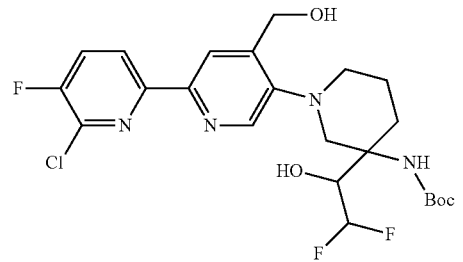 [SMILES: CC(C)(C)OC(=O)NC1(C(O)C(F)F)CCCN(c2cnc(-c3ccc(F)c(Cl)n3)cc2CO)C1] | 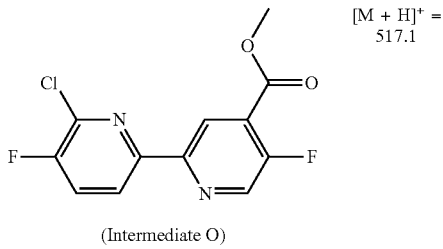(Intermediate O) | [M + H]⁺ = 517.1 |

Intermediate 168-3: tert-butyl (tert-butoxycarbonyl) (9-((5-(3-((tert-butoxycarbonyl)amino)-3-(2,2-difluoro-1-hydroxyethyl)piperidin-1-yl)-2-(2-chloro-4-methoxyphenyl)pyridin-4-yl)methyl)-9H-purin-6-yl) carbamate Intermediate 170-4: tert-butyl (tert-butoxycarbonyl) (9-((5-(3-((tert-butoxycarbonyl)amino)-3-(2,2-difluoro-1-hydroxyethyl)piperidin-1-yl)-2-(2-(difluoromethyl)-4,5-difluorophenyl) pyridin-4-yl)methyl)-9H-purin-6-yl)carbamate

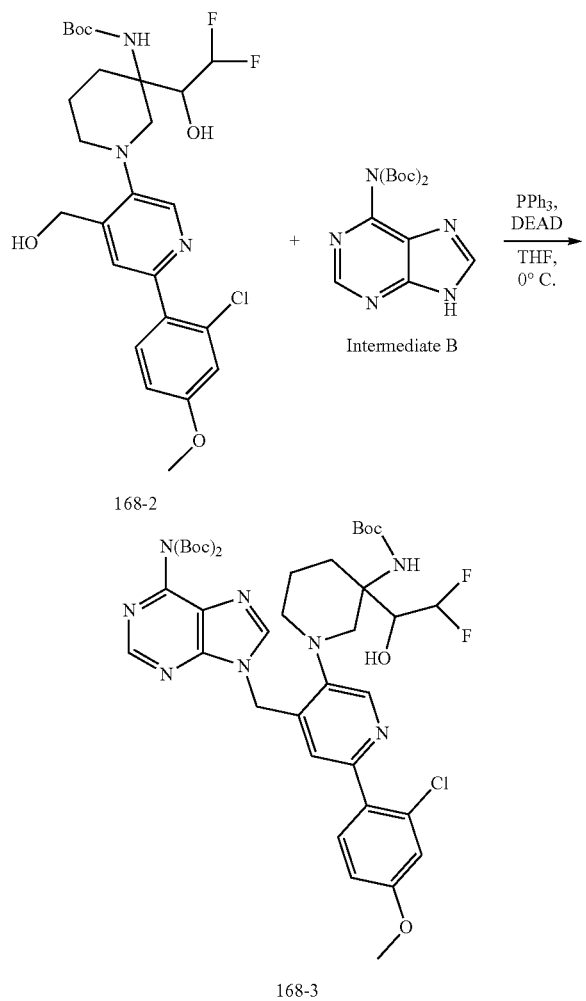

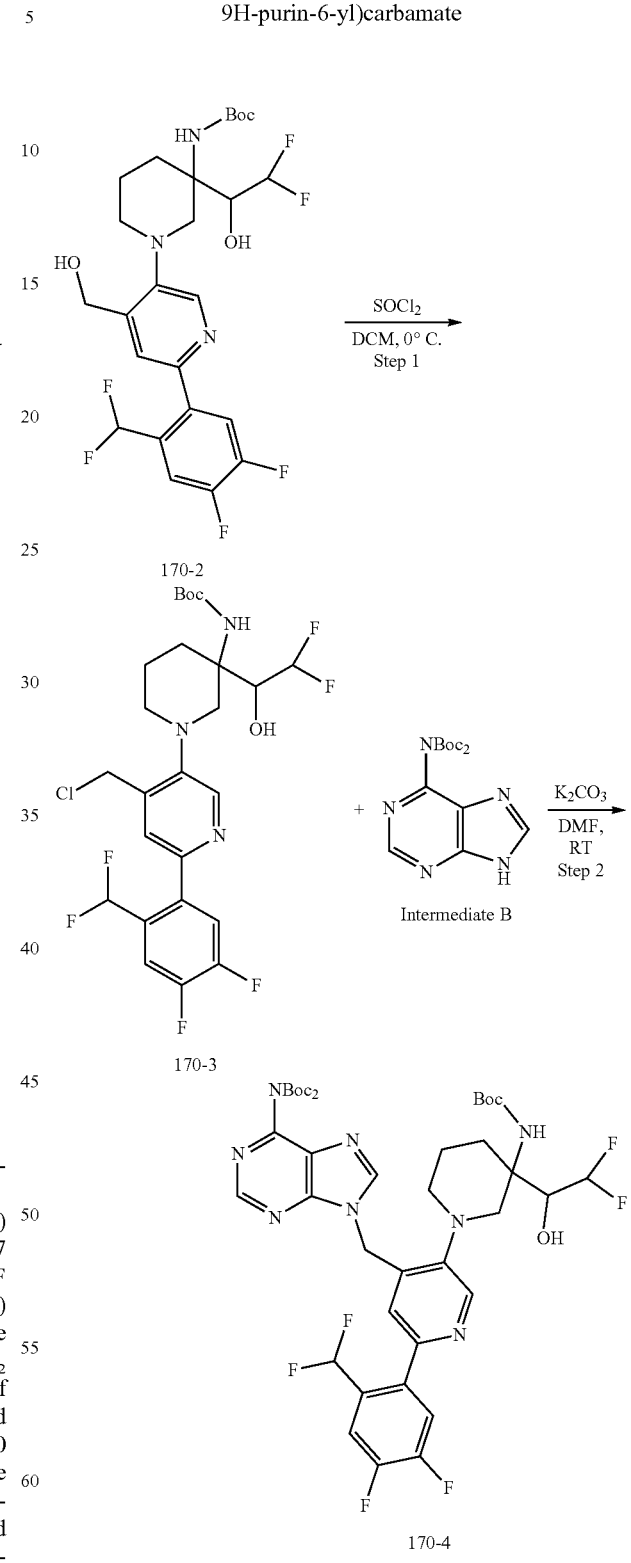

To a solution of tert-butyl (1-(6-(2-chloro-4-methoxyphenyl)-4-(hydroxymethyl)pyridin-3-yl)-3-(2,2-difluoro-1-hydroxyethyl)piperidin-3-yl)carbamate (Intermediate 168-2) (0.5 g, 0.947 mmol, 1.0 eq), Intermediate B (0.318 g, 0.947 mmol, 1.1 eq) and n-PPh$_3$ (0.745 g, 2.84 mmol, 3 eq) in THF (20 mL), was added DIAD (0.552 mL, 2.84 mmol, 3 eq) dropwise at 0° C. under N$_2$ over 20 min, after addition the reaction mixture was stirred at RT for 1 hr under N$_2$ atmosphere. The reaction mixture was diluted with 20 ml of water, extracted with EtOAc (20 mL*3). The combined organic layers were washed with water (20 mL), brine (20 mL), concentrated to give a crude product. The crude product was purified by flash chromatography (elution gradient: 20% to 70% EtOAc in n-hexane in 50 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(2-chloro-4-methoxyphenyl)pyridin-4-yl)methyl)-9H-purin-6-yl)carbamate (Intermediate 168-3). LC-MS: [M+H]$^+$=845.4.

Step 1. To a solution of tert-butyl (3-(2,2-difluoro-1-hydroxyethyl)-1-(6-(2-(difluoromethyl)-4,5-difluorophenyl)-4-(hydroxymethyl)pyridin-3-yl)piperidin-3-yl)carbamate (Intermediate 170-2) (0.22 g, 0.40 mmol, 1.0 eq) in dry DCM (5 mL) was added dropwise thionyl chloride (0.146 mL, 2.02 mmol) at 0° C. The reaction mixture diluted with sat. K$_2$CO$_3$ solution, extracted with DCM, washed with water (10 mL), brine (10 mL×2) and dried over Na$_2$SO$_4$, concentrated under reduced pressure to afford tert-butyl (1-(4-(chloromethyl)-6-(2-(difluoromethyl)-4,5-difluorophenyl)pyridin-3-yl)-3-(2,2-difluoro-1-hydroxyethyl)piperidin-3-yl)carbamate (Intermediate 170-3). LC-MS: [M+H]$^+$=568.1.

Step 2. A suspension of tert-butyl (1-(4-(chloromethyl)-6-(2-(difluoromethyl)-4,5-difluorophenyl)pyridin-3-yl)-3-(2,2-difluoro-1-hydroxyethyl)piperidin-3-yl)carbamate (Intermediate 170-3) (0.24 g, 0.42 mmol, 1.0 eq), intermediate B (0.14 g, 0.42 mmol) and K$_2$CO$_3$ (0.175 g, 1.27 mmol, 3.0 eq) in dry DMF (5 mL) was stirred at RT for 16 hours and quenched with water. The mixture was extracted with ethyl acetate (10 mL×3). The combined organic layers were washed with water (10 mL*3), brine (10 mL) and dried over Na$_2$SO$_4$. filtered and concentration. The crude product was purified by flash chromatography (elution gradient: 10% to 70% EtOAc in m-hexane 50 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(2-(difluoromethyl)-4,5-difluorophenyl)pyridin-4-yl)methyl)-9H-purin-6-yl)carbamate (Intermediate 170-4). LC-MS: [M+H]$^+$=867.3.

Intermediate 172-4: tert-butyl (tert-butoxycarbonyl)(9-((5-(3-((tert-butoxycarbonyl)amino)-3-(2,2-difluoro-1-hydroxyethyl)piperidin-1-yl)-2-(2,3,4-trifluorophenyl)pyridin-4-yl)methyl)-9H-purin-6-yl)carbamate

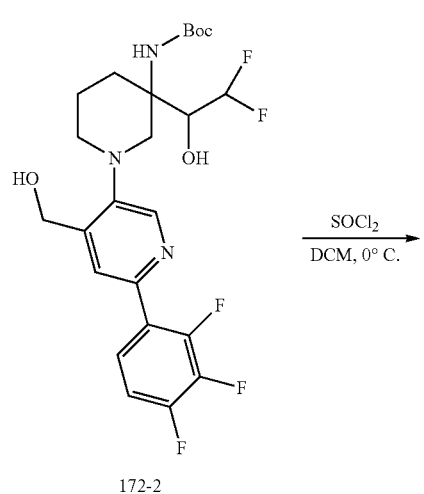

172-2

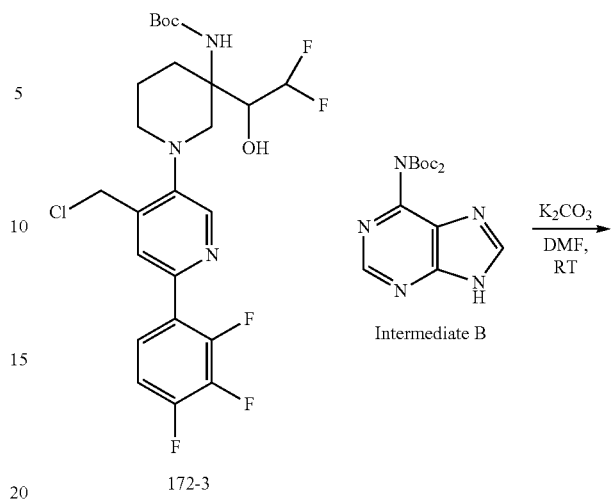

172-3

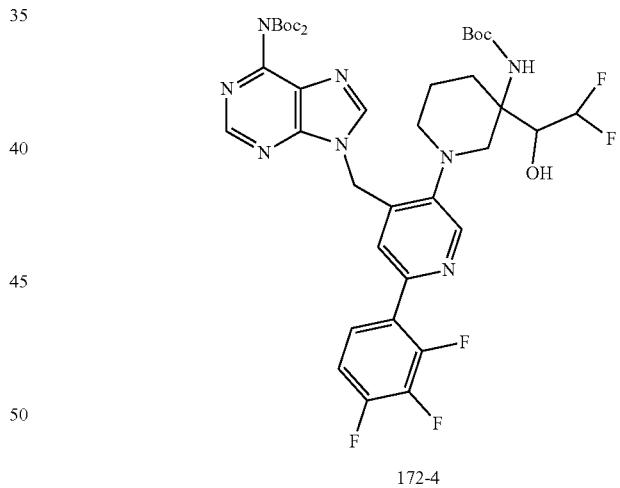

172-4 tert-butyl (tert-butoxycarbonyl)(9-((5-(3-((tert-butoxycarbonyl)amino)-3-(2,2-difluoro-1-hydroxyethyl)piperidin-1-yl)-2-(2,3,4-trifluorophenyl)pyridin-4-yl)methyl)-9H-purin-6-yl)carbamate (Intermediate 172-4) was obtained following analogous procedures described in Intermediate 170-4 from tert-butyl (3-(2,2-difluoro-1-hydroxyethyl)-1-(4-(hydroxymethyl)-6-(2,3,4-trifluorophenyl)pyridin-3-yl)piperidin-3-yl)carbamate (Intermediate 172-2). LC-MS: [M+H]$^+$=835.2.

Intermediate 174-3: tert-butyl (tert-butoxycarbonyl) (9-((5-(3-((tert-butoxycarbonyl)amino)-3-(2,2-difluoro-1-hydroxyethyl)piperidin-1-yl)-2-(4-fluoro-2-methoxyphenyl)pyridin-4-yl)methyl)-9H-purin-6-yl) carbamate

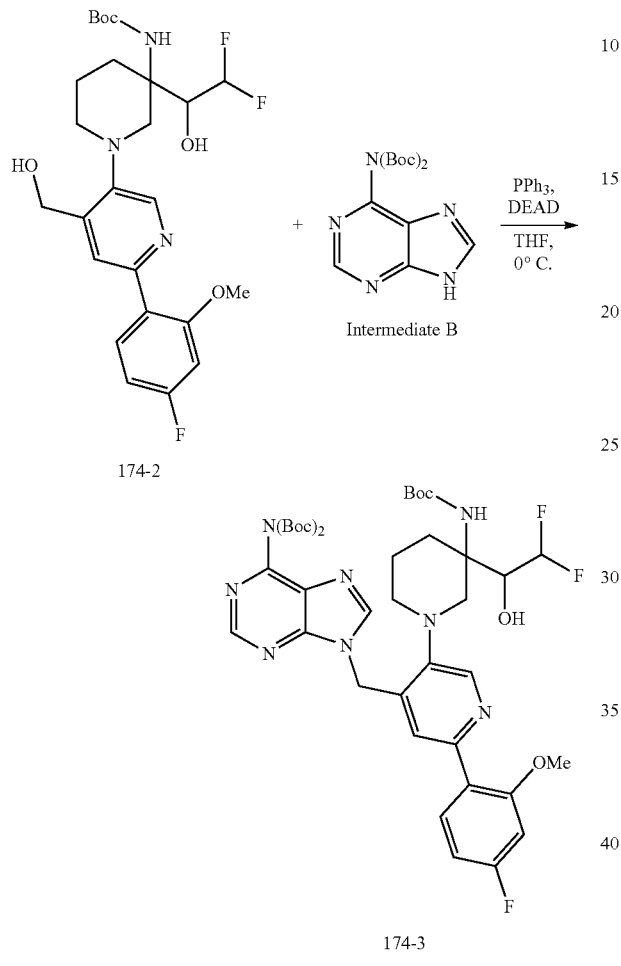

To a solution of tert-butyl (3-(2,2-difluoro-1-hydroxyethyl)-1-(6-(4-fluoro-2-methoxyphenyl)-4-(hydroxymethyl)pyridin-3-yl)piperidin-3-yl)carbamate (Intermediate 174-2) (310 mg, 0.61 mmol), Intermediate B (203 mg, 0.61 mmol) and PPh$_3$ (477 mg, 1.82 mmol) in THF (10 mL), was added DEAD (0.288 mL, 1.82 mmol) dropwise at 0° C., after addition the reaction mixture was stirred at RT for 0.5 hr under N$_2$ atmosphere. The reaction mixture was diluted with 20 ml of water, extracted with EtOAc (20 mL*3). The combined organic layers were washed with water (20 mL), brine (20 mL), concentrated to give a crude product. The crude product was purified by flash chromatography (elution gradient: 10% to 70% EtOAc in PE in 50 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(4-fluoro-2-methoxyphenyl)pyridin-4-yl)methyl)-9H-purin-6-yl)carbamate (Intermediate 174-3). LC-MS: [M+H]$^+$=829.2.

Intermediate 175-3: tert-butyl (tert-butoxycarbonyl) (9-((5-(3-((tert-butoxycarbonyl)amino)-3-(2,2-difluoro-1-hydroxyethyl)piperidin-1-yl)-6'-chloro-5'-fluoro-[2,2'-bipyridin]-4-yl)methyl)-9H-purin-6-yl) carbamate

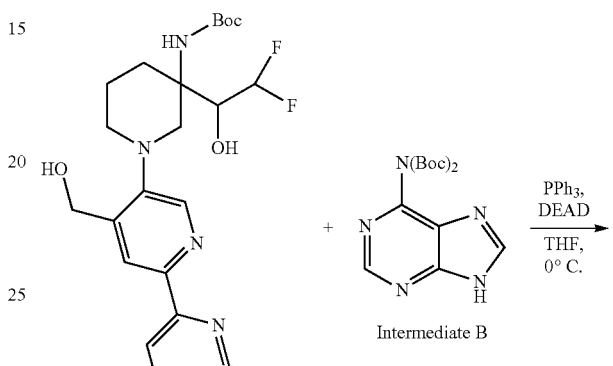

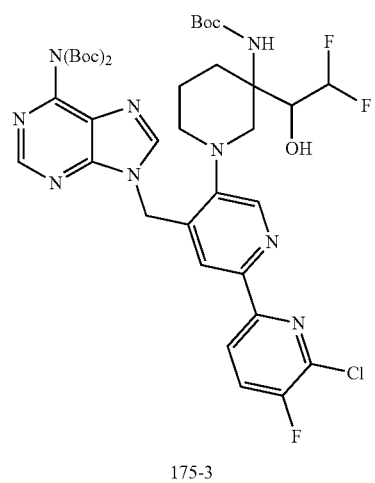

Tert-butyl (tert-butoxycarbonyl)(9-((5-(3-((tert-butoxycarbonyl)amino)-3-(2,2-difluoro-1-hydroxyethyl)piperidin-1-yl)-6'-chloro-5'-fluoro-[2,2'-bipyridin]-4-yl)methyl)-9H-purin-6-yl)carbamate (Intermediate 175-3) was obtained following procedures analogous to Intermediate 174-3. LC-MS: [M+H]$^+$=834.1.

Intermediate 177-4: Methyl (3-(6-methylpyridin-2-yl)piperidin-3-yl)carbamate hydrochloride Intermediates 177-5: Methyl 2-(3,4-difluorophenyl)-5-(3-((methoxycarbonyl)amino)-3-(6-methylpyridin-2-yl)piperidin-1-yl)isonicotinate Intermediate 177-6: Methyl (1-(6-(3,4-difluorophenyl)-4-(hydroxymethyl)pyridin-3-yl)-3-(6-methylpyridin-2-yl)piperidin-3-yl)carbamate Intermediate 177-7: tert-butyl (tert-butoxycarbonyl)(9-((2-(3,4-difluorophenyl)-5-(3-((methoxycarbonyl)amino)-3-(6-methylpyridin-2-yl)piperidin-1-yl)pyridin-4-yl)methyl)-9H-purin-6-yl)carbamate

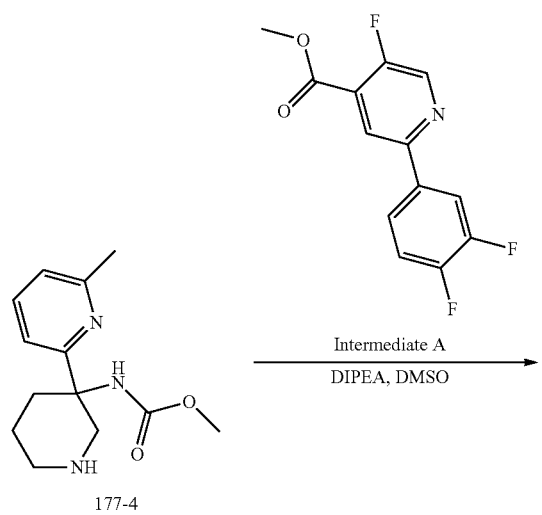

177-4

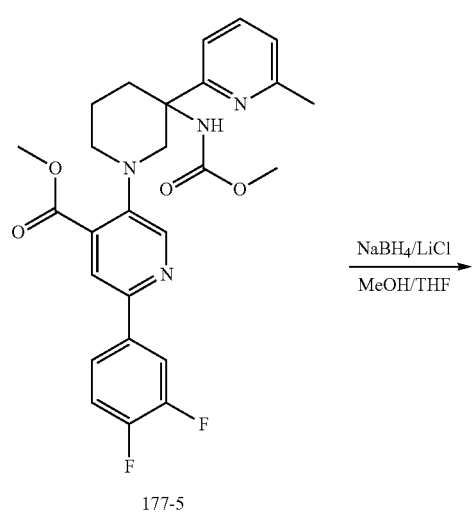

177-5

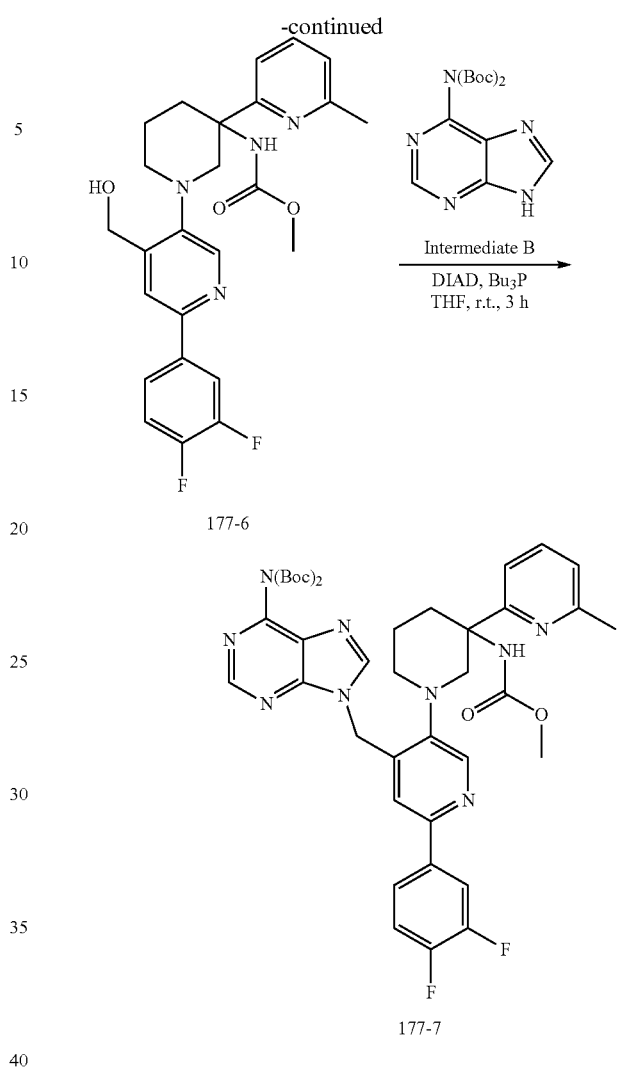

To a solution of tert-butyl 3-cyanopiperidine-1-carboxylate (3.00 g, 14.3 mmol, 1.0 eq.) and 2-fluoro-6-methylpyridine (1.66 g, 14.9 mmol, 1.05 eq.) in THF (30 mL) was added dropwise KHMDS (17 mL, 17 mmol, 1.2 eq., 1M in THF) at −70° C. under $N_2$ atmosphere. The resulting mixture was allowed to warm to 25° C. and stirred for 12 hours. The reaction was quenched with water (50 mL), and extracted with EtOAc (30 mL×3). The combined organic layers were dried over anhydrous $Na_2SO_4$, filtered and concentrated in vacuo. The residue was purified by combi flash (20% EtOAc in PE) to give tert-butyl 3-cyano-3-(6-methylpyridin-2-yl)piperidine-1-carboxylate (177-1). $^1$H NMR (400 MHz, $CDCl_3$) δ ppm 7.64 (t, J=7.6 Hz, 1H), 7.48 (d, J=7.6 Hz, 1H), 7.12 (d, J=8.0 Hz, 1H), 4.61-4.14 (m, 2H), 3.54-3.21 (m, 1H), 2.94-2.73 (m, 1H), 2.55 (s, 3H), 2.40-2.24 (m, 1H), 2.23-2.12 (m, 1H), 2.06-1.92 (m, 1H), 1.84-1.75 (m, 1H), 1.51 (s, 9H). LC-MS: [M+H]$^+$=302.0.

To a solution of tert-butyl 3-cyano-3-(6-methylpyridin-2-yl)piperidine-1-carboxylate (177-1) (2.70 g, 8.97 mmol, 1.0 eq.) in MeOH (30 mL) was added NaOH (10 mL, 1 M) and $H_2O_2$ (5 mL, 30%). The reaction mixture was stirred at 25° C. for 12 hours, quenched with sat·$Na_2SO_3$ (100 mL) and stirred at 25° C. for 1 hour. The resulting mixture was concentrated in vacuo to remove MeOH. The aqueous was extracted with EtOAc (1000 mL×3). The combined organic layers were dried over anhydrous $Na_2SO_4$, filtered and concentrated in vacuo. The residue was purified by silica gel (PE/EtOAc 5/1 to 1/1) to give tert-butyl 3-carbamoyl-3-(6-methylpyridin-2-yl)piperidine-1-carboxylate (177-2). $^1$H NMR (400 MHz, CDCl$_3$) δ ppm 7.54 (t, J=7.6 Hz, 1H), 7.34 (d, J=7.6 Hz, 1H), 7.03 (d, J=7.6 Hz, 1H), 5.48 (brs, 1H), 4.67-4.24 (m, 1H), 3.91-3.43 (m, 2H), 3.21-2.95 (m, 1H), 2.72-2.55 (m, 1H), 2.53 (s, 3H), 2.32-2.02 (m, 1H), 1.68-1.54 (m, 2H), 1.48 (s, 9H). LC-MS: [M+H]$^+$=320.1.

To a solution of tert-butyl 3-carbamoyl-3-(6-methylpyridin-2-yl)piperidine-1-carboxylate (177-2) (2.40 g, 7.51 mmol, 1.0 eq.) and KOH (1.05 g, 18.8 mmol, 2.5 eq.) in MeOH (30 mL) was added PhI(OAc)$_2$ (2.42 g, 7.51 mmol, 1.0 eq.) at 0° C. The resulting mixture was stirred at 25° C. for 16 hours. The reaction was concentrated in vacuo. The residue was purified by silica gel column (PE/EtOAc 10/1 to 3/1) to give tert-butyl 3-((methoxycarbonyl)amino)-3-(6-methylpyridin-2-yl)piperidine-1-carboxylate (177-3). $^1$H NMR (400 MHz, CDCl$_3$) δ ppm 7.55 (t, J=8.0 Hz, 1H), 7.26 (d, J=8.0 Hz, 1H), 7.01 (d, J=7.6 Hz, 1H), 4.31-3.98 (m, 2H), 3.62 (s, 3H), 3.14-2.82 (m, 1H), 2.53 (s, 3H), 2.48-2.09 (m, 1H), 1.82-1.67 (m, 2H), 1.66-1.57 (m, 1H), 1.50 (s, 9H). LC-MS: [M+H]$^+$=350.3.

To a mixture of tert-butyl 3-((methoxycarbonyl)amino)-3-(6-methylpyridin-2-yl)piperidine-1-carboxylate (177-3) (1.5 g, 4.30 mmol, 1.0 eq.) in DCM (10 mL) was added HCl/dioxane (10 mL, 4M), and the resulting mixture was stirred at 25° C. for 1 hour. The mixture was concentrated in vacuo to give methyl (3-(6-methylpyridin-2-yl)piperidin-3-yl)carbamate hydrochloride (Intermediate 177-4). $^1$H NMR (400 MHz, CD$_3$OD) δ ppm 8.48-8.39 (m, 1H), 7.92-7.78 (m, 2H), 4.33-4.25 (m, 1H), 4.09-4.01 (m, 1H), 3.68 (s, 3H), 3.50-3.39 (m, 1H), 3.30-3.17 (m, 1H), 2.91 (s, 3H), 2.44-2.31 (m, 1H), 2.30-2.14 (m, 2H), 2.06-1.94 (m, 1H). LC-MS: [M+H]$^+$=250.0.

To a solution of methyl (3-(6-methylpyridin-2-yl)piperidin-3-yl)carbamate hydrochloride (Intermediate 177-4) (1.22 g, 4.27 mmol, 1.0 eq.) in DMSO (10 mL) was added DIEA (3.86 g, 29.9 mmol, 7.0 eq.) and methyl 2-(3,4-difluorophenyl)-5-fluoroisonicotinate (Intermediate A) (1.14 g, 4.27 mmol, 1.0 eq.). The reaction mixture was stirred at 120° C. for 3 hours. The reaction mixture was diluted with water (100 mL) and extracted with EtOAc (20 mL×3). The combined organic layers were washed with brine (20 mL), dried over anhydrous sodium sulfate, filtered and concentrated in vacuo. The residue was purified by silica gel column chromatography (PE/EA 10/1 to 3/1) to give methyl 2-(3,4-difluorophenyl)-5-(3-((methoxycarbonyl)amino)-3-(6-methylpyridin-2-yl)piperidin-1-yl)isonicotinate (177-5). H NMR (400 MHz, CDCl$_3$) δ ppm 8.52 (s, 1H), 7.94 (s, 1H), 7.87-7.78 (m, 1H), 7.71-7.65 (m, 1H), 7.57 (t, J=7.6 Hz, 1H), 7.35 (d, J=8.0 Hz, 1H), 7.26 (d, J=7.6 Hz, 1H), 7.02 (d, J=7.6 Hz, 1H), 6.75 (brs, 1H), 4.09 (s, 3H), 3.67 (s, 3H), 3.49-3.34 (m, 2H), 3.12-2.95 (m, 2H), 2.86-2.74 (m, 1H), 2.54 (s, 3H), 2.40-2.28 (m, 1H), 2.16-1.98 (m, 1H), 1.86-1.81 (m, 1H). LC-MS: [M+H]$^+$=497.3.

To a mixture of methyl 2-(3,4-difluorophenyl)-5-(3-((methoxycarbonyl)amino)-3-(6-methylpyridin-2-yl)piperidin-1-yl)isonicotinate (177-5) (600 mg, 1.21 mmol, 1.0 eq.) and LiCl (512 mg, 12.1 mmol, 10 eq.) in MeOH/THF (20 mL, v/v=1/1) was added NaBH$_4$ (914 mg, 24.2 mmol, 20 eq.). The mixture was stirred at 25° C. for 1 hour. The reaction was quenched with water (50 mL), and extracted with EtOAc (20 mL×3). The combined organic layers were dried over Na$_2$SO$_4$ and concentrated in vacuo to give methyl (1-(6-(3,4-difluorophenyl)-4-(hydroxymethyl)pyridin-3-yl)-3-(6-methylpyridin-2-yl)piperidin-3-yl)carbamate (177-6). LC-MS: [M+H]$^+$=469.1.

To a solution of methyl (1-(6-(3,4-difluorophenyl)-4-(hydroxymethyl)pyridin-3-yl)-3-(6-methylpyridin-2-yl)piperidin-3-yl)carbamate (177-6) (500 mg, 1.07 mmol, 1.0 eq.), Intermediate B (537 mg, 1.60 mmol, 1.5 eq.) and Bu$_3$P (324 mg, 1.60 mmol, 1.5 eq.) in THF (10 mL) was added DIAD (324 mg, 1.60 mmol, 1.5 eq.). The mixture was stirred at 25° C. for 3 hours. The reaction was concentrated in vacuo and the residue was purified by silica gel column chromatography (Eluents: PE/EA 10/1 to 3:1) to give tert-butyl (tert-butoxycarbonyl)(9-((2-(3,4-difluorophenyl)-5-(3-((methoxycarbonyl)amino)-3-(6-methylpyridin-2-yl)piperidin-1-yl)pyridin-4-yl)methyl)-9H-purin-6-yl)carbamate (177-7). $^1$H NMR (400 MHz, CDCl$_3$) δ ppm 8.96 (s, 1H), 8.53 (s, 1H), 8.25 (s, 1H), 7.70-7.57 (m, 2H), 7.50-7.43 (m, 1H), 7.36 (d, J=8.0 Hz, 1H), 7.20-7.11 (m, 1H), 7.06 (d, J=8.4 Hz, 1H), 6.51 (s, 1H), 5.84 (d, J=15.6 Hz, 1H), 5.45 (d, J=15.2 Hz, 1H), 3.64-3.56 (m, 1H), 3.55 (s, 3H), 3.53-3.46 (m, 1H), 3.17-3.09 (m, 1H), 3.02-2.94 (m, 1H), 2.66-2.58 (m, 1H), 2.57 (s, 3H), 2.48-2.37 (m, 1H), 2.19-2.05 (m, 1H), 1.94-1.84 (m, 1H), 1.47 (s, 18H). LC-MS: [M+H]$^+$=786.3.

Intermediate 269-4: 3-(1-methyl-1H-pyrazol-4-yl)piperidin-3-amine

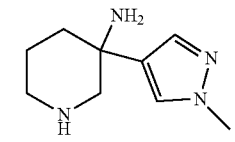

269-4

To a solution of 4-bromo-1H-pyrazole (10.0 g, 68 mmol, 1.0 eq) in DMF (100 mL) was added NaH (5.44 g, 136 mmol, 1.5 eq) at 10° C. After 30 min, MeI (15.0 g, 102 mmol, 2.0 eq) was added. The mixture was stirred at 30-35° C. for 2 hr, quenched with water (200 mL) and extracted with EtOAc (200 mL×3). The combined organic layer was dried over Na$_2$SO$_4$ and concentrated in vacuo to give 4-bromo-1-methyl-1H-pyrazole (269-1). $^1$H NMR (400 MHz, CDCl$_3$) δ ppm 7.43 (s, 1H), 7.37 (s, 1H), 3.88 (s, 3H).

To a solution of 4-bromo-1-methyl-1H-pyrazole (269-1) (10.6 g, 66.1 mmol, 1.1 eq) in THF (140 mL) was added n-BuLi (29.4 mL, 72.1 mmol, 1.2 eq, 2.5 M in THF) at −70° C. under N$_2$. After 30 min, a solution of benzyl 3-oxopiperidine-1-carboxylate (14.0 g, 60.1 mmol, 1.0 eq) in THF (10 mL) was added. The reaction was stirred at −70° C. for 2 hr. The reaction was quenched with water (200 mL), extracted with EtOAc (200 mL×3). The combined organic layer was dried over anhydrous Na$_2$SO$_4$ and concentrated in vacuo. The residue was purified by combi flash (70-90% EtOAc in PE) to give benzyl 3-hydroxy-3-(1-methyl-1H-pyrazol-4-yl)piperidine-1-carboxylate (269-2). LC-MS: [M+H]$^+$=316.1.

To a mixture of NaN$_3$ (1.3 g, 19 mmol, 2.0 eq.) in DCM (30 mL) was added TFA (6.00 g, 47.6 mmol, 5.0 eq) at 0° C. After 10 min, a solution of benzyl 3-hydroxy-3-(1-methyl-1H-pyrazol-4-yl)piperidine-1-carboxylate (intermediate 269-2) (3.00 g, 9.52 mmol, 1.0 eq.) in DCM (10 mL) was added. The resulting mixture was stirred at 30-35° C. for 16 hr. The reaction was quenched with NH$_3$·H$_2$O (3 mL), diluted with water (20 mL) and extracted with DCM (300 mL×3). The combined organic layers were dried over anhydrous Na$_2$SO$_4$ and concentrated in vacuo. The residue was purified by Combi Flash (40% EtOAc in PE) to give benzyl 3-azido-3-(1-methyl-1H-pyrazol-4-yl)piperidine-1-carboxylate (269-3). LC-MS: [M+H]⁺=341.1.

A mixture of benzyl 3-azido-3-(1-methyl-1H-pyrazol-4-yl)piperidine-1-carboxylate (269-3) (1.00 g, 2.9 mmol, 1.0 eq.) and Pd/C (100 mg, 10% wet) in EtOAc (10 mL) was stirred with H₂ balloon at 30-35° C. for 16 hr. The Pd/C was filtered off and the filtrate was concentrated in vacuo to give 3-(1-methyl-1H-pyrazol-4-yl)piperidin-3-amine (Intermediate 269-4).

Intermediate 269-6: methyl 2-(3,4-difluorophenyl)-5-(3-((methoxycarbonyl)amino)-3-(1-methyl-1H-pyrazol-4-yl)piperidin-1-yl)isonicotinate

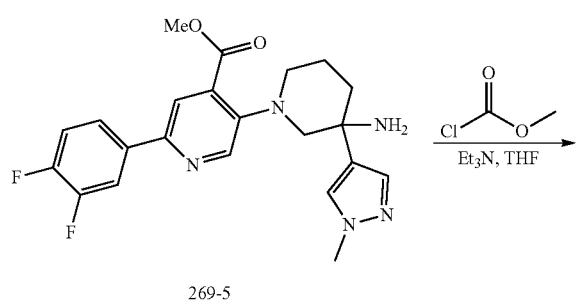

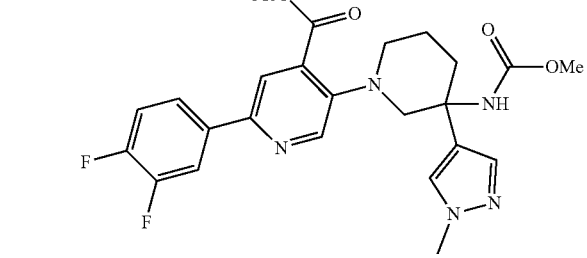

Methyl 5-(3-amino-3-(1-methyl-1H-pyrazol-4-yl)piperidin-1-yl)-2-(3,4-difluorophenyl)isonicotinate (Intermediate 269-5) was prepared following procedures analogous to the preparation of Intermediate 177-5 and corresponding intermediates. ¹H NMR (400 MHz, CDCl₃) δ ppm 8.46 (s, 1H), 7.88 (s, 1H), 7.75-7.85 (m, 1H), 7.65-7.70 (m, 1H), 7.53 (s, 1H), 7.50 (s, 1H), 7.15-7.25 (m, 1H), 3.97 (s, 3H), 3.89 (s. 3H), 3.10-3.30 (m, 3H), 2.90-3.00 (m, 1H), 2.05-2.15 (m, 1H), 1.65-1.90 (m, 3H).

To a solution of Intermediate 269-5 (500 mg, 1.17 mmol, 1.0 eq) and Et₃N (400 mg, 3.51 mmol, 3.0 eq) in THF (10 mL) was added methyl carbonochloridate (200 mg, 1.75 mmol, 1.5 eq) at 0° C. The reaction was stirred at 25-30° C. for 1 hr. The reaction was quenched with water (50 mL), extracted with EtOAc (50 mL×3). The combined organic layer was dried over Na₂SO₄ and concentrated in vacuo. The residue was purified by combi flash (60% EtOAc in PE) to give Intermediate 269-6. ¹H NMR (400 MHz, CDCl₃) δ ppm 8.51 (s, 1H), 7.95 (s, 1H), 7.80-7.90 (m, 1H), 7.60-7.70 (m, 1H), 7.40 (s, 1H), 7.35 (s, 1H), 7.15-7.25 (m, 1H), 6.66 (brs, 1H), 4.03 (s. 3H), 3.85 (s, 3H), 3.64 (s, 3H), 3.30-3.40 (m, 2H), 2.85-3.10 (m, 2H), 2.80 (d, J=12.0 Hz, 1H), 1.95-2.05 (m, 1H), 1.60-1.85 (m, 2H). LC-MS: [M+H]⁺= 486.3.

Intermediate 269-8: tert-butyl (tert-butoxycarbonyl) (1-((2-(3,4-difluorophenyl)-5-(3-((methoxycarbonyl) amino)-3-(1-methyl-1H-pyrazol-4-yl)piperidin-1-yl) pyridin-4-yl)methyl)-1H-imidazo[4,5-c]pyridin-4-yl) carbamate

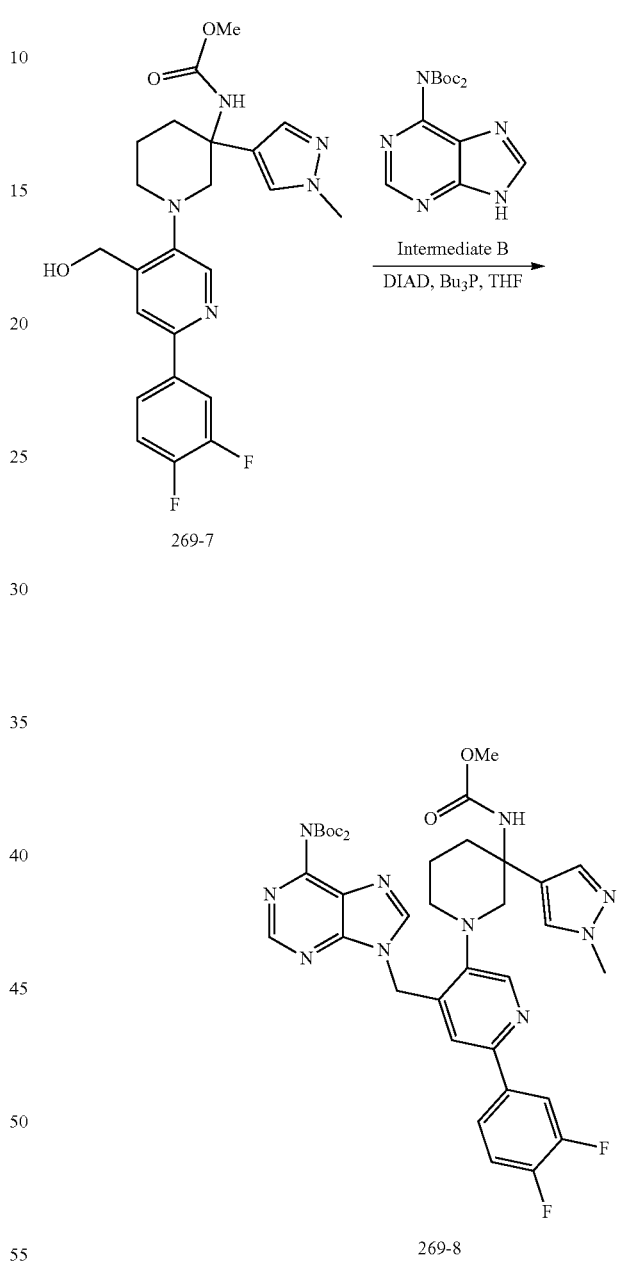

Methyl (1-(6-(3,4-difluorophenyl)-4-(hydroxymethyl) pyridin-3-yl)-3-(1-methyl-1H-pyrazol-4-yl)piperidin-3-yl) carbamate (Intermediate 269-7) was prepared following procedures analogous to the preparation of Intermediate 177-6 and corresponding intermediates. LC-MS: [M+H]⁺= 458.2.

Intermediate 269-8 was prepared by using a procedure similar to that of intermediate 177-7 in example 177 by replacing intermediate 177-6 with intermediate 269-7. LC-MS: [M+H]⁺=717.4.

Intermediate 271-7:
3-(pyridin-3-yl)piperidin-3-amine

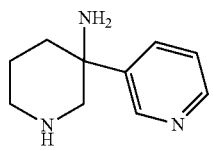

To a solution of nicotinaldehyde (17.85 g, 166.7 mmol, 1.0 eq.) in THF (250 mL) at −78° C. under N₂ atmosphere was added a solution of 3-butenylmagesium bromide (400 mL, 200 mmol, 0.5M, 1.2 eq.) dropwise. The reaction mixture was stirred at −78° C. for 2 h, quenched with saturated ammonium chloride solution (300 mL) and separated. The aqueous layer was extracted with ethyl acetate (100 mL*2). The combined organic layer was washed with brine (200 mL), dried over anhydrous sodium sulfate and concentrated in vacuo The residue was purified by Combi-flash (EA in PE: 30-50%) to give 1-(pyridin-3-yl)pent-4-en-1-ol (271-1). $^1$HNMR (CDCl₃ 400 MHz): δ 8.55 (d, J=1.6 Hz, 1H), 8.51 (dd, J=1.6 Hz and 4.8 Hz, 1H), 7.71 (dt, J=8.0 Hz and 2.0 Hz, 1H), 7.29 (dd, J=4.8 Hz and 8.0 Hz, 1H), 5.90-5.79 (m, 1H), 5.06 (dd, J=1.6 Hz and 17.2 Hz, 1H), 5.02 (dd, J=1.2 Hz and 10.4 Hz, 1H), 4.77 (dd, J=5.6 Hz and 8.0 Hz), 2.34 (brs, 1H), 2.24-2.10 (m, 2H), 1.98-1.88 (m, 1H), 1.86-1.77 (m, 1H).

To a solution of 1-(pyridin-3-yl)pent-4-en-1-ol (271-1) (10 g, 61.27 mmol, 1 eq) in CH₂Cl₂ (200 mL) was added Dess-Martin periodinane (38.98 g, 91.9 mmol, 1.5 eq) portionwise at 16-24° C., the suspension was stirred for 30 min at 16-24° C. The mixture was poured into a saturated sodium bicarbonate solution (300 mL) slowed and stirred for 30 min. The mixture was filtered and aqueous layer was extracted with CH₂Cl₂ (100 mL*2). The combined organic layer was washed with brine (100 mL), dried over anhydrous sodium sulfate and concentrated in vacuo. The residue was purified by Combi-flash (EA in PE: 20-30%) to give 1-(pyridin-3-yl)pent-4-en-1-one (271-2). $^1$HNMR (CDCl₃ 400 MHz): δ 9.18 (d, J=1.6 Hz, 1H), 8.78 (dd, J=1.6 Hz and 4.8 Hz, 1H), 8.23 (dt, J=8.0 Hz and 2.0 Hz, 1H), 7.43 (dd, J=4.8 Hz and 8.0 Hz, 1H), 5.94-5.84 (m, 1H), 5.12-5.06 (m, 1H), 5.05-5.01 (m, 1H), 2.10 (t, J=7.2 Hz, 2H), 2.55-2.48 (m, 2H).

To a mixture of 1-(pyridin-3-yl)pent-4-en-1-one (271-2) (8.64 g, 53.6 mmol, 1 eq) and 2-methylpropane-2-sulfinamide (12.99 g, 107.2 mmol, 2.0 eq) in anhydrous THF (120 ml) was added titanium ethoxide (30.57 g, 134.0 mmol, 2.5 eq), the reaction mixture was refluxed for 16 h at 80° C. The mixture was cooled to room temperature, poured into brine (300 ml) and stirred for 30 min. The mixture was filtered through a celite pad and the aqueous layer was extracted with ethyl acetate (200 mL*2). The combined organic layer was washed with brine (200 mL), dried over anhydrous sodium sulfate and concentrated. The residue was purified by Combi-flash (EA in PE: 20-30%) to give (E)-2-methyl-N-(1-(pyridin-3-yl)pent-4-en-1-ylidene)propane-2-sulfinamide (271-3). $^1$H NMR (CDCl₃ 400 MHz): δ 9.05 (s, 1H), 8.70 (dd, J=1.6 Hz and 4.8 Hz, 1H), 8.10 (d, J=7.6 Hz, 1H), 7.38 (dd, J=4.8 Hz and 8.0 Hz, 1H), 5.93-5.81 (m, 1H), 5.09-5.01 (m, 2H), 3.45-3.37 (m, 1H), 3.32-3.25 (m, 1H), 2.55-2.35 (m, 2H).

To a solution of (E)-2-methyl-N-(1-(pyridin-3-yl)pent-4-en-1-ylidene)propane-2-sulfinamide (271-3) (9.85 g, 37.3 mmol, 1 eq) in anhydrous THF (120 mL) at −78° C. was added a solution of vinylmagnesium bromide (90 mL, 90 mmol, 2.4 eq, 1M in Et₂O) dropwise, the resulting mixture was stirred for 2 h at −78° C. The reaction was quenched with saturated ammonium chloride (200 mL). The mixture was extracted with ethyl acetate (100 mL*3), the combined organic layer was washed with brine (100 ml), dried over anhydrous sodium sulfate and concentrated in vacuo. The residue was purified by Combi-flash (EA in PE: 30-70%) to give 2-methyl-N-(3-(pyridin-3-yl)hepta-1,6-dien-3-yl)propane-2-sulfinamide (271-4). $^1$H NMR (CDCl₃ 400 MHz): δ 8.89 (d, J=1.6 Hz, 1H), 8.53 (dd, J=1.6 Hz and 4.8 Hz, 1H), 7.82-7.78 (m, 1H), 7.29 (dd, J=4.8 Hz and 8.0 Hz, 1H), 6.03 (dd, J=10.8 Hz and 17.2 Hz, 1H), 5.87-5.78 (m, 1H), 5.37 (d, J=10.8 Hz, 1H), 5.30 (d, J=17.2 Hz, 1H), 5.05-4.96 (m, 2H), 3.75 (s, 1H), 2.43-2.35 (m, 1H), 2.26-2.18 (m, 1H), 2.07-1.97 (m, 2H), 1.24 (s, 9H).

To a solution of 2-methyl-N-(3-(pyridin-3-yl)hepta-1,6-dien-3-yl)propane-2-sulfinamide (271-4) (6.90 g, 23.6 mmol, 1.0 eq) in methanol (400 ml) at −78° C. was bubbled O₃ until the solution was blue. The excess O₃ was removed by N₂. The mixture was concentrated in vacuo to remove about 200 mL of methanol. Diphenylmethanylamine (6.48 g, 35.4 mmol, 1.5 eq), sodium cyanoborohydride (3.72 g, 59.0 mmol, 2.5 eq) and acetic acid (1.42 g, 23.6 mmol, 1.0 eq) were added to the above solution and the reaction mixture was stirred for 16 h at 11-17° C. The mixture was concentrated in vacuo, the residue was diluted with water (100 mL) and extracted with dichloromethane (100 ml*3). The combined organic layer was concentrated in vacuo, the residue was purified by Combi-flash (EA in PE: 30-100%) to give N-(1-benzhydryl-3-(pyridin-3-yl)piperidin-3-yl)-2-methylpropane-2-sulfinamide (271-6). $^1$H NMR (CDCl₃ 400 MHz): δ 8.57 (d, J=2.0 Hz, 1H), 8.47 (dd, J=1.6 Hz and 4.8 Hz, 1H), 7.64 (dt, J=8.0 Hz and 1.6 Hz, 1H), 7.40-7.37 (m, 4H), 7.33-7.28 (m, 4H), 7.25-7.20 (m, 3H), 5.53 (brs, 1H), 4.39 (s, 1H), 3.06-2.99 (m, 2H), 2.58 (d, J=12.8 Hz, 1H), 2.33-2.25 (m, 1H), 2.09-2.01 (m, 1H), 1.96-1.89 (m, 2H), 1.77-1.73 (m, 1H), 1.28 (s, 9H). LC-MS: M+H]⁺=448.2.

To a solution of N-(1-benzhydryl-3-(pyridin-3-yl)piperidin-3-yl)-2-methylpropane-2-sulfinamide (271-6) (2.34 g, 5.23 mmol, 1.0 eq.) in TFA (24 mL) was added Et₃SiH (4.68 mL), the reaction mixture was stirred for 16 h at 80° C. The mixture was concentrated in vacuo, the residue was diluted with water (50 mL) and extracted with ethyl acetate (30 mL*2) to remove impurities. The aqueous layer was neutralized with sodium hydroxide and concentrated in vacuo to give crude 3-(pyridin-3-yl)piperidin-3-amine (Intermediate 217-7). LC-MS: [M+H]⁺=177.9.

Intermediate 271-9: (5-(3-amino-3-(pyridin-3-yl)piperidin-1-yl)-2-(3,4-difluorophenyl)pyridin-4-yl)methanol

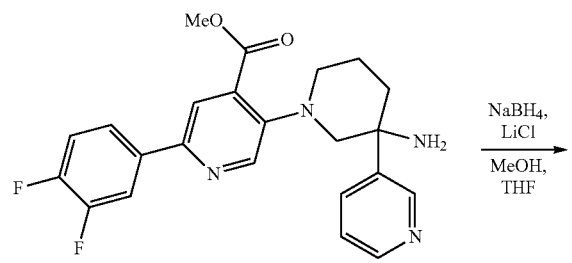

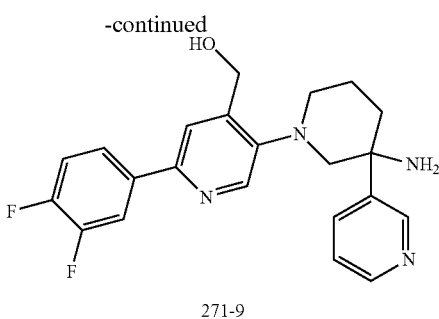

271-9

Methyl 5-(3-amino-3-(pyridin-3-yl)piperidin-1-yl)-2-(3,4-difluorophenyl)isonicotinate (Intermediate 271-8) was prepared following procedures analogous to the preparation of Intermediate 177-5 and corresponding intermediates. $^1$H NMR (CDCl$_3$ 400 MHz): δ 8.90 (d, J=2.0 Hz, 1H), 8.54 (dd, J=1.6 Hz and 4.8 Hz, 1H), 8.46 (s, 1H), 7.98 (dt, J=8.0 Hz and 1.6 Hz, 1H), 7.88 (s, 1H), 7.85-7.79 (m, 1H), 7.69-7.66 (m, 1H), 7.30 (dd, J=4.8 Hz and 8.0 Hz, 1H), 7.24-7.19 (m, 1H), 3.97 (s, 3H), 3.34-3.23 (m, 3H), 2.97 (td, J=12 Hz and 2.4 Hz, 1H), 2.21-2.15 (m, 1H), 2.08 (dt, J=12.8 Hz and 4.4 Hz, 1H), 1.88-1.84 (m, 1H), 1.82-1.76 (m, 1H). LC-MS: [M+H]$^+$=425.2.

Intermediate 271-9 was prepared by using a procedure similar to that of intermediate 177-6 in Example 177 by replacing intermediate 177-5 with intermediate 271-8. $^1$H NMR (CDCl$_3$ 400 MHz): δ 8.81 (d, J=2.0 Hz, 1H), 8.52 (dd, J=1.6 Hz and 4.8 Hz, 1H), 8.41 (s, 1H), 7.88 (dt, J=8.0 Hz and 1.6 Hz, 1H), 7.85-7.79 (m, 1H), 7.71 (s, 1H), 7.69-7.66 (m, 1H), 7.30 (dd, J=4.8 Hz and 8.0 Hz, 1H), 7.25-7.18 (m, 1H), 4.92 (d, J=14 Hz, 1H), 4.73 (d, J=14 Hz, 1H), 3.20 (t, J=11.6 Hz, 2H), 3.09 (d, J=11.6 Hz, 1H), 3.01-2.94 (m, 1H), 2.14-2.08 (m, 2H), 1.92-1.87 (m, 2H). LC-MS: [M+H]$^+$=397.3.

Intermediate 272-2: 1-Benzyl 3-methyl 2-oxopiperidine-1,3-dicarboxylate

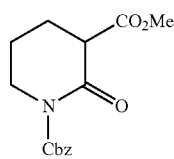

272-2

To a solution of piperidin-2-one (10 g, 100 mmol, 1.0 eq) in dry THF (200 mL) was added portions NaH (6 g, 60% wt, 150 mmol, 1.5 eq) below 0° C. The resulting mixture was stirred at 0° for 0.5 h and 30° C. for 1 h. Then a solution of benzyl carbonochloridate (26 g, 151.31 mmol, 1.5 eq) in dry THF (50 mL) was added into the suspension below 0° C. over 30 min, The resulting mixture was stirred at 30° C. for 3 h. The reaction was quenched by Sat. NH$_4$Cl (50 mL), extracted with EtOAc (50 mL×2). The combined organic layers were washed with brine (50 mL) and dried over Na$_2$SO$_4$. After filtration and concentration, the residue was purified by silica gel chromatography to give benzyl 2-oxopiperidine-1-carboxylate (272-1). $^1$H NMR (CDCl$_3$, 400 MHz): δ ppm 7.45-7.32 (m, 5H), 5.28 (s, 2H), 3.78-3.70 (m, 2H), 2.56-2.50 (m, 2H), 1.86-1.80 (m, 4H).

To a solution of benzyl 2-oxopiperidine-1-carboxylate (272-1) (9.1 g, 39.1 mmol, 1.0 eq) in dry THF (200 mL) was added LDA (30 mL, 2M, 60 mmol, 1.54 eq) below −70° C. over 30 min under N$_2$. After stirring for 1 h at −70°, methyl carbonochloridate (6.23 g, 65.93 mmol, 1.69 eq) was added into the mixture below −70° C. over 30 min. The resulting mixture was stirred at −70° C. for 1 h. The reaction mixture was quenched by Sat. NH$_4$Cl (50 mL) below −70° C. The mixture was extracted with EtOAc (100 mL×3). The combined organic layers were washed with brine (100 mL) and dried over Na2SO4. After filtration and concentration, the residue was purified by inversed phase chromatography to give 1-benzyl 3-methyl 2-oxopiperidine-1,3-dicarboxylate (Intermediate 272-2). $^1$H NMR (400 MHz, CDCl$_3$) δ ppm 7.45-7.32 (m, 2H), 5.29 (s, 2H), 3.80-3.79 (d, J=5.2 Hz, 1H), 3.77 (s, 3H), 3.76-3.74 (d, J=7.6 Hz, 1H), 3.58-3.54 (dd, J=6.8 Hz, J=8.0 Hz, 1H), 2.30-2.16 (m, 1H), 2.14-2.06 (m, 2H), 2.02-1.93 (m, 1H).

Intermediate 272-3: (2-methoxypyridin-3-yl)boronic acid

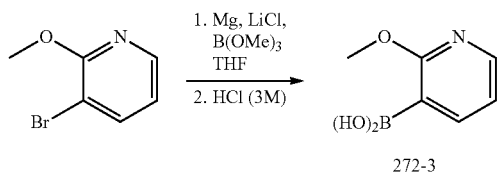

272-3

A suspension 3-bromo-2-methoxypyridine (9 g, 47.87 mmol, 1.0 eq), Mg (2.33 g, 95.73 mmol, 2.0 eq) and LiCl (2.54 g, 59.83 mmol, 1.25 eq) in dry THF (200 mL) was stirred at 35° C. for 2 hours under N$_2$. Then B(OMe)$_3$ (10 g, 96.23 mmol, 2.01 eq) was added into the reaction mixture below 0° C. Then resulting mixture was allowed to warm to 35° C. with stirring for 2 hours. The reaction was quenched with HCl (0.1M, 200 mL) to pH=6. The mixture was extracted with EtOAc (100 mL×3). The combined organic layers were washed with brine (100 mL) and dried over Na$_2$SO$_4$. After filtration and concentration, the residue was washed with chloroform (10 mL) to give (2-methoxypyridin-3-yl)boronic acid (Intermediate 272-3). $^1$H NMR (400 MHz, DMSO-d$_6$) δ ppm 8.19-8.17 (dd, J$_1$=2.0 Hz, J$_2$=4.8 Hz, 1H), 7.89-7.88 (d, J=2.0 Hz, 1H), 3.98-6.95 (dd, J$_1$=4.8 Hz, J$_2$=6.8 Hz, 1H), 3.87 (s, 3H).

Intermediate 272-5: 1-Benzyl 3-methyl 3-(2-methoxypyridin-3-yl)-2-oxopiperidine-1,3-dicarboxylate

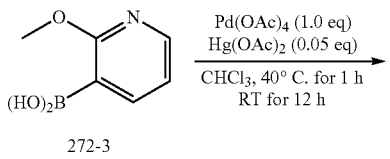

272-3

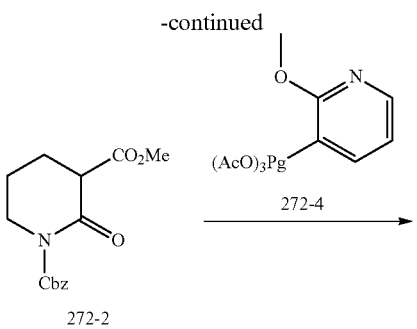

To a suspension of Pb(OAc)₄ (6.38 g, 14.39 mmol, 1.0 eq) and Hg(OAc)₂ (1.17 g, 3.67 mmol, 0.26 eq) in chloroform (20 mL) was added (2-methoxypyridin-3-yl)boronic acid (272-3) (2.2 g, 14.38 mmol. 1.0 eq) at 30° C. under N₂. The suspension was stirred at 40° C. for 1 hour and 30° for 16 hours under N₂. The reaction mixture of (2-methoxypyridin-3-yl)plumbanetriyl triacetate (272-4) was used in the next step directly. Then a solution of 1-benzyl 3-methyl 2-oxopiperidine-1,3-dicarboxylate (272-2) (3.9 g, 13.23 mmol, 0.93 eq) in chloroform (20 mL) and pyridine (3 mL) was added into the suspension. The resulting mixture was stirred at 40° C. for 12 hours under N₂. LC-MS showed intermediate 272-4 was consumed. The reaction mixture was cooled to room temperature and filtrated. The filtrate was washed with H₂SO₄ (1 M, 20 mL×4), water (20 mL×2) and dried over Na₂SO₄. After filtration and concentration, the residue was purified by Prep-HPLC (FA) to give 1-benzyl 3-methyl 3-(2-methoxypyridin-3-yl)-2-oxopiperidine-1,3-dicarboxylate (Intermediate 272-5). $^1$H NMR (400 MHz, CDCl₃) δ ppm 8.12-8.11 (m, 1H), 7.45-7.44 (m, 2H), 7.40-7.31 (m, 4H), 6.88-6.85 (m, 1H), 5.33 (s, 2H), 3.91 (s, 3H), 3.88-3.85 (m, 1H), 3.79 (s, 3H), 3.76-3.69 (m, 1H), 2.66-2.60 (m, 1H), 2.56-2.50 (m, 1H), 1.90-1.82 (m, 1H), 1.77-1.68 (m, 1H). LC-MS: [M+H]⁺=398.9.

Intermediate 272-10: Methyl (3-(2-methoxypyridin-3-yl)piperidin-3-yl)carbamate

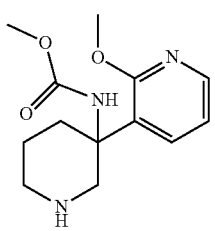

To a solution of 1-benzyl 3-methyl 3-(2-methoxypyridin-3-yl)-2-oxopiperidine-1,3-dicarboxylate (Intermediate 272-5) (1.7 g, 4.27 mmol, 1.0 eq) in dry THF (50 mL) and dry THF (50 mL) was added NaBH₄ (0.3 g, 7.93 mmol, 1.86 eq) below 0° C. After addition, the reaction mixture was allowed to stir at 30° C. for 2 hours. Then Pd/C (0.45 g, 0.427 mmol, 0.1 eq) was added into the mixture, the resulting mixture was stirred at 30° C. under H₂ (15 Psi) for 12 hours. The mixture was filtered, the filtrate was concentrated under reduced pressure to afford methyl 3-(2-methoxypyridin-3-yl)piperidine-3-carboxylate (272-6).

To a solution of methyl 3-(2-methoxypyridin-3-yl)piperidine-3-carboxylate (272-6) (2.2 g, 8.79 mmol, 1.0 eq) and Boc₂O (5.75 g, 26.37 mmol, 3.0 eq) in MeOH (10 mL) was stirred at 30° C. for 16 hours. The reaction mixture was concentrated, and the residue was purified by silica gel chromatography to give 1-(tert-butyl) 3-methyl 3-(2-methoxypyridin-3-yl)piperidine-1,3-dicarboxylate (272-7). $^1$H NMR (400 MHz, CDCl₃) δ ppm 8.08-8.07 (d, J=4.0 Hz, 1H), 7.63-7.61 (dd, J₁=1.6 Hz, J₂=8.6 Hz, 1H), 6.90-6.86 (dd, J₁=5.2 Hz, J₂=7.6 Hz, 1H), 4.15-4.10 (m, 1H), 3.92 (s, 3H), 3.82-3.66 (m, 2H), 3.61 (s, 3H), 3.22 (m, 1H), 2.23-2.19 (m, 2H), 1.71 (m, 4H), 1.32 (s, 9H). LC-MS: [M+H]⁺=351.0.

A solution of 1-(tert-butyl) 3-methyl 3-(2-methoxypyridin-3-yl)piperidine-1,3-dicarboxylate (272-7) (0.85 g, 2.43 mmol, 1.0 eq) and LiOH (0.233 g, 9.70 mmol, 4.0 eq) in MeOH (10 mL) and H₂O (2 mL) was heated to 40° C. with stirring for 2 hours and 80° C. for 4 hours. The reaction mixture was concentrated, the residue was acidified with HCl (2N) to pH=3-4. The mixture was extracted with chloroform/i-PrOH (v/v=3:1, 10 mL×4). The combined organic layers were washed with water (10 mL) and dried over Na₂SO₄. The mixture was filteredans the filtrate was concentrated to give 1-(tert-butoxycarbonyl)-3-(2-methoxypyridin-3-yl)piperidine-3-carboxylic acid (272-8). $^1$H NMR (400 MHz, CD₃OD) δ ppm 8.05-8.04 (d, J=3.2 Hz, 1H), 7.75-7.73 (dd, J₁=1.6 Hz, J₂=7.2 Hz, 1H), 6.96 (s, 1H), 4.14-4.10 (m, 1H), 4.10-3.89 (m, 4H), 3.62-3.58 (m, 1H), 3.30-3.28 (m, 1H), 2.33-2.28 (m, 2H), 1.83-1.79 (m, 2H), 1.27 (s, 9H).

To a solution of 1-(tert-butoxycarbonyl)-3-(2-methoxypyridin-3-yl)piperidine-3-carboxylic acid (272-8) (0.8 g, 2.38 mmol, 1.0 eq) in dry toluene (20 mL) was added DPPA (1.31 g, 4.76 mmol, 2.0 eq) and TEA (0.963 g, 9.51 mmol, 4.0 eq) in turns at 28° C. under N₂. The mixture was stirred at 80° C. for 12 hours. Then MeOH (20 mL) was added into the mixture and the mixture was stirred at 80° C. for 12 hours. The mixture was concentrated under reduced pressure and the residue was purified by silica gel chromatography to tert-butyl 3-((methoxycarbonyl)amino)-3-(2-methoxypyridin-3-yl)piperidine-1-carboxylate (272-9). $^1$H NMR (400 MHz, CDCl₃) δ ppm 8.098.074 (dd, J₁=2.0 Hz, J₂=5.2 Hz, 1H), 7.67-7.64 (dd, J₁=1.6 Hz, J₂=7.6 Hz, 1H), 6.92-6.88 (dd, J₁=4.8 Hz, J₂=7.6 Hz, 1H), 5.78-5.49 (m, 1H), 4.72-4.68 (d, 13.6 Hz, 1H), 3.99 (s, 3H), 3.53 (s, 3H), 2.98-2.80 (m, 3H), 1.91-1.71 (m, 4H), 1.83 (s, 9H).

To a solution of tert-butyl 3-((methoxycarbonyl)amino)-3-(2-methoxypyridin-3-yl)piperidine-1-carboxylate (272-9) (0.6 g, 1.64 mmol, 1.0 eq) in dry DCM (5 mL) was added TFA (1 mL) below 0° C. After addition, the mixture was allowed to warm to 30° C. with stirring for 3 hours. The mixture was concentrated under reduced pressure to methyl (3-(2-methoxypyridin-3-yl)piperidin-3-yl)carbamate (Intermediate 272-10). LC-MS: [M+H]⁺=266.2.

Intermediate 272-13: tert-butyl (tert-butoxycarbonyl)(9-((2-(3,4-difluorophenyl)-5-(3-((methoxycarbonyl)amino)-3-(2-methoxypyridin-3-yl)piperidin-1-yl)pyridin-4-yl)methyl)-9H-purin-6-yl)carbamate

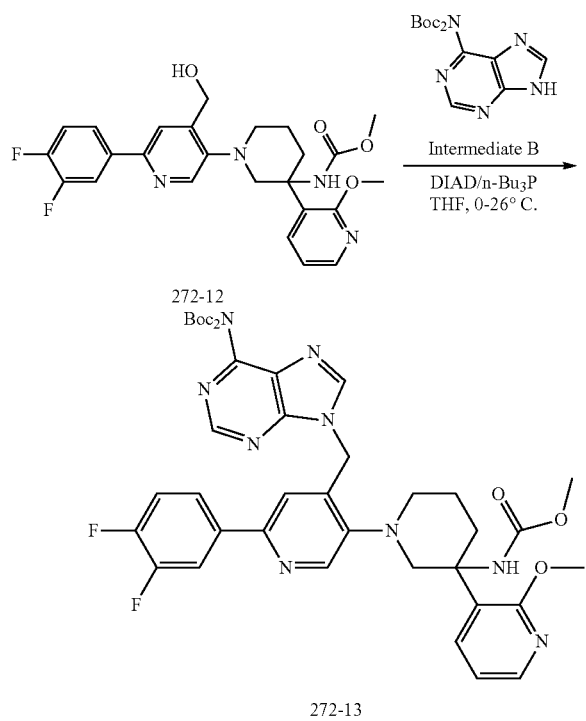

Intermediate 272-13 was prepared following procedures analogous to the preparation of Intermediate 177-7 and corresponding intermediates. $^1$H NMR (400 MHz, CDCl$_3$) δ ppm 8.93 (s, 1H), 8.50 (s, 1H), 8.27 (s, 1H), 8.14-8.12 (dd, J$_1$=1.6 Hz, J$_2$=5.2 Hz, 1H), 7.77-7.75 (dd, J$_1$=1.6 Hz, J$_2$=7.6 Hz, 1H), 7.70-7.64 (m, 1H), 7.48-7.46 (m, 1H), 7.20-7.13 (dd, J$_1$=5.2 Hz, J$_2$=7.6 Hz, 1H), 6.60 (s, 1H), 5.89-5.85 (d, J=15.6 Hz, 1H), 5.43-5.39 (d, J=15.6 Hz, 1H), 4.04-4.01 (m, 1H), 3.98 (s, 3H), 3.49 (s, 3H), 3.36-3.34 (m, 1H), 3.14-3.11 (m, 1H), 2.94-2.84 (m, 2H), 2.21-2.18 (m, 2H), 1.88-1.85 (m, 1H), 1.47 (s, 18H). LC-MS: [M+H]$^+$=802.5.

Intermediate 273-5a: tert-Butyl 3-cyano-3-(1-(difluoromethyl)-1H-pyrazol-3-yl)piperidine-1-carboxylate

Intermediate 273-5b: tert-Butyl 3-cyano-3-(1-(difluoromethyl)-1H-pyrazol-5-yl)piperidine-1-carboxylate

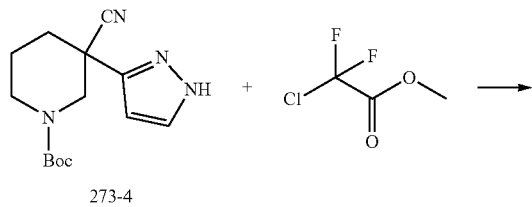

-continued

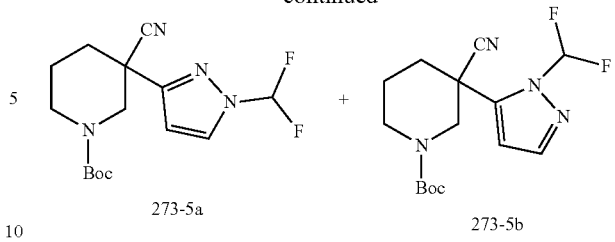

To a solution of tert-butyl 3-cyanopiperidine-1-carboxylate (25 g, 119.0 mmol, 1.0 eq.) in THF (300 mL) at −70° C. under N$_2$ atmosphere was added LiHMDS (178 mL, 178.57 mmol, 1.5 eq.) dropwise. The reaction mixture was stirred at −70° C. for 30 min, then CH$_3$CHO (7.85 g, 178.57 mmol, 3 eq.) was added. The reaction was quenched with aq·NH$_4$Cl (200 mL), extracted with EtOAc (100 mL*3). The combined organic layer was washed with brine (200 mL), dried over anhydrous sodium sulfate, filtered and concentrated. The residue was purified by Combi-flash (EtOAc in PE, 10-50%) to give tert-butyl 3-cyano-3-(1-hydroxyethyl)piperidine-1-carboxylate (273-1). $^1$H NMR (CDCl$_3$ 400 MHz): δ ppm 4.39-4.05 (m, 2H), 3.75-3.68 (m, 2H), 2.94-2.76 (m, 2H), 2.39-2.20 (m, 1H), 1.94-1.70 (m, 4H), 1.47 (s, 9H), 1.39 (t, J=6.4 Hz, 3H).

To a solution of tert-butyl 3-cyano-3-(1-hydroxyethyl)piperidine-1-carboxylate (273-1) (9 g, 35.43 mmol, 1.0 eq.) in DCM (150 mL) was added DMP (22.5 g, 53.15 mmol, 1.5 eq.). The mixture was stirred at 20° C. for 1 hour. The reaction was quenched with aq·NaHCO$_3$ (150 mL) and aq·Na$_2$SO$_3$ (150 mL), extracted with EtOAc (150 mL*3). The combined organic layers were washed with aq·NaHCO$_3$ (150 mL), dried over anhydrous sodium sulfate, filtered and concentrated to give crude tert-butyl 3-acetyl-3-cyanopiperidine-1-carboxylate (273-2). $^1$H NMR (CDCl$_3$ 400 MHz): δ 4.50-3.85 (m, 2H), 3.20-3.05 (m, 1H), 2.95-2.60 (m, 1H), 2.46 (s, 3H), 2.25-1.70 (m, 4H), 1.48 (s, 9H).

To a solution of tert-butyl 3-acetyl-3-cyanopiperidine-1-carboxylate (273-2) (12 g, 47.62 mmol, 1.0 eq.) in toluene (100 mL) was added DMF-DMA (28.3 g, 238.1 mmol, 5.0 eq.). The reaction was heated to 100° C. and stirred for 2 h. LC-MS showed a main product. The reaction was concentrated to give tert-butyl (E)-3-cyano-3-(3-(dimethylamino)acryloyl)piperidine-1-carboxylate (273-3). LCMS: [M+H]$^+$= 308.0.

A mixture of tert-butyl (E)-3-cyano-3-(3-(dimethylamino)acryloyl)piperidine-1-carboxylate (273-3) (5.6 g, 18.22 mmol) in EtOH (30 mL), was added hydrazine hydrate (8.85 mL, 182 mmol), then the mixture was stirred at 70° C. for 8 hr under Ar atmosphere. Water (50 ml) was added, the mixture was extracted with EtOAc, the combined organic phase was worked up under aqueous conditions and concentrated in vacuo. The residue was purified by flash chromatography (PE/EA, EA: 40% for 30 mins) to give tert-butyl 3-cyano-3-(1H-pyrazol-3-yl)piperidine-1-carboxylate (273-4). $^1$H NMR (400 MHz, CDCl$_3$) δ ppm 7.63 (d, J=2.0 Hz, 1H), 6.39 (d, J=2.8 Hz, 1H), 4.56-4.46 (m, 1H), 4.25-4.07 (m, 1H), 3.20 (d, J=12.0 Hz, 1H), 2.80-2.90 (m, 1H), 2.37 (d, J=13.2 Hz, 1H), 2.10-1.91 (m, 2H), 1.77 (d, J=11.0 Hz, 1H), 1.48 (s, 9H).

To a solution of tert-butyl 3-cyano-3-(1H-pyrazol-3-yl)piperidine-1-carboxylate (273-4) (500 mg, 1.809 mmol) and Cs$_2$CO$_3$ (2948 mg, 9.05 mmol) in DMF (10 mL), was added methyl 2-chloro-2,2-difluoroacetate (523 mg, 3.62 mmol) dropwise, and the reaction mixture was stirred at 60° C. for 24 hr. The reaction mixture was diluted with ammonium chloride solution, and the mixture was extracted with ethyl acetate. The organic layer was dried over sodium sulfate, and concentrated in vacuum, the residue was purified by flash chromatography (PE/EA, EA: 40% for 30 mins) to give tert-butyl 3-cyano-3-(1-(difluoromethyl)-1H-pyrazol-3-yl)piperidine-1-carboxylate (Intermediate 273-5a) and tert-butyl 3-cyano-3-(1-(difluoromethyl)-1H-pyrazol-5-yl)piperidine-1-carboxylate (Intermediate 273-5b). LC-MS: [M-100]⁺=227.1.

Intermediate 273-11: tert-Butyl tert-butoxycarbonyl (9-((5-(3-(1-(difluoromethyl)-1H-pyrazol-3-yl)-3-((methoxycarbonyl)amino)piperidin-1-yl)-2-(4-fluorophenyl)pyridin-4-yl)methyl)-9H-purin-6-yl) carbamate

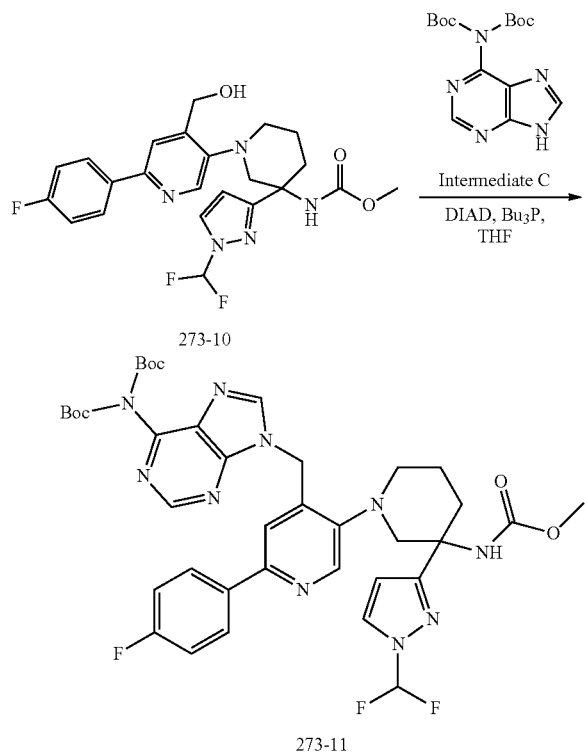

Intermediate 273-11 was prepared following procedures analogous to the preparation of Intermediate 177-7 and corresponding intermediates. LC-MS: [M+H]⁺=792.3.

Intermediate 281-7: Benzyl 3-carbamoyl-3-(2-chlorothiazol-4-yl)piperidine-1-carboxylate

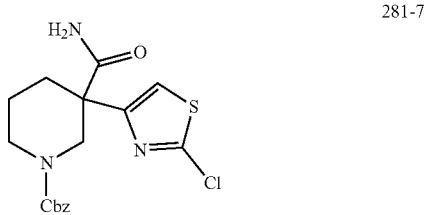 [SMILES: NC(=O)C1(c2csc(Cl)n2)CCCN(C(=O)OCc2ccccc2)C1]

A solution of 1-benzyl 3-methyl piperidine-1,3-dicarboxylate (20 g, 72.12 mmol, 1.0 eq) in THF (120 mL) was cooled to −78° C. and a solution of LiHMDS (108.18 mL, 108.18 mmol, 1.5 eq) was added dropwise over 20 minutes, and then stirred at −78° C. for 30 minutes, followed by the addition of CH₃CHO (3.81 g, 86.54 mmol, 1.2 eq). The resulting mixture was then stirred at 32° C. for 1 hour. The mixture was quenched with saturated NH₄Cl solution (150 mL), extracted with EtOAc (200 mL*3). The combined organic phase was washed with brine (400 mL), dried over anhydrous sodium sulfate, filtered and concentrated. The crude was purified by flash column (Petroleum ether:EtOAc=9:1-5:1) to give 1-benzyl 3-methyl 3-(1-hydroxyethyl)piperidine-1,3-dicarboxylate (281-1). ¹H NMR (CDCl₃ 400 MHz): δ 7.36-7.28 (m, 5H), 5.12 (s, 2H), 4.04-3.92 (m, 1H), 3.84-3.77 (m, 1H), 3.66-3.46 (m, 4H), 3.29-3.20 (m, 1H), 3.11-2.92 (m, 1H), 2.09-1.99 (m, 1H), 1.84-1.79 (m, 1H), 1.70-1.63 (m, 1H), 1.54-1.36 (m, 1H), 1.16 (d, J=6.4 Hz, 3H).

To a mixture of 1-benzyl 3-methyl 3-(1-hydroxyethyl)piperidine-1,3-dicarboxylate (281-1) (17 g, 52.9 mmol, 1.0 eq.) in CH₂Cl₂ (300 mL) was added Dess-Martin reagent (29.2 g, 68.8 mmol, 1.3 eq) in portions over 10 minutes at 0° C. Then, the mixture was stirred at 32° C. for 2 hours. The mixture was quenched with saturated NaHCO₃ solution (300 mL) and stirred for 30 minutes until pH to 8, diluted with CH₂Cl₂ (300 mL), continued to stir for 30 minutes, filtered, separated and concentrated the organic phase. The crude was purified by flash column (Petroleum ether:EtOAc=10:1) to give 1-benzyl 3-methyl 3-acetylpiperidine-1,3-dicarboxylate (281-2). ¹H NMR (CDCl₃ 400 MHz): 6.7.34-7.28 (m, 5H), 5.11 (s, 2H), 4.20-3.16 (m, 7H), 2.28-1.84 (m, 5H), 1.76-1.59 (m, 2H).

To a solution of 1-benzyl 3-methyl 3-acetylpiperidine-1,3-dicarboxylate (intermediate 281-2) (15.0 g, 46.9 mmol, 1.0 eq.) in MeOH (200 mL) was added Br₂ (2.6 ml, 51.67 mmol, 1.1 eq) in portions over 5 minutes. The resulting mixture was stirred at 60° C. for 1.5 hours. The mixture was concentrated and the crude was diluted with EtOAc (300 mL), washed with saturated Na₂SO₃ solution (300 mL), dried over anhydrous sodium sulfate, filtered and concentrated to give 1-benzyl 3-methyl 3-(2-bromoacetyl)piperidine-1,3-dicarboxylate (281-3). LCMS: [M+H]⁺=399.9.

To a mixture of 1-benzyl 3-methyl 3-(2-bromoacetyl) piperidine-1,3-dicarboxylate (281-3) (16 g, 32.14 mmol, 1.0 eq) and thiourea (4.89 g, 64.28 mmol, 2.0 eq) in EtOH (200 mL) was added NaHCO₃ (5.40 g, 64.28 mmol, 2.0 eq). The resulting mixture was heated at 90° C. for 1.5 hours with stirring, and the mixture was concentrated in vacuum. The residue was dissolved in EtOAc (300 mL), washed with saturated brine (300 mL*3), dried over anhydrous sodium sulfate, filtered and concentrated. The crude was purified by flash column (petroleum ether:EtOAc=8:1-1:1) to give 1-benzyl 3-methyl 3-(2-aminothiazol-4-yl)piperidine-1,3-dicarboxylate (281-4). ¹H NMR (CDCl₃ 400 MHz): 6.7.41-7.30 (m, 5H), 6.41-6.23 (m, 1H), 5.53-5.47 (m, 2H), 5.16 (s, 2H), 4.36-4.09 (m, 2H), 3.77-3.68 (m, 1H), 3.62-3.59 (m, 3H), 3.54-3.48 (m, 1H), 3.37-3.18 (m, 1H), 2.40-2.25 (m, 2H), 2.12-2.01 (m, 1H), 1.61-1.55 (m, 2H).

To a solution of 1-benzyl 3-methyl 3-(2-aminothiazol-4-yl)piperidine-1,3-dicarboxylate (281-4) (5 g2, 13.32 mmol2, 1.0 eq) in CH₃CN (50 mL) was added CuCl (3.30 g, 33.29 mmol, 2.5 eq) and heated to 60° C., followed by the addition of t-BuONO (3.43 g, 33.29 mmol, 2.5 eq) in portions over 5 minutes. The resulting mixture was then stirred at 80° C. under nitrogen for 1 hour. The mixture was cooled to 30° C., diluted with water (50 mL), extracted with EtOAc (60 ml*3), and the organic phase was washed with brine (200 mL), dried over anhydrous sodium sulfate, filtered and concentrated. Two batches with same scale was carried out and combined. The crude was purified by flash column (Petroleum ether:EtOAc=15:1~5:1) to give 1-benzyl 3-methyl 3-(2-chlorothiazol-4-yl)piperidine-1,3-dicarboxylate (281-5). ¹H NMR (DMSO-d6 400 MHz): δ. 7.57 (s, 1H), 7.37-7.31 (m, 5H), 5.07 (s, 2H), 4.28-4.13 (m, 1H), 3.69-3.63 (m, 1H), 3.55 (s, 3H), 3.58-3.51 (m, 1H), 3.28-3.18 (m, 1H), 2.32-2.27 (m, 1H), 2.12-2.02 (m, 1H), 1.61-1.42 (m, 2H).

To a solution of 1-benzyl 3-methyl 3-(2-chlorothiazol-4-yl)piperidine-1,3-dicarboxylate (281-5) (7.0 g, 17.73 mmol, 1.0 eq) in MeOH/H₂O (80 mL/10 mL) was added LiOH·H₂O (7.4 g, 177.27 mmol, 10.0 eq) and the resulting mixture was stirred at 30° C. for 2.0 hours. The mixture was acidified with 2N HCl to pH 5-6, diluted with water (40 mL), extracted with EtOAc (80 mL*3). The combined organic phase was washed with brine (250 mL), dried over anhydrous sodium sulfate, filtered and concentrated to give 1-((benzyloxy)carbonyl)-3-(2-chlorothiazol-4-yl)piperidine-3-carboxylic acid (281-6). LCMS: [M+Na]⁺=403.0.

To a solution of 1-((benzyloxy)carbonyl)-3-(2-chlorothiazol-4-yl)piperidine-3-carboxylic acid (281-6) (5.6 g, 14.70 mmol, 1.0 eq) and NH₄Cl (1.57 g, 29.41 mmol, 2.0 eq) in DMF (60 mL) was added DIEA (7.60 g, 58.82 mmol, 4.0 eq) and HATU (11.18 g, 29.41 mmol, 2.0 eq). The resulting mixture was stirred at 30° C. for 1 hour and the desired MS was observed by LC-MS. The mixture was diluted with water (40 mL), extracted with EtOAc (80 mL*3). The combined organic phase was washed with brine (200 mL*5), dried over anhydrous sodium sulfate, filtered and concentrated. The crude was purified by flash column (Petroleum ether:EtOAc=5:1~1:1) to give benzyl 3-carbamoyl-3-(2-chlorothiazol-4-yl)piperidine-1-carboxylate (Intermediate 281-7). ¹H NMR (DMSO-d₆ 400 MHz): δ. 7.44-7.31 (m, 6H), 7.13 (s, 1H), 7.01 (s, 1H), 5.06 (s, 2H), 4.07-4.03 (m, 1H), 3.78-3.63 (m, 1H), 3.58-3.46 (m, 1H), 3.18 (br s, 1H), 2.33-2.25 (m, 1H), 2.13-2.08 (m, 1H), 1.61-1.46 (m, 1H), 1.40-1.29 (m, 1H).

Intermediate 281-10: Methyl 5-(3-(2-chlorothiazol-4-yl)-3-((methoxycarbonyl)amino)piperidin-1-yl)-2-(4-fluorophenyl)isonicotinate

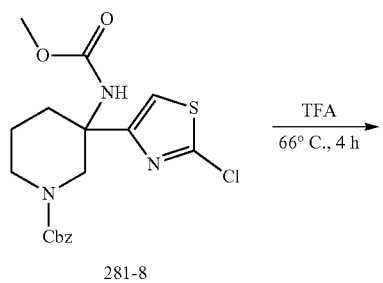

281-8

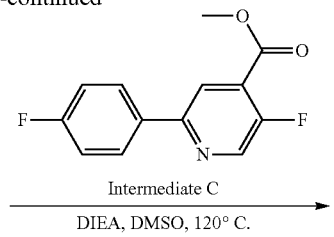

281-9

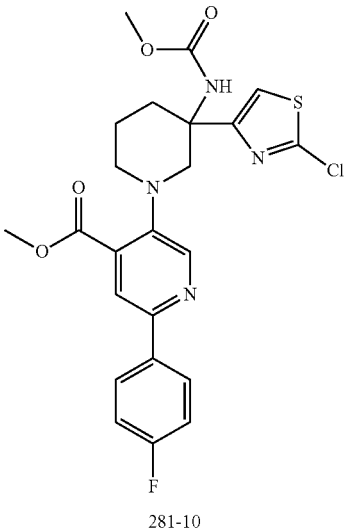

281-10

Benzyl 3-(2-chlorothiazol-4-yl)-3-((methoxycarbonyl)amino)piperidine-1-carboxylate (Intermediate 281-8) was prepared following procedures analogous to the preparation of Intermediate 177-3 and corresponding intermediates. ¹H NMR (CDCl₃ 400 MHz): δ. 7.37-7.30 (m, 5H), 7.18-7.07 (m, 1H), 5.44-5.11 (m, 3H), 4.23-4.08 (m, 1H), 3.92-3.89 (m, 1H), 3.74-3.56 (m, 4H), 3.14 (t, J=10.4 Hz, 1H), 2.71-2.50 (m, 1H), 2.25-2.12 (m, 1H), 1.71-1.65 (m, 1H), 1.60-1.49 (m, 1H).

A solution of benzyl 3-(2-chlorothiazol-4-yl)-3-((methoxycarbonyl)amino)piperidine-1-carboxylate (Intermediate 281-8) (1.5 g, 3.66 mmol, 1.0 eq) in TFA (12.0 mL) was stirred at 66° C. for 4.0 hours. The mixture was concentrated in vacuo and the residue was dissolved in EtOAc (20 mL), washed with saturated NaHCO₃ solution (40 mL*3), dried over anhydrous sodium sulfate, filtered and concentrated to give methyl (3-(2-chlorothiazol-4-yl)piperidin-3-yl)carbamate (281-9).

To a solution of methyl (3-(2-chlorothiazol-4-yl)piperidin-3-yl)carbamate (281-9) (1.3 g, 3.63 mmol, 1.0 eq) and Intermediate C (903.7 mg, 3.63 mmol, 1.0 eq) in DMSO (20 mL) was added DIEPA (1.87 g, 14.51 mmol, 4.0 eq). The reaction mixture was stirred at 120° C. for 12 hours. The desired MS was observed by LCMS. The mixture was cooled to 30° C., diluted with water (20 mL), extracted with EtOAc (30 mL*3). The organic phase was washed with brine (60 mL*3), dried over anhydrous sodium sulfate, filtered and concentrated. The crude was purified by flash column (Petroleum ether:EtOAc=15:1~6:1) to give methyl 5-(3-(2-chlorothiazol-4-yl)-3-((methoxycarbonyl)amino)piperidin-1-yl)-2-(4-fluorophenyl)isonicotinate (Intermediate 281-10). ¹H NMR (CDCl₃ 400 MHz): δ. 8.53 (s, 1H), 7.97 (s, 1H), 7.96-7.92 (m, 2H), 7.18-7.12 (m, 3H), 6.82 (brs, 1H), 4.04 (s, 3H), 3.66 (s, 3H), 3.50 (d, J=12.4 Hz, 1H), 3.32 (d, J=10.0 Hz, 1H), 3.10-2.98 (m, 2H), 2.93-2.84 (m, 1H), 2.06-1.95 (m, 2H), 1.87-1.76 (m, 1H).

Intermediate 281-12: tert-Butyl (tert-butoxycarbonyl)(9-((5-(3-(2-chlorothiazol-4-yl)-3-((methoxycarbonyl)amino)piperidin-1-yl)-2-(4-fluorophenyl)pyridin-4-yl)methyl)-9H-purin-6-yl)carbamate

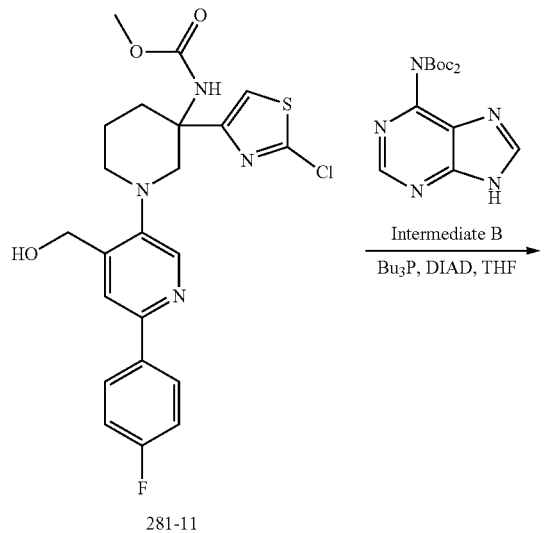

281-11

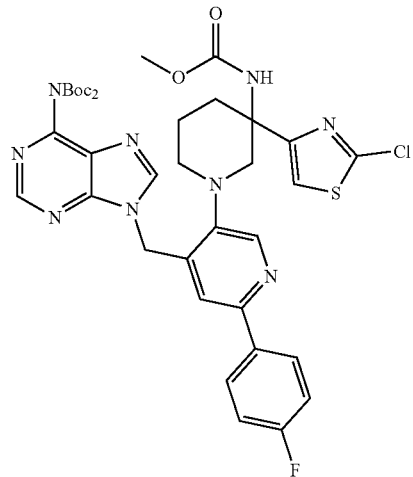

281-12

Methyl (3-(2-chlorothiazol-4-yl)-1-(6-(4-fluorophenyl)-4-(hydroxymethyl)pyridin-3-yl)piperidin-3-yl)carbamate (Intermediate 281-11) was prepared following procedures analogous to the preparation of Intermediate 177-6. ¹H NMR (CDCl₃ 400 MHz): δ. 8.45 (s, 1H), 7.94-7.90 (m, 2H), 7.64 (s, 1H), 7.15-7.11 (m, 3H), 7.15-7.10 (m, 2H), 5.75 (brs, 1H), 4.89-4.78 (m, 2H), 3.63 (s, 3H), 3.60-3.56 (m, 1H), 3.30-3.26 (m, 1H), 3.15-3.11 (m, 1H), 2.99-2.92 (m, 1H), 2.60-2.57 (m, 1H), 2.14-2.07 (m, 1H), 2.00-1.93 (m, 1H), 1.85-1.79 (m, 1H).

Intermediate 281-12 was prepared following procedures analogous to the preparation of Intermediate 177-7 and corresponding intermediates. LCMS: [M+H]⁺=794.4

Intermediate 282-4: 1-Benzyl 3-methyl 3-(2H-1,2,3-triazol-4-yl)piperidine-1,3-dicarboxylate

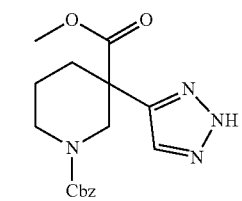

282-4

To a solution of 1-benzyl 3-methyl piperidine-1,3-dicarboxylate (30 g, 108 mmol, 1.0 eq) in THF (350 mL) was added LiHMDS (163 mL, 163 mmol, 1.5 eq) dropwise at −65° C. under N₂ atmosphere. After stirred for 30 min, paraformaldehyde (9.72 g, 324 mmol, 3.0 eq) was added. The reaction suspension was stirred at 13-23° C. for 1 hour. The reaction was quenched with water (300 mL), extracted with EtOAc (300 mL*3), washed with brine (500 mL*2). The combined organic layer was dried over Na₂SO₄, filtered and concentrated in vacuo. The residue was purified by CombiFlash (20-40% EtOAc in PE) to give 1-benzyl 3-methyl 3-(hydroxymethyl)piperidine-1,3-dicarboxylate (282-1). ¹H NMR (400 MHz, CDCl₃) δ ppm 7.40-7.26 (m, 5H), 5.15 (s, 2H), 4.06-3.80 (m, 1H), 3.75-3.60 (m, 6H), 3.50-3.25 (m, 1H), 3.15-2.85 (m, 1H), 1.84-1.71 (m, 1H), 1.70-1.62 (m, 1H), 1.61-1.50 (m, 2H). LC-MS: [M+H]⁺= 308.0.

To a solution of 1-benzyl 3-methyl 3-(hydroxymethyl) piperidine-1,3-dicarboxylate (282-1) (13.4 g, 43.6 mmol, 1.0 eq.) in dry DCM (150 mL) was added DMP (36.97 g, 87.21 mmol, 2.0 eq.) portion-wise at 0° C. The resulting mixture was stirred at 11-20° C. for 2 hours. The mixture was poured into saturated NaHCO₃ solution (300 mL) and extracted with DCM (300 mL*3), washed with NaHCO₃ aq. (400 mL*2), dried over Na₂SO₄, concentrated. The residue was purified by flash chromatography (PE/EA=80/20) to give 1-benzyl 3-methyl 3-formylpiperidine-1,3-dicarboxylate (282-2). ¹H NMR (400 MHz, CDCl₃) δ ppm 9.69-9.53 (m, 1H), 7.43-7.28 (m, 5H), 5.14 (s, 2H), 4.42-4.04 (m, 1H), 3.86-3.55 (m, 5H), 3.35-3.11 (m, 1H), 2.28-1.90 (m, 2H), 1.73-1.54 (m, 2H).

To a solution of 1-benzyl 3-methyl 3-formylpiperidine-1,3-dicarboxylate (282-2) (6.5 g, 21.29 mmol, 1.0 eq.) and comp dimethyl (1-diazo-2-oxopropyl)phosphonateound (8.17 g, 42.58 mmol, 2.0 eq.) in dry methanol (120 mL) was added K₂CO₃ (8.8 g, 63.87 mmol, 3.0 eq.). The mixture was stirred at 15-22° C. for 16 hours. The mixture was concentrated. The residue was purified by flash chromatography (PE/EA=60/40) to give 1-benzyl 3-methyl 3-ethynylpiperidine-1,3-dicarboxylate (282-3). ¹H NMR (400 MHz, CDCl₃) δ ppm 7.41-7.29 (m, 5H), 5.15 (s, 2H), 4.21-4.07 (m, 1H), 4.00-3.82 (m, 1H), 3.75 (s, 3H), 3.54-3.41 (m, 1H), 3.14-2.99 (m, 1H), 2.26-2.17 (m, 1H), 2.10-1.82 (m, 3H), 1.92-1.83 (m, 1H), 1.68-1.58 (m, 1H).

To a solution of 1-benzyl 3-methyl 3-ethynylpiperidine-1,3-dicarboxylate (intermediate 282-3) (4 g, 13.27 mmol, 1.0 eq.) in DMF/MeOH (40 mL/4 mL), TMSN₃ (2.3 g, 19.91 mmol. 1.5 eq.) was added. The mixture was stirred at 100-110° C. for 16 hours, diluted with water (100 mL), extracted with EA (100 mL*4), washed with brine (100 mL*3), dried over Na₂SO₄, filtered and concentrated to give crude compound, which was purified by CombiFlash (DCM/

MeOH=10/1) to give 1-benzyl 3-methyl 3-(2H-1,2,3-triazol-4-yl)piperidine-1,3-dicarboxylate (Intermediate 282-4). LC-MS: [M+H]⁺=345.0.

Intermediate 282-5a: 1-benzyl 3-methyl 3-(2-methyl-2H-1,2,3-triazol-4-yl)piperidine-1,3-dicarboxylate Intermediate 282-5b: 1-benzyl 3-methyl 3-(1-methyl-1H-1,2,3-triazol-4-yl)piperidine-1,3-dicarboxylate

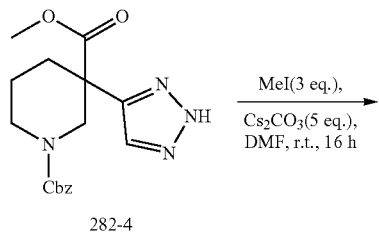

282-4

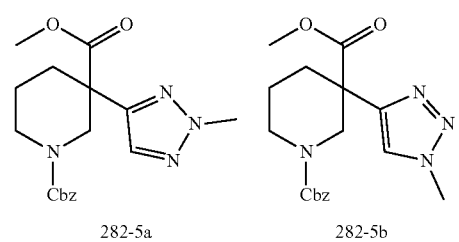

282-5a      282-5b

To a solution of 1-benzyl 3-methyl 3-(2H-1,2,3-triazol-4-yl)piperidine-1,3-dicarboxylate (intermediate 282-4) (3.3 g, 9.58 mmol, 1.0 eq.) in DMF (40 mL), Cs₂CO₃ (15.6 g, 47.9 mmol. 5 eq.) and MeI (9.3 g, 28.74 mmol, 3 eq.) were added. The mixture was stirred at 13-18° C. for 16 hours. The mixture was filtered and the filtrate was concentrated to give crude compound, which was purified by pre-HPLC to give 1-benzyl 3-methyl 3-(2-methyl-2H-1,2,3-triazol-4-yl) piperidine-1,3-dicarboxylate (Intermediate 282-5a) and 1-benzyl 3-methyl 3-(1-methyl-1H-1,2,3-triazol-4-yl)piperidine-1,3-dicarboxylate (Intermediate 282-5b).

Intermediate 282-5a: ¹H NMR (400 MHz, CD₃OD) δ ppm 7.63-7.47 (m, 1H), 7.44-7.27 (m, 5H), 5.15-5.07 (m, 2H), 4.40-4.15 (m, 1H), 4.09 (s, 3H), 3.90-3.70 (m, 1H), 3.60 (brs, 4H), 3.48-3.32 (m, 1H), 2.38 (brs, 1H), 2.26-2.10 (m, 1H), 1.70-1.55 (m, 2H). LC-MS: [M+H]⁺=359.3.

Intermediate 282-5b: ¹H NMR (400 MHz, CD₃OD) δ ppm 7.81 (s, 1H), 7.44-7.27 (m, 5H), 5.12 (s, 2H), 4.48-4.04 (m, 1H), 4.00 (s, 3H), 3.94-3.82 (m, 0.6H), 3.73-3.43 (m, 2H), 3.60 (s, 3H), 3.28-3.17 (m, 0.4H), 2.48-2.10 (m, 2H), 1.82-1.47 (m, 2H).

Intermediate 282-6: 1-((Benzyloxy)carbonyl)-3-(1-methyl-1H-1,2,3-triazol-4-yl)piperidine-3-carboxylic acid

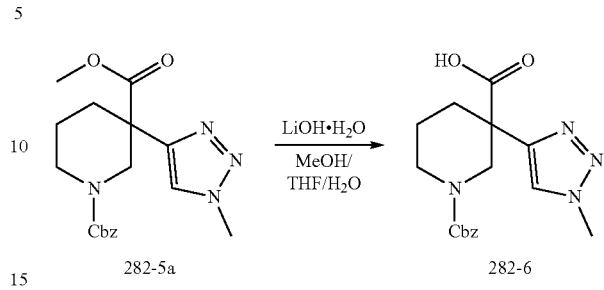

282-5a      282-6

Intermediate 282-6 was prepared by using a procedure similar to that of intermediate 281-6 in Example 281 by replacing intermediate 281-5 with intermediate 282-5a. LC-MS: [M+H]⁺=345.4.

Intermediate 282-7: Benzyl 3-carbamoyl-3-(1-methyl-1H-1,2,3-triazol-4-yl)piperidine-1-carboxylate

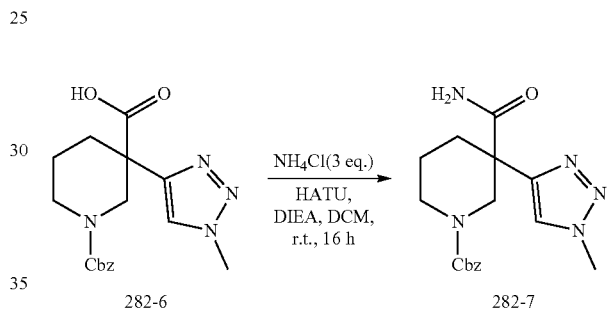

282-6      282-7

Intermediate 282-7 was prepared by using a procedure similar to that of intermediate 281-7 in Example 281 by replacing intermediate 281-6 with intermediate 282-6. LC-MS: [M+H]⁺=344.1.

Intermediate 282-8: Benzyl 3-((methoxycarbonyl)amino)-3-(1-methyl-1H-1,2,3-triazol-4-yl)piperidine-1-carboxylate

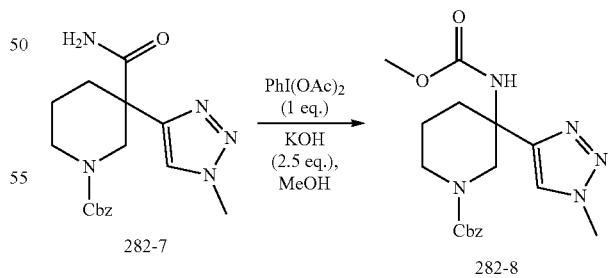

282-7      282-8

Intermediate 282-8 was prepared by using a procedure similar to that of intermediate 177-3 in Example 177 by replacing intermediate 177-3 with intermediate 281-7. ¹H NMR (400 MHz, CDCl₃) δ ppm 7.64-7.30 (m, 6H), 5.29-5.10 (m, 2H), 4.09-3.71 (m, 6H), 3.57 (s, 3H), 3.30 (brs, 1H), 2.69-2.45 (m, 1H), 2.37-2.15 (m, 1H), 1.82-1.65 (m, 1H), 1.55-1.45 (m, 1H). LC-MS: [M+H]⁺=374.1.

Intermediate 282-9: Methyl (3-(1-methyl-1H-1,2,3-triazol-4-yl)piperidin-3-yl)carbamate

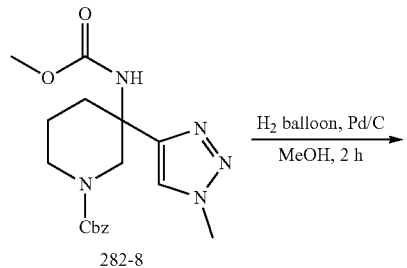

Intermediate 282-9 was prepared by using a procedure similar to that of intermediate 269-4 in Example 269 by replacing intermediate 269-3 with intermediate 281-8. $^1$H NMR (400 MHz, CD$_3$OD) δ ppm 7.81 (s, 1H), 4.06 (s, 3H), 3.56 (s, 3H), 3.40-3.32 (m, 1H), 3.13-2.89 (m, 2H), 2.71-2.62 (m, 1H), 2.39 (d, J=13.6 Hz, 1H), 2.08-1.99 (m, 1H), 1.79-1.66 (m, 1H), 1.57-1.47 (m, 1H).

Intermediate 282-10: Methyl 2-(3,4-difluorophenyl)-5-(3-((methoxycarbonyl)amino)-3-(1-methyl-1H-1,2,3-triazol-4-yl)piperidin-1-yl)isonicotinate

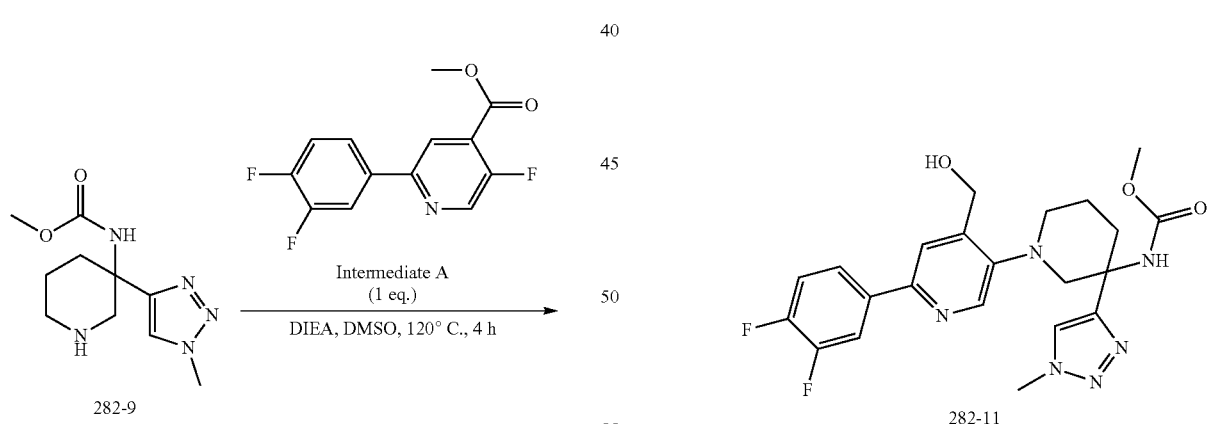

Intermediate 282-10 was prepared by using a procedure similar to that of intermediate 177-5 in example 177 by replacing intermediate 177-4 with intermediate 282-9. $^1$H NMR (400 MHz, CDCl$_3$) δ ppm 8.56 (s, 1H), 7.98 (s, 1H), 7.87-7.81 (m, 12 Hz, 1H), 7.72-7.67 (m, 1H), 7.64 (s, 1H), 7.27-7.20 (m, 1H), 6.87 (brs, 1H), 4.07 (s, 3H), 4.03 (s, 3H), 3.72-3.68 (m, 0.5H), 3.66 (s, 3H), 3.60-3.50 (m, 0.5H), 3.35 (d, J=11.2 Hz, 1H), 3.18 (d, J=12.4 Hz, 1H), 3.10 (td, J=11.6 Hz, 2.8 Hz, 1H), 2.94 (d, J=11.2 Hz, 1H), 2.09-1.70 (m, 3H). LC-MS: [M+H]$^+$=487.5.

Intermediate 282-11: methyl (1-(6-(3,4-difluorophenyl)-4-(hydroxymethyl)pyridin-3-yl)-3-(1-methyl-1H-1,2,3-triazol-4-yl)piperidin-3-yl)carbamate

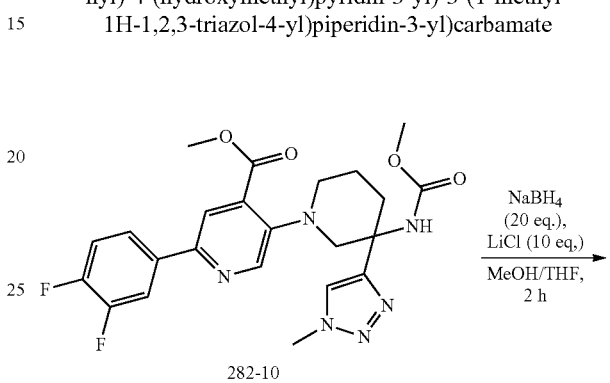

Intermediate 282-11 was prepared by using a procedure similar to that of intermediate 177-6 in example 177 by replacing intermediate 177-5 with intermediate 282-10. $^1$H NMR (400 MHz, CDCl$_3$) δ ppm 8.46 (s, 1H), 7.86-7.80 (m, 1H), 7.70-7.66 (m, 1H), 7.65 (s, 1H), 7.57 (s, 1H), 7.25-7.19 (m, 1H), 5.75 (brs, 1H), 4.85-4.77 (m, 2H), 4.08 (s, 3H), 3.95 (brs, 1H), 3.62 (s, 3H), 3.69-3.52 (m, 1H), 3.42 (d, J=11.2 Hz, 1H), 3.13 (d, J=11.6 Hz, 1H), 3.03-2.94 (m, 1H), 2.64-2.52 (m, 1H), 2.25-2.10 (m, 1H), 2.02-1.94 (m, 1H), 1.85-1.77 (m, 1H). LC-MS: [M+H]$^+$=459.1.

Intermediate 282-12: tert-Butyl (tert-butoxycarbonyl)(9-((2-(3,4-difluorophenyl)-5-(3-((methoxycarbonyl)amino)-3-(1-methyl-1H-1,2,3-triazol-4-yl)piperidin-1-yl)pyridin-4-yl)methyl)-9H-purin-6-yl)carbamate

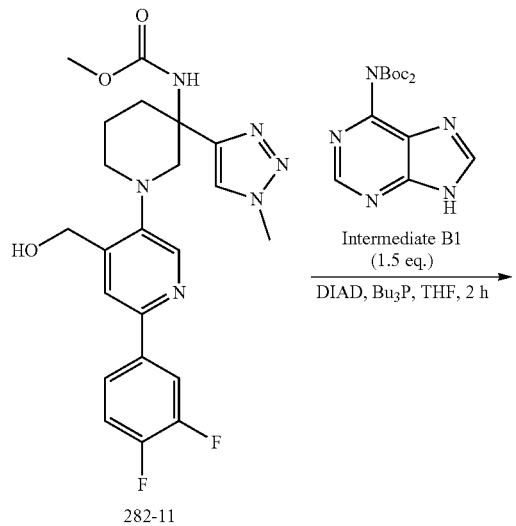

Intermediate B1 (1.5 eq.)
DIAD, Bu₃P, THF, 2 h

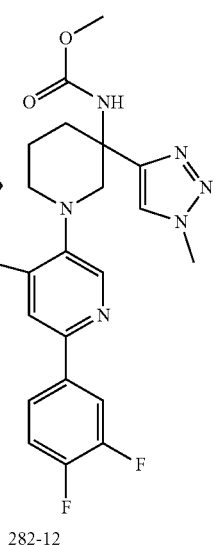

Intermediate 282-12 was prepared by using a procedure similar to that of intermediate 177-7 in example 177 by replacing intermediate 177-6 with intermediate 282-11. LC-MS: [M+H]⁺=776.3.

Intermediate: 284-4: 3-(5-methylisoxazol-3-yl)piperidin-3-amine

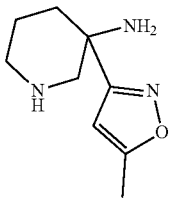

284-4

A mixture of benzyl 3-((tert-butoxycarbonyl)amino)-3-formylpiperidine-1-carboxylate (238 mg, 0.656 mmol) and hydroxylamine HCl (38 mg, 0.547 mmol) and K₂CO₃ (91 mg, 0.656 mmol) in EtOH/H₂O (1:1, 20 mL) was stirred at rt overnight, and the mixture was treated with EA (20 mL) and H₂O (10 mL). The layers were separated and the aqueous layers were extracted with EA (10 mL*2). The combined organic layers were washed with brine, dried over Na₂SO₄ and filtered. The filtrate was concentrated to give benzyl (E)-3-((tert-butoxycarbonyl)amino)-3-((hydroxyimino)methyl)piperidine-1-carboxylate (284-1). LC-MS: [M+H-100]*=277.9.

A mixture of benzyl (E)-3-((tert-butoxycarbonyl)amino)-3-((hydroxyimino)methyl)piperidine-1-carboxylate (284-1) (2 g, 5.3 mmol) in DMF (20 mL) was added NCS (1.061 g, 7.95 mmol). The mixture was stirred at 40° C. for 2 hrs. Then the mixture was treated with EA (20 mL) and H₂O (20 mL). The layers were separated and the aqueous layers were extracted with EA (20 mL*2). The combined organic layers were washed with brine, dried over Na₂SO₄ and filtered. The filtrate was concentrated to give crude benzyl (Z)-3-((tert-butoxycarbonyl)amino)-3-(chloro(hydroxyimino) methyl)piperidine-1-carboxylate (284-2).

To a mixture of crude benzyl (Z)-3-((tert-butoxycarbonyl)amino)-3-(chloro(hydroxyimino) methyl)piperidine-1-carboxylate (284-2) (2 g, 4.86 mmol) in DCM (50 mL) was added 2-chloroprop-1-ene (7.43 g, 97 mmol) and TEA (3.41 mL, 24.28 mmol). The mixture was heated to 40° C. for overnight. Then the mixture was concentrated. The residue was purified, eluting with EA in n-hexane (0 to 50%) to give benzyl 3-((tert-butoxycarbonyl)amino)-3-(5-methylisoxazol-3-yl)piperidine-1-carboxylate (284-3). LC-MS: [M+H]⁺= 415.9.

A mixture of benzyl 3-((tert-butoxycarbonyl)amino)-3-(5-methylisoxazol-3-yl)piperidine-1-carboxylate (284-3) (700 mg, 1.685 mmol) in HBr in HOAc (10 mL) was stirred at rt for 8 hrs. The mixture was concentrated and the residue was adjusted pH=10-12 with 1 M of aq. NaOH. The mixture was then extracted with i-PrOH/DCM (1:3 20 mL*3). The combined organic layers were dried over Na₂SO₄ and filtered. The filtrate was concentrated to 3-(5-methylisoxazol-3-yl)piperidin-3-amine (Intermediate 284-4). LC-MS: [M+H]⁺=182.0.

Intermediate 284-6: (5-(3-amino-3-(5-methylisoxa-zol-3-yl)piperidin-1-yl)-2-(3,4-difluorophenyl)pyri-din-4-yl)methanol

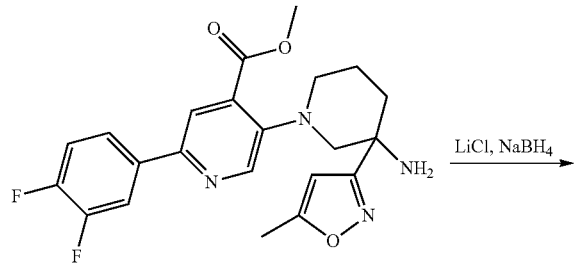

284-5

284-6

Methyl 5-(3-amino-3-(5-methylisoxazol-3-yl)piperidin-1-yl)-2-(3,4-difluorophenyl)isonicotinate (Intermediate 284-5) was prepared following procedures analogous to those described in Example 177-5 and from corresponding intermediates. LC-MS: [M+H]$^+$=428.9, 429.8.

Intermediate 284-6 was prepared by using a procedure similar to that of intermediate 177-6 in example 177 by replacing intermediate 177-5 with intermediate 284-5. LC-MS: [M+H]$^+$=400.9, 401.9.

Intermediate 285-4: 3-(2-(benzyloxy)-1-fluoroethyl)piperidin-3-amine 285-4

To a solution of 2-(benzyloxy)acetaldehyde (0.652 g, 4.34 mmol) in 0.025 M NaOH aqueous solution (15 mL, 0.375 mmol) was added 2-(benzyloxy)acetaldehyde (0.652 g, 4.34 mmol) and N,N,N-trimethylhexadecan-1-aminium chloride (0.139 g, 0.434 mmol) at rt, the mixture was stirred at rt for 3 h under N$_2$ atmosphere. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient: 0% to 30% EtOAc in PE in 30 mins) to afford the tert-butyl 3-(2-(benzyloxy)-1-hydroxyethyl)-3-nitropiperidine-1-carboxylate (285-1). $^1$H NMR (400 MHz, DMSO-d$_6$) δ ppm. 40-7.24 (m, 6H), 5.84 (dd, J=28.5, 6.2 Hz, 1H), 4.79-4.56 (m, 1H), 4.54-4.44 (m, 2H), 4.07-3.91 (m, 1H), 3.85 (s, 1H), 3.59 (ddd, J=27.8, 10.5, 4.9 Hz, 1H), 3.39 (ddd, J=12.0, 10.4, 6.3 Hz, 1H), 3.18 (dd, J=22.8, 13.2 Hz, 1H), 2.72 (s, 1H), 2.41 (t, J=15.6 Hz, 1H), 1.95-1.77 (m, 1H), 1.61 (dt, J=14.0, 3.9 Hz, 1H), 1.37 (d, J=2.5 Hz, 9H). LC-MS: [M+H-100]$^+$=281.2.

To a solution of tert-butyl 3-(2-(benzyloxy)-1-hydroxyethyl)-3-nitropiperidine-1-carboxylate (285-1) (0.93 g, 2.445 mmol) in DCM (20 mL), was added DAST (0.646 mL, 4.89 mmol) at 0° C., the mixture was stirred at 0° C. for 3 h under N$_2$ atmosphere. Then the reaction mixture was diluted with water, extracted with EtOAc (20 ml*3), and worked up in aqueous conditions to give a residue when concentrated in vacuum. The residue was purified by flash chromatography (elution gradient: 0% to 40% EtOAc in PE in 30 mins) to afford tert-butyl 3-(2-(benzyloxy)-1-fluoroethyl)-3-nitropiperidine-1-carboxylate (285-2). LC-MS: [M+H−100]+=383.1.

To a solution of tert-butyl 3-(2-(benzyloxy)-1-fluoroethyl)-3-nitropiperidine-1-carboxylate (285-2) (200 mg, 0.684 mmol) in EtOH (10 mL), was added Zn dust (44.7 mg, 0.684 mmol) at RT, then 4M HCl (2.281 mL, 6.84 mmol) was added dropwise at 0° C., after addition the mixture was stirred at 0° C. for 3 h under N$_2$ atmosphere. The reaction mixture was filtered and concentrated to give a residue. The residue was purified by flash chromatography (elution gradient: 0% to 40% EtOAc in PE in 30 mins) to afford tert-butyl 3-amino-3-(2-(benzyloxy)-1-fluoroethyl)piperidine-1-carboxylate (285-3). LC-MS: [M+H]$^+$=263.2.

To a solution of tert-butyl 3-amino-3-(2-(benzyloxy)-1-fluoroethyl)piperidine-1-carboxylate (285-3) (180 mg, 0.511 mmol) in DCM (15 mL), was added TFA (5 mL, 64.9 mmol) at rt, the mixture was stirred at rt for 1 h under N$_2$ atmosphere. Then the mixture was concentrated in vacuum to afford 3-(2-(benzyloxy)-1-fluoroethyl)piperidin-3-amine (Intermediate 285-4) as TFA salt. LC-MS: [M+H]$^+$=253.2.

Intermediate 287-6: 2,2,2-trifluoroacetaldehyde Compound with N-benzyl-3-(1,2-difluoroethyl)piperidin-3-amine (1:1)

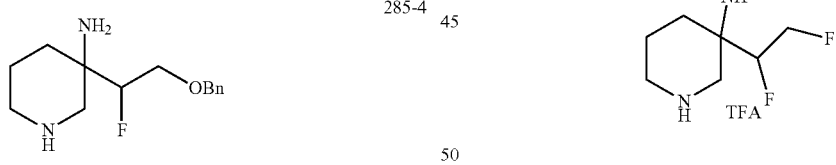

287-6

AlLiH$_4$ (13.42 g, 353.45 mmol) in THF (200 mL) was stirred at 80° C. for 2 h. Then the mixture was added to ethyl 2-fluoroacetate (150 g, 1.41 mol) in THF (100 mL) at −60° C. and stirred at −60° C. for 1 h. The mixture was quenched by EtOH (20 mL) at −60° C., poured into a solution of ice-water (500 mL) and H$_2$SO$_4$ (50 mL), and extracted with MTBE (150 mL*3). The organic layers were concentrated in vacuo (25° C.) to give residue. The residue was purified by distillation (−0.095 MPa, 25-50° C.) to give 1-ethoxy-2-fluoroethan-1-ol (287-1). $^1$H NMR (400 MHz, CD$_3$OD) δ=4.30-4.16 (m, 2H), 3.61 (q, J=7.1 Hz, 2H), 1.20-1.18 (m, 3H).

To a solution of tert-butyl 3-nitropiperidine-1-carboxylate (40 g, 173.72 mmol) in THF (40 mL) was added 1-ethoxy-2-fluoroethan-1-ol (287-1) (93.90 g, 868.58 mmol), K$_2$CO$_3$ (12.00 g, 86.86 mmol) and stirred at 40° C. for 4 h. The mixture was concentrated in vacuo to give a residue. The residue was purified by column chromatography (PE/EA=50:1-10:1) to give tert-butyl 3-(2-fluoro-1-hydroxyethyl)-3-nitropiperidine-1-carboxylate (287-2). $^1$H NMR (400 MHz, CDCl$_3$) δ=4.78-4.62 (m, 1H), 4.60-4.50 (m, 1H), 4.50-4.41 (m, 1H), 4.22-4.02 (m, 1H), 3.99-3.60 (m, 1H), 3.48-2.92 (m, 2H), 2.57-2.37 (m, 1H), 2.34-2.10 (m, 1H), 1.74-1.64 (m, 2H), 1.47 (m, 9H). LCMS: [M+H−56]$^+$=237.3.

To a solution of tert-butyl 3-(2-fluoro-1-hydroxyethyl)-3-nitropiperidine-1-carboxylate (287-2) (25 g, 85.53 mmol) in DCM (100 mL) was added BAST (85.15 g, 384.87 mmol) and stirred at 50° C. for 4 h. The mixture was quenched with aq·NaHCO$_3$ (1.0 L), extracted with EA (200 mL*3).

The organic layer was concentrated in vacuo to give a residue. The residue was purified by column chromatography (PE:EA=100:1-20:1) to give tert-butyl 3-(1,2-difluoroethyl)-3-nitropiperidine-1-carboxylate (287-3). LCMS: [M+H−56]$^+$=239.3.

To a solution of tert-butyl 3-(1,2-difluoroethyl)-3-nitropiperidine-1-carboxylate (287-3) (10.0 g, 33.98 mmol) in MeOH (100 mL) was added Pd/C (5.0 g, 10% purity) and stirred under H$_2$ (15 Psi) at 40° C. for 16 h. The mixture was filtered and concentrated in vacuo to give crude tert-butyl 3-amino-3-(1,2-difluoroethyl)piperidine-1-carboxylate (287-4). LCMS: [M+H−56]$^+$=209.3.

To a solution of tert-butyl 3-amino-3-(1,2-difluoroethyl)piperidine-1-carboxylate (287-4) (8.1 g, 30.65 mmol) and benzaldehyde (4.88 g, 45.97 mmol) in EtOH (100 mL) was stirred at 40° C. for 1 h. Then NaBH$_4$ (5.8 g, 153.23 mmol) was added to the mixture and stirred at 40° C. for 16 h. LCMS detected the reaction. The mixture was quenched by aq·NH$_4$Cl (100 mL), diluted with H$_2$O (200 mL), extracted with EA (50 mL*3). The organic layer was concentrated in vacuo to give tert-butyl 3-(benzylamino)-3-(1,2-difluoroethyl)piperidine-1-carboxylate (287-5). LCMS: [M+H]$^+$=355.4.

To a solution of tert-butyl 3-(benzylamino)-3-(1,2-difluoroethyl)piperidine-1-carboxylate (287-5) (7.0 g, 19.75 mmol) in DCM (20 mL) was added TFA (10 mL) and stirred at 40° C. for 3 h. The mixture was quenched by aq·NaHCO$_3$ (200 mL), extracted with DCM (50 mL*3). The organic layer was concentrated in vacuo to give 2,2,2-trifluoroacetaldehyde compound with N-benzyl-3-(1,2-difluoroethyl)piperidin-3-amine (1:1) (Intermediate 287-6). LCMS: [M+H]$^+$= 254.9.

Intermediate 288-9: 3-(6-methyl-1,4-dioxan-2-yl)piperidin-3-amine

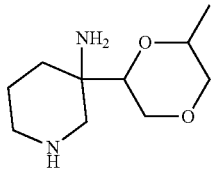

288-9

To a stirred solution of NaH (7.7 g, 180 mmol, 1.0 eq) in anhydrous THF (120 ml) at 0° C. was added prop-2-en-1-ol (10.4 g, 180 mmol, 1.0 eq) dropwise. The reaction mixture was stirred for 15 min at 0° C., and stirred at 15° C. for another 15 min. Besides, to another suspension of NaH (7.7 g, 180 mmol, 1.0 eq) and THF (60 mL) was added 2-chloroacetic acid in anhydrous at 0° C., after stirred at 0° C. for 15 mins, the previously prepared solution was added and the reaction mixture was stirred at 15° C. for 12 hours. The reaction mixture was quenched by water (100 mL), the aqueous layer was acidified and extracted with EA (200 mL*3), dried over anhydrous Na$_2$SO$_4$, filtered and concentrated to give 2-(allyloxy)acetic acid (288-1). $^1$H NMR (400 MHz, CDCl3) δ ppm 5.98-5.85 (m, 1H), 5.39-5.22 (m, 2H), 4.15 (s, 2H), 4.13 (m, 2H). LC-MS: [M+Na]+=161.1.

To a solution of 2-(allyloxy)acetic acid (288-1) (9.2 g, 79.23 mmol, 1.0 eq) in anhydrous DCM (60 mL) was added DMF (115 mg, 1.58 mmol, 0.02 eq) and (COCl)$_2$ (12.1 g, 95.07 mmol, 1.2 eq) dropwise at 15° C. The reaction mixture was stirred at 15° C. for 2 hours. The reaction mixture was concentrated in vacuum to give crude 2-(allyloxy)acetyl chloride (288-2). LC-MS: [M+C$_7$H$_9$N−HCl+H]+=206.2.

To a solution of 1-benzyl 3-methyl piperidine-1,3-dicarboxylate (16.9 g, 60.94 mmol, 1.0 eq) in anhydrous THF (170 mL) was added a solution of LiHMDS (61 mL, 60.94 mmol, 1.0 eq) dropwise at −78° C. The reaction mixture was stirred at −78° C. for 1 hour, 2-(allyloxy)acetyl chloride (288-2) (8.2 g, 60.94 mmol, 1.0 eq) was added dropwise at −78° C., the reaction was stirred at −78° C. for 1 hour and at 15° C. for another 1 hour. The reaction mixture was quenched with sat. NH$_4$Cl (200 mL), extracted with EA (100 mL*3), dried over Na$_2$SO$_4$, filtered, and concentrated to give crude 1-benzyl 3-methyl 3-(2-(allyloxy)acetyl)piperidine-1,3-dicarboxylate (288-3). LC-MS: [M+H]$^+$=376.2.

To a solution of 1-benzyl 3-methyl 3-(2-(allyloxy)acetyl)piperidine-1,3-dicarboxylate (288-3) (20.4 g, 53.34 mmol, 1.0 eq) in MeOH (100 mL) was added NaBH$_4$ (2.0 g, 53.34 mmol, 1.0 eq) portionwise at 15° C. The reaction was stirred at 15° C. for 3 hours. The reaction mixture was quenched with Sat. NH$_4$Cl (100 mL), acidified with 2N HCl to PH=4-5, extracted with EtOAc (100 ml*3), the combined organic phase was washed with water (100 ml), brine (100 ml), dried over anhydrous sodium sulfate, concentrated in vacuum to give a residue. The residue was purified by column chromatography (SiO$_2$, PE/EA=20:1 to 1:1) to give 1-benzyl 3-methyl 3-(2-(allyloxy)-1-hydroxyethyl)piperidine-1,3-dicarboxylate (288-4). LC-MS: [M+H]$^+$=378.3.

To a solution of 1-benzyl 3-methyl 3-(2-(allyloxy)-1-hydroxyethyl)piperidine-1,3-dicarboxylate (288-4) (10.4 g, 27.55 mmol, 1.0 eq) in dry MeCN (100 mL) was added NIS (10.6 g, 4.684 mmol, 1.7 eq). The reaction mixture was stirred at 90° C. for 3 hours. The reaction mixture was quenched with Sat. Na$_2$SO$_3$ (50 mL), extracted with EA (100 mL*3), dried over anhydrous Na$_2$SO$_4$, concentrated. The residue was purified by column chromatography (SiO$_2$, PE/EA=20/1 to 2/1) to give 1-benzyl 3-methyl 3-(6-(iodomethyl)-1,4-dioxan-2-yl)piperidine-1,3-dicarboxylate (288-5). LC-MS: [M+H]$^+$=504.2.

To a solution of 1-benzyl 3-methyl 3-(6-(iodomethyl)-1,4-dioxan-2-yl)piperidine-1,3-dicarboxylate (288-5) (4.3 g, 8.54 mmol, 1.0 eq) and n-Bu$_3$SnH (2.5 g, 8.54 mmol, 1.0 eq) and in anhydrous toluene (200 mL) was added AIBN (140 mg, 0.85 mmol, 0.1 eq), the reaction mixture was stirred under N$_2$ for 16 hours. The reaction mixture was quenched by a solution of KF (0.5 g, 8.54 mmol, 1.0 eq) in H$_2$O (50 mL), diluted with water (100 mL), extracted with EA (100 mL*3), dried over anhydrous Na$_2$SO$_4$, concentrated in vacuo to give residue. The residue was purified by column chromatography (SiO$_2$, PE/EA=20/1 to 1/1) to give 1-benzyl 3-methyl 3-(6-methyl-1,4-dioxan-2-yl)piperidine-1,3-dicarboxylate (288-6). LC-MS: [M+H]$^+$=378.3.

To a solution of 1-benzyl 3-methyl 3-(6-methyl-1,4-dioxan-2-yl)piperidine-1,3-dicarboxylate (288-6) (3.6 g, 9.54 mmol, 1.0 eq) in MeOH (50 mL) was added a solution of LiOH·H₂O (4.0 g, 95.38 mmol, 10.0 eq) in H₂O (50 mL) at RT. The reaction was stirred at RT for 16 hours. The reaction mixture was concentrated in vacuum to remove most of MeOH, diluted with 20 ml of water, the aqueous phase was washed with EA (10 mL*3). Then the aqueous phase was acidified with 2N HCl to PH=3-4, extracted with EA (50 mL*3), dried over anhydrous Na₂SO₄, concentrated in vacuo to give 1-((benzyloxy)carbonyl)-3-(6-methyl-1,4-dioxan-2-yl)piperidine-3-carboxylic acid (288-7). LC-MS: [M+H]⁺=364.3.

To a solution of 1-((benzyloxy)carbonyl)-3-(6-methyl-1,4-dioxan-2-yl)piperidine-3-carboxylic acid (288-7) (2.1 g, 5.78 mmol, 1.0 eq) in anhydrous THF (800 mL) was added TEA (1.7 g, 17.34 mmol, 3.0 eq) and DPPA (2.2 g, 8.09 mmol, 1.4 eq) at 20° C., the reaction mixture was stirred at 70° C. for 2 hours and cooled to 20° C. then a solution of KOH (1.0 g, 17.34 mmol, 3.0 eq) in H₂O (10 mL) was added. The reaction mixture was stirred at 20° C. for 2 hours. The reaction mixture was concentrated, extracted with EA (50 mL*3), washed with water (50 mL), brine (50 mL). The organic layer was dried over Na₂SO₄, concentrated in vacuo. The crude was purified by column chromatography (SiO₂, PE/EA=20/1 to EA) to give a not pure product, which was further purified by Prep-HPLC to give benzyl 3-amino-3-(6-methyl-1,4-dioxan-2-yl)piperidine-1-carboxylate (288-8). ¹H NMR (400 MHz, CDCl₃) δ ppm 7.39-7.21 (m, 5H), 5.06 (m, 2H), 3.96-2.86 (m, 10H), 1.82-1.61 (m, 2H), 1.52-1.31 (m, 2H), 1.30-0.96 (m, 3H). LC-MS: [M+H]⁺=335.3.

To a solution of benzyl 3-amino-3-(6-methyl-1,4-dioxan-2-yl)piperidine-1-carboxylate (288-8) (1.0 g, 2.99 mmol, 1.0 eq) in MeOH (10 ml) was added Pd(OH)₂ (104 mg, 10% wt), the reaction mixture was stirred at 20° C. under H₂ atmosphere (16 Psi) for 8 hours. The reaction mixture was filtered and concentrated in vacuum to give crude 3-(6-methyl-1,4-dioxan-2-yl)piperidin-3-amine (Intermediate 288-9).

Intermediate 292-3:
3-oxa-1,7-diazaspiro[4.5]decan-2-one

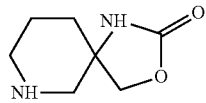

To a solution of 1-benzyl 3-ethyl 3-(hydroxymethyl)piperidine-1,3-dicarboxylate (intermediate 22-2) (2.0 g, 6.97 mmol, 1.0 eq.) in THF/MeOH/H₂O (1:1:1, 30 mL) was added LiOH H₂O (0.87 g, 20.9 mmol, 3.0 eq.) at 20° C. The mixture was stirred at 20° C. for 8 h. Water (50 mL) was added and the mixture was extracted with EtOAc (100 mL*3). The aqueous phase was acidified by 1M HCl to pH=2-3 and then extracted with EtOAc (100 mL*3). The combined organic layers were washed with brine, dried over anhydrous sodium sulfate, filtered and concentrated to give 1-(tert-butoxycarbonyl)-3-(hydroxymethyl)piperidine-3-carboxylic acid (292-1). ¹H NMR (CDCl₃ 400 MHz): δ 4.05-3.85 (m, 1H), 3.85-3.65 (m, 3H), 3.45-3.20 (m, 1H), 3.14-2.95 (m, 1H), 1.97-1.85 (m, 1H), 1.80-1.70 (m, 1H), 1.62-1.52 (m, 2H), 1.44 (s, 9H).

To a solution of 1-(tert-butoxycarbonyl)-3-(hydroxymethyl)piperidine-3-carboxylic acid (292-1) (1.8 g, 6.94 mmol, 1.0 eq) in toluene (40 mL) was added TEA (1.4 g, 13.9 mmol, 2.0 eq) and DPPA (2.7 g, 10.4 mmol, 1.5 eq.) under N₂ at 20° C. Then the reaction mixture was stirred at 110° C. for 8 h. H₂O (100 mL) was added and the mixture was extracted with EtOAc (100 mL*3). The combined organic layers were washed with brine, dried over anhydrous sodium sulfate, filtered and concentrated. The residue was purified by silica gel column chromatography (PE:EA=1:1) to give tert-butyl 2-oxo-3-oxa-1,7-diazaspiro[4.5]decane-7-carboxylate (292-2). ¹H NMR (CDCl₃ 400 MHz): δ 5.87 (brs, 1H), 4.22 (d, J=8.8 Hz, 1H), 4.07 (d, J=8.8 Hz, 1H), 3.66-3.42 (m, 2H), 3.38-3.18 (m, 2H), 1.85-1.78 (m, 2H), 1.75-1.65 (m, 1H), 1.60-1.52 (m, 1H), 1.48 (s, 9H).

A solution of tert-butyl 2-oxo-3-oxa-1,7-diazaspiro[4.5]decane-7-carboxylate (292-2) (0.6 g, 2.34 mmol, 1.0 eq.) in HCl/dioxane (5 mL, 4N) was stirred at 20° C. for 2 h. The mixture was concentrated to give crude 3-oxa-1,7-diazaspiro[4.5]decan-2-one (Intermediate 292-3).

Intermediate 293-8: 3-(1,1-difluoroprop-1-en-2-yl)piperidin-3-amine

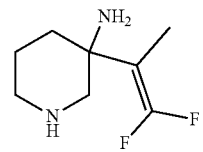

To a solution of tert-butyl 3-cyanopiperidine-1-carboxylate (25 g, 119.0 mmol, 1.0 eq.) in THF (300 mL) at −70° C. under N₂ atmosphere was added LiHMDS (178 mL, 178.57 mmol, 1.5 eq.) dropwise. The reaction mixture was stirred at −70° C. for 30 min, then CH₃CHO (7.85 g, 178.57 mmol, 3 eq.) was added. The reaction was quenched with aq·NH₄Cl (200 mL), extracted with EtOAc (100 mL×3). The combined organic layer was washed with brine (200 mL), dried over anhydrous sodium sulfate, filtered and concentrated. The residue was purified by Combi-flash (EtOAc in PE, 10%-50%) to afford tert-butyl 3-(1-hydroxyethyl)-3-methylpiperidine-1-carboxylate (293-1).

To a solution of tert-butyl 3-(1-hydroxyethyl)-3-methylpiperidine-1-carboxylate (intermediate 293-1) (9 g, 35.43 mmol, 1.0 eq.) in DCM (150 mL) was added DMP (22.5 g, 53.15 mmol, 1.5 eq.). The mixture was stirred at 20° C. for 1 hour. The reaction was quenched with aq. NaHCO₃ (150 mL) and aq. Na₂SO₃ (150 mL), extracted with EtOAc (150 mL×3). The combined organic layers were washed with aq·NaHCO₃ (150 mL), dried over anhydrous sodium sulfate, filtered and concentrated to afford tert-butyl 3-acetyl-3-cyanopiperidine-1-carboxylate (293-2). H NMR (400 MHz, CDCl₃) δ ppm 4.50-3.85 (m, 2H), 3.20-3.05 (m, 1H), 2.95-2.60 (m, 1H), 2.46 (s, 3H), 2.25-1.70 (m, 4H), 1.48 (s, 9H).

To a solution of tert-butyl 3-acetyl-3-cyanopiperidine-1-carboxylate (293-2) (5 g, 19.84 mmol, 1.0 eq.) in DCM (100 mL) was added TFA (15 mL). The mixture was stirred at 20° C. for 2 hours. The reaction mixture was then concentrated. The residue was diluted with EtOAc (150 mL), and aq·NaHCO₃ (150 mL) was added. Then CbzCl (4.0 g, 23.81 mmol, 1.2 eq) was added. The reaction mixture was stirred at 20° C. for another 1 h. The product was extracted with EtOAc (50 mL×3). The combined organic layers were washed with brine (50 mL), dried over anhydrous Na₂SO₄, filtered and concentrated. The residue was purified by combi-flash (EtOAc in PE, 0%-30%) to afford benzyl 3-acetyl-3-cyanopiperidine-1-carboxylate (293-3). ¹H NMR (400 MHz, CDCl₃) δ ppm 7.45-7.30 (m, 5H), 5.25-5.10 (m, 2H), 4.50-4.05 (m, 2H), 3.20 (d, J=13.6 MHz, 1H), 2.95-2.75 (m, 1H), 2.47 (d, J=16.8 MHz, 3H), 2.25-1.60 (m, 4H).

To a solution of benzyl 3-acetyl-3-cyanopiperidine-1-carboxylate (293-3) (5 g, 17.46 mmol, 1.0 eq.) and 2-((difluoromethyl)sulfonyl)pyridine (5 g, 26.19 mmol, 1.5 eq.) in THF (50 mL) was added KHMDS (26 mL, 26.19 mmol, 1.5 eq.) dropwise at −70° C. under N₂ atmosphere. The mixture was stirred at −70° C. for 2 hours. The reaction was quenched with aq. NH₄Cl (50 mL) and extracted with EtOAc (50 mL×3). The organic layers were washed with brine (100 mL), dried over anhydrous Na₂SO₄, filtered and concentrated to afford benzyl 3-cyano-3-(1,1-difluoro-2-hydroxy-1-(pyridin-2-ylsulfonyl)propan-2-yl)piperidine-1-carboxylate (293-4). LC-MS: [M+H]⁺=480.0.

To a solution of benzyl 3-cyano-3-(1,1-difluoro-2-hydroxy-1-(pyridin-2-ylsulfonyl)propan-2-yl)piperidine-1-carboxylate (293-4) (12 g, crude) in DMF (30 mL) was added sat. NH₄Cl (30 mL) and aq. HCl (30 mL, 6M). The reaction mixture was stirred at 80° C. for 48 hours. The reaction was cooled and diluted with H₂O (50 mL). The product was extracted with EtOAc (50 mL×3). The organic layers were washed with brine (100 mL), dried over Na₂SO₄, filtered and concentrated. The residue was purified by combi-flash (EtOAc in PE, 0%-20%) to afford benzyl 3-cyano-3-(1,1-difluoroprop-1-en-2-yl)piperidine-1-carboxylate (293-5). H NMR (400 MHz, CDCl₃) δ ppm 7.45-7.30 (m, 5H), 5.30-5.15 (m, 2H), 4.65-4.15 (m, 2H), 3.10-2.70 (m, 2H), 2.25 (d, J=11.2 MHz, 1H), 2.10-1.60 (m, 6H). LC-MS: [M+H]⁺=320.9.

To a mixture of benzyl 3-cyano-3-(1,1-difluoroprop-1-en-2-yl)piperidine-1-carboxylate (293-5) (2.7 g, 8.44 mmol, 1.0 eq), 1 M NaOH solution (12.6 mL, 1.5 eq) in MeOH (100 mL) was added H₂O₂ (30%, 6.68 g, 59 mmol, 7.0 eq). The reaction was stirred at 18° C. for 36 hrs. The reaction was quenched with saturated Na₂S₂O₃ (50 mL). The aqueous layer was extracted with EtOAc (50 mL×3). The combined organic layers were dried over Na₂SO₄, filtered and concentrated into dryness. The residue was purified by combi-flash (EtOAc in PE, 0-40%) to afford benzyl 3-carbamoyl-3-(1,1-difluoroprop-1-en-2-yl)piperidine-1-carboxylate (293-6). ¹H NMR (CDCl₃ 400 MHz): δ ppm 7.42-7.30 (m, 5H), 5.22-5.08 (m, 2H), 4.48 (brs, 1H), 3.99 (brs, 1H), 3.17-2.88 (m, 2H), 2.53 (brs, 1H), 1.76-1.46 (m, 7H).

To a solution of benzyl 3-carbamoyl-3-(1,1-difluoroprop-1-en-2-yl)piperidine-1-carboxylate (293-6) (1.34 g, 4 mmol, 1.0 eq) and KOH (560 mg, 10 mmol, 2.5 eq) in MeOH (30 mL) was added PhI(OAc)₂ (1.53 g, 4.8 mmol, 1.2 eq) at 0° C. The resulting mixture was stirred at 15° C. for 3 hr. The reaction was quenched with sat. NH₄Cl solution (50 mL). The aqueous layer was extracted with EtOAc (50 mL×3). The combined organic layers were dried over Na₂SO₄, filtered and concentrated. The residue was purified by combi-flash (EtOAc in PE, 0-30%) to afford benzyl 3-(1,1-difluoroprop-1-en-2-yl)-3-((methoxycarbonyl)amino)piperidine-1-carboxylate (293-7). ¹H NMR (400 MHz, CDCl₃) δ ppm 7.42-7.30 (m, 5H), 5.24-5.08 (m, 2H), 4.30 (d, J=14.2 Hz, 1H), 4.18-4.04 (m, 1H), 3.60 (s, 3H), 2.82 (brs, 2H), 1.73-1.60 (m, 4H), 1.57 (s, 3H). LC-MS: [M+H]⁺=369.0.

To a solution of benzyl 3-(1,1-difluoroprop-1-en-2-yl)-3-((methoxycarbonyl)amino)piperidine-1-carboxylate (293-7) (600 mg, 1.63 mmol, 1.0 eq) in DCM (15 mL) was added TMSI (977 mg, 4.89 mmol, 3.0 eq). The reaction was stirred at 16° C. for 18 hr. The reaction was quenched with water (10 mL). The aqueous layer was adjusted to pH=4-5 by 1 M HCl solution. The mixture was partitioned between DCM and water. The aqueous layer was lyophilized to afford 3-(1,1-difluoroprop-1-en-2-yl)piperidin-3-amine HCl salt (Intermediate 293-8). ¹H NMR (400 MHz, DMSO-d₆) δ ppm 3.73 (d, J=13.4 Hz, 1H), 3.17 (d, J=12.8 Hz, 2H), 2.98 (t, J=10.2 Hz, 1H), 2.27 (d, J=13.6 Hz, 1H), 2.01-1.78 (m, 2H), 1.71 (t, J=3.4 Hz, 3H), 1.65-1.50 (m, 1H). LC-MS: [M+H]⁺=177.1

Intermediate 295-6:
3-(1-fluoroethyl)piperidin-3-amine

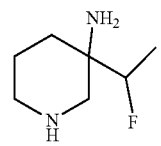

295-6

To solution of 1-benzyl 3-methyl 3-((tert-butoxycarbonyl)amino)piperidine-1,3-dicarboxylate (160 mg, 0.41 mmol) in MeOH (10 ml) was added LiCl (510 mg, 12.3 mmol) and NaBH₄ (462 mg, 12.3 mmol) at room temperature. The reaction mixture was stirred at this temperature until no starting material left. The reaction mixture was diluted with EA, washed with 1 N HCl and brine. The organic layer was dried over Na₂SO₄ and concentrated under vacuum to give the crude alcohol. LC-MS: [M+H-100]⁺=265.0.

To a solution of the alcohol (560 mg, 1.537 mmol) in DCM (15 ml) was added Dess-Martin reagent (782 mg, 1.844 mmol). The mixture was stirred at rt for 2 hrs. The mixture was treated with aq. NaHCO₃ (10 ml) and the layers were separated. The aqueous layer was extracted with DCM (10 ml*2). The combined organic layers were washed with brine, dried over Na₂SO₄ and filtered. The filtrate was concentrated. The residue was purified, eluting with EA in n-hexane (0 to 50%) to give benzyl 3-((tert-butoxycarbonyl)amino)-3-formylpiperidine-1-carboxylate (295-1). LC-MS: [M+H-100]⁺=624.8.

To a solution of benzyl 3-((tert-butoxycarbonyl)amino)-3-formylpiperidine-1-carboxylate (295-1) (100 mg, 0.276 mmol) in THF (10 ml) was added dropwise aq. CH₃MgBr in 2-Me THF (3M, 0.138 ml, 0.414 mmol) at −78° C. The mixture was stirred at −78° C. for another 1 hr and was allowed to warm to 0° C. for another 2 hr. The mixture was quenched with aq. NH₄Cl (10 ml) and was extracted with EA (20 ml*3). The combined organic layers were washed with brine, dried over Na₂SO₄ and filtered. The filtrate was concentrated. The residue was purified, eluting with EA in n-hexane (0 to 50%) to give the alcohol. LC-MS: [M+H-100]+=279.0. To a solution of the alcohol (100 mg, 0.264 mmol) in DCM (3 ml) was added TFA (0.5 ml). The resulting mixture was stirred at rt for 2 hrs. The mixture was concentrated under vacuum (below 40° C.) to give benzyl 3-amino-3-(1-hydroxyethyl)piperidine-1-carboxylate (295-2). LC-MS [M+H]⁺=279.0.

To a solution of benzyl 3-amino-3-(1-hydroxyethyl)piperidine-1-carboxylate (295-2) (330 mg, 1.186 mmol), DMAP (14.48 mg, 0.119 mmol) and DIPEA (0.958 mL, 5.34 mmol) in DCM (20 mL) was added NsCl (657 mg, 2.96 mmol) in portions. The mixture was stirred at rt under N₂ overnight. The reaction was treated with aq. NaHCO₃ (20 mL). The layers were separated. The aqueous layer was extracted with DCM (20 mL*2). The combined organic layers were washed with brine, dried over Na₂SO₄ and filtered. The filtrate was concentrated. The residue was purified, eluting with n-hexane in EA (0 to 30%) to give benzyl 2-methyl-1-((4-nitrophenyl)sulfonyl)-1,5-diazaspiro[2.5]octane-5-carboxylate (295-3). LC-MS: [M+H]⁺=445.8.

To a solution of benzyl 2-methyl-1-((4-nitrophenyl)sulfonyl)-1,5-diazaspiro[2.5]octane-5-carboxylate (295-3) (420 mg, 0.943 mmol) in THF (10 mL) was added 1 M TBAF in THF (0.606 ml, 0.606 mmol) under $N_2$. The mixture was heated to 45° C. overnight. The mixture was cooled to rt and was treated with EA (15 mL) and $H_2O$ (10 mL). The layers were separated and the aqueous layer was extracted with EA (15 mL*3). The combined organic layers were washed with brine, dried over $Na_2SO_4$ and filtered. The filtrate was concentrated and was purified via prep. HPLC to give benzyl 3-(1-fluoroethyl)-3-((4-nitrophenyl)sulfonamido)piperidine-1-carboxylate (295-4). LC-MS: [M+H]⁺=465.8.

A mixture of thioglycolic acid (71.2 mg, 0.773 mmol) and DBU 235 (98 mg, 1.547 mmol) in $CH_3CN$ (10 mL) was stirred under $N_2$ for 5 min. Then benzyl 3-(1-fluoroethyl)-3-((4-nitrophenyl)sulfonamido)piperidine-1-carboxylate (295-4) (120 mg, 0.258 mmol) in $CH_3CN$ (2 mL) was added. The mixture was stirred at rt overnight and concentrated. The residue was treated with EA (10 ml) and was washed with aq. $NaHCO_3$ (5 mL*2), $H_2O$ (10 mL) and brine, dried over $Na_2SO_4$ and filtered. The filtrate was concentrated and the residue purified via prep. HPLC to give benzyl 3-amino-3-(1-fluoroethyl)piperidine-1-carboxylate (295-5). LC-MS: [M+H]⁺=281.1.

To a solution of benzyl 3-amino-3-(1-fluoroethyl)piperidine-1-carboxylate (295-5) (120 mg, 0.428 mmol) in MeOH (15 ml) was added Pd(OH)₂ (60 mg) under $N_2$. The mixture was then stirred under $H_2$ balloon for 3 hr. The mixture was filtered and the filtrate was concentrated to give 3-(1-fluoroethyl)piperidin-3-amine (Intermediate 295-6). LC-MS: [M+H]⁺=147.1

Intermediate 297-6: 3-((methylthio)methyl)piperidin-3-amine

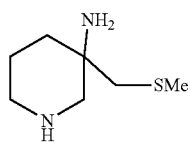

To a solution of 1-benzyl 3-ethyl 3-((((trifluoromethyl)sulfonyl)oxy)methyl)piperidine-1,3-dicarboxylate (22-3) (18.0 g, 39.7 mmol, 1.0 eq.) in THF (200 mL) was added MeSNa (11.0 g, 159 mmol, 4.0 eq) at 0° C. The resulting mixture was stirred at 15-20° C. for 16 hr. The reaction was quenched with water (300 mL), and extracted with EtOAc (300 mL×3). The combined organic layers were dried over anhydrous $Na_2SO_4$ and concentrated in vacuo. The residue was purified by Combi Flash (30% EtOAc in PE) to give 1-benzyl 3-ethyl 3-((methylthio)methyl)piperidine-1,3-dicarboxylate (297-1). ¹H NMR (400 MHz, CDCl₃) δ ppm 7.25-7.45 (5H, m), 5.13 (2H, s), 4.05-4.25 (2H, m), 3.80-4.00 (1H, m), 3.25-3.60 (3H, m), 2.60-2.85 (2H, m), 2.00-2.15 (4H, m), 1.55-1.75 (3H, m), 1.10-1.30 (3H, m).

A mixture of 1-benzyl 3-ethyl 3-((methylthio)methyl) piperidine-1,3-dicarboxylate (297-1) (10.0 g, 28.5 mmol, 1.0 eq.) and LiOH $H_2O$ (12.0 g, 285 mmol, 10.0 eq.) in MeOH/THF/$H_2O$ (120 mL, v/v/v=1/1/1) was stirred at 20° C. for 16 hr. The reaction was concentrated in vacuo. The residue was diluted with water (200 mL), and extracted with MTBE (100 mL). Then the pH of the aqueous layer was adjusted to 5 by 1H HCl, and extracted with EtOAc (200 mL×3). The combined organic layers were dried over anhydrous $Na_2SO_4$ and concentrated in vacuo to give crude 1-((benzyloxy)carbonyl)-3-((methylthio)methyl)piperidine-3-carboxylic acid (297-2). LC-MS: [M+H]⁺=324.1.

A mixture of 1-((benzyloxy)carbonyl)-3-((methylthio)methyl)piperidine-3-carboxylic acid (297-2) (8.00 g, 24.7 mmol, 1.0 eq.), DPPA (7.50 g, 27.2 mmol, 1.1 eq.) and $Et_3N$ (5.00 g, 48.5 mmol, 2.0 eq.) in toluene (100 mL) was stirred at 80° C. under $N_2$ for 1 hr. Then the reaction was concentrated in vacuo. The residue was dissolved in dioxane (50 mL) and 6N HCl (50 mL), and the mixture was stirred for 16 hr at 25-30° C. The reaction was concentrated in vacuo. The pH of the aqueous layer was adjusted to 9 by 1 N NaOH. Then the mixture was extracted with EtOAc (200 mL×3). The combined organic layers were dried over anhydrous $Na_2SO_4$ and concentrated in vacuo. The residue was dissolved in DCM (100 mL), DIPEA (10.0 g, 74.2 mmol, 3.0 eq) and Boc₂O (11.0 g, 48.4 mmol) were added. The resulting mixture was stirred at 25-30° C. for 16 hr. The reaction was concentrated in vacuo. The residue was purified by Combi Flash (20% EtOAc in PE) to give benzyl 3-((tert-butoxycarbonyl)amino)-3-((methylthio)methyl) piperidine-1-carboxylate (297-5). LC-MS: [M+H-100]*=295.1.

To a solution of benzyl 3-((tert-butoxycarbonyl)amino)-3-((methylthio)methyl)piperidine-1-carboxylate (297-5) (2.37 g, 6.00 mmol, 1 eq.) in $CH_3CN$ (50 mL) was added dropwise TMSI (3.60 g, 18 mmol, 3 eq.) at about 0° C. After addition, the reaction mixture was stirred at the same temperature for 2 h. The reaction mixture was carefully quenched with MeOH (20 mL) and HCl/dioxane (5 mL, 4M). The reaction mixture was concentrated. Water (20 mL) was added and the mixture was extracted with MTBE (40 mL*4). The aqueous layer was lyophilized to give crude 3-((methylthio)methyl)piperidin-3-amine (Intermediate 297-6).

Intermediate 299-3: 2,2,2-Trifluoroacetaldehyde compound with 1-(3-aminopiperidin-3-yl)-2,2,2-trifluoroethan-1-ol (1:1)

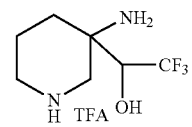

To a mixture of tert-butyl 3-nitropiperidine-1-carboxylate (5.0 g, 21.71 mmol, 1.0 eq) and 2,2,2-trifluoroethane-1,1-diol (10.08 g, 86.86 mmol, 4.0 eq) in THF (50 mL) was added $K_2CO_3$ (1.8 g, 13.03 mmol, 0.6 eq) at 60° C. for 16 hours. 1N HCl (10 mL) was added to the mixture, and extracted with EA (40 mL*3). The combined organic layer was washed with brine (30 mL), dried over $Na_2SO_4$, filtered and concentrated in vacuo to give tert-butyl 3-nitro-3-(2,2,2-trifluoro-1-hydroxyethyl)piperidine-1-carboxylate (299-1). H NMR: ¹H NMR (400 MHz, CDCl₃) δ ppm 5.01-4.71 (m, 2H), 4.67-4.34 (m, 1H), 4.07-3.35 (m, 2H), 2.88-2.13 (m, 2H), 1.95-1.52 (m, 2H), 1.50-1.36 (m, 9H). LCMS: [M+H-56]⁺=273.3.

To a solution of tert-butyl 3-nitro-3-(2,2,2-trifluoro-1-hydroxyethyl)piperidine-1-carboxylate (299-1) (4.0 g, 12.89 mmol, 1.0 eq) and NH$_4$Cl (3.45 g, 64.45 mmol, 5.0 eq) in EtOH/H$_2$O (40 mL, v/v=4:1) was added Zn (8.43 g, 128.91 mmol, 10.0 eq) at 25° C. under N$_2$. The mixture was stirred at 80° C. for 16 h, worked up under aqueous conditions, filtered and concentrated in vacuo. The crude was purified by column chromatography (PE:EA=10:1) to give tert-butyl 3-amino-3-(2,2,2-trifluoro-1-hydroxyethyl)piperidine-1-carboxylate (299-2). H NMR: $^1$H NMR (400 MHz, CDCl$_3$) δ ppm 4.05-3.93 (m, 1H), 3.69-3.50 (m, 2H), 3.22-2.74 (m, 2H), 1.90-1.70 (m, 2H), 1.68-1.60 (m, 2H), 1.47 (s, 9H).

To a solution of tert-butyl 3-amino-3-(2,2,2-trifluoro-1-hydroxyethyl)piperidine-1-carboxylate (299-2) (1.2 g, crude) in DCM (10 mL) was added TFA (2 mL) dropwise under the protection of nitrogen and the mixture was stirred at 25° C. for 2 hours. The mixture was concentrated to give 2,2,2-trifluoroacetaldehyde compound with 1-(3-aminopiperidin-3-yl)-2,2,2-trifluoroethan-1-ol (1:1) (Intermediate 299-3).

Intermediate 300-6: (5-(3-amino-3-(1,2,2-trifluoroethyl)piperidin-1-yl)-2-(3,4-difluorophenyl)pyridin-4-yl)methanol

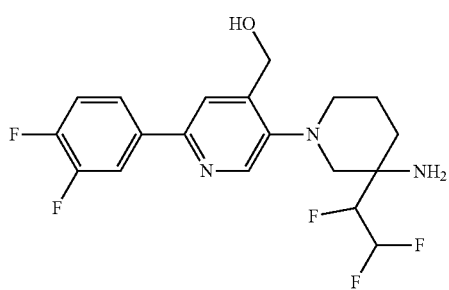

To a solution of tert-butyl 3-nitropiperidine-1-carboxylate (3 g, 13.03 mmol) in THF (30 mL), was added K$_2$CO$_3$ (0.540 g, 3.91 mmol) and 1-ethoxy-2,2-difluoroethanol (4.93 g, 39.1 mmol), the reaction mixture was stirred at 55° C. for 18 h under N$_2$ atmosphere. he reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient: 0% to 40% EtOAc in PE in 30 mins) to afford tert-butyl 3-(2,2-difluoro-1-hydroxyethyl)-3-nitropiperidine-1-carboxylate (300-1). LC-MS: [M+H]$^+$=311.1

A solution of tert-butyl 3-(2,2-difluoro-1-hydroxyethyl)-3-nitropiperidine-1-carboxylate (300-1) (2.0 g, 6.45 mmol) in BAST (20 mL) was stirred at 60° C. for 4 hours under N$_2$ atmosphere. The reaction mixture was diluted with water, extracted with EtOAc, the combined organic phase was washed with water, sat. NaHCO$_3$ solution, brine, dried over sodium sulfate, concentrated to give a crude product. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The crude product was purified by flash chromatography (elution gradient: 0% to 30% EtOAc in PE in 30 mins) to afford tert-butyl 3-nitro-3-(1,2,2-trifluoroethyl)piperidine-1-carboxylate (300-2). LC-MS: [M+H]$^+$=313.1

To a solution of tert-butyl 3-nitro-3-(1,2,2-trifluoroethyl)piperidine-1-carboxylate (300-2) (1.36 g, 4.35 mmol) in EtOH (30 mL) and water (15 mL), was added Fe (2.432 g, 43.5 mmol) and NH$_4$Cl (1.165 g, 21.77 mmol), the reaction mixture was stirred at 60° C. for 18 h under N$_2$ atmosphere. The reaction mixture was filtered and the filtrate was diluted with water, extracted with EtOAc (30 ml*3), the combined organic phase was washed with water (20 ml), brine (20 ml), dried over anhydrous sodium sulfate, concentrated in vacuum to give a residue. The crude product was purified by flash chromatography (elution gradient: 0% to 50% EtOAc in PE in 30 mins) to afford tert-butyl 3-amino-3-(1,2,2-trifluoroethyl)piperidine-1-carboxylate (300-3). LC-MS: [M+H]$^+$=283.2.

To a solution of tert-butyl 3-amino-3-(1,2,2-trifluoroethyl)piperidine-1-carboxylate (300-3) (700 mg, 2.480 mmol) in DCM (12 mL), was added TFA (4 mL), the reaction mixture was stirred at rt for 1 h under N$_2$ atmosphere. The reaction mixture was concentrated to give 3-(1,2,2-trifluoroethyl)piperidin-3-amine (300-4). LC-MS: [M+H]$^+$=183.2.

To a solution of methyl 2-(3,4-difluorophenyl)-5-fluoroisonicotinate (Intermediate A) (0.847 g, 3.17 mmol) and 3-(1,2,2-trifluoroethyl)piperidin-3-amine (300-4) (1.3 g, 3.17 mmol) in DMSO (30 mL) was added DIPEA (15 mL) at RT, the reaction mixture was stirred at 80° C. for 8 hr under N$_2$ atmosphere. The reaction mixture was diluted with water, extracted with EtOAc (20 ml*3), worked up under aqueous conditions, and concentrated in vacuum to give a residue. The crude product was purified by flash chromatography (elution gradient: 0% to 30% EtOAc in PE in 30 mins) to afford methyl 5-(3-amino-3-(1,2,2-trifluoroethyl)piperidin-1-yl)-2-(3,4-difluorophenyl)isonicotinate (300-5). LC-MS: [M+H]$^+$=430.1.

To a solution of methyl 5-(3-amino-3-(1,2,2-trifluoroethyl)piperidin-1-yl)-2-(3,4-difluorophenyl)isonicotinate (300-5) (0.65 g, 1.514 mmol) in THF (20 mL) and Methanol (20 mL), was added lithium chloride (1.284 g, 30.3 mmol) and sodium tetrahydroborate (1.145 g, 30.3 mmol) at RT, the reaction mixture was stirred at rt for 3 h under N$_2$ atmosphere. The reaction mixture was diluted with water, extracted with EtOAc (20 ml*3), the combined organic phase was washed with water (20 mL), brine (20 mL), dried over anhydrous sodium sulfate, concentrated in vacuum to give a residue. The crude product was purified by flash chromatography (elution gradient: 10% to 40% EtOAc in PE in 30 mins) to afford (5-(3-amino-3-(1,2,2-trifluoroethyl)piperidin-1-yl)-2-(3,4-difluorophenyl)pyridin-4-yl)methanol (Intermediate 300-6). LC-MS: [M+H]$^+$=402.2.

Intermediate 300-7

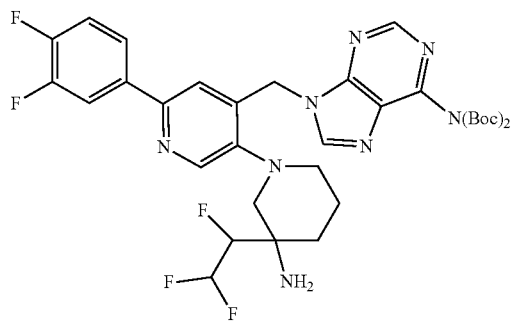

To a solution of (5-(3-amino-3-(1,2,2-trifluoroethyl)piperidin-1-yl)-2-(3,4-difluorophenyl)pyridin-4-yl)methanol (Intermediate 300-6) (500 mg, 1.246 mmol), Intermediate B (501 mg, 1.495 mmol) and triphenylphosphine (980 mg, 3.74 mmol) in THF (90 mL), was added DEAD (0.592 mL, 3.74 mmol) dropwise at 0° C., the reaction mixture was stirred at 0° C. for 0.5 hr under $N_2$ atmosphere. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The crude product was purified by flash chromatography (elution gradient: 0% to 10% MeOH in DCM in 50 mins) to afford Intermediate 300-7. LC-MS: $[M+H]^+$=719.2.

Intermediate 301-8: 3-amino-1-(4-(chloromethyl)-6-(3,4-difluorophenyl)pyridin-3-yl)-3-(2,2-difluoroethyl)piperidin-4-ol

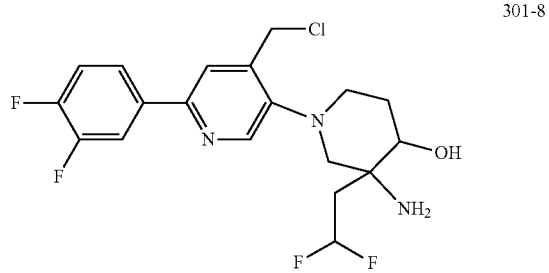 [SMILES: NC1(CC(F)F)CN(c2cnc(-c3ccc(F)c(F)c3)cc2CCl)CCC1O]

To a solution of LDA (6.94 mL, 13.88 mmol) in THF (9 mL) was added a solution of 1-(tert-butyl) 3-methyl 4-hydroxypiperidine-1,3-dicarboxylate (1.5 g, 5.78 mmol) in THF at −78° C. under $N_2$ atmosphere, after stirred for 10 min at this temperature, a solution of 1,1-difluoro-2-iodoethane (1.443 g, 7.52 mmol) in HMPA (5 mL, 28.7 mmol) was added −15° C., the reaction mixture was stirred at RT for 30 mins under $N_2$ atmosphere. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient: 0% to 30% EtOAc in PE in 30 mins) to afford 1-(tert-butyl) 3-methyl 3-(2,2-difluoroethyl)-4-hydroxypiperidine-1,3-dicarboxylate (301-1). LC-MS: $[M+H]^+$=324.1.

To a solution of 1-(tert-butyl) 3-methyl 3-(2,2-difluoroethyl)-4-hydroxypiperidine-1,3-dicarboxylate (301-1) (0.6 g, 1.856 mmol) in methanol (5 mL) was added a solution of LiOH (700 mg, 29.2 mmol) in Water (5 mL) at RT under $N_2$ atmosphere, the reaction was stirred at RT for 5 hr. The pH of the reaction mixture was adjusted to 4 by addition of 3M HCl solution, extracted with EtOAc (20 ml*3), the combined organic phase was washed with water (20 ml), brine (20 ml), dried over anhydrous sodium sulfate, concentrated in vacuum to give crude 1-(tert-butoxycarbonyl)-3-(2,2-difluoroethyl)-4-hydroxypiperidine-3-carboxylic acid (301-2). LC-MS: $[M+H]^+$=310.1.

To a solution of 1-(tert-butoxycarbonyl)-3-(2,2-difluoroethyl)-4-hydroxypiperidine-3-carboxylic acid (301-2) (0.4 g, 1.293 mmol) in Toluene (10 mL) was added DPPA (0.534 g, 1.940 mmol) and TEA (0.721 mL, 5.17 mmol) at RT under $N_2$ atmosphere, the reaction was stirred at 100° C. for 18 hr. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient: 0% to 50% EtOAc in PE in 30 mins) to afford tert-butyl 3a-(2,2-difluoroethyl)-2-oxohexahydrooxazolo[4,5-c]pyridine-5(4H)-carboxylate (303-3). $^1$H NMR (400 MHz, DMSO-$d_6$) δ 8.12 (s, 1H), 6.43-5.89 (m, 1H), 4.41-4.15 (m, 2H), 4.13 (dt, J=12.9, 2.5 Hz, 1H), 3.03-2.75 (m, 2H), 2.03-1.74 (m, 4H), 1.39 (s, 9H). LC-MS: $[M+H]^+$=307.1.

To a solution of tert-butyl 3a-(2,2-difluoroethyl)-2-oxohexahydrooxazolo[4,5-c]pyridine-5(4H)-carboxylate (301-3) (400 mg, 1.306 mmol) in DCM (9 mL) was added TFA (3 mL, 38.9 mmol) at RT under $N_2$ atmosphere, the reaction was stirred at RT for 1 hr. The reaction mixture was concentrated in vacuum to give crude 3a-(2,2-difluoroethyl)hexahydrooxazolo[4,5-c]pyridin-2(3H)-one (301-4). LC-MS: $[M+H]^+$=207.1.

To a solution of methyl 2-(3,4-difluorophenyl)-5-fluoroisonicotinate (Intermediate A) (259 mg, 0.970 mmol) and 3a-(2,2-difluoroethyl)hexahydrooxazolo[4,5-c]pyridin-2(3H)-one (301-4) in DMSO (10 mL) was added DIPEA (10 mL, 57.3 mmol) at RT under $N_2$ atmosphere, the reaction was stirred at 120° C. for 18 hr. The reaction mixture was diluted with water, extracted with EtOAc (20 ml*3), the combined organic phase was washed with water (20 ml*3), brine (20 ml), dried over anhydrous sodium sulfate, concentrated in vacuum to give a residue. The residue was purified by flash chromatography (elution gradient: 0% to 10% MeOH in DCM in 30 mins) to afford methyl 5-(3a-(2,2-difluoroethyl)-2-oxohexahydrooxazolo[4,5-c]pyridin-5(4H)-yl)-2-(3,4-difluorophenyl)isonicotinate (301-5). LC-MS: $[M+H]^+$=454.1.

To a solution of methyl 5-(3a-(2,2-difluoroethyl)-2-oxohexahydrooxazolo[4,5-c]pyridin-5(4H)-yl)-2-(3,4-difluorophenyl)isonicotinate (301-5) (40 mg, 0.088 mmol) in THF (5 ml) and Methanol (5 ml) was added LiCl (74.8 mg, 1.764 mmol) and $NaBH_4$ (33.4 mg, 0.882 mmol) at RT under $N_2$ atmosphere, the reaction was stirred at RT for 5 hr. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient: 0% to 10% MeOH in DCM in 30 mins) to afford 3a-(2,2-difluoroethyl)-5-(6-(3,4-difluorophenyl)-4-(hydroxymethyl)pyridin-3-yl)hexahydrooxazolo[4,5-c]pyridin-2(3H)-one (301-6). LC-MS: $[M+H]^+$=426.2.

To a solution of 3a-(2,2-difluoroethyl)-5-(6-(3,4-difluorophenyl)-4-(hydroxymethyl)pyridin-3-yl)hexahydrooxazolo[4,5-c]pyridin-2(3H)-one (301-6) (100 mg, 0.235 mmol) in MeOH (10 mL) and Water (10 mL) was added KOH (132 mg, 2.351 mmol) at RT under $N_2$ atmosphere, the reaction was stirred at 100° C. for 18 hr. The reaction mixture was diluted with water, extracted with EtOAc (20 ml*3), the combined organic phase was washed with water (20 ml), brine (20 ml), dried over anhydrous sodium sulfate, concentrated in vacuum to give a residue. The residue was purified by flash chromatography (elution gradient 0% to 10% MeOH in DCM in 30 mins) to afford 3-amino-3-(2,2-difluoroethyl)-1-(6-(3,4-difluorophenyl)-4-(hydroxymethyl)pyridin-3-yl)piperidin-4-ol (301-7). LC-MS: $[M+H]^+$= 400.1.

To a solution of 3-amino-3-(2,2-difluoroethyl)-1-(6-(3,4-difluorophenyl)-4-(hydroxymethyl)pyridin-3-yl)piperidin-4-ol (301-7) (130 mg, 0.325 mmol) in DCM (10 mL) was added thionyl chloride (0.119 mL, 1.627 mmol) at 0° C. under $N_2$ atmosphere, the reaction was stirred at RT for 5 hr. The reaction was quenched with 5 ml of sat. $K_2CO_3$ aqueous solution at 0° C. The reaction mixture was extracted with DCM (20 ml*3), the combined organic phase was washed with water (20 mL), brine (20 mL), dried over anhydrous sodium sulfate, concentrated in vacuum to give crude 3-amino-1-(4-(chloromethyl)-6-(3,4-difluorophenyl)pyridin-3-yl)-3-(2,2-difluoroethyl)piperidin-4-ol (Intermediate 301-8). LC-MS: $[M+H]^+=418.1$.

Intermediate 302-9: 3-amino-3-(6-chloropyridin-2-yl)-1-(6-(3,4-difluorophenyl)-4-(hydroxymethyl)pyridin-3-yl)piperidin-4-ol

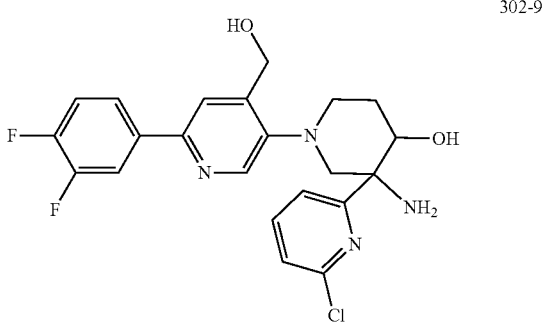 [SMILES: NC1(c2cccc(Cl)n2)CN(c2cnc(-c3ccc(F)c(F)c3)cc2CO)CCC1O]

302-9

To a solution of m-CPBA (23.17 g, 94 mmol) and 2-chloro-6-iodopyridine (15 g, 62.6 mmol) in DCM (450 mL) was added TfOH (22.25 mL, 251 mmol) dropwise at 0° C. And then the reaction mixture was stirred at RT for 2 hr, mesitylene (9.54 mL, 68.9 mmol) was added dropwise at 0° C., the reaction mixture was stirred at RT for 18 hr under $N_2$ atmosphere. The solvent was removed in vacuo to give a crude product. The crude product was recrystallized in $Et_2O$ at −20° C. to afford (6-chloropyridin-2-yl)(mesityl)iodonium trifluoromethanesulfonate (302-1). LC-MS: $[M+H]^+=358$.

To a solution of 1-tert-butyl 3-methyl 4-oxopiperidine-1,3-dicarboxylate (1.3 g, 5.05 mmol) in DMF (30 mL) was added potassium tert-butoxide (0.680 g, 6.06 mmol) at RT, after the reaction mixture was stirred at RT for 10 mins, (6-chloropyridin-2-yl)(mesityl)iodonium trifluoromethanesulfonate (intermediate 302-1) (3.52 g, 5.56 mmol) was added at rt, the reaction mixture was stirred at rt for 18 hr under $N_2$ atmosphere. The reaction mixture was diluted with water, extracted with EtOAc, the combined organic phase was washed with water, brine, dried over sodium sulfate, concentrated to give a crude product. The crude product was purified by flash chromatography (elution gradient: 0% to 30% EtOAc in Hexane in 30 mins) to afford 1-(tert-butyl) 3-methyl 3-(6-chloropyridin-2-yl)-4-oxopiperidine-1,3-dicarboxylate (302-2). LC-MS: $[M+H]^+=369.0$ To a solution of 1-(tert-butyl) 3-methyl 3-(6-chloropyridin-2-yl)-4-oxopiperidine-1,3-dicarboxylate (intermediate 302-2) (1.0 g, 2.71 mmol) in MeOH (30 mL) was added sodium tetrahydroborate (0.205 g, 5.42 mmol) at 0° C., the reaction mixture was stirred at 0° C. for 30 mins. The reaction mixture was diluted with water, extracted with EtOAc, the combined organic phase was washed with water, brine, dried over sodium sulfate, concentrated to give a crude product. The crude product was purified by flash chromatography (elution gradient: 0% to 30% EtOAC in Hexane in 30 mins) to afford 1-(tert-butyl) 3-methyl 3-(6-chloropyridin-2-yl)-4-hydroxypiperidine-1,3-dicarboxylate (302-3). LC-MS: $[M+H]^+=371.0$ To a solution of 1-(tert-butyl) 3-methyl 3-(6-chloropyridin-2-yl)-4-hydroxypiperidine-1,3-dicarboxylate (302-3) (0.9 g, 2.427 mmol) in methanol (5 mL) and water (5 mL) was added LiOH (0.581 g, 24.27 mmol) at RT, the reaction mixture was stirred at RT for 5 hr under $N_2$ atmosphere. The pH of reaction mixture was adjusted to 4 by addition of 5M HCl aqueous solution, extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford 1-(tert-butoxycarbonyl)-3-(6-chloropyridin-2-yl)-4-hydroxypiperidine-3-carboxylic acid (302-4). LC-MS: $[M+H]^+=357.1$.

To a solution of 1-(tert-butoxycarbonyl)-3-(6-chloropyridin-2-yl)-4-hydroxypiperidine-3-carboxylic acid (302-4) (0.8 g, 2.242 mmol) in toluene (20 mL) and was added DPPA (0.926 g, 3.36 mmol) and TEA (1.250 mL, 8.97 mmol) at RT, after the reaction mixture was stirred at 100° C. for 3 h under $N_2$ atmosphere, methanol (0.091 mL, 2.242 mmol) was added, the reaction mixture was stirred at 100° C. for 18 hr under $N_2$ atmosphere. The reaction mixture was diluted with water, extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford tert-butyl 3a-(6-chloropyridin-2-yl)-2-oxohexahydrooxazolo[4,5-c]pyridine-5(4H)-carboxylate (302-5). LC-MS: $[M+H]^+=354.1$.

To a solution of tert-butyl 3a-(6-chloropyridin-2-yl)-2-oxohexahydrooxazolo[4,5-c]pyridine-5(4H)-carboxylate (302-5) (400 mg, 0.113 mmol) in DCM (9 mL) and was added TFA (3 ml) at rt, the reaction mixture was stirred at rt for 3 h. The reaction mixture was concentrated to give crude 3a-(6-chloropyridin-2-yl)hexahydrooxazolo[4,5-c]pyridin-2(3H)-one (302-6). LC-MS: $[M+H]^+=254.1$ To a solution of methyl 2-(3,4-difluorophenyl)-5-fluoroisonicotinate (Intermediate A) (87 mg, 0.326 mmol) and 3a-(6-chloropyridin-2-yl)hexahydrooxazolo[4,5-c]pyridin-2(3H)-one (302-6) (120 mg, 0.326 mmol) in DMSO (5 mL), was added DIPEA (5 mL), the reaction mixture was stirred at 100° C. for 5 hr under $N_2$ atmosphere. The reaction mixture was diluted with water, extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford methyl 5-(3a-(6-chloropyridin-2-yl)-2-oxohexahydrooxazolo[4,5-c]pyridin-5(4H)-yl)-2-(3,4-difluorophenyl)isonicotinate (302-7). LC-MS: $[M+H]^+=501.1$ To a solution of methyl 5-(3a-(6-chloropyridin-2-yl)-2-oxohexahydrooxazolo[4,5-c]pyridin-5(4H)-yl)-2-(3,4-difluorophenyl)isonicotinate (302-7) (70 mg, 0.140 mmol) in methanol (5 mL) and THF (5 mL), was added lithium chloride (59.2 mg, 1.398 mmol) and sodium tetrahydroborate (52.9 mg, 1.398 mmol), the reaction mixture was stirred at rt for 5 hr under $N_2$ atmosphere. The reaction mixture was diluted with water, extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford 3a-(6-chloropyridin-2-yl)-5-(6-(3,4-difluorophenyl)-4-(hydroxymethyl)pyridin-3-yl)hexahydrooxazolo[4,5-c]pyridin-2(3H)-one (302-8). LC-MS: [M+H]⁺=473.1.

To a solution of 3a-(6-chloropyridin-2-yl)-5-(6-(3,4-difluorophenyl)-4-(hydroxymethyl)pyridin-3-yl)hexahydrooxazolo[4,5-c]pyridin-2(3H)-one (302-8) (50 mg, 0.106 mmol) in methanol (5 mL) and was added a solution of KOH (59.3 mg, 1.057 mmol) in Water (5 ml) at rt, the reaction mixture was stirred at 100° C. for 8 hr under N₂ atmosphere. The reaction mixture was diluted with water, extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford 3-amino-3-(6-chloropyridin-2-yl)-1-(6-(3,4-difluorophenyl)-4-(hydroxymethyl)pyridin-3-yl)piperidin-4-ol (Intermediate 302-9). LC-MS: [M+H]⁺= 447.1

Intermediate 303-3:
3-(2,2,2-trifluoroethyl)piperidin-3-amine

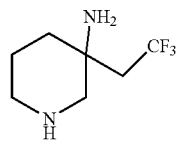

303-3

Togni reagent (6.42 g, 19.46 mmol) and tetrakis(acetonitrile)copper(I) hexafluorophosphate (483 mg, 1.297 mmol) were dissolved in DMA (50 ml) under N₂. Then reagent 1 (3 g, 12.97 mmol) and TMSN₃ (2.99 g, 25.9 mmol) was added. The mixture was stirred at rt overnight. The mixture was treated with EA (50 ml) and H₂O (50 ml). The layers were separated and the aqueous layer was extracted with EA (30 ml*3). The combined organic layers were washed with brine (20 ml), dried over Na₂SO₄ and filtered. The filtrate was concentrated and the residue was purified, eluting with EA in n-hexane (0 to 20%) to give benzyl 3-azido-3-(2,2,2-trifluoroethyl)piperidine-1-carboxylate (303-1). ¹H NMR (400 MHz, CDCl₃ 7.31-7.51 (m, 1H), 5.03-5.34 (m, 1H), 3.86 (d, J=12.80 Hz, 1H), 3.20 (d, J=13.55 Hz, 1H), 2.39 (br. s., 1H), 1.92-2.01 (m, 1H), 1.81 (d, J=9.54 Hz, 2H)), 1.54-1.72 (m, 1H).

To a solution of benzyl 3-azido-3-(2,2,2-trifluoroethyl) piperidine-1-carboxylate (303-1) (1.3 g, 0.15 mmol) in MeOH (20 ml) was added indium powder (1.3 g, 11.4 mmol) and NH₄Cl (0.609 g, 11.38 mmol). The mixture was heated to reflux under a sealed tube for 2 hrs. The mixture was cooled to rt and filtered. The filtrate was concentrated. The residue was purified via prep. HPLC to give benzyl 3-amino-3-(2,2,2-trifluoroethyl)piperidine-1-carboxylate TFA salt (303-2). LC-MS: [M+H]⁺=316.9.

To a solution of benzyl 3-amino-3-(2,2,2-trifluoroethyl) piperidine-1-carboxylate (303-2) (500 mg, 1.58 mmol) in MeOH (40 ml) was added Pd(OH)₂ (222 mg, 1.581 mmol) under N₂. The mixture was then stirred under H₂ balloon for 3 hr. The mixture was filtered and the filtrate was concentrated to 3-(2,2,2-trifluoroethyl)piperidin-3-amine (Intermediate 303-3). ¹H NMR (CDCl₃) δ: 3.57-3.35 (m, 4H), 3.02-2.84 (m, 2H), 2.43 (q, J=11.1 Hz, 2H), 2.25 (dddd, J=17.3, 13.2, 8.6, 4.2 Hz, 1H), 1.96 (d, J=13.1 Hz, 1H), 1.84-1.59 (m, 2H) LC-MS: [M+H]⁺=183.0.

Intermediate 304-7: Methyl (1-(6-(3,4-difluorophenyl)-4-(hydroxymethyl)pyridin-3-yl)-3-ethynylpiperidin-3-yl)carbamate

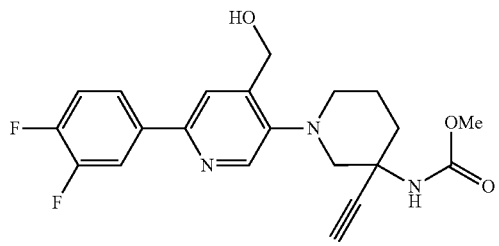

304-7

To a solution of 1-benzyl 3-ethyl 3-formylpiperidine-1,3-dicarboxylate (6.5 g, 20.4 mmol, 1.0 eq.) and dimethyl (1-diazo-2-oxopropyl)phosphonate (7.8 g, 40.8 mmol, 2.0 eq.) in dry methanol (120 mL) was added K₂CO₃ (8.5 g, 61.2 mmol, 3.0 eq.). The mixture was stirred at 1~7° C. for 18 h, filtered and the filtrate was concentrated. The residue was purified by flash chromatography (PE/EA=70/30) to give 1-benzyl 3-methyl 3-ethynylpiperidine-1,3-dicarboxylate (304-1). ¹H NMR (CDCl₃ 400 MHz): δ 7.48-7.28 (m, 5H), 5.14 (s, 2H), 4.25-4.09 (m, 1H), 4.00-3.84 (m, 1H), 3.73 (s, 3H), 3.48 (d, J=12.8 Hz, 1H), 3.14-2.97 (m, 1H), 2.20 (s, 1H), 2.06-1.80 (m, 3H), 1.64-1.60 (m, 1H).

To a solution of 1-benzyl 3-methyl 3-ethynylpiperidine-1,3-dicarboxylate (intermediate 304-1) (3.1 g, 10.3 mmol, 1.0 eq.) in THF (50 mL) and water (15 mL) was added LiOH·H₂O (1.7 g, 41.1 mmol, 4.0 eq.). The mixture was stirred at 50° C. for 2 h. The mixture was diluted with water (100 mL), extracted with EA (80 mL). The aqueous layer was acidified to pH=2 with 1 N HCl (aq.). The suspension was extracted with DCM (80 mL*2), dried over Na₂SO₄, concentrated to give crude 1-((benzyloxy)carbonyl)-3-ethynylpiperidine-3-carboxylic acid (304-2). ¹H NMR (CDCl₃ 400 MHz): δ 10.03 (brs, 1H), 7.40-7.31 (m, 5H), 5.17 (s, 2H), 4.29-4.16 (m, 1H), 4.02-3.88 (m, 1H), 3.49 (d, J=12 Hz, 1H), 3.15-2.98 (m, 1H), 2.24 (s, 1H), 2.12-2.06 (m, 1H), 2.04-1.92 (m, 2H), 1.67-1.64 (m, 1H).

To a solution of 1-((benzyloxy)carbonyl)-3-ethynylpiperidine-3-carboxylic acid (304-2) (2.7 g, 9.4 mmol, 1.0 eq.) in DCM (125 mL) was added NH₄Cl (1 g, 18.8 mmol, 2.0 eq.), HATU (7.1 g, 18.8 mmol, 2.0 eq.) and DIEA (4.9 g, 37.6 mmol, 4 eq.). The resulting mixture was stirred at 25° C. for 16 h. The mixture was washed with water (100 mL) and brine (150 mL), dried over Na₂SO₄, concentrated. The residue was purified by flash chromatography (PE/EA=50/50) to give benzyl 3-carbamoyl-3-ethynylpiperidine-1-carboxylate (304-3). ¹H NMR (400 MHz, CDCl₃): δ 7.35-7.21 (m, 5H), 6.68-6.59 (d, J=36.8 Hz, 1H), 5.87 (s, 1H), 5.11-5.01 (m, 2H), 4.25-4.02 (m, 2H), 3.20-3.14 (m, 1H), 2.89-2.64 (m, 1H), 2.26 (d, J=20.8 Hz, 1H), 2.12-1.71 (m, 3H), 1.57 (d, J=10 Hz, 1H).

To a solution of benzyl 3-carbamoyl-3-ethynylpiperidine-1-carboxylate (304-3) (2.5 g, 8.7 mmol, 1.0 eq.) in methanol (100 mL) was added KOH (1.2 g, 21.8 mmol, 2.5 eq.). Then PhI(OAc)₂ (2.8 g, 8.7 mmol, 1.0 eq.) was added. The resulting mixture was stirred at 3-10° C. for 30 min. The color turned from colorless to yellow. The reaction was concentrated, diluted with water (150 mL), extracted with EA (100 mL*2), dried over Na₂SO₄ and concentrated. The residue was purified by flash chromatography (PE/EA=70/

30) to give benzyl 3-ethynyl-3-((methoxycarbonyl)amino) piperidine-1-carboxylate (304-4). ¹H NMR (400 MHz, CD₃OD): δ 7.48-7.30 (m, 5H), 5.20-4.86 (m, 3H), 4.13-3.83 (m, 2H), 3.65 (s, 3H), 3.51-3.22 (m, 2H), 2.69-2.30 (m, 2H), 1.95-1.64 (m, 3H).

A mixture of benzyl 3-ethynyl-3-((methoxycarbonyl) amino)piperidine-1-carboxylate (304-4) (800 mg, 2.53 mmol, 1.0 eq.) and TFA (10 mL) in DCM (10 mL) was stirred at 75° C. for 12 h. The mixture was concentrated and diluted with DCM (20 mL), poured into saturated NaHCO₃ solution (50 mL), extracted with CHCl₃/i-PrOH=3/1 (50 mL*4), dried over Na₂SO₄, concentrated to give crude methyl (3-ethynylpiperidin-3-yl)carbamate (304-5). LCMS: [M+H]⁺=182.9.

To a mixture of methyl (3-ethynylpiperidin-3-yl)carbamate (304-5) (600 mg, 2.53 mmol, 1.0 eq.) and methyl 2-(3,4-difluorophenyl)-5-fluoroisonicotinate (Intermediate A) (670 mg, 2.53 mmol, 1.0 eq.) in DMSO (10 mL) was added DIEA (2.3 g, 7.0 eq.). Then the mixture was stirred at 120° C. for 2.5 h. The mixture was cooled and diluted with water (100 mL), extracted with EA (50 mL*2), washed with brine (100 mL), dried over Na₂SO₄, concentrated. The residue was purified by flash chromatography (PE/EA=10/1 to 70/30) to give methyl 2-(3,4-difluorophenyl)-5-(3-ethynyl-3-((methoxycarbonyl)amino)piperidin-1-yl)isonicotinate (304-6). LCMS: [M+H]⁺=430.2.

To a solution of methyl 2-(3,4-difluorophenyl)-5-(3-ethynyl-3-((methoxycarbonyl)amino) piperidin-1-yl)isonicotinate (intermediate 304-6) (280 mg, 0.652 mmol, 1.0 eq.) in dry THF (12 mL) was added L-selectride (3.9 mL) dropwise at 0° C. under N₂. The solution was stirred at 0° C. for 30 min. The mixture was quenched with saturated NH₄Cl solution (30 mL) and diluted with water (100 mL), extracted with EA (50 mL*2), dried over Na₂SO₄, concentrated. The residue was purified by flash chromatography (PE/EA=1/1) to give methyl (1-(6-(3,4-difluorophenyl)-4-(hydroxymethyl)pyridin-3-yl)-3-ethynylpiperidin-3-yl)carbamate (Intermediate 304-7). LCMS: 402.1 [M+H]⁺=402.1.

Intermediate 305-5:
3-(difluoromethyl)piperidin-3-amine

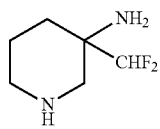

305-5

To a solution of 1-benzyl 3-ethyl 3-formylpiperidine-1,3-dicarboxylate (7.0 g, 21.9 mmol, 1.0 eq.) in DCM (100 mL) at 0° C. under N₂ atmosphere was added DAST (14.1 g, 87.8 mmol, 4.0 eq.) dropwise. The reaction was allowed to warm to 10° C. and stirred for 16 h. The reaction was cooled to 0° C. and quenched with aq·NaHCO₃ (100 mL) carefully. The mixture was extracted with DCM (50 mL×3). The combined organic layers were dried over Na₂SO₄, filtered and concentrated in vacuo. The residue was purified by silica gel column (PE/EA=10/1) to afford 4.0 g crude product, which was further purified by prep-HPLC (0.1% TFA as additive) to give 1-benzyl 3-ethyl 3-(difluoromethyl)piperidine-1,3-dicarboxylate (305-1). ¹H NMR (400 MHz, CDCl₃): δ 7.45-7.28 (m, 5H), 5.89 (t, J=15.2 Hz, 1H), 5.16 (s, 2H), 4.55-4.37 (m, 1H), 4.27-4.05 (m, 2H), 4.04-3.87 (m, 1H), 3.28-3.10 (m, 1H), 3.05-2.90 (m, 1H), 2.25-2.10 (m, 1H), 1.80-1.60 (m, 3H), 1.30-1.12 (m, 3H).

To a mixture of 1-benzyl 3-ethyl 3-(difluoromethyl)piperidine-1,3-dicarboxylate (305-1) (2.6 g, 7.62 mmol, 1 eq.) in THF (10 mL), MeOH (10 mL) and H₂O (10 mL) was added LiOH·H₂O (3.2 g, 76.2 mmol, 10 eq.). The reaction was stirred at 40° C. for 16 h. The reaction mixture was cooled and acidified to pH=3 with 6M HCl, then extracted with DCM (30 mL×3). The combined organic layers were washed with brine (50 mL), dried over Na₂SO₄, filtered and concentrated to give 1-((benzyloxy)carbonyl)-3-(difluoromethyl)piperidine-3-carboxylic acid (305-2). 1H NMR (400 MHz, CDCl₃): δ 7.45-7.25 (m, 5H), 5.93 (t, J=15.6 Hz, 1H), 5.17 (s, 2H), 4.55-4.42 (m, 1H), 4.05-3.95 (m, 1H), 3.25-3.15 (m, 1H), 3.05-2.95 (m, 1H), 2.28-2.15 (m, 1H), 1.85-1.68 (m, 3H). LCMS: [M+H]⁺=314.

To a mixture of 1-((benzyloxy)carbonyl)-3-(difluoromethyl)piperidine-3-carboxylic acid (305-2) (3.4 g, 10.9 mmol, 1.0 eq.) and Et₃N (2.2 g, 21.72 mmol, 2.0 eq.) in toluene (50 mL) under N₂ atmosphere was added DPPA (3.3 g, 11.9 mmol, 1.1 eq.). The reaction was heated and stirred at 60° C. for 3 h. The reaction mixture was cooled and diluted with EtOAc (100 mL), then washed with H₂O (50 mL×2). The organic layer was dried over Na₂SO₄, filtered and concentrated to give the crude benzyl 3-(difluoromethyl)-3-isocyanatopiperidine-1-carboxylate (305-3).

To a solution of benzyl 3-(difluoromethyl)-3-isocyanatopiperidine-1-carboxylate (305-3) (3.4 g, 10.9 mmol, 1.0 eq.) in dioxane (10 mL) was added 6M HCl (10 mL). The reaction was stirred at 40° C. for 16 h. The reaction mixture was concentrated to remove dioxane, then diluted with H₂O (20 mL) and extracted with EtOAc (20 mL). The aqueous phase was basified to pH=10 with aq. NaOH. The mixture was extracted with DCM (50 mL×3). The combined organic layers were dried over Na₂SO₄, filtered and concentrated to give benzyl 3-amino-3-(difluoromethyl)piperidine-1-carboxylate (305-4). ¹H NMR (400 MHz, CDCl₃): δ 7.45-7.28 (m, 5H), 5.56 (t, J=16.0 Hz, 1H), 5.15 (s, 2H), 3.88-3.80 (m, 1H), 3.65-3.50 (m, 1H), 3.35-3.00 (m, 2H), 1.87-1.65 (m, 4H), 1.30-1.15 (m, 2H). LCMS: [M+H]⁺=285.

A mixture of benzyl 3-amino-3-(difluoromethyl)piperidine-1-carboxylate (intermediate 305-4) (1.8 g, 6.33 mmol, 1 eq.) and Pd/C (10%, 1.5 g) in EtOH (36 mL) was hydrogenated under H₂ balloon for 3 h. The reaction mixture was filtered and the filtrate was concentrated to dryness to give 3-(difluoromethyl)piperidin-3-amine (Intermediate 305-5). ¹H NMR (400 MHz, CD₃OD): δ 5.68 (t, J=16.4 Hz, 1H), 5.15 (s, 2H), 2.88-2.75 (m, 1H), 2.80-2.65 (m, 1H), 2.63-2.52 (m, 2H), 1.80-1.65 (m, 2H), 1.62-1.51 (m, 2H).

Intermediate 306-9: tert-butyl (tert-butoxycarbonyl) (9-((5-((3R,5R)-3-((tert-butoxycarbonyl)amino)-5-(fluoromethyl)piperidin-1-yl)-2-(3-fluoro-4-methoxyphenyl)pyridin-4-yl)methyl)-9H-purin-6-yl) carbamate

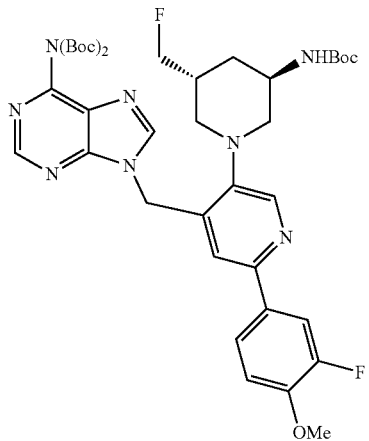

A mixture of ethyl 5-bromonicotinate (20.0 g, 86.9 mmol, 1 eq.), NH$_2$Boc (12.2 g, 104 mmol, 1.2 eq.), Xant-Phos (1.60 g, 2.77 mmol, 0.03 eq.), Pd$_2$(dba)$_3$ (1.60 g, 1.75 mmol, 0.02 eq.) and Cs$_2$CO$_3$ (40.0 g, 123 mmol, 1.4 eq.) and dioxane (300 mL) was stirred at 110° C. under N$_2$ atmosphere for 16 h. Then the reaction mixture was concentrated to dryness. Water (800 mL) was added and the reaction mixture was extracted with EtOAc (300 mL*2). The combined organic layers were dried over anhydrous sodium sulfate, filtered and concentrated in vacuo. The residue was purified by combi flash (EtOAc/PE=0-40%) to give ethyl 5-((tert-butoxycarbonyl)amino)nicotinate (306-1). $^1$H NMR (400 MHz, CDCl$_3$): δ 8.89 (d, J=2.0 Hz, 1H), 8.72 (d, J=2.8 Hz, 1H), 8.47 (s, 1H), 6.99 (brs, 1H), 4.41 (q, J=7.6 Hz, 2H), 1.54 (s, 9H), 1.40 (t, J=7.2 Hz, 3H).

To a solution of LAH (3.05 g, 80.3 mmol, 1.6 eq.) in THF (200 mL) was added dropwise a solution of ethyl 5-((tert-butoxycarbonyl)amino)nicotinate (306-1) (13.5 g, 50.7 mmol, 1 eq.) in THF (200 mL) at 0° C. After addition, the reaction mixture was stirred at about 0° C. for 2 h. The reaction mixture was carefully quenched with water (3 mL), 10% NaOH (3 mL) and water (10 mL). The reaction mixture was filtered and the filtrate was concentrated to dryness. The residue was purified by combi flash (EtOAc/PE=0-100%) to give tert-butyl (5-(hydroxymethyl)pyridin-3-yl)carbamate (306-2). $^1$HNMR (400 MHz, CDCl$_3$): δ 8.33 (d, J=2.4 Hz, 1H), 8.22 (d, J=1.6 Hz, 1H), 8.01 (s, 1H), 7.23 (brs, 1H), 4.69 (s, 2H), 1.53 (s, 9H).

A mixture of tert-butyl (5-(hydroxymethyl)pyridin-3-yl) carbamate (intermediate 306-2) (10.0 g, 44.6 mmol, 1 eq.) and PtO$_2$ (3.0 g) in AcOH (3 mL) and EtOH (300 mL) was hydrogenated under H$_2$ atmosphere (50 psi) at 50° C. for 7 days. The reaction mixture was filtered and the filtrate was concentrated to dryness to give tert-butyl (5-(hydroxymethyl)piperidin-3-yl)carbamate (306-3). LC-MS: [M+H]$^+$=230.1

To a suspension of tert-butyl (5-(hydroxymethyl)piperidin-3-yl)carbamate (306-3) (10.0 g, impure, 1 eq.) and NaHCO$_3$ (10.9 g, 130 mmol, 3 eq.) in THF (100 mL) and H$_2$O (100 mL) was added dropwise CbzCl (8.20 g, 47.4 mmol, 1.1 eq.) at about 0° C. After addition, the reaction mixture was stirred at about 20° C. for 16 h. The reaction mixture was poured into water (400 mL) and extracted with EtOAc (200 mL*3). The combined organic layers were dried over Na$_2$SO$_4$, and concentrated to dryness. The residue was purified by combi flash (EtOAc/PE=0-70%) to give benzyl 3-((tert-butoxycarbonyl)amino)-5-(hydroxymethyl) piperidine-1-carboxylate (306-4). $^1$H NMR (400 MHz, CDCl$_3$): δ 7.40-7.25 (m, 5H), 5.25-5.05 (m, 2H), 4.80-4.10 (m, 3H), 3.65-3.40 (m, 4H), 2.60-2.45 (m, 1H), 2.15-2.00 (m, 1H), 1.98-1.65 (m, 2H), 1.43 (s, 9H), 1.15-1.00 (m, 1H). LC-MS: [M+Na]$^+$=387.1.

To a mixture of benzyl 3-((tert-butoxycarbonyl)amino)-5-(hydroxymethyl)piperidine-1-carboxylate (306-4) (3.50 g, 9.60 mmol, 1.0 eq.) in THF (60 mL) was added Et$_3$N (13.6 g, 134 mmol, 14.0 eq.), FSO$_2$(CF$_2$)$_3$CF$_3$ (5.80 g, 19.2 mmol, 2.0 eq.) and TEA·3HF (6.19 g, 38.4 mmol, 4.0 eq.). The reaction mixture was stirred at 25° C. for 12 hours. The reaction mixture was concentrated in vacuo. The residue was purified by silica gel column chromatography (Eluents: PE/EA 10/1 to 3/1) to give benzyl 3-((tert-butoxycarbonyl)amino)-5-(fluoromethyl)piperidine-1-carboxylate (306-5). LC-MS: [M+Na]$^+$=389.1.

To a solution of benzyl 3-((tert-butoxycarbonyl)amino)-5-(fluoromethyl)piperidine-1-carboxylate (306-5) (2.50 g, 6.83 mmol, 1.0 eq.) in MeOH (30 mL) was added Pd(OH)$_2$/C (250 mg, 10% wt). The reaction mixture was stirred at 25° C. for 1 hour. The mixture was filtered and the filtrate was concentrated in vacuo to give tert-butyl (5-(fluoromethyl)piperidin-3-yl)carbamate (305-6). LC-MS: [M+H]$^+$=233.1. To a solution of tert-butyl (5-(fluoromethyl)piperidin-3-yl)carbamate (306-6) (1.50 g, 6.51 mmol, 1.0 eq.) in DMSO (15 mL) was added DIEA (5.89 g, 45.6 mmol, 7.0 eq.) and methyl 5-fluoro-2-(3-fluoro-4-methoxyphenyl) isonicotinate (Intermediate D) (1.82 g, 6.51 mmol, 1.0 eq.). The reaction mixture was stirred at 120° C. under N$_2$ for 3 hours. The reaction mixture was diluted with water (100 mL) and extracted with EtOAc (20 mL×3). The combined organic layers were washed with brine (20 mL), dried over anhydrous sodium sulfate, filtered and concentrated in vacuo. The residue was purified by silica gel column chromatography (PE/EA 10/1 to 2/1) and further purified by prep-HPLC (0.05% NH$_3$·H$_2$O as additive) to afford methyl 5-((3R,5R)-3-((tert-butoxycarbonyl)amino)-5-(fluoromethyl)piperidin-1-yl)-2-(3-fluoro-4-methoxyphenyl)isonicotinate (306-7). $^1$H NMR (400 MHz, CD$_3$OD): δ 8.45 (s, 1H), 7.93 (s, 1H), 7.76-7.67 (m, 2H), 7.19 (t, J=8.4 Hz, 1H), 4.51 (d, J=6.0 Hz, 1H), 4.39 (d, J=6.0 Hz, 1H), 4.02 (s, 3H), 3.94 (s, 3H), 3.92-3.86 (m, 1H), 3.35-3.24 (m, 1H), 3.20-3.08 (m, 2H), 3.01-2.92 (m, 1H), 2.46-2.31 (m, 1H), 1.84-1.76 (m, 1H), 1.64-1.54 (m, 1H), 1.42-1.41 (m, 10H). LC-MS: [M+H]$^+$=492.2

To a mixture of methyl 5-((3R,5R)-3-((tert-butoxycarbonyl)amino)-5-(fluoromethyl)piperidin-1-yl)-2-(3-fluoro-4-methoxyphenyl)isonicotinate (306-7) (120 mg, 0.24 mmol, 1.0 eq.) and LiCl (102 mg, 2.44 mmol, 10 eq.) in THF (2 mL) and MeOH (2 mL) was added NaBH$_4$ (181 mg, 4.88 mmol, 20 eq.) in small portions. After addition, the mixture was stirred at 25° C. for 1 hour. Then water (20 mL) was added, and the mixture was extracted with EtOAc (10 mL×3). The combined organic phases were washed with brine (10 mL×2), dried over anhydrous Na$_2$SO$_4$, filtered and concentrated in vacuo to give tert-butyl ((3R,5R)-1-(6-(3-fluoro-4-methoxyphenyl)-4-(hydroxymethyl)pyridin-3-yl)-5-(fluoromethyl)piperidin-3-yl)carbamate (306-8). LC-MS: [M+H]$^+$=464.3

To a mixture of tert-butyl ((3R,5R)-1-(6-(3-fluoro-4-methoxyphenyl)-4-(hydroxymethyl)pyridin-3-yl)-5-(fluoromethyl)piperidin-3-yl)carbamate (intermediate 306-8) (100 mg, 0.22 mmol, 1.0 eq.), Intermediate B (109 mg, 0.32 mmol, 1.5 eq.), n-Bu₃P (66.0 mg, 0.32 mmol, 1.5 eq.) and THF (10 mL) was added DIAD (66.0 mg, 0.32 mmol, 1.5 eq.) dropwise. After addition, the mixture was stirred at 25° C. for 12 hours under N₂. The mixture was concentrated in vacuo. The residue was purified by silica gel column (PE/EA=5:1 to 1:1) to give tert-butyl (tert-butoxycarbonyl)(9-((5-((3R,5R)-3-((tert-butoxycarbonyl)amino)-5-(fluoromethyl)piperidin-1-yl)-2-(3-fluoro-4-methoxyphenyl)pyridin-4-yl)methyl)-9H-purin-6-yl)carbamate (Intermediate 306-9). LC-MS: [M+Na]⁺=803.4

Intermediate 311-11: Methyl 5-(3-(benzyl(methoxycarbonyl)amino)-2-((difluoromethoxy)methyl)piperidin-1-yl)-2-(3,4-difluorophenyl)isonicotinate 311-11

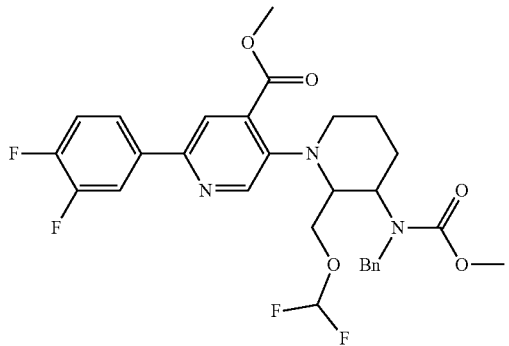

To a solution of 3-aminopicolinic acid (50 g, 360 mmol, 1.0 eq) in anhydrous MeOH (500 mL) was added conc·H₂SO₄ (106 g, 1090 mmol, 3.0 eq) dropwise. The reaction was stirred at 80° C. for 48 h. SOCl₂ (130 g, 1090 mmol, 3.0 eq) was added to the reaction and stirred at 80° C. for another 48 h. The reaction was concentrated and diluted with water (500 mL), basified with K₂CO₃(s) to PH=9, extracted with EA (500 mL×3), washed with brine (500 mL), dried over Na₂SO₄, concentrated to give methyl 3-aminopicolinate (311-1). ¹H NMR (400 MHz, CDCl₃) δ=8.04 (d, J=4.3 Hz, 1H), 7.20 (dd, J=4.3, 8.4 Hz, 1H), 7.04 (dd, J=1.3, 8.4 Hz, 1H), 5.76 (br s, 2H), 3.98-3.92 (m, 3H).

To a solution of methyl 3-aminopicolinate (311-1) (27 g, 180 mmol, 1.0 eq) and K₂CO₃ (48 g, 350 mmol, 2.0 eq) in MeCN (500 mL) was added methyl carbonochloridate (33 g, 350 mmol, 2.0 eq) at 20° C. for 18 h. The reaction mixture was diluted with water (500 mL), concentrated. The residue was acidified with 1N HCl to PH=3, extracted with EA (500 mL×3), washed with sat·NaHCO₃ (500 mL) and brine (300 mL), dried over Na₂SO₄, concentrated to give methyl 3-((methoxycarbonyl)amino)picolinate (311-2). ¹H NMR (400 MHz, CDCl₃) δ=10.39 (br s, 1H), 8.82 (dd, J=1.4, 8.7 Hz, 1H), 8.34 (dd, J=1.5, 4.4 Hz, 1H), 7.51-7.40 (m, 1H), 3.99 (s, 3H), 3.78 (s, 3H).

A solution of methyl 3-((methoxycarbonyl)amino)picolinate (intermediate 311-2) (22 g, 105 mmol, 1.0 eq) and PtO₂ (5 g, 23% wt) in AcOH (220 mL) was stirred at 25° C. and 5 MPa under H₂ for 144 h. The reaction mixture was filtered and concentrated to give methyl (2S,3R)-3-((methoxycarbonyl)amino)piperidine-2-carboxylate (311-3).

To a solution of methyl (2S,3R)-3-((methoxycarbonyl)amino)piperidine-2-carboxylate (311-3) (30 g, about 105 mmol, 1.0 eq) in THF (300 mL) was added TEA (53 g, 525 mmol, 5.0 eq) and Boc₂O (69 g, 315 mmol, 3.0 eq) at 20° C. for 18 h. The reaction mixture was concentrated and diluted with water (100 mL), acidified with 1 N HCl to PH=3, extracted with EA (100 mL×3), washed with brine (100 mL), dried over Na₂SO₄, concentrated. The residue was purified by combi-flash (EA %=0%-50%) to give 1-(tert-butyl) 2-methyl (2S,3R)-3-((methoxycarbonyl)amino)piperidine-1,2-dicarboxylate (311-4).

To a solution of 1-(tert-butyl) 2-methyl (2S,3R)-3-((methoxycarbonyl)amino)piperidine-1,2-dicarboxylate (311-4) (33 g, 104 mmol, 1.0 eq) in anhydrous THF (660 mL) was added LiAlH₄ (5.15 g, 136 mmol, 1.3 eq) at −78° C.~−10° C. for 2 h. The reaction mixture was poured into sat·NH₄Cl (700 mL), acidified with 1 N HCl to PH=5, extracted with EA (500 mL×3), washed with brine (500 mL), dried over Na₂SO₄, concentrated. The residue was purified by combi-flash (EA %=0%-70%) to give tert-butyl (2S,3R)-2-(hydroxymethyl)-3-((methoxycarbonyl)amino)piperidine-1-carboxylate (311-5). ¹H NMR (400 MHz, CDCl₃) δ: 5.70 (br s, 1H), 4.44 (br d, J=5.5 Hz, 1H), 3.92 (br d, J=10.9 Hz, 2H), 3.86-3.71 (m, 2H), 3.64 (br s, 3H), 2.98-2.64 (m, 2H), 1.92-1.80 (m, 1H), 1.73-1.63 (m, 1H), 1.61-1.50 (m, 2H), 1.44 (s, 9H). LC-MS: [M+H]⁺=289.2.

To a mixture of tert-butyl (2S,3R)-2-(hydroxymethyl)-3-((methoxycarbonyl)amino)piperidine-1-carboxylate (311-5) (5 g, 17 mmol, 1.0 eq), BnBr (12 g, 69 mmol, 1.0 eq) and TBAI (3.1 g, 9 mmol, 0.5 eq) in anhydrous THF (50 mL) was added NaH (2.6 g, 65 mmol, 3.8 eq) at 20° C.

After the addition, the reaction was stirred at 60° C. for 2 h. The reaction mixture was poured into a solution of sat·NH₄Cl (200 mL), extracted with EA (100 mL×3), washed with brine (50 mL), dried over Na₂SO₄, concentrated. The residue was purified by combi-flash (EA %=0%-50%) to give tert-butyl (2S,3R)-3-(benzyl(methoxycarbonyl)amino)-2-((benzyloxy)methyl)piperidine-1-carboxylate (311-6). ¹H NMR (400 MHz, CDCl₃) δ: 7.53-6.90 (m, 10H), 4.90-3.31 (m, 12H), 3.08-2.74 (m, 1H), 1.97-1.79 (m, 1H), 1.62-1.50 (m, 1H), 1.50-1.42 (m, 1H), 1.41-1.28 (m, 9H). LC-MS: [M+H]⁺=469.4.

A solution of tert-butyl (2S,3R)-3-(benzyl(methoxycarbonyl)amino)-2-((benzyloxy)methyl)piperidine-1-carboxylate (intermediate 311-6) (7.2 g, 15 mmol, 1.0 eq) in DCM (40 mL) and TFA (20 mL) was stirred at 20° C. for 20 h. The reaction mixture was diluted with H₂O (100 mL), basified with K₂CO₃(s) to PH=9, extracted with EA (100 mL×3), washed with brine, dried over Na₂SO₄, concentrated to give methyl benzyl((2S,3R)-2-((benzyloxy)methyl)piperidin-3-yl)carbamate (311-7). LC-MS: [M+H]⁺=369.5.

A mixture of methyl 2-(3,4-difluorophenyl)-5-fluoroisonicotinate (Intermediate A) (30 g, 0.112 mmol, 1.0 eq) and m-CPBA (30 g, 0.174 mmol, 1.55 eq) in CDCl₃ (500 mL) was stirred at 65° C. for 20 h. More m-CPBA (30 g, 0.174 mmol, 1.55 eq) was added to the reaction mixture and the reaction was stirred at 65° C. for 72 h. The reaction mixture was diluted with water (300 mL), basified with K₂CO₃(s) to PH=8, extracted with EA (300 mL×3), washed with brine (300 mL), dried over Na₂SO₄, and concentrated. The crude was purified by trituration with PE/MTBE=1/1 (100 mL) to give 2-(3,4-difluorophenyl)-5-fluoro-4-(methoxycarbonyl)pyridine 1-oxide (311-7A). LC-MS: [M+H]⁺=284.2.

To a mixture of methyl benzyl((2S,3R)-2-((benzyloxy)methyl)piperidin-3-yl)carbamate (311-7) (17 g, 0.06 mol, 4.0 eq) and 2-(3,4-difluorophenyl)-5-fluoro-4-(methoxycarbonyl)pyridine 1-oxide (311-7A) (6 g, about 15 mmol, 1.0 eq) in DIPEA (40 mL) and DMSO (40 mL) was stirred at 120° C. for 5 h. The reaction mixture was diluted with H₂O (100 mL), extracted with EA (50 mL×3), washed with brine (20 mL), dried over Na₂SO₄, concentrated. The residue was purified by combi-flash (EA %=10%-100%) to give 5-(3-(benzyl(methoxycarbonyl)amino)-2-((benzyloxy)methyl) piperidin-1-yl)-2-(3,4-difluorophenyl)-4-(methoxycarbonyl)pyridine 1-oxide (311-8). LCMS: [M+H]⁺=632.5.

To a mixture of 5-(3-(benzyl(methoxycarbonyl)amino)-2-((benzyloxy)methyl)piperidin-1-yl)-2-(3,4-difluorophenyl)-4-(methoxycarbonyl)pyridine 1-oxide (311-8) (5200 mg, about 4.69 mmol, 1.0 eq) and Pd(OH)₂ (2000 mg, 38% wt) in MeOH (25 mL) and EA (25 mL) was stirred at 60° C. and 50 Psi for 20 h. The reaction mixture was filtered and concentrated. The residue was purified by combi-flash (EA %=0%-60%) to give methyl 5-(3-(benzyl(methoxycarbonyl) amino)-2-((benzyloxy)methyl) piperidin-1-yl)-2-(3,4-difluorophenyl)isonicotinate (311-9). LCMS: [M+H]+=616.7.

To a mixture of methyl 5-(3-(benzyl(methoxycarbonyl) amino)-2-((benzyloxy)methyl)piperidin-1-yl)-2-(3,4-difluorophenyl)isonicotinate (311-9) (1500 mg, 2.44 mmol, 1.0 eq) and Pd(OH)₂ (1500 mg, 100% wt) in EA (45 mL) was stirred at 60° C. and 50 Psi for 18 h. The reaction mixture was filtered and concentrated. The residue was purified by combi-flash (EA %=0%-50%) to give methyl 5-(3-(benzyl (methoxycarbonyl)amino)-2-(hydroxymethyl)piperidin-1-yl)-2-(3,4-difluorophenyl)isonicotinate (311-10). LCMS: [M+H]⁺=526.5.

To a solution of methyl 5-(3-(benzyl(methoxycarbonyl) amino)-2-(hydroxymethyl)piperidin-1-yl)-2-(3,4-difluorophenyl)isonicotinate (311-10) (300 mg, 0.571 mmol) and CuI (21.74 mg, 0.114 mmol) in MeCN (10 mL), was added 2,2-difluoro-2-(fluorosulfonyl)acetic acid (0.113 mL, 1.142 mmol) dropwise at 55° C., the reaction mixture was stirred at 55° C. for 2 hr. The reaction mixture was diluted with EA, washed with water and brine. The organic layer was dried over Na₂SO₄ and concentrated under vacuum to give the crude product. The crude product was purified by flash chromatography (elution gradient:0% to 40% EtOAc in PE in 30 mins) to give methyl 5-(3-(benzyl(methoxycarbonyl) amino)-2-((difluoromethoxy)methyl)piperidin-1-yl)-2-(3,4-difluorophenyl)isonicotinate (Intermediate 311-11). LCMS: [M+H]+=576.3.

EXAMPLES

Example 1: (R)-9-((5-(3-aminopiperidin-1-yl)-2-(3-fluoro-4-methoxyphenyl)pyridin-4-yl)methyl)-9H-purin-6-amine

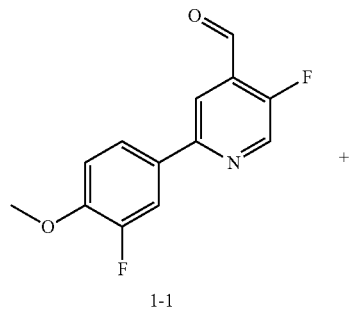

1-1

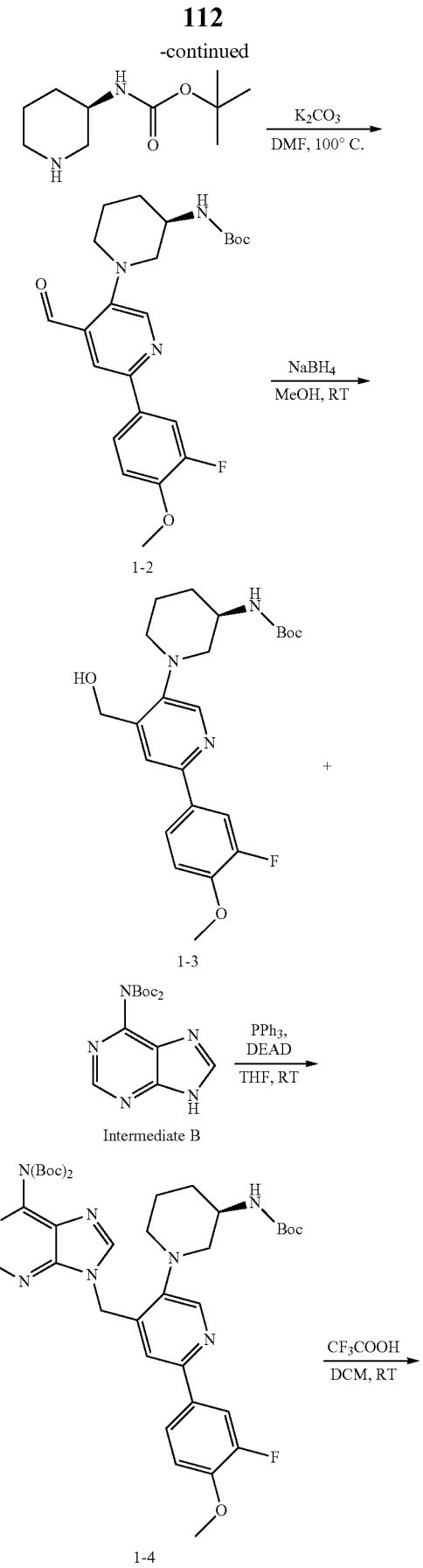

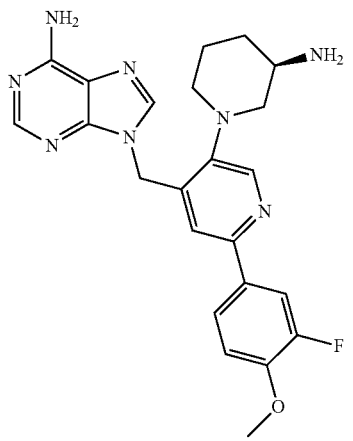

Example 1

A suspension of 5-fluoro-2-(3-fluoro-4-methoxyphenyl) isonicotinaldehyde (intermediate 1-1) (800 mg, 3.21 mmol), (R)-tert-butyl piperidin-3-ylcarbamate (643 mg, 3.21 mmol), and potassium carbonate (887 mg, 6.42 mmol) in DMF (15 mL) was stirred at 100° C. for 20 hr. The mixture was diluted with H$_2$O (30 mL), extracted with EtOAc (20 mL*3). The combined organic layers were washed with H$_2$O (20 mL*2), brine (20 mL), dried over anhydrous Na$_2$SO$_4$, filtered and concentrated in vacuo. The residue was purified by silica gel column chromatography (0-30% EtOAc in PE in 30 mins) to give tert-butyl (R)-(1-(6-(3-fluoro-4-methoxyphenyl)-4-formylpyridin-3-yl)piperidin-3-yl)carbamate (1-2). 1H NMR (400 MHz, DMSO-d6) δ 10.24 (s, 1H), 8.63 (s, 1H), 8.01 (s, 1H), 7.93-7.83 (m, 2H), 7.27 (t, J=8.8 Hz, 1H), 7.04 (d, J=7.5 Hz, 1H), 3.90 (s, 3H), 3.63 (s, 1H), 3.42-3.37 (m, 1H), 3.30-3.23 (m, 1H), 3.06-2.94 (m, 1H), 2.84 (dd, J=11.7, 9.0 Hz, 1H), 1.85 (d, J=11.2 Hz, 2H), 1.70 (d, J=10.5 Hz, 1H), 1.40 (s, 10H). LC-MS: [M+H]$^+$=429.9.

To a suspension of tert-butyl (R)-(1-(6-(3-fluoro-4-methoxyphenyl)-4-formylpyridin-3-yl)piperidin-3-yl)carbamate (1-2) (260 mg, 0.605 mmol) in MeOH (15 mL) was added sodium borohydride (22.9 mg, 0.605 mmol). The mixture was stirred at RT for 30 min and the solvent removed in reduced pressure. The residue was redissolved in DCM (30 mL), worked up under aqueous conditions and concentrated. The residue was purified by flash chromatography (10-50% EtOAc in PE in 30 mins) to afford tert-butyl (R)-(1-(6-(3-fluoro-4-methoxyphenyl)-4-(hydroxymethyl) pyridin-3-yl)piperidin-3-yl)carbamate (1-3). $^1$H NMR (400 MHz, CD$_3$OD) δ 8.26 (s, 1H), 7.93 (s, 1H), 7.75-7.62 (m, 2H), 7.21 (t, J=8.5 Hz, 1H), 5.52 (s, 1H), 4.88-4.72 (m, 2H), 3.95 (s, 3H), 3.71 (dt, J=9.5, 4.8 Hz, 1H), 3.21 (dd, J=11.2, 3.7 Hz, 1H), 3.07 (d, J=11.6 Hz, 1H), 2.83 (t, J=10.7 Hz, 1H), 2.66 (t, J=10.0 Hz, 1H), 2.06-1.86 (m, 2H), 1.78 (q, J=13.1, 11.6 Hz, 1H), 1.47 (s, 9H). LC-MS: [M+H]$^+$=431.9.

To a solution of tert-butyl (R)-(1-(6-(3-fluoro-4-methoxyphenyl)-4-(hydroxymethyl)pyridin-3-yl)piperidin-3-yl)carbamate (1-3) (370 mg, 0.857 mmol), Intermediate B (300 mg, 0.895 mmol) and PPh$_3$ (704 mg, 2.68 mmol) in THF (15 mL) was added DEAD (0.425 mL, 2.68 mmol) dropwise at 0° C., The mixture was stirred at rt for 1 hr. The mixture was diluted with H$_2$O (20 mL), extracted with EtOAc (20 mL*3). The combined organic layers were washed with brine (20 mL), dried over anhydrous Na$_2$SO$_4$, filtered and concentrated in vacuo. The residue was purified by silica gel column chromatography (10-50% EtOAc in hexane in 40 mins) to give tert-butyl (R)-(tert-butoxycarbonyl)(9-((5-(3-((tert-butoxycarbonyl)amino)piperidin-1-yl)-2-(3-fluoro-4-methoxyphenyl)pyridin-4-yl)methyl)-9H-purin-6-yl)carbamate (1-4). $^1$H NMR (400 MHz, CD$_3$OD) b 8.88 (s, 1H), 8.76 (s, 1H), 8.45 (s, 1H), 7.54-7.44 (m, 2H), 7.26 (s, 1H), 7.13 (t, J=8.6 Hz, 1H), 5.90-5.72 (m, 2H), 3.90 (s, 3H), 3.85 (d, J=4.6 Hz, 1H), 3.42-3.37 (m, 1H), 3.18-3.09 (m, 1H), 2.99 (t, J=10.1 Hz, 1H), 2.88 (d, J=10.1 Hz, 1H), 1.97 (d, J=10.2 Hz, 2H), 1.82 (d, J=6.8 Hz, 1H), 1.64-1.54 (m, 1H), 1.44 (s, 9H), 1.36 (s, 18H). LC-MS: [M+H]$^+$=749.0.

To a solution of tert-butyl (R)-(tert-butoxycarbonyl)(9-((5-(3-((tert-butoxycarbonyl)amino)piperidin-1-yl)-2-(3-fluoro-4-methoxyphenyl)pyridin-4-yl)methyl)-9H-purin-6-yl)carbamate (1-4) (360 mg, 0.481 mmol) in DCM (9 mL) was added TFA (3 mL). The mixture was stirred at RT for 1 hr. The mixture was concentrated in vacuum. The residue was purified by Prep-HPLC (Basic condition, NH$_3$H$_2$O %=0.05%, MECN/H$_2$O=0-95% in 12 mins) to give (R)-9-((5-(3-aminopiperidin-1-yl)-2-(3-fluoro-4-methoxyphenyl) pyridin-4-yl)methyl)-9H-purin-6-amine (Example 1). $^1$H NMR (400 MHz, CD$_3$OD) δ 8.59-8.32 (m, 3H), 7.69-7.53 (m, 2H), 7.37 (s, 1H), 7.17 (td, J=8.6, 1.7 Hz, 1H), 5.85-5.63 (m, 2H), 3.93 (d, J=1.8 Hz, 3H), 3.62 (s, 1H), 3.56-3.44 (m, 1H), 3.19-3.07 (m, 2H), 3.04 (d, J=9.5 Hz, 1H), 2.22-2.12 (m, 1H), 2.04 (s, 1H), 1.89 (dd, J=9.0, 4.2 Hz, 1H), 1.76 (d, J=10.1 Hz, 1H). LC-MS: [M+H]$^+$=449.1.

Example 2-21 can be prepared following procedures analogous to those described in Example 1.

| Example # | Structure | ¹H NMR & MS |
|---|---|---|
| 2 | 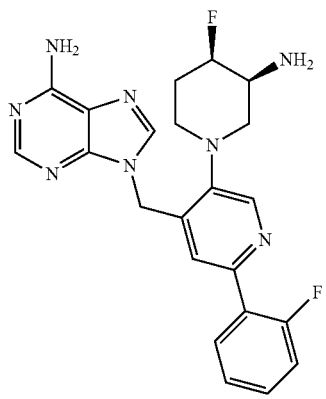 [SMILES: Nc1ncnc2c1ncn2Cc1cc(-c2ccccc2F)ncc1N1CC[C@@H](F)[C@@H](N)C1] | ¹H NMR (400 MHz, CD₃OD) δ ppm 8.56 (s, 1 H) 8.26 (s, 1 H) 8.11 (s, 1 H) 7.85 (td, J = 8.03, 1.76 Hz, 1 H) 7.35-7.43 (m, 1 H) 7.32 (s, 2 H) 7.17-7.29 (m, 2 H) 6.97 (s, 1 H) 5.42-5.68 (m, 2 H) 4.66-4.94 (m, 1 H) 2.86-3.19 (m, 4 H) 1.87-2.23 (m, 2 H) 1.73 (br. s., 1 H). LC-MS: [M + H]+ = 436.9, 437.9. |
| 3 | 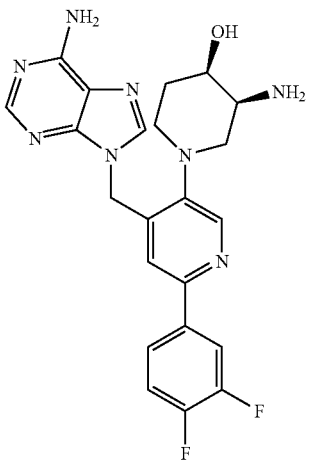 [SMILES: Nc1ncnc2c1ncn2Cc1cc(-c2ccc(F)c(F)c2)ncc1N1CC[C@@H](O)[C@@H](N)C1] | ¹H NMR (400 MHz, CD₃OD) δ ppm 8.49 (s, 1H), 8.22 (d, J = 4.7 Hz, 2H), 7.73 (ddd, J = 12.1, 7.8, 2.2 Hz, 1H), 7.52 (ddt, J = 8.2, 3.8, 1.6 Hz, 1H), 7.28 (d, J = 11.2 Hz, 2H), 5.63 (d, J = 1.4 Hz, 2H), 3.90 (dt, J = 7.4, 3.5 Hz, 1H), 3.25-2.98 (m, 4H), 2.89 (ddd, J = 11.5, 7.4, 3.8 Hz, 1H), 1.90 (dddd, J = 33.5, 13.2, 6.7, 3.6 Hz, 2H). LC-MS: [M + H]⁺ = 453.2, 454.2. |
| 4 | 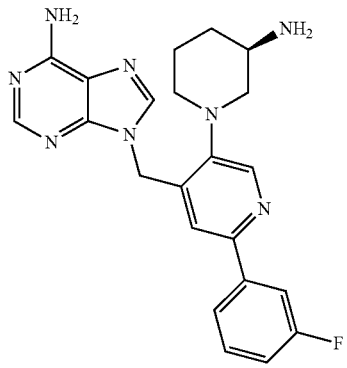 [SMILES: Nc1ncnc2c1ncn2Cc1cc(-c2cccc(F)c2)ncc1N1CCC[C@@H](N)C1] | ¹H NMR (400 MHz, CD₃OD) δ 8.57 (d, J = 6.2 Hz, 1H), 8.47 (d, J = 6.0 Hz, 1H), 8.37 (d, J = 5.8 Hz, 1H), 7.68-7.56 (m, 2H), 7.50-7.39 (m, 2H), 7.15 (td, J = 8.2, 7.7, 2.3 Hz, 1H), 5.85-5.67 (m, 2H), 3.62 (tt, J = 8.1, 3.7 Hz, 1H), 3.51 (dd, J = 11.4, 3.7 Hz, 1H), 3.14 (dq, J = 10.5, 6.5, 4.5 Hz, 2H), 3.05 (td, J = 8.5, 4.2 Hz, 1H), 2.24-2.11 (m, 1H), 2.05 (dtt, J = 9.5, 6.1, 3.1 Hz, 1H), 1.90 (ddq, J = 13.2, 8.8, 4.0 Hz, 1H), 1.82-1.69 (m, 1H). LC-MS: [M + H]⁺ = 418.9. |

| Example # | Structure | ¹H NMR & MS |
|---|---|---|
| 5 | 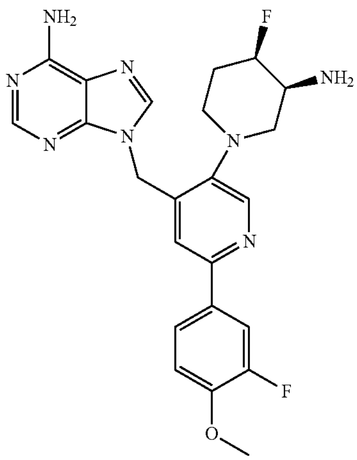 [SMILES: COc1ccc(-c2cc(Cn3cnc4c(N)ncnc43)c(N3CC[C@@H](F)[C@@H](N)C3)cn2)cc1F] | ¹H NMR (400 MHz, CD₃OD) δ ppm 8.49 (s, 1H), 8.24 (d, J = 1.5 Hz, 2H), 7.58 (dd, J = 12.6, 2.2 Hz, 1H), 7.48 (ddd, J = 8.5, 2.3, 1.2 Hz, 1H), 7.25 (s, 1H), 7.13 (t, J = 8.6 Hz, 1H), 5.64 (s, 2H), 4.79 (dd, J = 5.4, 2.6 Hz, 1H), 3.91 (s, 3H), 3.22-3.02 (m, 4H), 3.02-2.88 (m, 1H), 2.20 (ddd, J = 15.0, 9.6, 4.9 Hz, 1H), 2.03 (ddd, J = 36.1, 14.0, 10.3 Hz, 1H). LC-MS: [M + H]⁺ = 466.9, 467.9. |
| 6 | 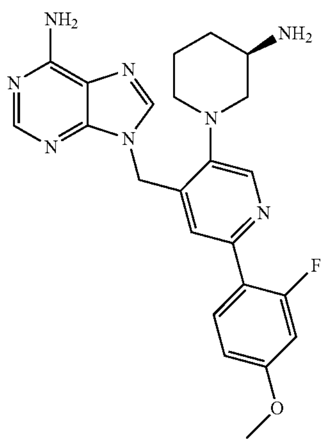 [SMILES: COc1ccc(-c2cc(Cn3cnc4c(N)ncnc43)c(N3CCC[C@@H](N)C3)cn2)c(F)c1] | ¹H NMR (400 MHz, CD₃OD) δ 8.55 (s, 1H), 8.41 (s, 1H), 8.34 (s, 1H), 7.71 (t, J = 9.0 Hz, 1H), 7.17 (d, J = 1.6 Hz, 1H), 6.86 (dd, J = 8.8, 2.5 Hz, 1H), 6.75 (dd, J = 13.3, 2.5 Hz, 1H), 5.84-5.67 (m, 2H), 3.84 (s, 3H), 3.63 (dt, J = 8.3, 4.5 Hz, 1H), 3.55-3.48 (m, 1H), 3.19-3.11 (m, 2H), 3.05 (t, J = 8.8 Hz, 1H), 2.23-2.13 (m, 1H), 2.11-2.02 (m, 1H), 1.91 (ddq, J = 13.2, 8.6, 4.3 Hz, 1H), 1.77 (d, J = 9.2 Hz, 1H). LC-MS: [M + H]⁺ = 448.9. |
| 7 | 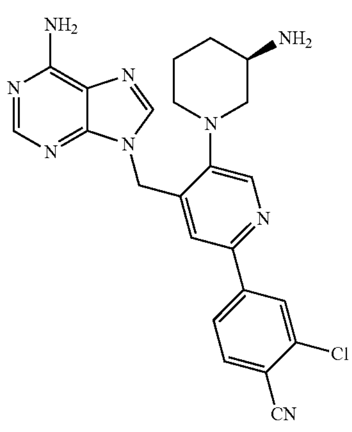 [SMILES: N#Cc1ccc(-c2cc(Cn3cnc4c(N)ncnc43)c(N3CCC[C@@H](N)C3)cn2)cc1Cl] | 1H NMR (40 0MHz, CDCl₃): 8.61 (s, 1H), 8.43 (s, 1H), 8.33 (s, 1H), 8.17 (d, J = 1.8 Hz, 1H), 7.92 (dd, J = 8.3, 1.7 Hz, 1H), 7.81 (d, J = 8.1 Hz, 1H), 7.50 (s, 1H), 5.92-5.49 (m, 2H), 3.60 (tt, J = 7.7, 3.5 Hz, 1H), 3.50 (dd, J = 11.5, 3.4 Hz, 1H), 3.23-2.97 (m, 3H), 2.09 (dddd, J = 41.4, 10.0, 7.1, 3.5 Hz, 2H), 1.92-1.62 (m, 2H) LC-MS: [M + H]+ = 459.8 |

-continued
| Example # | Structure | ¹H NMR & MS |
|---|---|---|
| 8 | 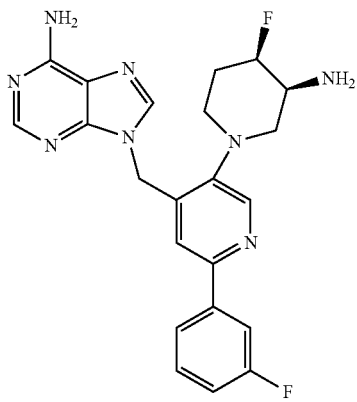 [SMILES: Nc1ncnc2c1ncn2Cc1cc(-c2cccc(F)c2)ncc1N1CC[C@@H](F)[C@@H](N)C1] | ¹H NMR (400 MHz, CD$_3$OD) δ ppm 8.54 (s, 1H), 8.24 (d, J = 3.3 Hz, 2H), 7.60-7.50 (m, 2H), 7.43 (td, J = 8.3, 6.1 Hz, 1H), 7.31 (s, 1H), 7.12 (tt, J = 7.7, 1.5 Hz, 1H), 5.66 (s, 2H), 4.80-4.57 (m, 1H), 3.25-3.06 (m, 4H), 3.06-2.91 (m, 1H), 2.21 (td, J = 11.0, 10.3, 5.7 Hz, 1H), 2.04 (ddd, J = 36.2, 14.1, 10.4 Hz, 1H). LC-MS: [M + H]+ = 436.9, 437.9. |
| 9 | 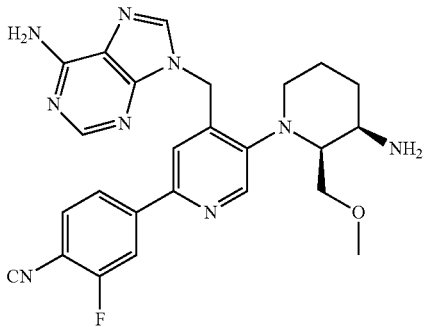 | ¹H NMR (400 MHz, CD$_3$OD) δ ppm 8.80 (s, 1H), 8.35 (s, 1H), 8.28 (s, 1H), 8.07 (dd, J = 10.8, 1.5 Hz, 1H), 8.01 (dd, J = 8.2, 1.6 Hz, 1H), 7.96 (s, 1 H), 7.88 (dd, J = 8.2, 6.7 Hz, 1H), 6.03 (d, J = 15.3 Hz, 1H), 5.43 (d, J = 15.3 Hz, 1H), 3.88 (d, J = 4.0 Hz, 1H), 3.64-3.50 (m, 2H), 3.42-3.34 (m, 1H), 3.16 (s, 3H), 3.11-2.95 (m, 2H), 2.15-1.97 (m, 2H), 1.69-1.57 (m, 1H), 1.57-1.39 (m, 1H). LC-MS: [M + H]+ = 487.9, 488.9. |
| 10 | 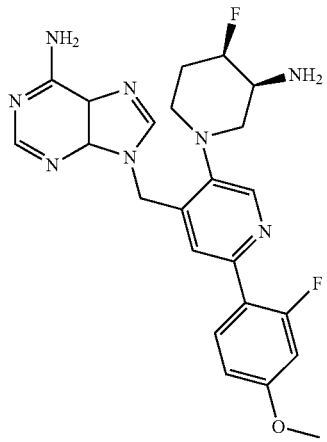 [SMILES: COc1ccc(-c2cc(CN3C=NC4C(N)=NC=NC43)c(N3CC[C@@H](F)[C@@H](N)C3)cn2)c(F)c1] | ¹H NMR (400 MHz, CD$_3$OD) δ ppm 8.52 (s, 1H), 8.26 (s, 1H), 8.11 (s, 1H), 7.81 (t, J = 9.3 Hz, 1H), 7.32 (s, 2H), 6.91-6.71 (m, 3H), 5.54 (s, 2H), 4.81 (ddt, J = 49.4, 5.4, 2.5 Hz, 1H), 3.77 (s, 3H), 3.18-2.83 (m, 5H), 2.20-1.88 (m, 2H), 1.85-1.58 (m, 2H). LC-MS: [M + H]+ = 466.9, 470.9. |

| Example # | Structure | ¹H NMR & MS |
|---|---|---|
| 11 | 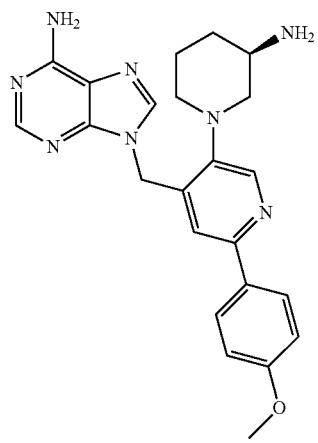 [SMILES: COc1ccc(-c2cc(Cn3cnc4c(N)ncnc43)c(N3CCC[C@@H](N)C3)cn2)cc1] | ¹H NMR (400 MHz, CD₃OD) δ: 8.50 (d, J = 26.4 Hz, 2H), 8.36 (s, 1H), 7.73 (d, J = 8.9 Hz, 2H), 7.40 (s, 1H), 7.14-6.93 (m, 2H), 5.93-5.62 (m, 2H), 3.85 (s, 3H), 3.57 (ddd, J = 44.7, 9.9, 3.8 Hz, 2H), 3.22-3.01 (m, 3H), 2.22-1.99 (m, 2H), 1.94-1.69 (m, 2H). LC-MS: [M + H]+ = 430.9 |
| 12 | 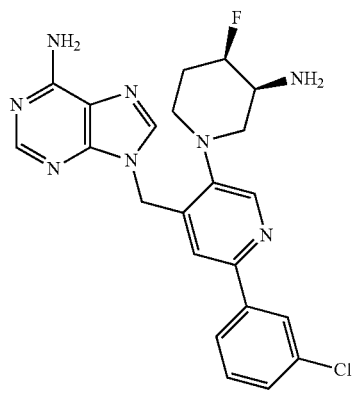 [SMILES: Nc1ncnc2c1ncn2Cc1cc(-c2cccc(Cl)c2)ncc1N1CC[C@@H](F)[C@@H](N)C1] | ¹H NMR (400 MHz, CD₃OD) δ ppm 8.57 (d, J = 2.3 Hz, 1H), 8.32-8.17 (m, 2H), 7.87 (p, J = 1.6 Hz, 1H), 7.67 (ddt, J = 5.1,3.2, 1.8 Hz, 1H), 7.47-7.30 (m, 3H), 5.65 (s, 2H), 5.15-4.95 (m, 1H), 3.63 (dd, J = 39.0, 22.1 Hz, 1H), 3.38 (d, J = 6.0 Hz, 1H), 3.26 (s, 1H), 3.22-3.13 (m, 1H), 3.04 (dq, J = 12.6, 4.5 Hz, 1H), 2.32-2.04 (m, 2H). LC-MS: [M + H]+ = 452.9, 453.9. |
| 13 | 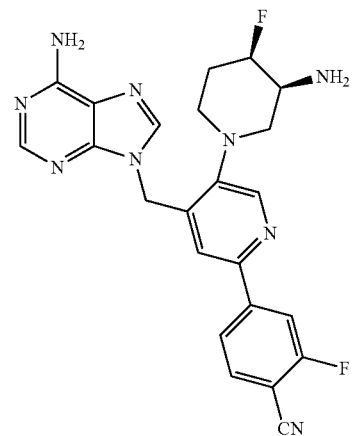 [SMILES: N#Cc1ccc(-c2cc(Cn3cnc4c(N)ncnc43)c(N3CC[C@@H](F)[C@@H](N)C3)cn2)cc1F] | ¹H NMR (400 MHz, CD₃OD) δ ppm 8.6 (s, 1H), 8.23 (d, 2H), 7.9 (d, 1H), 7.79 (m, 2H), 7.45 (s, 1H), 5.6 (s, 2H), 4.9 4.81 (m, 1H), 3.83 (s, 3H), 3.21-3.12 (m, 4H), 3.05-3.01 (m, 1H), 2.19 (m, 1H), 2.14-1.88 (m, 1H). LC-MS: [M + H]+ = 461.9, 462.9. |

| Example # | Structure | ¹H NMR & MS |
|---|---|---|
| 14 | 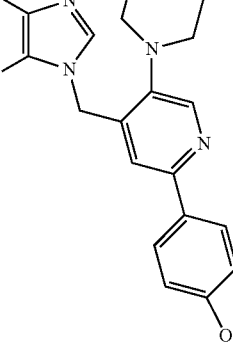 | ¹H NMR (400 MHz, CD₃OD) δ ppm 8.45 (s, 1H), 8.23 (d, J = 1.3 Hz, 2H), 7.61 (d, J = 1.8 Hz, 1H), 7.46 (dd, J = 8.3, 1.9 Hz, 1H), 7.18 (s, 1H), 6.76 (d, J = 8.4 Hz, 1H), 5.64 (s, 2H), 4.65 (s, 1H), 4.58 (t, J = 8.7 Hz, 2H), 3.23 (t, J = 8.7 Hz, 2H), 3.20-3.04 (m, 4H), 3.00-2.92 (m, 1H), 2.26-2.13 (m, 1H), 2.12-1.93 (m, 1H). LC-MS: [M + H]+ = 460.9, 461.9. |
| 15 | 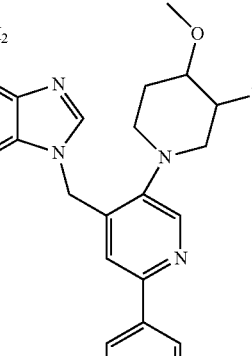 | ¹H NMR (400 MHz, CD₃OD) δ ppm 8.44 (s, 1H), 8.23 (d, J = 1.3 Hz, 2H), 7.56 (dd, J = 12.7, 2.2 Hz, 1H), 7.45 (ddd, J = 8.5, 2.3, 1.1 Hz, 1H), 7.24 (s, 1H), 7.09 (t, J = 8.7 Hz, 1H), 5.62 (s, 2H), 3.48 (dt, J = 7.1, 3.3 Hz, 1H), 3.44 (s, 3H), 3.22-2.95 (m, 4H), 2.85 (ddd, J = 11.4, 7.4, 3.6 Hz, 1H), 2.06 (ddt, J = 18.0, 7.4, 3.0 Hz, 1H), 1.87-1.73 (m, 1H). LC-MS: [M + H]+ = 478.9, 479.9. |
| 16 | 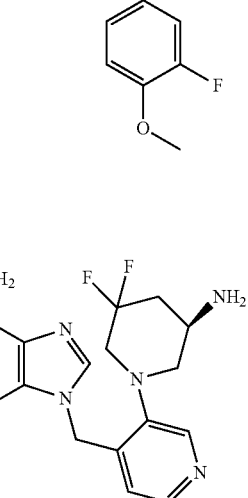 | ¹H NMR (400 MHz, DMSO-d₆) δ: 8.52 (s, 1H), 8.25 (s, 1H), 8.12 (s, 1H), 7.67 (dd, J = 13.0, 2.1 Hz, 1H), 7.52 (s, 1H), 7.31 (s, 1H), 7.27-7.07 (m, 2H), 5.50 (d, J = 2.7 Hz, 2H), 3.85 (s, 3H), 3.32-3.09 (m, 3H), 2.71 (t, J = 10.2 Hz, 1H), 2.36 (d, J = 12.1 Hz, 1H), 2.09-1.54 (m, 3H), 1.06 (t, J = 7.0 Hz, 1H) LC-MS: [M + H]+ = 485.1 |

| Example # | Structure | ¹H NMR & MS |
|---|---|---|
| 17 | 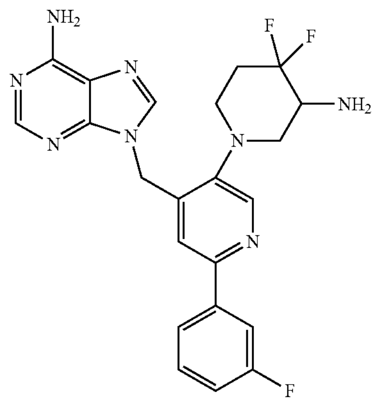 [SMILES: Nc1ncnc2c1ncn2Cc1cc(-c2cccc(F)c2)ncc1N1CCC(F)(F)C(N)C1] | ¹H NMR (400 MHz, CD₃OD) δ: 8.64 (s, 1H), 8.47 (s, 1H), 8.36 (s, 1H), 7.67-7.55 (m, 2H), 7.52-7.35 (m, 2H), 7.22-7.02 (m, 1H), 5.87-5.64 (m, 2H), 4.10 (ddt, J = 18.1, 9.6, 4.6 Hz, 1H), 3.63 (d, J = 11.8 Hz, 1H), 3.46-3.37 (m, 1H), 3.32-3.26 (m, 2H), 2.57-2.37 (m, 2H) LC-MS: [M + H]+ = 454.9 |
| 18 | 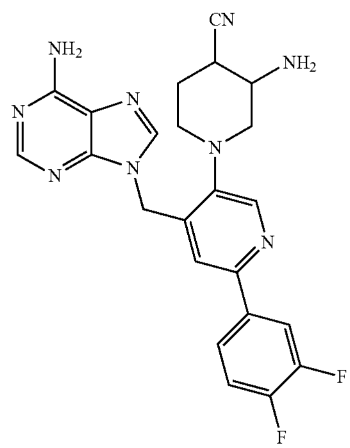 [SMILES: N#CC1CCN(c2cnc(-c3ccc(F)c(F)c3)cc2Cn2cnc3c(N)ncnc32)CC1N] | ¹H NMR (400 MHz, DMSO-d₆): d 8.51 (s, 1H), 8.48 (s, 1H), 8.24 (s, 1H), 7.95-7.85 (m, 1H), 7.67-7.57 (m, 1H), 7.49 (q, J = 8.8 Hz, 1H), 7.38 (s, 1H), 7.28 (s, 2H), 5.49 (s, 2H), 3.27-3.15 (m, 1H), 3.14-3.05 (m, 1H), 3.04-2.97 (m, 1H), 2.86-2.77 (m, 1H), 2.70-2.55 (m, 2H), 2.20-2.02 (m, 3H), 1.95-1.80 (m, 1H). LC-MS: [M + H]+ = 462.3 |
| 19 | 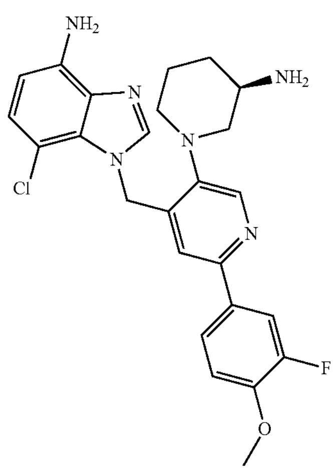 | ¹H NMR (400 MHz, CD₃OD) δ: 8.54 (s, 1H), 8.48 (s, 1H), 7.79-7.45 (m, 3H), 7.23 (s, 1H), 7.14 (t, J = 8.6 Hz, 1H), 7.00 (d, J = 7.1 Hz, 1H), 5.92-5.61 (m, 2H), 3.91 (s, 3H), 3.62-3.51 (m, 1H), 3.47 (dd, J = 11.4, 3.5 Hz, 1H), 3.12 (dq, J = 14.0, 4.9, 4.0 Hz, 2H), 3.04-2.94 (m, 1H), 2.17 (dt, J = 10.4, 5.0 Hz, 1H), 2.10-1.98 (m, 1H), 1.97-1.81 (m, 1H), 1.72 (d, J = 10.5 Hz, 1H) LC-MS: [M + H]+ = 447.8 |

| Example # | Structure | ¹H NMR & MS |
|---|---|---|
| 20 | 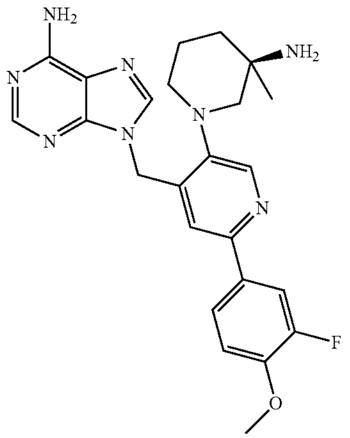 [SMILES: COc1ccc(-c2cc(Cn3cnc4c(N)ncnc43)c(N3CCC[C@@](C)(N)C3)cn2)cc1F] | ¹H NMR (400 MHz, CD₃OD) δ 8.55 (s, 1H), 8.46 (s, 1H), 8.34 (s, 1H), 7.61 (dd, J = 12.6, 2.2 Hz, 1H), 7.55 (dt, J = 8.8, 1.6 Hz, 1H), 7.28 (s, 1H), 7.14 (t, J = 8.6 Hz, 1H), 5.76 (q, J = 16.4 Hz, 2H), 3.91 (s, 3H), 3.26 (s, 2H), 3.20-3.13 (m, 1H), 2.96 (t, J = 10.9 Hz, 1H), 1.98 (t, J = 10.9 Hz, 3H), 1.89-1.80 (m, 1H), 1.52 (s, 3H). LC-MS: [M + H]⁺ = 462.9. |
| 21 | 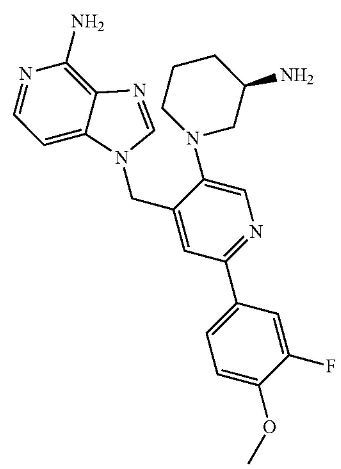 [SMILES: COc1ccc(-c2cc(Cn3cnc4c(N)nccc43)c(N3CCC[C@@H](N)C3)cn2)cc1F] | ¹H NMR (400 MHz, CD₃OD) δ: 8.54 (s, 1H), 8.48 (s, 1H), 7.66-7.41 (m, 3H), 7.23 (s, 1H), 7.14 (t, J = 8.6 Hz, 1H), 7.00 (d, J = 7.1 Hz, 1H), 5.89-5.68 (m, 2H), 3.91 (s, 3H), 3.58 (tt, J = 8.3, 4.0 Hz, 1H), 3.47 (dd, J = 11.3, 3.5 Hz, 1H), 3.20-3.08 (m, 2H), 3.04 (d, J = 3.2 Hz, 1H), 2.17 (dt, J = 10.4, 5.0 Hz, 1H), 2.10-1.99 (m, 1H), 1.90 (qt, J = 9.4, 4.2 Hz, 1H), 1.80-1.62 (m, 1H). LC-MS: [M + H]+ = 447.8 |
Example 22: (R)-9-((5-(3-amino-3-(cyclopropoxymethyl)piperidin-1-yl)-2-(3,4-difluorophenyl)pyridin-4-yl)methyl)-9H-purin-6-amine
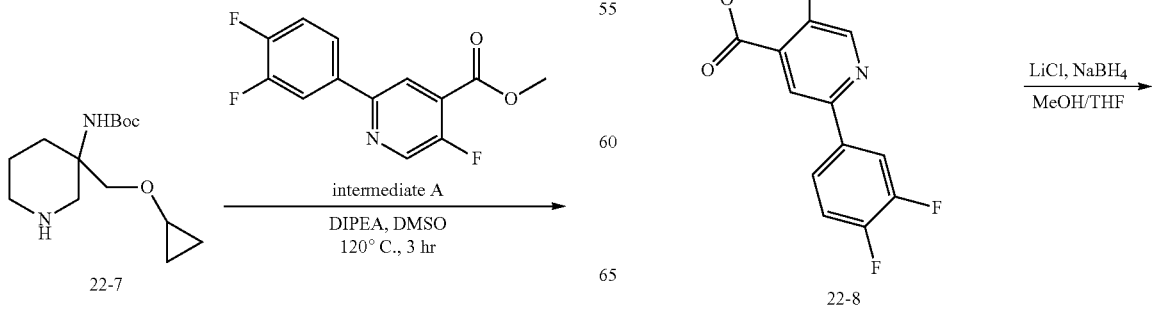

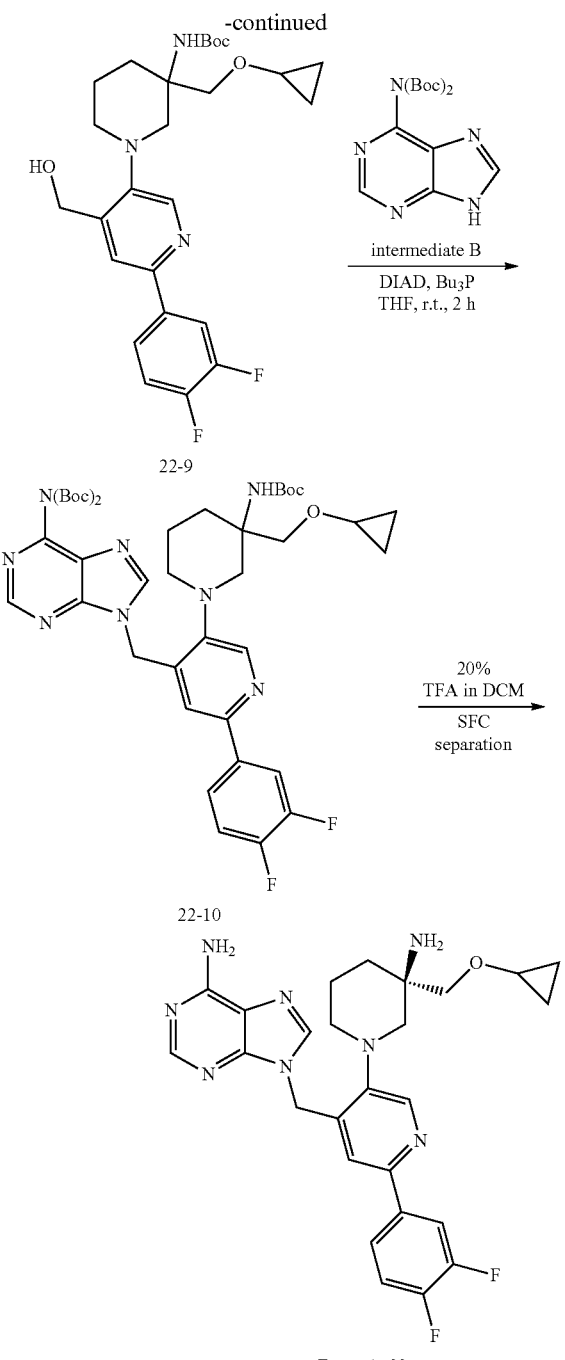

Example 22

A mixture of tert-butyl (3-(cyclopropoxymethyl)piperidin-3-yl)carbamate (Intermediate 22-7) (300 mg, 1.11 mmol, 1.0 eq), methyl 2-(3,4-difluorophenyl)-5-fluoroisonicotinate (intermediate A) (296 mg, 1.11 mmol, 1.0 eq) and DIPEA (1.00 g, 7.77 mmol, 7.0 eq) in DMSO (3 mL) was stirred at 120° C. under N₂ for 3 hr. The mixture was quenched with water (200 mL) at 10° C., and extracted with EtOAc (100 mL×3). The combined organic layers were dried over anhydrous Na₂SO₄ and concentrated in vacuo. The residue was purified by Combi Flash (20% EtOAc in PE) to give methyl 5-(3-((tert-butoxycarbonyl)amino)-3-(cyclopropoxymethyl)piperidin-1-yl)-2-(3,4-difluorophe- nyl)isonicotinate (22-8). ¹H NMR (400 MHz, CDCl₃) δ ppm 8.48 (1H, s), 7.86 (1H, s), 7.83 (1H, dd, J=10.0, 2.0 Hz), 7.67 (1H, d, J=8.4 Hz), 7.23 (1H, dd, J=8.4, 1.6 Hz), 5.63 (1H, brs), 3.80-4.05 (4H, m), 3.57 (1H, d, J=9.6 Hz), 3.15-3.35 (3H, m), 2.80-2.95 (2H, m), 2.30-2.45 (1H, m), 1.85-2.00 (1H, m), 1.65-1.75 (1H, m), 1.46 (9H, s), 1.25-1.40 (1H, m), 0.40-0.60 (4H, m).

To a solution of methyl 5-(3-((tert-butoxycarbonyl)amino)-3-(cyclopropoxymethyl)piperidin-1-yl)-2-(3,4-difluorophenyl)isonicotinate (22-8) (330 mg, 0.638 mmol, 1.0 eq) in THF/MeOH (10 mL, v/v=1/1) was added LiCl (270 mg, 6.38 mmol, 10.0 eq) followed by NaBH₄ (480 mg, 12.75 mmol, 20.0 eq) at 15-20° C. The resulting mixture was stirred at 30° C. for 2 hr. The reaction was quenched with water (100 mL), and extracted with EtOAc (100 mL×3). The combined organic layer was dried over anhydrous Na₂SO₄ and concentrated in vacuo to give crude tert-butyl (3-(cyclopropoxymethyl)-1-(6-(3,4-difluorophenyl)-4-(hydroxymethyl)pyridin-3-yl)piperidin-3-yl)carbamate (22-9). ¹H NMR (400 MHz, CDCl₃) δ ppm 8.43 (1H, s), 7.75-7.85 (1H, m), 7.60-7.70 (2H, m), 7.15-7.25 (1H, m), 4.79 (2H, s), 4.76 (1H, brs), 3.65-3.85 (3H, m), 3.35-3.45 (1H, m), 3.25-3.35 (1H, m), 3.05-3.15 (1H, m), 2.80-2.95 (2H, m), 2.05-2.15 (1H, m), 1.85-1.95 (1H, m), 1.65-1.75 (1H, m), 1.55-1.60 (1H, m), 1.44 (9H, s), 0.40-0.60 (4H, m).

To a solution of tert-butyl (3-(cyclopropoxymethyl)-1-(6-(3,4-difluorophenyl)-4-(hydroxymethyl)pyridin-3-yl)piperidin-3-yl)carbamate (22-9) (300 mg, 0.613 mmol, 1.0 eq.), Intermediate B (310 mg, 0.919 mmol, 1.5 eq.) and Bu₃P (372 mg, 1.84 mmol, 3.0 eq.) in THF (10 mL) was added DIAD (372 mg, 1.84 mmol, 3.0 eq.) at 0° C. The mixture was stirred at 20-30° C. for 2 hr. The reaction was concentrated in vacuo. The residue was purified by Combi Flash (30-40% EtOAc in PE) to give tert-butyl (tert-butoxycarbonyl)(9-((5-(3-((tert-butoxycarbonyl)amino)-3-(cyclopropoxymethyl)piperidin-1-yl)-2-(3,4-difluorophenyl)pyridin-4-yl)methyl)-9H-purin-6-yl)carbamate (22-10). ¹H NMR (400 MHz, CDCl₃) δ ppm 8.88 (1H, s), 8.52 (1H, s), 8.25 (1H, s), 7.60-7.70 (1H, m), 7.35-7.45 (1H, m), 7.10-7.25 (2H, m), 5.70 (1H, d, J=15.6 Hz), 5.53 (1H, d, J=15.6 Hz), 5.19 (1H, brs), 3.75-3.90 (2H, m), 3.40-3 intermediate. 50 (1H, m), 3.25-3.35 (1H, m), 2.90-3.10 (3H, m), 2.15-2.30 (1H, m), 1.90-2.00 (1H, m), 1.70-1.80 (1H, m), 1.55-1.65 (1H, m), 1.45 (18H, s), 1.35 (9H, s), 0.40-0.60 (4H, m).

A solution of tert-butyl (tert-butoxycarbonyl)(9-((5-(3-((tert-butoxycarbonyl)amino)-3-(cyclopropoxymethyl)piperidin-1-yl)-2-(3,4-difluorophenyl)pyridin-4-yl)methyl)-9H-purin-6-yl)carbamate (22-10) (270 mg, 0.335 mmol) in 20% TFA in DCM (7.5 mL) was stirred at 15-20° C. for 2 hr. Then the pH of the reaction was adjusted to 8-9 by NH₃·H₂O, and extracted with DCM (100 mL×3). The combined organic layers were dried over anhydrous Na₂SO₄ and concentrated in vacuo. The residue was purified by Prep-HPLC (0.1% NH₃·H₂O as additive) and SFC to give (R)-9-((5-(3-amino-3-(cyclopropoxymethyl)piperidin-1-yl)-2-(3,4-difluorophenyl)pyridin-4-yl)methyl)-9H-purin-6-amine (Example 22). ¹H NMR (400 MHz, CD₃OD) b ppm 8.51 (1H, s), 8.25 (1H, d, J=4.0 Hz), 7.70-7.80 (1H, m), 7.50-7.60 (1H, m), 7.25-7.40 (2H, 3), 5.66 (2H, s), 3.60-3.80 (1H, n), 3.45-3.55 (4H, d, J=9.6 Hz), 2.90-3.15 (4H, in), 1.55-2.00 (4H, in), 1.25-1.40 (1H, m), 0.35-0.65 (4H, m). LC-MS: [M+H]=506.8.

Example 23-46 can be prepared following procedures analogous to those described in Example 22.

| Example # | Structure | ¹H NMR & MS |
|---|---|---|
| 23 | 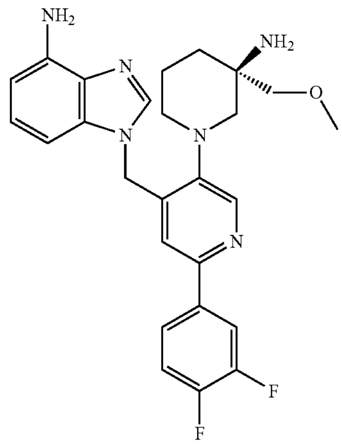 [SMILES: COC[C@@]1(N)CCCN(c2cnc(-c3ccc(F)c(F)c3)cc2Cn2cnc3c(N)cccc32)C1] | ¹H NMR (400 MHz, CDCl₃) δ ppm 8.50 (s, 1H), 8.36 (br s, 1H), 8.16 (br s, 1H), 7.76-7.91 (m, 2H), 7.65 (br d, J = 7.0 Hz, 1H), 7.20-7.27 (m, 1H), 5.71 (br d, J = 12.8 Hz, 1H), 5.47 (br s, 1H), 3.58-3.70 (m, 2H), 3.54 (br d, J = 12.0 Hz, 1H), 3.45 (s, 3H), 2.93-3.06 (m, 1H), 2.86 (br s, 2H), 2.28 (brd, J = 14.3 Hz, 1H), 2.05 (brs, 1H), 1.75 (brd, J = 13.8 Hz, 1H), 1.56-1.68 (m, 1H), 1.18-1.39 (m, 3H), 0.80-0.95 (m, 1H). LC-MS: [M + H]⁺ = 480.9. |
| 24 | 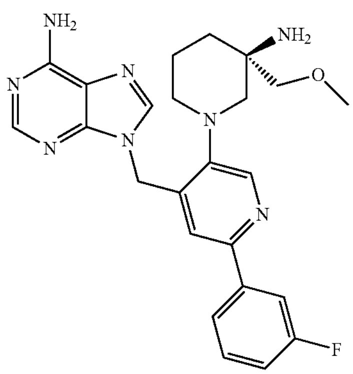 [SMILES: COC[C@@]1(N)CCCN(c2cnc(-c3cccc(F)c3)cc2Cn2cnc3c(N)ncnc32)C1] | ¹H NMR (400 MHz, CD₃OD) δ ppm 1.40-1.82 (4H, m), 2.68-3.05 (4H, m), 3.20 (1H, t), 3.26 (3H, s), 3.42 (1H, d), 5.56 (3H, t), 7.01 (1H, t), 7.15 (1H, s), 7.25-7.44 (2H, m), 8.12 (2H, d), 8.38 (1H, s). LC-MS: [M + H]⁺ = 463.1. |
| 25 | 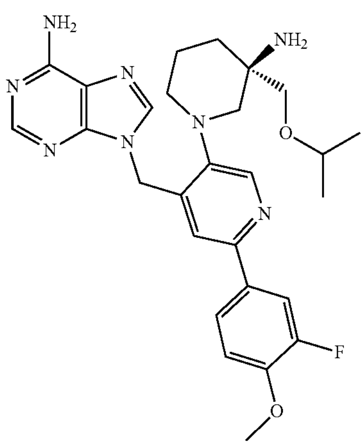 [SMILES: COc1ccc(-c2cc(Cn3cnc4c(N)ncnc43)c(N3CCC[C@](N)(COC(C)C)C3)cn2)cc1F] | ¹H NMR (400 MHz, CD₃OD) δ ppm 8.45 (s, 1H), 8.24 (d, J = 6.4 Hz, 2H), 7.56 (dd, J = 12.8, 2.2 Hz, 1H), 7.45 (dt, J = 8.6, 1.6 Hz, 1H), 7.18 (s, 1H), 7.11 (t, J = 8.6 Hz, 1H), 5.67 (s, 2H), 3.90 (s, 3H), 3.74-3.53 (m, 2H), 3.14 (d, J = 11.3 Hz, 1H), 3.10-2.93 (m, 2H), 2.87 (d, J = 11.4 Hz, 1H), 2.00-1.74 (m, 2H), 1.73-1.48 (m, 2H), 1.17 (d, J = 6.0 Hz, 3H), 1.12 (d, J = 6.1 Hz, 3H). LC-MS: [M + H]⁺ = 520.8, 521.8. |
| 26 | 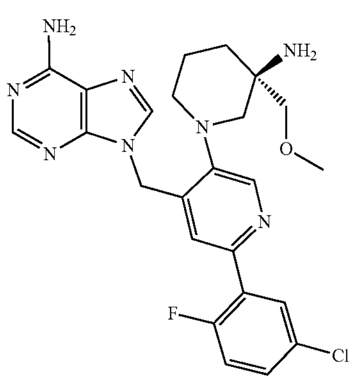 [SMILES: COC[C@@]1(N)CCCN(c2cnc(-c3cc(Cl)ccc3F)cc2Cn2cnc3c(N)ncnc32)C1] | ¹H NMR (400 MHz, DMSO-d₆) δ ppm 8.53 (s, 1H), 8.29 (s, 1H), 8.11 (s, 1H), 7.88 (dd, J = 6.8, 2.8 Hz, 1 H), 7.45 (ddd, J = 8.7, 4.1, 2.8 Hz, 1H), 7.40-7.22 (m, 3H), 7.00 (d, J = 1.5 Hz, 1H), 5.63-5.47 (m, 2H), 3.46 (d, J = 8.8 Hz, 1H), 3.28 (s, 3H), 3.23 (d, J = 8.8 Hz, 1H), 3.08-2.93 (m, 3H), 2.75 (d, J = 11.3 Hz, 1H), 1.88 (d, J = 13.0 Hz, 1H), 1.72 (s, 3H), 1.61 (td, J = 8.7, 4.5 Hz, 1H), 1.40 (dt, J = 12.6, 5.2 Hz, 1H). LC-MS: [M + H]⁺ = 496.8, 497.8. |

| Example # | Structure | ¹H NMR & MS |
|---|---|---|
| 27 | 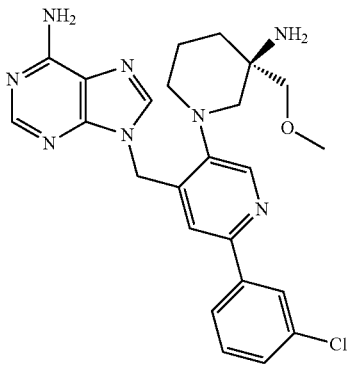 [SMILES: COC[C@@]1(N)CCCN(c2cnc(-c3cccc(Cl)c3)cc2Cn2cnc3c(N)ncnc32)C1] | ¹H NMR (400 MHz, DMSO-d$_6$) δ ppm 8.50 (s, 1H), 8.33 (s, 1H), 8.13 (s, 1H), 7.89 (t, J = 1.9 Hz, 1H), 7.71 (dt, J = 7.2, 1.8 Hz, 1H), 7.51-7.38 (m, 2H), 7.32 (d, J = 13.0 Hz, 3H), 5.61-5.42 (m, 2H), 3.41 (d, J = 8.8 Hz, 1H), 3.26 (s, 3H), 3.21 (d, J = 8.8 Hz, 1H), 3.04-2.86 (m, 3H), 2.73 (d, J = 11.2 Hz, 1H), 1.92-1.52 (m, 5H), 1.37 (ddt, J = 10.6, 8.0, 3.9 Hz, 1H). LC-MS: [M + H]$^+$ = 478.9, 479.9. |
| 28 | 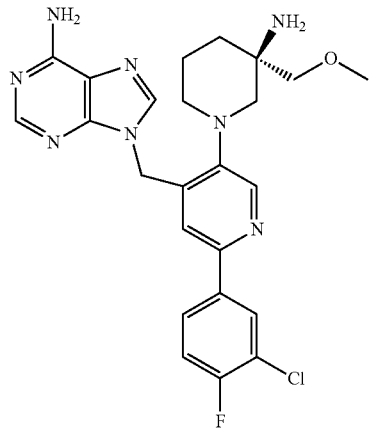 [SMILES: COC[C@@]1(N)CCCN(c2cnc(-c3ccc(F)c(Cl)c3)cc2Cn2cnc3c(N)ncnc32)C1] | ¹H NMR (400 MHz, CD$_3$OD) δ ppm 8.50 (s, 1H), 8.22-8.27 (m, 2H), 7.96 (d, J = 6.7 Hz, 1H), 7.64-7.71 (m, 2H), 7.28 (s, 1H), 5.67 (s, 2H), 3.57 (br d, J = 9.3 Hz, 1H), 3.36-3.39 (m, 4H), 3.04-3.16 (m, 2H), 2.86-3.04 (m, 2H), 1.75-1.93 (m, 2H), 1.50-1.73 (m, 2H). LC-MS: [M + H]$^+$ = 496.8. |
| 29 | 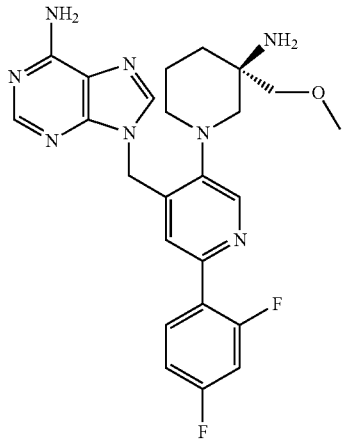 [SMILES: COC[C@@]1(N)CCCN(c2cnc(-c3ccc(F)cc3F)cc2Cn2cnc3c(N)ncnc32)C1] | ¹H NMR (400 MHz, CDCl$_3$) δ ppm 8.55 (s, 1H), 8.42 (s, 1H), 7.92 (s, 1H), 7.88 (td, J = 8.8, 6.7 Hz, 1H), 6.96 (td, J = 8.3, 2.0 Hz, 1H), 6.84 (ddd, J = 11.3, 8.8, 2.5 Hz, 1H), 5.48-5.65 (m, 2H), 3.53-3.61 (m, 1H), 3.38 (s, 3H), 3.29-3.35 (m, 1H), 2.91-3.09 (m, 4H), 1.88-2.01 (m, 2H), 1.63 (br s, 2H). LC-MS: [M + H]$^+$ = 480.9. |

| Example # | Structure | ¹H NMR & MS |
|---|---|---|
| 30 | 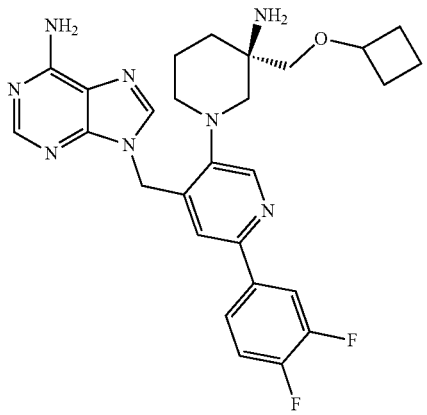 [SMILES: Nc1ncnc2c1ncn2Cc1cc(-c2ccc(F)c(F)c2)ncc1N1CCC[C@](N)(COC2CCC2)C1] | ¹H NMR (400 MHz, CD₃OD) δ ppm 8.51 (s, 1H), 8.24 (s, 1H), 8.24 (s, 1H), 7.78-7.72 (m, 1H), 7.54-7.52 (m, 2H), 7.33-7.26 (m, 2H), 5.67 (s, 1H), 3.98-3.94 (m, 1H), 3.56-3.54 (m, 1H), 3.32 (d, J = 6.Hz, 1H), 3.12-2.94 (m, 3H), 1.93-1.50 (m, 8H). LC-MS: [M + H]⁺ = 520.7. |
| 31 | 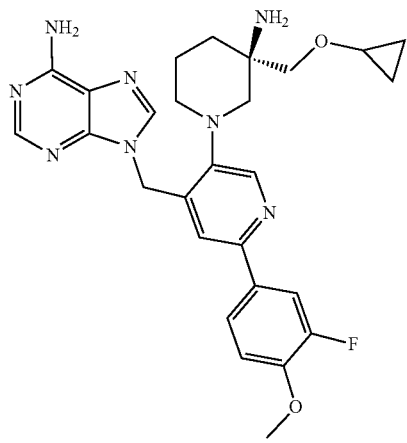 [SMILES: COc1ccc(-c2cc(Cn3cnc4c(N)ncnc43)c(N3CCC[C@](N)(COC4CC4)C3)cn2)cc1F] | ¹H NMR (400 MHz, DMSO-d₆) δ ppm 8.44 (1H, s), 8.31 (1H, s), 8.12 (1H, s), 7.66 (1H, dd, J = 13.2, 2.0 Hz), 7.50 (1 H, d, J = 8.4 Hz), 7.30 (2H, brs), 7.15-7.25 (2H, m), 5.45-5.60 (2H, m), 3.84 (3H, s), 3.53 (1H, d, J = 8.8 Hz), 3.20-3.35 (2H, m), 2.85-2.95 (3H, m), 2.68 (1H, d, J = 11.2 Hz), 1.25-1.85 (6H, m), 0.25-0.50 (4H, m). LC-MS: [M + H]⁺ = 519.1. |
| 32 | 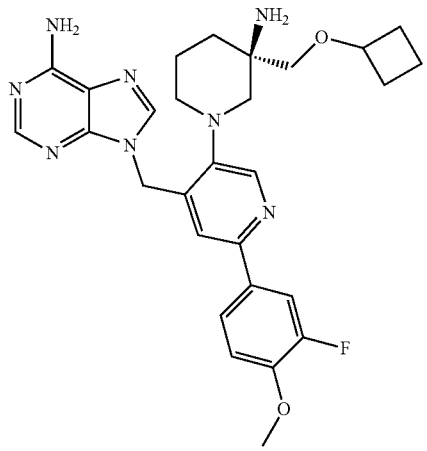 [SMILES: COc1ccc(-c2cc(Cn3cnc4c(N)ncnc43)c(N3CCC[C@](N)(COC4CCC4)C3)cn2)cc1F] | ¹H NMR (400 MHz, CD₃OD) δ ppm 8.33 (s, 1H), 8.13 (s, 1H), 8.12 (s, 1H), 7.43 (dd, J = 2.0, 12.8 Hz, 1H), 7.32 (d, J = 8.4 Hz, 1H), 7.06 (s, 1H), 7.00-6.97 (m, 1H), 5.59-5.50 (m, 2H), 3.86-3.79 (m, 1 H), 3.77 (s, 3H), 3.44 (d, J = 8.0 Hz, 1H), 3.12 (d, J = 8.8 Hz), 3.04-3.01 (m, 1H), 2.95-2.86 (m, 2H), 2.75-2.72 (m, 1H), 2.09-2.00 (m, 2H), 1.84-1.74 (m, 3H), 1.68-1.16 (m, 5H). LC-MS: [M + H]⁺ = 533.2. |

| Example # | Structure | ¹H NMR & MS |
|---|---|---|
| 33 | 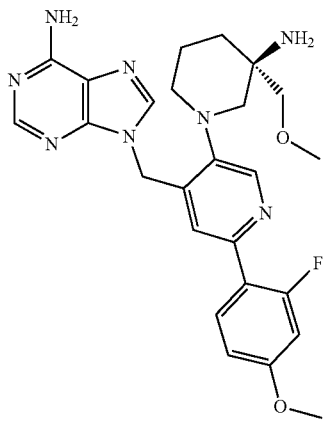 [SMILES: COC[C@@]1(N)CCCN(c2cnc(-c3ccc(OC)cc3F)cc2Cn2cnc3c(N)ncnc32)C1] | ¹H NMR (400 MHz, DMSO-d₆) δ ppm 8.48 (s, 1H), 8.29 (s, 1H), 8.11 (s, 1H), 7.80 (t, J = 9.3 Hz, 1H), 7.32 (s, 2H), 6.90-6.75 (m, 3H), 5.61-5.43 (m, 2H), 3.77 (s, 3H), 3.47 (d, J = 8.8 Hz, 1H), 3.28 (s, 3H), 3.24 (d, J = 8.8 Hz, 1H), 2.98 (t, J = 11.8 Hz, 3H), 2.75-2.66 (m, 1H), 1.94-1.77 (m, 1H), 1.72 (s, 3H), 1.60 (ddd, J = 13.0, 8.6, 4.3 Hz, 1H), 1.39 (ddd, J = 12.3, 7.4, 4.4 Hz, 1H). LC-MS: [M + H]⁺ = 492.9, 493.9. |
| 34 | 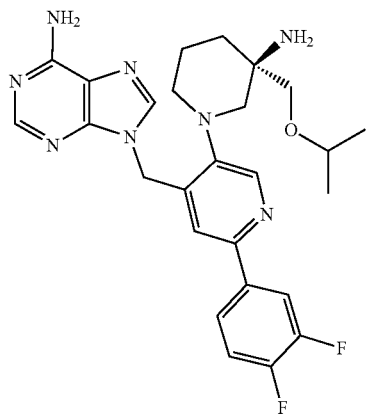 [SMILES: CC(C)OC[C@@]1(N)CCCN(c2cnc(-c3ccc(F)c(F)c3)cc2Cn2cnc3c(N)ncnc32)C1] | ¹H NMR (400 MHz, DMSO-d₆) δ ppm 8.49 (s, 1H), 8.31 (s, 1H), 8.12 (s, 1H), 7.87 (ddd, J = 12.2, 8.0, 2.2 Hz, 1 H), 7.60 (d, J = 8.8 Hz, 1H), 7.48 (dt, J = 10.8, 8.5 Hz, 1H), 7.29 (d, J = 5.8 Hz, 3H), 5.64-5.38 (m, 2H), 3.60-3.41 (m, 2H), 3.21 (d, J = 8.8 Hz, 1H), 3.08-2.85 (m, 3H), 2.70 (d, J = 11.5 Hz, 1H), 1.83 (s, 1H), 1.68 (s, 3H), 1.58 (ddd, J = 13.0, 8.7, 4.2 Hz, 1H), 1.46-1.31 (m, 1H), 1.07 (d, J = 6.0 Hz, 3H), 1.02 (d, J = 6.0 Hz, 3H). LC-MS: [M + H]⁺ = 508.9, 509.9. |
| 35 | 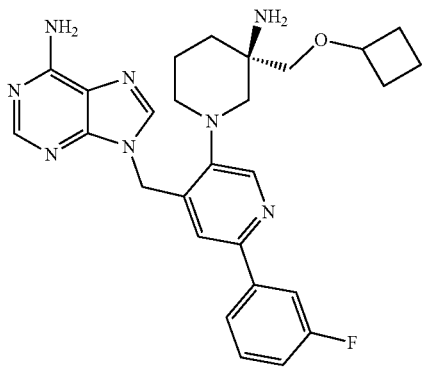 [SMILES: Nc1ncnc2c1ncn2Cc1cc(-c2cccc(F)c2)ncc1N1CCC[C@](N)(COC2CCC2)C1] | ¹H NMR (400 MHz, CD₃OD) δ ppm 1.73-2.05 (7H, m), 2.84-2.90 (1H, m), 3.03-3.07 (2H, m), 3.84 (3H, s), 3.88 (3H,s), 5.49-5.59 (2H, m), 7.01 (1H, t, J = 8.4 Hz), 7.21 (1H, s), 7.38 (1H, d, J = 8.4 Hz), 7.48 (1H, dd, J = 8.8 Hz, 2.4 Hz), 8.14 (1H, d, J = 7.2Hz), 8.38 (1H, s). LC-MS: [M + H]⁺ = 503.3. |

| Example # | Structure | ¹H NMR & MS |
|---|---|---|
| 36 | 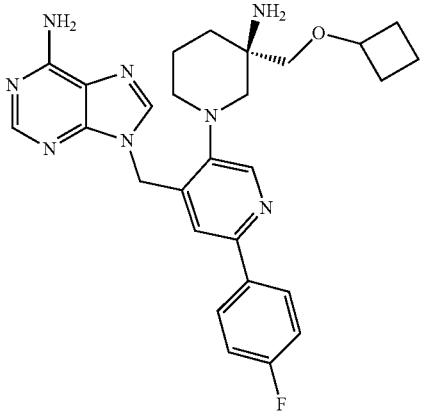 [SMILES: Nc1ncnc2c1ncn2Cc1cc(-c2ccc(F)cc2)ncc1N1CCC[C@](N)(COC2CCC2)C1] | ¹H NMR (400 MHz, CD₃OD) δ ppm 8.49 (s, 1H), 8.25 (s, 1H), 8.24 (s, 1H), 7.19 (s, 1H), 7.15 (t, J = 6.8Hz, 2H), 5.69 (dd, J1 = 13.2 Hz, J2 = 15.2 Hz, 2H), 4.00-3.91 (m, 1H), 3.58 (br, 1H), 3.25 (d, J = 7.2 Hz, 1H), 3.22-3.15 (m, 1H), 3.13-2.97 (m, 2H), 2.93-2.83 (m, 1H), 2.26-2.17 (m, 1H), 2.16-2.07 (m, 1H), 1.97-1.75 (m, 4H), 1.72-1.45 (m, 4H). LC-MS: [M + H]⁺ = 503.2. |
| 37 | 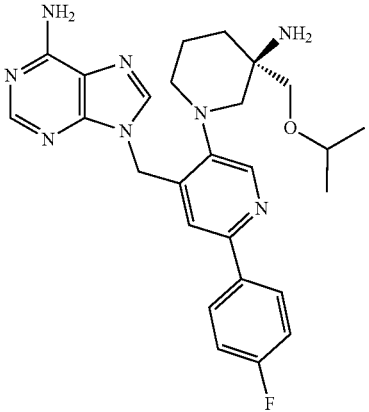 [SMILES: CC(C)OC[C@@]1(N)CCCN(c2cnc(-c3ccc(F)cc3)cc2Cn2cnc3c(N)ncnc32)C1] | ¹H NMR (400 MHz, CD₃OD) δ ppm 8.50 (s, 1H), 8.25 (d, J = 7.2 Hz, 2H), 7.86-7.70 (m, 2H), 7.25 (s, 1H), 7.21-7.08 (m, 2H), 5.68 (s, 2H), 3.78-3.55 (m, 2H), 3.41 (d, J = 9.3 Hz, 1H), 3.24-3.15 (m, 1H), 3.11-2.86 (m, 3H), 2.01-1.77(m, 2H), 1.71 (dd, J = 9.0, 5.0 Hz, 2H), 1.17 (dd, J = 18.3, 6.0 Hz, 6H). LC-MS: [M + H]⁺ = 490.9, 491.9. |
| 38 | 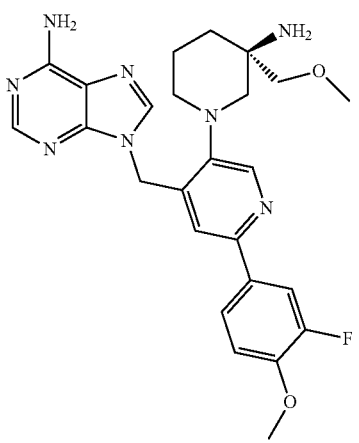 [SMILES: COC[C@@]1(N)CCCN(c2cnc(-c3ccc(OC)c(F)c3)cc2Cn2cnc3c(N)ncnc32)C1] | ¹H NMR (400 MHz, CD₃OD) δ ppm 1.46-1.85 (4H, m), 2.80-3.00 (4H, m), 3.20 (1H, t), 3.26 (3H, s), 3.46 (1H, d), 3.78 (3H, s), 5.53 (3H, s), 7.00 (1H, t), 7.09 (1H, s), 7.33-7.46 (2H, m), 8.12 (2H, d), 8.34 (1H, s). LC-MS: [M + H]⁺ = 493.1. |

| Example # | Structure | ¹H NMR & MS |
|---|---|---|
| 39 | 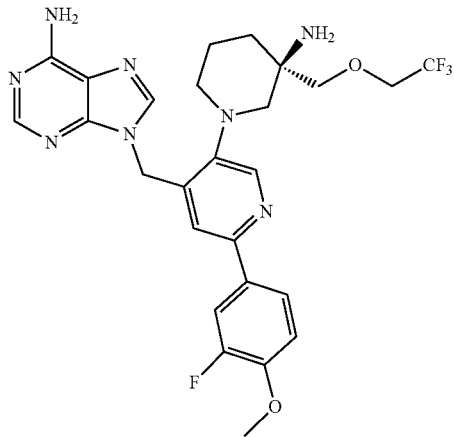 [SMILES: COc1ccc(-c2cc(Cn3cnc4c(N)ncnc43)c(N3CCC[C@](N)(COCC(F)(F)F)C3)cn2)cc1F] | ¹H NMR (400 MHz, CD₃OD) δ ppm 8.46 (s, 1H), 8.24 (d, J = 2.7 Hz, 2H), 7.57 (dd, J = 12.8, 2.2 Hz, 1H), 7.52-7.39 (m, 1H), 7.19 (s, 1H), 7.12 (t, J = 8.6 Hz, 1H), 5.66 (s, 2H), 4.02 (q, J = 9.0 Hz, 2H), 3.59 (d, J = 9.0 Hz, 1H), 3.15 (d, J = 11.3 Hz, 1H), 3.10-2.86 (m, 3H), 1.97-1.85 (m, 1H), 1.85-1.50 (m, 3H). LC-MS: [M + H]⁺ = 560.8, 561.8. |
| 40 | 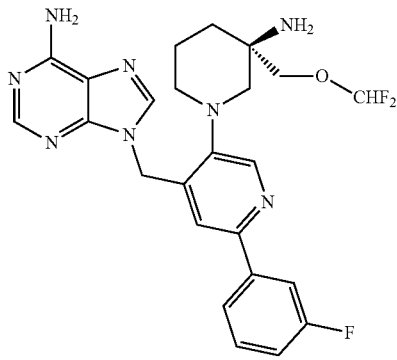 [SMILES: Nc1ncnc2c1ncn2Cc1cc(-c2cccc(F)c2)ncc1N1CCC[C@](N)(COC(F)F)C1] | ¹H NMR (400 MHz, CD₃OD) δ ppm 1.60-1.92 (4H, m), 2.94-3.14 (4H, m), 3.84-4.04 (2H, dd), 5.66 (2H, s), 6.46 (1H, t), 7.07-7.11 (1H, m), 7.25 (1H, s), 7.37-7.54 (3H, m), 8.23 (2H, d), 8.50 (1H,s). LC-MS: [M + H]+ = 499.1. |
| 41 | 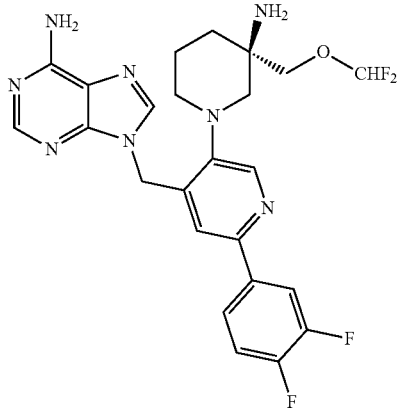 [SMILES: Nc1ncnc2c1ncn2Cc1cc(-c2ccc(F)c(F)c2)ncc1N1CCC[C@](N)(COC(F)F)C1] | ¹H NMR (400 MHz, CD₃OD) δ ppm 8.40 (s, 1H), 8.12 (d, J = 2.4 Hz, 2H), 7.65-7.60 (m, 1H), 7.43-7.41 (m, 1H), 7.20-7.13 (m, 1H), 6.54-6.17 (m, 1H), 5.54 (s, 2H), 3.93 (d, J = 9.6 Hz, 1H), 3.75 (d, J = 10.0 Hz, 1H), 3.02 (d, J = 11.6 Hz, 1H), 2.90-2.84 (m, 3H), 1.80-1.48 (m, 4H). LC-MS: [M + H]+ = 517.2. |

| Example # | Structure | ¹H NMR & MS |
|---|---|---|
| 42 | 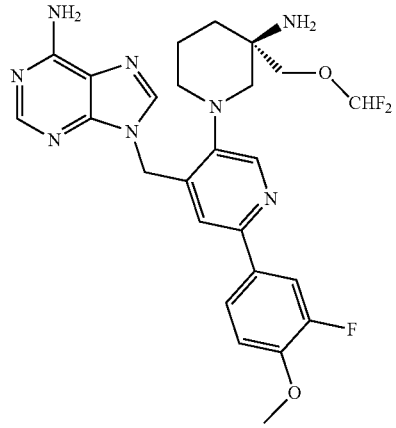 [SMILES: COc1ccc(-c2cc(Cn3cnc4c(N)ncnc43)c(N3CCC[C@](N)(COC(F)F)C3)cn2)cc1F] | ¹H NMR (400 MHz, CD₃OD) δ 1.58-1.90 (4H, m), 2.98-3.14 (4H, m), 3.84-4.05 (5H, m), 5.65 (2H, s), 6.46 (1H, t), 7.11 (1H, m), 7.19 (1H, s), 7.55 (2H, q), 8.23 (2H, d), 8.46 (1H, s). LC-MS: [M + H]+ = 529.1. |
| 43 | 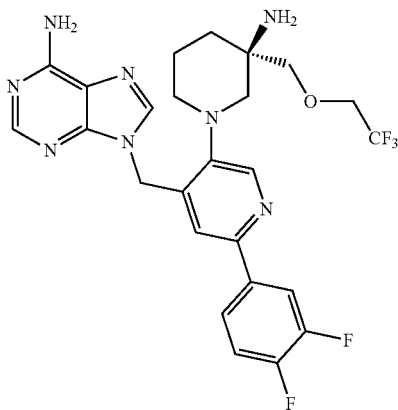 [SMILES: Nc1ncnc2c1ncn2Cc1cc(-c2ccc(F)c(F)c2)ncc1N1CCC[C@](N)(COCC(F)(F)F)C1] | ¹H NMR (400 MHz, CD₃OD) δ ppm 8.51 (s, 1H), 8.24 (d, J = 1.4 Hz, 2H), 7.75 (ddd, J = 12.0, 7.8, 2.2 Hz, 1H), 7.53 (ddt, J = 8.2, 4.0, 1.7 Hz, 1H), 7.37-7.23 (m, 2H), 5.66 (s, 2H), 4.02 (q, J = 9.0 Hz, 2H), 3.86 (d, J = 9.0 Hz, 1H), 3.58 (d, J = 9.1 Hz, 1H), 3.16 (d, J = 11.2 Hz, 1H), 3.11-2.83 (m, 3H), 1.92 (s, 1H), 1.86-1.66 (m, 2H), 1.66-1.51 (m, 1H). LC-MS: [M + H]+ = 548.8, 549.8. |
| 44 | 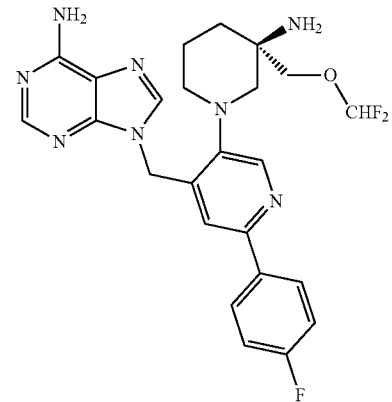 [SMILES: Nc1ncnc2c1ncn2Cc1cc(-c2ccc(F)cc2)ncc1N1CCC[C@](N)(COC(F)F)C1] | ¹H NMR (400 MHz, CD₃OD) δ ppm 1.59-1.94 (4H, m), 2.95-3.15 (4H, m), 3.85-4.05 (2H, dd), 5.66 (2H, s), 6.46 (1H, t), 7.10-7.15 (2H, m), 7.20 (1H, s), 7.73-7.76 (2H, m), 8.23 (2H, d), 8.49 (1H, s). LC-MS: [M + H]+ = 499.1. |

| Example # | Structure | ¹H NMR & MS |
|---|---|---|
| 45 | 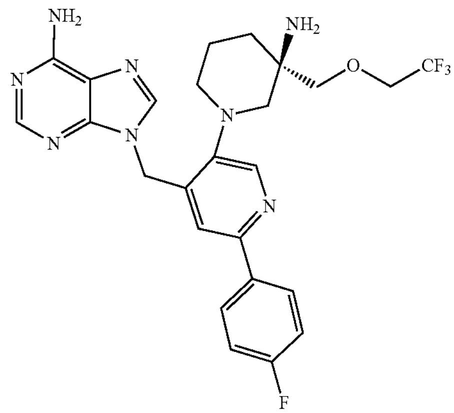 [SMILES: Nc1ncnc2c1ncn2Cc1cc(-c2ccc(F)cc2)ncc1N1CCC[C@](N)(COCC(F)(F)F)C1] | ¹H NMR (400 MHz, CD₃OD) δ ppm 8.49 (s, 1H), 8.24 (s, 2H), 7.82-7.70 (m, 2H), 7.23-7.09 (m, 3H), 5.67 (s, 2H), 4.03 (q, J = 9.0 Hz, 2H), 3.86 (d, J = 8.9 Hz, 1H), 3.59 (d, J = 9.0 Hz, 1H), 3.16 (d, J = 11.3 Hz, 1H), 3.09-2.85 (m, 3H), 1.92 (s, 1H), 1.86-1.51 (m, 3H). LC-MS: [M + H]+ = 530.8, 531.8. |
| 46 | 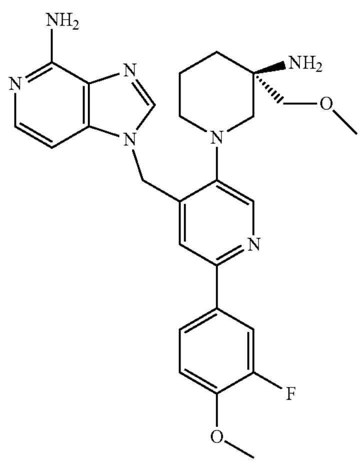 [SMILES: COC[C@@]1(N)CCCN(c2cnc(-c3ccc(OC)c(F)c3)cc2Cn2cnc3c(N)nccc32)C1] | ¹H NMR (400 MHz, CD₃OD) δ ppm 8.34 (s, 1H), 8.12 (d, 2H), 7.46-7.33 (m, 2H), 7.09 (s, 1H), 7.00 (t, 1H), 5.53 (s, 3H), 3.78 (s, 3H), 3.46 (d, 1H), 3.26 (s, 3H), 3.20 (t, 1H), 3.00-2.80 (m, 4H), 1.85-1.46 (m, 4H). LC-MS: [M + H]+ = 493.1. |

Example 47: (S)-9-((5-(3-amino-3-(2,2-difluoro-ethyl)piperidin-1-yl)-2-(3,4-difluorophenyl)pyridin-4-yl)methyl)-9H-purin-6-amine

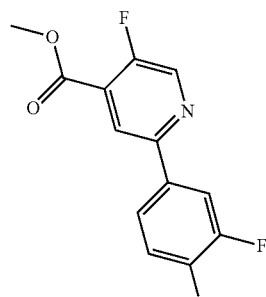

Intermediate A

+

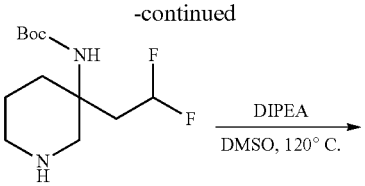

47-6

$\xrightarrow{\text{DIPEA}}{\text{DMSO, 120° C.}}$

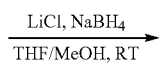

47-7

$\xrightarrow{\text{LiCl, NaBH}_4}{\text{THF/MeOH, RT}}$

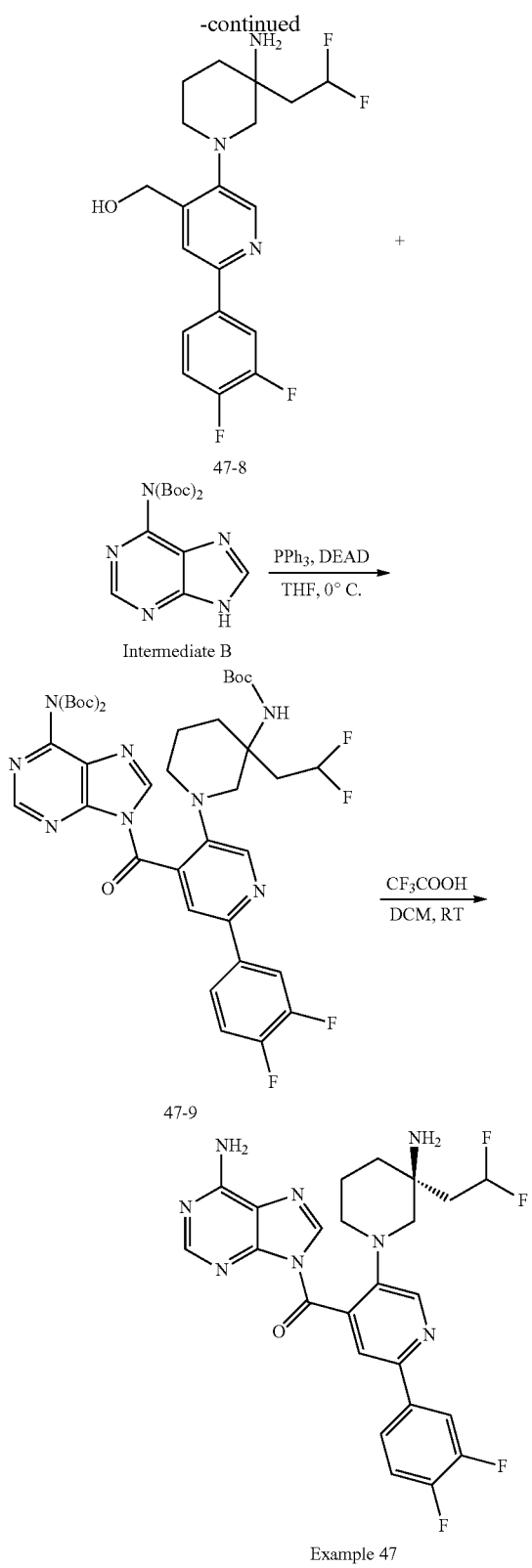

To a solution of methyl 2-(3,4-difluorophenyl)-5-fluoroisonicotinate (Intermediate A) (1.35 g, 5.05 mmol) and tert-butyl (3-(2,2-difluoroethyl)piperidin-3-yl)carbamate (Intermediate 47-6) (1.3 g, 5.05 mmol) in DMSO (30 mL) was added DIPEA (20 mL) at rt, the reaction mixture was stirred at 120° C. for 8 hr under N$_2$ atmosphere. The reaction mixture was diluted with water, extracted with EtOAc (20 mL*3), the combined organic phase was washed with water (20 mL), brine (20 mL), dried over anhydrous sodium sulfate, concentrated to give a crude product. The crude product was purified by flash chromatography (elution gradient: 0% to 30% EtOAc in PE in 30 mins) to afford methyl 5-(3-((tert-butoxycarbonyl)amino)-3-(2,2-difluoroethyl)piperidin-1-yl)-2-(3,4-difluorophenyl)isonicotinate (47-7). LC-MS: [M+H]$^+$=512.0.

To a solution of methyl 5-(3-((tert-butoxycarbonyl)amino)-3-(2,2-difluoroethyl)piperidin-1-yl)-2-(3,4-difluorophenyl)isonicotinate (47-7) (1.2 g, 2.346 mmol) in THF (30 mL) and Methanol (30 mL), was added lithium chloride (1.97 g, 46.9 mmol) and sodium tetrahydroborate (1.78 g, 46.9 mmol) at rt, the reaction mixture was stirred at rt for 5 h under N$_2$ atmosphere. The reaction mixture was diluted with water (20 mL), extracted with EtOAc (20 mL*3), the combined organic phase was washed with water (20 mL), brine (20 mL), dried over anhydrous sodium sulfate, concentrated to give a residue. The residue was purified by flash chromatography (elution gradient: 10% to 50% EtOAc in hexane in 30 mins) to afford tert-butyl (3-(2,2-difluoroethyl)-1-(6-(3,4-difluorophenyl)-4-(hydroxymethyl)pyridin-3-yl)piperidin-3-yl)carbamate (47-8). LC-MS: [M+H]$^+$= 484.2.

To a solution of tert-butyl (3-(2,2-difluoroethyl)-1-(6-(3,4-difluorophenyl)-4-(hydroxymethyl)pyridin-3-yl)piperidin-3-yl)carbamate (47-8) (865 mg, 1.789 mmol), Intermediate B (600 mg, 1.789 mmol) and triphenylphosphine (939 mg, 3.58 mmol) and in THF (20 mL), was added DEAD (0.567 mL, 3.58 mmol) dropwise at 0° C., the reaction mixture was stirred at 0° C. for 0.5 hr under N$_2$ atmosphere. The reaction mixture was diluted with water (20 mL), extracted with EtOAc (20 mL*3), the combined organic phase was washed with water (10 mL), brine (20 mL), dried over sodium sulfate, concentrated to give a crude product. The crude product was purified by flash chromatography (elution gradient: 0% to 10% MeOH in DCM in 30 mins) to afford tert-butyl (tert-butoxycarbonyl)(9-((5-(3-((tert-butoxycarbonyl)amino)-3-(2,2-difluoroethyl)piperidin-1-yl)-2-(3,4-difluorophenyl)pyridin-4-yl)methyl)-9H-purin-6-yl)carbamate (47-9). LC-MS: [M+H]$^+$=801.1.

To a solution of tert-butyl (tert-butoxycarbonyl)(9-((5-(3-((tert-butoxycarbonyl)amino)-3-(2,2-difluoroethyl)piperidin-1-yl)-2-(3,4-difluorophenyl)pyridin-4-yl)methyl)-9H-purin-6-yl)carbamate (47-9) (700 mg, 0.875 mmol) in DCM (18 mL) was added TFA (6 mL), the reaction mixture was stirred at RT for 2 hr under N$_2$ atmosphere. The reaction mixture was concentrated in vacuo to give the crude product. The crude product was purified by Pre-HPLC (Basic condition, NH$_3$H$_2$O %=0.05%, MECN/H$_2$O=0-95% in 12 mins) to afford the pure racemic product. The racemic product was isolated by SFC to afford (S)-9-((5-(3-amino-3-(2,2-difluoroethyl)piperidin-1-yl)-2-(3,4-difluorophenyl)pyridin-4-yl)methyl)-9H-purin-6-amine (Example 47). $^1$H NMR (400 MHz, CD$_3$OD) δ 8.49 (s, 1H), 8.23 (d, J=3.9 Hz, 2H), 7.75 (ddd, J=12.2, 7.8, 2.2 Hz, 1H), 7.53 (s, 1H), 7.34-7.22 (m, 2H), 6.38-6.02 (m, 1H), 5.73-5.52 (m, 2H), 3.00 (d, J=9.4 Hz, 3H), 2.92 (d, J=10.5 Hz, 1H), 2.11 (q, J=18.5, 18.0 Hz, 2H), 1.92 (s, 1H), 1.73 (d, J=28.9 Hz, 3H). LC-MS: [M+H]$^+$= 501.3.

Example 48-77 can be prepared following procedures analogous to those described in Example 47, from corresponding intermediates.

| Example # | Structure | ¹H NMR & MS |
|---|---|---|
| 48 | 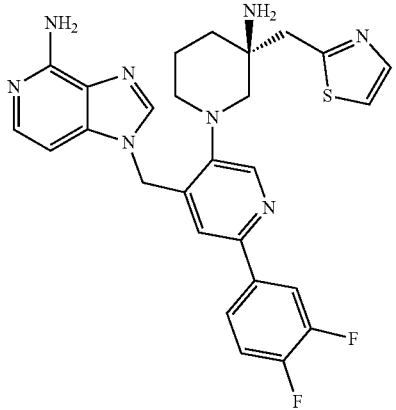 [SMILES: Nc1nccc2c1ncn2Cc1cc(-c2ccc(F)c(F)c2)ncc1N1CCC[C@](N)(Cc2nccs2)C1] | ¹H NMR (400 MHz, CD₃OD) δ: 8.47-8.58 (m, 1H), 8.26 (s, 1H), 7.76 (d, J = 3.5 Hz, 1H), 7.68 (d, J = 6.0 Hz, 2H), 7.48 (d, J = 3.5 Hz, 1H), 7.38-7.46 (m, 1H), 7.24 (dt, J = 10.3, 8.5 Hz, 1H), 6.69 (d, J = 6.0 Hz, 1H), 5.64-5.77 (m, 2H), 3.25-3.42 (m, 4H), 3.13 (br d, J = 11.0 Hz, 1H), 2.93-3.05 (m, 3H), 1.86-1.99 (m, 2H), 1.65-1.77 (m, 1H), 1.52-1.64 (m, 1H). LC-MS: [M + H]+ = 533.1. |
| 49 | 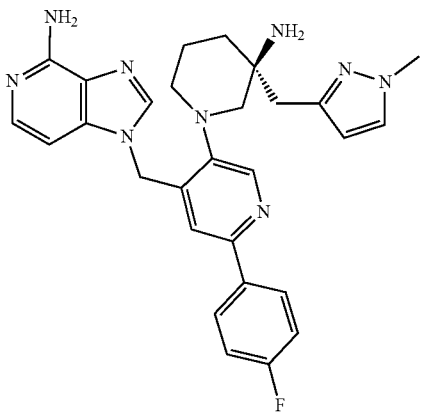 [SMILES: Cn1ccc(C[C@@]2(N)CCCN(c3cnc(-c4ccc(F)cc4)cc3Cn3cnc4c(N)nccc43)C2)n1] | ¹H NMR (400 MHz, CD₃OD) δ ppm 8.49 (s, 1H), 8.25 (s, 1H), 7.69 (q, J = 4.1, 2.3 Hz, 3H), 7.50 (d, J = 2.1 Hz, 1H), 7.21-6.94 (m, 3H), 6.69 (d, J = 6.1 Hz, 1H), 6.16 (d, J = 2.2 Hz, 1H), 5.70 (s, 2H), 3.85 (s, 3H), 3.07 (dd, J = 11.7, 6.3 Hz, 2H), 2.91 (d, J = 21.9 Hz, 4H), 1.92 (dtq, J = 29.4, 10.3, 5.0, 4.6 Hz, 2H), 1.63 (dtd, J = 29.5, 13.2, 4.8 Hz, 2H). LC-MS: [M + H]+ = 512.1, 513.0. |
| 50 | 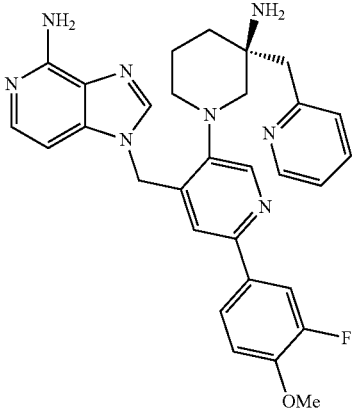 [SMILES: COc1ccc(-c2cc(Cn3cnc4c(N)nccc43)c(N3CCC[C@](N)(Cc4ccccn4)C3)cn2)cc1F] | ¹H NMR (400 MHz, DMSO-d₆) δ ppm 8.51 (d, J = 4.4 Hz, 1H), 8.44 (s, 1H), 8.23 (s, 1H), 7.76 (t, J = 7.6 Hz, 1H), 7.68 (d, J = 6.0 Hz, 1H), 7.49 (dd, J = 12.4 Hz, 2.0 Hz, 1H), 7.35 (d, J = 7.2 Hz, 1H), 7.29 (t, J = 8.0 Hz, 1H), 7.06 (t, J = 8.4 Hz, 1H), 7.00 (s, 1H), 6.68 (d, J = 6.0 Hz, 1H), 5.68 (s, 2H), 3.86 (s, 3H), 3.13-3.00 (m, 4H), 2.97-2.85 (m, 2H), 2.00-1.80 (m, 2H), 1.72-1.52 (m, 2H). LC-MS: [M + H]+ = 539.3. |

| Example # | Structure | ¹H NMR & MS |
|---|---|---|
| 51 | 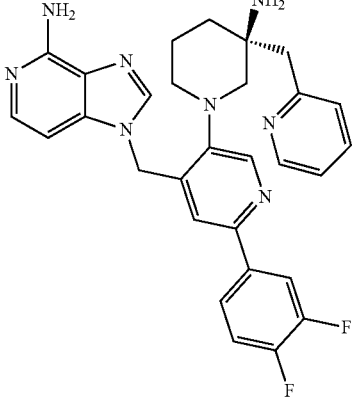 | ¹H NMR (400 MHz, DMSO-d$_6$) δ ppm 8.55-8.46 (m, 2H), 8.24 (s, 1H), 7.76 (t, J = 7.6 Hz, 1H), 7.71-7.63 (m, 2H), 7.47-7.40 (m, 1H), 7.36 (d, J = 7.6 Hz, 1H), 7.31-7.21 (m, 2H), 7.07 (s, 1H), 6.67 (d, J = 6.0 Hz, 1H), 5.69 (s, 2H), 3.16-3.02 (m, 4H), 2.95-2.88 (m, 2H), 2.02-1.81 (m, 2H), 1.71-1.54 (m, 2H).LC-MS: [M + H]+ = 527.2 [M + H]+. |
| 52 | 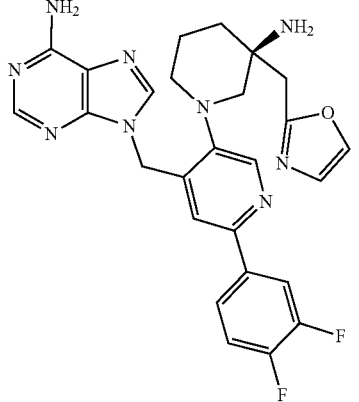 [SMILES: Nc1ncnc2c1ncn2Cc1cc(-c2ccc(F)c(F)c2)ncc1N1CCC[C@](N)(Cc2ncco2)C1] | ¹H NMR (400 MHz, DMSO-d$_6$) δ ppm 8.48 (s, 1H), 8.29 (s, 1H), 8.11 (s, 1H), 8.01 (s, 1H), 7.97-7.80 (m, 1H), 7.61 (d, J = 8.1 Hz, 1H), 7.56-7.43 (m, 1H), 7.31 (d, J = 14.8 Hz, 3H), 7.13 (s, 1H), 5.71-5.44 (m, 2H), 3.13-2.82 (m, 6H), 2.06-1.63 (m, 4H), 1.65-1.40 (m, 2H). LC-MS: [M + H]⁺ = 518.2, 519.2. |
| 53 | 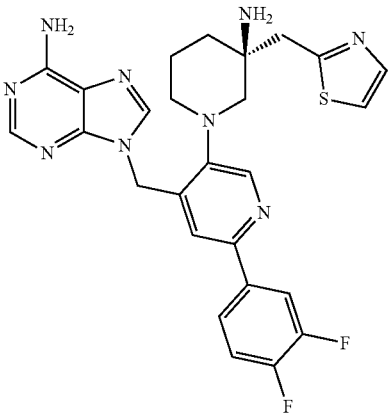 [SMILES: Nc1ncnc2c1ncn2Cc1cc(-c2ccc(F)c(F)c2)ncc1N1CCC[C@](N)(Cc2nccs2)C1] | ¹H NMR (400 MHz, DMSO-d$_6$) δ ppm 8.46 (s, 1H), 8.29 (s, 1H), 8.12 (s, 1H), 7.90-7.84 (m, 1H), 7.71 (d, J = 3.2 Hz, 1H), 7.63-7.55 (m,2H), 7.51-7.44 (m, 1H), 7.30 (d, J = 10.8 Hz, 2H), 5.61-5.59 (m, 2H), 3.31 (m, 2H), 3.18 (d, J = 14.4 Hz, 1H), 2.95-2.82 (m, 4H), 1.85-1.70 (m, 2H), 1.58-1.48 (m, 1H), 1.46-1.39 (m, 1H). LC-MS: [M + H]⁺ = 534.1. |

| Example # | Structure | ¹H NMR & MS |
|---|---|---|
| 54 | 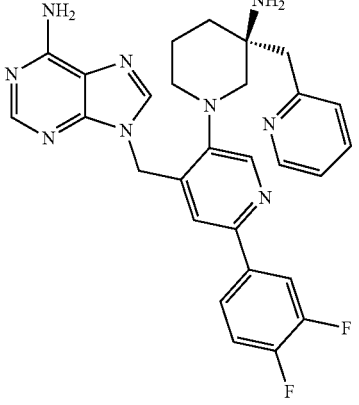 | ¹H NMR (400 MHz, DMSO-d₆) δ ppm 8.47 (d, J = 3.6 Hz, 1H), 8.43 (s, 1H), 8.29 (s, 1H), 8.09 (s, 1H), 7.88-7.81 (m, 1H), 7.66 (dt, J = 2.0 Hz, 7.6 Hz, 1H), 7.61-7.55 (m, 1H), 7.50-7.41 (m, 1H), 7.33 (d, J = 7.6 Hz, 1H), 7.30-7.22 (m, 2H), 7.21-7.16 (m, 2H), 5.55 (q, J = 16.4 Hz, 2H), 3.01-2.75 (m, 6H), 2.05 (brs, 2H), 1.85-1.70 (m, 2H), 1.55-1.43 (m, 1H), 1.42-1.30 (m, 1H). LC-MS: [M + H]⁺ = 528.2. |
| 55 | 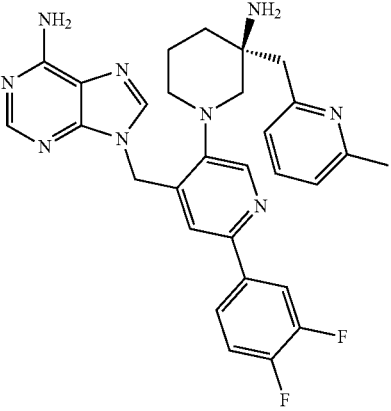 | ¹H NMR (400 MHz, DMSO-d₆) δ ppm 8.51 (s, 1H), 8.23 (s, 1H), 7.81-7.74 (m, 2H), 7.61 (t, J = 7.6 Hz, 1 H), 7.59 (d, J = 6.0 Hz, 1H), 7.54 (d, J = 7.6 Hz, 1H), 7.25-7.16 (m, 2H), 7.13-7.05 (m, 2H), 6.54 (d, J = 6.0 Hz, 1H), 6.19 (s, 2H), 5.54 (s, 2H), 3.53-3.45 (m, 1H), 3.18-3.09 (m, 1H), 3.04-2.99 (m, 1H), 2.98-2.89 (m, 1H), 2.48 (s, 3H), 2.34-2.16 (m, 3H), 2.15-2.04 (m, 1H), 1.81-1.72 (m, 1H), 1.70-1.63 (m, 1H). LC-MS: [M + H]⁺ = 509.3. |
| 56 | 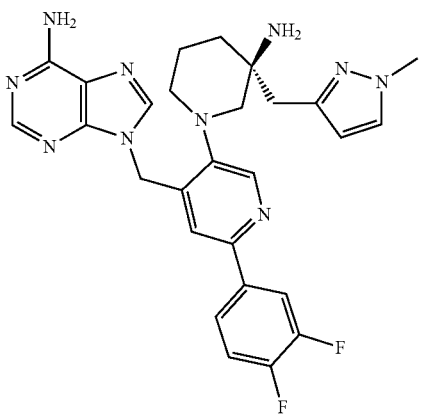 [SMILES: Cn1ccc(C[C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.49 (s, 1H), 8.23 (d, J = 3.8 Hz, 2H), 7.74 (ddd, J = 12.1, 7.7, 2.2 Hz, 1H), 7.51 (dd, J = 14.3, 4.2 Hz, 2H), 7.29 (d, J = 10.3 Hz, 2H), 6.17 (d, J = 2.2 Hz, 1H), 5.74-5.56 (m, 2H), 3.86 (s, 3H), 3.03 (d, J = 11.2 Hz, 2H), 2.88 (d, J = 26.8 Hz, 4H), 2.00-1.74 (m, 2H), 1.62 (q, J = 5.8, 5.4 Hz, 2H). LC-MS: [M + H]⁺ = 531.0, 532.0. |

| Example # | Structure | ¹H NMR & MS |
|---|---|---|
| 57 | 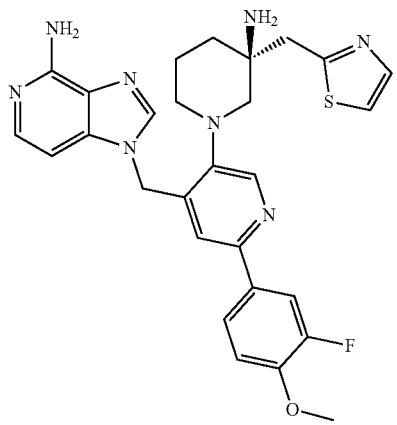 [SMILES: COc1ccc(-c2cc(Cn3cnc4c(N)nccc43)c(N3CCC[C@](N)(Cc4nccs4)C3)cn2)cc1F] | ¹H NMR (400 MHz, CD$_3$OD) δ ppm 8.39 (s, 1H), 8.21 (s, 1H), 7.72 (d, J = 3.2 Hz, 1H), 7.66 (d, J = 6 Hz, 1H), 7.50-7.49 (m, 2H), 7.31 (d, J = 8.8 Hz, 1H), 6.96 (t, J = 7.6 Hz, 2H), 6.67 (d, J = 6.0 Hz, 1H), 5.72-5.59 (m, 2H), 3.79 (s, 3H), 3.40-3.20 (m, 2H), 3.05 (d, J = 11.2 Hz, 1H), 2.95-2.85 (m, 3H), 1.95-1.76 (m, 2H), 1.70-1.60 (m, 1H), 1.55-1.45 (m, 1H). LC-MS: [M + H]+ = 545.2 |
| 58 | 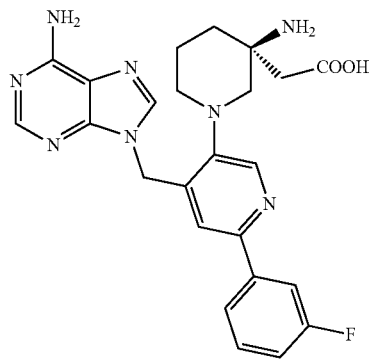 [SMILES: Nc1ncnc2c1ncn2Cc1cc(-c2cccc(F)c2)ncc1N1CCC[C@](N)(CC(=O)O)C1] | ¹H NMR (400 MHz, CD$_3$OD) δ ppm 8.50 (s, 1 H), 8.32 (s, 1 H), 8.23 (s, 1 H), 7.52-7.47 (m, 2 H), 7.42-7.36 (m, 1H), 7.20 (s, 1 H), 7.11-7.07 (m, 1H), 5.72-5.63 (m, 2 H), 3.15-2.94 (m, 4 H), 2.56-2.47 (m, 2 H), 1.96-1.64 (m, 4 H). LC-MS: [M + H]$^+$ = 477.1. |
| 60 | 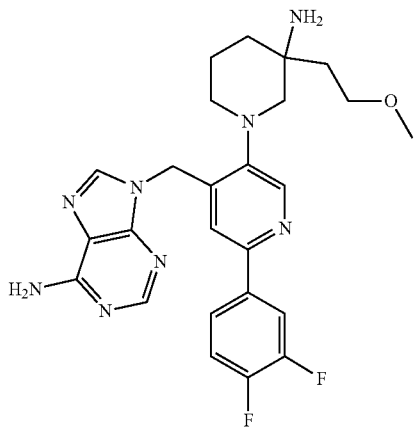 [SMILES: COCCC1(N)CCCN(c2cnc(-c3ccc(F)c(F)c3)cc2Cn2cnc3c(N)ncnc32)C1] | ¹H NMR (400MHz, CD$_3$OD) δ : 8.51 (s, 1H), 8.24 (d, J = 4.0 Hz, 2H), 7.76 (ddd, J = 12.1, 7.8, 2.2 Hz, 1H), 7.60-7.47 (m, 1H), 7.39-7.16 (m, 2H), 5.89-5.55 (m, 2H), 3.60 (td, J = 6.4, 2.3 Hz, 2H), 3.35 (s, 3H), 2.97 (dp, J = 24.6, 11.2 Hz, 4H), 2.04-1.71 (m, 4H), 1.65 (d, J = 7.3 Hz, 2H). LC-MS: [M + H]+ = 495.2 |

| Example # | Structure | ¹H NMR & MS |
|---|---|---|
| 61 | 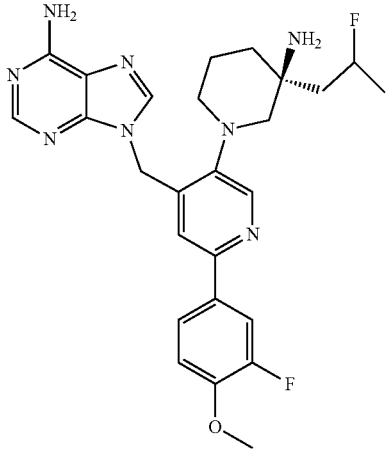 | ¹H NMR (400 MHz, CD₃OD) δ 8.46 (d, J = 2.5 Hz, 1H), 8.32-8.16 (m, 2H), 7.58 (dt, J = 12.7, 1.8 Hz, 1H), 7.53-7.42 (m, 1H), 7.25 (s, 1H), 7.20-6.97 (m, 1H), 6.41-6.00 (m, 1H), 5.83-5.51 (m, 2H), 3.90 (d, J = 1.4 Hz, 3H), 3.07-2.80 (m, 4H), 2.33 -1.99 (m, 2H), 1.93 (s, 1H), 1.82-1.55 (m, 3H). LC-MS: [M + H]⁺ = 512.8, 513.8. |
| 62 | 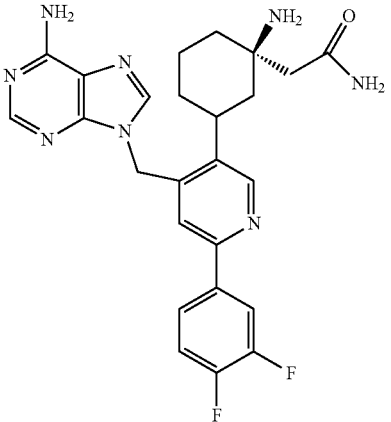 [SMILES: NC(=O)C[C@@]1(N)CCCC(c2cnc(-c3ccc(F)c(F)c3)cc2Cn2cnc3c(N)ncnc32)C1] | ¹H NMR (400 MHz, CDCl₃) δ ppm 8.52 (s, 1H), 8.39 (s, 1H), 7.92 (s, 1H), 7.66-7.77 (m, 2H), 7.48 (br d, J = 8.0 Hz, 1H), 7.19 (s, 1H), 5.76 (br s, 2H), 5.47-5.58 (m, 2H), 2.92-3.12 (m, 4H), 2.42-2.49 (m, 1H), 2.15 (d, J = 4.3 Hz, 1H), 1.59-1.79 (m, 4H). LC-MS: [M + H]⁺ = 493.8. |
| 63 | 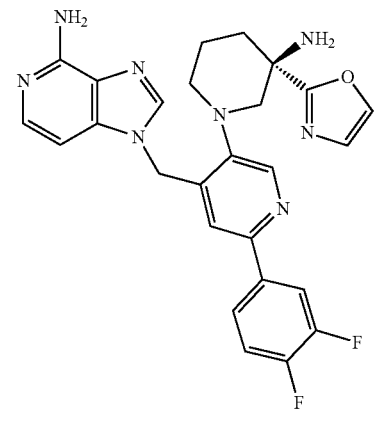 [SMILES: Nc1nccc2c1ncn2Cc1cc(-c2ccc(F)c(F)c2)ncc1N1CCC[C@](N)(c2ncco2)C1] | ¹H NMR (400 MHz, CD₃OD) δ ppm 8.52 (s, 1H), 8.27 (s, 1H), 7.87 (s, 1H), 7.74-7.64 (m, 2H), 7.45 (ddt, J = 8.3, 4.0, 1.7 Hz, 1H), 7.27 (dt, J = 10.6, 8.4 Hz, 1H), 7.15 (s, 1H), 7.07 (s, 1H), 6.70 (d, J = 6.0 Hz, 1H), 5.80-5.60 (m, 2H), 3.24-3.04 (m, 4H), 3.04-2.99 (m, 2H), 2.01-1.88 (m, 2H), 1.68 (dp, J = 28.2, 7.3, 6.5 Hz, 2H). LC-MS: [M + H]+ = 517.2, 518.2. |

| Example # | Structure | ¹H NMR & MS |
|---|---|---|
| 64 | 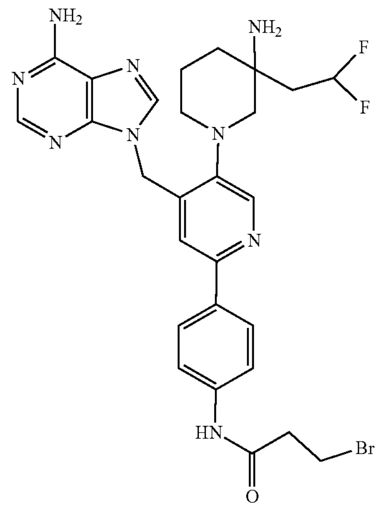 [SMILES: Nc1ncnc2c1ncn2Cc1cc(-c2ccc(NC(=O)CCBr)cc2)ncc1N1CCCC(N)(CC(F)F)C1] | ¹H NMR (400 MHz, CD₃OD) δ ppm 8.55-8.61 (m, 1H), 8.52 (s, 1H), 8.38 (s, 1H), 7.74-7.80 (m, 2H), 7.66-7.73 (m, 2H), 7.39 (s, 1H), 6.21-6.53 (m, 1H), 5.85 (br d, J = 12.5 Hz, 2H), 3.73 (t, J = 6.4 Hz, 2H), 3.42 (s, 2H), 3.01 (t, J = 6.4 Hz, 2H), 2.42-2.62 (m, 2H), 1.94-2.18 (m, 4H), 1.35-1.41 (m, 2H). LC-MS: [M + H]+ = 613.9. |
| 65 | 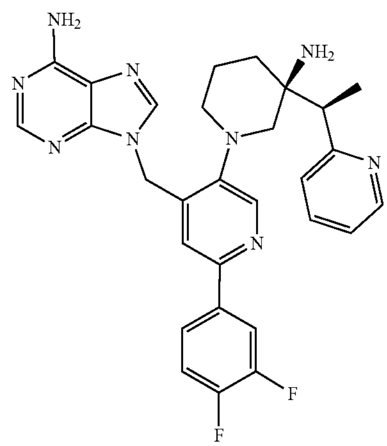 [SMILES: C[C@@H](c1ccccn1)[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.62-8.40 (m, 2H), 8.25 (s, 2H), 7.77 (q, J = 7.7 Hz, 2H), 7.56 (q, J = 3.4 Hz, 1H), 7.44-7.14 (m, 4H), 5.82-5.55 (m, 2H), 3.18-3.08 (m, 2H), 3.00 (dd, J = 11.9, 6.2 Hz, 2H), 2.87 (t, J = 10.4 Hz, 1H), 1.88 (t, J = 9.8 Hz, 1H), 1.80-1.65 (m, 1H), 1.55 (td, J = 12.3, 10.9, 4.5 Hz, 1H), 1.34 (t, J = 11.2 Hz, 4H). LC-MS: [M + H]⁺ = 542.0, 543.0. |
| 66 | 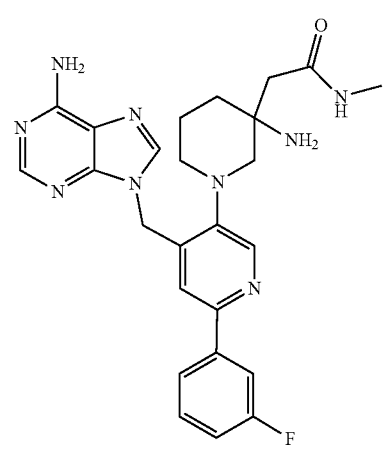 [SMILES: CNC(=O)CC1(N)CCCN(c2cnc(-c3cccc(F)c3)cc2Cn2cnc3c(N)ncnc32)C1] | ¹H NMR (400 MHz, CD₃OD) δ 8.49 (s, 1H), 8.27 (s, 1H), 8.23 (s, 1H), 7.54-7.49 (m, 2H), 7.43-7.37 (m, 1H), 7.24 (s, 1H), 7.11-7.07 (m, 1H), 5.72-5.63 (m, 2H), 3.10-2.94 (m, 4H), 2.72 (s, 3H), 2.49 (s, 2H), 1.90-1.66 (m, 4H). LC-MS: [M + H]+ = 490.2 |

-continued

| Example # | Structure | ¹H NMR & MS |
|---|---|---|
| 67 | 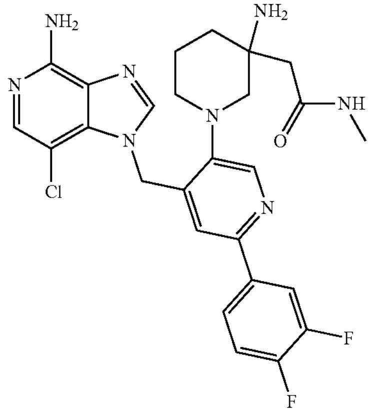 [SMILES: CNC(=O)CC1(N)CCCN(c2cnc(-c3ccc(F)c(F)c3)cc2Cn2cnc3c(N)ncc(Cl)c32)C1] | ¹H NMR (400 MHz, CD₃OD) δ: 8.49 (s, 1H), 8.32 (s, 1H), 7.73-7.55 (m, 2H), 7.38 (d, J = 8.7 Hz, 1H), 7.26 (dt, J = 10.4, 8.4 Hz, 1H), 6.79 (s, 1H), 5.95 (s, 2H), 3.19-2.99 (m, 4H), 2.74 (s, 3H), 2.55 (q, J = 14.9 Hz, 2H), 1.93 (d, J = 39.7 Hz, 2H), 1.70 (s, 2H). LC-MS: [M + H]+ = 540.8 |
| 68 | 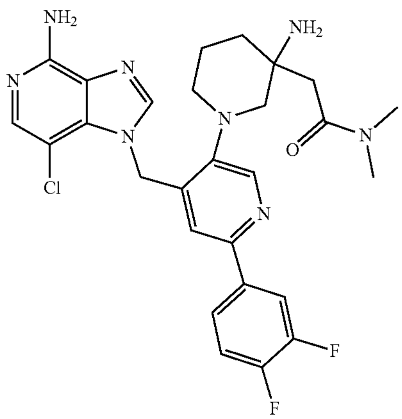 [SMILES: CN(C)C(=O)CC1(N)CCCN(c2cnc(-c3ccc(F)c(F)c3)cc2Cn2cnc3c(N)ncc(Cl)c32)C1] | ¹H NMR (400 MHz, CD₃OD) δ ppm 8.48 (d, J = 6.1 Hz, 1H), 8.32 (d, J = 6.1 Hz, 1H), 7.63 (h, J = 6.6 Hz, 2H), 7.37 (s, 1H), 7.26 (q, J = 8.4 Hz, 1H), 6.79 (d, J = 6.2 Hz, 1H), 5.90 (d, J = 6.5 Hz, 2H), 3.07 (dd, J = 14.0, 7.4 Hz, 2H), 2.96-2.75 (m, 4H), 2.61 (dd, J = 16.5, 6.4 Hz, 1H), 1.94 (d, J = 25.0 Hz, 2H), 1.74 (s, 2H). LC-MS: [M + H]+ = 554.8, 556.7. |
| 69 | 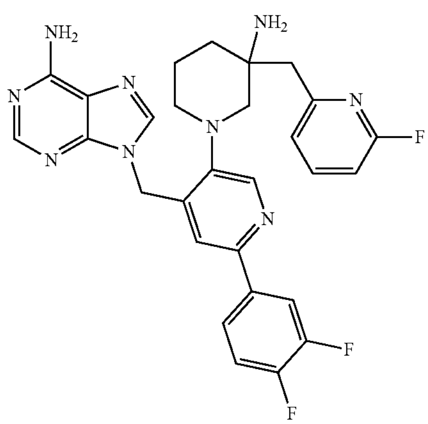 [SMILES: Nc1ncnc2c1ncn2Cc1cc(-c2ccc(F)c(F)c2)ncc1N1CCCC(N)(Cc2cccc(F)n2)C1] | ¹H NMR (400 MHz, CD₃OD) δ ppm 8.45 (s, 1H), 8.22 (s, 1H), 8.21 (s, 1H), 7.86 (q, J = 8.0 Hz, 1H), 7.76-7.65 (m, 1H), 7.54-7.46 (m, 1H), 7.30-7.20 (m, 3H), 6.90 (dd, J = 2.4, 8.0 Hz, 1H), 5.76-5.58 (m, 2H), 3.09-2.86 (m, 6H), 1.96-1.76 (m, 2H), 1.72-1.51 (m, 2H). LC-MS: [M + H]+ = 546.4. |
| 70 | 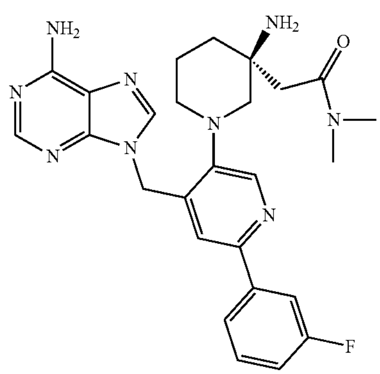 [SMILES: CN(C)C(=O)C[C@@]1(N)CCCN(c2cnc(-c3cccc(F)c3)cc2Cn2cnc3c(N)ncnc32)C1] | ¹H NMR (400 MHz, CD₃OD) δ 8.38 (s, 1H), 8.14 (s, 1H), 8.12 (s, 1H), 7.43-7.38 (m, 2H), 7.31-7.26 (m, 1H), 7.14 (s, 1H), 7.00-6.96 (m, 1H), 5.54-5.51 (m, 2H), 3.09-2.92 (m, 6H), 2.88-2.78 (m, 4H), 2.67-2.60 (m, 1H), 2.52-2.48 (m, 1H), 1.88-1.57 (m, 4H). LC-MS: [M + H]+ = 504.2. |

| Example # | Structure | ¹H NMR & MS |
|---|---|---|
| 71 | 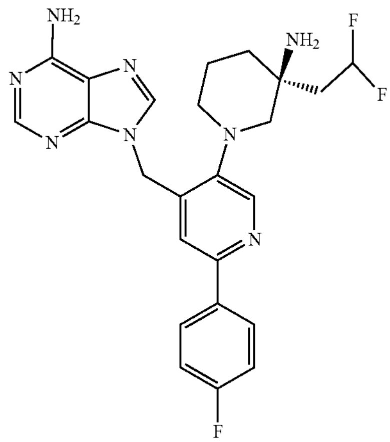 [SMILES: Nc1ncnc2c1ncn2Cc1cc(-c2ccc(F)cc2)ncc1N1CCC[C@](N)(CC(F)F)C1] | ¹H NMR (400 MHz, CD₃OD) δ ppm 8.49 (s, 1H), 8.24 (t, J = 3.0 Hz, 2H), 7.78 (dt, J = 8.4, 4.3 Hz, 2H), 7.25 (s, 1H), 7.15 (t, J = 8.5 Hz, 2H), 6.22 (tt, J = 56.3, 4.7 Hz, 1H), 5.93-5.53 (m, 2H), 3.13-2.79 (m, 4H), 2.34-1.86 (m, 3H), 1.86-1.54 (m, 3H). LC-MS: [M + H]+ = 482.9, 483.9. |
| 72 | 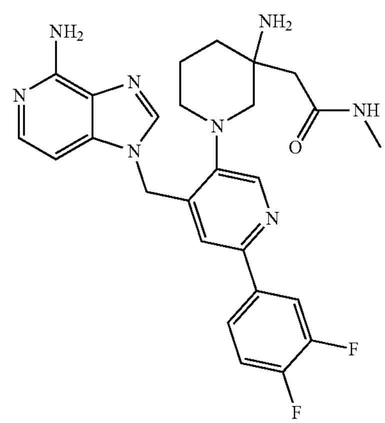 [SMILES: CNC(=O)CC1(N)CCCN(c2cnc(-c3ccc(F)c(F)c3)cc2Cn2cnc3c(N)nccc32)C1] | ¹H NMR (400 MHz, CD₃OD) δ ppm 8.52 (s, 1H), 8.28 (s, 1H), 7.76-7.63 (m, 2H), 7.44 (ddt, J = 8.3, 3.9, 1.6 Hz, 1H), 7.27 (dt, J = 10.5, 8.5 Hz, 1H), 7.04 (s, 1H), 6.66 (d, J = 6.0 Hz, 1H), 5.71 (s, 2H), 3.21-2.91 (m, 4H), 2.74 (s, 3H), 2.55 (s, 2H), 1.97 (d, J = 11.2 Hz, 1H), 1.88 (d, J = 5.2 Hz, 1H), 1.72 (d, J = 4.7 Hz, 2H). LC-MS: [M + H]+ = 506.9, 507.9. |
| 73 | 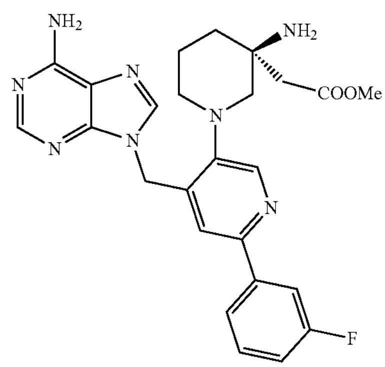 [SMILES: COC(=O)C[C@@]1(N)CCCN(c2cnc(-c3cccc(F)c3)cc2Cn2cnc3c(N)ncnc32)C1] | ¹H NMR (400 MHz, CD₃OD) δ ppm 8.37 (s, 1 H), 8.13 (s, 1 H), 8.10 (s, 1 H), 7.44-7.39 (m, 2 H), 7.31-7.26 (m, 1H), 7.18 (s, 1 H), 7.00-6.96 (m, 1H), 5.60-5.49 (m, 2 H), 3.57 (s, 3 H), 2.98-2.86 (m, 4 H), 2.56-2.45 (m, 2 H), 1.82-1.56 (m, 4 H). LC-MS: [M + H]+ = 491.2. |

| Example # | Structure | ¹H NMR & MS |
|---|---|---|
| 74 | 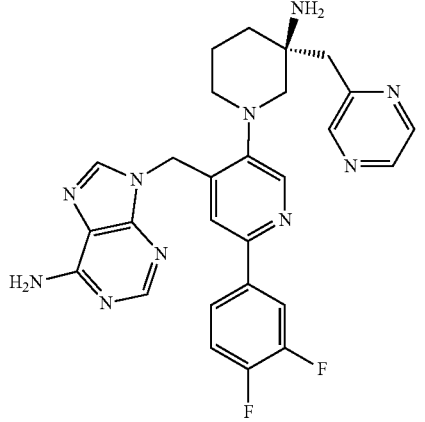 [SMILES: Nc1ncnc2c1ncn2Cc1cc(-c2ccc(F)c(F)c2)ncc1N1CCC[C@](N)(Cc2cnccn2)C1] | ¹H NMR (400 MHz, CD₃OD) δ ppm 8.68-8.56 (m, 2H), 8.56-8.43 (m, 2H), 8.24 (d, J = 3.5 Hz, 2H), 7.76 (ddd, J = 12.0, 7.8, 2.2 Hz, 1H), 7.54 (ddt, J = 8.2, 3.8, 1.7 Hz, 1H), 7.38-7.17 (m, 2H), 5.82-5.51 (m, 2H), 3.21-3.05 (m, 3H), 2.97 (t, J = 8.5 Hz, 3H), 1.88 (d, J = 9.1 Hz, 2H), 1.70 (dt, J = 13.8, 6.5 Hz, 1H), 1.61 (q, J = 7.6, 6.4 Hz, 1H). LC-MS: [M + H]+ = 529.2, 530.2. |
| 75 | 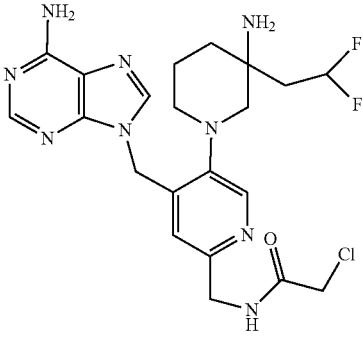 [SMILES: Nc1ncnc2c1ncn2Cc1cc(CNC(=O)CCl)ncc1N1CCCC(N)(CC(F)F)C1] | ¹H NMR (400 MHz, CD₃OD) δ ppm 8.55 (s, 1H), 8.35 (s, 1H), 8.25 (s, 1H), 7.79 (br d, J = 8.0 Hz, 2H), 7.47 (s, 1H), 7.39 (br d, J = 8.0 Hz, 2H), 6.20-6.53 (m, 1H), 5.65 (br d, J = 3.0 Hz, 2H), 4.46 (s, 2H), 4.11 (s, 2H), 3.06 (br s, 2H), 2.98 (br s, 2H), 2.40-2.54 (m, 2H), 1.87-2.03 (m, 4H). LC-MS: [M + H]+ = 570.0. |
| 76 | 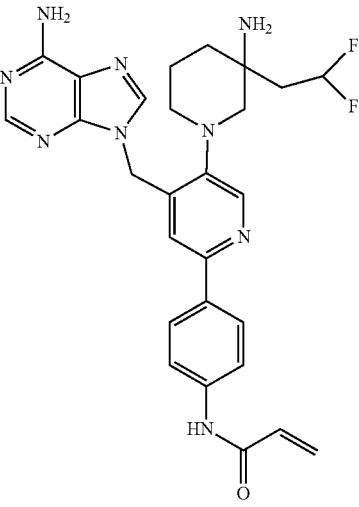 [SMILES: C=CC(=O)Nc1ccc(-c2cc(Cn3cnc4c(N)ncnc43)c(N3CCCC(N)(CC(F)F)C3)cn2)cc1] | ¹H NMR (400 MHz, CD₃OD) δ ppm 8.55-8.59 (m, 1H), 8.47-8.51 (m, 1H), 8.36 (s, 1H), 7.73-7.81 (m, 4H), 7.37 (s, 1H), 6.42-6.48 (m, 1H), 6.41 (d, J = 2.5 Hz, 1H), 6.21-6.39 (m, 1H), 5.77-5.84 (m, 3H), 3.40 (br d, J = 4.3 Hz, 2H), 3.12-3.22 (m, 1H), 3.01-3.09 (m, 1H), 2.43-2.60 (m, 2H), 2.04 (br d, J = 11.0 Hz, 4H) LC-MS: [M + H]+ = 534.0. |

| Example # | Structure | ¹H NMR & MS |
|---|---|---|
| 77 | 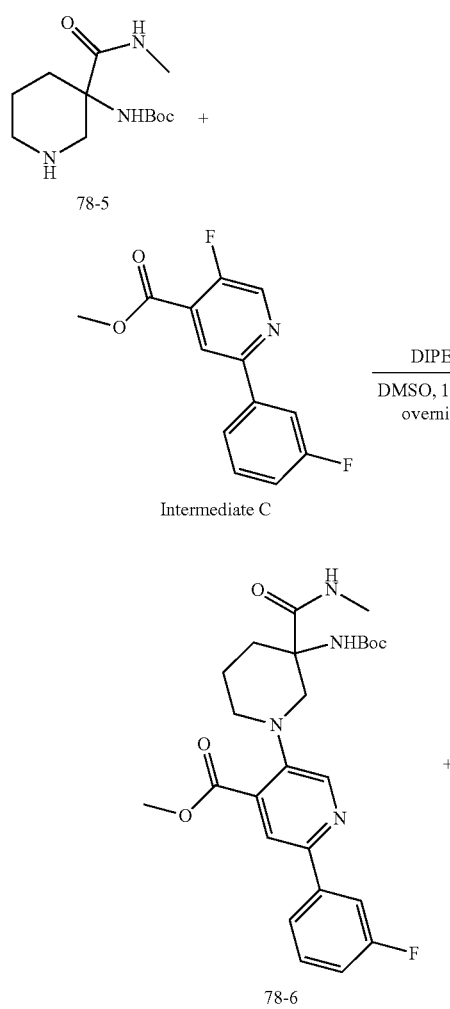 | ¹H NMR (CD₃OD) δ: 8.55 (s, 1H), 8.28 (d, J = 20.9 Hz, 2H), 7.80 (t, J = 10.0 Hz, 1H), 7.59 (s, 1H), 7.45-7.23 (m, 2H), 5.66 (s, 2H), 3.22 (t, J = 9.4 Hz, 2H), 3.08-2.86 (m, 4H), 2.23 (s, 2H), 1.90 (d, J = 8.8 Hz, 4H) LC-MS: [M + H]+ = 475.8 |

Example 78: (R)-3-amino-1-(4-((6-amino-9H-purin-9-yl)methyl)-6-(3-fluorophenyl)pyridin-3-yl)-N-methylpiperidine-3-carboxamide

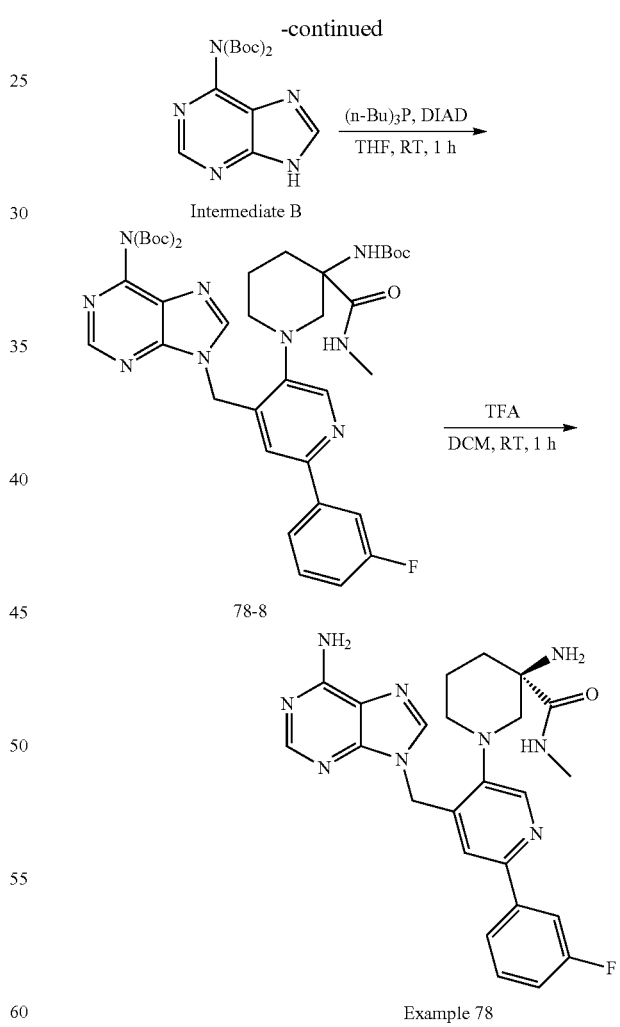

To a solution of methyl tert-butyl 3-(methylcarbamoyl)piperidin-3-ylcarbamate (Intermediate 78-5) (200 mg, 0.777 mmol), methyl 5-fluoro-2-(3-fluorophenyl)isonicotinate (Intermediate C) (161 mg, 0.648 mmol) in DMSO (4 mL) was added DIPEA (4 mL) at RT, the reaction mixture was stirred at 120° C. overnight. The reaction mixture was diluted with water, extracted with EtOAc, the combined organic phase was washed with water (20 mL), brine (20 mL), dried over anhydrous sodium sulfate, concentrated to give a residue. The residue was purified by flash chromatography (elution gradient: 0% to 30% EtOAc in PE in 30 mins) to afford methyl 5-(3-(tert-butoxycarbonylamino)-3-(methylcarbamoyl)piperidin-1-yl)-2-(3-fluorophenyl) isonicotinate (78-6). LC-MS: [M+H]⁺=487.3.

To a mixture of methyl 5-(3-(tert-butoxycarbonylamino)-3-(methylcarbamoyl)piperidin-1-yl)-2-(3-fluorophenyl) isonicotinate (78-6) (150 mg, 0.308 mmol), LiCl (130 mg, 3.08 mmol), THF (5 mL) and MeOH (5 mL) was added NaBH₄ (232 mg, 6.16 mmol) portionwise. After addition, the mixture was stirred at RT for 3 h. Then water (10 mL) was added to quench the reaction, extracted with EtOAc, the combined organic phase was washed with water (20 mL), brine, dried over anhydrous sodium sulfate, concentrated to give a residue. The residue was purified by flash chromatography (elution gradient: 10% to 50% EtOAc in PE in 30 mins) to give tert-butyl 1-(6-(3-fluorophenyl)-4-(hydroxymethyl)pyridin-3-yl)-3-(methylcarbamoyl)piperidin-3-ylcarbamate (78-7). LC-MS: [M+H]⁺=459.2.

To a solution of tert-butyl 1-(6-(3-fluorophenyl)-4-(hydroxymethyl)pyridin-3-yl)-3-(methylcarbamoyl)piperidin-3-ylcarbamate (78-7) (129 mg, 0.282 mmol), Intermediate B (142 mg, 0.423 mmol), n-Bu3P (171 mg, 0.845 mmol) in THF (5 mL) was added DIAD (171 mg, 0.845 mmol) dropwise at RT under N₂ atmosphere, after addition, the mixture was stirred at RT for 1 h under N₂, quenched with water and extracted with EtOAc. The combined organic phase was worked up under aqueous conditions and concentrated to give a residue. The residue was purified by flash chromatography (elution gradient: 10% to 70% EtOAc in PE in 30 mins) to afford tert-butyl (tert-butoxycarbonyl)(9-((5-(3-((tert-butoxycarbonyl)amino)-3-(methylcarbamoyl) piperidin-1-yl)-2-(3-fluorophenyl)pyridin-4-yl)methyl)-9H-purin-6-yl)carbamate (78-8). LC-MS: [M+H]⁺=776.3

To a solution of tert-butyl (tert-butoxycarbonyl)(9-((5-(3-((tert-butoxycarbonyl)amino)-3-(methylcarbamoyl) piperidin-1-yl)-2-(3-fluorophenyl)pyridin-4-yl)methyl)-9H-purin-6-yl)carbamate (78-8) (100 mg, 0.232 mmol) in DCM (9 mL), was added TFA (3 mL) at RT. The reaction mixture was stirred at RT for 1 h. The mixture was concentrated in vacuo to give a residue. The residue was purified by Pre-HPLC (Basic condition, NH₃.H₂O %=0.05%, MEOH/H₂O=0-95% in 12 mins) to afford 40 mg of pure racemic product. The racemic product was isolated by SFC to give (R)-3-amino-1-(4-((6-amino-9H-purin-9-yl)methyl)-6-(3-fluorophenyl)pyridin-3-yl)-N-methylpiperidine-3-carboxamide (Example 78). ¹H NMR (400 MHz, CD₃OD) δ 8.39 (s, 1H), 8.17 (s, 1H), 8.11 (s, 1H), 7.44-7.39 (m, 2H), 7.32-7.27 (m, 1H), 7.18 (s, 1H), 7.01-6.97 (m, 1H), 5.62-5.51 (m, 2H), 3.32-3.29 (m, 1H), 3.02-2.99 (m, 1H), 2.91-2.78 (m, 2H), 2.69 (s, 3H), 2.09-2.01 (m, 1H), 1.97-1.87 (m, 1H), 1.70-1.67 (m, 1H), 1.55-1.51 (m, 1H). LC-MS: [M+H]⁺=476.2

Example 79-88 can be prepared following procedures analogous to those described in Example 78.

| Example # | Structure | ¹H NMR & MS |
|---|---|---|
| 79 | 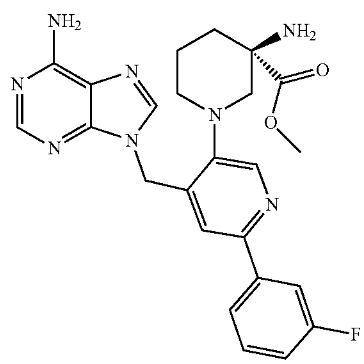 [SMILES: COC(=O)[C@@]1(N)CCCN(c2cnc(-c3cccc(F)c3)cc2Cn2cnc3c(N)ncnc32)C1] | ¹H NMR (400 MHz, CDCl₃) δ ppm 8.54 (s, 1H), 8.41 (s, 1H), 7.94 (s, 1H), 7.59-7.47 (m, 2H), 7.40-7.30 (m, 2H), 7.04 (td, J = 8.2, 2.1 Hz, 1H), 5.67 (s, 2H), 5.60-5.46 (m, 2H), 3.79 (s, 3H), 3.48 (d, J = 11.4 Hz, 1H), 3.01 (dd, J = 13.7, 8.4 Hz, 3H), 2.21 (d, J = 5.4 Hz, 1H), 2.04-1.86 (m, 2H), 1.67-1.59 (m, 1H). LC-MS: [M + H]⁺ = 477.1. |
| 80 | 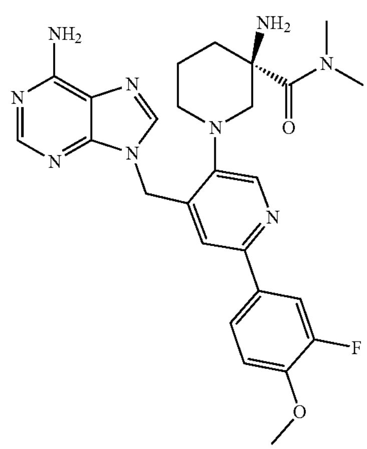 [SMILES: COc1ccc(-c2cc(Cn3cnc4c(N)ncnc43)c(N3CCC[C@](N)(C(=O)N(C)C)C3)cn2)cc1F] | ¹H NMR (400 MHz, CD₃OD) δ 8.37 (1H, s), 8.17 (1H, s), 8.12 (1H, s), 7.45 (1H, dd, J = 8.4 Hz, 2.0 Hz), 7.35 (1 H, d, J = 8.8 Hz), 7.12 (1H, s), 6.99 (1H, t, J = 8.8 Hz), 5.48-5.62 (2H, m), 3.78 (3H, s), 3.34-3.37 (1H, m), 2.98-3.20 (8H, m), 2.68-2.74 (1H, m), 1.86-1.96 (2H, m), 1.67-1.82 (2H, m). LC-MS: [M + H]⁺ = 520.2. |

| Example # | Structure | ¹H NMR & MS |
|---|---|---|
| 81 | 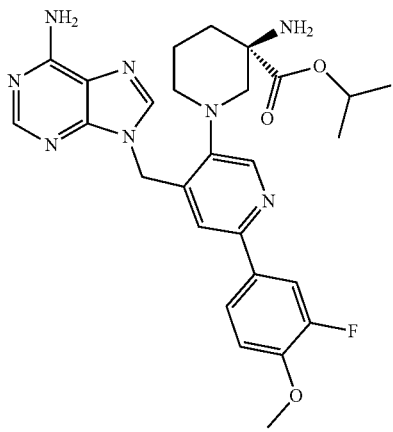 [SMILES: COc1ccc(-c2cc(Cn3cnc4c(N)ncnc43)c(N3CCC[C@](N)(C(=O)OC(C)C)C3)cn2)cc1F] | ¹H NMR (400 MHz, CD₃OD) δ 8.36 (s, 1H), 8.13 (s, 2H), 7.47-7.43 (m, 1H), 7.35-7.33 (m, 1H), 7.13 (s, 1H), 7.01-6.97 (m, 1H), 5.56-5.47 (m, 2H), 4.98-4.92 (m, 1H), 3.77 (s, 3H), 3.38 (d, J = 11.2 Hz, 1H), 2.89-2.86 (m, 3H), 2.08-2.04 (m, 1H), 1.83-1.77 (m, 2H), 1.59-1.57 (m, 1H), 1.19-1.16 (m, 6H). LC-MS: [M + H]⁺ = 535.2. |
| 82 | 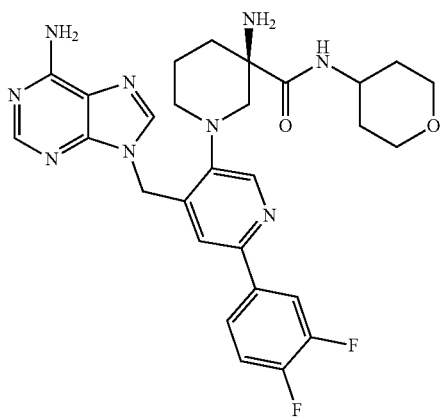 [SMILES: Nc1ncnc2c1ncn2Cc1cc(-c2ccc(F)c(F)c2)ncc1N1CCC[C@](N)(C(=O)NC2CCOCC2)C1] | ¹H NMR (400 MHz, CD₃OD) δ ppm 8.48 (s, 1H), 8.23 (d, J = 15.0 Hz, 2H), 7.74 (ddd, J = 12.1, 7.8, 2.2 Hz, 1H), 7.52 (ddt, J = 7.5, 3.5, 1.7 Hz, 1H), 7.39-7.21 (m, 2H), 6.05-5.41 (m, 2H), 3.90 (tdd, J = 15.3, 7.9, 4.1 Hz, 3H), 3.62-3.33 (m, 3H), 3.15-3.04 (m, 1H), 3.00-2.79 (m, 2H), 2.27-1.91 (m, 2H), 1.90-1.73 (m, 3H), 1.57 (dddd, J = 17.4, 15.8, 8.9, 5.2 Hz, 3H). LC-MS: [M + H]⁺ = 564.2, 565.2. |
| 83 | 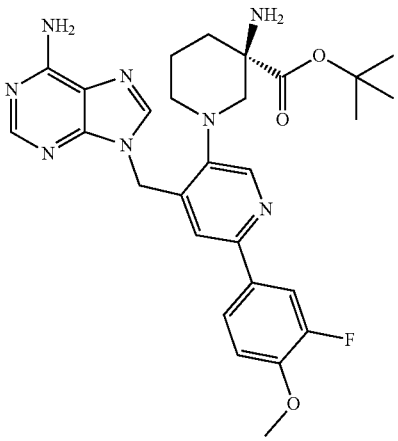 [SMILES: COc1ccc(-c2cc(Cn3cnc4c(N)ncnc43)c(N3CCC[C@](N)(C(=O)OC(C)(C)C)C3)cn2)cc1F] | ¹H NMR (400 MHz, CD₃OD) δ ppm 8.48 (s, 1H), 8.24 (d, J = 5.3 Hz, 2H), 7.56 (dd, J = 12.7, 2.1 Hz, 1H), 7.45 (d, J = 8.6 Hz, 1H), 7.21 (s, 1H), 7.11 (t, J = 8.7 Hz, 1H), 5.73-5.52 (m, 2H), 3.89 (s, 3H), 3.46 (d, J = 11.3 Hz, 1H), 3.08-2.88 (m, 3H), 2.14 (s, 3H), 1.91 (d, J = 17.6 Hz, 2H), 1.67 (s, 1H), 1.51 (s, 9H). LC-MS: [M + H]⁺ = 549.1. |

| Example # | Structure | ¹H NMR & MS |
|---|---|---|
| 84 | 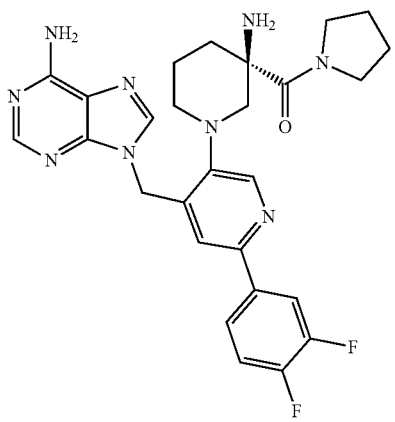 [SMILES: Nc1ncnc2c1ncn2Cc1cc(-c2ccc(F)c(F)c2)ncc1N1CCC[C@](N)(C(=O)N2CCCC2)C1] | ¹H NMR (400 MHz, CD₃OD) δ ppm 8.52 (s, 1H), 8.39-8.14 (m, 2H), 7.64 (d, J = 86.3 Hz, 2H), 7.30 (s, 2H), 5.65 (q, J = 15.9 Hz, 2H), 3.84 (d, J = 55.4 Hz, 2H), 3.50 (d, J = 12.3 Hz, 3H), 3.11 (d, J = 11.1 Hz, 2H), 2.86 (s, 1H), 1.89 (d, J = 47.7 Hz, 8H). LC-MS: [M + H]⁺ = 534.3, 535.3. |
| 85 | 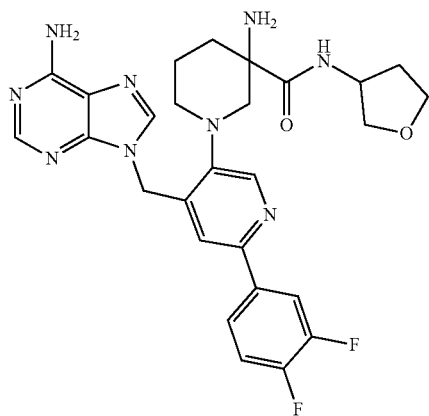 [SMILES: Nc1ncnc2c1ncn2Cc1cc(-c2ccc(F)c(F)c2)ncc1N1CCCC(N)(C(=O)NC2CCOC2)C1] | ¹H NMR (400 MHz, CD₃OD) δ 8.48 (s, 1H), 8.25 (s, 1H), 8.22 (s, 1H), 7.81-7.63 (m, 1H), 7.55-7.44 (m, 1H), 7.36-7.19 (m, 2H), 5.77-5.57 (m, 2H), 4.44-4.32 (m, 1H), 3.97-3.74 (m, 3H), 3.68-3.62 (m, 1H), 3.39 (d, J = 11.2 Hz, 1H), 3.13-2.81 (m, 3H), 2.31-1.54 (m, 6H). LC-MS: [M + Na]⁺ = 572.1 |
| 86 | 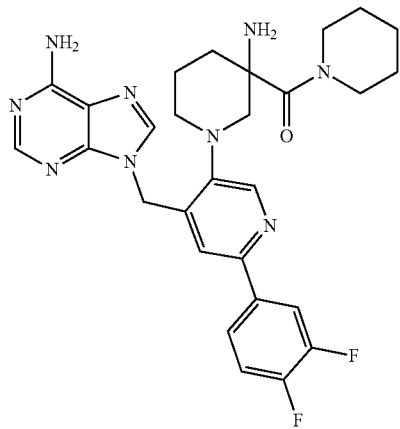 [SMILES: Nc1ncnc2c1ncn2Cc1cc(-c2ccc(F)c(F)c2)ncc1N1CCCC(N)(C(=O)N2CCCCC2)C1] | 1H NMR (400 MHz, CD₃OD): δ 8.52 (s, 1H), 8.27 (s, 1H), 8.21 (s, 1H), 7.78-7.69 (m, 1H), 7.56-7.49 (m, 1H), 7.34-7.22 (m, 2H), 5.75-5.56 (m, 2H), 3.81 (br s, 4H), 3.46 (d, J = 12.0 Hz, 1H), 3.20-3.06 (m, 2H), 2.92-2.74 (m, 1H), 2.10-1.54 (m, 10H). LC-MS: [M + H]⁺ = 548.1. |

| Example # | Structure | ¹H NMR & MS |
|---|---|---|
| 87 | 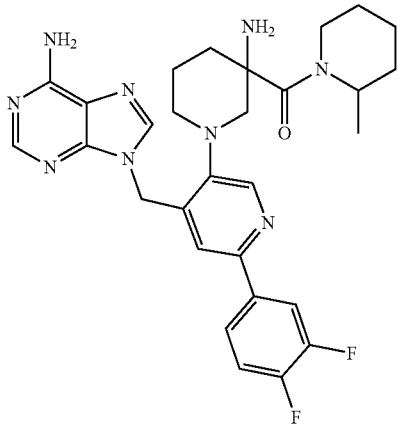 [SMILES: CC1CCCCN1C(=O)C1(N)CCCN(c2cnc(-c3ccc(F)c(F)c3)cc2Cn2cnc3c(N)ncnc32)C1] | 1H NMR (400 MHz, CD₃OD): δ 8.52 (s, 1H), 8.26 (d, J = 2.0 Hz, 1H), 8.21 (s, 1H), 7.80-7.67 (m, 1H), 7.58-7.45 (m, 1H), 7.34-7.21 (m, 2H), 5.77-5.55 (m, 2H), 5.47-4.90 (m, 1H), 4.83-4.22 (m, 1H), 3.53-3.35 (m, 1H), 3.19-2.68 (m, 4H), 2.10-1.17 (m, 13H). LC-MS: [M + H] = 562.2 |
| 88 | 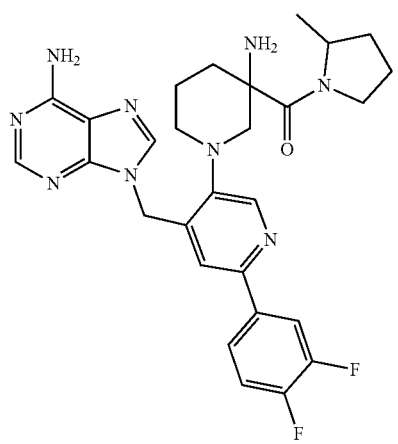 [SMILES: CC1CCCN1C(=O)C1(N)CCCN(c2cnc(-c3ccc(F)c(F)c3)cc2Cn2cnc3c(N)ncnc32)C1] | 1H NMR (400 MHz, CD₃OD) δ ppm 8.79-8.49 (m, 1H), 8.27 (dd, J = 31.2, 5.8 Hz, 2H), 7.86-7.50 (m, 2H), 7.34 (s, 2H), 5.65 (q, J = 16.2 Hz, 2H), 4.23 (s, 1H), 4.03 (s, 1H), 3.90-3.73 (m, 1H), 3.57 (d, J = 11.7 Hz, 1H), 3.23-3.04 (m, 2H), 2.92 (d, J = 10.1 Hz, 1H), 2.11-1.80 (m, 7H), 1.55 (s, 1H), 1.21 (d, J = 6.4 Hz, 3H). LC-MS: [M + H]⁺ = 548.3, 549.3. |
Example 89: 1-(3-amino-1-(4-((6-amino-9H-purin-9-yl)methyl)-6-(3,4-difluorophenyl)pyridin-3-yl)piperidin-3-yl)-2,3-dimethylbutan-1-one
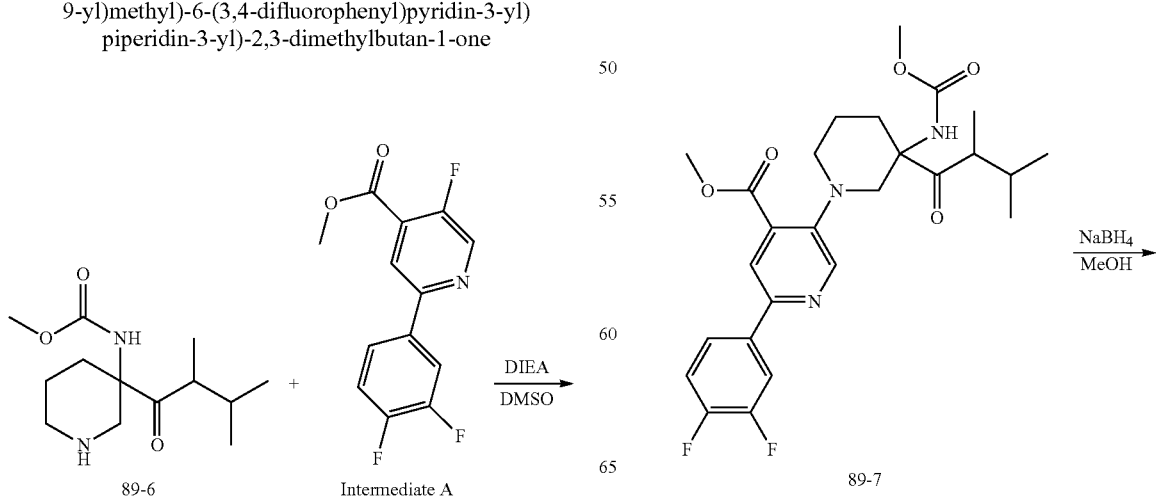

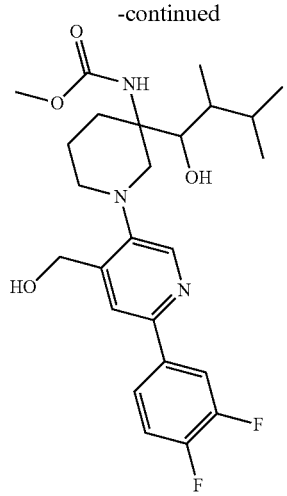

89-8

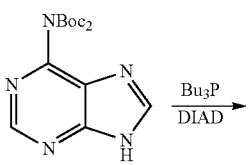

Intermediate B

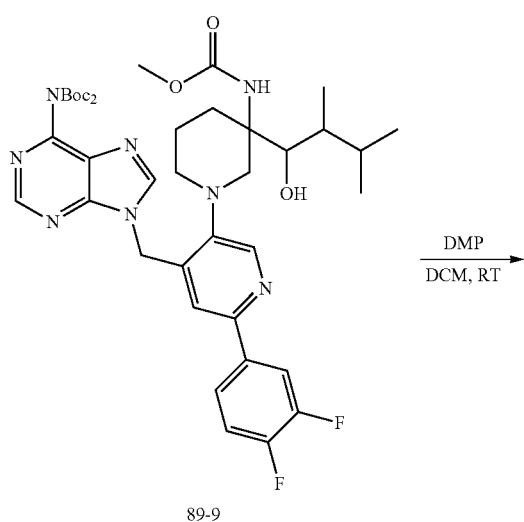

89-9

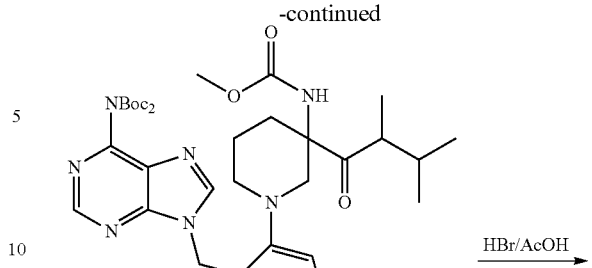

89-10

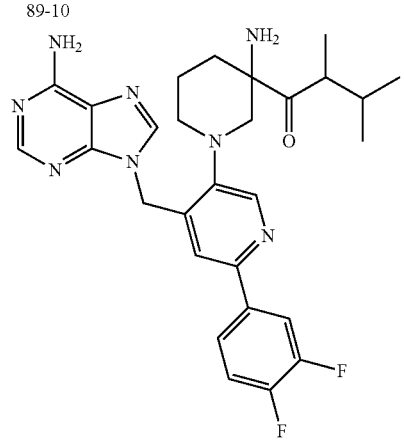

Example 89

To a solution of methyl (3-(2,3-dimethylbutanoyl)piperidin-3-yl)carbamate (Intermediate 89-6) (367 mg, 1.4 mmol, 1.0 eq.) and methyl 2-(3,4-difluorophenyl)-5-fluoroisonicotinate (Intermediate A) (383 mg, 1.4 mmol, 1.0 eq.) in DMSO (10 mL) was added DIPEA (724 mg, 5.6 mmol, 4.0 eq.). The mixture was stirred at 120° C. for 5 hours under $N_2$ atmosphere. The mixture was diluted with $H_2O$ (20 mL), extracted with EtOAc (20 mL*2). The combined organic layers were washed with brine (30 mL), dried over anhydrous $Na_2SO_4$, filtered and concentrated in vacuo. The residue was purified by silica gel column chromatography (30% EtOAc in PE) to give methyl 2-(3,4-difluorophenyl)-5-(3-(2,3-dimethylbutanoyl)-3-((methoxycarbonyl)amino) piperidin-1-yl)isonicotinate (89-7). $^1$H NMR (400 MHz, $CD_3OD$) δ ppm 8.52 (s, 0.5H), 8.50 (s, 0.5H), 8.02 (s, 0.5H), 7.98 (s, 0.5H), 7.94-7.86 (m, 1H), 7.80-7.73 (m, 1H), 7.39-7.30 (m, 1H), 4.00 (s, 1.5H), 3.99 (s, 1.5H), 3.75 (d, J=12.4 Hz, 0.5H), 3.67 (d, J=12.0 Hz, 0.5H), 3.59 (s, 1.5H), 3.54 (s, 1.5H), 3.42-3.34 (m, 1H), 3.23 (d, J=12.4 Hz, 0.5H), 3.13-3.00 (m, 1.5H), 2.97-2.88 (m, 1H), 2.30-2.20 (m, 1H), 2.01-1.82 (m, 3H), 1.78-1.66 (m, 1H), 0.99-0.94 (m, 3H), 0.90-0.84 (m, 6H). LC-MS: [M+H]$^+$=504.2.

To a mixture of methyl 2-(3,4-difluorophenyl)-5-(3-(2,3-dimethylbutanoyl)-3-((methoxycarbonyl)amino) piperidin-1-yl)isonicotinate (89-7) (416 mg, 0.82 mmol, 1.0 eq.) in $CH_3OH$ (10 mL) was added $NaBH_4$ (312 mg, 8.2 mmol, 10 eq.) at RT. The mixture was stirred at RT for 20 minutes. Another $NaBH_4$ (312 mg, 8.2 mmol, 10 eq.) was added and the mixture was stirred at RT for another 20 minutes. The mixture was diluted with H₂O (20 mL), extracted with EtOAc (20 mL*2). The combined organic layers were washed with brine (20 mL), dried over anhydrous Na₂SO₄, filtered and concentrated in vacuo. The residue was purified by silica gel column chromatography (30% EtOAc in hexane) to give methyl (1-(6-(3,4-difluorophenyl)-4-(hydroxymethyl)pyridin-3-yl)-3-(1-hydroxy-2,3-dimethylbutyl)piperidin-3-yl)carbamate (89-8). 1H NMR (400 MHz, CD₃OD) δ ppm 8.34 (s, 0.4H), 8.33 (s, 0.6H), 7.91 (s, 0.4H), 7.90 (s, 0.6H), 7.88-7.81 (m, 1H), 7.76-7.70 (m, 1H), 7.39-7.32 (m, 1H), 4.84-4.69 (m, 1H), 3.90-3.64 (m, 1H), 3.63-3.55 (m, 3H), 3.49-3.43 (m, 0.3H), 3.28-3.23 (m, 0.6H), 3.18-3.02 (m, 2H), 2.86-2.76 (m, 1H), 2.31-2.15 (m, 1H), 2.00-1.86 (m, 1H), 1.82-1.54 (m, 3H), 1.21-1.20 (m, 1H), 0.95-0.78 (m, 9H). LC-MS: [M+H]⁺=478.2.

To a solution of methyl (1-(6-(3,4-difluorophenyl)-4-(hydroxymethyl)pyridin-3-yl)-3-(1-hydroxy-2,3-dimethylbutyl)piperidin-3-yl)carbamate (intermediate 89-8) (273 mg, 0.57 mmol, 1.0 eq.), Intermediate B (192 mg 0.57 mmol 1.0 eq.) and Bu₃P (578 mg, 2.86 mmol, 5.0 eq.) in THF (15 mL) was added DIEA (578 mg, 2.86 mmol, 5.0 eq.) dropwise at 0° C. under N₂. Then the reaction mixture was stirred at RT for 1 hour under N₂. The mixture was diluted with H₂O (20 mL), extracted with EtOAc (20 mL*2). The combined organic layers were washed with brine (30 mL), dried over anhydrous Na₂SO₄, filtered and concentrated in vacuo. The residue was purified by silica gel column chromatography (50% EtOAc in PE) to give tert-butyl (tert-butoxycarbonyl)(9-((2-(3,4-difluorophenyl)-5-(3-(1-hydroxy-2,3-dimethylbutyl)-3-((methoxycarbonyl)amino)piperidin-1-yl)pyridin-4-yl)methyl)-9H-purin-6-yl)carbamate (89-9). 1H NMR (400 MHz, CD₃OD) δ ppm 8.91-8.81 (m, 1H), 8.80-8.70 (m, 1H), 8.56-8.50 (m, 1H), 7.76-7.67 (m, 1H), 7.59-7.51 (m, 1H), 7.36-7.23 (m, 2H), 5.92-5.64 (m, 2H), 4.04-3.65 (m, 2H), 3.60-3.48 (m, 3H), 3.30-2.75 (m, 3H), 2.33-2.13 (m, 2H), 1.88-1.70 (m, 4H), 1.36 (s, 18H), 0.98-0.93 (m, 9H). LC-MS: [M+H]⁺=795.3.

A mixture of tert-butyl (tert-butoxycarbonyl)(9-((2-(3,4-difluorophenyl)-5-(3-(1-hydroxy-2,3-dimethylbutyl)-3-((methoxycarbonyl)amino)piperidin-1-yl)pyridin-4-yl)methyl)-9H-purin-6-yl)carbamate (89-9) (279 mg, 0.37 mmol, 1.0 eq.) and DMP (237 mg 0.56 mmol, 1.5 eq.) in DCM (10 ml) was stirred at RT for 4 hours. The mixture was quenched with sat. aq. NaHCO₃ (30 mL), extracted with DCM (30 mL*2). The combined organic layers were washed with sat. aq. NaHCO₃ (20 mL*2), brine (30 mL), dried over anhydrous Na₂SO₄, filtered and concentrated in vacuo to give a residue. The residue was purified by silica gel column chromatography (50% EtOAc in PE) to give tert-butyl (tert-butoxycarbonyl)(9-((2-(3,4-difluorophenyl)-5-(3-(2,3-dimethylbutanoyl)-3-((methoxycarbonyl)amino)piperidin-1-yl)pyridin-4-yl)methyl)-9H-purin-6-yl)carbamate (89-10). LC-MS: [M+H]⁺=793.5.

A mixture of tert-butyl (tert-butoxycarbonyl)(9-((2-(3,4-difluorophenyl)-5-(3-(2,3-dimethylbutanoyl)-3-((methoxycarbonyl)amino)piperidin-1-yl)pyridin-4-yl)methyl)-9H-purin-6-yl)carbamate (89-10) (280 mg, crude, 0.34 mmol, 1 eq.) and 10 ml of 35% HBr in acetic acid was stirred at RT for 20 hours. LC-MS showed most of starting material was consumed. The reaction mixture was concentrated in vacuo and diluted with H₂O (30 mL), washed with EtOAc (30 mL*3) to remove impurities. The aqueous layer was basified by NH₃·H₂O to pH=11, extracted with EtOAc (30 mL*2), The organic layers were dried over Na₂SO₄, filtered and concentrated to give the crude product, which was purified by prep-HPLC to give 1-(3-amino-1-(4-((6-amino-9H-purin-9-yl)methyl)-6-(3,4-difluorophenyl) pyridin-3-yl)piperidin-3-yl)-2,3-dimethylbutan-1-one (Example 89). ¹H NMR (400 MHz, CD₃OD) 8.52 (d, J=4.0 Hz, 1H), 8.32-8.17 (i, 2H), 7.83-7.65 (n, 1 OH), 7.60-7.48 (, 1H), 7.37-7.15 (i, 2H), 5.67 (d, J=3.6 Hz, 2H), 3.41 (t, J=12.0 Hz, 1H), 3.14-2.87 (, 4H), 2.08-1.61 (, 5H), 1.06 (t, J=8.0 Hz, 3H), 0.95 (d, J=6.8 Hz, 3H), 0.90 (d, J=6.8 Hz, 3H). LC-MS: [M+H]⁺=535.3.

Example 90-112 can be prepared following procedures analogous to those described in Example 89.

| Example # | Structure | ¹H NMR & MS |
|---|---|---|
| 90 | ![structure] | ¹H NMR (400 MHz, CD₃OD) δ 8.48 (dd, J = 13.4, 7.8 Hz, 1H), 8.36-8.15 (m, 2H), 7.66-7.36 (m, 2H), 7.27 (dd, J = 13.5, 7.9 Hz, 1H), 7.14 (dd, J = 14.3, 7.0 Hz, 1H), 5.77-5.51 (m, 2H), 4.02-3.82 (m, 3H), 3.70 (d, J = 14.0 Hz, 1H), 3.21-3.00 (m, 2H), 3.00-2.75 (m, 2H), 1.96 (s, 1H), 1.73 (d, J = 37.1 Hz, 3H), 1.25 (p, J = 7.4, 6.2 Hz, 3H). LC-MS: [M + H]⁺ = 493.0 |

| Example # | Structure | ¹H NMR & MS |
|---|---|---|
| 91 | 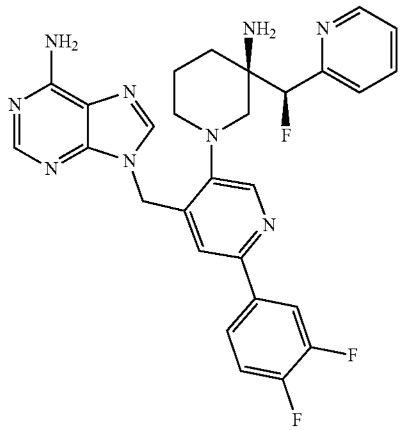 [SMILES: Nc1ncnc2c1ncn2Cc1cc(-c2ccc(F)c(F)c2)ncc1N1CCC[C@](N)([C@H](F)c2ccccn2)C1] | ¹H NMR (400 MHz, CD₃OD) δ 8.57-8.51 (m, 1H), 8.45 (s, 1H), 8.25 (s, 1H), 8.21 (s, 1H), 7.86 (td, J = 7.8, 1.8 Hz, 1H), 7.73 (ddd, J = 12.0, 7.7, 2.2 Hz, 1H), 7.59 (dd, J = 8.0, 1.2 Hz, 1 H), 7.51 (dddd, J = 8.5, 3.9, 2.2, 1.3 Hz, 1H), 7.37 (ddd, J = 7.7, 4.9, 1.1 Hz, 1H), 7.32-7.22 (m, 2H), 5.77-5.56 (m, 3H), 3.18 (d, J = 11.4 Hz, 1H), 2.96 (tq, J = 18.3, 9.1, 8.2 Hz, 3H), 2.02-1.82 (m, 3H), 1.71 (dd, J = 11.0, 6.0 Hz, 1H). LC-MS: [M + H]⁺ = 546.3 |
| 92 | 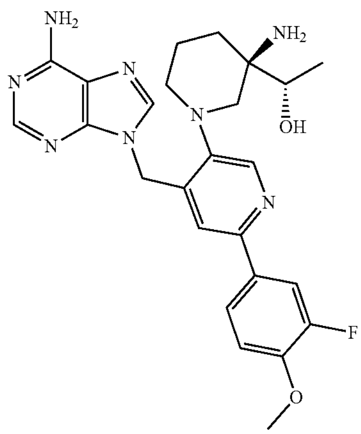 [SMILES: COc1ccc(-c2cc(Cn3cnc4c(N)ncnc43)c(N3CCC[C@](N)([C@H](C)O)C3)cn2)cc1F] | ¹H NMR (400 MHz, CD₃OD) δ 8.47 (s, 1H), 8.27 (d, J = 13.6 Hz, 2H), 7.57 (dd, J = 12.6, 2.3 Hz, 1H), 7.53-7.42 (m, 1H), 7.21 (s, 1H), 7.13 (t, J = 8.7 Hz, 1H), 5.69 (d, J = 2.7 Hz, 2H), 3.90 (s, 4H), 3.06 (d, J = 16.7 Hz, 3H), 2.92 (d, J = 10.5 Hz, 1H), 1.93 (d, J = 21.6 Hz, 1H), 1.79 (d, J = 4.6 Hz, 1H), 1.62 (s, 2H), 1.25 (d, J = 6.5 Hz, 3H). LC-MS: [M + H]+ = 493.0 |
| 93 | 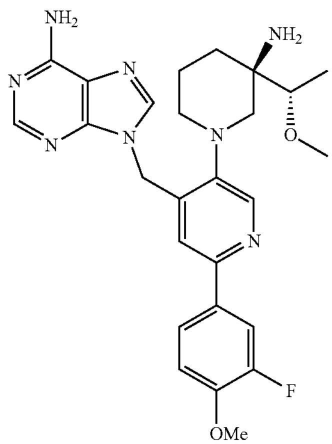 [SMILES: COc1ccc(-c2cc(Cn3cnc4c(N)ncnc43)c(N3CCC[C@](N)([C@H](C)OC)C3)cn2)cc1F] | ¹H NMR (400 MHz, CD₃OD) δ ppm 8.46 (s, 1H), 8.25 (d, J = 3.4 Hz, 2H), 7.58 (d, J = 12.7 Hz, 1H), 7.47 (d, J = 8.6 Hz, 1H), 7.24 (s, 1H), 7.13 (t, J = 8.6 Hz, 1H), 5.83-5.52 (m, 2H), 3.90 (s, 3H), 3.41 (s, 2H), 3.04 (d, J = 9.6 Hz, 3H), 2.91 (t, J = 11.3 Hz, 1H), 2.07-1.83 (m, 1H), 1.75 (d, J = 15.2 Hz, 1 H), 1.59 (t, J = 5.2 Hz, 2H), 1.20 (d, J = 6.2 Hz, 3H). LC-MS: [M + H]⁺ = 506.8, 507.8. |

-continued
| Example # | Structure | ¹H NMR & MS |
|---|---|---|
| 94 | 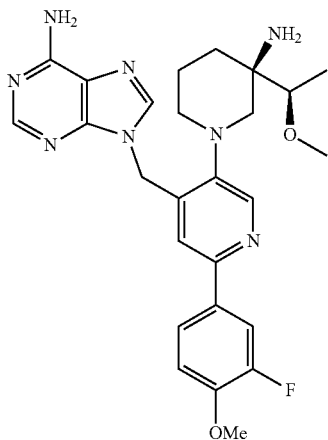 [SMILES: COc1ccc(-c2cc(Cn3cnc4c(N)ncnc43)c(N3CCC[C@](N)([C@@H](C)OC)C3)cn2)cc1F] | ¹H NMR (400 MHz, CD₃OD) δ ppm 8.46 (s, 1H), 8.24 (d, J = 9.4 Hz, 2H), 7.59 (dd, J = 12.8, 2.2 Hz, 1H), 7.49 (dd, J = 8.5, 2.4 Hz, 1H), 7.29 (s, 1H), 7.13 (t, J = 8.7 Hz, 1H), 5.85-5.44 (m, 2H), 3.90 (s, 3H), 3.38 (s, 3H), 3.25 (q, J = 6.3 Hz, 1H), 3.06 (dd, J = 23.5, 11.4 Hz, 2H), 2.96-2.70 (m, 2H), 1.92 (dd, J = 15.7, 9.1 Hz, 1H), 1.69 (tdd, J = 24.3, 10.4, 6.2 Hz, 3H), 1.18 (d, J = 6.3 Hz, 3H). LC-MS: [M + H]⁺ = 506.8, 507.8. |
| 95 | 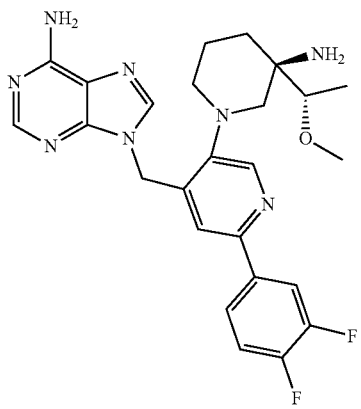 [SMILES: CO[C@@H](C)[C@@]1(N)CCCN(c2cnc(-c3ccc(F)c(F)c3)cc2Cn2cnc3c(N)ncnc32)C1] | ¹H NMR (400 MHz, CD₃OD) δ 8.50 (s, 1H), 8.25 (d, J = 8.0 Hz, 2H), 7.76 (ddd, J = 12.1, 7.8, 2.2 Hz, 1H), 7.55 (ddt, J = 8.0, 3.8, 1.7 Hz, 1H), 7.37-7.26 (m, 2H), 5.73-5.61 (m, 2H), 3.47-3.39 (m, 1 H), 3.05 (d, J = 8.1 Hz, 3H), 2.99-2.87 (m, 1H), 1.91 (tt, J = 9.6, 4.8 Hz, 1H), 1.84-1.70 (m, 1H), 1.59 (dt, J = 10.4, 5.3 Hz, 2H), 1.20 (d, J = 6.3 Hz, 3H). LC-MS: [M + H]⁺ = 495.2. |
| 96 | 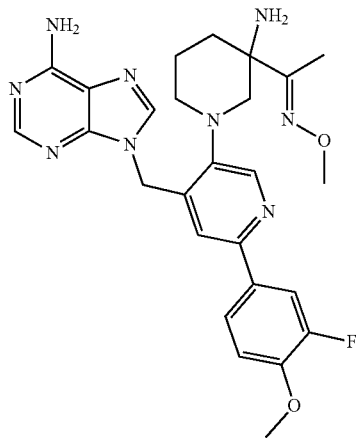 [SMILES: CO/N=C(\C)C1(N)CCCN(c2cnc(-c3ccc(OC)c(F)c3)cc2Cn2cnc3c(N)ncnc32)C1] | ¹H NMR (400 MHz, CD₃OD) δ 1.65-1.74 (2H, m), 1.79-1.91 (5H, m), 2.73-2.83 (1H, m), 2.90-3.00 (2H, m), 3.23-3.27 (1H, m), 3.75 (3H, s), 3.77-3.78 (3H, m), 5.48-5.60 (2H, m), 6.96-7.05 (1H, m), 7.20 (1H, s), 7.38 (1H, d, J = 8.8 Hz), 7.47 (1H, dd, J = 8.8 Hz, 1.6 Hz), 8.14 (1H, d, J = 5.6 Hz), 8.37 (1H, s). LC-MS: [M + H]⁺ = 520.3. |

| Example # | Structure | ¹H NMR & MS |
|---|---|---|
| 97 | 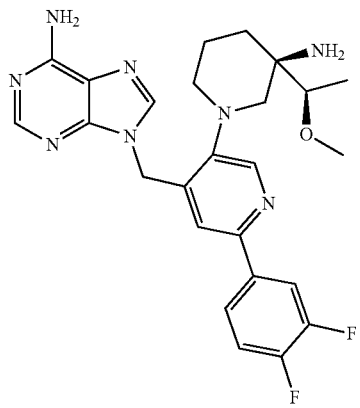 [SMILES: CO[C@H](C)[C@@]1(N)CCCN(c2cnc(-c3ccc(F)c(F)c3)cc2Cn2cnc3c(N)ncnc32)C1] | ¹H NMR (CD$_3$OD) δ: 8.50 (s, 1H), 8.24 (d, J = 4.8 Hz, 2H), 7.86-7.52 (m, 2H), 7.46-7.12 (m, 2H), 5.88-5.49 (m, 2H), 3.38 (s, 3H), 3.30-3.14 (m, 2H), 3.15-2.65 (m, 4H), 2.06-1.47 (m, 4H), 1.18 (d, J = 6.4 Hz, 3H) LC-MS: [M + H]+ = 495.2 |
| 98 | 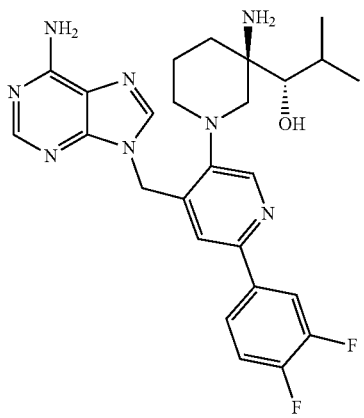 [SMILES: CC(C)[C@H](O)[C@@]1(N)CCCN(c2cnc(-c3ccc(F)c(F)c3)cc2Cn2cnc3c(N)ncnc32)C1] | ¹H NMR (400 MHz, CD$_3$OD) δ ppm 8.48 (s, 1H), 8.27 (s, 1H), 8.21 (s, 1H), 7.72 (ddd, J = 12.0, 7.8, 2.2 Hz, 1H), 7.54-7.44 (m, 1H), 7.33-7.19 (m, 2H), 5.65 (d, J = 2.3 Hz, 2H), 3.48 (d, J = 4.7 Hz, 1H), 3.16-2.97 (m, 3H), 2.86 (t, J = 10.6 Hz, 1H), 2.11-1.88 (m, 2H), 1.81-1.57 (m, 3H), 1.02 (dd, J = 18.3, 6.8 Hz, 6H). LC-MS: [M + H]$^+$ = 509.3, 510.3. |
| 99 | 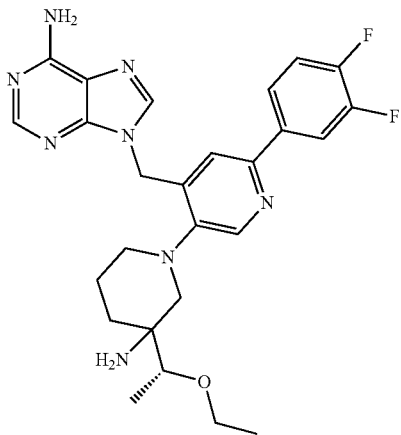 [SMILES: CCO[C@H](C)C1(N)CCCN(c2cnc(-c3ccc(F)c(F)c3)cc2Cn2cnc3c(N)ncnc32)C1] | ¹H NMR (400 MHz, CD$_3$OD) δ ppm 8.48 (s, 1H), 8.23 (s, 1H), 8.21 (s, 1H), 7.80-7.70 (m, 1H), 7.59-7.50 (m, 1H), 7.34 (s, 1H), 7.32-7.24 (m, 1H), 5.64 (q, J = 12 Hz, 1H), 3.74-3.63 (m, 1H), 3.43-3.32 (m, 2H), 3.13-3.06 (m, 1H), 3.05-2.98 (m, 1H), 2.95-2.87 (m, 1H), 2.86-2.75 (m, 1H), 2.02-1.85 (m, 1H), 1.79-1.57 (m, 3H), 1.23-1.11 (m, 6H). LC-MS: [M + H]$^+$ = 509.2. |

| Example # | Structure | ¹H NMR & MS |
|---|---|---|
| 100 | 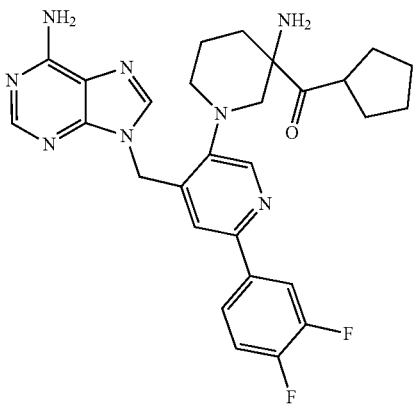 [SMILES: Nc1ncnc2c1ncn2Cc1cc(-c2ccc(F)c(F)c2)ncc1N1CCCC(N)(C(=O)C2CCCC2)C1] | ¹H NMR (400 MHz, CD₃OD) δ 8.52 (s, 1H), 8.23 (d, J = 11.6 Hz, 2H), 7.75 (ddd, J = 12.0, 7.8, 2.2 Hz, 1H), 7.58-7.46 (m, 1H), 7.37-7.16 (m, 2H), 5.65 (d, J = 2.9 Hz, 2H), 3.57-3.42 (m, 2H), 2.99 (h, J = 10.8, 9.9 Hz, 3H), 2.10-1.94 (m, 2H), 1.94-1.79 (m, 3H), 1.79-1.57 (m, 7H). LC-MS: [M + H]⁺ = 533.3 |
| 101 | 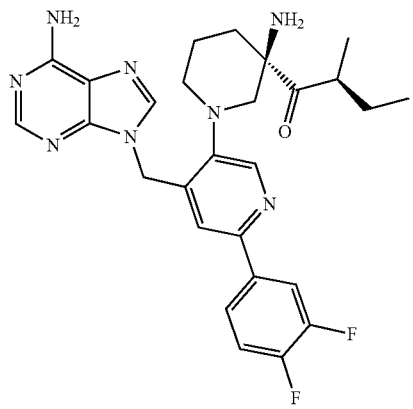 [SMILES: CC[C@H](C)C(=O)[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.52 (s, 1H), 8.24 (d, J = 13.6 Hz, 2H), 7.74 (ddd, J = 12.0, 7.8, 2.2 Hz, 1 H), 7.53 (dddd, J = 8.8, 3.9, 2.3, 1.4 Hz, 1H), 7.38-7.08 (m, 2H), 5.65 (s, 2H), 3.44 (d, J = 11.3 Hz, 1H), 3.24 (p, J = 6.8 Hz, 1H), 3.10-2.85 (m, 3H), 2.22-1.87 (m, 2H), 1.87-1.62 (m, 3H), 1.39 (dt, J = 13.8, 7.0 Hz, 1H), 1.09 (d, J = 6.7 Hz, 3H), 0.90 (t, J = 7.4 Hz, 3H). LC-MS: [M + H]⁺ = 521.3, 522.3. |
| 102 | 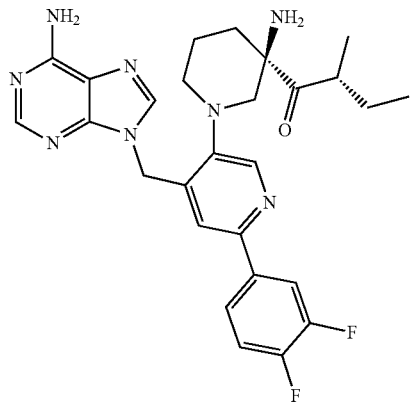 [SMILES: CC[C@@H](C)C(=O)[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.53 (s, 1H), 8.24 (d, J = 15.4 Hz, 2H), 7.75 (ddd, J = 12.0, 7.8, 2.2 Hz, 1H), 7.53 (ddt, J = 8.2, 3.4, 1.6 Hz, 1H), 7.40-7.14 (m, 2H), 5.66 (s, 2H), 3.42 (d, J = 11.3 Hz, 1H), 3.23 (q, J = 6.8 Hz, 1H), 3.12-2.90 (m, 3H), 2.12-1.94 (m, 2H), 1.87-1.78 (m, 1H), 1.74-1.60 (m, 2H), 1.39 (dp, J = 14.3, 7.3 Hz, 1H), 1.08 (d, J = 6.7 Hz, 3H), 0.89 (t, J = 7.4 Hz, 3H). LC-MS: [M + H]⁺ = 521.3, 522.3. |

| Example # | Structure | ¹H NMR & MS |
|---|---|---|
| 103 | 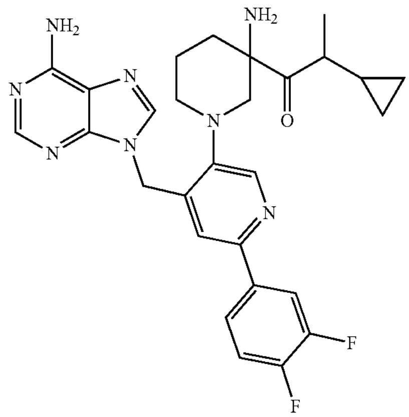 [SMILES: CC(C(=O)C1(N)CCCN(c2cnc(-c3ccc(F)c(F)c3)cc2Cn2cnc3c(N)ncnc32)C1)C1CC1] | ¹H NMR (400 MHz, CD₃OD) δ ppm 8.52 (s, 1H), 8.26 (d, J = 4.8 Hz, 1H), 8.22 (s, 1H), 7.77-7.72 (m, 1H), 7.56-7.52 (m, 1H), 7.34-7.25 (m, 2H), 5.72-5.61 (m, 2H), 3.46-3.38 (m, 1H), 3.06-2.92 (m, 3H), 2.62-2.54 (m, 1H), 2.04-1.97 (m, 2H), 1.82-1.64 (m, 2H), 1.19 (t, J = 6.4 Hz, 3H), 1.03-0.95 (m, 1H), 0.58-0.38 (m, 2H), 0.31-0.17 (m, 2H). LC-MS: [M + H]⁺ = 533.1. |
| 104 | 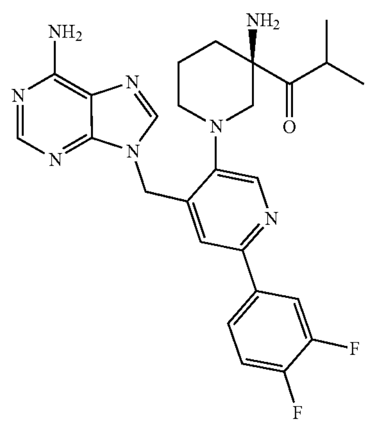 [SMILES: CC(C)C(=O)[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.54 (d, J = 4.3 Hz, 1H), 8.26 (s, 1H), 8.22 (s, 1H), 7.75 (ddd, J = 12.0, 7.8, 2.2 Hz, 1H), 7.54 (ddt, J = 7.9, 3.8, 1.7 Hz, 1H), 7.38-7.21 (m, 2H), 5.65 (s, 2H), 3.51-3.36 (m, 2H), 3.01 (q, J = 12.6, 12.2 Hz, 3H), 2.13-1.92 (m, 2H), 1.85-1.67 (m, 2H), 1.10 (dd, J = 6.7, 4.1 Hz, 6H). LC-MS: [M + H]⁺ = 507.3, 508.3. |
| 105 | 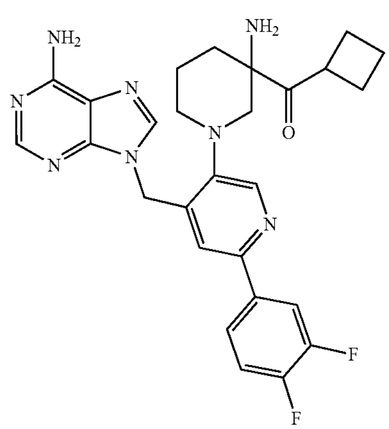 [SMILES: Nc1ncnc2c1ncn2Cc1cc(-c2ccc(F)c(F)c2)ncc1N1CCCC(N)(C(=O)C2CCC2)C1] | ¹H NMR (400 MHz, CD₃OD) δ ppm 8.51 (s, 1H), 8.24 (d, J = 9.2 Hz, 2H), 7.82-7.70 (m, 1H), 7.57-7.50 (m, 1H), 7.35-7.21 (m, 2H), 5.64 (s, 2H), 4.06-3.87 (m, 1H), 3.40 (d, J = 11.2 Hz, 1H), 3.08-2.86 (m, 3H), 2.38-2.24 (m, 2H), 2.19-1.95 (m, 5H), 1.89-1.72 (m, 2H), 1.68-1.59 (m, 1H). LC-MS: [M + H]⁺ = 519.1. |

| Example # | Structure | ¹H NMR & MS |
|---|---|---|
| 106 | 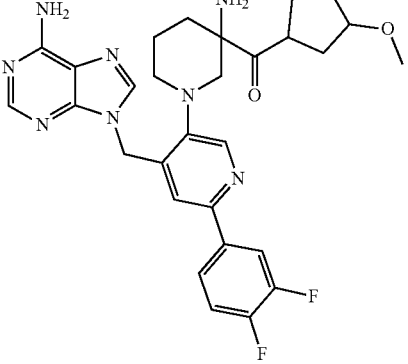 | ¹H NMR (400 MHz, CD₃OD) δ ppm 8.53 (s, 1H), 8.26 (d, J = 2.0 Hz, 1H), 8.23 (s, 1H), 7.80-7.69 (m, 1H), 7.58-7.49 (m, 1H), 7.37-7.23 (m, 2H), 5.71-5.56 (m, 2H), 3.99-3.84 (m, 1H), 3.78-3.42 (m, 2H), 3.30-3.25 (m, 3H), 3.08-2.91 (m, 3H), 2.32-1.60 (m, 10H). LC-MS: [M + H]⁺ = 563.1. |
| 107 | 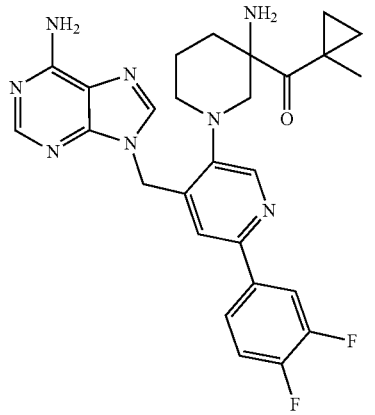 [SMILES: CC1(C(=O)C2(N)CCCN(c3cnc(-c4ccc(F)c(F)c4)cc3Cn3cnc4c(N)ncnc43)C2)CC1] | ¹H NMR (400 MHz, CD₃OD): δ 8.50 (s, 1H), 8.26 (s, 1H), 8.22 (s, 1H), 7.75-7.70 (m, 1H), 7.52-7.50 (m, 1H), 7.30 (s, 1H), 7.29-7.23 (m, 1H), 5.70-5.60 (m, 2H), 3.45 (d, J = 11.6 Hz, 1H), 3.10-3.02 (m, 2H), 2.90-2.85 (m, 1H), 2.12-2.00 (m, 2H), 1.94-1.88 (m, 1H), 1.80-1.76 (m, 1H), 1.60 (s, 3H), 1.28-1.12 (m, 2H), 0.67-0.60 (m, 2H). LC-MS: [M + H]⁺ = 519.2. |
| 108 | 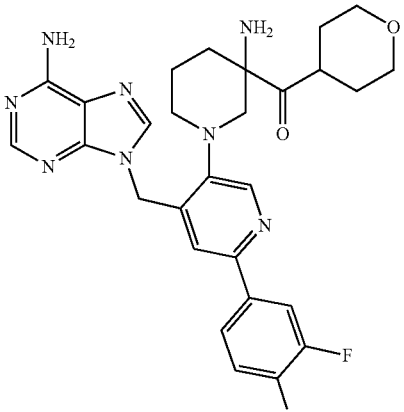 | ¹H NMR (400 MHz, CD₃OD) δ ppm 8.53 (s, 1H), 8.26 (s, 1H), 8.22 (s, 1H), 7.77-7.71 (m, 1H), 7.55-7.50 (m, 1H), 7.32-7.25 (m, 2H), 5.69-5.60 (m, 2H), 3.99-3.92 (m, 2H), 3.55-3.41 (m, 4H), 3.05-2.93 (m, 3H), 2.10-1.94 (m, 2H), 1.84-1.60 (m, 6H). LC-MS: [M + H]⁺ = 549.1. |

| Example # | Structure | ¹H NMR & MS |
|---|---|---|
| 109 | 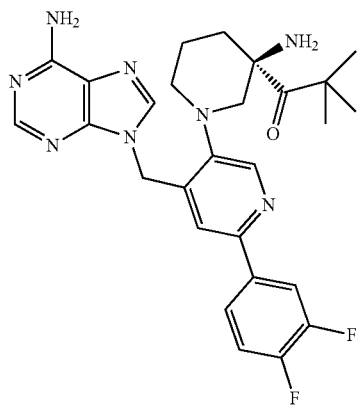 [SMILES: CC(C)(C)C(=O)[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.49 (s, 1H), 8.26 (s, 1H), 8.22 (s, 1H), 7.73 (ddd, J = 12.0, 7.8, 2.2 Hz, 1H), 7.51 (ddt, J = 7.9, 3.8, 1.6 Hz, 1H), 7.34-7.17 (m, 2H), 5.75-5.55 (m, 2H), 3.37 (d, J = 11.3 Hz, 1H), 3.14-3.00 (m, 2H), 2.84 (td, J = 11.4, 2.9 Hz, 1H), 2.15-1.97 (m, 2H), 1.88-1.78 (m, 1H), 1.74 (dq, J = 11.9, 3.2, 2.5 Hz, 1H), 1.34 (s, 9H). LC-MS: [M + H]⁺ = 521.3, 522.3. |
| 110 | 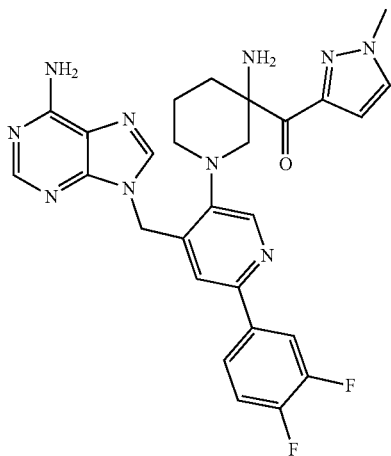 [SMILES: Cn1ccc(C(=O)C2(N)CCCN(c3cnc(-c4ccc(F)c(F)c4)cc3Cn3cnc4c(N)ncnc43)C2)n1] | ¹H NMR (400 MHz, CD₃OD) δ ppm 8.51 (s, 1H), 8.22 (s, 1H), 8.11 (s, 1H), 7.74-7.68 (m, 1H), 7.59 (d, J = 2.4 Hz, 1H), 7.50-7.47 (m, 1H), 7.30-7.21 (m, 2H), 6.81 (d, J = 2.4 Hz, 1H), 5.50-5.35 (m, 2H), 3.99 (s, 3H), 3.93-3.91 (m, 1H), 3.24-3.21 (m, 1H), 3.13-3.00 (m, 2H), 2.37-2.31 (m, 1H), 2.05-1.99 (m, 2H), 1.87-1.81 (m, 1H). LC-MS: [M + H]⁺ = 545.4. |
| 111 | 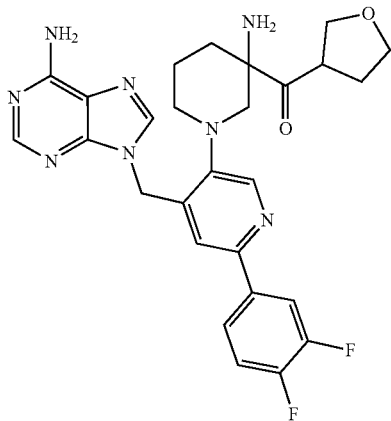 [SMILES: Nc1ncnc2c1ncn2Cc1cc(-c2ccc(F)c(F)c2)ncc1N1CCCC(N)(C(=O)C2CCOC2)C1] | 1H NMR (CD₃OD) δ: 8.57-8.43 (m, 1H), 8.31-8.06 (m, 2H), 7.78 (dddd, J = 12.7, 7.5, 5.1, 2.2 Hz, 1H), 7.59 (ddd, J = 9.0, 4.4, 2.3 Hz, 1H), 7.48-7.19 (m, 2H), 5.75-5.44 (m, 2H), 3.84 (ddd, J = 13.8, 11.2, 5.7 Hz, 1H), 3.63-3.45 (m, 1H), 3.43-3.32 (m, 1H), 3.24 (dt, J = 12.6, 4.1 Hz, 2H), 3.05-2.74 (m, 4H), 2.42-1.97 (m, 2H), 1.94-1.80 (m, 1H), 1.75-1.60 (m, 2H), 1.58-1.37 (m, 1H) LC-MS: [M + H]⁺ = 535.3 |

| Example # | Structure | ¹H NMR & MS |
|---|---|---|
| 112 | 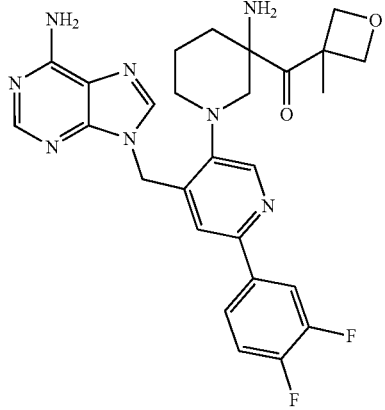 [SMILES: CC1(C(=O)C2(N)CCCN(c3cnc(-c4ccc(F)c(F)c4)cc3Cn3cnc4c(N)ncnc43)C2)COC1] | ¹H NMR (400 MHz, CD₃OD): δ 8.44 (s, 1H), 8.41 (s, 1H), 8.22 (s, 1H), 7.79-7.67 (m, 1H), 7.57-7.49 (m, 1H), 7.34-7.19 (m, 2H), 5.84-5.48 (m, 2H), 3.82-3.67 (m, 2H), 3.54-3.43 (m, 1H), 3.30-3.10 (m, 4H), 3.00-2.86 (m, 1H), 2.12-1.81 (m, 4H), 1.13 (s, 3H). LC-MS: [M + H]⁺ = 535.0 |

Example 113 and Example 114: (R)-1-((R)-3-amino-1-(4-((6-amino-9H-purin-9-yl)methyl)-6-(3,4-difluorophenyl)pyridin-3-yl)piperidin-3-yl)-2,2-difluoroethan-1-ol and (S)-1-((R)-3-amino-1-(4-((6-amino-9H-purin-9-yl)methyl)-6-(3,4-difluorophenyl)pyridin-3-yl)piperidin-3-yl)-2,2-difluoroethan-1-ol

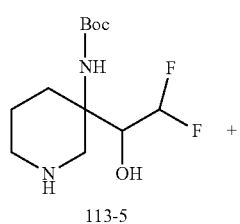

113-5

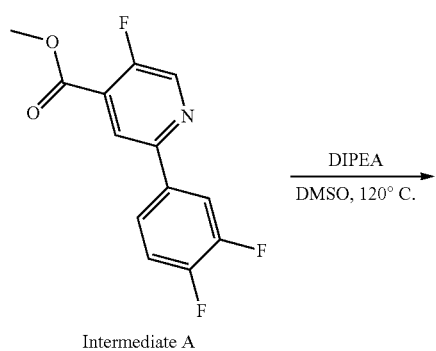

Intermediate A $\xrightarrow{\text{DIPEA}}{\text{DMSO, 120° C.}}$

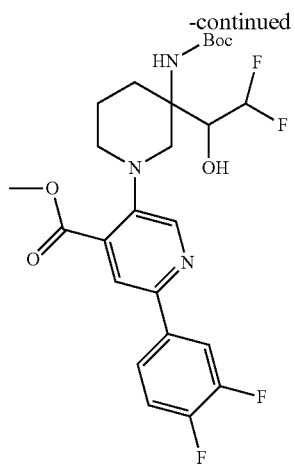

113-6

$\xrightarrow{\text{LiCl, NaBH}_4}{\text{THF/MeOH, RT}}$

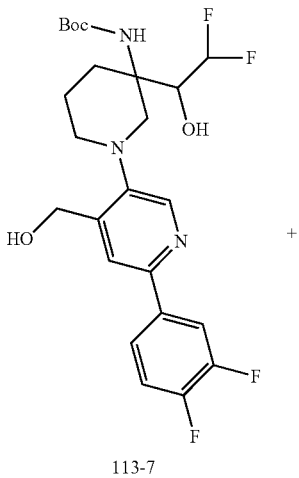

113-7

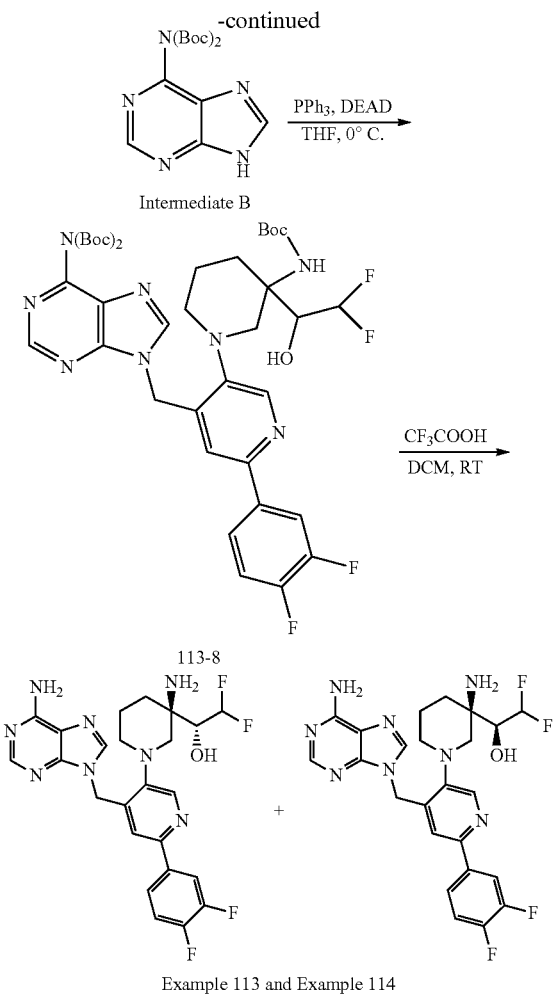

Example 113 and Example 114

To a solution of tert-butyl (3-(2,2-difluoro-1-hydroxyethyl)piperidin-3-yl)carbamate (Intermediate 113-5) (1.2 g, 4.28 mmol) and methyl 2-(3,4-difluorophenyl)-5-fluoroisonicotinate (Intermediate A) (1.144 g, 4.28 mmol) in DMSO (30 mL) was added DIPEA (14.95 mL, 86 mmol) at rt, the reaction mixture was stirred at 120° C. for 8 hr under $N_2$ atmosphere. The reaction mixture was diluted with water (40 mL), extracted with EtOAc (30 mL*3). The combined organic layers were washed with water (20 mL*3), brine (20 mL), dried over anhydrous $Na_2SO_4$, filtered and concentrated to give a residue. The residue was purified by flash chromatography (elution gradient: 10% to 50% EtOAc in PE in 40 mins) to afford methyl 5-(3-((tert-butoxycarbonyl)amino)-3-(2,2-difluoro-1-hydroxyethyl)piperidin-1-yl)-2-(3,4-difluorophenyl)isonicotinate (113-6). LC-MS: [M+H]$^+$= 528.2.

To a solution of methyl 5-(3-((tert-butoxycarbonyl)amino)-3-(2,2-difluoro-1-hydroxyethyl)piperidin-1-yl)-2-(3,4-difluorophenyl)isonicotinate (113-6) (1.2 g, 2.275 mmol) in THF (30 mL) and MeOH (30 mL), was added lithium chloride (1.929 g, 45.5 mmol) and sodium tetrahydroborate (1.721 g, 45.5 mmol) at 0° C., the reaction mixture was stirred at rt for 4 hours under $N_2$ atmosphere. The reaction mixture was diluted with 30 ml of water, extracted with EtOAc (20 mL*3). The combined organic layers were washed with water (20 mL), brine (20 mL), concentrated to give a crude product. The crude product was purified by flash chromatography (elution gradient: 20% to 70% EtOAc in PE in 40 mins) to afford tert-butyl (3-(2,2-difluoro-1-hydroxyethyl)-1-(6-(3,4-difluorophenyl)-4-(hydroxymethyl)pyridin-3-yl)piperidin-3-yl)carbamate (113-7). LC-MS: [M+H]$^+$=500.2.

To a solution of tert-butyl (3-(2,2-difluoro-1-hydroxyethyl)-1-(6-(3,4-difluorophenyl)-4-(hydroxymethyl)pyridin-3-yl)piperidin-3-yl)carbamate (intermediate 113-7) (800 mg, 1.602 mmol), Intermediate B (645 mg, 1.922 mmol) and triphenylphosphine (1260 mg, 4.80 mmol) in THF (20 mL), was added DEAD (0.761 mL, 4.80 mmol) dropwise at 0° C., after addition the reaction mixture was stirred at 0° C. for 0.5 hr under $N_2$ atmosphere. The reaction mixture was diluted with 20 ml of water, extracted with EtOAc (20 mL*3). The combined organic layers were washed with water (20 mL), brine (20 mL), concentrated to give a crude product. The crude product was purified by flash chromatography (elution gradient: 20% to 70% EtOAc in PE in 50 mins) to afford tert-butyl (tert-butoxycarbonyl)(9-((5-(3-((tert-butoxycarbonyl)amino)-3-(2,2-difluoro-1-hydroxyethyl)piperidin-1-yl)-2-(3,4-difluorophenyl)pyridin-4-yl)methyl)-9H-purin-6-yl)carbamate (113-8). LC-MS: [M+H]$^+$=817.2.

To a solution of tert-butyl (tert-butoxycarbonyl)(9-((5-(3-((tert-butoxycarbonyl)amino)-3-(2,2-difluoro-1-hydroxyethyl)piperidin-1-yl)-2-(3,4-difluorophenyl)pyridin-4-yl)methyl)-9H-purin-6-yl)carbamate (113-8) (600 mg, 0.735 mmol) in DCM (30 mL), was added TFA (10 mL), the reaction mixture was stirred at rt for 2 hr under $N_2$ atmosphere. The reaction mixture was concentrated in vacuo to give the crude product. The crude product was purified by Pre-HPLC (Basic condition, NH3H2O %=0.05%, MEOH/H2O=0-95% in 10 mins) to afford 330 mg of pure racemic product. The racemic product was isolated by SFC to afford (R)-1-((R)-3-amino-1-(4-((6-amino-9H-purin-9-yl)methyl)-6-(3,4-difluorophenyl)pyridin-3-yl) piperidin-3-yl)-2,2-difluoroethan-1-ol (Example 113) and (S)-1-((R)-3-amino-1-(4-((6-amino-9H-purin-9-yl)methyl)-6-(3,4-difluorophenyl)pyridin-3-yl) piperidin-3-yl)-2,2-difluoroethan-1-ol (Example 114).

Example 113: $^1$H NMR (O$_3$M, H400 MHz) C (ppm): 8.48 (s, 1H), 8.22 (d, 2H), 7.71-7.77 (m, 1H), 7.51-7.54 (m, 1H), 7.29 (s, 1H), 7.24-7.27 (t, 1H), 5.91-6.19 (t, 1H), 5.65 (s, 2H), 3.65 (br, 1H), 3.20 (d, 1H), 2.99 (m, 2H), 2.84 (t, 1H), 1.93-1.99 (i, 1H), 1.66-1.86 (m, 3H). LC-MS: [M+H]$^+$= 517.2.

Example 114: $^1$H NMR (CD$_3$OD-d6, 400M Hz) δ (ppm): 8.49 (s, 1H), 8.22 (d, 2H), 7.69-7.75 (m, 1H), 7.48-7.51 (m, 1H), 7.24-7.31 (t, 1H), 7.21 (s, 1H)), 5.89-6.18 (t, 1H), 5.65 (s, 2H), 3.95 (br, 1H), 3.25 (d, 1H), 2.90-3.10 (b, 3H), 1.82-1.88 (m, 3H), 1.63 (br, 1H). LC-MS: [M+H]-517.2.

Example 115-155 can be prepared following procedures analogous to those described in Example 113 and 114.

| Example # | Structure | ¹H NMR & MS |
|---|---|---|
| 115 | 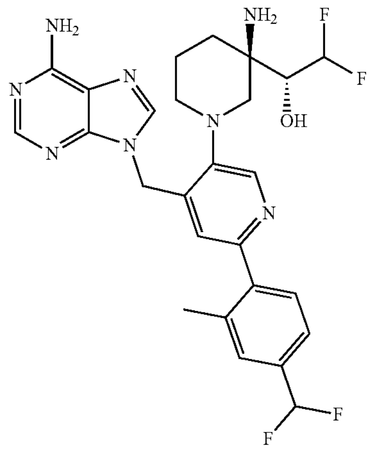 [SMILES: Cc1cc(C(F)F)ccc1-c1cc(Cn2cnc3c(N)ncnc32)c(N2CCC[C@](N)([C@@H](O)C(F)F)C2)cn1] | ¹H NMR (400 MHz, CD₃OD): δ 8.49 (s, 1H), 8.23-8.20 (d, J = 104 Hz, 2H), 7.38-7.30 (m, 3H), 6.86-6.58 (m, 2H), 6.22-5.93 (m, 1H), 5.70 (s, 2H), 3.73-3.68 (m, 1H), 3.26-3.23 (m, 1H), 3.15-3.05 (m, 2H), 2.92-2.86 (m, 1H), 2.11 (s, 3H), 2.03-2.01 (m, 1H), 1.89-1.70 (m, 3H). LC-MS: [M + H] = 545.4. |
| 116 | 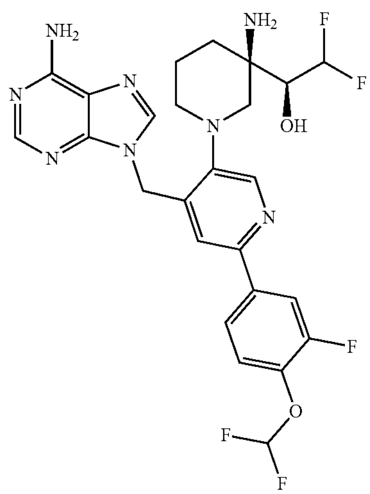 [SMILES: Nc1ncnc2c1ncn2Cc1cc(-c2ccc(OC(F)F)c(F)c2)ncc1N1CCC[C@](N)([C@H](O)C(F)F)C1] | ¹H NMR (400 MHz, CD₃OD) δ ppm 8.43 (s, 1H), 8.17 (d, J = 14.2 Hz, 2H), 7.81-7.39 (m, 2H), 7.31-7.11 (m, 2H), 6.80 (t, J = 73.3 Hz, 1H), 5.98 (td, J = 55.4, 4.4 Hz, 1H), 5.60 (s, 2H), 3.90 (s, 1H), 3.17 (d, J = 11.3 Hz, 1H), 3.02-2.79 (m, 3H), 1.92-1.51 (m, 4H). LC-MS: [M + H]⁺ = 565.2, 566.2. |
| 117 | 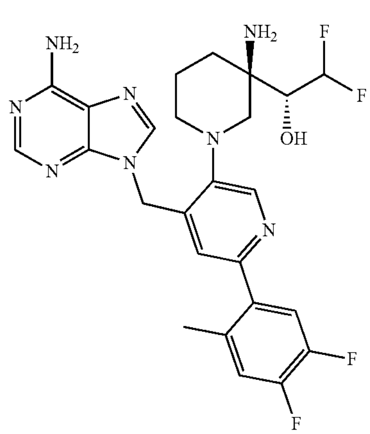 [SMILES: Cc1cc(F)c(F)cc1-c1cc(Cn2cnc3c(N)ncnc32)c(N2CCC[C@](N)([C@@H](O)C(F)F)C2)cn1] | ¹H NMR (400 MHz, CD₃OD): δ 8.50 (s, 1H), 8.25 (s, 1H), 8.22 (s, 1H), 7.15 (dt, J = 8.0, 11.2 Hz, 2H), 6.80 (s, 1H), 6.26-5.92 (m, 1H), 5.70 (s, 2H), 3.83-3.65 (m, 1H), 3.29-3.21 (m, 1H), 3.19-3.05 (m, 2H), 2.97-2.83 (m, 1H), 2.11-2.05 (m, 1H), 2.03 (s, 3H), 1.94-1.80 (m, 2H), 1.78-1.69 (m, 1H). LC-MS: [M + H]⁺ = 531.4. |

| Example # | Structure | ¹H NMR & MS |
|---|---|---|
| 118 | 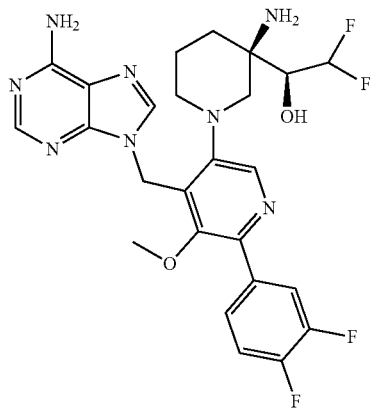 [SMILES: COc1c(-c2ccc(F)c(F)c2)ncc(N2CCC[C@](N)([C@H](O)C(F)F)C2)c1Cn1cnc2c(N)ncnc21] | ¹H NMR (400 MHz, CD₃OD) δ = 8.37 (s, 1H), 8.26 (s, 1H), 8.10 (s, 1H), 7.75 (ddd, J = 2.1, 7.9, 11.6 Hz, 1H), 7.67 (br d, J = 5.9 Hz, 1H), 7.42-7.31 (m, 1H), 6.18-5.84 (m, 1H), 5.62 (q, J = 14.1 Hz, 2H), 3.82 (br s, 1H), 3.37 (s, 3H), 3.20-3.11 (m, 1H), 2.99 (br d, J = 9.8 Hz, 1H), 2.94-2.87 (m, 1H), 2.85-2.76 (m, 1H), 1.91-1.60 (m, 4H). LC-MS: [M + H]⁺ = 547.5. |
| 119 | 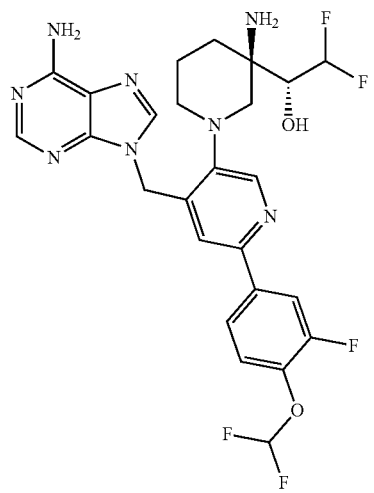 [SMILES: Nc1ncnc2c1ncn2Cc1cc(-c2ccc(OC(F)F)c(F)c2)ncc1N1CCC[C@](N)([C@@H](O)C(F)F)C1] | ¹H NMR (400 MHz, CD₃OD) δ ppm 8.49 (s, 1H), 8.24 (d, J = 7.9 Hz, 2H), 7.85-7.44 (m, 2H), 7.41-7.18 (m, 2H), 6.86 (t, J = 73.3 Hz, 1H), 6.05 (td, J = 55.1, 3.9 Hz, 1H), 5.65 (s, 2H), 3.67 (dd, J = 16.5, 6.6 Hz, 1H), 3.22 (d, J = 11.4 Hz, 1H), 3.02 (t, J = 13.5 Hz, 2H), 2.91-2.79 (m, 1H), 2.09-1.91 (m, 1H), 1.89-1.62 (m, 3H). LC-MS: [M + H]⁺ = 565.2, 566.2. |
| 120 | 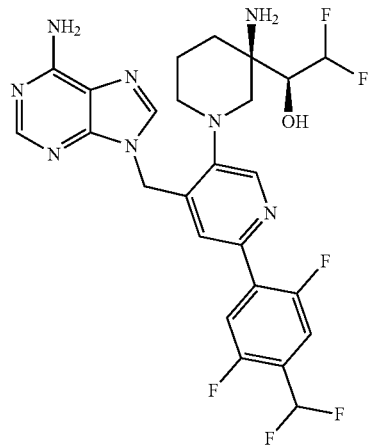 [SMILES: Nc1ncnc2c1ncn2Cc1cc(-c2cc(F)c(C(F)F)cc2F)ncc1N1CCC[C@](N)([C@H](O)C(F)F)C1] | ¹H NMR (400 MHz, CD₃OD) δ = 8.57 (s, 1H), 8.23 (s, 1H), 8.20 (s, 1H), 7.74 (br dd, J = 5.9, 10.7 Hz, 1H), 7.35 (dd, J = 5.6, 10.7 Hz, 1H), 7.16 (s, 1H), 7.12-6.79 (m, 1H), 6.23-5.88 (m, 1H), 5.69 (s, 2H), 3.99 (br s, 1H), 3.27 (br s, 1H), 3.16-2.90 (m, 3H), 2.03-1.79 (m, 3H), 1.66 (br s, 1H). LC-MS: [M + H]⁺ = 567.4. |

| Example # | Structure | ¹H NMR & MS |
|---|---|---|
| 121 | 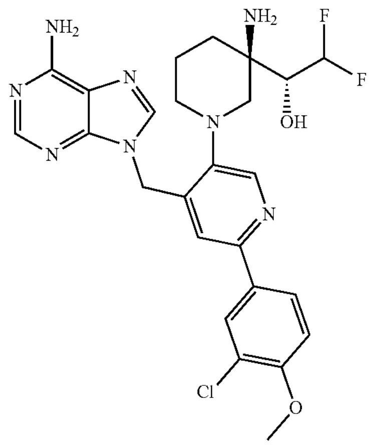 [SMILES: COc1ccc(-c2cc(Cn3cnc4c(N)ncnc43)c(N3CCC[C@](N)([C@@H](O)C(F)F)C3)cn2)cc1Cl] | ¹H NMR (400 MHz, CD₃OD) δ ppm 8.43 (s, 1H), 8.24 (d, J = 2.1 Hz, 2H), 7.82 (d, J = 2.0 Hz, 1H), 7.60 (dd, J = 2.0, 8.6 Hz, 1H), 7.24 (s, 1H), 7.08 (d, J = 8.7 Hz, 1H), 6.23-5.86 (m, 1H), 5.64 (s, 2H), 3.89 (s, 3H), 3.74-3.61 (m, 1H), 3.20 (br d, J = 11.5 Hz, 1H), 3.07-2.94 (m, 2H), 2.88=275 (m, 1H), 2.04-1.90 (m, 1H), 1.88-1.60 (m, 3H). LC-MS: [M + H]⁺ = 545.4. |
| 122 | 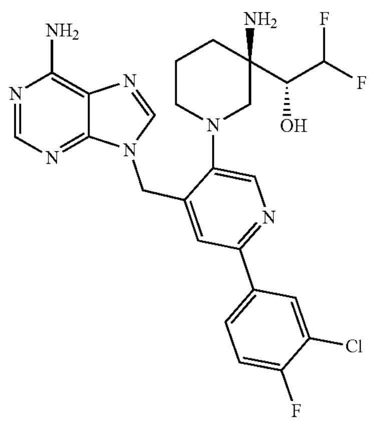 [SMILES: Nc1ncnc2c1ncn2Cc1cc(-c2ccc(F)c(Cl)c2)ncc1N1CCC[C@](N)([C@@H](O)C(F)F)C1] | ¹H NMR (400 MHz, CD₃OD) δ ppm 8.47 (s, 1H), 8.24 (d, 2H), 7.93 (t, 1H), 7.65-7.7.68 (m, 1H), 7.32 (s, H), 7.24 (t, H), 5.90-6.19 (t, 1H), 5.64 (s, 2H), 3.65 (br, 1H), 3.2 (d, 1H), 3.00 (m, 2H), 2.83 (t, 1H), 1.97 (m, 1H), 1.66-1.86 (m, 3H). LC-MS: [M + H]⁺ = 532.9, 533.9. |
| 123 | 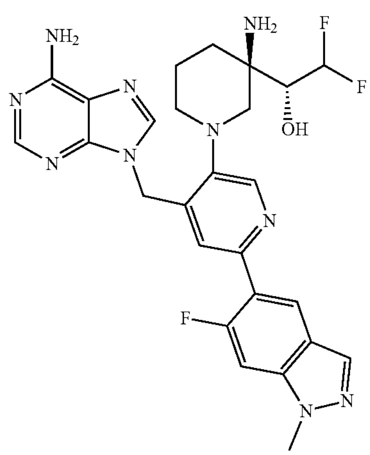 [SMILES: Cn1ncc2cc(-c3cc(Cn4cnc5c(N)ncnc54)c(N4CCC[C@](N)([C@@H](O)C(F)F)C4)cn3)c(F)cc21] | ¹H NMR (400 MHz, CD₃OD) δ = 8.51 (s, 1H), 8.22 (d, J = 3.7 Hz, 2H), 8.10-7.97 (m, 2H), 7.31 (d, J = 11.5 Hz, 1 H), 7.10 (d, J = 1.8 Hz, 1H), 6.27-5.90 (m, 1H), 5.69 (s, 2H), 4.01 (s, 3H), 3.78-3.64 (m, 1H), 3.24 (brd, J = 11.5 Hz, 1H), 3.13 (br d, J = 1 0.9 Hz, 1H), 3.05 (br d, J = 11.4 Hz, 1H), 2.89 (br t, J = 10.3 Hz, 1H), 2.09-1.96 (m, 1H), 1.92-1.76 (m, 2H), 1.70 (br d, J = 10.4 Hz, 1H). LC-MS: [M + H]⁺ = 553.5. |

| Example # | Structure | ¹H NMR & MS |
|---|---|---|
| 124 | 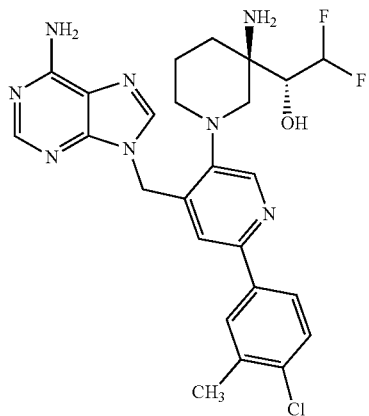 | ¹H NMR (400 MHz, CD₃OD) δ ppm 8.50 (s, 1H), 8.24-8.23 (d, J = 6.0 Hz, 2H), 7.74-7.71 (m, 1H), 7.56-7.54 (m, 1H), 7.51-7.49 (m, 1H), 7.36 (s, 1H), 6.19-5.91 (m, 1H), 5.66 (s, 2H), 3.70-3.65 (m, 1H), 3.23-3.21 (d, J = 11.6 Hz, 1H), 3.07-3.00 (m, 2H), 2.87-2.82 (m, 1H), 2.01-1.98 (m, 1H), 1.86-1.70 (m, 3H). LC-MS: [M + H]⁺ = 533.4. |
| 125 | 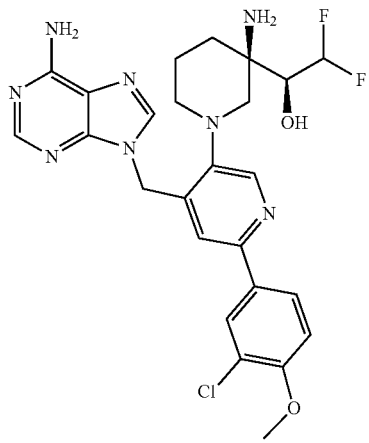 [SMILES: COc1ccc(-c2cc(Cn3cnc4c(N)ncnc43)c(N3CCC[C@](N)([C@H](O)C(F)F)C3)cn2)cc1Cl] | ¹H NMR (400 MHz, CD₃OD) δ ppm 8.45 (s, 1H), 8.23 (d, J = 8.8 Hz, 2H), 7.80 (d, J = 2.1 Hz, 1H), 7.57 (dd, J = 2.1, 8.6 Hz, 1H), 7.15 (s, 1H), 7.07 (d, J = 8.7 Hz, 1H), 6.22-5.86 (m, 1H), 5.65 (s, 2H), 4.05-3.85 (m, 4H), 3.21 (br d, J = 11.0 Hz, 1H), 3.05-2.90 (m, 3H), 1.96-1.72 (m, 3H), 1.71-1.56 (m, 1H). LC-MS: [M + H]⁺ = 545.4. |
| 126 | 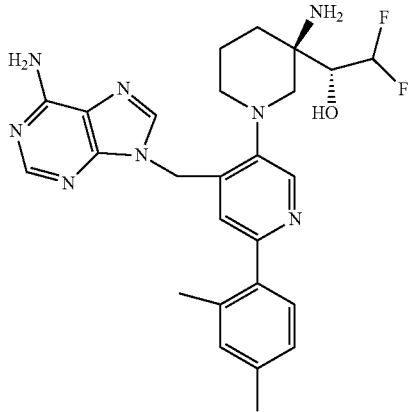 [SMILES: Cc1ccc(-c2cc(Cn3cnc4c(N)ncnc43)c(N3CCC[C@](N)([C@@H](O)C(F)F)C3)cn2)c(C)c1] | ¹H NMR (400 MHz, CD₃OD): δ 8.44 (s, 1H), 8.22-8.17 (d, J = 7.6 Hz, 2H), 7.08-7.00 (m, 3H), 6.72 (s, 1H), 6.22-5.93 (m, 1H), 5.68 (s, 2H), 3.71 (m, 1H), 3.25-3.22 (m, 1H), 3.13-3.04 (m, 2H), 2.90-2.85 (m, 1H), 2.29 (s, 3H), 2.11-2.09 (m, 1H), 2.01 (s, 3H), 1.89-1.70 (m, 3H). LC-MS: [M + H]⁺ = 509.4 |

| Example # | Structure | ¹H NMR & MS |
|---|---|---|
| 127 | 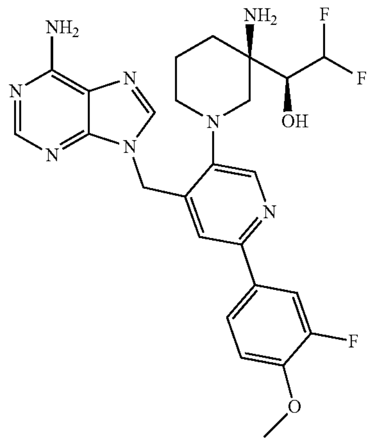 [SMILES: COc1ccc(-c2cc(Cn3cnc4c(N)ncnc43)c(N3CCC[C@](N)([C@H](O)C(F)F)C3)cn2)cc1F] | ¹H NMR (400 MHz, CD₃OD) δ ppm 8.45 (s, 1H), 8.23 (d, J = 9.2 Hz, 2H), 7.54 (dd, J = 12.7, 2.2 Hz, 1H), 7.43 (dd, J = 8.7, 1.6 Hz, 1H), 7.11 (dd, J = 17.6, 9.0 Hz, 2H), 6.04 (td, J = 55.4, 4.5 Hz, 1H), 5.65 (s, 2H), 3.95 (s, 1H), 3.88 (s, 3H), 3.22 (d, J = 11.0 Hz, 1H), 2.96 (d, J = 15.1 Hz, 3H), 1.86 (d, J = 13.5 Hz, 3H), 1.64 (s, 1H). LC-MS: [M + H]⁺ = 529.0, 530.0. |
| 128 | 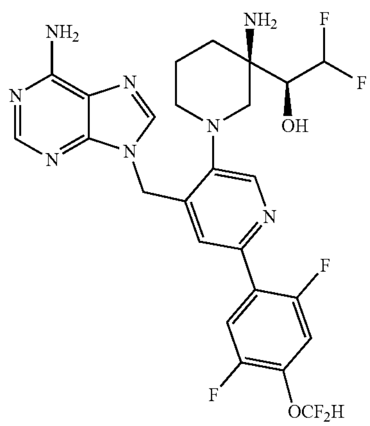 | ¹H NMR (400 MHz, DMSO-d₆) δ ppm 8.53 (s, 1H), 8.26 (s, 1H), 8.11 (s, 1H), 7.83 (dd, J = 11.5, 7.2 Hz, 1H), 7.52-7.04 (m, 4H), 6.98 (d, J = 1.6 Hz, 1H), 6.18 (td, J = 55.8, 4.0 Hz, 1H), 5.72 (s, 1H), 5.56 (d, J = 2.4 Hz, 2H), 3.77 (s, 1H), 3.08 (dd, J = 30.6, 8.8 Hz, 2H), 2.93 (t, J = 9.6 Hz, 1H), 2.79 (d, J = 11.3 Hz, 1H), 1.80 (q, J = 27.0, 21.6 Hz, 5H), 1.48 (d, J = 9.8 Hz, 1H). LC-MS: [M + H]⁺ = 582.9, 583.8. |
| 129 | 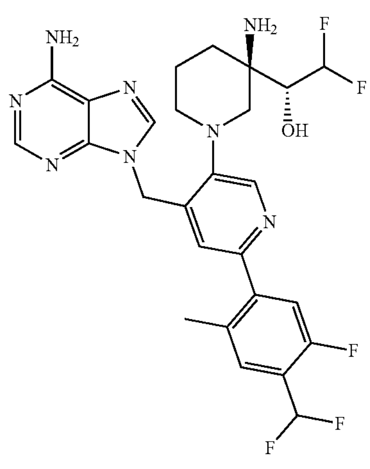 [SMILES: Cc1cc(C(F)F)c(F)cc1-c1cc(Cn2cnc3c(N)ncnc32)c(N2CCC[C@](N)([C@@H](O)C(F)F)C2)cn1] | ¹H NMR (400 MHz, CD₃OD) δ = 8.50 (s, 1H), 8.23 (s, 1H), 8.20-8.14 (m, 1H), 7.42 (d, J = 7.0 Hz, 1H), 7.10 (d, J = 10.8 Hz, 1H), 7.07-6.75 (m, 2H), 6.24-5.90 (m, 1H), 5.69 (s, 2H), 3.70 (ddd, J = 4.1, 8.3, 12.2 Hz, 1H), 3.24 (d, J = 11.5 Hz, 1H), 3.13 (br d, J = 11.4 Hz, 1H), 3.06 (br d, J = 11.4 Hz, 1H), 2.94-2.84 (m, 1H), 2.06 (s, 3H), 2.04-1.98 (m, 1H), 1.91-1.77 (m, 2H), 1.72 (br d, J = 1 5.3 Hz, 1H). LC-MS: [M + H]⁺ = 563.4. |

| Example # | Structure | ¹H NMR & MS |
|---|---|---|
| 130 | 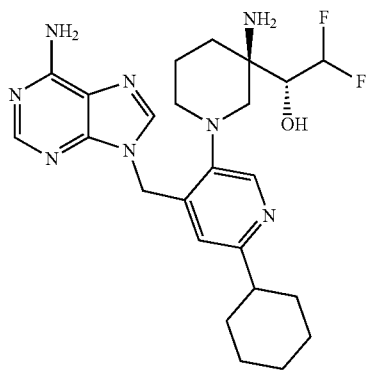 [SMILES: Nc1ncnc2c1ncn2Cc1cc(C2CCCCC2)ncc1N1CCC[C@](N)([C@@H](O)C(F)F)C1] | ¹H NMR (400 MHz, CD₃OD) δ ppm 8.29 (s, 1H), 8.22 (s, 1H), 8.17 (s, 1H), 6.68 (s, 1H), 6.03 (td, J = 55.1, 3.9 Hz, 1H), 5.71-5.33 (m, 2H), 3.65 (d, J = 15.2 Hz, 1H), 3.15 (d, J = 11.4 Hz, 1H), 2.95 (dd, J = 19.0, 11.6 Hz, 2H), 2.78 (t, J = 10.6 Hz, 1H), 2.62-2.48 (m, 1H), 1.95 (q, J = 11.3, 10.8 Hz, 1H), 1.74 (d, J = 18.8 Hz, 7H), 1.40-1.24 (m, 5H), 1.22-0.84 (m, 1H). LC-MS: [M + H]⁺ = 487.3, 488.3. |
| 131 | 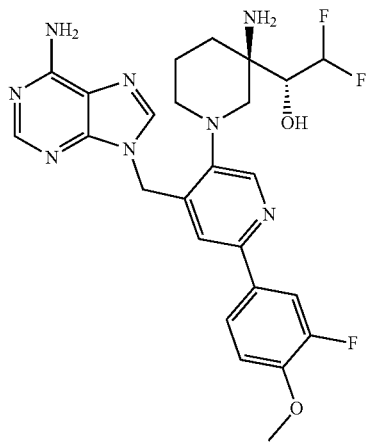 [SMILES: COc1ccc(-c2cc(Cn3cnc4c(N)ncnc43)c(N3CCC[C@](N)([C@@H](O)C(F)F)C3)cn2)cc1F] | ¹H NMR (400 MHz, CD₃OD) δ ppm 8.44 (s, 1H), 8.23 (d, J = 1.9 Hz, 2H), 7.56 (dd, J = 12.7, 2.2 Hz, 1H), 7.45 (ddd, J = 8.6, 2.3, 1.2 Hz, 1H), 7.24 (s, 1H), 7.10 (t, J = 8.7 Hz, 1H), 6.05 (td, J = 55.1, 3.9 Hz, 1H), 5.64 (d, J = 2.6 Hz, 2H), 3.75-3.60 (m, 1H), 3.20 (d, J = 11.4 Hz, 1H), 3.00 (t, J = 13.6 Hz, 2H), 2.88-2.75 (m, 1H), 1.97 (d, J = 12.3 Hz, 1H), 1.88-1.61 (m, 3H). LC-MS: [M + H]⁺ = 529.0, 530.0. |
| 132 | 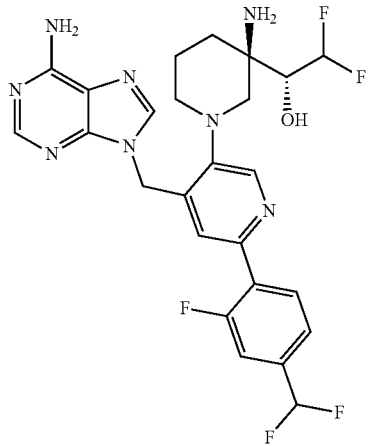 [SMILES: Nc1ncnc2c1ncn2Cc1cc(-c2ccc(C(F)F)cc2F)ncc1N1CCC[C@](N)([C@@H](O)C(F)F)C1] | ¹H NMR (400 MHz, CD₃OD) δ = 8.54 (d, J = 1.6 Hz, 1H), 8.22 (s, 1H), 8.21 (s, 1H), 7.92-7.84 (m, 1H), 7.45-7.36 (m, 1H), 7.33-7.25 (m, 1H), 7.18 (s, 1H), 6.94-6.60 (m, 1H), 6.23-5.92 (m, 1H), 5.68 (s, 2H), 3.79-3.64 (m, 1H), 3.28-3.21 (m, 1H), 3.18-3.03 (m, 2H), 2.94-2.83 (m, 1H), 2.11-1.97 (m, 1H), 1.93-1.67 (m, 3H). LC-MS: [M + H]⁺ = 549.5. |

| Example # | Structure | ¹H NMR & MS |
|---|---|---|
| 133 | 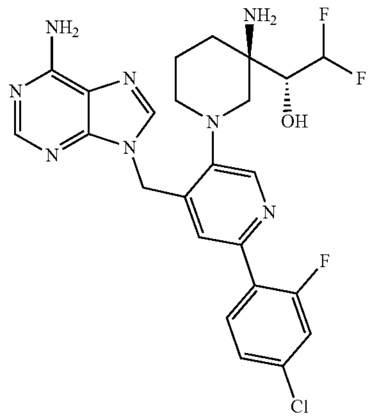 [SMILES: Nc1ncnc2c1ncn2Cc1cc(-c2ccc(Cl)cc2F)ncc1N1CCC[C@](N)([C@@H](O)C(F)F)C1] | ¹H NMR (400 MHz, CD₃OD) δ ppm 8.42 (s, 1H), 8.11 (d, J = 4.3 Hz, 2H), 7.78 (t, J = 8.4 Hz, 1H), 7.23-7.07 (m, 2H), 7.02 (s, 1H), 6.15-5.80 (m, 1H), 5.58 (s, 2H), 3.68-3.50 (m, 1H), 3.25 (s, 1H), 3.14 (d, J = 11.4 Hz, 1H), 3.03 (d, J = 10.9 Hz, 1H), 2.96 (d, J = 11.4 Hz, 1H), 2.83-2.64 (m, 1H), 2.01-1.82 (m, 1H), 1.91-1.63 (m, 3H). LC-MS: [M + H]⁺ = 533.4. |
| 134 | 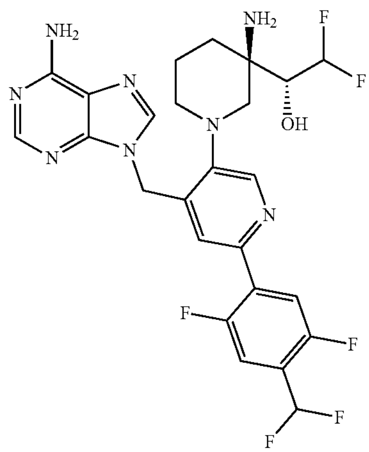 [SMILES: Nc1ncnc2c1ncn2Cc1cc(-c2cc(F)c(C(F)F)cc2F)ncc1N1CCC[C@](N)([C@@H](O)C(F)F)C1] | ¹H NMR (400 MHz, CD₃OD) δ = 8.58 (s, 1H), 8.25 (s, 1H), 8.21 (s, 1H), 7.80-7.70 (m, 1H), 7.40-7.32 (m, 1H), 7.27 (s, 1H), 7.13-6.80 (m, 1H), 6.26-5.94 (m, 1H), 5.77-5.61 (m, 2H), 3.85-3.72 (m, 1H), 3.28-3.09 (m, 3H), 2.97-2.86 (m, 1H), 2.10-2.00 (m, 1H), 1.97-1.80 (m, 3H) LC-MS: [M + H]⁺ = 567.4, |
| 135 | 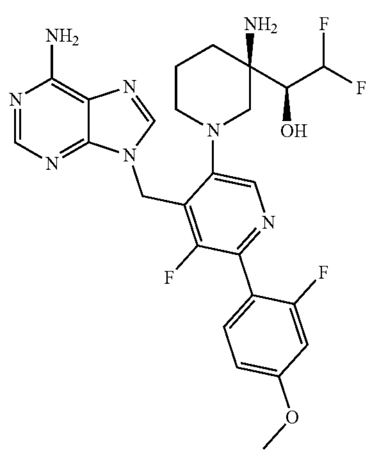 [SMILES: COc1ccc(-c2ncc(N3CCC[C@](N)([C@H](O)C(F)F)C3)c(Cn3cnc4c(N)ncnc43)c2F)c(F)c1] | ¹H NMR (400 MHz, CD₃OD) δ = 8.39 (s, 1H), 8.24 (s, 1H), 8.10 (d, J = 2.0 Hz, 1H), 7.43 (t, J = 8.5 Hz, 1H), 6.87 (dd, J = 2.4, 8.6 Hz, 1H), 6.79 (dd, J = 2.4, 12.2 Hz, 1H), 6.21-5.88 (m, 1H), 5.77-5.58 (m, 2H), 3.97-3.77 (m, 4H), 3.25-3.17 (m, 1H), 3.15-3.06 (m, 1H), 3.05-2.96 (m, 1H), 2.95-2.85 (m, 1H), 2.01-1.87 (m, 1H), 1.86-1.66 (m, 3H).). LC-MS: [M + H]⁺ = 547.5. |

| Example # | Structure | ¹H NMR & MS |
|---|---|---|
| 136 | 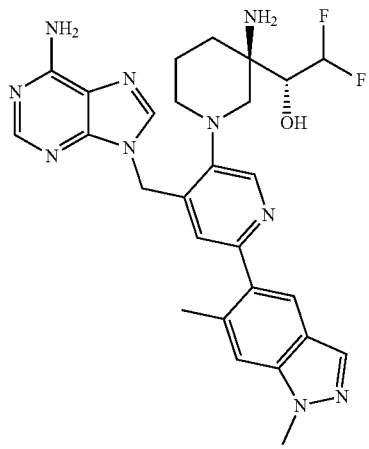 [SMILES: Cc1cc2c(cnn2C)cc1-c1cc(Cn2cnc3c(N)ncnc32)c(N2CCC[C@](N)([C@@H](O)C(F)F)C2)cn1] | ¹H NMR (400 MHz, CD₃OD): δ 8.54 (s, 1H), 8.22 (d, J = 5.6 Hz, 1H), 8.23-8.21 (m, 1H), 7.00-6.85 (m, 3H), 6.27-5.93 (m, 1H), 5.71 (s, 2H), 3.84-3.67 (m, 1H), 3.31-3.25 (m, 1H), 3.21-3.15 (m, 1H), 3.14-3.08 (m, 1H), 2.97-2.88 (m, 1H), 2.14-2.02 (m, 1H), 1.96-1.81 (m, 2H), 1.81-1.72 (m, 1H). LC-MS: [M + H]⁺ = 549.4. |
| 137 | 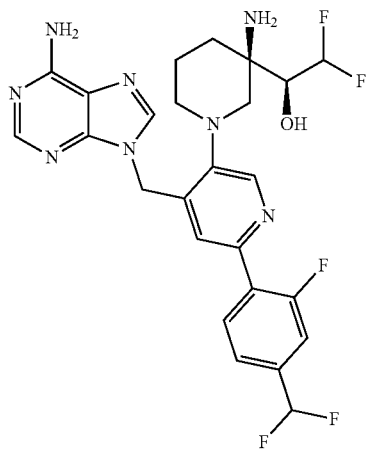 [SMILES: Nc1ncnc2c1ncn2Cc1cc(-c2ccc(C(F)F)cc2F)ncc1N1CCC[C@](N)([C@H](O)C(F)F)C1] | ¹H NMR (400 MHz, CD₃OD): δ 8.57 (s, 1H), 8.30-8.20 (m, 2H), 7.92 (t, J = 8.0 Hz, 1H), 7.44 (d, J = 8.0 Hz, 1H), 7.33 (d, J = 11.2 Hz, 1H), 7.13 (s, 1H), 6.98-6.64 (m, 1H), 6.26-5.92 (m, 1H), 5.72 (s, 2H), 4.17-3.93 (m, 1H), 3.32-3.24 (m, 1H), 3.16-2.94 (m, 3H), 2.06-1.82 (m, 3H), 1.75-1.59 (m, 1H). LC-MS: [M + H]⁺ = 549.4. |
| 138 | 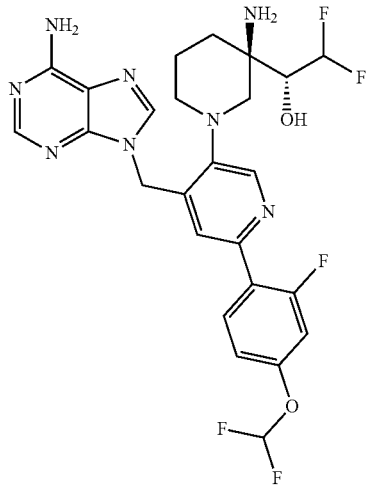 [SMILES: Nc1ncnc2c1ncn2Cc1cc(-c2ccc(OC(F)F)cc2F)ncc1N1CCC[C@](N)([C@@H](O)C(F)F)C1] | ¹H NMR (400 MHz, CD₃OD) δ ppm 8.51 (s, 1H), 8.21 (d, J = 2.2 Hz, 2H), 7.81 (t, J = 8.8 Hz, 1H), 7.10 (d, J = 1.7 Hz, 1H), 7.08-6.71 (m, 3H), 6.06 (td, J = 55.1, 3.9 Hz, 1H), 5.68 (s, 2H), 3.70 (dd, J = 15.8, 8.2 Hz, 1H), 3.23 (d, J = 11.4 Hz, 1H), 3.12 (d, J = 11.1 Hz, 1H), 3.04 (d, J = 11.4 Hz, 1H), 2.88 (t, J = 10.6 Hz, 1H), 2.02 (t, J = 11.6 Hz, 1H), 1.91-1.75 (m, 2H), 1.70 (d, J = 13.5 Hz, 1H). LC-MS: [M + H]⁺ = 565.2, 566.2. |

| Example # | Structure | ¹H NMR & MS |
|---|---|---|
| 139 | 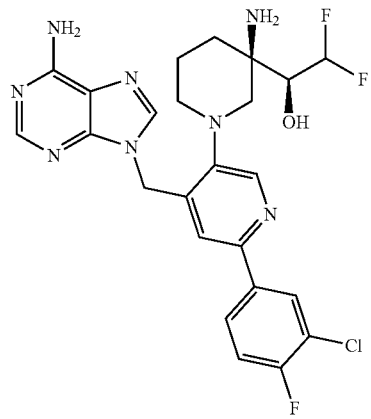 | ¹H NMR (400 MHz, CD₃OD) δ ppm 8.49 (s, 1H), 8.21-8.24 (d, 2H), 7.91-7.93 (t, 1H), 7.65 (br, 1H), 7.22-7.28 (br, 2H), 5.89-6.18 (t, 1H), 5.65 (s, 2H), 3.94 (br, 1H), 3.25 (d, 1H), 2.95 (b, 3H), 1.88 (m, 3H), 1.63 (m, 1H). LC-MS: [M + H]⁺ = 532.9, 533.9. |
| 140 | 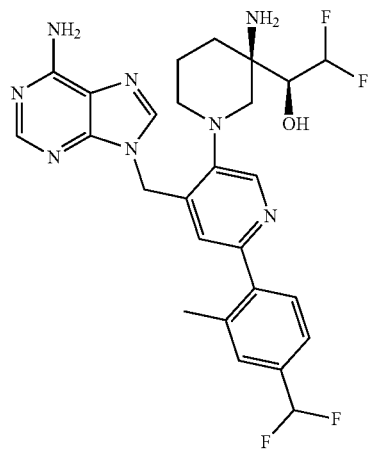 [SMILES: Cc1cc(C(F)F)ccc1-c1cc(Cn2cnc3c(N)ncnc32)c(N2CCC[C@](N)([C@H](O)C(F)F)C2)cn1] | ¹H NMR: (400 MHz, CD₃CN): δ 8.51 (s, 1H), 8.19 (s, 1H), 7.97 (s, 1H), 7.40-7.34 (m, 3H), 6.91-6.59 (m, 2H), 6.19-5.87 (m, 3H), 5.54 (s, 2H), 3.80 (m, 1H), 3.14 (m, 1H), 3.07-2.98 (m, 1H), 2.90 (m, 2H), 2.11 (s, 3H), 2.09 (m, 1H), 1.84-1.71 (m, 2H), 1.62-1.50 (m, 1H). LC-MS: [M + H]⁺ = 545.5. |
| 141 | 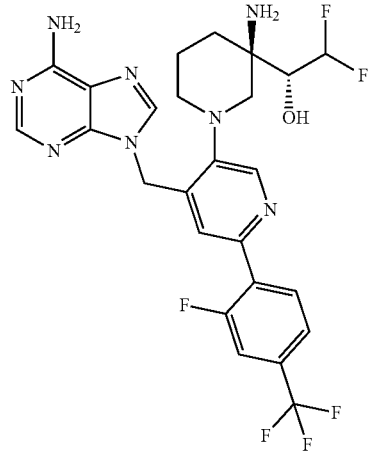 [SMILES: Nc1ncnc2c1ncn2Cc1cc(-c2ccc(C(F)(F)F)cc2F)ncc1N1CCC[C@](N)([C@@H](O)C(F)F)C1] | ¹H NMR (400 MHz, CD₃OD): δ 8.56 (s, 1H), 8.23 (s, 1H), 8.21 (s, 1H), 8.02-7.98 (m, 1H), 7.56-7.54 (d, J = 8.0 Hz, 1H), 7.48-7.45 (d, J = 11.2 Hz, 1H), 7.21 (s, 1H), 6.22-5.93 (m, 1H), 5.69 (s, 2H), 3.73-3.67 (m, 1H), 3.27-3.24 (d, J = 11.6 Hz, 1H), 3.16-3.14 (m, 1H), 3.09-3.06 (d, J = 11.2 Hz, 1H), 2.92-2.87 (m, 1H), 2.07-2.02 (m, 1H), 1.89-1.79 (m, 2H), 1.74-1.70 (m, 1H). LC-MS: [M + H]⁺ = 567.4. |

| Example # | Structure | ¹H NMR & MS |
|---|---|---|
| 142 | 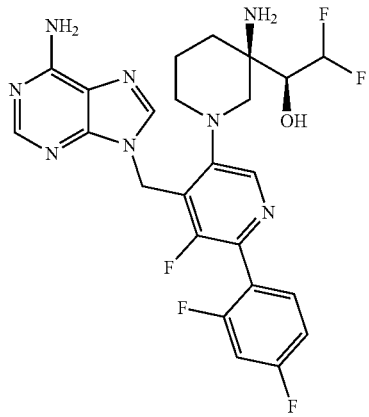 [SMILES: Nc1ncnc2c1ncn2Cc1c(N2CCC[C@](N)([C@H](O)C(F)F)C2)cnc(-c2ccc(F)cc2F)c1F] | ¹H NMR (400 MHz, CD₃OD) δ = 8.52 (s, 1H), 8.46 (s, 1H), 8.29 (s, 1H), 8.17 (d, J = 2.4 Hz, 1H), 7.58 (dt, J = 6.5, 8.5 Hz, 1H), 7.17-7.04 (m, 2H), 6.31-5.98 (m, 1H), 5.76-5.57 (m, 2H), 4.08-3.91 (m, 1 H), 3.46-3.35 (m, 1H), 3.30-3.25 (m, 1H), 3.16-3.06 (m, 1H), 3.06-2.94 (m, 1H), 2.11-1.82 (m, 4H). LC-MS: [M + H]⁺ = 535.4. |
| 143 | 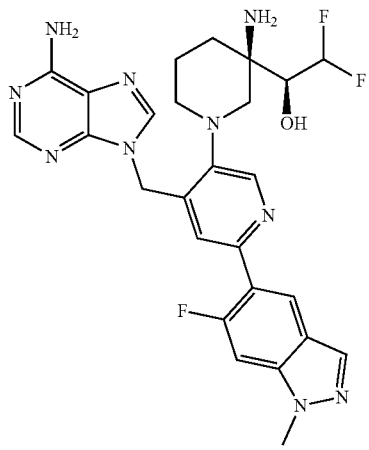 [SMILES: Cn1ncc2cc(-c3cc(Cn4cnc5c(N)ncnc54)c(N4CCC[C@](N)([C@H](O)C(F)F)C4)cn3)c(F)cc21] | ¹H NMR (400 MHz, CD₃OD) δ = 8.52 (s, 1H) 8.24 (s, 1H), 8.20 (s, 1H), 8.07-8.03 (m, 2H), 7.31 (d, J = 11.5 Hz, 1H), 7.01 (d, J = 2.0 Hz, 1H), 6.24-5.88 (m, 1H), 5.74-5.67 (m, 2H), 4.01 (s, 3H), 3.23-3.29 (m, 1H), 3.16-2.91 (m, 3H), 2.20-2.15 (m, 1H), 1.93-1.80 (m, 3H), 1.74-1.57 (m, 1H). LC-MS: [M + H]⁺ = 553.4. |
| 144 | 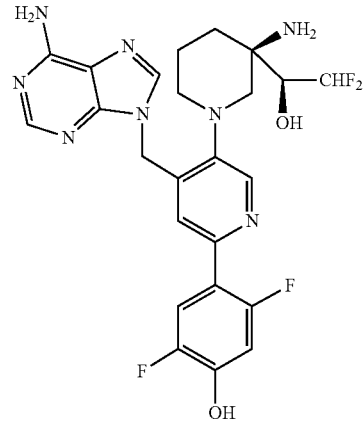 [SMILES: Nc1ncnc2c1ncn2Cc1cc(-c2cc(F)c(O)cc2F)ncc1N1CCC[C@](N)([C@H](O)C(F)F)C1] | ¹H NMR (400 MHz, CD₃OD) δ = 8.45 (s, 1H), 8.20 (d, J = 9.6 Hz, 2H), 7.50 (m, 1H), 7.04 (s, 1H), 6.58 (m, 1H) , 6.20-5.92 (m, 1H), 5.65 (s, 2H), 4.0 (s, 1H), 3.26-3.23 (m, 1H), 3.01-2.99 (m, 3H), 1.91-1.88 (m, 3H), 1.70 (br s, 1H). LC-MS: [M + H]⁺ = 533.3. |

| Example # | Structure | ¹H NMR & MS |
|---|---|---|
| 145 | 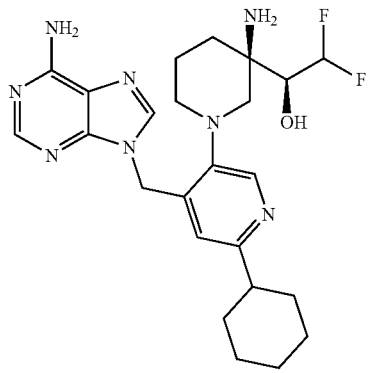 [SMILES: Nc1ncnc2c1ncn2Cc1cc(C2CCCCC2)ncc1N1CCC[C@](N)([C@H](O)C(F)F)C1] | ¹H NMR (400 MHz, CD₃OD) δ ppm 8.29 (s, 1H), 8.20 (s, 1H), 8.18 (s, 1H), 6.59 (s, 1H), 6.03 (td, J = 55.4, 4.3 Hz, 1H), 5.61 (s, 2H), 3.95 (s, 1H), 3.19-3.11 (m, 1H), 2.91 (d, J = 18.5 Hz, 3H), 2.62-2.45 (m, 1H), 1.89-1.61 (m, 9H), 1.36-1.22 (m, 5H). LC-MS: [M + H]⁺ = 487.3, 488.3. |
| 146 | 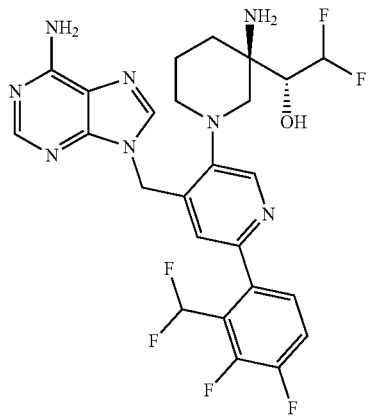 [SMILES: Nc1ncnc2c1ncn2Cc1cc(-c2ccc(F)c(F)c2C(F)F)ncc1N1CCC[C@](N)([C@@H](O)C(F)F)C1] | ¹H NMR (400 MHz, CD₃OD) δ = 8.56 (s, 1H), 8.23 (d, J = 10.0 Hz, 2H), 7.70 (t, J = 7.4 Hz, 1H), 7.43 (br t, J = 7.2 Hz, 1H), 7.19 (d, J = 1.0 Hz, 1H), 7.16-6.85 (m, 1H), 6.24-5.91 (m, 1H), 5.70 (s, 2H), 3.78-3.63 (m, 1H), 3.26 (m, 1H), 3.19-3.04 (m, 2H), 2.95-2.85 (m, 1H), 2.14-1.98 (m, 1H), 1.93-1.65 (m, 1H), 1.93-1.65 (m, 3H). LC-MS: [M + H]⁺ = 567.4. |
| 147 | 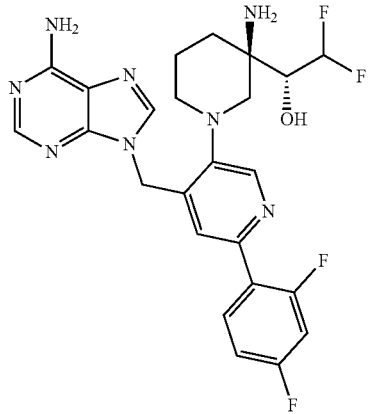 [SMILES: Nc1ncnc2c1ncn2Cc1cc(-c2ccc(F)cc2F)ncc1N1CCC[C@](N)([C@@H](O)C(F)F)C1] | ¹H NMR (400 MHz, CD₃OD) δ 8.51 (s, 1H), 8.21 (d, J = 15.3 Hz, 2H), 7.78 (td, J = 8.8, 6.5 Hz, 1H), 7.15-6.70 (m, 3H), 6.05 (td, J = 55.4, 4.4 Hz, 1H), 5.69 (s, 2H), 3.99 (s, 1H), 3.15-2.81 (m, 3H), 1.89 (d, J = 16.2 Hz, 3H), 1.65 (s, 1H). LC-MS: [M + H]⁺ = 517.2, 518.2. |

| Example # | Structure | ¹H NMR & MS |
|---|---|---|
| 148 | 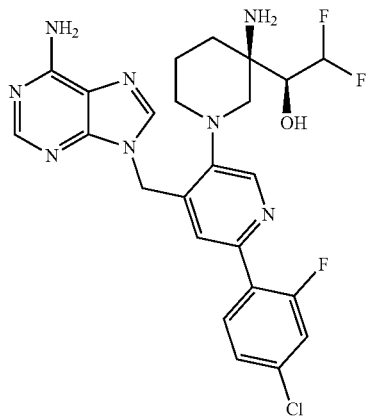 | ¹H NMR (400 MHz, CD₃OD) δ ppm 8.52 (s, 1H), 8.21 (d, J = 13.9 Hz, 2H), 7.77 (t, J = 8.4 Hz, 1H), 7.31-7.16 (m, 2H), 7.05 (s, 1H), 6.24-5.88 (m, 1H), 5.69 (s, 2H), 4.11-3.88 (m, 1H), 3.26 (m, 1H), 3.16-2.90 (m, 3H), 1.90 (m, 3H), 1.67 (m, 1H). LC-MS: [M + H]⁺ = 533.4. |
| 149 | 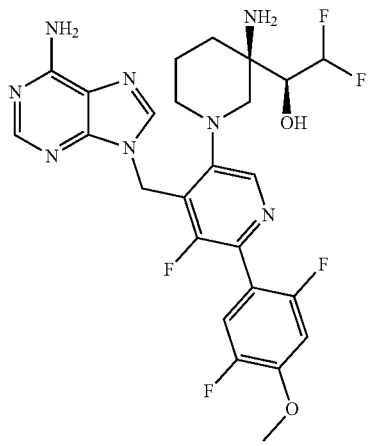 | ¹H NMR (400 MHz, CD₃OD) δ = 8.40 (s, 1H), 8.24 (s, 1H), 8.11 (s, 1H), 7.28 (dd, J = 6.7, 11.3 Hz, 1H), 7.01 (dd, J = 7.1, 11.4 Hz, 1H), 6.23-5.88 (m, 1H), 5.76-5.56 (m, 2H), 4.0-3.80 (m, 4H), 3.26-3.18 (m, 1H), 3.18-3.08 (m, 1H), 3.08-2.97 (m, 1H), 2.97-2.84 (m, 1H), 2.06-1.88 (m, 1H), 1.88-1.66 (m, 3H) LCMS: [M + H]⁺ = 565.4 |
| 150 | 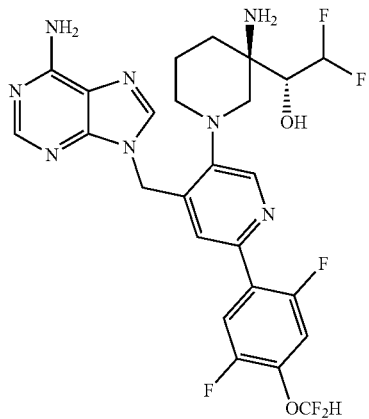 | ¹H NMR (400 MHz, DMSO-d₆) δ ppm 8.52 (s, 1H), 8.26 (s, 1H), 8.11 (s, 1H), 7.83 (dd, J = 11.5, 7.2 Hz, 1H), 7.56-7.07 (m, 4H), 7.02 (d, J = 1.6 Hz, 1H), 6.19 (td, J = 55.4, 3.1 Hz, 1H), 5.62 (s, 1H), 5.58 (s, 2H), 3.54 (dd, J = 17.7, 9.3 Hz, 1H), 3.09 (d, J = 11.4 Hz, 2H), 2.94-2.75 (m, 2H), 1.98 (d, J = 12.5 Hz, 3H), 1.76-1.64 (m, 2H), 1.54 (d, J = 12.8 Hz, 1H). LC-MS: [M + H]⁺ = 582.9, 583.8. |

| Example # | Structure | ¹H NMR & MS |
|---|---|---|
| 151 | 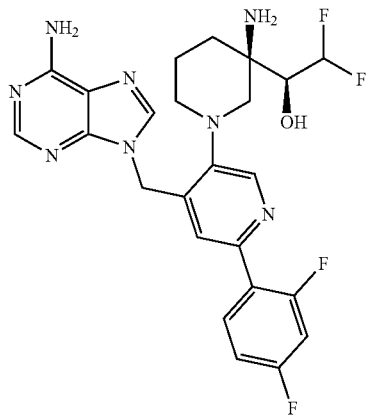 [SMILES: Nc1ncnc2c1ncn2Cc1cc(-c2ccc(F)cc2F)ncc1N1CCC[C@](N)([C@H](O)C(F)F)C1] | ¹H NMR (400 MHz, CD₃OD) δ 8.51 (s, 1H), 8.21 (d, J = 15.4 Hz, 2H), 7.78 (td, J = 8.9, 6.6 Hz, 1H), 7.09-6.87 (m, 3H), 6.05 (td, J = 55.4, 4.5 Hz, 1H), 5.69 (s, 2H), 3.99 (s, 1H), 3.25 (d, J = 1.9 Hz, 1H), 3.12-2.83 (m, 3H), 2.02-1.77 (m, 3H), 1.65 (s, 1H). LC-MS: [M + H]⁺ = 517.2, 518.2. |
| 152 | 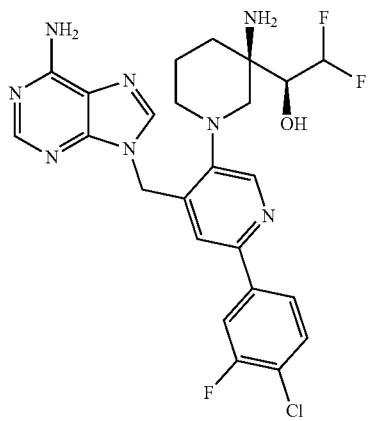 [SMILES: Nc1ncnc2c1ncn2Cc1cc(-c2ccc(Cl)c(F)c2)ncc1N1CCC[C@](N)([C@H](O)C(F)F)C1] | ¹HNMR (400 MHz, CD₃OD) δ ppm 8.51 (s, 1H), 8.25-8.22 (d, J = 10.8 Hz, 2H), 7.72-7.69 (m, 1H), 7.54-7.49 (m, 2H), 7.27 (s, 1H), 6.18-5.90 (m, 1H), 5.66 (s, 2H), 3.95 (m, 1H), 3.24-3.22 (d, J = 11.2 Hz, 1H), 2.98 (m, 3H), 1.89-1.83 (m, 3H), 1.66 (m, 1H). LC-MS: [M + H]⁺ = 533.4. |
| 153 | 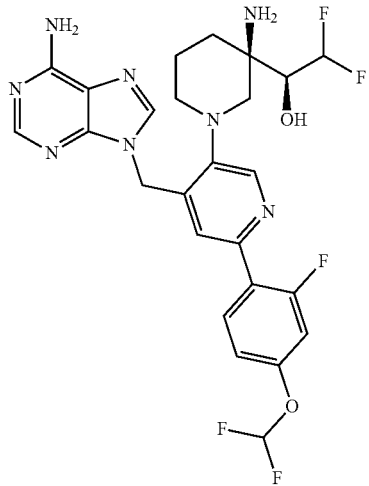 [SMILES: Nc1ncnc2c1ncn2Cc1cc(-c2ccc(OC(F)F)cc2F)ncc1N1CCC[C@](N)([C@H](O)C(F)F)C1] | ¹H NMR (400 MHz, CD₃OD) δ ppm 8.51 (s, 1H), 8.21 (d, J = 10.4 Hz, 2H), 7.80 (t, J = 8.8 Hz, 1H), 7.12-6.67 (m, 4H), 6.05 (td, J = 55.5, 4.4 Hz, 1H), 5.68 (s, 2H), 3.99 (s, 1H), 3.26 (d, J = 11.5 Hz, 1H), 3.00 (dd, J = 29.4, 14.5 Hz, 3H), 1.89 (d, J = 13.5 Hz, 3H), 1.65 (s, 1H). LC-MS: [M + H]⁺ = 565.2, 566.2. |

| Example # | Structure | ¹H NMR & MS |
|---|---|---|
| 154 | 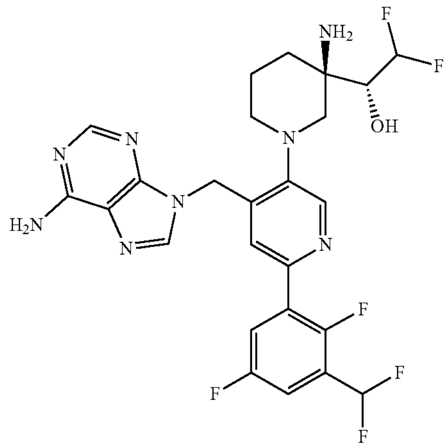 [SMILES: Nc1ncnc2c1ncn2Cc1cc(-c2cc(F)cc(C(F)F)c2F)ncc1N1CCC[C@](N)([C@@H](O)C(F)F)C1] | ¹H NMR (400 MHz, CD₃OD) δ = 8.59 (s, 1H), 8.35-8.25 (m, 1H), 8.21 (s, 1H), 7.80-7.70 (m, 1H), 7.40-7.31 (m, 1H), 7.30-7.20 (m, 1H), 7.12-6.78 (m, 1H), 6.32-5.88 (m, 1H), 5.82-5.58 (m, 2H), 3.97-3.80 (m, 1H), 3.33-3.32 (m, 1H), 3.21-3.10 (m, 1H), 3.00-2.80 (m, 1H), 2.18-1.79 (m, 4H) LC-MS: [M + H]⁺ = 567.4, |
| 155 | 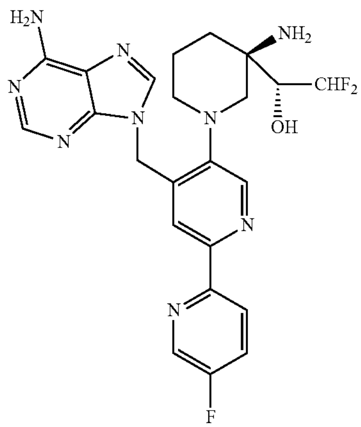 [SMILES: Nc1ncnc2c1ncn2Cc1cc(-c2ccc(F)cn2)ncc1N1CCC[C@](N)([C@@H](O)C(F)F)C1] | ¹H NMR (400 MHz, CD₃OD) δ = 8.50 (s, 1H), 8.39 (d, J = 2.8 Hz, 1H), 8.31 (dd, J = 4.6, 8.9 Hz, 1H), 8.26 (s, 1H), 8.22 (s, 1H), 7.76 (s, 1H), 7.65 (dt, J = 2.9, 8.6 Hz, 1H), 6.24-5.93 (m, 1H), 5.70 (s, 2H), 3.78-3.63 (m, 1H), 3.26 (d, J = 11.5 Hz, 1H), 3.18-3.12 (m, 1H), 3.10-3.04 (m, 1H), 2.96-2.84 (m, 1H), 2.14-1.98 (m, 1H), 1.93-1.76 (m, 2H), 1.76-1.65 (m, 1H). LC-MS: [M + H]⁺ = 500.2. |

Example 156 and Example 157: (R)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol and (S)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol

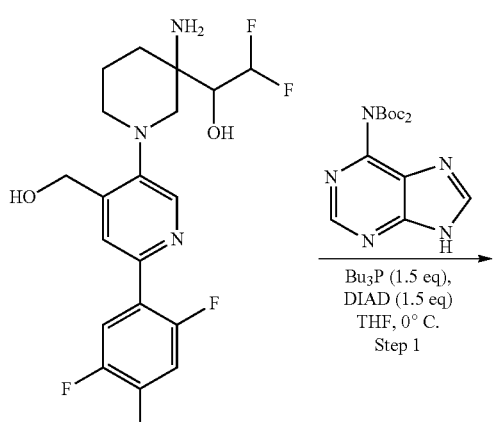

156-2

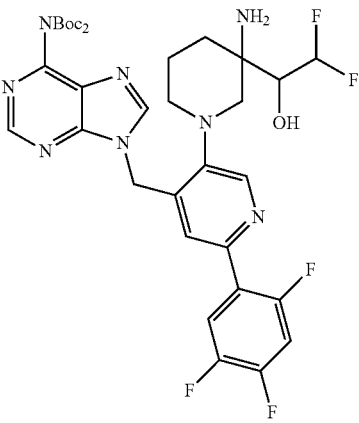

156-3

1. TFA, DCM
2. SFC

Step 2

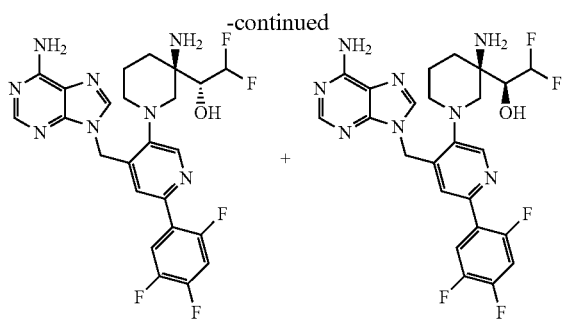

Example 156 and Example 157

Step 1. To a solution of 1-(3-amino-1-(4-(hydroxymethyl)-6-(2,4,5-trifluorophenyl)pyridin-3-yl)piperidin-3-yl)-2,2-difluoroethan-1-ol (Intermediate 156-2) (700 mg, 1.677 mmol, 1.0 eq), Intermediate B (80 mg, 0.240 mmol, 1.5 eq) and n-Bu₃P (509 mg, 2.516 mmol, 1.5 eq) in anhydrous THF (7 mL) was added DIAD (509 mg, 2.516 mmol, 1.5 eq) under nitrogen at 0° C. The reaction mixture was stirred at 0° C. for 30 min. The reaction mixture was concentrated in vacuum and the residue was purified by Prep-HPLC (base) to give Intermediate 156-3. $^1$H NMR (400 MHz, CDCl₃) δ=8.93-8.85 (m, 1H), 8.57 (s, 1H), 8.22-8.14 (m, 1H), 7.92-7.76 (m, 1H), 7.45-7.32 (m, 1H), 7.01-6.83 (m, 1H), 6.20-5.80 (m, 1H), 5.72-5.53 (m, 2H), 3.82-3.63 (m, 1H), 3.26-3.06 (m, 2H), 3.05-2.89 (m, 2H), 2.28-2.12 (m, 1H), 1.89-1.79 (m, 2H), 1.75-1.63 (m, 1H), 1.49-1.36 (m, 18H). LCMS: [M+H]⁺=735.5.

Step 2. To a solution of Intermediate 156-3 (630 mg, 0.858 mmol) in anhydrous DCM (15 mL) was added TFA (5 mL) and the reaction was stirred at 20° C. for 3 hours. The reaction mixture was concentrated in vacuum and basified with ammonium hydroxide to pH=8, concentrated in vacuum. The residue was purified by Prep-HPLC (base) and SFC to give (R)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol (Example 156) and (S)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol (Example 157).

Example 156: $^1$H NMR (400 MHz, CD3OD) δ ppm 8.52 (d, J=1.9 Hz, 1H), 8.20 (dd, J=5.6, 2.0 Hz, 2H), 7.78 (dddd, J=11.4, 9.2, 7.1, 2.0 Hz, 1H), 7.42-7.05 (m, 2H), 6.35-5.80 (m, 1H), 5.67 (d, J=2.0 Hz, 2H), 3.68 (d, J=14.0 Hz, 1H), 3.22 (s, 1H), 3.14-3.00 (m, 2H), 2.88 (t, J=11.2 Hz, 1H), 2.03 (t, J=11.5 Hz, 1H), 1.82 (t, J=12.9 Hz, 2H), 1.71 (d, J=13.0 Hz, 1H). LC-MS: [M+H]+=535.2.

Example 157: $^1$H NMR (400 MHz, CD3OD) δ ppm 8.55 (s, 1H), 8.25 (s, 1H), 8.21 (s, 1H), 7.87-7.74 (m, 1H), 7.25-7.15 (m, 1H), 7.09 (s, 1H), 6.26-5.88 (m, 1H), 5.70 (s, 2H), 4.10-3.90 (m, 1H), 3.30-3.20 (m, 1H), 3.17-2.87 (m, 3H), 2.03-1.80 (m, 3H), 1.75-1.60 (m, 1H). LC-MS: [M+H]+=535.4.

Examples 158 and 159 were prepared following procedures analogous to the preparation of Examples 156 and 157 (Step 2).

| Example No. | | $^1$H NMR |
|---|---|---|
| 158 | ![structure] | $^1$H NMR (400 MHz, CD3OD) δ ppm 8.51 (s, 1H), 8.20 (d, J = 2.5 Hz, 2H), 7.47-7.34 (m, 2H), 7.27 (td, J = 8.5, 2.5 Hz, 1H), 7.01-6.63 (m, 2H), 6.06 (td, J = 55.1, 3.8 Hz, 1H), 5.68 (s, 2H), 3.78-3.57 (m, 1H), 3.23 (d, J = 11.5 Hz, 1H), 3.12 (d, J = 11.3 Hz, 1H), 3.05 (d, J = 11.5 Hz, 1H), 2.88 (t, J = 10.8 Hz, 1H), 2.02 (dd, J = 13.6, 9.3 Hz, 1H), 1.83 (td, J = 14.9, 13.8, 6.8 Hz, 2H), 1.71 (d, J = 14.7 Hz, 1H). LC-MS: [M + H]+ = 549.2. | or

| Example No. | | ¹H NMR |
|---|---|---|
| 159 | 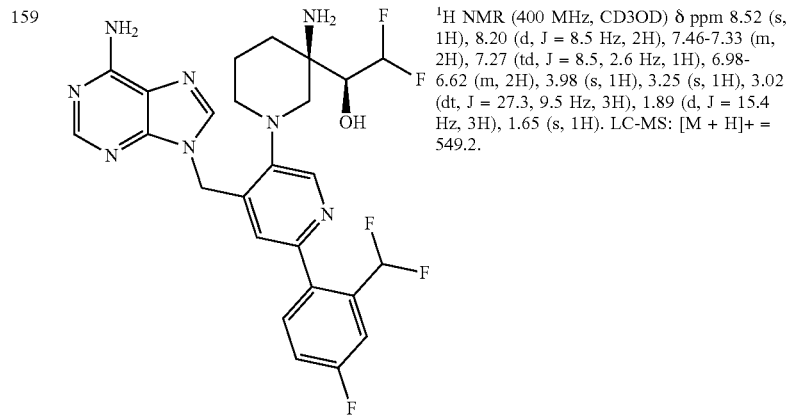 | ¹H NMR (400 MHz, CD3OD) δ ppm 8.52 (s, 1H), 8.20 (d, J = 8.5 Hz, 2H), 7.46-7.33 (m, 2H), 7.27 (td, J = 8.5, 2.6 Hz, 1H), 6.98-6.62 (m, 2H), 3.98 (s, 1H), 3.25 (s, 1H), 3.02 (dt, J = 27.3, 9.5 Hz, 3H), 1.89 (d, J = 15.4 Hz, 3H), 1.65 (s, 1H). LC-MS: [M + H]+ = 549.2. |

Example 160 and Example 161: (R)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol and (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol

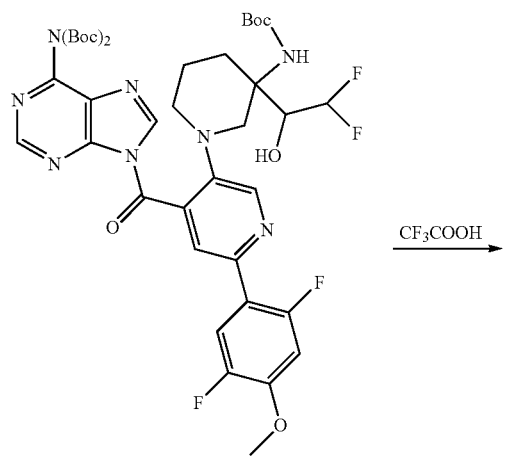

160-3

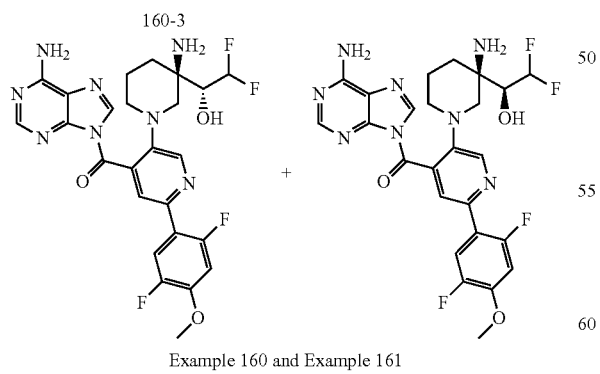

Example 160 and Example 161

To a solution of tert-butyl (tert-butoxycarbonyl)(9-((5-(3-((tert-butoxycarbonyl)amino)-3-(2,2-difluoro-1-hydroxyethyl)piperidin-1-yl)-2-(2,5-difluoro-4-methoxyphenyl)pyridin-4-yl)methyl)-9H-purin-6-yl)carbamate (Intermediate 160-3) (200 mg, 0.237 mmol) in DCM (18 mL), was added TFA (36 mL), and the reaction mixture was stirred at rt for 30 min under N₂ atmosphere. The reaction mixture was concentrated in vacuo to give the crude product. The crude product was purified by Pre-HPLC and SFC to afford (R)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (Example 160) and (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol (Example 161).

Example 160: ¹H NMR (400 MHz, CD₃OD) δ ppm 8.48 (s, 1H), 8.20 (d, J=1.6 Hz, 2H), 7.58 (dd, J=12.2, 7.3 Hz, 1H), 7.11 (d, J=1.3 Hz, 1H), 6.90 (dd, J=12.6, 7.1 Hz, 1H), 6.06 (td, J=55.1, 3.9 Hz, 1H), 5.67 (s, 2H), 3.87 (s, 3H), 3.75-3.58 (m, 1H), 3.25-2.75 (m, 4H), 2.26-1.60 (m, 4H). LC-MS: [M+H]⁺=547.2, 548.2.

Example 161: ¹H NMR (400 MHz, CD₃OD) δ=8.51-8.44 (m, 1H), 8.24-8.16 (m, 2H), 7.62-7.48 (m, 1H), 7.03 (s, 1H), 6.93-6.79 (m, 1H), 6.25-5.86 (m, 1H), 5.71-5.59 (m, 2H), 4.00 (m, 1H), 3.88-3.80 (m, 3H), 3.28-2.87 (m, 4H), 1.99-1.56 (m, 4H). LC-MS: [M+H]+=547.4.

Example 162 and Example 163: (R)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol and (S)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol

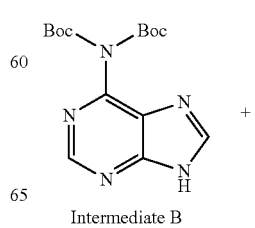

Intermediate B

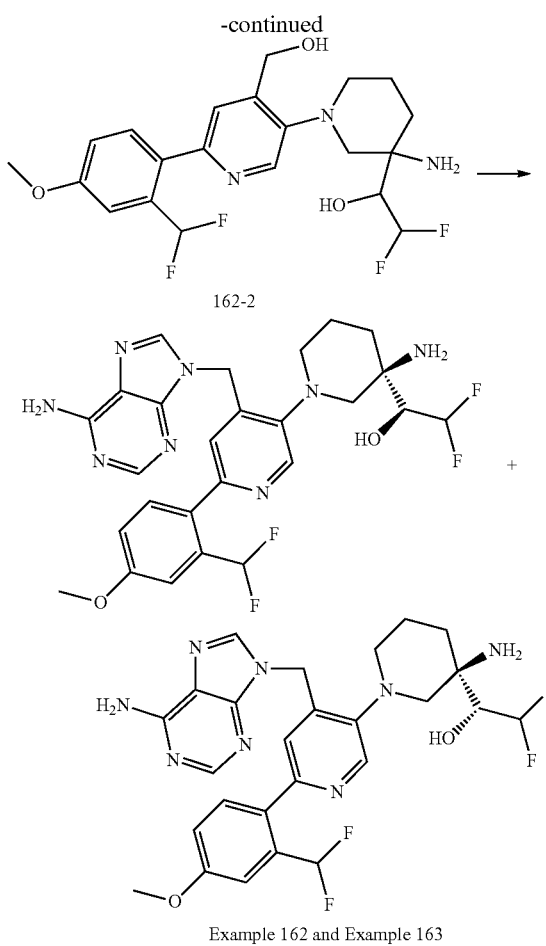

Example 162 and Example 163

To a solution of intermediate 162-2 (57 mg, 0.129 mmol) Intermediate B (43.1 mg, 0.129 mmol) and PPh₃ (101 mg, 0.386 mmol) in THF (5 mL) was added DEAD (0.061 mL, 0.386 mmol). The reaction mixture was stirred at 0° C. for 30 min under N₂ atmosphere. The reaction mixture was quenched with water and extracted with EtOAc, the combined organic phase was washed with water, brine, dried over sodium sulfate, concentrated to give a crude product. The crude product was purified by flash chromatography (elution gradient: 0% to 10% MeOH in DCM in 30 mins) to afford the intermediate. LC-MS: [M+H]+=761.

To a solution of the intermediate (200 mg, 0.263 mmol) in DCM (18 mL) was added TFA (36 mL, 467 mmol), the reaction mixture was stirred at rt for 30 min under N₂ atmosphere. The crude product was purified by Pre-HPLC (Basic condition, NH₃H₂O %=0.05%, MeOH/H₂O=0-95% in 10 mins) to afford the pure product, and then further purified by to afford (R)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol (Example 162) and (S)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol (Example 163).

Example 162: ¹H NMR (400 MHz, CD₃OD) δ ppm 8.48 (s, 1H), 8.21 (d, J=3.7 Hz, 2H), 7.34-7.26 (m, 1H), 7.17 (d, J=2.6 Hz, 1H), 7.07 (dt, J=8.6, 1.8 Hz, 1H), 6.95-6.61 (m, 2H), 6.07 (td, J=55.1, 3.9 Hz, 1H), 5.68 (s, 2H), 3.76-3.61 (m, 1H), 3.22 (d, J=11.4 Hz, 1H), 3.17-3.08 (m, 1H), 3.04 (d, J=11.4 Hz, 1H), 2.93-2.81 (m, 1H), 2.02 (dd, J=13.9, 8.9 Hz, 1H), 1.91-1.75 (m, 2H), 1.70 (d, J=12.7 Hz, 1H). LC-MS: [M+H]+=560.9, 562.0.

Example 163: ¹H NMR (400 MHz, CD₃OD) δ ppm 8.55 (s, 1H), 8.30 (d, J=14.6 Hz, 2H), 7.34 (d, J=8.6 Hz, 1H), 7.20 (d, J=2.6 Hz, 1H), 7.10 (dd, J=8.6, 2.6 Hz, 1H), 7.01 (s, 1H), 6.85 (t, J=55.3 Hz, 1H), 6.19 (td, J=53.9, 2.6 Hz, 1H), 5.68 (d, J=3.3 Hz, 2H), 4.20 (s, 1H), 3.50-3.34 (m, 2H), 3.19-2.98 (m, 2H), 2.02 (d, J=42.5 Hz, 4H). LC-MS: [M+H]+=560.9, 562.0.

Examples 164-167 were prepared from Intermediate B and corresponding intermediates following procedures analogous to the preparation of Examples 162 and 163.

| Example No. | | Intermediate | LC-MS and/or ¹H NMR |
|---|---|---|---|
| 164 | [structure] or | [structure 164-2] | ¹H NMR (400 MHz, CD₃OD) δ ppm 8.46 (s, 1H), 8.23 (d, J = 6.6 Hz, 2H), 7.56-7.37 (m, 2H), 7.32 (s, 1H), 6.05 (td, J = 55.1, 3.9 Hz, 1H), 5.64 (d, J = 2.0 Hz, 2H), 3.97 (d, J = 1.1 Hz, 3H), 3.66 (ddd, J = 16.7, 8.5, 3.6 Hz, 1H), 3.20 (d, J = 11.4 Hz, 1H), 3.09-2.89 (m, 2H), 2.82 (td, J = 11.1, 2.7 Hz, 1H), 2.10-1.86 (m, 1H), 1.85-1.58 (m, 3H). LC-MS: [M + H]+ = 547.2, 548.2 |

| Example No. | Intermediate | LC-MS and/or ¹H NMR |
|---|---|---|
| 165 | | ¹H NMR (400 MHz, CD₃OD) δ ppm 8.48 (s, 1H), 8.23 (d, J = 11.8 Hz, 2H), 7.41 (d, J = 9.3 Hz, 2H), 7.22 (s, 1H), 6.03 (td, J = 55.5, 4.5 Hz, 1H), 5.64 (s, 2H), 3.97 (s, 4H), 3.22 (d, J = 11.1 Hz, 1H), 3.05-2.92 (m, 3H), 1.84 (d, J = 22.8 Hz, 3H), 1.63 (s, 1H). LC-MS: [M + H]+ = 547.2, 548.2 |
| 166 | 166-2 | ¹H NMR (400 MHz, CD₃OD) δ ppm 8.64 (d, J = 5.5 Hz, 1H), 8.53 (s, 1H), 8.21 (d, J = 11.1 Hz, 2H), 7.75 (ddd, J = 12.1, 7.8, 2.2 Hz, 1H), 7.67-7.48 (m, 2H), 7.38-7.17 (m, 2H), 5.70-5.47 (m, 2H), 3.62 (d, J = 11.3 Hz, 1H), 3.14 (d, J = 11.3 Hz, 2H), 3.01 (t, J = 10.1 Hz, 1H), 2.68 (s, 3H), 2.35-1.97 (m, 2H), 1.89-1.68 (m, 2H). LC-MS: [M + H]+ = 579.2, 580.2 |
| 167 | | ¹H NMR (400 MHz, CD₃OD) δ ppm 8.42 (s, 1H), 8.18 (d, J = 3.0 Hz, 2H), 7.51-7.00 (m, 3H), 6.70 (s, 1H), 6.08 (td, J = 55.0, 3.8 Hz, 1H), 5.68 (s, 2H), 3.85 (s, 3H), 3.79-3.53 (m, 1H), 3.28-3.03 (m, 3H), 2.88 (t, J = 11.1 Hz, 1H), 2.07 (d, J = 12.0 Hz, 1H), 1.94-1.59 (m, 3H). LC-MS: [M + H]+ = 579.2, 580.2. |

Examples 168-176 were prepared from corresponding intermediates following procedures analogous to the preparation of Example 168 and Example 169.

| Example No. | | Intermediate | LC-MS and/or ¹H NMR |
|---|---|---|---|
| 168 | 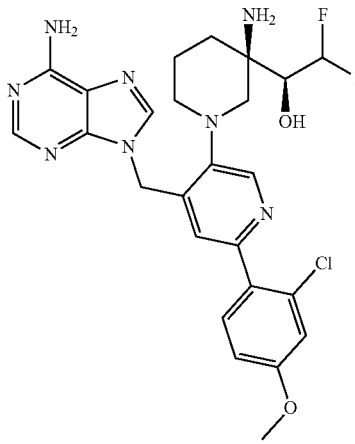 or | 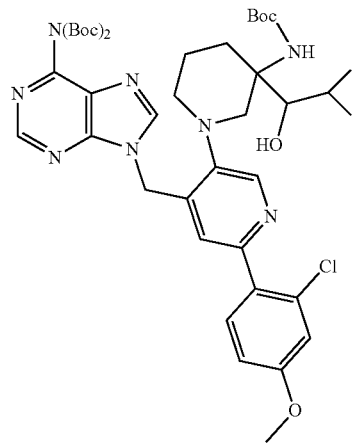 168-3 | ¹H NMR (400 MHz, CD₃OD) δ 8.54 (s, 1H), 8.29 (d, J = 13.7 Hz, 2H), 7.34 (d, J = 8.6 Hz, 1H), 7.20 (d, J = 2.6 Hz, 1H), 7.10 (dd, J = 8.6, 2.6 Hz, 1H), 7.02 (s, 1H), 6.92 (d, J = 55.4 Hz, 1H), 6.34-6.01 (m, 1H), 5.67 (d, J = 2.2 Hz, 2H), 4.19 (s, 1H), 3.85 (s, 3H), 3.49-3.37 (m, 2H), 3.16-3.02 (m, 2H), 2.02 (d, J = 43.7 Hz, 4H). LC-MS: [M + H]⁺ = 545.2, 546.2. |
| 169 | 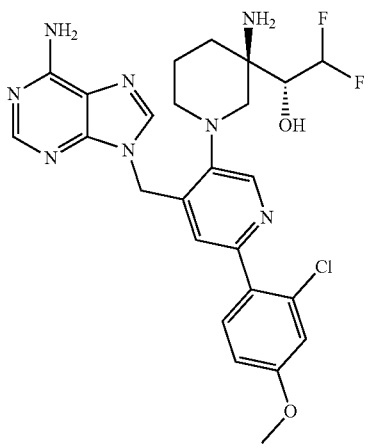 [SMILES: COc1ccc(-c2cc(Cn3cnc4c(N)ncnc43)c(N3CCC[C@](N)([C@@H](O)C(F)F)C3)cn2)c(Cl)c1] | | ¹H NMR (400 MHz, CD₃OD) δ 8.44 (s, 1H), 8.20 (d, J = 11.9 Hz, 2H), 7.38 (d, J = 8.6 Hz, 1H), 6.98-6.87 (m, 3H), 6.08 (td, J = 55.0, 3.9 Hz, 1H), 5.69 (s, 2H), 3.80 (s, 3H), 3.69 (d, J = 14.0 Hz, 1H), 3.23 (d, J = 11.5 Hz, 1H), 3.18-3.11 (m, 1H), 3.05 (d, J = 11.5 Hz, 1H), 2.88 (t, J = 11.0 Hz, 1H), 2.03 (dd, J = 24.0, 9.4 Hz, 1H), 1.84 (q, J = 13.7 Hz, 2H), 1.72 (d, J = 14.5 Hz, 1H). [M + H]⁺ = 545.2, 546.2. |
| 170 | 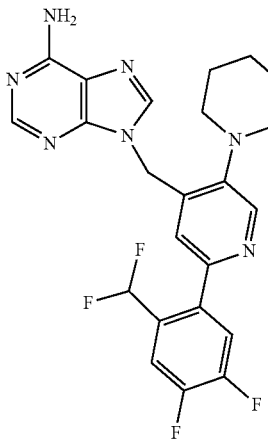 or | 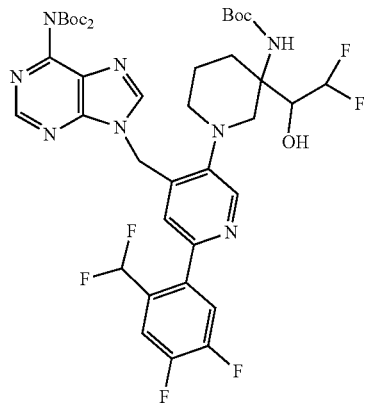 170-4 | ¹H NMR (400 MHz, CD₃OD): δ 8.53 (s, 1H), 8.22 (s. 1H), 8.21 (s, 1H), 7.62-7.57 (m, 1H), 7.39-7.35 (m. 1H), 6.95-6.68 (m, 2H), 6.21-5.93 (m, 1H), 5.68 (s, 2H), 3.71 (m, 1H), 3.27-3.24 (m, 2H), 3.10-3.07 (m, 1H), 2.92-2.87 (m, 1H), 2.05-2.00 (m, 1H), 1.89-1.72 (m, 3H). LC-MS: [M + H]⁺ = 567.2. |

| Example No. | | Intermediate | LC-MS and/or ¹H NMR |
|---|---|---|---|
| 171 | 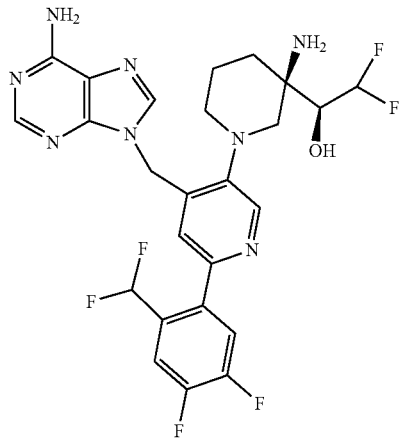 [SMILES: Nc1ncnc2c1ncn2Cc1cc(-c2cc(F)c(F)cc2C(F)F)ncc1N1CCC[C@](N)([C@H](O)C(F)F)C1] | | ¹H NMR (400 MHz, CD₃OD): δ 8.54 (s, 1H), 8.23 (s, 1H), 8.20 (s, 1H), 7.61-7.57 (m, 1H), 7.38-7.34 (m, 1H), 6.94-6.66 (m, 2H), 5.68 (s, 2H), 4.10-4.01 (m, 1H), 3.27 (m, 1H), 3.07-3.02 (m, 3H), 1.93-1.71 (m, 4H). LC-MS: [M + H]⁺ = 567.2. |
| 172 | 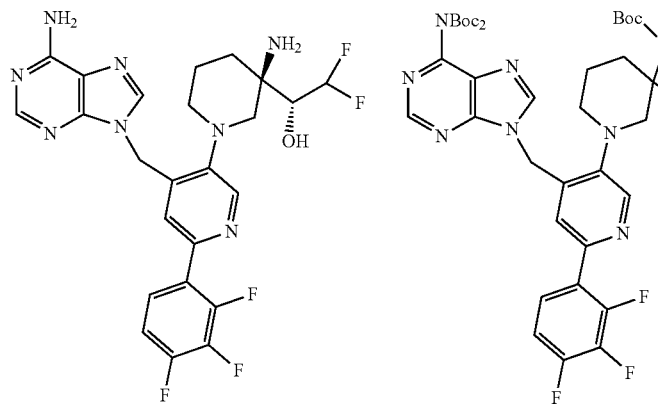 | | ¹H NMR (400 MHz, CD₃OD) δ 8.54 (s, 1H), 8.25 (s. 1H), 8.23 (s, 1H), 7.62-7.56 (m, 1H), 7.25-7.14 (m, 1H), 7.13 (d, J = 1.3 Hz, 1H), 6.26-5.92 (m, 1H), 5.70 (s, 2H), 3.79-3.66 (m, 1H), 3.30-3.23 (m, 1H), 3.20-3.04 (m, 2H), 2.96-2.85 (m, 1H), 2.15-1.99 (m, 1H), 1.94-1.78 (m, 2H), 1.76-1.68 (m, 1H). LC-MS: [M + H]⁺ = 535.4. |
| | | 172-4 | |
| 173 | 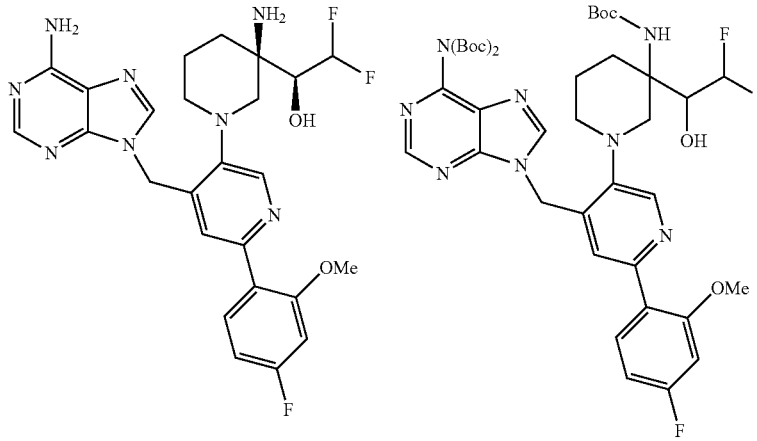 | | ¹H NMR (400 MHz, DMSO-d6) δ ppm 8.44 (s, 1H), 8.26 (s, 1H), 8.14 (s, 1H), 7.77 (dd, J = 8.7, 7.2 Hz, 1H), 7.34 (s, 2H), 6.95 (s, 1H), 6.89 (dd, J = 11.4, 2.5 Hz, 1H), 6.81 (td, J = 8.4, 2.5 Hz, 1H), 6.19 (td, J = 55.8, 4.0 Hz, 1H), 5.74 (s, 1H), 5.54 (d, J = 2.9 Hz, 2H), 3.79 (s, 1H), 3.45 (s, 3H), 3.17-2.98 (m, 2H), 2.92 (d, J = 8.5 Hz, 1H), 2.75 (d, J = 11.3 Hz, 1H), 2.05-1.62 (m, 5H), 1.47 (d, J = 5.5 Hz, 1H). LC-MS: [M + H]⁺ = 529.0, 530.0. |
| or | | 173-3 | |

| Example No. | Intermediate | LC-MS and/or ¹H NMR |
|---|---|---|
| 174 | | ¹H NMR (400 MHz, DMSO-d6) δ ppm 8.43 (s, 1H), 8.26 (s, 1H), 8.14 (s, 1H), 7.77 (dd, J = 8.6, 7.2 Hz, 1H), 7.34 (s, 2H), 6.98 (s, 1H), 6.89 (dd, J = 11.5, 2.5 Hz, 1H), 6.81 (td, J = 8.4, 2.5 Hz, 1H), 6.20 (td, J = 55.4, 3.1 Hz, 1H), 5.64 (d, J = 4.7 Hz, 1H), 5.56 (s, 2H), 3.53 (d, J = 15.7 Hz, 1H), 3.46 (s, 3H), 3.06 (t, J = 11.1 Hz, 2H), 2.95-2.71 (m, 2H), 1.99 (s, 3H), 1.68 (dd, J = 13.1, 8.3 Hz, 2H), 1.53 (d, J = 12.6 Hz, 1H). LC-MS: [M + H]⁺ = 529.0, 530.0. |
| 175 | 175-3 | ¹HNMR (400 MHz, CD₃OD) δ 8.50 (s, 1H), 8.30-8.24 (m, 2H), 8.21 (s, 1H), 7.73 (t, J = 8.3 Hz, 1H), 7.69 (s, 1H), 6.21-5.89 (m, 1H), 5.68 (s, 2H), 4.07-3.90 (m, 1H), 3.29-3.23 (m, 1H), 3.12-2.92 (m, 3H), 2.00-1.88 (m, 3H), 1.72-1.58 (m, 1H) LC-MS: [M + H]⁺ = 534.2. |
| 176 | | ¹H NMR (400 MHz, CD₃OD) δ 8.50 (s, 1H), 8.33-8.25 (m, 2H), 8.24 (s, 1H), 7.82-7.70 (m, 2H), 6.24-5.92 (m, 1H), 5.70 (s, 2H), 3.78-3.64 (m, 1H), 3.26 (d, J = 11.5 Hz, 1H), 3.19-3.10 (m, 1H), 3.10-3.03 (m, 1H), 2.95-2.83 (m, 1H), 2.13-1.96 (m, 1H), 1.95-1.77 (m, 2H), 1.76-1.65 (m, 1H). LC-MS: [M + H]⁺ = 534.4. |

Example 177: 9-((5-(3-amino-3-(6-methylpyridin-2-yl)piperidin-1-yl)-2-(3,4-difluorophenyl)pyridin-4-yl)methyl)-9H-purin-6-amine

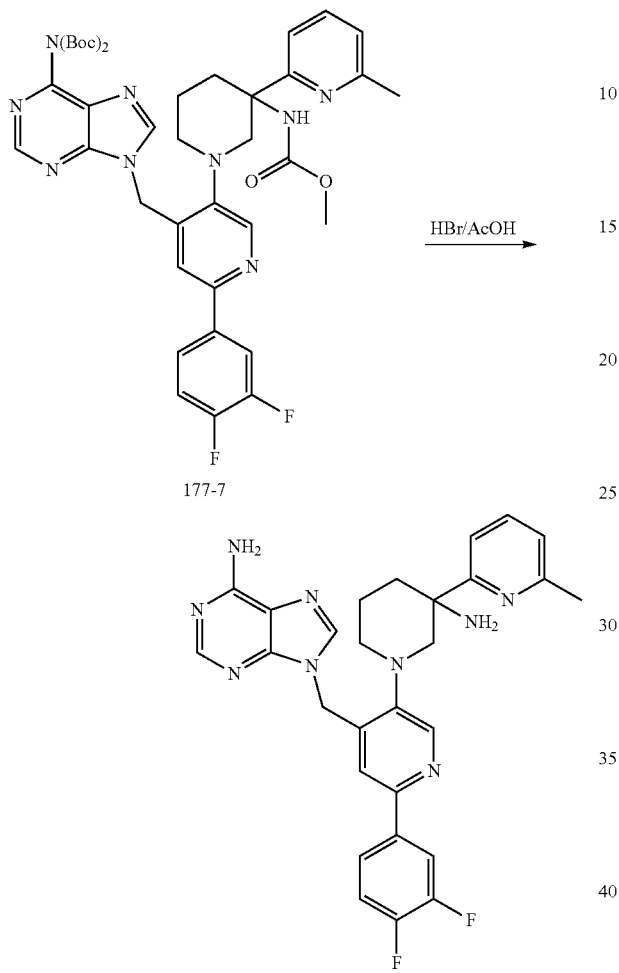

A solution of tert-butyl (tert-butoxycarbonyl)(9-((2-(3,4-difluorophenyl)-5-(3-((methoxycarbonyl)amino)-3-(6-methylpyridin-2-yl)piperidin-1-yl)pyridin-4-yl)methyl)-9H-purin-6-yl)carbamate (177-7) (700 mg, 0.89 mmol, 1.0 eq) in HBr/AcOH (33%, 10 mL) was stirred at 25-30° C. for 16 hours. The reaction was concentrated in vacuo. The residue was purified by prep-HPLC (0.1% NH$_4$HCO$_3$ as additive) to give 9-((5-(3-amino-3-(6-methylpyridin-2-yl)piperidin-1-yl)-2-(3,4-difluorophenyl)pyridin-4-yl)methyl)-9H-purin-6-amine (Example 177). NMR (400 MHz, DMSO-d$_6$) δ ppm 8.53 (s, 1H), 8.29 (s, 1H), 8.14 (s, 1H), 7.93-7.82 (m, 1H), 7.72-7.65 (m, 1H), 7.64-7.59 (n, 1H), 7.56 (d, J=7.6 Hz, 1H), 7.52-7.42 (m, 1H), 7.37 (s, 1H), 7.29 (brs, 2H), 7.12 (d, J=7.6 Hz, 1H), 5.55 (dd, J=16.0 Hz, 28.4 Hz, 2H), 3.44 (d, J=11.2 Hz, 1H), 3.17-3.08 (n, 1H), 3.06-3.01 (m, 11H), 3.00-2.90 (m, 1H), 2.47 (s, 3H), 2.24-2.14 (m, 1H), 2.13-1.99 (m, 1H), 1.77-1.65 (l, 1H). LC-MS: [M+H]$^+$=528.3.

Examples 178-284 were prepared following procedures analogous to the preparation of Example 177 and corresponding intermediates.

| Example # | Structure | ¹H NMR & LC-MS |
|---|---|---|
| 178 | 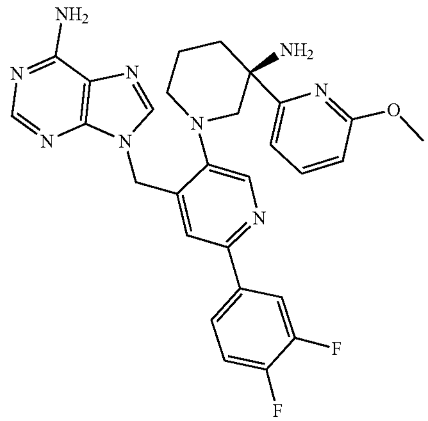 [SMILES: COc1cccc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.52 (s, 1H), 8.23 (s, 1H), 8.16 (s, 1H), 7.74 (ddd, J = 12.1, 7.8, 2.2 Hz, 1H), 7.68 (dd, J = 8.3, 7.4 Hz, 1H), 7.53 (ddd, J = 10.2, 5.0, 2.9 Hz, 1H), 7.34-7.24 (m, 2H), 7.20 (d, J = 7.4 Hz, 1H), 6.67 (d, J = 8.2 Hz, 1H), 5.69-5.53 (m, 2H), 3.93 (s, 3H), 3.54 (d, J = 11.4 Hz, 1H), 3.23-3.11 (m, 2H), 2.97 (t, J = 10.2 Hz, 1H), 2.27 (t, J = 11.2 Hz, 1H), 2.16-2.01 (m, 1H), 1.97-1.80 (m, 2H). LC-MS: [M + H]⁺ = 544.3, 545.3 |
| 179 | 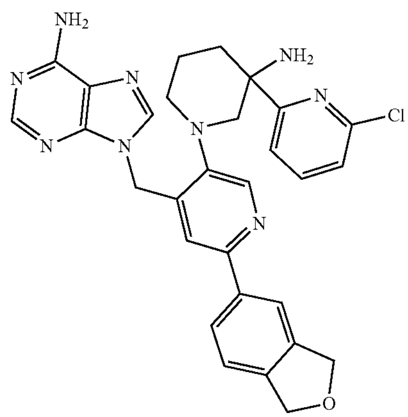 [SMILES: Nc1ncnc2c1ncn2Cc1cc(-c2ccc3c(c2)COC3)ncc1N1CCCC(N)(c2cccc(Cl)n2)C1] | ¹H NMR (400 MHz, CD₃OD) δ ppm 8.52 (s, 1H), 8.20 (d, J = 14.3 Hz, 2H), 7.82 (t, J = 7.8 Hz, 1H), 7.70-7.57 (m, 3H), 7.31 (t, J = 7.9 Hz, 2H), 7.24 (s, 1H), 5.74-5.54 (m, 2H), 5.07 (s, 4H), 3.61 (d, J = 11.5 Hz, 1H), 3.20-3.10 (m, 2H), 3.01 (t, J = 9.7 Hz, 1H), 2.28 (s, 1H), 2.15-1.99 (m, 1H), 1.86 (dq, J = 9.5, 4.8 Hz, 2H). LC-MS: [M + H]⁺ = 514.2, 516.1. |
| 180 | 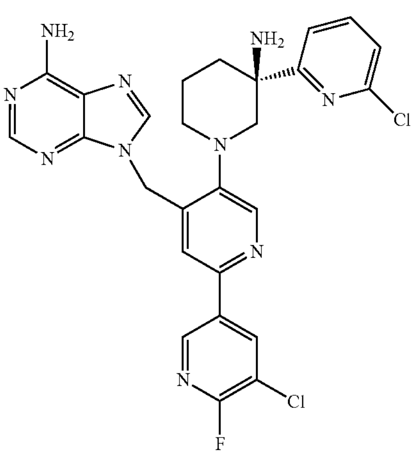 [SMILES: Nc1ncnc2c1ncn2Cc1cc(-c2cnc(F)c(Cl)c2)ncc1N1CCC[C@](N)(c2cccc(Cl)n2)C1] | ¹H NMR (400 MHz, CD₃OD) δ ppm 8.52 (s, 1H), 8.44 (s, 1H), 8.41-8.37 (m, 1H), 8.17-8.10 (m, 2H), 7.76 (s, 1H), 7.58 (d, J = 7.6 Hz, 1H), 7.42 (s, 1H), 7.29 (d, J = 8.0 Hz, 1H), 5.61-5.42 (m, 2H), 4.48 (s, 2H), 3.55 (d, J = 11.1 Hz, 1H), 3.14 (m, 1H), 3.08-2.91 (m, 2H), 2.32-1.75 (m, 4H). LC-MS: [M + H]⁺ = 565.3. |

| Example # | Structure | ¹H NMR & LC-MS |
|---|---|---|
| 181 | 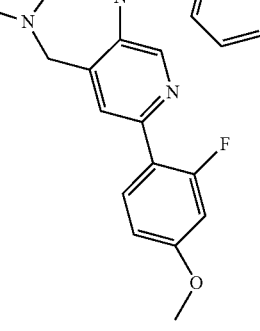 | ¹H NMR (400 MHz, CD₃OD) δ ppm 8.51 (s, 1H), 8.19 (d, J = 15.0 Hz, 2H), 7.82 (t, J = 7.8 Hz, 1H), 7.78-7.59 (m, 2H), 7.32 (d, J = 7.9 Hz, 1H), 7.02 (d, J = 1.7 Hz, 1H), 6.80 (dd, J = 8.7, 2.5 Hz, 1H), 6.68 (dd, J = 13.3, 2.5 Hz, 1H), 5.65 (t, J = 13.3 Hz, 2H), 3.79 (s, 3H), 3.66-3.54 (m, 1H), 3.18 (dt, J = 18.0, 7.7 Hz, 2H), 3.03 (dt, J = 12.4, 6.2 Hz, 1H), 2.30 (t, J = 10.0 Hz, 1H), 2.10 (d, J = 12.2 Hz, 1H), 1.88 (q, J = 6.8, 5.8 Hz, 2H). LC-MS: [M + H]⁺ = 560.3, 561.3. |
| 182 | 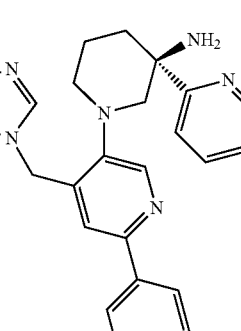 | ¹H NMR (400 MHz, CD₃OD) δ ppm 8.47 (s, 1H), 8.23 (s, 1H), 8.12 (s, 1H), 7.78-7.69 (m, 2H), 7.62 (t, J = 7.8 Hz, 1H), 7.37 (dd, J = 7.9, 0.9 Hz, 1H), 7.23 (s, 1H), 7.16-7.06 (m, 3H), 5.59 (s, 2H), 3.50 (d, J = 11.3 Hz, 1H), 3.13 (dd, J = 15.6, 11.4 Hz, 2H), 3.02-2.84 (m, 1H), 2.31-2.15 (m, 1H), 2.15-1.95 (m, 2H), 1.87 (t, J = 7.9 Hz, 2H), 1.07-0.86 (m, 4H). LC-MS: [M + H]⁺ = 536.3, 537.3. |
| 183 | 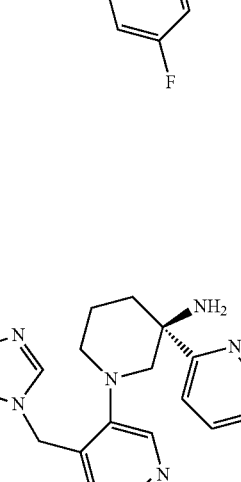 | ¹H NMR (400 MHz, CD₃OD) δ ppm 8.62-8.39 (m, 1H), 8.22 (q, J = 3.4 Hz, 1H), 8.19-8.04 (m, 1H), 7.86 (dd, J = 9.7, 5.6 Hz, 1H), 7.74 (qd, J = 7.7, 6.5, 3.8 Hz, 2H), 7.62 (q, J = 7.3, 5.7 Hz, 1H), 7.40 (dd, J = 7.5, 3.9 Hz, 1H), 7.23 (d, J = 6.1 Hz, 1H), 7.18-6.96 (m, 2H), 5.80-5.47 (m, 3H), 3.68-3.47 (m, 1H), 3.17 (d, J = 11.3 Hz, 2H), 2.97 (d, J = 11.6 Hz, 1H), 2.27 (s, 1H), 2.08 (s, 1H), 1.89 (s, 2H), 1.73-1.54 (m, 3H). LC-MS: [M + H]⁺ = 542.3, 543.3 |

| Example # | Structure | ¹H NMR & LC-MS |
|---|---|---|
| 184 | 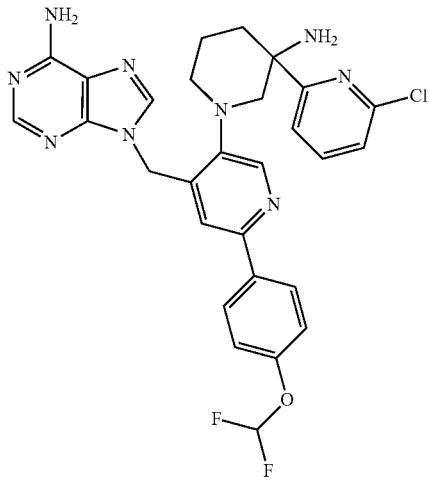 [SMILES: Nc1ncnc2c1ncn2Cc1cc(-c2ccc(OC(F)F)cc2)ncc1N1CCCC(N)(c2cccc(Cl)n2)C1] | ¹H NMR (400 MHz, CD₃OD) δ ppm 8.54 (s, 1H), 8.32-8.06 (m, 3H), 7.97 (d, J = 1.4 Hz, 1H), 7.81 (t, J = 7.8 Hz, 1H), 7.74-7.58 (m, 3H), 7.43-7.22 (m, 2H), 5.65 (q, J = 16.2 Hz, 2H), 3.90 (s, 3H), 3.61 (d, J = 11.3 Hz, 1H), 3.14 (d, J = 11.5 Hz, 2H), 3.06-2.88 (m, 1H), 2.28 (t, J = 10.6 Hz, 1H), 2.05 (dq, J = 13.6, 5.3, 4.2 Hz, 1H), 1.92-1.78 (m, 2H). LC-MS: [M + H]⁺ = 566.3, 568.3. |
| 185 | 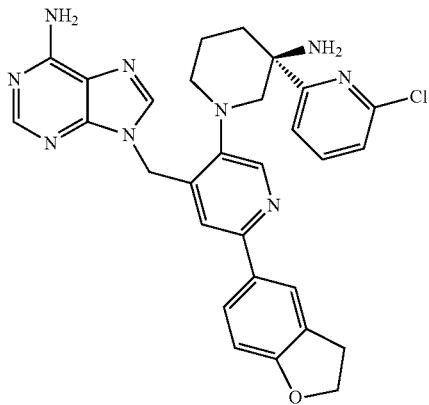 [SMILES: Nc1ncnc2c1ncn2Cc1cc(-c2ccc3c(c2)CCO3)ncc1N1CCC[C@](N)(c2cccc(Cl)n2)C1] | ¹H NMR (400 MHz, CD₃OD) δ ppm 8.45 (s, 1H), 8.20 (d, J = 25.6 Hz, 2H), 7.81 (t, J = 7.8 Hz, 1H), 7.72-7.55 (m, 2H), 7.43 (dd, J = 8.4, 2.0 Hz, 1H), 7.31 (d, J = 7.8 Hz, 1H), 7.15 (s, 1H), 6.72 (d, J = 8.3 Hz, 1H), 5.61 (q, J = 16.3 Hz, 2H), 4.55 (t, J = 8.7 Hz, 2H), 3.58 (d, J = 11.3 Hz, 1H), 3.19 (t, J = 8.7 Hz, 2H), 3.11 (d, J = 11.3 Hz, 2H), 3.03-2.92 (m, 1H), 2.26 (d, J = 9.2 Hz, 1H), 2.11-1.99 (m, 1H), 1.92-1.77 (m, 2H). LC-MS: [M + H]⁺ = 554.3, 555.2. |
| 186 | 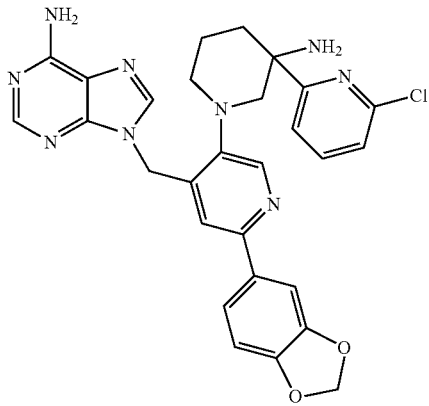 [SMILES: Nc1ncnc2c1ncn2Cc1cc(-c2ccc3c(c2)OCO3)ncc1N1CCCC(N)(c2cccc(Cl)n2)C1] | ¹H NMR (400 MHz, CD₃OD) δ ppm 8.46 (s, 1H), 8.20 (d, J = 21.9 Hz, 2H), 7.81 (t, J = 7.8 Hz, 1H), 7.64 (d, J = 7.6 Hz, 1H), 7.32 (d, J = 7.8 Hz, 1H), 7.24 (d, J = 1.8 Hz, 1H), 7.20-7.12 (m, 2H), 6.82 (d, J = 8.1 Hz, 1H), 5.96 (s, 2H), 5.61 (q, J = 16.3 Hz, 2H), 3.58 (d, J = 11.3 Hz, 1H), 3.18-3.03 (m, 2H), 3.03-2.94 (m, 1H), 2.27 (s, 1H), 2.04 (dt, J = 11.1, 5.6 Hz, 1H), 1.84 (td, J = 12.2, 11.2, 4.7 Hz, 2H). LC-MS: [M + H]⁺ = 556.3, 557.2. |

| Example # | Structure | ¹H NMR & LC-MS |
|---|---|---|
| 187 | 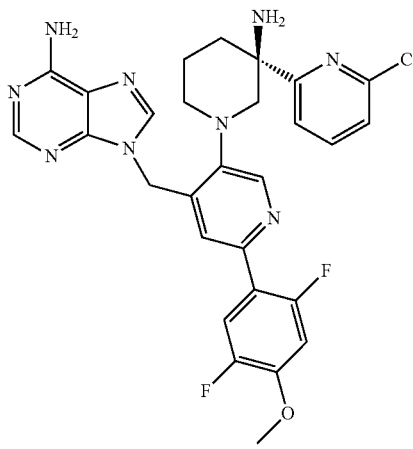 | ¹H NMR (400 MHz, CD₃OD) δ ppm 8.53 (s, 1H) 8.20 (s, 1H), 8.17 (s, 1H), 7.87-7.78 (m, 1H), 7.66 (d, J = 7.6 Hz, 1H), 7.58 (m, 1H), 7.32 (d, J = 8.0 Hz, 1H), 7.09 (s, 1H), 6.89 (m, 1H), 5.72-5.55 (m, 2H), 3.86 (s, 3H), 3.69-3.54 (m, 1H), 3.25-3.12 (m, 2H), 3.10-2.97 (m, 1H), 2.36-2.23 (m, 1H), 2.19-2.04 (m, 1H), 1.88 (m, 2H). LC-MS: [M + H]⁺ = 578.4. |
| 188 | 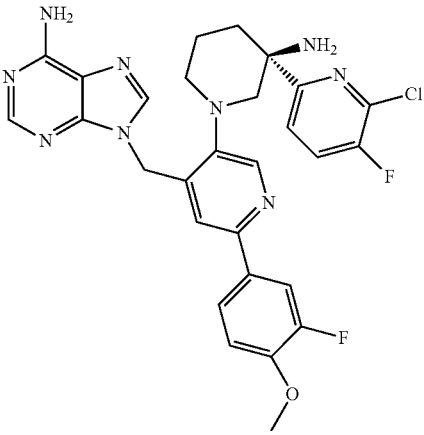 [SMILES: COc1ccc(-c2cc(Cn3cnc4c(N)ncnc43)c(N3CCC[C@](N)(c4ccc(F)c(Cl)n4)C3)cn2)cc1F] | ¹H NMR (400 MHz, CD₃OD) δ ppm 8.47 (s, 1H), 8.21 (d, J = 15.8 Hz, 2H), 7.70 (d, J = 5.7 Hz, 2H), 7.54 (dd, J = 12.7, 2.2 Hz, 1H), 7.44 (dt, J = 8.6, 1.5 Hz, 1H), 7.22 (s, 1H), 7.08 (t, J = 8.6 Hz, 1H), 5.82-5.45 (m, 2H), 3.86 (s, 3H), 3.54 (d, J = 11.4 Hz, 1H), 3.11 (dd, J = 17.2, 8.3 Hz, 2H), 3.02-2.89 (m, 1H), 2.33-2.16 (m, 1H), 2.12-1.94 (m, 1H), 1.92-1.71 (m, 2H). LC-MS: [M + H]⁺ = 578.3, 579.3 |
| 189 | 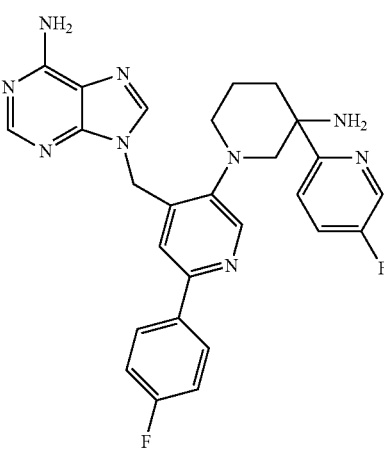 [SMILES: Nc1ncnc2c1ncn2Cc1cc(-c2ccc(F)cc2)ncc1N1CCCC(N)(c2ccc(F)cn2)C1] | ¹H NMR (400 MHz, CD₃OD) δ ppm 8.52 (s, 1H), 8.49 (s, 1H), 8.25 (s, 1H), 8.21 (s, 1H), 7.79-7.76 (m, 3H), 7.64-7.60 (m, 1H), 7.28 (s, 1H), 7.14 (t, J = 8.8 Hz, 1H), 5.70-5.61 (m, 2H), 3.56 (d, J = 11.0 Hz, 1H), 3.23-3.15 (m, 2H), 3.00 (t, J = 10 Hz, 1H), 2.33-2.21 (m, 1H), 2.16-2.05 (m, 1H), 1.95-1.85 (m, 2H). LC-MS: [M + H]⁺ = 514.3. |

| Example # | Structure | ¹H NMR & LC-MS |
|---|---|---|
| 190 | 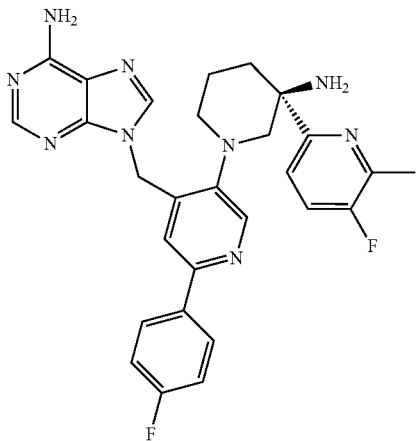 [SMILES: Cc1nc([C@@]2(N)CCCN(c3cnc(-c4ccc(F)cc4)cc3Cn3cnc4c(N)ncnc43)C2)ccc1F] | ¹H NMR (400 MHz, CD₃OD) δ ppm 8.49 (s, 1H), 8.23 (s, 1H), 8.16 (s, 1H), 7.84-7.68 (m, 2H), 7.57-7.41 (m, 2H), 7.25 (s, 1H), 7.16-7.04 (m, 2H), 5.73-5.47 (m, 2H), 3.53 (d, J = 11.4 Hz, 1H), 3.15 (d, J = 11.3 Hz, 2H), 2.97 (td, J = 11.2, 10.5, 2.9 Hz, 1H), 2.48 (d, J = 3.0 Hz, 3H), 2.36-2.19 (m, 1H), 2.06 (dtt, J = 13.8, 8.3, 4.4 Hz, 1H), 1.95-1.76 (m, 2H). LC-MS: [M + H]⁺ = 527.8, 528.8. |
| 191 | 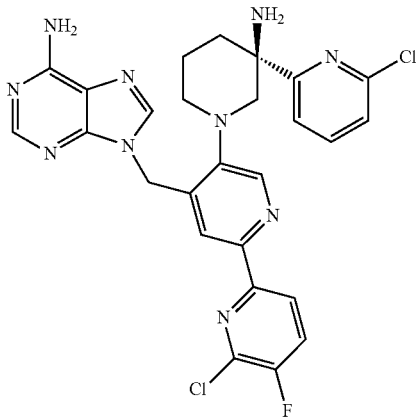 [SMILES: Nc1ncnc2c1ncn2Cc1cc(-c2ccc(F)c(Cl)n2)ncc1N1CCC[C@](N)(c2cccc(Cl)n2)C1] | ¹H NMR (400 MHz, CD₃OD) δ ppm 8.54 (s, 1H), 8.29-8.24 (m, 1H), 8.24-8.19 (m, 2H), 7.85-7.79 (m, 1H), 7.77-7.70 (m, 2H), 7.66 (d, J = 7.7 Hz, 1H), 7.33 (d, J = 7.7 Hz, 1H), 5.73-5.56 (m, 2H), 3.69-3.59 (m, 1H), 3.27-3.16 (m, 2H), 3.10-2.98 (m, 1H), 2.38-2.24 (m, 1H), 2.19-2.02 (m, 1H), 1.94-1.81 (m, 2H). LC-MS: [M + H]⁺ = 565.1. |
| 192 | 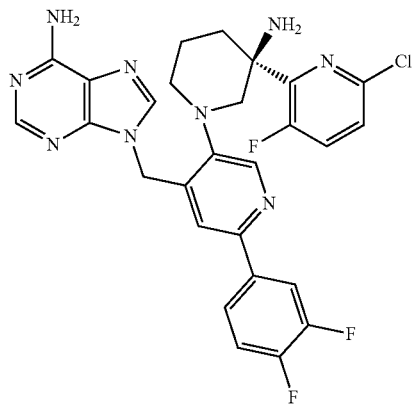 [SMILES: Nc1ncnc2c1ncn2Cc1cc(-c2ccc(F)c(F)c2)ncc1N1CCC[C@](N)(c2nc(Cl)ccc2F)C1] | ¹H NMR (400 MHz, CD₃OD) δ ppm 8.55 (s, 1H), 8.19 (d, J = 18.0 Hz, 2H), 7.74 (dd, J = 11.9, 8.1 Hz, 1H), 7.62 (t, J = 9.8 Hz, 1H), 7.57-7.49 (m, 1H), 7.44-7.35 (m, 1H), 7.29 (d, J = 16.6 Hz, 2H), 5.61 (s, 2H), 3.73 (d, J = 11.5 Hz, 1H), 3.25 (d, J = 11.6 Hz, 1H), 3.14 (d, J = 11.7 Hz, 1H), 2.99 (t, J = 10.5 Hz, 1H), 2.31 (d, J = 12.5 Hz, 1H), 2.11 (d, J = 10.7 Hz, 1H), 1.99 (d, J = 13.1 Hz, 1H), 1.87 (d, J = 12.5 Hz, 1H). LC-MS: [M + H]⁺ = 566.2, 567.2. |

| Example # | Structure | ¹H NMR & LC-MS |
|---|---|---|
| 193 | 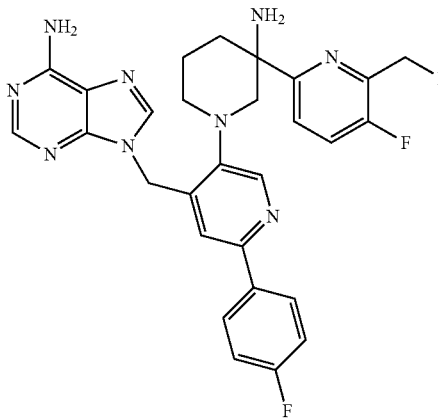 | ¹H NMR (400 MHz, CD₃OD) δ ppm 8.51 (s, 1H), 8.23 (s, 1H), 8.17 (s, 1H), 7.83-7.71 (m, 3H), 7.70-7.61 (m, 1H), 7.23 (s, 1H), 7.13 (t, J = 8.8 Hz, 2H), 5.72-5.40 (m, 4H), 3.67-3.54 (m, 1H), 3.22-3.09 (m, 2H), 3.00 (t, J = 8.8 Hz, 1H), 2.39-2.23 (m, 1H), 2.13-2.02 (m, 1H), 1.94-1.79 (m, 2H). LC-MS: [M + H]⁺ = 546.1. |
| 194 | 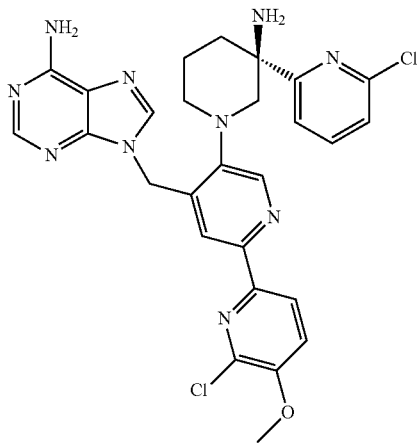 [SMILES: COc1ccc(-c2cc(Cn3cnc4c(N)ncnc43)c(N3CCC[C@](N)(c4cccc(Cl)n4)C3)cn2)nc1Cl] | ¹H NMR (400 MHz, CD₃OD) δ ppm 8.51 (s, 1H), 8.25-8.21 (m, 2H), 8.18-8.13 (d, J = 8.8 Hz, 1H), 7.85-7.78 (t, J = 8.0 Hz, 1H), 7.72 (s, 1H), 7.68-7.63 (d, J = 8.0 Hz, 1H), 7.54-7.48 (d, J = 8.0 Hz, 1H), 7.34-7.31 (d, J = 8.0 Hz, 1H), 5.71-5.59 (m, 2H), 3.94 (s, 3H), 3.67-3.57 (m, 1H), 3.22-7.15 (m, 2H), 3.09-2.99 (m, 1H), 2.35-2.25 (m, 1H), 2.15-2.04 (m, 1H), 1.94-1.83 (m, 2H). LC-MS: [M + H]⁺ = 577.3. |
| 195 | 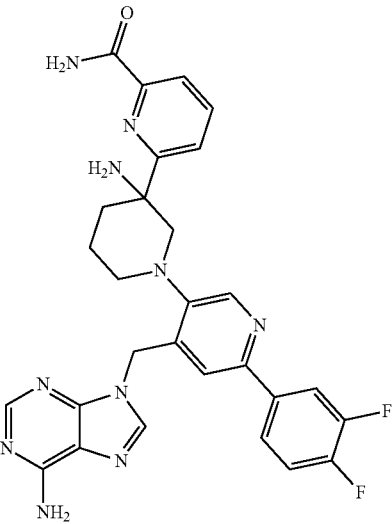 [SMILES: NC(=O)c1cccc(C2(N)CCCN(c3cnc(-c4ccc(F)c(F)c4)cc3Cn3cnc4c(N)ncnc43)C2)n1] | ¹H NMR (400 MHz, CD₃OD): δ 8.59 (s, 1H), 8.25-8.20 (m, 2H), 8.05-8.01 (m, 2H), 7.91 (d, J = 6.8 Hz, 1H), 7.79-7.74 (m, 1H), 7.57-7.54 (m, 1H), 7.32-7.27 (m, 2H), 5.70-5.56 (m, 2H), 3.68 (d, J = 11.6 Hz, 1H), 3.28-3.05 (m, 3H), 2.40-2.31 (m, 1H), 2.12-1.90 (m, 3H). LC-MS: [M + H]⁺ = 557.1 |

| Example # | Structure | ¹H NMR & LC-MS |
|---|---|---|
| 196 | 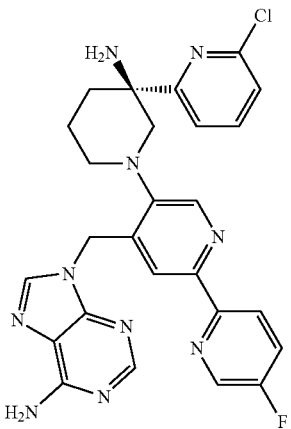 [SMILES: Nc1ncnc2c1ncn2Cc1cc(-c2ccc(F)cn2)ncc1N1CCC[C@](N)(c2cccc(Cl)n2)C1] | ¹H NMR (400 MHz, CD₃OD) δ ppm 8.56 (s, 1H), 8.40 (d, J = 2.3 Hz, 1H), 8.31 (dd, J = 4.6, 9.0 Hz, 1H), 8.23 (d, J = 5.5 Hz, 2H), 7.89-7.82 (m, 1H), 7.76 (s, 1H), 7.72-7.60 (m, 2H), 7.35 (d, J = 7.9 Hz, 1H), 5.76-5.59 (m, 2H), 3.66 (d, J = 11.0 Hz, 1H), 3.29-3.19 (m, 2H), 3.12-3.03 (m, 1H), 2.40-2.25 (m, 1H), 2.20-2.05 (m, 1H), 1.93-1.90 (m). LC-MS: [M + H]⁺ = 531.3. |
| 197 | 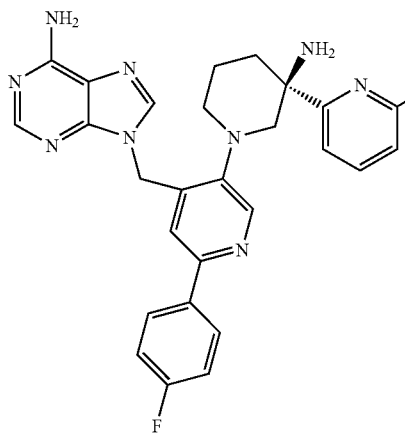 | ¹H NMR (400 MHz, CD₃OD) δ ppm 8.51 (s, 1H), 8.22 (s, 1H), 8.15 (s, 1H), 7.95 (t, J = 7.9 Hz, 1H), 7.84-7.67 (m, 3H), 7.59 (dd, J = 7.8, 0.9 Hz, 1H), 7.22 (s, 1H), 7.18-7.02 (m, 2H), 5.79-5.43 (m, 2H), 3.60 (d, J = 11.3 Hz, 1H), 3.24-3.09 (m, 2H), 3.04-2.90 (m, 1H), 2.35-2.24 (m, 1H), 2.11 (t, J = 5.0 Hz, 1H), 2.01 (t, J = 18.7 Hz, 3H), 1.94-1.82 (m, 2H). LC-MS: [M + H]⁺ = 560.3, 561.3. |
| 198 | 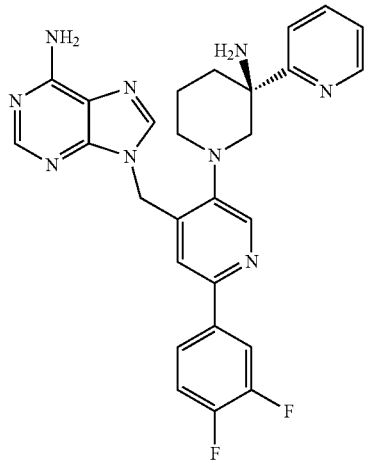 [SMILES: Nc1ncnc2c1ncn2Cc1cc(-c2ccc(F)c(F)c2)ncc1N1CCC[C@](N)(c2ccccn2)C1] | ¹H NMR (400 MHz, DMSO-d₆) δ ppm 8.50-8.56 (2H, m), 8.28 (1H, s), 8.13 (1H, s), 7.85-7.95 (1H, m), 7.78 (2H, d, J = 3.6 Hz), 7.55-7.65 (1H, m), 7.40-7.50 (1H, m), 7.36 (1H, s), 7.20-7.35 (3H, m), 5.55 (2H, dd, J = 23.2, 16.4 Hz), 3.45 (1H, d, J = 11.2 Hz), 3.15-3.07 (1H, m), 3.04 (1H, d, J = 11.2 Hz), 2.93 (1H, t, J = 10.8 Hz), 2.00-2.25 (2H, m), 1.60-1.80 (2H, m), 1.10-1.30 (2H, m). LC-MS: [M + H]⁺ = 514.2. |

| Example # | Structure | ¹H NMR & LC-MS |
|---|---|---|
| 199 | 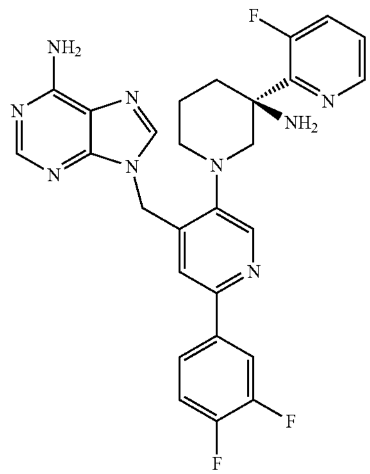 [SMILES: Nc1ncnc2c1ncn2Cc1cc(-c2ccc(F)c(F)c2)ncc1N1CCC[C@](N)(c2ncccc2F)C1] | ¹H NMR (400 MHz, DMSO-d₆) δ ppm 8.57 (s, 1H), 8.41-8.38 (m, 1H), 8.23 (s, 1H), 8.12 (s, 1H), 7.93-7.85 (m, 1H), 7.72-7.60 (m, 2H), 7.53-7.45 (m, 1H), 7.43-7.38 (m, 1H), 7.37 (s, 1H), 7.28 (s, 2H), 5.55-5.44 (m, 2H), 3.57 (d, J = 11.6 Hz, 1H), 3.25 (d, J = 11.6 Hz, 1H), 3.13-3.05 (m, 1H), 2.94 (t, J = 8.8 Hz, 1H), 2.20-2.07 (m, 2H), 1.94 (brs, 1H), 1.81-1.74 (m, 1H). LC-MS: [M + H]⁺ = 532.1. |
| 200 | 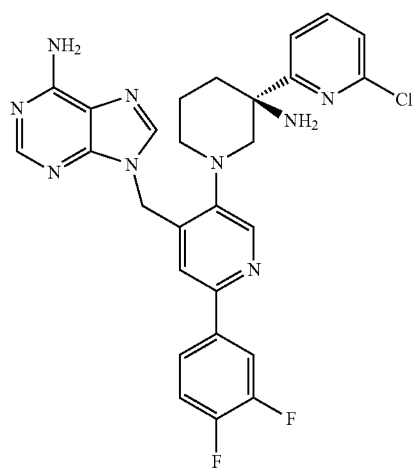 [SMILES: Nc1ncnc2c1ncn2Cc1cc(-c2ccc(F)c(F)c2)ncc1N1CCC[C@](N)(c2cccc(Cl)n2)C1] | ¹H NMR (400 MHz, CD₃OD) δ ppm 8.54 (s, 1H), 8.24 (s, 1H), 8.19 (s, 1H), 7.83 (t, J = 7.6 Hz, 1H), 7.77-7.72 (m, 1H), 7.66 (d, J = 8.0 Hz, 1H), 7.57-7.50 (m, 1H), 7.35-7.24 (m, 3H), 5.67 (d, J = 16.0 Hz, 1H), 5.60 (d, J = 16.0 Hz, 1H), 3.61 (d, J = 11.2 Hz, 1H), 3.19-3.11 (m, 2H), 3.01 (t, J = 9.2 Hz, 1H), 2.34-2.24 (m, 1H), 2.14-2.02 (m, 1H), 1.94-1.82 (m, 2H). LC-MS: [M + H]⁺ = 548.3. |
| 201 | 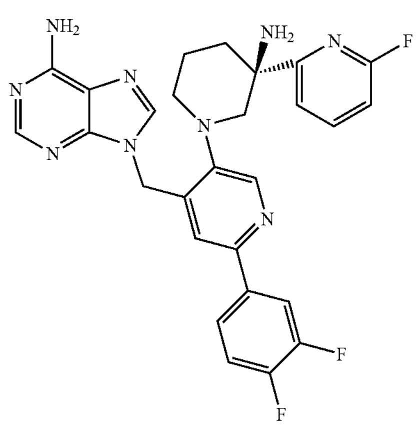 [SMILES: Nc1ncnc2c1ncn2Cc1cc(-c2ccc(F)c(F)c2)ncc1N1CCC[C@](N)(c2cccc(F)n2)C1] | ¹H NMR (400 MHz, CD₃OD) δ ppm 8.55 (s, 1H), 8.22 (d, J = 19.8 Hz, 2H), 7.96 (q, J = 8.1 Hz, 1H), 7.75 (ddd, J = 12.1, 7.8, 2.3 Hz, 1H), 7.64-7.49 (m, 2H), 7.41-7.19 (m, 2H), 6.95 (dd, J = 8.1, 2.9 Hz, 1H), 5.86-5.56 (m, 2H), 3.57 (d, J = 11.3 Hz, 1H), 3.16 (dd, J = 14.3, 10.2 Hz, 2H), 3.06-2.93 (m, 1H), 2.27 (dq, J = 14.8, 6.5, 5.3 Hz, 1H), 2.09 (tdd, J = 13.4, 8.4, 4.1 Hz, 1H), 1.95-1.68 (m, 2H). LC-MS: [M + H]⁺ = 532.0, 533.0. |

| Example # | Structure | ¹H NMR & LC-MS |
|---|---|---|
| 202 | 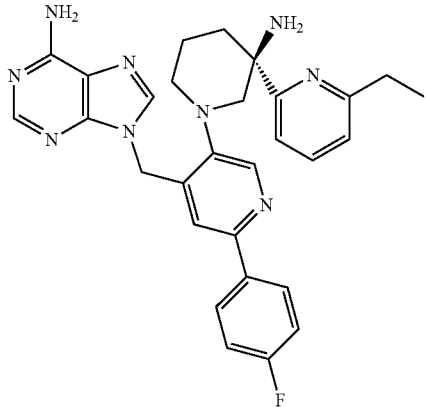 [SMILES: CCc1cccc([C@@]2(N)CCCN(c3cnc(-c4ccc(F)cc4)cc3Cn3cnc4c(N)ncnc43)C2)n1] | ¹H NMR (400 MHz, CD₃OD) δ ppm 8.52 (d, J = 4.6 Hz, 1H), 8.22 (d, J = 34.2 Hz, 2H), 7.78 (ddd, J = 13.6, 7.9, 5.0 Hz, 3H), 7.50 (d, J = 7.9 Hz, 1H), 7.31 (s, 1H), 7.16 (td, J = 9.6, 8.7, 4.3 Hz, 3H), 5.63 (t, J = 10.3 Hz, 2H), 3.59 (d, J = 11.6 Hz, 1H), 3.24-3.15 (m, 2H), 3.03 (dt, J = 11.3, 5.9 Hz, 1H), 2.84 (q, J = 7.6 Hz, 2H), 2.32 (t, J = 11.3 Hz, 1H), 2.17-2.02 (m, 1H), 2.01-1.82 (m, 2H), 1.30 (q, J = 6.2, 4.7 Hz, 3H). LC-MS: [M + H]⁺ = 524.0, 525.0. |
| 203 | 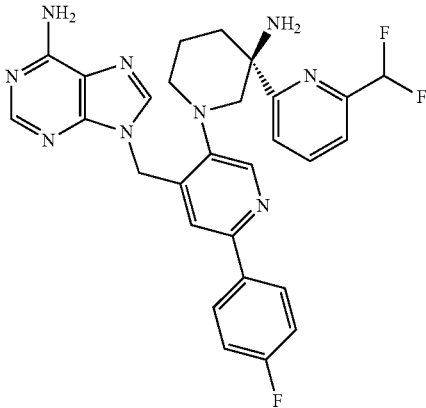 [SMILES: Nc1ncnc2c1ncn2Cc1cc(-c2ccc(F)cc2)ncc1N1CCC[C@](N)(c2cccc(C(F)F)n2)C1] | ¹H NMR (400 MHz, CD₃OD) δ ppm 8.53 (s, 1H), 8.30-8.20 (m, 1H), 8.17 (d, J = 7.5 Hz, 1H), 8.00 (q, J = 7.2, 6.5 Hz, 1H), 7.86 (d, J = 8.0 Hz, 1H), 7.77 (ddd, J = 9.2, 5.7, 2.9 Hz, 2H), 7.60 (d, J = 7.7 Hz, 1H), 7.23 (d, J = 7.5 Hz, 1H), 7.14 (td, J = 8.9, 4.5 Hz, 2H), 6.72 (td, J = 55.4, 7.7 Hz, 1H), 5.77-5.49 (m, 2H), 3.65 (d, J = 11.4 Hz, 1H), 3.19 (t, J = 9.9 Hz, 2H), 3.09-2.91 (m, 1H), 2.33 (q, J = 9.5, 6.1 Hz, 1H), 2.12 (dp, J = 14.5, 4.3 Hz, 1H), 1.99-1.80 (m, 2H). LC-MS: [M + H]⁺ = 546.0, 547.0. |
| 204 | 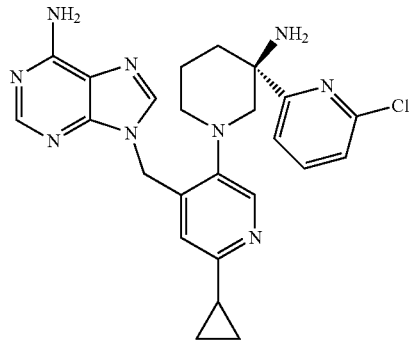 [SMILES: Nc1ncnc2c1ncn2Cc1cc(C2CC2)ncc1N1CCC[C@](N)(c2cccc(Cl)n2)C1] | ¹H NMR (CD₃OD) δ: 8.24 (d, J = 18.9 Hz, 2H), 8.12 (s, 1H), 7.80 (t, J = 7.8 Hz, 1H), 7.63 (d, J = 7.8 Hz, 1H), 7.31 (d, J = 7.9 Hz, 1H), 6.61 (s, 1H), 5.54 (q, J = 16.5 Hz, 2H), 3.51 (d, J = 11.4 Hz, 1H), 3.04 (d, J = 11.2 Hz, 2H), 2.92 (t, J = 10.5 Hz, 1H), 2.25 (s, 1H), 2.00 (d, J = 10.4 Hz, 1H), 1.93-1.72 (m, 3H), 0.89 (dt, J = 8.3, 3.2 Hz, 2H), 0.84-0.67 (m, 2H) LC-MS [M + H]⁺ = 476.3 |
| 205 | 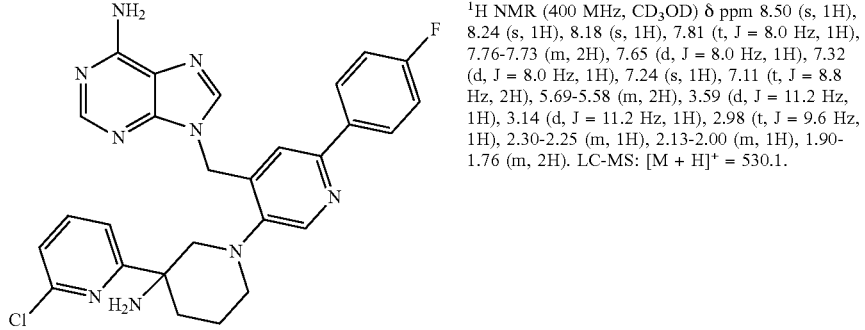 | ¹H NMR (400 MHz, CD₃OD) δ ppm 8.50 (s, 1H), 8.24 (s, 1H), 8.18 (s, 1H), 7.81 (t, J = 8.0 Hz, 1H), 7.76-7.73 (m, 2H), 7.65 (d, J = 8.0 Hz, 1H), 7.32 (d, J = 8.0 Hz, 1H), 7.24 (s, 1H), 7.11 (t, J = 8.8 Hz, 2H), 5.69-5.58 (m, 2H), 3.59 (d, J = 11.2 Hz, 1H), 3.14 (d, J = 11.2 Hz, 1H), 2.98 (t, J = 9.6 Hz, 1H), 2.30-2.25 (m, 1H), 2.13-2.00 (m, 1H), 1.90-1.76 (m, 2H). LC-MS: [M + H]⁺ = 530.1. |

| Example # | Structure | ¹H NMR & LC-MS |
|---|---|---|
| 206 | 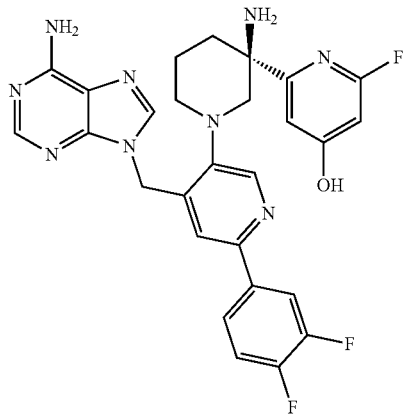 [SMILES: Nc1ncnc2c1ncn2Cc1cc(-c2ccc(F)c(F)c2)ncc1N1CCC[C@](N)(c2cc(O)cc(F)n2)C1] | ¹H NMR (400 MHz, CD₃OD): ☐ 8.57 (s, 1H), 8.26 (d, J = 3.2 Hz, 2H), 7.83-7.73 (m, 1H), 7.67-7.52 (m, 1H), 7.45 (s, 1H), 7.35-7.21 (m, 1H), 6.67 (s, 1H), 6.00 (s, 1H), 5.68-5.56 (m, 2H), 3.54-3.44 (m, 1H), 3.14-2.97 (m, 2H), 2.28-2.15 (m, 1H), 2.10-1.95 (m, 2H), 1.89-1.85 (m, 2H). LC-MS: [M + H]⁺ = 548.3. |
| 207 | 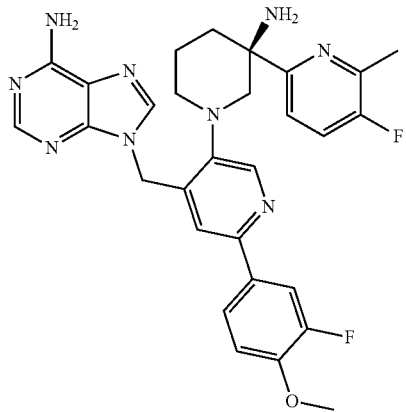 [SMILES: COc1ccc(-c2cc(Cn3cnc4c(N)ncnc43)c(N3CCC[C@](N)(c4ccc(F)c(C)n4)C3)cn2)cc1F] | ¹H NMR (400 MHz, CD₃OD) δ ppm 8.45 (s, 1H), 8.23 (d, J = 6.2 Hz, 1H), 8.18 (s, 1H), 7.59-7.40 (m, 4H), 7.23 (s, 1H), 7.06 (t, J = 8.6 Hz, 1H), 5.68-5.49 (m, 2H), 3.86 (s, 3H), 3.49 (d, J = 11.3 Hz, 1H), 3.11 (dd, J = 11.6, 5.1 Hz, 2H), 2.92 (td, J = 15.9, 14.2, 8.1 Hz, 1H), 2.47 (d, J = 2.9 Hz, 3H), 2.21 (q, J = 8.5, 5.8 Hz, 1H), 2.04 (qd, J = 10.4, 9.8, 5.0 Hz, 1H), 1.92-1.74 (m, 2H). LC-MS: [M + H]⁺ = 558.4. |
| 208 | 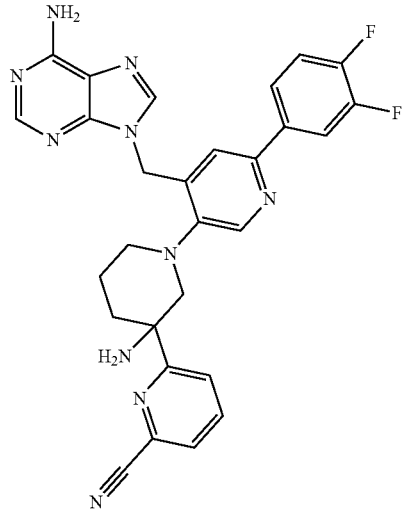 [SMILES: N#Cc1cccc(C2(N)CCCN(c3cnc(-c4ccc(F)c(F)c4)cc3Cn3cnc4c(N)ncnc43)C2)n1] | ¹H NMR (400 MHz, CD₃OD) δ ppm 8.55 (s, 1H), 8.23 (d, J = 9.6 Hz, 2H), 8.03 (d, J = 3.6 Hz, 2H), 7.77-7.72 (m, 2H), 7.53 (s, 1H), 7.30-7.25 (m, 2H), 5.69-5.59 (m, 2H), 3.66 (d, J = 11.2 Hz, 1H), 3.21-3.13 (m, 2H), 3.03 (t, J = 10.0 Hz, 1H), 2.35-2.29 (m, 1H), 2.18-2.05 (m, 1H), 1.91-1.83 (m, 2H). LC-MS: 561.1 [M + Na]+. |

| Example # | Structure | ¹H NMR & LC-MS |
|---|---|---|
| 209 | 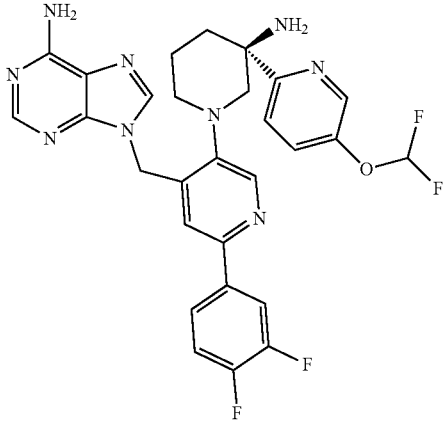 [SMILES: Nc1ncnc2c1ncn2Cc1cc(-c2ccc(F)c(F)c2)ncc1N1CCC[C@](N)(c2ccc(OC(F)F)cn2)C1] | ¹H NMR (400 MHz, CD$_3$OD) δ ppm 8.53 (s, 1H), 8.46 (d, J = 2.7 Hz, 1H), 8.22 (d, J = 9.8 Hz, 2H), 7.84-7.71 (m, 2H), 7.65 (dd, J = 8.7, 2.8 Hz, 1H), 7.54 (ddd, J = 8.0, 4.0, 1.9 Hz, 1H), 7.39-7.19 (m, 2H), 6.92 (t, J = 73.1 Hz, 1H), 5.63 (s, 2H), 3.56 (d, J = 11.4 Hz, 1H), 3.18 (dd, J = 25.0, 11.9 Hz, 2H), 3.06-2.92 (m, 1H), 2.25 (q, J = 13.9, 12.5 Hz, 1H), 2.08 (q, J = 12.2 Hz, 1H), 2.01-1.82 (m, 2H). LC-MS: [M + H]$^+$ = 580.3, 581.3. |
| 210 | 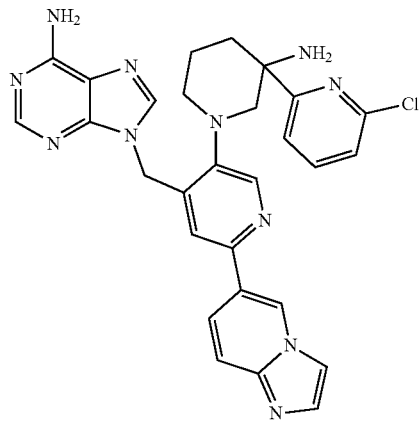 [SMILES: Nc1ncnc2c1ncn2Cc1cc(-c2ccc3nccn3c2)ncc1N1CCCC(N)(c2cccc(Cl)n2)C1] | ¹H NMR (400 MHz, CD$_3$OD) δ ppm 8.90 (d, J = 1.5 Hz, 1H), 8.54 (s, 1H), 8.21 (d, J = 15.3 Hz, 2H), 7.94-7.76 (m, 2H), 7.75-7.60 (m, 2H), 7.59-7.49 (m, 2H), 7.36 (s, 1H), 7.31 (d, J = 7.9 Hz, 1H), 5.84-5.50 (m, 2H), 3.60 (d, J = 11.3 Hz, 1H), 3.14 (dd, J = 11.4, 4.5 Hz, 2H), 3.02-2.90 (m, 1H), 2.26 (q, J = 9.5, 6.1 Hz, 1H), 2.06 (tp, J = 7.9, 4.4, 3.7 Hz, 1H), 1.84 (q, J = 7.8, 4.3 Hz, 2H). LC-MS: [M + H]$^+$ = 552.3, 553.2. |
| 211 | 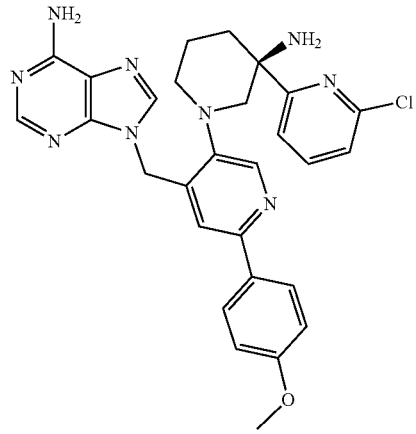 [SMILES: COc1ccc(-c2cc(Cn3cnc4c(N)ncnc43)c(N3CCC[C@](N)(c4cccc(Cl)n4)C3)cn2)cc1] | ¹H NMR (400 MHz, CD$_3$OD) δ ppm 8.47 (s, 1H), 8.21 (d, J = 20.6 Hz, 2H), 7.82 (t, J = 7.8 Hz, 1H), 7.71-7.56 (m, 3H), 7.33 (d, J = 7.6 Hz, 1H), 7.17 (s, 1H), 7.01-6.83 (m, 2H), 5.62 (q, J = 16.4 Hz, 2H), 3.80 (s, 3H), 3.59 (d, J = 11.3 Hz, 1H), 3.12 (d, J = 11.4 Hz, 2H), 2.99 (t, J = 10.4 Hz, 1H), 2.27 (s, 1H), 2.04 (d, J = 9.8 Hz, 1H), 1.92-1.75 (m, 2H). LC-MS: [M + H]$^+$ = 542.3, 544.3. |

-continued

| Example # | Structure | ¹H NMR & LC-MS |
|---|---|---|
| 212 | 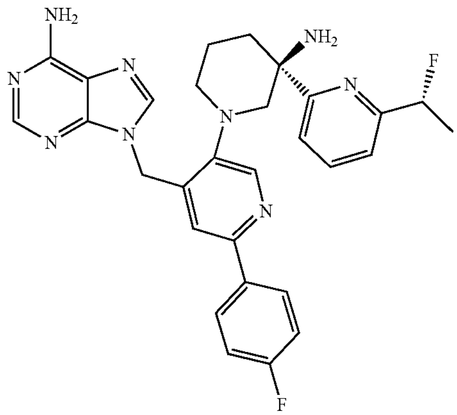 [SMILES: C[C@@H](F)c1cccc([C@@]2(N)CCCN(c3cnc(-c4ccc(F)cc4)cc3Cn3cnc4c(N)ncnc43)C2)n1] | ¹H NMR (400 MHz, CD₃OD) δ ppm 8.50 (d, J = 4.2 Hz, 1H), 8.29-8.18 (m, 1H), 8.13 (s, 1H), 7.86 (dd, J = 10.1, 6.1 Hz, 1H), 7.75 (dd, J = 8.8, 5.0 Hz, 2H), 7.62 (d, J = 7.7 Hz, 1H), 7.39 (d, J = 7.4 Hz, 1H), 7.22 (d, J = 5.9 Hz, 1H), 7.18-7.00 (m, 2H), 5.79-5.50 (m, 3H), 3.57 (d, J = 11.3 Hz, 1H), 3.16 (d, J = 10.8 Hz, 2H), 3.01 (d, J = 13.3 Hz, 1H), 2.29 (s, 1H), 2.07 (s, 1H), 1.89 (d, J = 11.2 Hz, 2H), 1.77-1.55 (m, 3H). LC-MS: [M + H]⁺ = 542.3, 543.3. |
| 213 | 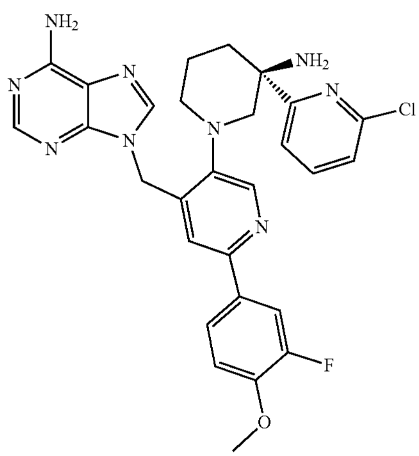 [SMILES: COc1ccc(-c2cc(Cn3cnc4c(N)ncnc43)c(N3CCC[C@](N)(c4cccc(Cl)n4)C3)cn2)cc1F] | ¹H NMR (400 MHz, CD₃OD) δ ppm 8.48 (s, 1H), 8.23 (s, 1H), 8.18 (s, 1H), 7.81 (t, J = 7.8 Hz, 1H), 7.64 (d, J = 7.7 Hz, 1H), 7.54 (dd, J = 12.7, 2.2 Hz, 1H), 7.44 (ddd, J = 8.6, 2.2, 1.1 Hz, 1H), 7.31 (d, J = 7.8 Hz, 1H), 7.21 (s, 1H), 7.08 (t, J = 8.7 Hz, 1H), 5.61 (q, J = 16.3 Hz, 2H), 3.87 (s, 3H), 3.66-3.50 (m, 1H), 3.12 (d, J = 11.4 Hz, 2H), 2.96 (d, J = 9.6 Hz, 1H), 2.25 (d, J = 10.5 Hz, 1H), 2.04 (ddt, J = 13.6, 9.6, 4.8 Hz, 1H), 1.88-1.68 (m, 2H). LC-MS: [M + H]⁺ = 560.3, 561.2. |
| 214 | 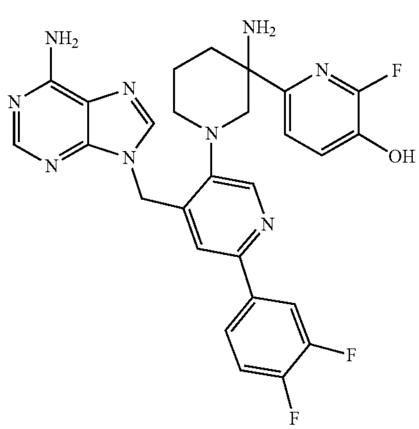 [SMILES: Nc1ncnc2c1ncn2Cc1cc(-c2ccc(F)c(F)c2)ncc1N1CCCC(N)(c2ccc(O)c(F)n2)C1] | ¹H NMR (400 MHz, CD₃OD) δ ppm 8.60 (s, 1H), 8.32 (s, 1H), 8.28 (s, 1H), 7.81 (ddd, J = 2.0, 7.9, 11.8 Hz, 1H), 7.62 (brd, J = 8.4 Hz, 1H), 7.52 (s, 1H), 7.46-7.39 (m, 2H), 7.37-7.26 (m, 1H), 5.65 (m, 2H), 3.59-3.52 (m, 1H), 3.48-3.41 (m, 1H), 3.13-3.01 (m, 2H), 2.38-2.17 (m, 2H), 2.09-1.91 (m, 2H). LC-MS: [M + H]⁺ = 548.0. |

| Example # | Structure | ¹H NMR & LC-MS |
|---|---|---|
| 215 | 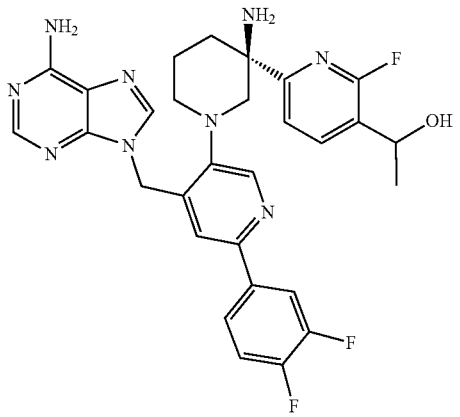 [SMILES: CC(O)c1ccc([C@@]2(N)CCCN(c3cnc(-c4ccc(F)c(F)c4)cc3Cn3cnc4c(N)ncnc43)C2)nc1F] | ¹H NMR (400 MHz, CD₃OD) δ ppm 8.56 (s, 1H), 8.26 (s, 1H), 8.19 (s, 1H), 8.12-8.02 (m, 1H), 7.83-7.73 (m, 1H), 7.62 (d, J = 7.6 Hz, 1H), 7.59-7.50 (m, 1H), 7.36-7.25 (m, 2H), 5.74-5.59 (m, 2H), 5.10-5.00 (m, 1H), 3.65-3.53 (m, 1H), 3.23-3.12 (m, 2H), 3.10-2.95 (m, 1H), 2.37-2.22 (m, 1H), 2.14-2.00 (m, 1H), 1.94-1.81 (m, 2H), 1.45 (d, J = 6.8 Hz, 1H), 1.41 (d, J = 6.4 Hz, 2H). LC-MS: [M + H]⁺ = 576.3. |
| 216 | 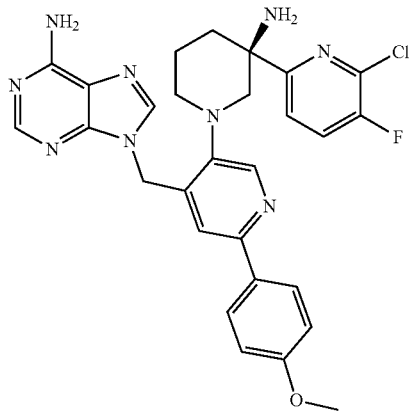 [SMILES: COc1ccc(-c2cc(Cn3cnc4c(N)ncnc43)c(N3CCC[C@](N)(c4ccc(F)c(Cl)n4)C3)cn2)cc1] | ¹H NMR (400 MHz, CD₃OD) δ ppm 8.47 (s, 1H), 8.21 (d, J = 16.6 Hz, 2H), 7.71 (d, J = 5.8 Hz, 2H), 7.68-7.56 (m, 2H), 7.17 (s, 1H), 7.03-6.81 (m, 2H), 5.71-5.49 (m, 2H), 3.55 (d, J = 11.4 Hz, 1H), 3.11 (td, J = 9.8, 8.6, 4.4 Hz, 2H), 3.04-2.91 (m, 1H), 2.26 (t, J = 10.9 Hz, 1H), 2.04 (dq, J = 13.1, 8.6, 7.5 Hz, 1H), 1.91-1.74 (m, 2H). LC-MS: [M + H]⁺ = 560.3, 561.3 |
| 217 | 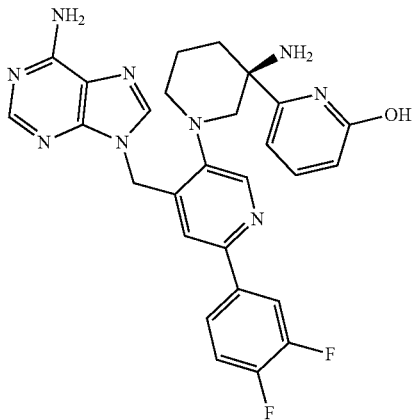 [SMILES: Nc1ncnc2c1ncn2Cc1cc(-c2ccc(F)c(F)c2)ncc1N1CCC[C@](N)(c2cccc(O)n2)C1] | ¹H NMR (400 MHz, CD₃OD) δ ppm 8.52 (s, 1H), 8.29 (s, 1H), 8.23 (s, 1H), 7.75 (ddd, J = 11.8, 7.9, 2.1 Hz, 1H), 7.67 (dd, J = 8.9, 7.2 Hz, 1H), 7.54 (d, J = 8.8 Hz, 1H), 7.30 (dt, J = 16.6, 5.6 Hz, 2H), 6.78 (s, 1H), 6.51 (d, J = 8.9 Hz, 1H), 5.76-5.60 (m, 2H), 3.39 (d, J = 11.6 Hz, 1H), 3.21 (d, J = 11.3 Hz, 1H), 3.14 (d, J = 12.1 Hz, 1H), 3.01 (t, J = 10.8 Hz, 1H), 2.16 (d, J = 10.1 Hz, 2H), 1.89 (d, J = 17.2 Hz, 2H). LC-MS: [M + H]⁺ = 530.3, 531.3. |

| Example # | Structure | ¹H NMR & LC-MS |
|---|---|---|
| 218 | 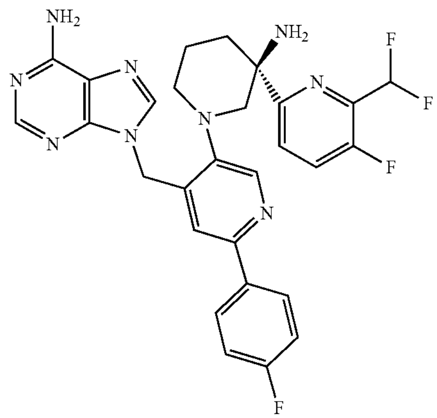 [SMILES: Nc1ncnc2c1ncn2Cc1cc(-c2ccc(F)cc2)ncc1N1CCC[C@](N)(c2ccc(F)c(C(F)F)n2)C1] | ¹H NMR (400 MHz, CD₃OD) δ ppm 8.51 (s, 1H), 8.23 (s, 1H), 8.18 (s, 1H), 7.92 (dd, J = 9.0, 3.6 Hz, 1H), 7.80-7.68 (m, 3H), 7.22 (s, 1H), 7.12 (t, J = 8.8 Hz, 2H), 6.87 (t, J = 53.6 Hz, 1H), 5.71-5.51 (m, 2H), 3.60 (d, J = 11.3 Hz, 1H), 3.15 (d, J = 17.2 Hz, 2H), 3.00 (t, J = 10.7 Hz, 1H), 2.30 (t, J = 11.7 Hz, 1H), 2.08 (d, J = 12.7 Hz, 1H), 1.94-1.79 (m, 2H). LC-MS: [M + H]⁺ = 563.9. |
| 219 | 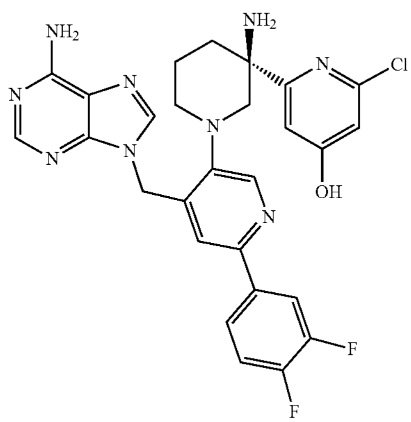 [SMILES: Nc1ncnc2c1ncn2Cc1cc(-c2ccc(F)c(F)c2)ncc1N1CCC[C@](N)(c2cc(O)cc(Cl)n2)C1] | ¹H NMR (400 MHz, CD₃OD) δ ppm 7.83-7.78 (m, 1H), 7.63-7.61 (m, 1H), 7.51 (s, 1H), 7.34-7.27 (m, 1H), 6.72-6.71 (d, J = 1.6 Hz, 1H), 6.49-6.48 (d, J = 1.6 Hz, 1H), 5.67-5.59 (t, J₁ = 16.4 Hz, J₂ = 33.6 Hz, 2H), 3.55-3.52 (d, J = 12.0 Hz, 1H), 3.35 (s, 1H), 3.08-3.06 (m, 2H), 2.28-2.22 (m, 1H), 2.13-2.09 (m, 1H), 2.00-1.91 (m, 2H). LC-MS: [M + H]⁺ = 564.3 |
| 220 | 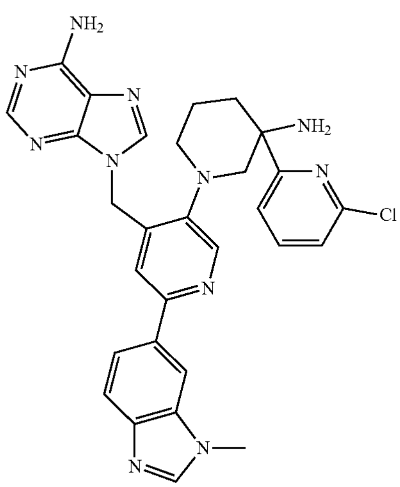 [SMILES: Cn1cnc2ccc(-c3cc(Cn4cnc5c(N)ncnc54)c(N4CCCC(N)(c5cccc(Cl)n5)C4)cn3)cc21] | ¹H NMR (400 MHz, CD₃OD) δ ppm 8.54 (s, 1H), 8.32-8.06 (m, 3H), 7.97 (d, J = 1.4 Hz, 1H), 7.81 (t, J = 7.8 Hz, 1H), 7.74-7.58 (m, 3H), 7.43-7.22 (m, 2H), 5.65 (q, J = 16.2 Hz, 2H), 3.90 (s, 3H), 3.61 (d, J = 11.3 Hz, 1H), 3.14 (d, J = 11.5 Hz, 2H), 3.06-2.88 (m, 1H), 2.28 (t, J = 10.6 Hz, 1H), 2.05 (dq, J = 13.6, 5.3, 4.2 Hz, 1H), 1.92-1.78 (m, 2H). LC-MS: [M + H]⁺ = 566.3, 568.3. |

| Example # | Structure | ¹H NMR & LC-MS |
|---|---|---|
| 221 | 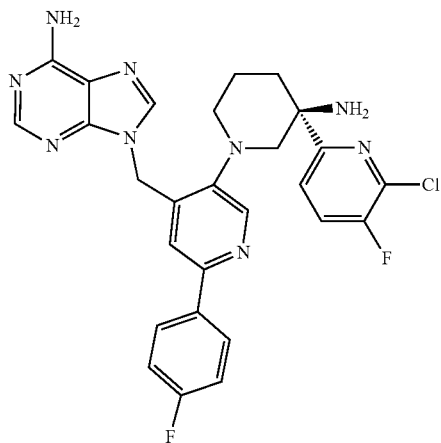 [SMILES: Nc1ncnc2c1ncn2Cc1cc(-c2ccc(F)cc2)ncc1N1CCC[C@](N)(c2ccc(F)c(Cl)n2)C1] | ¹H NMR (400 MHz, CD₃OD) δ 8.51 (s, 1H), 8.21 (d, J = 11.4 Hz, 2H), 7.80-7.66 (m, 4H), 7.23 (s, 1H), 7.18-7.08 (m, 2H), 5.71-5.52 (m, 2H), 3.57 (d, J = 11.4 Hz, 1H), 3.14 (t, J = 11.0 Hz, 2H), 2.99 (td, J = 10.7, 9.6, 2.8 Hz, 1H), 2.25 (d, J = 9.7 Hz, 1H), 2.12-1.97 (m, 1H), 1.91-1.77 (m, 2H). LC-MS: [M + H]⁺ = 547.7. |
| 222 | 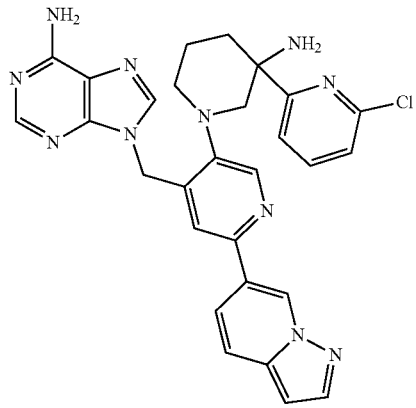 [SMILES: Nc1ncnc2c1ncn2Cc1cc(-c2ccc3ccnn3c2)ncc1N1CCCC(N)(c2cccc(Cl)n2)C1] | ¹H NMR (400 MHz, CD₃OD) δ ppm 8.99 (t, J = 4.9 Hz, 1H), 8.58 (q, J = 4.7 Hz, 1H), 8.22 (dq, J = 16.5, 4.4 Hz, 2H), 8.01-7.91 (m, 1H), 7.81 (dd, J = 11.4, 6.7 Hz, 1H), 7.65 (dh, J = 14.1, 7.6, 6.2 Hz, 3H), 7.44-7.24 (m, 2H), 6.61 (d, J = 6.6 Hz, 1H), 5.66 (d, J = 9.9 Hz, 2H), 3.62 (s, 1H), 3.15 (q, J = 7.6, 6.8 Hz, 2H), 3.02 (d, J = 9.4 Hz, 1H), 2.36-2.15 (m, 2H), 2.07 (s, 1H), 1.87 (s, 2H). LC-MS: [M + H]⁺ = 552.3, 554.3. |
| 223 | 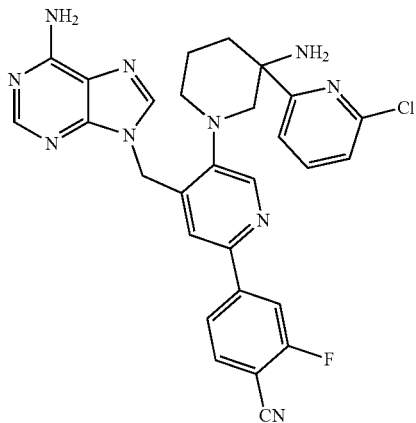 [SMILES: N#Cc1ccc(-c2cc(Cn3cnc4c(N)ncnc43)c(N3CCCC(N)(c4cccc(Cl)n4)C3)cn2)cc1F] | ¹H NMR (400 MHz, CD₃OD) δ ppm 8.60 (s, 1H), 8.20 (d, J = 7.6 Hz, 2H), 7.90-7.77 (m, 2H), 7.76 (d, J = 5.5 Hz, 2H), 7.65 (dd, J = 7.8, 0.7 Hz, 1H), 7.43 (s, 1H), 7.37-7.27 (m, 1H), 5.79-5.42 (m, 2H), 3.64 (d, J = 11.3 Hz, 1H), 3.18 (dd, J = 11.6, 6.3 Hz, 2H), 3.09-2.91 (m, 1H), 2.36-2.20 (m, 1H), 2.20-2.03 (m, 1H), 1.87 (dd, J = 11.3, 6.1 Hz, 2H). LC-MS: [M + H]⁺ = 555.3, 557.2. |

| Example # | Structure | ¹H NMR & LC-MS |
|---|---|---|
| 224 | 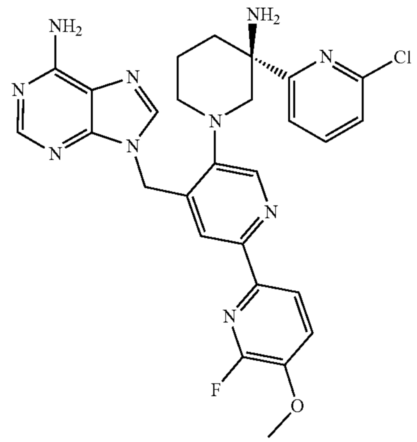 [SMILES: COc1ccc(-c2cc(Cn3cnc4c(N)ncnc43)c(N3CCC[C@](N)(c4cccc(Cl)n4)C3)cn2)nc1F] | ¹H NMR (400 MHz, CD₃OD) δ ppm 8.50 (s, 1H), 8.23-8.20 (m, 2H), 8.10-8.06 (d, J = 8.0 Hz, 1H), 7.85-7.79 (t, J = 8.0 Hz, 1H), 7.68-7.65 (d, J = 8.0 Hz, 1H), 7.62-7.55 (m, 2H), 7.34-7.31 (d, J = 8.0 Hz, 1H), 5.67-5.61 (m, 2H), 3.92 (s, 3H), 3.65-3.58 (m, 1H), 3.52-3.45 (m, 1H), 3.25-2.98 (m, 2H), 2.38-2.23 (m, 1H), 2.20-2.03 (m, 1 H), 1.94-1.82 (m, 2H). LC-MS: [M + H]⁺ = 561.3. |
| 225 | 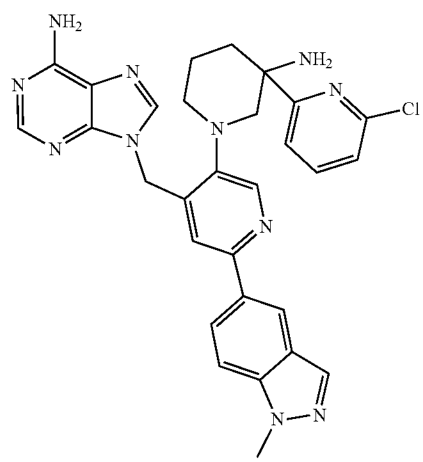 [SMILES: Cn1ncc2cc(-c3cc(Cn4cnc5c(N)ncnc54)c(N4CCCC(N)(c5cccc(Cl)n5)C4)cn3)ccc21] | ¹H NMR (CD₃OD) δ: 8.51 (s, 1H), 8.22 (d, J = 13.4 Hz, 2H), 8.05 (dd, J = 27.2, 1.0 Hz, 2H), 7.93-7.74 (m, 2H), 7.60 (dd, J = 39.0, 8.3 Hz, 2H), 7.43-7.19 (m, 2H), 5.64 (q, J = 16.4 Hz, 2H), 4.04 (s, 3H), 3.59 (d, J = 11.4 Hz, 1H), 3.13 (d, J = 11.4 Hz, 2H), 3.07-2.83 (m, 1H), 2.32-1.99 (m, 2H), 1.84 (td, J = 11.9, 10.8, 4.6 Hz, 2H) LC-MS : [M + H]⁺ = 566.3 : [M + H + 2]⁺ = 568.3. |
| 226 | 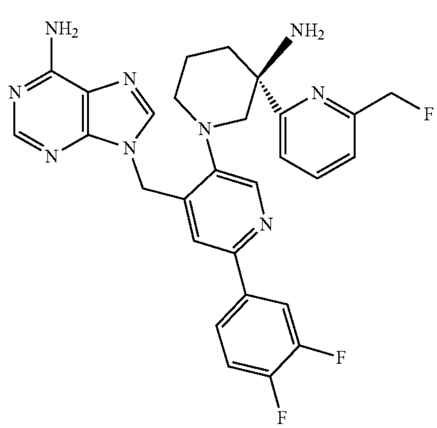 [SMILES: Nc1ncnc2c1ncn2Cc1cc(-c2ccc(F)c(F)c2)ncc1N1CCC[C@](N)(c2cccc(CF)n2)C1] | ¹H NMR (400 MHz, CD₃OD) δ ppm 8.52 (s, 1H), 8.23 (s, 1H), 8.15 (s, 1H), 7.88 (t, J = 7.8 Hz, 1H), 7.74 (ddd, J = 12.1, 7.8, 2.3 Hz, 1H), 7.65 (d, J = 8.0 Hz, 1H), 7.53 (ddt, J = 8.2, 4.0, 1.6 Hz, 1H), 7.40 (d, J = 7.7 Hz, 1H), 7.33-7.22 (m, 2H), 5.68-5.52 (m, 2H), 5.51 (s, 1H), 5.39 (s, 1H), 3.59 (d, J = 11.6 Hz, 1H), 3.16 (dd, J = 11.7, 6.2 Hz, 2H), 3.00 (t, J = 10.0 Hz, 1H), 2.30 (t, J = 11.0 Hz, 1H), 2.08 (d, J = 9.5 Hz, 1H), 1.97-1.80 (m, 2H). LC-MS: [M + H]⁺ = 545.9, 546.9. |

| Example # | Structure | ¹H NMR & LC-MS |
|---|---|---|
| 227 | 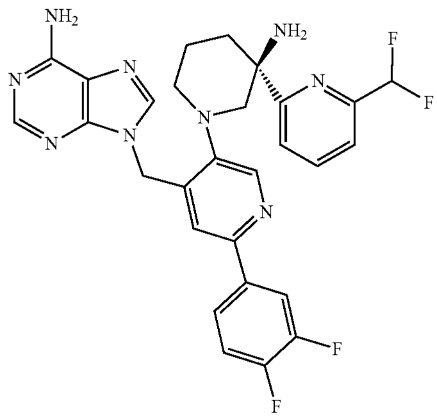 [SMILES: Nc1ncnc2c1ncn2Cc1cc(-c2ccc(F)c(F)c2)ncc1N1CCC[C@](N)(c2cccc(C(F)F)n2)C1] | ¹H NMR (400 MHz, CD₃OD) δ ppm 8.53 (s, 1H), 8.22 (s, 1H), 8.16 (s, 1H), 7.99 (t, J = 7.8 Hz, 1H), 7.84 (d, J = 8.0 Hz, 1H), 7.73 (ddd, J = 11.8, 7.8, 2.1 Hz, 1H), 7.58 (d, J = 7.7 Hz, 1H), 7.56-7.43 (m, 1H), 7.27 (d, J = 9.6 Hz, 2H), 6.71 (t, J = 55.4 Hz, 1H), 5.72-5.50 (m, 2H), 3.63 (d, J = 11.4 Hz, 1H), 3.17 (t, J = 11.6 Hz, 2H), 3.09-2.94 (m, 1H), 2.31 (t, J = 11.5 Hz, 1H), 2.16-1.98 (m, 1H), 1.95-1.79 (m, 2H). LC-MS: [M + H]⁺ = 564.3, 565.3. |
| 228 | 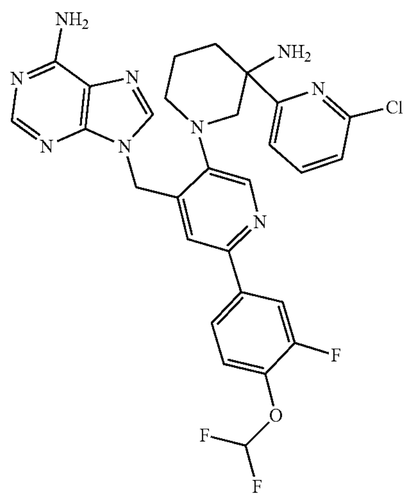 [SMILES: Nc1ncnc2c1ncn2Cc1cc(-c2ccc(OC(F)F)c(F)c2)ncc1N1CCCC(N)(c2cccc(Cl)n2)C1] | ¹H NMR (400 MHz, CD₃OD) δ ppm 8.54 (s, 1H), 8.20 (d, J = 16.4 Hz, 2H), 7.81 (t, J = 7.8 Hz, 1H), 7.77-7.68 (m, 1H), 7.65 (d, J = 7.8 Hz, 1H), 7.54 (d, J = 8.6 Hz, 1H), 7.40-7.24 (m, 3H), 6.87 (t, J = 73.3 Hz, 1H), 5.72-5.49 (m, 2H), 3.61 (d, J = 11.4 Hz, 1H), 3.14 (d, J = 11.1 Hz, 2H), 3.00 (t, J = 10.5 Hz, 1H), 2.35-2.17 (m, 1H), 2.06 (d, J = 10.1 Hz, 1H), 1.86 (q, J = 11.0, 8.6 Hz, 2H). LC-MS: [M + H]⁺ = 596.3, 597.2. |
| 229 | 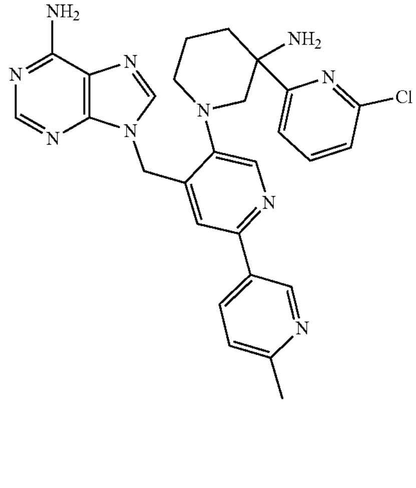 [SMILES: Cc1ccc(-c2cc(Cn3cnc4c(N)ncnc43)c(N3CCCC(N)(c4cccc(Cl)n4)C3)cn2)cn1] | ¹H NMR (400 MHz, CD₃OD) δ ppm 8.79 (d, J = 2.3 Hz, 1H), 8.57 (s, 1H), 8.21 (d, J = 13.1 Hz, 2H), 8.08 (dd, J = 8.2, 2.4 Hz, 1H), 7.82 (t, J = 7.8 Hz, 1H), 7.65 (dd, J = 7.8, 0.7 Hz, 1H), 7.40-7.20 (m, 3H), 5.72-5.54 (m, 2H), 3.62 (d, J = 11.4 Hz, 1H), 3.15 (d, J = 11.0 Hz, 2H), 3.02 (t, J = 10.5 Hz, 1H), 2.29 (s, 1H), 2.08 (d, J = 12.8 Hz, 1H), 1.87 (d, J = 7.5 Hz, 2H). LC-MS: [M + H]⁺ = 527.3, 528.3. |

| Example # | Structure | ¹H NMR & LC-MS |
|---|---|---|
| 230 | 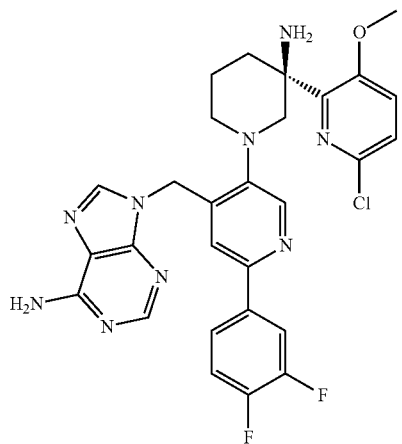 [SMILES: COc1ccc(Cl)nc1[C@@]1(N)CCCN(c2cnc(-c3ccc(F)c(F)c3)cc2Cn2cnc3c(N)ncnc32)C1] | ¹H NMR (400 MHz, CD₃OD) δ ppm 8.53 (s, 1H), 8.23 (s, 1H), 8.13 (s, 1H), 7.75-7.70 (m, 1H), 7.53-7.48 (m, 2H), 7.31-7.23 (m, 3H), 5.63-5.53 (q, 2H), 3.95 (s, 3H), 3.76-3.73 (m, 1H), 3.27 (s, 1H), 3.17-3.14 (m, 1H), 3.00-2.95 (m, 1H), 2.30-2.27 (m, 1H), 2.09-1.96 (m, 3H). LC-MS: [M + H]⁺ = 578.4. |
| 231 | 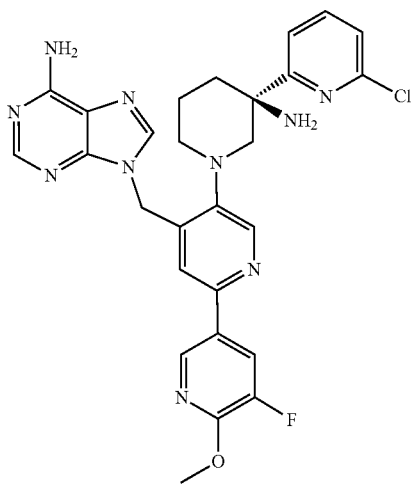 [SMILES: COc1ncc(-c2cc(Cn3cnc4c(N)ncnc43)c(N3CCC[C@](N)(c4cccc(Cl)n4)C3)cn2)cc1F] | ¹H NMR (400 MHz, CD₃OD) δ ppm 8.54 (s, 1H), 8.30 (d, J = 1.9 Hz, 1H), 8.24 (s, 1H), 8.22 (s, 1H), 7.93 (dd, J = 1.9, 11.4 Hz, 1H), 7.88 (br t, J = 7.9 Hz, 1H), 7.70 (br d, J = 7.7 Hz, 1H), 7.39 (br d, J = 7.9 Hz, 1H), 7.35 (s, 1H), 5.80-5.49 (m, 2H), 4.01 (s, 3H), 3.58 (br d, J = 10.3 Hz, 1H), 3.20 (br d, J = 10.5 Hz, 1H), 3.12 (br d, J = 10.3 Hz, 1H), 3.06-2.96 (m, 1H), 2.39-2.24 (m, 1H), 2.14-1.80 (m, 4H). LCMS: [M + H]⁺ = 561.4 |
| 232 | 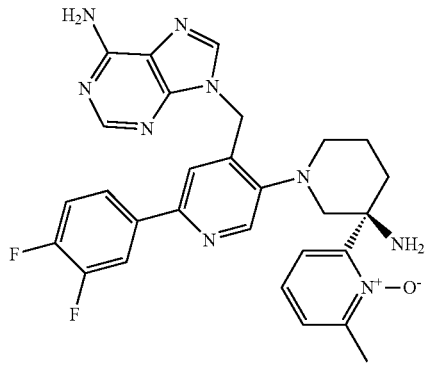 [SMILES: Cc1cccc([C@@]2(N)CCCN(c3cnc(-c4ccc(F)c(F)c4)cc3Cn3cnc4c(N)ncnc43)C2)[n+]1[O-]] | ¹H NMR (400 MHz, CD₃OD) δ ppm 8.51 (s, 1H), 8.20 (s, 2H), 7.82-7.58 (m, 2H), 7.53-7.39 (m, 3H), 7.26 (dt, J = 10.4, 8.4 Hz, 1H), 7.19 (s, 1H), 5.84-5.33 (m, 2H), 3.87-3.39 (m, 2H), 3.13 (t, J = 5.3 Hz, 2H), 2.47 (s, 4H), 2.25-1.77 (m, 3H). LC-MS: [M + H]⁺ = 544.2, 545.3 |

| Example # | Structure | ¹H NMR & LC-MS |
|---|---|---|
| 233 | 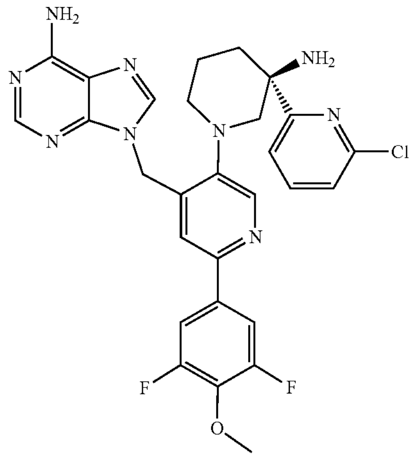 [SMILES: COc1c(F)cc(-c2cc(Cn3cnc4c(N)ncnc43)c(N3CCC[C@](N)(c4cccc(Cl)n4)C3)cn2)cc1F] | ¹H NMR (400 MHz, CD₃OD) δ ppm 8.50 (s, 1H), 8.29-8.21 (m, 1H), 8.17 (s, 1H), 7.81 (t, J = 7.8 Hz, 1H), 7.64 (d, J = 8.0 Hz, 1H), 7.47-7.36 (m, 2H), 7.35-7.27 (m, 2H), 5.68-5.52 (m, 2H), 3.96 (s, 3H), 3.63-3.54 (m, 1H), 3.18-3.06 (m, 2H), 3.02-2.92 (m, 1H), 2.33-2.19 (m, 1H), 2.12-1.98 (m, 1H), 1.92-1.79 (m, 2H). LC-MS: [M + H]⁺ = 578.0. |
| 234 | 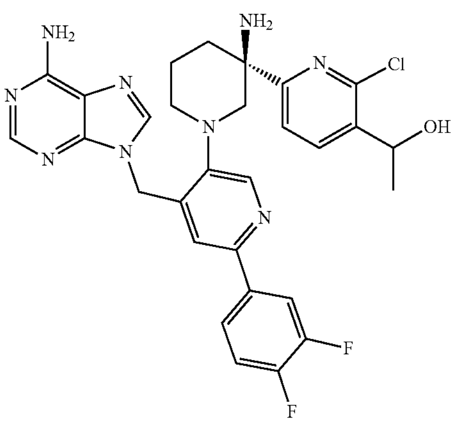 [SMILES: CC(O)c1ccc([C@@]2(N)CCCN(c3cnc(-c4ccc(F)c(F)c4)cc3Cn3cnc4c(N)ncnc43)C2)nc1Cl] | ¹H NMR (400 MHz, CD₃OD) δ ppm 8.56 (s, 1H), 8.25 (s, 1H), 8.17 (s, 1H), 8.07 (d, J = 8.2 Hz, 1H), 7.80-7.71 (m, 2H), 7.55 (br s, 1H), 7.35-7.27 (m, 2H), 5.66-5.57 (m, 2H), 5.11 (m, 1H), 3.66 (m, 1H), 3.22-3.14 (m, 2H), 3.05 (m, 1H), 2.34 (m, 1H), 2.08 (m, 1H), 1.91 (m, 2H), 1.35 (m, 3H). LC-MS: [M + H]⁺ = 592.4 |
| 235 | 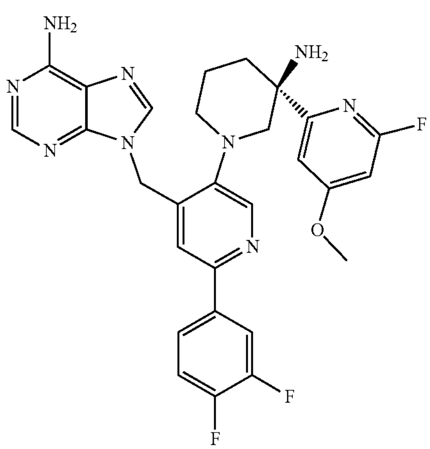 [SMILES: COc1cc(F)nc([C@@]2(N)CCCN(c3cnc(-c4ccc(F)c(F)c4)cc3Cn3cnc4c(N)ncnc43)C2)c1] | ¹H NMR (400 MHz, CD₃OD) δ ppm 8.52 (s, 1H), 8.23 (s, 1H), 8.18 (s, 1H), 7.73 (ddd, J = 12.0, 7.8, 2.2 Hz, 1H), 7.58-7.44 (m, 1H), 7.32 (s, 1H), 7.27 (dt, J = 10.3, 8.4 Hz, 1H), 7.11 (d, J = 1.7 Hz, 1H), 6.49 (d, J = 1.8 Hz, 1H), 5.72-5.54 (m, 2H), 3.91 (s, 3H), 3.51 (d, J = 11.4 Hz, 1H), 3.11 (d, J = 10.8 Hz, 2H), 2.96 (t, J = 10.7 Hz, 1H), 2.21 (t, J = 10.8 Hz, 1H), 2.13-1.95 (m, 1H), 1.89-1.73 (m, 2H). LC-MS: [M + H]⁺ = 562.0, 563.0. |

| Example # | Structure | ¹H NMR & LC-MS |
|---|---|---|
| 236 | 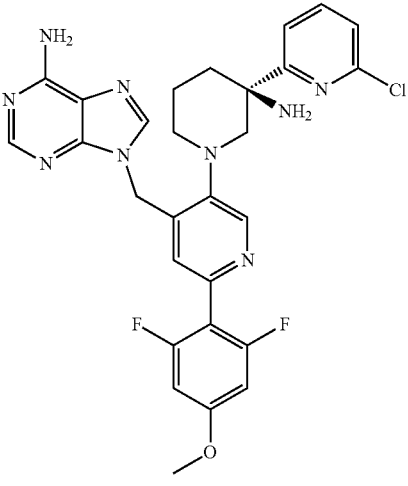 [SMILES: COc1cc(F)c(-c2cc(Cn3cnc4c(N)ncnc43)c(N3CCC[C@](N)(c4cccc(Cl)n4)C3)cn2)c(F)c1] | ¹H NMR (400 MHz, CD₃OD): ): δ 8.55 (s, 1H), 8.22 (s, 1H), 8.18 (s, 1H), 7.86-7.82 (t, J = 8.0 Hz, 1H), 7.69-7.68 (d, J = 7.6 Hz, 1H), 7.35-7.34 (d, J = 7.6 Hz, 1H), 6.82 (s, 1H), 6.63-6.60 (m, 2H), 5.72-5.62 (m, 2H), 3.82 (s, 3H), 3.69-3.61 (m, 1H), 3.27-3.20 (m, 2H), 3.10-3.05 (m, 1H), 2.35-2.31 (m, 1H), 2.16-2.14 (m, 1H), 1.92-1.90 (m, 2H). LCMS: [M + H]⁺ = 578.3. |
| 237 | 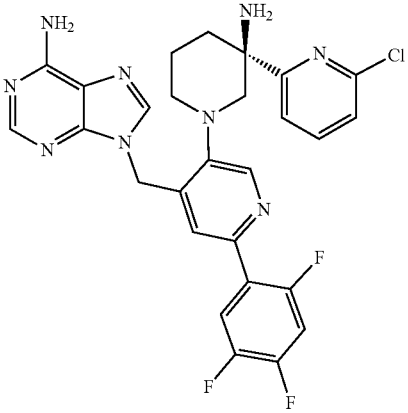 [SMILES: Nc1ncnc2c1ncn2Cc1cc(-c2cc(F)c(F)cc2F)ncc1N1CCC[C@](N)(c2cccc(Cl)n2)C1] | ¹H NMR (400 MHz, CD₃OD) δ ppm 8.57 (s, 1H), 8.20 (s, 1H), 8.18 (s, 1H), 7.85-7.81 (t, J = 8.0 Hz, 1H), 7.79-7.74 (m, 1H), 7.68-7.66 (d, J = 7.6 Hz, 1H), 7.34-7.32 (d, J = 8.0 Hz, 1H), 7.20-7.15 (m, 1H), 7.13 (br, 1H), 5.69-5.60 (m, 2H), 3.65-3.62 (d, J = 11.2 Hz, 1H), 3.24-3.18 (m, 2H), 3.08-3.03 (m, 1H), 2.34-2.27 (m, 1H), 2.17-2.11 (m, 1H), 1.91-1.88 (m, 2H). LC-MS: [M + H]⁺ = 566.4. |
| 238 | 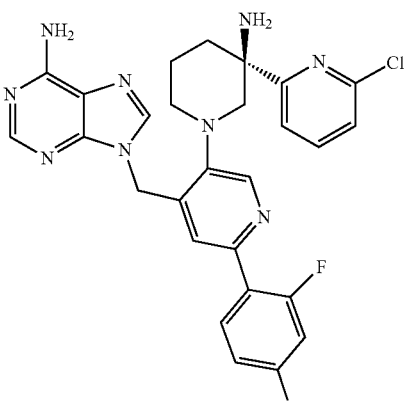 | ¹H NMR (400 MHz, CD₃OD) δ ppm 8.56 (s, 1H), 8.20 (s, 1H), 8.17 (s, 1H), 7.85-7.76 (m, 2H), 7.68-7.66 (d, J = 8.0 Hz, 1H), 7.34-7.32 (d, J = 7.6 Hz, 1H), 7.07-6.94 (m, 3H), 5.70-5.60 (m, 2H), 3.65-3.62 (d, J = 11.2 Hz, 1H), 3.23-3.13 (m, 2H), 3.07-3.02 (m, 1H), 2.31-2.28 (m, 1H), 2.13-2.11 (m, 1H), 1.90-1.88 (m, 2H). LC-MS: [M + H]⁺ = 548.4. |

| Example # | Structure | ¹H NMR & LC-MS |
|---|---|---|
| 239 | 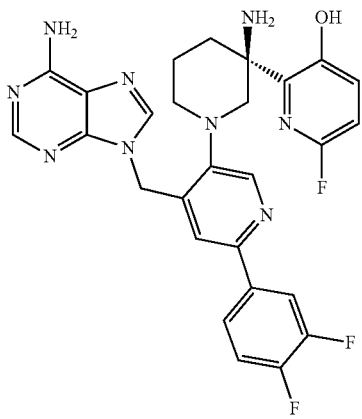 [SMILES: Nc1ncnc2c1ncn2Cc1cc(-c2ccc(F)c(F)c2)ncc1N1CCC[C@](N)(c2nc(F)ccc2O)C1] | ¹H NMR (400 MHz, CD₃OD) δ ppm 8.49 (s, 1H), 8.27 (s, 1H), 8.22 (s, 1H), 7.74 (m, 1H), 7.58-7.51 (m, 1H), 7.34 (s, 1H), 7.27 (q, J = 8.4 Hz, 1H), 7.17 (dd, J = 6.8, 8.8 Hz, 1H), 6.77 (dd, J = 3.6, 8.4 Hz, 1H), 5.75-5.62 (m, 2H), 3.39-3.33 (m, 2H), 3.20-3.13 (m, 1H), 2.90 (dt, J = 2.8, 12.0 Hz, 1H), 2.43-2.42 (m, 1H), 2.19-2.07 (m, 1H), 1.99-1.82 (m, 2H). LC-MS: [M + H]⁺ = 548.3. |
| 240 | 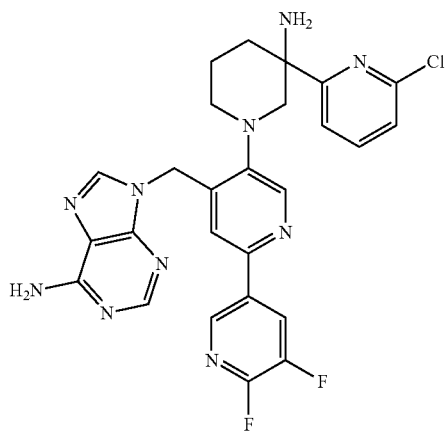 [SMILES: Nc1ncnc2c1ncn2Cc1cc(-c2cnc(F)c(F)c2)ncc1N1CCCC(N)(c2cccc(Cl)n2)C1] | ¹H NMR (400 MHz, CD₃OD) δ ppm 8.59 (s, 1H), 8.38 (m, 1H), 8.28-8.23 (m, 1H), 8.24 (s, 1H), 8.18 (s, 1H), 7.83-7.80 (t, J = 8.0 Hz, 1H), 7.66-7.64 (d, J = 7.6 Hz, 1H), 7.23 (s, 1H), 7.33-7.31 (d, J = 7.6 Hz, 1H), 5.68-5.81 (m, 2H), 3.64-3.61 (d, J = 11.2 Hz, 1H), 3.18-3.13 (m, 2H), 3.04-3.00 (m, 1H), 2.32-2.27 (m, 1H), 2.10-2.06 (m, 1H), 1.86 (m, 2H). LC-MS: [M + H]+ = 549.2. |
| 241 | 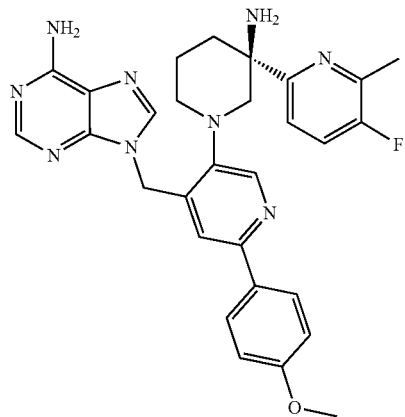 [SMILES: COc1ccc(-c2cc(Cn3cnc4c(N)ncnc43)c(N3CCC[C@](N)(c4ccc(F)c(C)n4)C3)cn2)cc1] | ¹H NMR (400 MHz, CD₃OD) δ ppm 8.45 (s, 1H), 8.24 (s, 1H), 8.16 (s, 1H), 7.79-7.55 (m, 2H), 7.55-7.35 (m, 2H), 7.18 (s, 1H), 7.04-6.72 (m, 2H), 5.79-5.51 (m, 2H), 3.80 (s, 3H), 3.52 (d, J = 11.4 Hz, 1H), 3.13 (d, J = 11.3 Hz, 2H), 3.03-2.92 (m, 1H), 2.48 (d, J = 2.9 Hz, 3H), 2.24 (s, 1H), 2.13-1.97 (m, 1H), 1.86 (tq, J = 8.3, 4.4 Hz, 2H). LC-MS: [M + H]⁺ = 540.3, 541.3. |

| Example # | Structure | ¹H NMR & LC-MS |
|---|---|---|
| 242 | 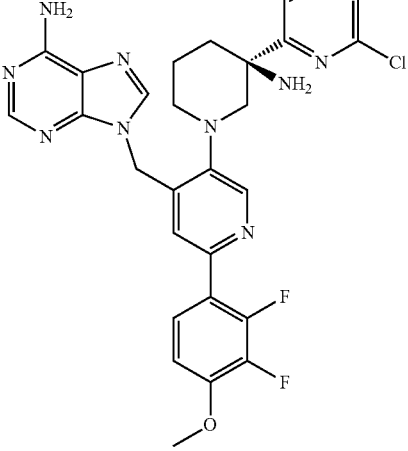 | ¹H NMR (400 MHz, CD₃OD) δ ppm 8.54 (s, 1H), 8.22 (s, 1H), 8.19 (s, 1H), 7.88-7.80 (m, 1H), 7.70-7.65 (d, J = 7.8 Hz, 1H), 7.53-7.44 (dt, J = 2.3, 8.7 Hz, 1H), 7.36-7.30 (m, 1H), 7.05 (s, 1H), 7.02-6.95 (m, 1H), 5.73-5.58 (m, 2H), 3.91 (s, 3H), 3.67-6.64 (m, 1H), 3.26-3.15 (m, 2H), 3.10-3.00 (m, 1H), 2.38-2.25 (m, 1H), 2.20-2.06 (m, 1H), 1.95-1.90 (m, 2H). LC-MS: [M + H]⁺ = 578.3. |
| 243 | 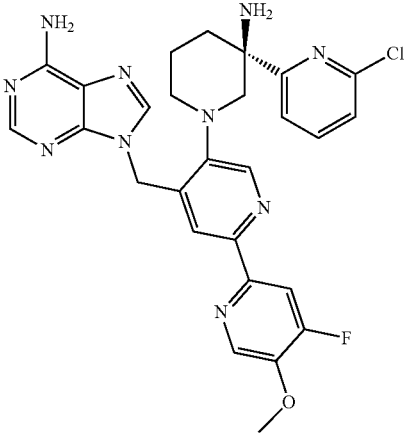 [SMILES: COc1cnc(-c2cc(Cn3cnc4c(N)ncnc43)c(N3CCC[C@](N)(c4cccc(Cl)n4)C3)cn2)cc1F] | ¹H NMR (400 MHz, CD₃OD) δ ppm 7.25 (s, 1 H) 7.02 (d, J = 9.95 Hz, 1 H) 6.94 (s, 1 H) 6.92 (s, 1 H) 6.73 (d, J = 12.35 Hz, 1 H) 6.57 (t, J = 7.51 Hz, 1 H) 6.45 (s, 1 H) 6.40 (d, J = 7.55 Hz, 1 H) 6.08 (d, J = 7.82 Hz, 1 H) 4.31-4.41 (m, 2 H) 2.68-2.72 (m, 3 H) 2.36 (br d, J = 11.49 Hz, 1 H) 1.90-1.99 (m, 2 H) 1.72-1.82 (m, 1 H) 1.00-1.08 (m, 1 H) 0.78-0.90 (m, 1 H). LC-MS: [M + H]⁺ = 561.3. |
| 244 | 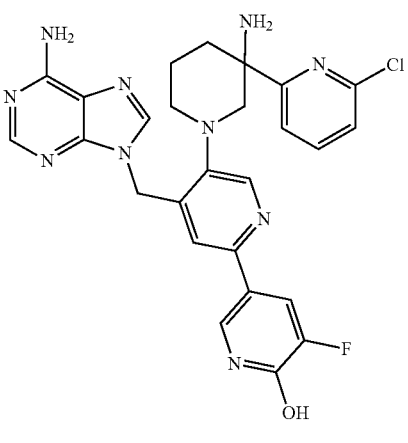 [SMILES: Nc1ncnc2c1ncn2Cc1cc(-c2cnc(O)c(F)c2)ncc1N1CCCC(N)(c2cccc(Cl)n2)C1] | ¹H NMR (400 MHz, DMSO-d₆) δ ppm 8.42 (s, 1H), 8.23 (s, 1H), 8.10 (s, 1H), 7.85-7.79 (m, 2H), 7.78-7.73 (m, 1H), 7.69 (m, 1H), 7.34 (d, J = 8.0 Hz, 1H), 7.23 (s, 3H), 5.57-5.36 (m, 2H), 3.05-2.78 (m, 4H), 2.19-1.91 (m, 2H), 1.64 (m, 2H). LC-MS: [M + H]⁺ = 547.3. |

-continued

| Example # | Structure | ¹H NMR & LC-MS |
|---|---|---|
| 245 | 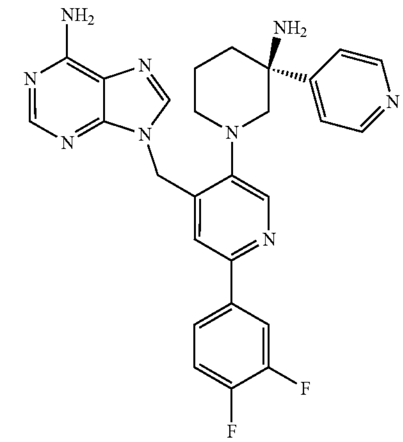 [SMILES: Nc1ncnc2c1ncn2Cc1cc(-c2ccc(F)c(F)c2)ncc1N1CCC[C@](N)(c2ccncc2)C1] | ¹H NMR (400 MHz, CD₃OD) δ ppm 8.65-8.42 (m, 3H), 8.25 (d, J = 2.4 Hz, 2H), 7.84-7.63 (m, 3H), 7.60-7.47 (m, 1H), 7.39-7.20 (m, 2H), 5.67 (q, J = 16.3 Hz, 2H), 3.49 (d, J = 11.4 Hz, 1H), 3.16 (dd, J = 24.6, 11.6 Hz, 2H), 3.04 (dt, J = 11.3, 5.6 Hz, 1H), 2.24-1.96 (m, 2H), 1.86 (ddd, J = 32.2, 9.6, 4.8 Hz, 2H). LC-MS: [M + H]⁺ = 514.0, 515.0. |
| 246 | 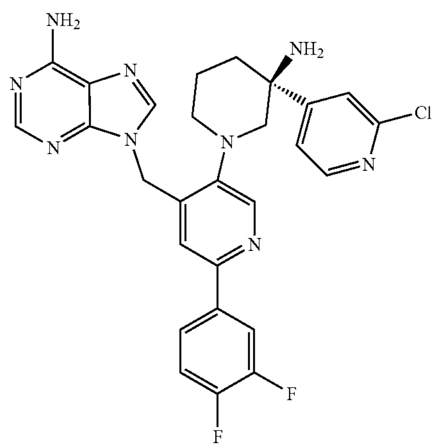 [SMILES: Nc1ncnc2c1ncn2Cc1cc(-c2ccc(F)c(F)c2)ncc1N1CCC[C@](N)(c2ccnc(Cl)c2)C1] | ¹H NMR (400 MHz, CD₃OD) δ ppm 8.59 (s, 1H), 8.37 (d, J = 5.4 Hz, 1H), 8.25 (s, 2H), 7.85-7.72 (m, 2H), 7.67 (dd, J = 5.4, 1.6 Hz, 1H), 7.55 (t, J = 5.9 Hz, 1H), 7.39-7.20 (m, 2H), 5.84-5.57 (m, 2H), 3.47 (d, J = 11.3 Hz, 1H), 3.21-2.92 (m, 3H), 2.22-1.96 (m, 2H), 1.86 (dt, J = 20.8, 9.4 Hz, 2H). LC-MS: [M + H]⁺ = 547.9, 549.0. |
| 247 | 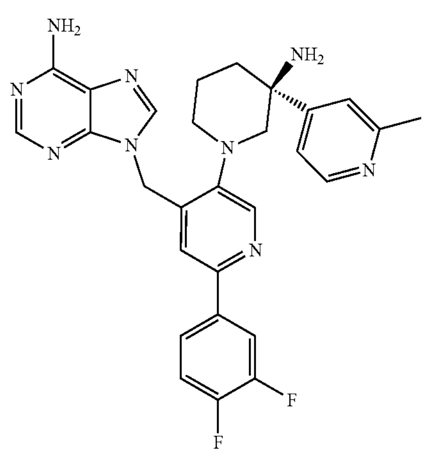 [SMILES: Cc1cc([C@@]2(N)CCCN(c3cnc(-c4ccc(F)c(F)c4)cc3Cn3cnc4c(N)ncnc43)C2)ccn1] | ¹H NMR (400 MHz, CD₃OD) δ ppm 8.58 (s, 1H), 8.41 (d, J = 5.5 Hz, 1H), 8.25 (d, J = 4.9 Hz, 2H), 7.77 (ddd, J = 11.9, 7.8, 2.1 Hz, 1H), 7.65-7.44 (m, 3H), 7.41-7.18 (m, 2H), 5.87-5.53 (m, 2H), 3.60-3.42 (m, 1H), 3.16 (t, J = 11.3 Hz, 2H), 3.07-2.90 (m, 1H), 2.25-1.97 (m, 2H), 1.97-1.75 (m, 2H). LC-MS: [M + H]⁺ = 528.0, 529.0. |

| Example # | Structure | ¹H NMR & LC-MS |
|---|---|---|
| 248 | 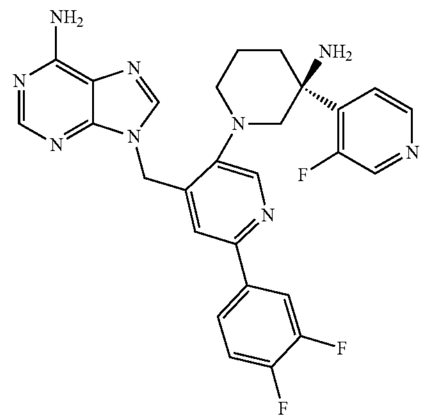 [SMILES: Nc1ncnc2c1ncn2Cc1cc(-c2ccc(F)c(F)c2)ncc1N1CCC[C@](N)(c2ccncc2F)C1] | ¹H NMR (400 MHz, CD₃OD) δ ppm 8.56 (s, 1H), 8.43 (d, J = 5.5 Hz, 1H), 8.23 (d, J = 4.9 Hz, 2H), 7.54-7.51 (m, 1H), 7.65-7.44 (m, 3H), 7.3-7.25 (m, 2H), 5.68-5.59 (m, 2H), 3.67 (m, 1H), 3.3 (m, 1H), 3.12-3.0 (m, 2H), 2.3-2.0 (m, 2H), 1.93-1.87 (m, 2H). LC-MS: [M + H]⁺ = 532.0, 532.9. |
| 249 | 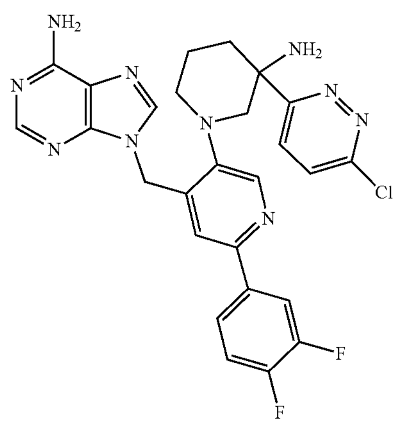 [SMILES: Nc1ncnc2c1ncn2Cc1cc(-c2ccc(F)c(F)c2)ncc1N1CCCC(N)(c2ccc(Cl)nn2)C1] | ¹H NMR (400 MHz, CD₃OD) δ 8.55 (s, 1H), 8.22 (s, 2H), 8.06 (d, J = 9.1 Hz, 1H), 7.81 (d, J = 9.1 Hz, 1H), 7.75 (ddd, J = 12.0, 7.8, 2.1 Hz, 1H), 7.57-7.48 (m, 1H), 7.34-7.22 (m, 2H), 5.61 (s, 2H), 3.72 (d, J = 11.5 Hz, 1H), 3.28 (s, 1H), 3.17-3.08 (m, 1H), 3.05-2.92 (m, 1H), 2.34 (d, J = 12.0 Hz, 1H), 2.16-2.04 (m, 1H), 1.94 (dd, J = 8.4, 5.0 Hz, 1H), 1.82 (dd, J = 9.3, 4.5 Hz, 1H). LC-MS: [M + H]⁺ = 548.7. |
| 250 | 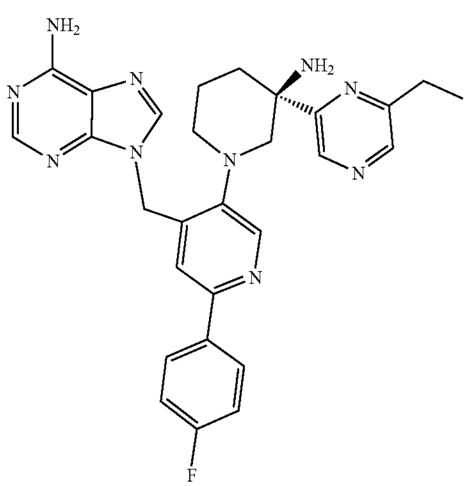 [SMILES: CCc1cncc([C@@]2(N)CCCN(c3cnc(-c4ccc(F)cc4)cc3Cn3cnc4c(N)ncnc43)C2)n1] | ¹H NMR (400 MHz, CD₃OD) δ ppm 8.73 (s, 1H), 8.52 (s, 1H), 8.40 (s, 1H), 8.20 (d, J = 19.5 Hz, 2H), 7.89-7.61 (m, 2H), 7.24 (s, 1H), 7.21-7.01 (m, 2H), 5.79-5.47 (m, 2H), 3.62 (d, J = 11.3 Hz, 1H), 3.24-3.08 (m, 2H), 3.01 (t, J = 10.7 Hz, 1H), 2.87 (q, J = 7.6 Hz, 2H), 2.33 (t, J = 11.0 Hz, 1H), 2.09 (dt, J = 14.0, 6.8 Hz, 1H), 1.95-1.79 (m, 2H), 1.32 (t, J = 7.6 Hz, 3H). LC-MS: [M + H]⁺ = 525.3, 526.3. |

| Example # | Structure | ¹H NMR & LC-MS |
|---|---|---|
| 251 | 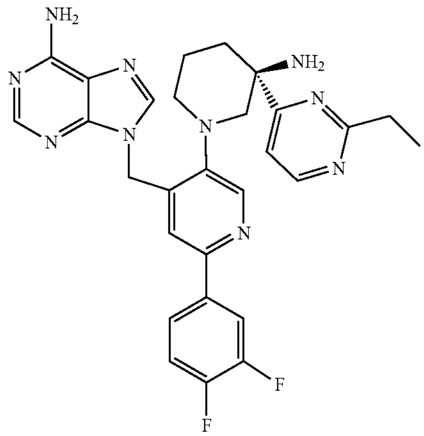 [SMILES: CCc1nccc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.67 (d, J = 5.4 Hz, 1H), 8.52 (s, 1H), 8.21 (d, J = 12.9 Hz, 2H), 7.73 (ddd, J = 12.0, 7.8, 2.2 Hz, 1H), 7.65-7.46 (m, 2H), 7.40-7.03 (m, 2H), 5.81-5.43 (m, 2H), 3.62 (d, J = 11.2 Hz, 1H), 3.14 (t, J = 10.2 Hz, 2H), 2.96 (p, J = 7.6 Hz, 3H), 2.29 (t, J = 10.8 Hz, 1H), 2.08 (dq, J = 12.0, 7.5, 6.8 Hz, 1H), 1.93-1.72 (m, 2H), 1.34 (t, J = 7.6 Hz, 3H). LC-MS: [M + H]⁺ = 543.5, 544.4. |
| 252 | 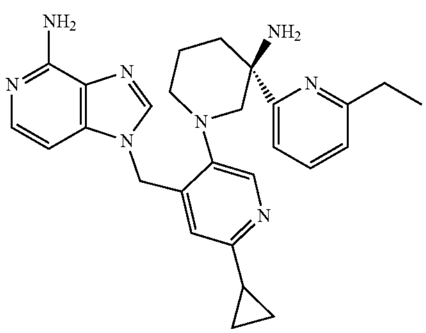 [SMILES: CCc1cccc([C@@]2(N)CCCN(c3cnc(C4CC4)cc3Cn3cnc4c(N)nccc43)C2)n1] | ¹H NMR (400 MHz, CD₃OD) δ 8.54 (s, 1H), 8.28 (s, 1H), 7.68-7.73 (m, J = 7.9 Hz, 2H), 7.45 (d, J = 8.0 Hz, 1H), 7.14 (d, J = 6.0 Hz, 1H), 6.60 (d, J = 7.7 Hz, 1H), 6.46 (s, 1H), 5.53 (d, J = 9.4 Hz, 2H), 3.57 (d, J = 11.4 Hz, 1H), 3.10 (t, J = 11.5 Hz, 2H), 2.92 (td, J = 11.6, 10.5, 3.0 Hz, 1H), 2.78 (t, 2H), 2.30 (b, 1H), 2.10 (b, 1H), 1.97-1.75 (m, 3H), 1.28 (t, 3H), 0.94-0.80 (m, 2H), 0.79-0.65 (m, 2H). LC-MS: [M + H]⁺ = 469.0, 470.0. |
| 253 | 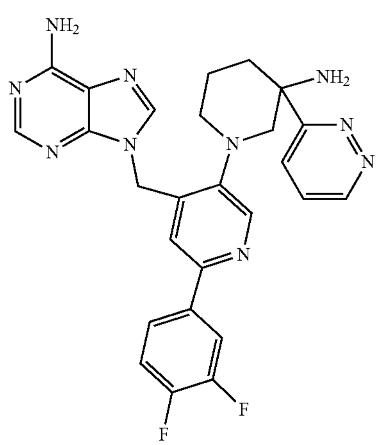 [SMILES: Nc1ncnc2c1ncn2Cc1cc(-c2ccc(F)c(F)c2)ncc1N1CCCC(N)(c2cccnn2)C1] | ¹H NMR (CD₃OD) δ: 9.10 (d, J = 4.9 Hz, 1H), 8.56 (s, 1H), 8.21 (d, J = 12.6 Hz, 2H), 8.06 (dd, J = 8.8, 1.5 Hz, 1H), 7.88-7.64 (m, 2H), 7.53 (s, 1H), 7.42-7.09 (m, 2H), 5.62 (s, 2H), 3.75 (d, J = 11.7 Hz, 1H), 3.20-2.85 (m, 3H), 2.37 (s, 2H), 2.02-1.69 (m, 2H) LCMS:[M + H]⁺ = 514.9. |

| Example # | Structure | ¹H NMR & LC-MS |
|---|---|---|
| 254 | 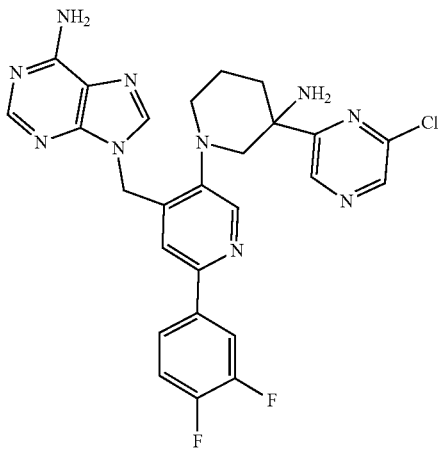 [SMILES: Nc1ncnc2c1ncn2Cc1cc(-c2ccc(F)c(F)c2)ncc1N1CCCC(N)(c2cncc(Cl)n2)C1] | ¹H NMR (CD₃OD) δ: 8.89 (s, 1H), 8.57 (d, J = 10.5 Hz, 2H), 8.21 (d, J = 7.0 Hz, 2H), 7.89-7.70 (m, 1H), 7.53 (s, 1H), 7.29 (d, J = 15.7 Hz, 2H), 5.85-5.31 (m, 2H), 3.64 (d, J = 11.4 Hz, 1H), 3.16-3.01 (m, 3H), 2.42-2.04 (m, 2H), 2.00-1.74 (m, 2H) LC-MS: [M + H]⁺ = 549.2 |
| 255 | 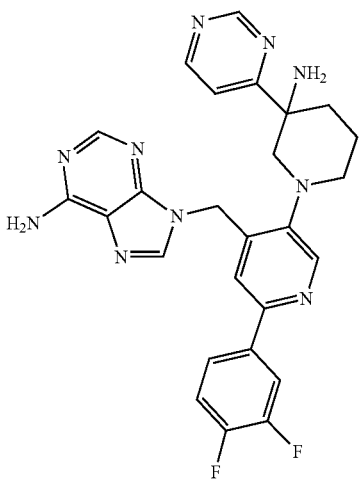 [SMILES: Nc1ncnc2c1ncn2Cc1cc(-c2ccc(F)c(F)c2)ncc1N1CCCC(N)(c2ccncn2)C1] | ¹H NMR (400 MHz, CD₃OD) δ ppm 9.16 (s, 1H), 8.77 (d, J = 5.6 Hz, 1H), 8.53 (s, 1H), 8.23 (s, 1H), 8.21 (s, 1H), 7.82 (d, J = 5.2 Hz, 1H), 7.76-7.71 (m, 1H), 7.54-7.52 (m, 1H), 7.32 (s, 1H), 7.27-7.23 (m, 1H), 5.66-5.57 (m, 2H), 3.63 (d, J = 11.2 Hz, 1H), 3.19 (d, J = 11.2 Hz, 1H), 3.13-3.09 (m, 1H), 3.02-2.97 (m, 1H), 2.31-2.26 (m, 1H), 2.09-2.03 (m, 1H), 1.88-1.81 (m, 2H). LC-MS: [M + H]⁺ = 515.1. |
| 256 | 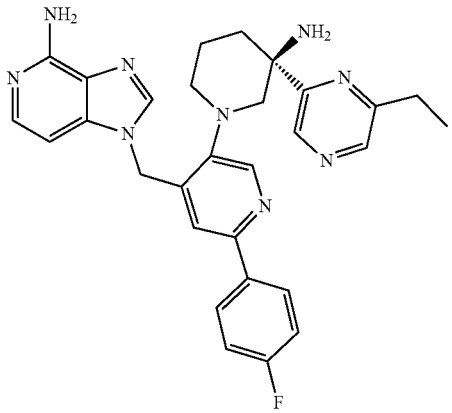 [SMILES: CCc1cncc([C@@]2(N)CCCN(c3cnc(-c4ccc(F)cc4)cc3Cn3cnc4c(N)nccc43)C2)n1] | ¹H NMR (400 MHz, CD₃OD) δ ppm 8.73 (s, 1H), 8.53 (s, 1H), 8.40 (s, 1H), 8.19 (s, 1H), 7.68 (ddd, J = 7.1, 5.3, 1.7 Hz, 3H), 7.15-7.04 (m, 2H), 7.01 (s, 1H), 6.60 (d, J = 6.0 Hz, 1H), 5.64 (t, J = 12.5 Hz, 2H), 3.69 (d, J = 11.4 Hz, 1H), 3.21 (d, J = 11.4 Hz, 2H), 3.02 (ddd, J = 12.0, 9.6, 2.9 Hz, 1H), 2.87 (q, J = 7.6 Hz, 2H), 2.39 (t, J = 10.0 Hz, 1H), 2.16 (td, J = 12.4, 9.7, 5.7 Hz, 1H), 1.91 (t, J = 9.9 Hz, 2H), 1.35-1.30 (m, 3H). LC-MS: [M + H]⁺ = 524.3, 525.3. |

| Example # | Structure | ¹H NMR & LC-MS |
|---|---|---|
| 257 | 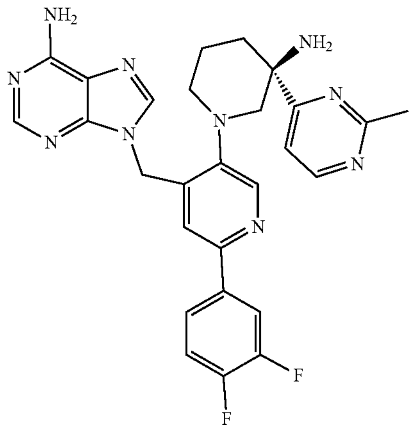 [SMILES: Cc1nccc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.51 (s, 1H), 8.21 (d, J = 15.3 Hz, 2H), 7.78 (td, J = 8.8, 6.5 Hz, 1H), 7.15-6.71 (m, 3H), 6.05 (td, J = 55.4, 4.4 Hz, 1H), 5.69 (s, 2H), 3.99 (s, 1H), 3.25 (d, J = 1.6 Hz, 1H), 3.13-2.91 (m, 3H), 1.89 (d, J = 16.2 Hz, 3H), 1.65 (s, 3H). LC-MS: [M + H]⁺ = 529.3, 530.3. |
| 258 | 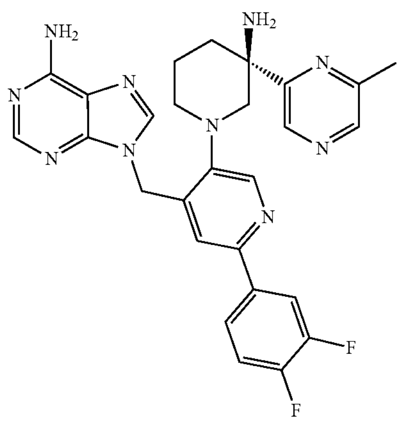 [SMILES: Cc1cncc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.71 (s, 1H), 8.53 (s, 1H), 8.39 (s, 1H), 8.20 (d, J = 17.0 Hz, 2H), 7.73 (ddd, J = 12.0, 7.8, 2.2 Hz, 1H), 7.57-7.46 (m, 1H), 7.41-7.14 (m, 2H), 5.74-5.45 (m, 2H), 3.62 (d, J = 11.4 Hz, 1H), 3.16 (dd, J = 15.7, 11.5 Hz, 2H), 3.06-2.89 (m, 1H), 2.56 (s, 3H), 2.32 (t, J = 10.4 Hz, 1H), 2.18-2.02 (m, 1H), 1.96-1.79 (m, 2H). LC-MS: [M + H]⁺ = 528.8, 529.8. |
| 259 | 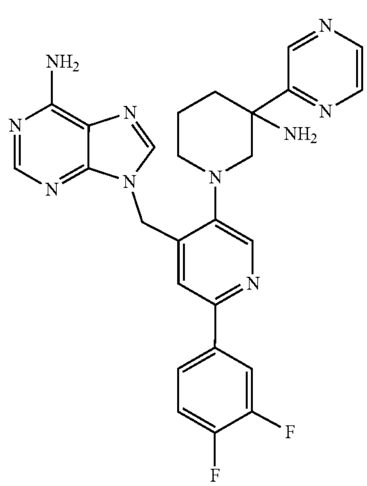 [SMILES: Nc1ncnc2c1ncn2Cc1cc(-c2ccc(F)c(F)c2)ncc1N1CCCC(N)(c2cnccn2)C1] | ¹H NMR (400 MHz, CD₃OD): δ 8.95 (1H, s), 8.65 (1H, s), 8.54 (1H, s), 8.51 (1H, s), 8.23 (1H, s), 8.20 (1H, s), 7.70-7.80 (1H, m), 7.45-7.56 (1H, m), 7.25-7.35 (2H, m), 5.45-5.80 (2H, m), 3.55-3.65 (1H, m), 3.10-3.25 (2H, m), 2.90-3.05 (1H, m), 2.25-2.40 (1H, m), 2.05-2.20 (1H, m), 1.75-1.90 (2H, m). LC-MS: [M + H]⁺ = 515.2. |

| Example # | Structure | ¹H NMR & LC-MS |
|---|---|---|
| 260 | 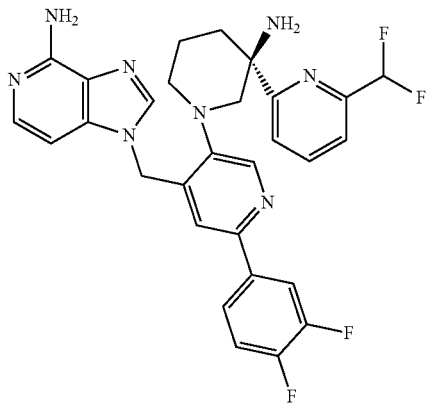 [SMILES: Nc1nccc2c1ncn2Cc1cc(-c2ccc(F)c(F)c2)ncc1N1CCC[C@](N)(c2cccc(C(F)F)n2)C1] | ¹H NMR (400 MHz, CD₃OD) δ ppm 8.54 (s, 1H), 8.16 (s, 1H), 7.98 (t, J = 7.8 Hz, 1H), 7.83 (d, J = 8.0 Hz, 1H), 7.72-7.62 (m, 2H), 7.57 (d, J = 7.7 Hz, 1H), 7.48-7.37 (m, 1H), 7.24 (dt, J = 10.3, 8.4 Hz, 1H), 7.07 (s, 1H), 6.88-6.52 (m, 2H), 5.59 (t, J = 12.3 Hz, 2H), 3.70 (d, J = 11.4 Hz, 1H), 3.20 (t, J = 9.4 Hz, 2H), 3.07-2.94 (m, 1H), 2.37 (t, J = 10.6 Hz, 1H), 2.21-2.05 (m, 1H), 2.01-1.83 (m, 2H). LC-MS: [M + H]⁺ = 563.3, 564.2. |
| 261 | 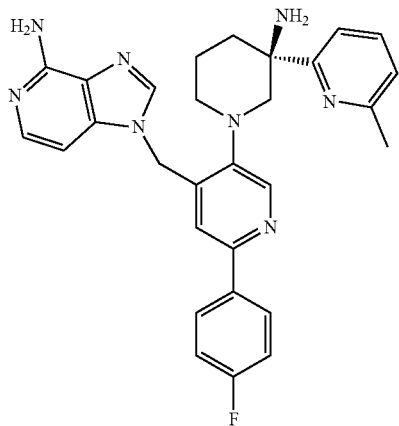 [SMILES: Cc1cccc([C@@]2(N)CCCN(c3cnc(-c4ccc(F)cc4)cc3Cn3cnc4c(N)nccc43)C2)n1] | ¹H NMR (CD₃OD) δ: 8.51 (s, 1H), 8.15 (s, 1H), 7.68 (ddd, J = 7.7, 6.4, 3.6 Hz, 4H), 7.45 (d, J = 7.9 Hz, 1H), 7.22-6.96 (m, 4H), 6.62 (d, J = 6.0 Hz, 1H), 5.81-5.48 (m, 2H), 3.63 (d, J = 11.2 Hz, 1H), 3.33 (p, J = 1.6 Hz, 1H), 3.22-3.15 (m, 1H), 2.97 (ddd, J = 11.9, 9.3, 2.8 Hz, 1H), 2.51 (s, 3H), 2.38-2.25 (m, 1H), 2.17-2.09 (m, 1H), 1.90 (ddt, J = 19.9, 13.6, 4.8 Hz, 2H) LC-MS: [M + H]⁺ = 509.0 |
| 262 | 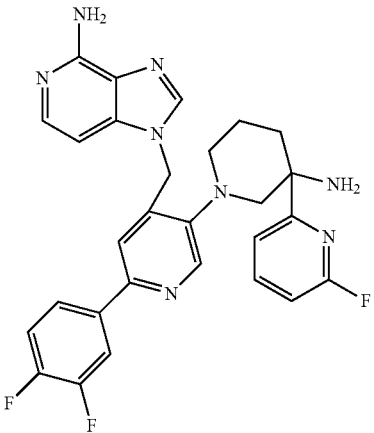 [SMILES: Nc1nccc2c1ncn2Cc1cc(-c2ccc(F)c(F)c2)ncc1N1CCCC(N)(c2cccc(F)n2)C1] | ¹H NMR (400 MHz, CD₃OD) δ ppm 8.57 (s, 1H), 8.20 (s, 1H), 7.96 (q, J = 8.1 Hz, 1H), 7.79-7.50 (m, 3H), 7.51-7.38 (m, 1H), 7.27 (dt, J = 10.4, 8.5 Hz, 1H), 7.09 (s, 1H), 6.96 (dd, J = 8.2, 2.8 Hz, 1H), 6.60 (d, J = 6.1 Hz, 1H), 5.77-5.53 (m, 2H), 3.67 (d, J = 11.4 Hz, 1H), 3.25-3.11 (m, 2H), 3.08-2.94 (m, 1H), 2.35 (t, J = 10.5 Hz, 1H), 2.23-2.06 (m, 1H), 1.91 (td, J = 12.1, 10.2, 5.6 Hz, 2H). LC-MS: [M + H]⁺ = 531.0, 532.0. |

| Example # | Structure | ¹H NMR & LC-MS |
|---|---|---|
| 263 | 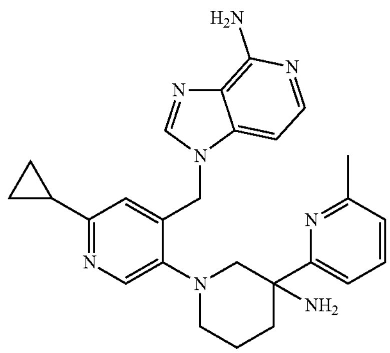 [SMILES: Cc1cccc(C2(N)CCCN(c3cnc(C4CC4)cc3Cn3cnc4c(N)nccc43)C2)n1] | ¹H NMR (400 MHz, CD₃OD): δ 8.28 (s, 1H), 8.10 (s, 1H), 7.73-7.65 (m, 2H), 7.45 (d, J = 7.6 Hz, 1H), 7.13 (d, J = 7.6 Hz, 1H), 6.59 (d, J = 6.0 Hz, 1H), 6.46 (s, 1H), 5.60-5.45 (m, 2H), 3.57 (d, J = 10.8 Hz, 1H), 3.17-3.03 (m, 2H), 2.92 (t, J = 9.6 Hz, 1H), 2.52 (s, 3H), 2.37-2.24 (m, 1H), 2.15-2.03 (m, 1H), 1.97-1.80 (m, 3H), 0.93-0.84 (m, 2H), 0.77-0.70 (m, 2H). LC-MS: [M + H]⁺ = 455.3 |
| 264 | 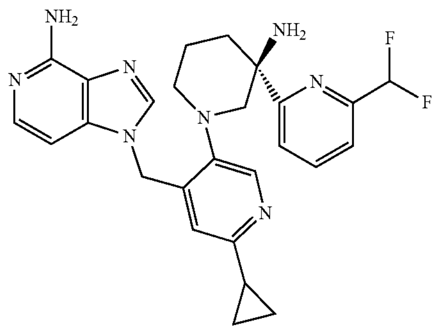 [SMILES: Nc1nccc2c1ncn2Cc1cc(C2CC2)ncc1N1CCC[C@](N)(c2cccc(C(F)F)n2)C1] | ¹H NMR (CD₃OD) δ: 8.28 (s, 1H), 8.10 (s, 1H), 7.97 (t, J = 7.9 Hz, 1H), 7.81 (d, J = 8.1 Hz, 1H), 7.66 (d, J = 6.0 Hz, 1H), 7.57 (d, J = 7.7 Hz, 1H), 6.87-6.48 (m, 2H), 6.43 (s, 1H), 5.49 (d, J = 9.4 Hz, 2H), 3.60 (d, J = 11.4 Hz, 1H), 3.10 (t, J = 11.6 Hz, 2H), 2.92 (td, J = 11.7, 10.5, 3.1 Hz, 1H), 2.33 (s, 1H), 2.16-2.03 (m, 1H), 1.99-1.64 (m, 3H), 0.92-0.81 (m, 2H), 0.78-0.65 (m, 2H) LC-MS: [M + H]⁺ = 491.0 |
| 265 | 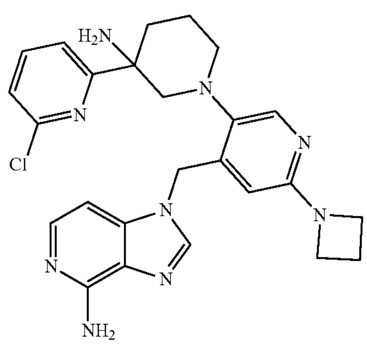 [SMILES: Nc1nccc2c1ncn2Cc1cc(N2CCC2)ncc1N1CCCC(N)(c2cccc(Cl)n2)C1] | ¹H NMR (400 MHz, CD₃OD): δ 8.18 (s, 1H), 7.87-7.83 (m, 1H), 7.73-7.65 (m, 3H), 7.35 (d, J = 8.0 Hz, 1H), 6.70 (d, J = 5.2 Hz, 1H), 5.92 (s, 1H), 4.24 (t, J = 5.6 Hz, 2H), 3.61-3.47 (m, 1H), 3.38 (t, J = 5.6 Hz, 2H), 3.24-3.10 (m, 1H), 3.02 (d, J = 11.2 Hz, 1H), 2.88 (t, J = 9.6 Hz, 1H), 2.39-2.23 (m, 1H), 2.15-2.10 (m, 3H), 1.91-1.86 (m, 2H). LC-MS: [M + H]⁺ = 490.1 |
| 266 | 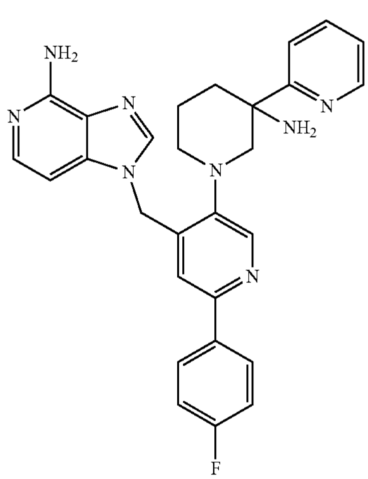 [SMILES: Nc1nccc2c1ncn2Cc1cc(-c2ccc(F)cc2)ncc1N1CCCC(N)(c2ccccn2)C1] | ¹H NMR (400 MHz, CDCl₃): δ 8.58 (d, J = 4.4 Hz, 1H), 8.53 (s, 1H), 8.25 (s, 1H), 7.88-7.70 (m, 4H), 7.61 (d, J = 6.0 Hz, 1H), 7.32-7.26 (m, 1H), 7.22 (t, J = 8.8 Hz, 2H), 7.08 (s, 1H), 6.54 (d, J = 5.6 Hz, 1H), 6.24 (brs, 2H), 5.58 (m, 2H), 3.62-3.50 (m, 1H), 3.17-3.06 (m, 2H), 2.95-2.85 (m, 1H), 2.38-2.06 (m, 2H), 1.88-1.73 (m, 2H). LC-MS: [M + H]⁺ = 495.3 |

| Example # | Structure | ¹H NMR & LC-MS |
|---|---|---|
| 267 | 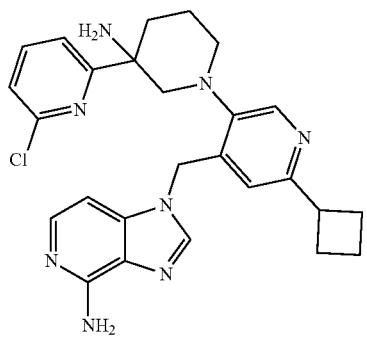 [SMILES: Nc1nccc2c1ncn2Cc1cc(C2CCC2)ncc1N1CCCC(N)(c2cccc(Cl)n2)C1] | ¹H NMR (400 MHz, CD₃OD) δ ppm 8.40 (s, 1H), 8.16 (s, 1H), 7.83 (t, J = 7.6 Hz, 1H), 7.75-7.65 (m, 2H), 7.34 (d, J = 7.2 Hz, 1H), 6.56 (d, J = 6.0 Hz, 1H), 6.51 (s, 1H), 5.65-5.50 (m, 2H), 3.75-3.60 (m, 1H), 3.55-3.40 (m, 1H), 3.20-2.95 (m, 3H), 2.43-1.70 (m, 10H). LC-MS: [M + H]⁺ = 489.2. |
| 268 | 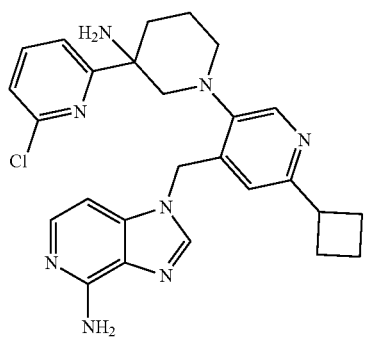 [SMILES: Nc1nccc2c1ncn2Cc1cc(C2CCC2)ncc1N1CCCC(N)(c2cccc(Cl)n2)C1] | ¹H NMR (400 MHz, CD₃OD): δ 8.28 (s, 1H), 8.12 (s, 1H), 7.81 (t, J = 8.0 Hz, 1H), 7.72-7.58 (m, 2H), 7.31 (d, J = 8.4 Hz, 1H), 6.55 (d, J = 6.0 Hz, 1H), 6.43 (s, 1H), 5.60-5.43 (m, 2H), 3.69-3.55 (m, 1H), 3.18-3.01 (m, 2H), 2.97-2.88 (m, 1H), 2.39-2.25 (m, 1H), 2.13-1.98 (m, 1H), 1.90-1.79 (m, 3H), 0.92-0.84 (m, 2H), 0.77-0.69 (m, 2H). LC-MS: [M + H]⁺ = 475.1 |
| 269 | 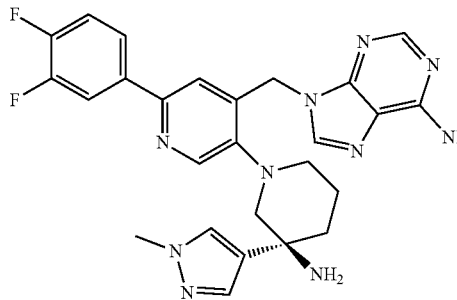 | 1H NMR (DMSO 400 MHz): δ 8.49 (s, 1H), 8.31 (s, 1H), 8.12 (s, 1H), 7.80-7.90 (m, 1H), 7.66 (s, 1H), 7.60-7.65 (m, 1H), 7.40-7.55 (m, 2H), 7.33 (s, 1H), 7.28 (brs, 2H), 5.45-5.65 (m, 2H), 3.77 (s. 3H), 3.00-3.10 (m, 3H), 3.80-3.90 (m, 1H), 1.95-2.05 (m, 1H), 1.65-1.85 (m, 3H). LC-MS: [M + H]⁺ = 517.2. |
| 270 | 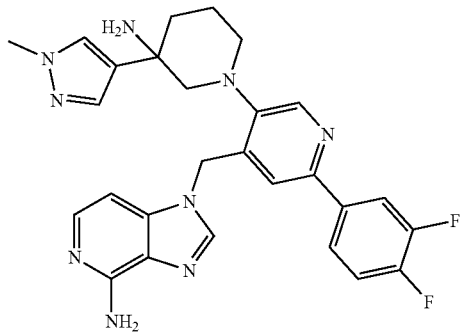 [SMILES: Cn1cc(C2(N)CCCN(c3cnc(-c4ccc(F)c(F)c4)cc3Cn3cnc4c(N)nccc43)C2)cn1] | ¹H NMR (400 MHz, CD3OD) δ ppm 8.53 (s, 1H), 8.23 (d, J = 13.8 Hz, 2H), 7.75 (ddd, J = 12.0, 7.8, 2.2 Hz, 1H), 7.69 (s, 1H), 7.61 (s, 1H), 7.54 (ddd, J = 9.2, 4.3, 2.2 Hz, 1H), 7.29 (d, J = 9.3 Hz, 2H), 5.78-5.49 (m, 2H), 3.88 (s, 3H), 3.27 (s, 1H), 3.19 (d, J = 11.3 Hz, 1H), 3.10 (d, J = 11.8 Hz, 1H), 3.02-2.87 (m, 1H), 2.13-1.87 (m, 3H), 1.82 (dq, J = 12.2, 4.0 Hz, 1H). LC-MS: [M + H]⁺ = 516.3. |

| Example # | Structure | ¹H NMR & LC-MS |
|---|---|---|
| 271 | 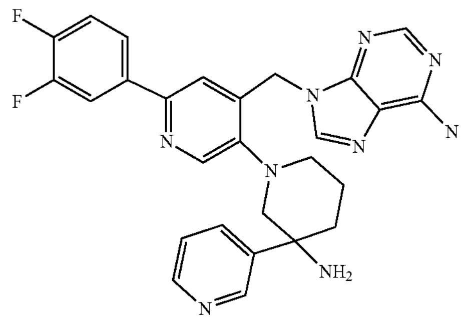 | ¹H NMR (CDCl₃ 400 MHz): δ 8.85 (s, 1H), 8.56 (s, 1H), 8.46 (d, J = 4.4 Hz, 1H), 8.23 (s, 2H), 8.12 (d, J = 8.0 Hz, 1H), 7.76-7.70 (m, 1H), 7.53-7.50 (m, 1H), 7.46 (dd, J = 4.8 Hz and 8.0 Hz, 1H), 7.30 (s, 1H), 7.28-7.22 (m, 1H), 5.69 (d, J = 16 Hz, 1H), 5.62 (d, J = 16 Hz, 1H), 3.48 (d, J = 11.6 Hz, 2H), 3.24 (d, J = 11.6 Hz, 2H), 3.11 (d, J = 11.2 Hz, 1H), 3.01 (t, J = 10.8 Hz, 1H), 2.16-2.08 (m, 2H), 1.96-1.93 (m, 1H), 1.84-1.79 (m, 2H). LCMS: [M + H]⁺ = 514.1 |
| 272 | 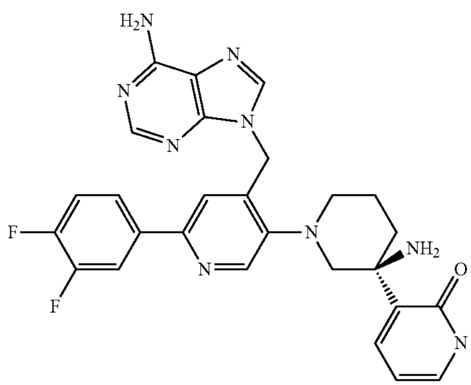 [SMILES: Nc1ncnc2c1ncn2Cc1cc(-c2ccc(F)c(F)c2)ncc1N1CCC[C@](N)(c2ccc[nH]c2=O)C1] | ¹H NMR (400 MHz, CD₃OD) δ ppm 8.53 (s, 1H), 8.29 (s, 1H), 8.25 (s, 1H), 7.85-7.83 (m, 2H), 7.78-7.73 (m, 1H), 7.54-7.50 (m, 1H), 7.36 (s, 1H), 7.32-7.26 (m, 1H), 6.52-6.49 (t, J = 6.8 Hz, 1H), 5.68 (s, 2H), 3.77-3.74 (m, 1H), 3.38-3.35 (m, 1H), 3.17-3.14 (m, 1H), 3.04-2.99 (m, 1H), 2.27-2.07 (m, 3H), 1.96-1.93 (m, 1H). LC-MS: [M + H]⁺ = 530.4. |
| 273 | 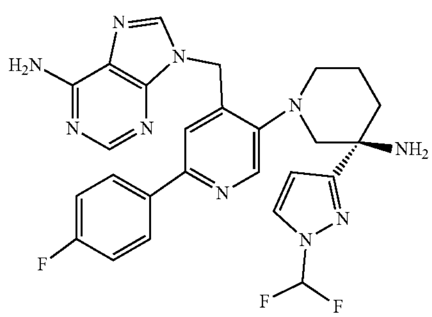 [SMILES: Nc1ncnc2c1ncn2Cc1cc(-c2ccc(F)cc2)ncc1N1CCC[C@](N)(c2ccn(C(F)F)n2)C1] | ¹H NMR (400 MHz, CD₃OD) δ ppm 8.51 (s, 1H), 8.22 (s, 1H), 8.13 (s, 1H), 8.00 (d, J = 2.8 Hz, 1H), 7.81-7.70 (m, 2H), 7.45 (t, J = 59.9 Hz, 1H), 7.25 (s, 1H), 7.13 (t, J = 8.8 Hz, 2H), 6.67 (d, J = 2.8 Hz, 1H), 5.63 (s, 2H), 3.51 (d, J = 11.5 Hz, 1H), 3.15 (dd, J = 19.7, 9.0 Hz, 2H), 2.97 (t, J = 10.2 Hz, 1H), 2.26-2.10 (m, 1H), 2.03 (s, 1H), 1.97-1.77 (m, 2H). LC-MS: [M + H]⁺ = 535.3, 536.3. |
| 274 | 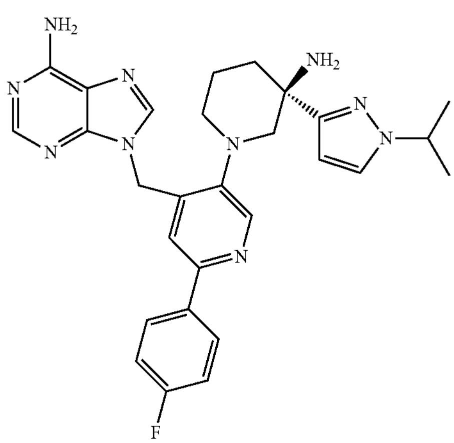 [SMILES: CC(C)n1ccc([C@@]2(N)CCCN(c3cnc(-c4ccc(F)cc4)cc3Cn3cnc4c(N)ncnc43)C2)n1] | ¹H NMR (400 MHz, CD₃OD) δ ppm 8.49 (t, J = 6.3 Hz, 1H), 8.33-8.14 (m, 1H), 8.06 (s, 1H), 7.76 (ddd, J = 8.7, 5.5, 3.0 Hz, 2H), 7.58 (tt, J = 6.3, 2.9 Hz, 1H), 7.30 (dd, J = 8.0, 4.9 Hz, 1H), 7.13 (td, J = 8.5, 5.6 Hz, 2H), 6.38 (td, J = 6.1, 2.8 Hz, 1H), 5.76-5.48 (m, 2H), 4.48 (dt, J = 9.4, 4.9 Hz, 1H), 3.46 (d, J = 11.4 Hz, 1H), 3.14 (dd, J = 11.4, 6.0 Hz, 2H), 2.95 (d, J = 10.9 Hz, 1H), 2.17 (s, 1H), 2.03 (s, 1H), 1.96-1.79 (m, 2H), 1.43 (q, J = 7.2, 6.7 Hz, 6H). LC-MS: [M + H]⁺ = 527.3, 528.3. |

| Example # | Structure | ¹H NMR & LC-MS |
|---|---|---|
| 275 | 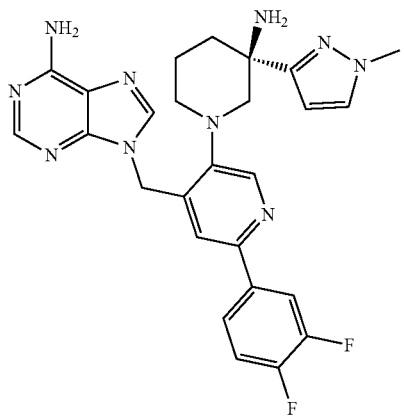 [SMILES: Cn1ccc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.53 (s, 1H), 8.25 (s, 1H), 8.11 (s, 1H), 7.77 (ddd, J = 12.0, 7.8, 2.3 Hz, 1H), 7.65-7.46 (m, 2H), 7.39 (s, 1H), 7.31 (dt, J = 10.4, 8.5 Hz, 1H), 6.39 (d, J = 2.3 Hz, 1H), 5.86-5.36 (m, 2H), 3.87 (s, 3H), 3.58-3.42 (m, 1H), 3.17 (t, J = 10.8 Hz, 2H), 3.07-2.84 (m, 1H), 2.19 (dd, J = 23.5, 9.1 Hz, 1H), 2.06 (dd, J = 10.4, 4.1 Hz, 1H), 1.92 (q, J = 11.0, 9.3 Hz, 2H). LC-MS: [M + H]⁺ = 517.0, 518.0. |
| 276 | 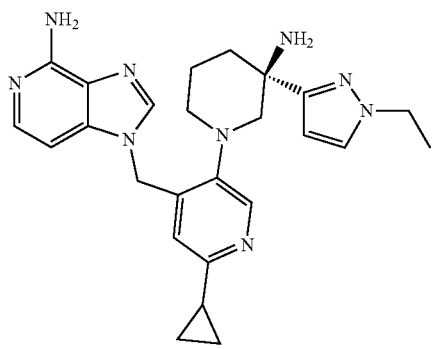 | ¹H NMR (400 MHz, CD₃OD) δ ppm 8.41-8.18 (m, 1H), 8.05 (s, 1H), 7.79-7.41 (m, 2H), 6.62 (d, J = 5.9 Hz, 1H), 6.50 (d, J = 4.6 Hz, 1H), 6.37 (d, J = 3.1 Hz, 1H), 5.67-5.41 (m, 2H), 4.13 (ddd, J = 13.9, 9.0, 5.2 Hz, 2H), 3.40 (s, 1H), 3.07 (s, 2H), 2.86 (s, 1H), 2.10 (d, J = 66.2 Hz, 2H), 1.96-1.73 (m, 2H), 1.37-1.28 (m, 4H), 0.99-0.66 (m, 4H). LC-MS: [M + H]⁺ = 458.3, 459.4. |
| 277 | 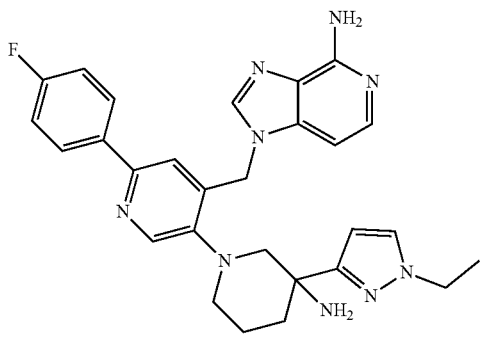 [SMILES: CCn1ccc(C2(N)CCCN(c3cnc(-c4ccc(F)cc4)cc3Cn3cnc4c(N)nccc43)C2)n1] | ¹H NMR (400 MHz, CD₃OD) δ ppm 8.52 (s, 1H), 8.13 (s, 1H), 7.75-7.64 (m, 3H), 7.59 (d, J = 2.0 Hz, 1H), 7.16-7.05 (m, 3H), 6.67 (d, J = 5.6 Hz, 1H), 6.41 (d, J = 2.0 Hz, 1H), 5.77-5.68 (m, 1H), 5.65-5.53 (m, 1H), 4.14 (q, J = 7.2 Hz, 2H), 3.57-3.46 (m, 1H), 3.25-3.14 (m, 2H), 3.03-2.92 (m, 1H), 2.32-2.19 (m, 1H), 2.16-2.04 (m, 1H), 2.02-1.83 (m, 2H), 1.39 (t, J = 7.2 Hz, 3H). LC-MS: [M + H]⁺ = 512.3. |
| 278 | 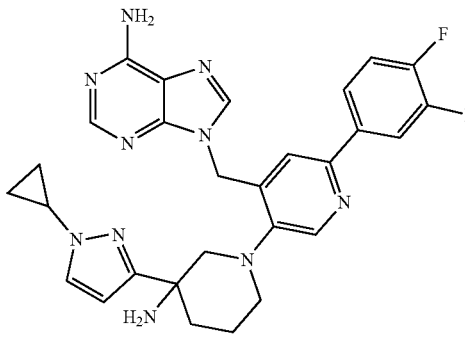 | ¹H NMR (400 MHz, CD₃OD) δ ppm 8.51 (s, 1H), 8.23 (s, 1H), 8.08 (br.s, 1H), 7.77-7.72 (m, 1H), 7.58 (d, J = 2.3 Hz, 1H), 7.54 (d, J = 6.8 Hz, 1H), 7.36 (s, 1H), 7.32-7.25 (m, 1H), 6.36 (d, J = 2.3 Hz, 1H), 5.69-5.59 (m, 2H), 3.61-3.55 (m, 1H), 3.46 (d, J = 11.5 Hz, 1H), 3.14 (d, J = 11.5 Hz, 2H), 2.94 (t, J = 9.5 Hz, 1H), 2.18-2.14 (m, 1H), 2.06-2.00 (m, 1H), 1.91-1.87 (m, 2H), 1.06-0.96 (m, 4H). LC-MS: [M + H]⁺ = 543.1. |

| Example # | Structure | ¹H NMR & LC-MS |
|---|---|---|
| 279 | 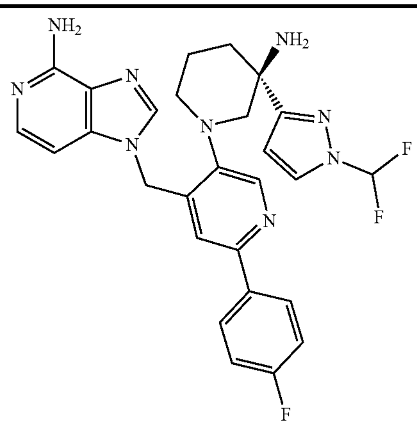 | ¹H NMR (400 MHz, CD₃OD) δ ppm 8.52 (s, 1H), 8.14 (s, 1H), 8.01 (d, J = 2.7 Hz, 1H), 7.74-7.61 (m, 3H), 7.43 (t, J = 59.8 Hz, 1H), 7.09 (dd, J = 17.5, 8.6 Hz, 3H), 6.65 (dd, J = 19.9, 4.4 Hz, 2H), 5.74-5.47 (m, 2H), 3.56 (d, J = 11.4 Hz, 1H), 3.18 (d, J = 11.2 Hz, 2H), 2.96 (t, J = 9.0 Hz, 1H), 2.26 (dd, J = 27.5, 15.2 Hz, 1H), 2.06 (s, 1H), 1.98-1.83 (m, 2H). LC-MS: [M + H]⁺ = 534.3, 535.3. |
| 280 | 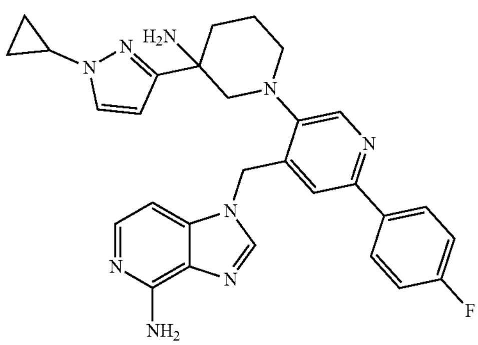 [SMILES: Nc1nccc2c1ncn2Cc1cc(-c2ccc(F)cc2)ncc1N1CCCC(N)(c2ccn(C3CC3)n2)C1] | ¹H NMR (400 MHz, CD₃OD): δ 8.50 (s, 1H), 8.12 (s, 1H), 7.71-7.66 (m, 3H), 7.58 (d, J = 2.3 Hz, 1H), 7.10 (t, J = 9.6 Hz, 3H), 6.66 (d, J = 6.0 Hz, 1H), 6.37 (d, J = 2.4 Hz, 1H), 5.73-5.56 (m, 2H), 3.58-3.49 (m, 2H), 3.19-3.12 (m, 2H), 2.98-2.93 (t, J = 8.8 Hz, 1H), 2.25-2.20 (m, 1H), 2.09-2.04 (m, 1H), 1.94-1.85 (m, 2H), 1.02-0.93 (m, 4H). LC-MS: [M + H]⁺ = 524.1 |
| 281 | 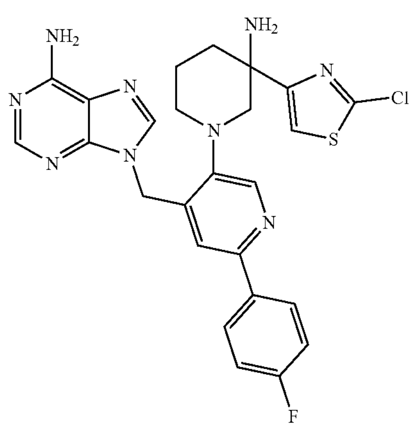 [SMILES: Nc1ncnc2c1ncn2Cc1cc(-c2ccc(F)cc2)ncc1N1CCCC(N)(c2csc(Cl)n2)C1] | ¹H NMR (400 MHz, CD₃OD): δ. 8.50 (s, 1H), 8.23 (s, 1H), 8.20 (s, 1H), 7.77-7.73 (m, 2H), 7.52 (s, 1H), 7.24 (s, 1H), 7.15-7.10 (m, 2H), 5.67-5.56 (m, 2H), 3.52-3.49 (m, 1H), 3.21-3.17 (m, 1H), 3.12-3.08 (m, 1H), 3.02-2.97 (m, 1H), 2.26-2.21 (m, 1H), 2.07-1.99 (m, 1H), 1.92-1.83 (m, 2H). LCMS: 536.3 [M + H]⁺. = 536.3 |
| 282 | 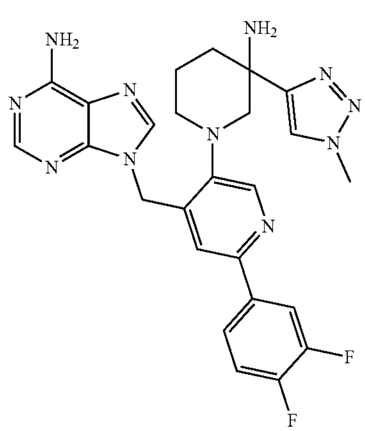 [SMILES: Cn1cc(C2(N)CCCN(c3cnc(-c4ccc(F)c(F)c4)cc3Cn3cnc4c(N)ncnc43)C2)nn1] | ¹H NMR (400 MHz, CD₃OD) δ ppm 8.51 (s, 1H), 8.23 (s, 1H), 8.17 (s, 1H), 7.98 (s, 1H), 7.73 (ddd, J = 2 Hz, 7.6 Hz, 11.6 Hz, 1H), 7.55-7.50 (m, 1H), 7.31-7.23 (m, 2H), 5.66-5.56 (m, 2H), 4.09 (s, 3H), 3.49 (d, J = 11.2 Hz, 1H), 3.23 (d, J = 11.2 Hz, 1H), 3.12-3.05 (m, 1H), 3.02-2.95 (m, 1H), 2.25-2.15 (m, 1H), 2.09-1.99 (m, 1H), 1.96-1.89 (m, 1H), 1.86-1.78 (m, 1H). LC-MS: [M + H]⁺ = 518.1. |

-continued

| Example # | Structure | ¹H NMR & LC-MS |
|---|---|---|
| 283 | 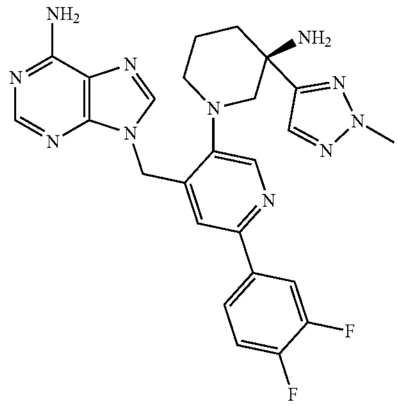 [SMILES: Cn1ncc([C@@]2(N)CCCN(c3cnc(-c4ccc(F)c(F)c4)cc3Cn3cnc4c(N)ncnc43)C2)n1] | ¹H NMR (400 MHz, CD₃OD) δ ppm 8.52 (s, 1H), 8.23 (s, 1H), 8.16 (s, 1H), 7.74 (ddd, J = 12.1, 7.8, 2.2 Hz, 1H), 7.53 (ddd, J = 8.0, 4.1, 2.0 Hz, 1H), 7.35 (s, 1H), 7.28 (dt, J = 10.4, 8.4 Hz, 1H), 6.31 (s, 1H), 5.61 (s, 2H), 3.46 (d, J = 11.4 Hz, 1H), 3.22 (d, J = 11.3 Hz, 1H), 3.12-3.05 (m, 1H), 2.97 (td, J = 11.8, 10.5, 3.2 Hz, 1H), 2.40 (s, 3H), 2.28-2.08 (m, 1H), 2.03 (d, J = 11.7 Hz, 1H), 1.98-1.80 (m, 2H). LC-MS: [M + H]⁺ = 517.8, 518.8. |
| 284 | 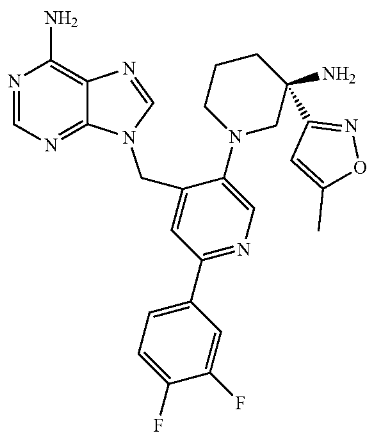 [SMILES: Cc1cc([C@@]2(N)CCCN(c3cnc(-c4ccc(F)c(F)c4)cc3Cn3cnc4c(N)ncnc43)C2)no1] | ¹H NMR (400 MHz, CD₃OD) δ ppm 8.52 (s, 1H), 8.23 (s, 1H), 8.16 (s, 1H), 7.74 (ddd, J = 12.1, 7.8, 2.2 Hz, 1H), 7.53 (ddd, J = 8.0, 4.1, 2.0 Hz, 1H), 7.35 (s, 1H), 7.28 (dt, J = 10.4, 8.4 Hz, 1H), 6.31 (s, 1H), 5.61 (s, 2H), 3.46 (d, J = 11.4 Hz, 1H), 3.22 (d, J = 11.3 Hz, 1H), 3.12-3.05 (m, 1H), 2.97 (td, J = 11.8, 10.5, 3.2 Hz, 1H), 2.40 (s, 3H), 2.28-2.08 (m, 1H), 2.03 (d, J = 11.7 Hz, 1H), 1.98-1.80 (m, 2H). LC-MS: [M + H]⁺ = 517.8, 518.8. |

Examples 285-291 were prepared following procedures analogous to those described in Example 47 from corresponding intermediates.

| Example # | Structure | ¹H NMR & MS |
|---|---|---|
| 285 | 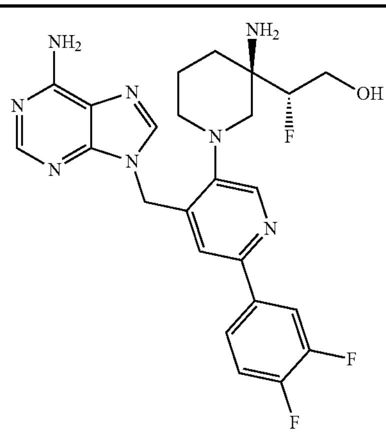 | ¹H NMR (400 MHz, CD₃OD) δ ppm 8.46 (s, 1H), 8.20 (d, J = 10.0 Hz, 2H), 7.75-7.66 (m, 1H), 7.49 (s, 1H), 7.24 (d, J = 10.2 Hz, 2H), 5.69-5.53 (m, 2H), 4.40 (s, 1H), 3.96-3.73 (m, 2H), 3.15 (d, J = 11.5 Hz, 1H), 2.98 (d, J = 11.3 Hz, 2H), 2.85 (t, J = 10.7 Hz, 1H), 1.92 (s, 1H), 1.75 (d, J = 12.0 Hz, 2H), 1.67 (s, 1H). LC-MS: [M + H]⁺ = 499.2. |

| Example # | Structure | ¹H NMR & MS |
|---|---|---|
| 286 | 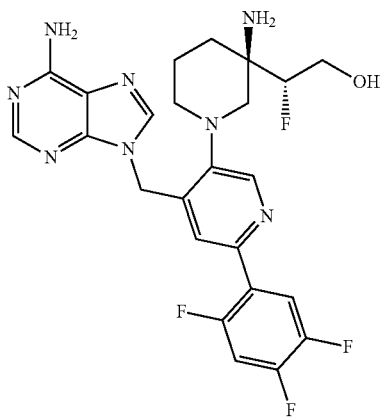 [SMILES: Nc1ncnc2c1ncn2Cc1cc(-c2cc(F)c(F)cc2F)ncc1N1CCC[C@](N)([C@@H](F)CO)C1] | ¹H NMR (400 MHz, CD₃OD) δ 8.54 (s, 1H), 8.21 (d, J = 11.9 Hz, 2H), 7.78 (ddd, J = 11.5, 9.1, 7.1 Hz, 1H), 7.17 (td, J = 10.5, 6.6 Hz, 1H), 7.13-7.11 (m, 1H), 5.71-5.63 (m, 2H), 4.62-4.43 (m, 1H), 4.01-3.81 (m, 2H), 3.21 (d, J = 11.3 Hz, 1H), 3.13-3.03 (m, 2H), 2.93 (t, J = 10.6 Hz, 1H), 2.08-1.96 (m, 1H), 1.82 (t, J = 10.7 Hz, 2H), 1.71 (d, J = 11.7 Hz, 1H). [M + H]⁺ = 517.1 |
| 287 | 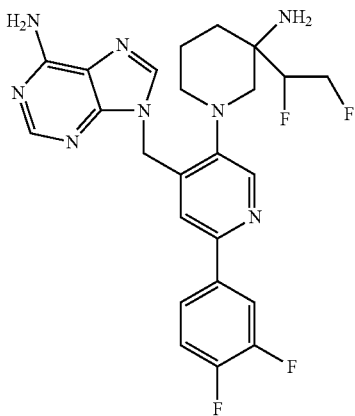 [SMILES: Nc1ncnc2c1ncn2Cc1cc(-c2ccc(F)c(F)c2)ncc1N1CCCC(N)(C(F)CF)C1] | ¹H NMR: (400 MHz, CD₃OD): δ 8.53-8.48 (m, 1H), 8.26-8.19 (m, 2H), 7.78-7.70 (m, 1H), 7.57-7.50 (m, 1H), 7.34-7.23 (m, 2H), 5.70-5.59 (m, 2H), 3.18 (brd, J = 11.1 Hz, 1H), 3.07-2.85 (m, 3H), 2.02-1.88 (m, 1H), 1.87-1.71 (m, 2H), 1.70-1.54 (m, 1H). LC-MS: [M + H]⁺ = 501.4. |
| 288 | 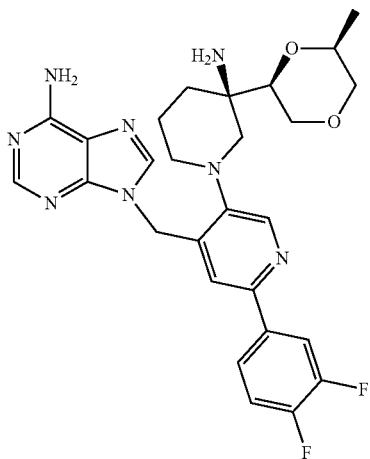 [SMILES: C[C@H]1COC[C@@H]([C@@]2(N)CCCN(c3cnc(-c4ccc(F)c(F)c4)cc3Cn3cnc4c(N)ncnc43)C2)O1] | ¹H NMR (400 MHz, CD₃OD) δ ppm 8.49 (s, 1H), 8.23 (s, 2H), 7.76 (m, 1H), 7.54 (m, 1H), 7.34 (s, 1H), 7.29 (m, 1H), 5.74-5.55 (m, 2H), 3.85 (m, 1H), 3.77-3.65 (m, 2H), 3.63-3.56 (m, 1H), 3.55-3.47 (m, 1H), 3.17-3.07 (m, 2H), 3.01 (m, 1H), 2.95 (m, 1H), 2.91-2.79 (m, 1H), 2.00-1.86 (m, 1H), 1.83-1.70 (m, 2H), 1.69-1.57 (m, 1H), 1.10 (d, J = 6.0 Hz, 3H). LC-MS: [M + H]⁺ = 537.4 |

-continued
| Example # | Structure | ¹H NMR & MS |
|---|---|---|
| 285 | 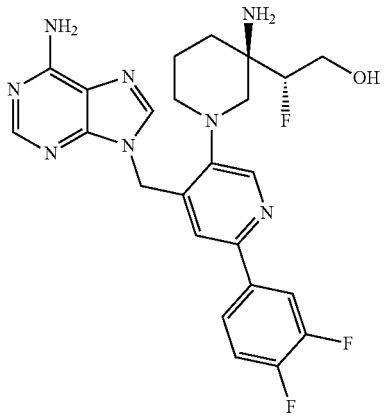 [SMILES: Nc1ncnc2c1ncn2Cc1cc(-c2ccc(F)c(F)c2)ncc1N1CCC[C@](N)([C@@H](F)CO)C1] | ¹H NMR (400 MHz, CD₃OD) δ ppm 8.46 (s, 1H), 8.20 (d, J = 10.0 Hz, 2H), 7.75-7.66 (m, 1H), 7.49 (s, 1H), 7.24 (d, J = 10.2 Hz, 2H), 5.69-5.53 (m, 2H), 4.40 (s, 1H), 3.96-3.73 (m, 2H), 3.15 (d, J = 11.5 Hz, 1H), 2.98 (d, J = 11.3 Hz, 2H), 2.85 (t, J = 10.7 Hz, 1H), 1.92 (s, 1H), 1.75 (d, J = 12.0 Hz, 2H), 1.67 (s, 1H). LC-MS: [M + H]⁺ = 499.2. |
| 290 | 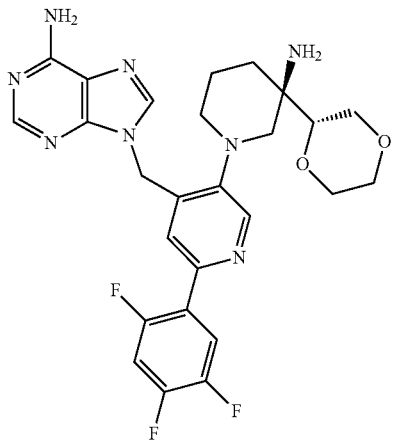 [SMILES: Nc1ncnc2c1ncn2Cc1cc(-c2cc(F)c(F)cc2F)ncc1N1CCC[C@](N)([C@@H]2COCCO2)C1] | ¹H NMR (400 MHz, CD₃OD) δ8.52 (s, 1H), 8.20 (s, 2H), 7.82-7.75 (m, 1H), 7.21-7.09 (m, 2H), 5.68-5.62 (m, 2H), 3.91-3.81 (m, 2H), 3.78-3.54 (m, 5H), 3.19-3.11 (m, 2H), 3.00-2.97 (M, 1H), 2.91-2.86 (m, 1 H). LC-MS: [M + H]⁺ = 541.4. |
| 291 | 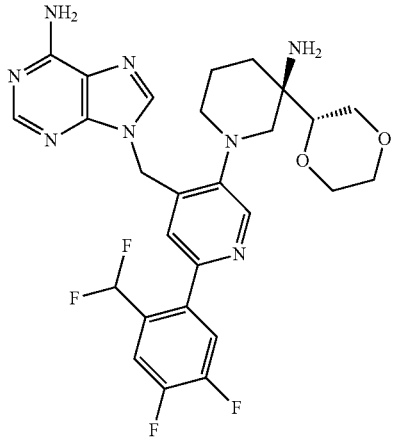 [SMILES: Nc1ncnc2c1ncn2Cc1cc(-c2cc(F)c(F)cc2C(F)F)ncc1N1CCC[C@](N)([C@@H]2COCCO2)C1] | ¹H NMR (, 400 MHz, CD₃OD): δ 8.64 (s, 1H), 8.30 (s, 1H), 8.22 (s, 1H), 7.65-7.60 (m, 1H), 7.44-7.40 (m, 1H), 7.09 (s, 1H), 7.01-6.74 (d, J1 = 54.8 Hz, J2 = 109.6 Hz, 1H), 5.72-5.62 (m, 2H), 4.00-3.95 (m, 2H), 3.84-3.60 (m, 5H), 3.45-3.42 (m, 1H), 3.35 (m, 1H), 3.13-3.10 (m, 1H), 2.99-2.90 (m, 1H), 2.05-1.85 (m, 4H). [M + H]⁺ = 573.4 |

| Example # | Structure | ¹H NMR & MS |
|---|---|---|
| 292 | 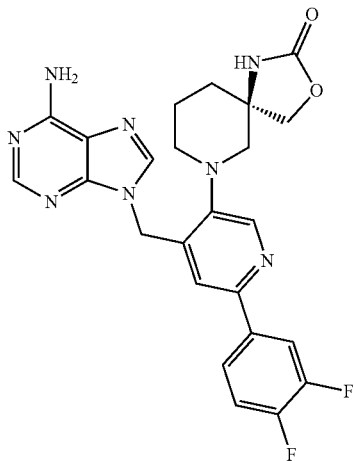 [SMILES: Nc1ncnc2c1ncn2Cc1cc(-c2ccc(F)c(F)c2)ncc1N1CCC[C@]2(COC(=O)N2)C1] | ¹H NMR (400 MHz, DMSO-d$_6$): δ 8.48 (s, 1H), 8.36 (brs, 1H), 8.26 (s, 1H), 8.14 (s, 1H), 7.90-7.80 (m, 1H), 7.65-7.57 (m, 1H), 7.46 (t, J = 8.8 Hz, 1H), 7.35-7.25 (m, 3H), 5.53 (s, 2H), 4.24 (d, J = 8.4 Hz, 1H), 4.07 (d, J = 8.8 Hz, 1H), 3.15-3.03 (m, 2H), 2.95-2.80 (m, 2H), 1.85-1.77 (m, 1H), 1.76-1.60 (m, 3H). LC-MS: [M + H]$^+$ = 493.2. |
| 293 | 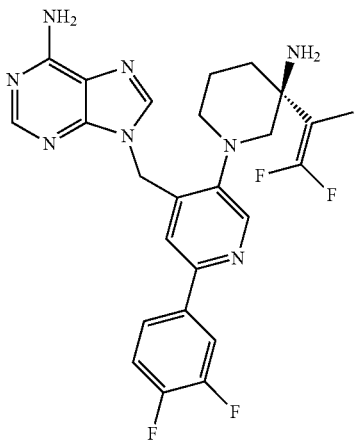 [SMILES: CC(=C(F)F)[C@@]1(N)CCCN(c2cnc(-c3ccc(F)c(F)c3)cc2Cn2cnc3c(N)ncnc32)C1] | ¹H NMR (400 MHz, CD$_3$OD) δ ppm 8.50 (s, 1H), 8.22 (d, J = 1.7 Hz, 2H), 7.75 (ddd, J = 12.0, 7.8, 2.2 Hz, 1H), 7.54 (d, J = 9.1 Hz, 1H), 7.39-7.07 (m, 2H), 6.00-5.41 (m, 2H), 3.25 (s, 1H), 3.13 (d, J = 11.3 Hz, 1H), 2.95 (dt, J = 20.7, 11.5 Hz, 2H), 2.10-1.79 (m, 3H), 1.71 (t, J = 3.4 Hz, 4H). LC-MS: [M + H]$^+$ = 513.3, 514.3. |
| 294 | 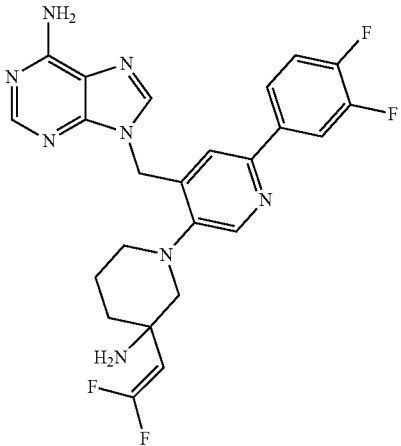 [SMILES: Nc1ncnc2c1ncn2Cc1cc(-c2ccc(F)c(F)c2)ncc1N1CCCC(N)(C=C(F)F)C1] | ¹H NMR (400 MHz, CD$_3$OD) δ ppm 8.49 (s, 1H), 8.21 (s, 2H), 7.78-7.70 (m, 1H), 7.57-7.49 (m, 1H), 7.35-7.25 (m, 2H), 5.72-5.55 (m, 2H), 4.70-4.60 (m, 1H), 3.20-2.90 (m, 4H), 2.00-1.70 (m, 4H). LC-MS: [M + H]$^+$ = 499.2. |

| Example # | Structure | ¹H NMR & MS |
|---|---|---|
| 295 | 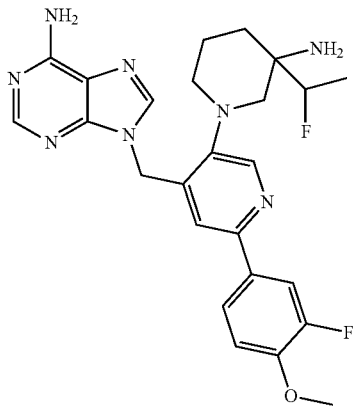 [SMILES: COc1ccc(-c2cc(Cn3cnc4c(N)ncnc43)c(N3CCCC(N)(C(C)F)C3)cn2)cc1F] | ¹H NMR (400 MHz, CD₃OD) δ ppm 8.48 (s, 1H), 8.26 (s, 2H), 7.69-7.35 (m, 2H), 7.23 (s, 1H), 7.13 (t, J = 8.6 Hz, 1H), 5.88-5.54 (m, 2H), 3.90 (s, 3H), 3.21-2.87 (m, 4H), 1.93 (dt, J = 9.1, 4.4 Hz, 1H), 1.78-1.48 (m, 3H), 1.39 (dd, J = 25.1, 6.4 Hz, 4H). LC-MS: [M + H]⁺ = 495.2, 496.2. |
| 296 | 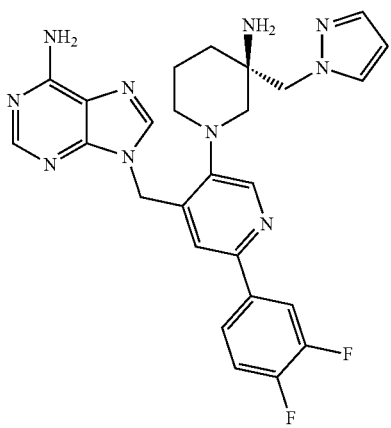 [SMILES: Nc1ncnc2c1ncn2Cc1cc(-c2ccc(F)c(F)c2)ncc1N1CCC[C@](N)(Cn2cccn2)C1] | ¹H NMR (400 MHz, CDCl₃) δ ppm 8.49 (s, 1H), 8.39 (s, 1H), 7.92 (s, 1H), 7.70-7.65 (m, 1H), 7.51 (s, 1H), 7.49-7.40 (m, 1H), 7.20-7.10 (m, 2H), 6.26 (s, 1H), 5.70-5.60 (m, 3H), 5.48 (d, J = 16 Hz, 1H), 4.45-4.35 (m, 1H), 4.19 (d, J = 14 Hz, 1H), 3.05-2.30 (m, 4H), 1.95-1.50 (m, 4H). LC-MS: [M + H]⁺ = 517.3. |
| 297 | 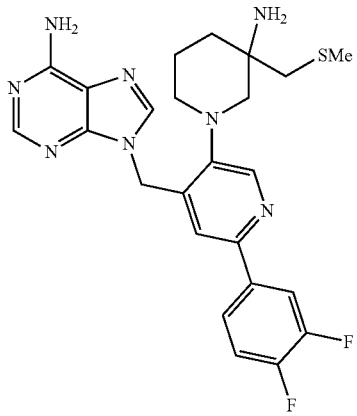 [SMILES: CSCC1(N)CCCN(c2cnc(-c3ccc(F)c(F)c3)cc2Cn2cnc3c(N)ncnc32)C1] | ¹H NMR (400 MHz, DMSO-d₆) δ ppm 8.50 (s, 1H), 8.30 (s, 1H), 8.13 (s, 1H), 7.90-7.80 (m, 1H), 7.63-7.55 (m, 1H), 7.52-7.42 (m, 1H), 7.36 (s, 1H), 7.28 (brs, 2H), 5.55 (s, 2H), 2.98-2.80 (m, 4H), 2.72 (s, 2H), 1.90-1.75 (m, 3H), 1.73-1.55 (m, 2H), 1.54-1.40 (m, 1H). LC-MS: [M + H]⁺ = 497.2. |

| Example # | Structure | ¹H NMR & MS |
|---|---|---|
| 298 | 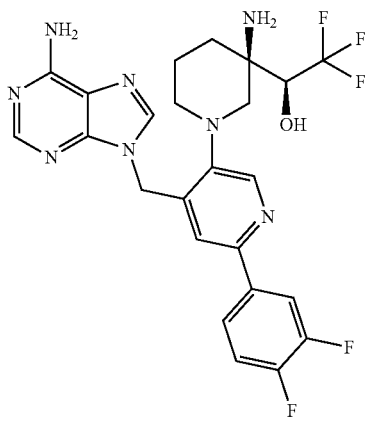 [SMILES: Nc1ncnc2c1ncn2Cc1cc(-c2ccc(F)c(F)c2)ncc1N1CCC[C@](N)([C@H](O)C(F)(F)F)C1] | ¹H NMR (400 MHz, DMSO-d$_6$): δ 8.49 (s, 1H), 8.29 (s, 1H), 8.15 (s, 1H), 7.95-7.82 (m, 1H), 7.65-7.60 (m, 1H), 7.51 (q, J = 8.8 Hz, 1H), 7.38 (s, 1H), 7.30 (brs, 2H), 5.56 (s, 2H), 3.60-3.40 (m, 2H), 3.11 (s, 3H), 3.10-2.97 (m, 2H), 2.95-2.80 (m, 2H), 2.48-2.10 (m, 1H), 1.95-1.50 (m, 4H). LC-MS: [M + H]$^+$ = 529.2 |
| 299 | 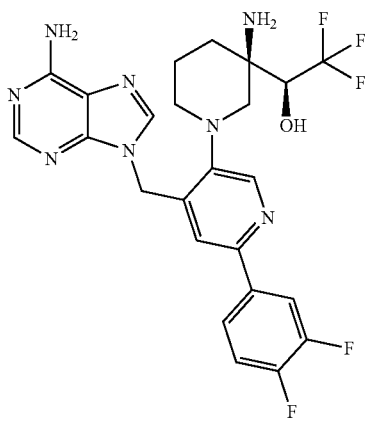 [SMILES: Nc1ncnc2c1ncn2Cc1cc(-c2ccc(F)c(F)c2)ncc1N1CCC[C@](N)([C@H](O)C(F)(F)F)C1] | ¹H NMR (400 MHz, CDCl$_3$) δ ppm 8.52 (s, 1H), 8.27 (s, 1H), 8.23 (s, 1H), 7.76-7.70 (m, 1H), 7.56-7.50 (m, 1H), 7.35-7.22 (m, 2H), 7.23-7.21 (m, 1H), 5.75-5.55 (m, 2H), 4.34 (s, 1H), 3.30-3.13 (m, 1H), 3.00 (s, 3H), 2.00-1.90 (m, 2H), 1.87-1.67 (m, 2H). LC-MS: [M + H]$^+$ = 535.4. |
| 300 | 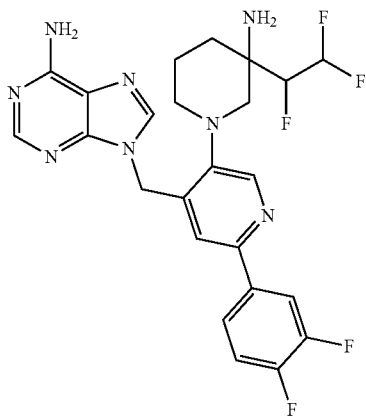 [SMILES: Nc1ncnc2c1ncn2Cc1cc(-c2ccc(F)c(F)c2)ncc1N1CCCC(N)(C(F)C(F)F)C1] | ¹H NMR (400 MHz, CD$_3$OD) δ 8.50 (d, J = 6.6 Hz, 1H), 8.27-8.20 (m, 2H), 7.75 (ddd, J = 12.0, 7.8, 2.2 Hz, 1H), 7.57-7.50 (m, 1H), 7.35-7.23 (m, 2H), 6.45-6.08 (m, 1H), 5.64 (d, J = 3.4 Hz, 2H), 4.89-4.41 (m, 1H), 3.21 (d, J = 11.4 Hz, 1H), 3.07-2.82 (m, 3H), 2.04-1.60 (m, 4H). LC-MS: [M + H]$^+$ = 519.2. |

Example 301: 3-amino-1-(4-((6-amino-9H-purin-9-yl)methyl)-6-(3,4-difluorophenyl)pyridin-3-yl)-3-(2,2-difluoroethyl)piperidin-4-ol

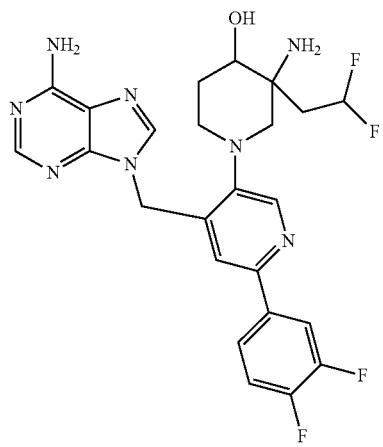 [SMILES: Nc1ncnc2c1ncn2Cc1cc(-c2ccc(F)c(F)c2)ncc1N1CCC(O)C(N)(CC(F)F)C1]

To a solution of Intermediate B (104 mg, 0.311 mmol) and intermediate 301-8 (130 mg, 0.311 mmol) in DMF (10 mL) was added K$_2$CO$_3$ (215 mg, 1.556 mmol) at rt under N$_2$ atmosphere, the reaction was stirred at RT for 18 hr. The reaction mixture was diluted with water, extracted with EtOAc (20 ml*3), the combined organic phase was washed with water (20 mL*3), brine (20 ml), dried over anhydrous sodium sulfate, concentrated in vacuum to give a residue. The residue was purified by flash chromatography (elution gradient: 0% to 10% MeOH in DCM in 30 mins) to afford intermediate 301-9. LC-MS: [M+H]$^+$=311.1.

To a solution of intermediate 301-9 (60 mg, 0.084 mmol) in DCM (9 mL) was added TFA (3 ml, 38.9 mmol) at RT under N$_2$ atmosphere, the reaction was stirred at RT for 2 hr. The reaction mixture was concentrated in vacuum to give a residue. The residue was purified by Pre-HPLC (Basic condition, NH$_3$H$_2$O %=0.05%, MeCN/H$_2$O=0-95% in 12 mins) to afford 3-amino-1-(4-((6-amino-9H-purin-9-yl)methyl)-6-(3,4-difluorophenyl)pyridin-3-yl)-3-(2,2-difluoroethyl)piperidin-4-ol (Example 301). $^1$H NMR (400 MHz, CD$_3$OD) δ 8.58 (s, 1H), 8.36 (s, 1H), 8.27 (s, 1H), 7.82 (ddd, J=11.2, 8.1, 2.2 Hz, 1H), 7.63 (dt, J=5.8, 2.9 Hz, 1H), 7.47 (s, 1H), 7.31 (dt, J=10.2, 8.4 Hz, 1H), 6.41 (tt, J=55.3, 4.7 Hz, 1H), 5.65 (s, 2H), 3.94 (dd, J=10.4, 5.3 Hz, 1H), 3.50-3.38 (m, 2H), 3.11-2.93 (m, 2H), 2.69-2.36 (m, 2H), 2.07 (dd, J=14.1, 4.8 Hz, 1H), 2.01-1.84 (m, 12H). LC-MS: [M+H]+=517.2.

Examples 302-310 were prepared following procedures analogous to the preparation of Example 47 and the corresponding intermediates.

| Example # | Structure | $^1$H NMR & MS |
|---|---|---|
| 302 | 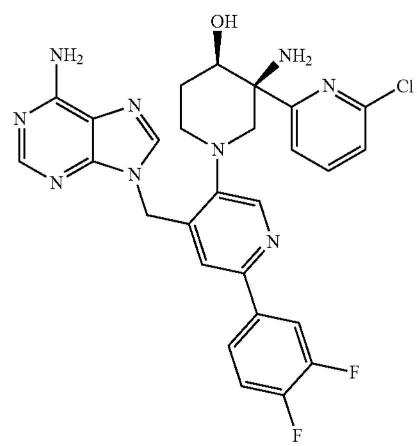 [SMILES: Nc1ncnc2c1ncn2Cc1cc(-c2ccc(F)c(F)c2)ncc1N1CC[C@@H](O)[C@](N)(c2cccc(Cl)n2)C1] | $^1$H NMR (400 MHz, CD$_3$OD) δ 8.54 (d, J = 5.6 Hz, 1H), 8.26 (d, J = 9.3 Hz, 2H), 7.83-7.68 (m, 3H), 7.52 (dddd, J = 8.6, 3.8, 2.2, 1.3 Hz, 1H), 7.33-7.23 (m, 3H), 5.79-5.61 (m, 2H), 4.39 (dd, J = 11.0, 5.1 Hz, 1H), 3.57 (d, J = 11.8 Hz, 1H), 3.18 (ddd, J = 7.2, 5.6, 2.4 Hz, 1H), 3.11 (td, J = 11.5, 2.7 Hz, 2H), 2.10-2.01 (m, 1H), 1.96 (ddt, J = 13.0, 5.7, 3.0 Hz, 1H). [M + H]$^+$ = 564.2. |
| 303 | 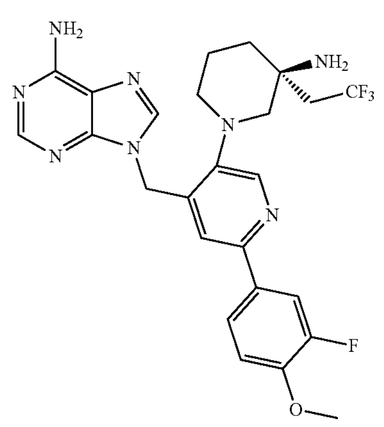 [SMILES: COc1ccc(-c2cc(Cn3cnc4c(N)ncnc43)c(N3CCC[C@](N)(CC(F)(F)F)C3)cn2)cc1F] | $^1$H NMR (CD$_3$OD) δ 8.46 (s, 1H), 8.24 (d, J = 8.7 Hz, 2H), 7.58 (dd, J = 12.8, 2.2 Hz, 1H), 7.48 (dt, J = 8.6, 1.6 Hz, 1H), 7.27 (s, 1H), 7.11 (t, J = 8.6 Hz, 1H), 5.81-5.51 (m, 2H), 3.89 (s, 3H), 3.15-2.80 (m, 4H), 2.68-2.35 (m, 2H), 1.93 (d, J = 11.3 Hz, 1H), 1.76 (dt, J = 11.9, 6.4 Hz, 3H). LC-MS: [M + H]$^+$ = 530.8. |

| Example # | Structure | ¹H NMR & MS |
|---|---|---|
| 304 | 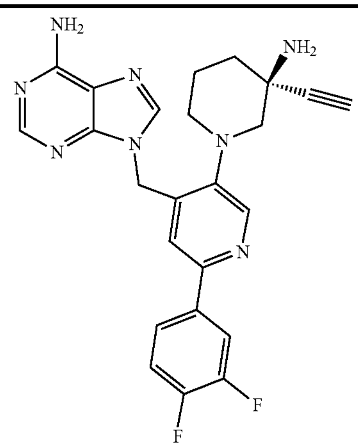 | ¹H NMR (400 MHz, CD₃OD) δ ppm 8.49 (s, 1H), 8.26 (d, J = 29.8 Hz, 2H), 7.73 (ddd, J = 11.3, 7.9, 2.0 Hz, 1H), 7.51 (q, J = 3.7 Hz, 1H), 7.43-7.12 (m, 2H), 5.95-5.47 (m, 2H), 3.35 (d, J = 11.6 Hz, 1H), 3.12 (d, J = 11.4 Hz, 1H), 3.01 (t, J = 9.8 Hz, 1H), 2.90 (d, J = 11.3 Hz, 1H), 2.84 (s, 1H), 1.98 (dd, J = 59.1, 12.9 Hz, 3H), 1.69 (t, J = 11.5 Hz, 1H). LC-MS: [M + H]⁺ = 461.2, 462.2. |
| 305 | 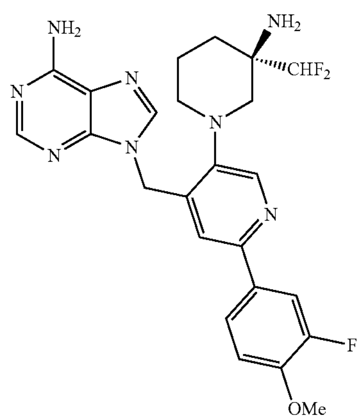 [SMILES: COc1ccc(-c2cc(Cn3cnc4c(N)ncnc43)c(N3CCC[C@](N)(C(F)F)C3)cn2)cc1F] | ¹H NMR (400 MHz, DMSO-d₆): δ 8.49 (s, 1H), 8.35 (s, 1H), 8.14 (s, 1H), 7.71 (d, J = 2.0 Hz, 1H), 7.68 (d, J = 2.0 Hz, 1H), 7.32 (s, 1H), 7.29 (brs, 2H), 7.24 (t, J = 8.8 Hz, 1H), 6.04 (t, J = 16.8 Hz, 1H), 5.53 (s, 2H), 3.86 (s, 3H), 3.05-2.80 (m, 4H), 2.05-1.85 (m, 3H), 1.75-1.60 (m, 2H), 1.55-1.43 (m, 1H). LC-MS: [M + H]⁺ = 499.2. |

Example 306: 9-((5-((3R,5R)-3-amino-5-(fluoromethyl)piperidin-1-yl)-2-(3-fluoro-4-methoxyphenyl)pyridin-4-yl)methyl)-9H-purin-6-amine To a mixture of tert-butyl (tert-butoxycarbonyl)(9-((5-((3R,5R)-3-((tert-butoxycarbonyl)amino)-5-(fluoromethyl)piperidin-1-yl)-2-(3-fluoro-4-15 methoxyphenyl)pyridin-4-yl)methyl)-9H-purin-6-yl)carbamate (Intermediate 306-9) (0.15 g, 0.19 mmol) in DCM (1 mL) was added HCl/Dioxane (10.0 mL, 4M), and the resulting mixture was stirred at 25° C. for 4 hours. The mixture was concentrated in vacuo. The residue was purified by prep-HPLC (0.1% NH₄HCO₃ as additive as additive) to afford 9-((5-((3R,5R)-3-amino-5-(fluoromethyl)piperidin-1-yl)-2-(3-fluoro-4-methoxyphenyl)pyridin-4-yl)methyl)-9H-purin-6-amine (Example 306). ¹H NMR (400 MHz, DMSO-d₆): δ 8.48 (s, 1H), 8.33 (s, 1H), 8.14 (s, 1H), 7.67 (dd, J=2.0 Hz, 12.8 Hz, 1H), 7.51 (d, J=8.8 Hz, 1H), 7.30 (brs, 2H), 7.34-7.17 (m, 2H), 5.54 (s, 2H), 4.64-4.37 (m, 2H), 3.85 (s, 3H), 3.18-3.03 (m, 3H), 2.92-2.77 (m, 2H), 2.48-2.32 (m, 1H), 1.68-1.49 (m, 2H). LC-MS: [M+Na]⁺=481.2

Example 307-310 were prepared following procedures analogous to the preparation of Example 306 and the corresponding intermediates.

| Example # | Structure | ¹H NMR & MS |
|---|---|---|
| 307 | 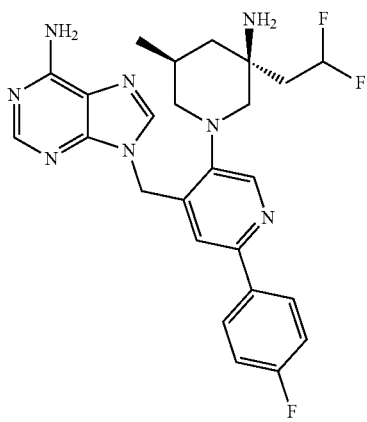 [SMILES: C[C@@H]1CN(c2cnc(-c3ccc(F)cc3)cc2Cn2cnc3c(N)ncnc32)C[C@@](N)(CC(F)F)C1] | ¹HNMR (400 MHz, CD$_3$OD): δ 8.47 (s, 1H), 8.22 (s, 1H), 8.13 (s, 1H), 7.79-7.75 (m, 2H), 7.24 (s, 1H), 7.16-7.12 (m, 2H), 6.14 (tt, J = 56.8 Hz, 4.0 Hz, 1H), 5.61 (s, 2H), 3.08-3.06 (m, 2H), 2.83-2.80 (m, 1H), 2.52-2.38 (m, 1H), 2.33-2.27 (m, 1H), 2.25-2.16 (m, 1H), 2.03-2.00 (m, 1H), 1.95-1.91 (m, 1H), 1.09-1.02 (m, 1H), 0.91 (d, J = 6.8 Hz, 3H). LC-MS: [M + H]$^+$ = 497.3 |
| 308 | 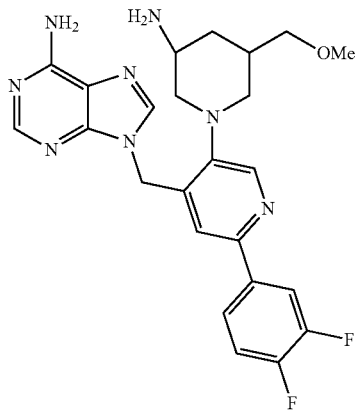 [SMILES: COCC1CC(N)CN(c2cnc(-c3ccc(F)c(F)c3)cc2Cn2cnc3c(N)ncnc32)C1] | ¹HNMR (400 MHz, DMSO-d$_6$): δ 8.48 (s, 1H), 8.32 (s, 1H), 8.13 (s, 1H), 7.90-7.80 (m, 1H), 7.63-7.55 (m, 1H), 7.47 (q, J = 8.4 Hz, 1H), 7.33 (s, 1H), 7.29 (brs, 2H), 5.54 (d, J = 2.0 Hz, 2H), 3.35-3.10 (m, 4H), 3.09-2.95 (m, 4H), 2.87-2.75 (m, 2H), 2.35-2.20 (m, 1H), 1.60-1.44 (m, 2H). LC-MS: [M + H]$^+$ = 481.2. |
| 309 | 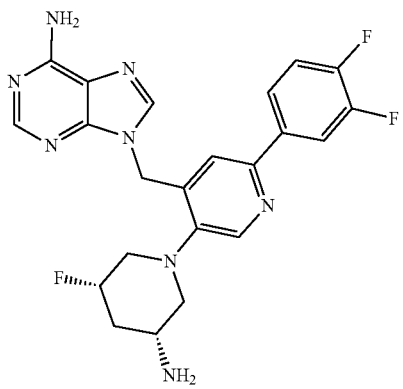 [SMILES: Nc1ncnc2c1ncn2Cc1cc(-c2ccc(F)c(F)c2)ncc1N1C[C@H](N)C[C@H](F)C1] | ¹H NMR (400 MHz, CD$_3$OD): δ 8.51 (s, 1H), 8.21 (s, 1H), 8.20 (s, 1H), 7.72 (ddd, J = 2.4 Hz, 8 Hz, 10 Hz, 1H), 7.54-7.47 (m, 1H), 7.32-7.22 (m, 2H), 5.72-5.55 (m, 2H), 4.81-4.75 (m, 1H), 3.39-3.34 (m, 1H), 3.28-3.25 (m, 1H), 3.17-3.07 (m, 2H), 2.91-2.80 (m, 1H), 2.36-2.24 (m, 1H), 1.80-1.65 (m, 1H). LC-MS: [M + H]$^+$ = 455.2. |

| Example # | Structure | ¹H NMR & MS |
|---|---|---|
| 310 | 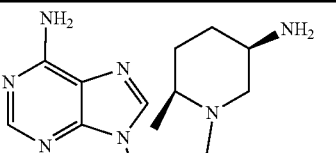 | ¹H NMR (400 MHz, CD₃OD): δ 8.55 (s, 1H), 8.28 (s, 1H), 8.21 (s, 1H), 7.88-7.81 (m, 1H), 7.69-7.64 (m, 1H), 7.61 (s, 1H), 7.37-7.29 (m, 1H), 5.80 (d, J = 15.6 Hz, 1H), 5.37 (d, J = 15.6 Hz, 1H), 3.28-3.24 (m, 2H), 3.17-3.08 (m, 2H), 1.95-1.72 (m, 4H), 1.60-1.45 (m, 1H), 0.95-0.81 (m, 2H), 0.61 (d, J = 6 Hz, 3H). LC-MS: [M + H]⁺ = 451.1. |

Example 311-321 were prepared following procedures analogous to the preparation of Example 47 and the corresponding intermediates.

| Example # | Structure | ¹H NMR & MS |
|---|---|---|
| 311 | 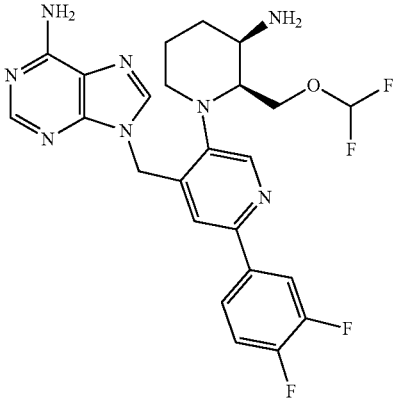 [SMILES: Nc1ncnc2c1ncn2Cc1cc(-c2ccc(F)c(F)c2)ncc1N1CCC[C@@H](N)[C@H]1COC(F)F] | ¹H NMR (400 MHz, CD₃OD) δ 8.61 (s, 1H), 8.24 (s, 1H), 8.16 (s, 1H), 7.80 (ddd, J = 12.1, 7.8, 2.2 Hz, 1H), 7.64-7.57 (m, 1H), 7.47 (s, 1H), 7.31 (dt, J = 10.4, 8.4 Hz, 1H), 6.21 (t, J = 75.3 Hz, 1H), 5.72-5.50 (m, 2H), 3.99-3.85 (m, 2H), 3.54 (td, J = 5.8, 3.1 Hz, 1H), 3.25 (dt, J = 6.7, 3.5 Hz, 1H), 3.00-2.84 (m, 2H), 1.76 (ddd, J = 15.8, 10.3, 5.7 Hz, 3H), 1.60-1.47 (m, 1H). LC-MS: [M + H]⁺ = 517.2. |
| 312 | 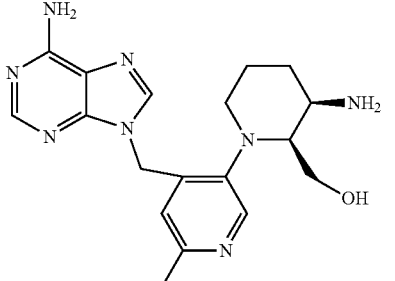 | ¹H NMR (CD₃OD): δ 8.62 (s, 1H), 8.21 (d, J = 36.6 Hz, 2H), 7.83 (ddd, J = 12.0, 7.8, 2.2 Hz, 1H), 7.72-7.51 (m, 2H), 7.32 (dt, J = 10.3, 8.5 Hz, 1H), 5.79 (d, J = 15.6 Hz, 1H), 5.54 (d, J = 15.5 Hz, 1H), 3.72-3.45 (m, 2H), 3.43-3.31 (m, 2H), 3.00-2.71 (m, 2H), 1.87-1.75 (m, 2H), 1.73-1.43 (m, 2H) LC-MS: [M + H]⁺ = 467.2. |

-continued
| Example # | Structure | ¹H NMR & MS |
|---|---|---|
| 313 | 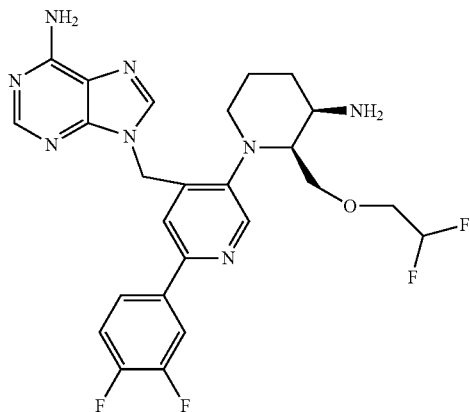 [SMILES: Nc1ncnc2c1ncn2Cc1cc(-c2ccc(F)c(F)c2)ncc1N1CCC[C@@H](N)[C@H]1COCC(F)F] | ¹H NMR (DMSO-d₆): δ 8.60 (d, J = 5.0 Hz, 1H), 8.19 (dd, J = 44.6, 5.3 Hz, 2H), 7.89-7.14 (m, 4H), 5.95-5.36 (m, 3H), 3.70-3.36 (m, 5H), 3.24 (s, 1H), 2.98-2.68 (m, 2H), 1.98-1.41 (m, 4H). LC-MS: [M + H]⁺ = 531.2. |
| 314 | 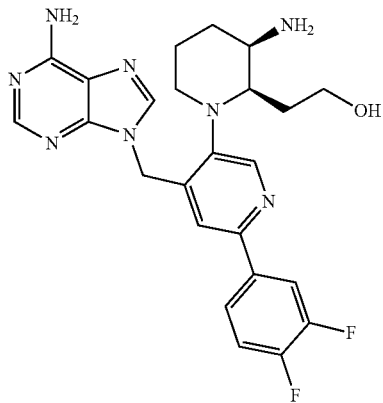 [SMILES: Nc1ncnc2c1ncn2Cc1cc(-c2ccc(F)c(F)c2)ncc1N1CCC[C@@H](N)[C@H]1CCO] | ¹H NMR (400 MHz, CD₃OD): δ 8.58 (d, J = 17.0 Hz, 2H), 8.27 (t, J = 17.6 Hz, 2H), 7.84 (ddd, J = 11.9, 7.8, 2.1 Hz, 1H), 7.64 (dd, J = 11.4, 4.7 Hz, 1H), 7.54 (s, 1H), 7.39-7.28 (m, 1H), 5.79-5.61 (m, 1H), 5.52 (t, J = 20.8 Hz, 1H), 3.67-3.36 (m, 5H), 2.91 (d, J = 11.9 Hz, 1H), 2.24 (d, J = 13.8 Hz, 1H), 1.91 (dd, J = 31.4, 16.3 Hz, 4H). LC-MS: [M + H]⁺ = 481.1. |
| 315 | 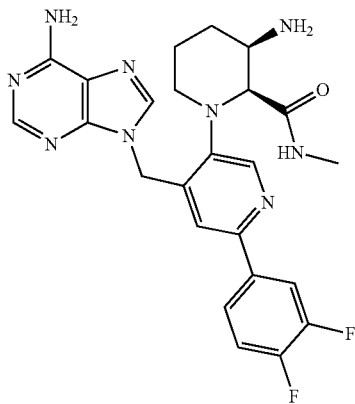 [SMILES: CNC(=O)[C@@H]1[C@H](N)CCCN1c1cnc(-c2ccc(F)c(F)c2)cc1Cn1cnc2c(N)ncnc21] | ¹H NMR (400 MHz, CD₃OD): δ 8.47 (s, 1H), 8.27 (d, J = 3.0 Hz, 2H), 7.78 (ddd, J = 12.0, 7.8, 2.2 Hz, 1H), 7.58 (ddd, J = 10.4, 5.0, 2.4 Hz, 1H), 7.46 (s, 1H), 7.30 (dt, J = 10.4, 8.4 Hz, 1H), 5.74 (q, J = 15.8 Hz, 2H), 3.94 (d, J = 2.8 Hz, 1H), 3.25 (q, J = 2.8 Hz, 1H), 3.02 (d, J = 11.7 Hz, 1H), 2.75 (t, J = 9.9 Hz, 1H), 2.57 (s, 3H), 1.93 (d, J = 3.4 Hz, 1H), 1.79 (d, J = 9.2 Hz, 2H), 1.53 (d, J = 8.4 Hz, 1H). LC-MS: [M + H]⁺ = 494.1. |

| Example # | Structure | ¹H NMR & MS |
|---|---|---|
| 316 | 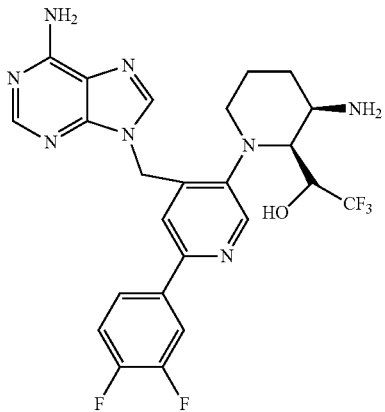 [SMILES: Nc1ncnc2c1ncn2Cc1cc(-c2ccc(F)c(F)c2)ncc1N1CCC[C@@H](N)[C@H]1C(O)C(F)(F)F] | ¹H NMR (CD₃OD): δ 8.59 (s, 1H), 8.24 (s, 1H), 8.07 (s, 1H), 7.70 (ddd, J = 12.1, 7.8, 2.2 Hz, 1H), 7.53-7.34 (m, 1H), 7.37-7.17 (m, 2H), 5.78-5.44 (m, 2H), 4.59 (qd, J = 8.4, 3.1 Hz, 1H), 3.82 (dd, J = 11.7, 3.4 Hz, 1H), 3.66 (dd, J = 4.9, 3.2 Hz, 1H), 3.37 (dd, J = 11.9, 6.3 Hz, 1H), 3.03 (dt, J = 11.8, 4.3 Hz, 1H), 1.92-1.61 (m, 4H). . LC-MS: [M + H]⁺ = 535.2. |
| 317 | 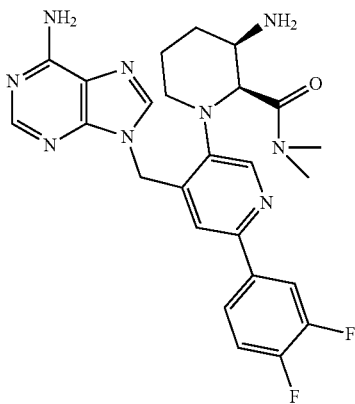 [SMILES: CN(C)C(=O)[C@@H]1[C@H](N)CCCN1c1cnc(-c2ccc(F)c(F)c2)cc1Cn1cnc2c(N)ncnc21] | ¹H NMR (400 MHz, CDOD): δ 8.46 (s, 1H), 8.27 (d, J = 9.7 Hz, 2H), 7.79 (ddd, J = 12.0, 7.8, 2.2 Hz, 1H), 7.63-7.54 (m, 1H), 7.48 (s, 1H), 7.30 (dt, J = 10.4, 8.4 Hz, 1H), 5.79 (dd, J = 99.4, 15.7 Hz,2H), 4.62 (d, J = 2.5 Hz, 1H), 3.27 (d, J = 4.4 Hz, 1H), 3.20-3.09 (m, 3H), 2.95 (s, 16H), 2.80 (s, 5H), 2.01-1.88 (m, 1H), 1.82 (td, J = 12.4, 3.8 Hz, 1H), 1.71 (d, J = 11.9 Hz, 1H), 1.52-1.40 (m, 1H).. LC-MS: [M + H]⁺ = 508.2 |
| 318 | 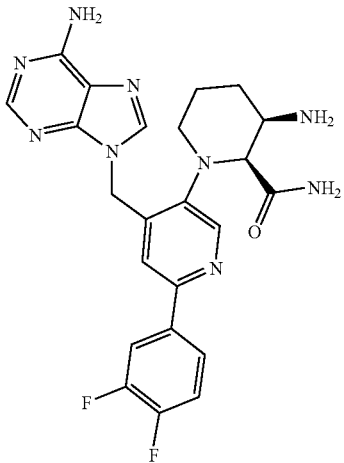 [SMILES: NC(=O)[C@@H]1[C@H](N)CCCN1c1cnc(-c2ccc(F)c(F)c2)cc1Cn1cnc2c(N)ncnc21] | ¹H NMR (CD₃OD): δ 8.53 (d, J = 12.3 Hz, 1H), 8.25 (d, J = 10.5 Hz, 2H), 7.84-7.70 (m, 1H), 7.67-7.53 (m, 1H), 7.46 (s, 1H), 7.30 (dt, J = 10.4, 8.4 Hz, 1H), 5.86-5.50 (m, 2H), 4.03 (d, J = 2.7 Hz, 1H), 3.48 (p, J = 1.7 Hz, 1H), 3.13 (p, J = 1.6 Hz, 1H), 2.98-2.71 (m, 1H), 1.93 (s, 1H), 1.81 (s, 2H), 1.53 (s, 1H) LC-MS: [M + H]⁺ = 480.1. |

-continued
| Example # | Structure | ¹H NMR & MS |
|---|---|---|
| 319 | 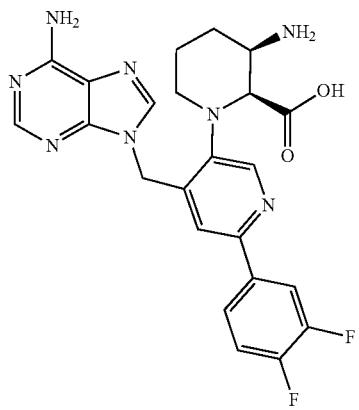 [SMILES: Nc1ncnc2c1ncn2Cc1cc(-c2ccc(F)c(F)c2)ncc1N1CCC[C@@H](N)[C@H]1C(=O)O] | ¹H NMR (400 MHz, DMSO-d$_6$): δ 8.57 (s, 1H), 8.26 (s, 1H), 8.15 (s, 1H), 7.89-7.71 (m, 1H), 7.56-7.49 (m, 1H), 7.49-7.39 (m, 1H), 7.29 (s, 2H), 7.11 (br s, 1H), 5.59-5.33 (m, 2H), 3.71 (brd, J = 2.9 Hz, 1H), 3.60-3.50 (m, 1H), 3.05-2.90 (m, 2H), 2.00-1.85 (m, 1H), 1.85-1.70 m, 1H),1.65-1.47 (m, 2H) LC-MS: [M + H]$^+$ = 481.3 |
| 320 | 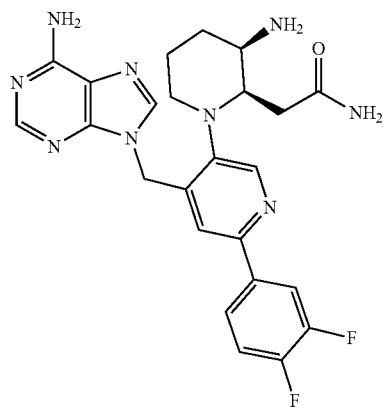 [SMILES: NC(=O)C[C@@H]1[C@H](N)CCCN1c1cnc(-c2ccc(F)c(F)c2)cc1Cn1cnc2c(N)ncnc21] | ¹H NMR (CD$_3$OD): δ 8.54 (d, J = 7.8 Hz, 1H), 8.28 (d, J = 4.6 Hz, 1H), 8.17 (d, J = 3.7 Hz, 1H), 7.85-7.60 (m, 1H), 7.58-7.39 (m, 1H), 7.36-7.02 (m, 2H), 5.92-5.39 (m, 2H), 4.28-3.96 (m, 1H), 3.72-3.40 (m, 2H), 3.20-2.90 (m, 1H), 2.69-2.14 (m, 2H), 2.21-1.76 (m, 4H). LC-MS: [M + H]$^+$ = 494.1 |
| 321 | 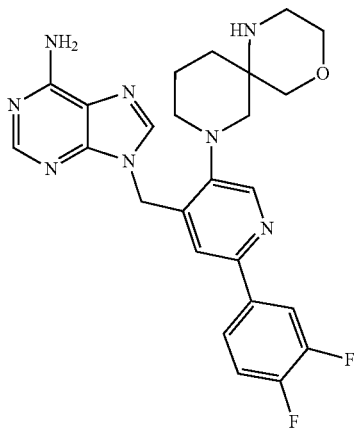 [SMILES: Nc1ncnc2c1ncn2Cc1cc(-c2ccc(F)c(F)c2)ncc1N1CCCC2(COCCN2)C1] | ¹HNMR (400 MHz, DMSO-d$_6$): δ 8.55 (s, 1H), 8.27 (s, 1H), 8.15 (s, 1H), 7.98-7.85 (m, 1H), 7.70-7.60 (m, 1H), 7.57-7.45 (m, 1H), 7.42 (s, 1H), 7.33 (brs, 2H), 5.54 (s, 2H), 3.85-3.50 (m, 3H), 3.49-3.37 (m, 1H), 3.28-3.13 (m, 1H), 3.10-2.70 (m, 5H), 1.85-1.48 (m, 4H). LC-MS: [M + H]$^+$ = 493.2. |

Example 322: (S)-3-(3-amino-1-(4-((6-amino-9H-purin-9-yl)methyl)-6-(3,4-difluorophenyl)pyridin-3-yl)piperidin-3-yl)-N,N-dimethylpropanamide

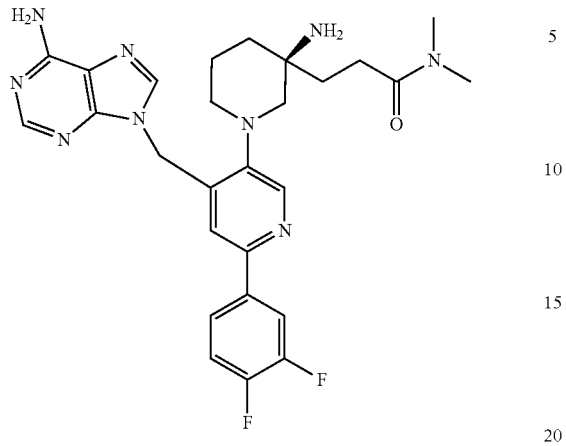

Example 322 was prepared following procedures analogous to the preparation of Example 89 and the corresponding intermediate. $^1$H NMR (400 MHz, CD$_3$OD) δ: 8.50 (s, 1H), 8.24 (d, J=10.8 Hz, 2H), 7.73 (ddd, J=12.3, 7.7, 2.3 Hz, 1H), 7.51 (t, J=5.7 Hz, 1H), 7.28 (d, J=8.5 Hz, 2H), 5.85-5.51 (m, 2H), 3.10 (s, 3H), 2.99 (d, J=19.4 Hz, 4H), 2.93 (s, 3H), 2.53 (t, J=8.1 Hz, 2H), 2.08-1.71 (m, 4H), 1.71-1.41 (m, 2H). LC-MS: [M+H]$^+$=535.8, 536.8.

Example 323-325 were prepared following procedures analogous to the preparation of Example 1 and the corresponding intermediates.

| Example # | Structure | $^1$H NMR & MS |
|---|---|---|
| 323 | 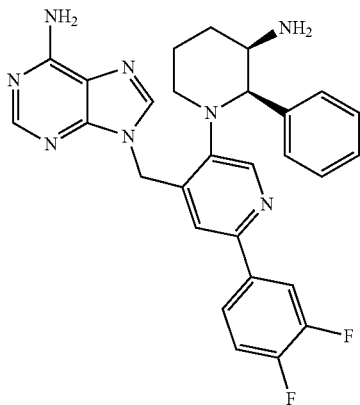 [SMILES: Nc1ncnc2c1ncn2Cc1cc(-c2ccc(F)c(F)c2)ncc1N1CCC[C@@H](N)[C@H]1c1ccccc1] | $^1$HNMR (400 MHz, CD$_3$OD): δ d 8.51 (s, 2H), 8.44 (s, 1H), 8.27 (s, 1H), 8.16 (s, 1H), 7.68 (ddd, J = 2.0, 8.0, 12.0 Hz, 1H), 7.53-7.47 (m, 1H), 7.39-7.33 (m, 3H), 7.29-7.23 (m, 3H), 7.23-7.17 (m, 1H), 5.61 (s, 2H), 4.20 (d, J = 9.6 Hz, 1H), 3.53-3.44 (m, 1H), 3.18-3.07 (m, 1H), 2.94-2.85 (m, 1H), 2.39-2.27 (m, 1H), 2.07-1.87 (m, 2H), 1.81-1.71 (m, 1H). LC-MS: [M + H]$^+$ = 513.2. |
| 324 | 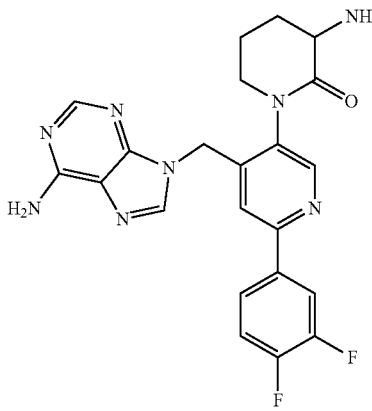 | $^1$HNMR (400 MHz, CD$_3$OD): δ 8.57 (s, 1H), 8.23 (s, 0.4H), 8.22 (s, 1H), 8.15 (s, 0.6H), 7.94-7.83 (m, 1H), 7.77-7.63 (m, 1.6H), 7.58 (s, 0.4H), 7.40-7.28 (m, 1H), 7.52-7.46 (m, 1H), 5.34 (d, J = 15.6 Hz, 1H), 3.86-3.75 (m, 1H), 3.60-3.51 (m, 1H), 3.48-3.41 (m, 0.6H), 3.36-3.34 (m, 0.4H), 2.29-1.72 (m, 4H). LC-MS: [M + H]$^+$ = 451.1. |

-continued

| Example # | Structure | ¹H NMR & MS |
|---|---|---|
| 325 | 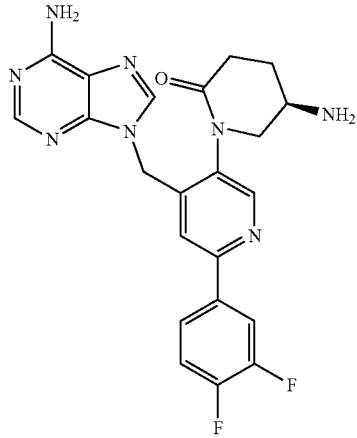 [SMILES: Nc1ncnc2c1ncn2Cc1cc(-c2ccc(F)c(F)c2)ncc1N1C[C@H](N)CCC1=O] | ¹H NMR (400 MHz, CD$_3$OD): δ 8.29 (d, J = 9.8 Hz, 2H), 8.13 (s, 1H), 7.72 (ddd, J = 12.3, 7.8, 2.2 Hz, 1H), 7.60-7.54 (m, 1H), 7.49 (s, 1H), 7.27 (dt, J = 10.4, 8.4 Hz, 1H), 5.42 (d, J = 2.0 Hz, 2H), 4.15-3.93 (m, 1H), 3.40 (qd, J = 13.1, 6.0 Hz, 2H), 2.53-2.23 (m, 3H), 2.04-1.80 (m, 1H) LC-MS: [M + H]$^+$= 450.9. |

Biological Assays

The compounds of the present invention may be evaluated for their ability to inhibit NSD2 using assays described below, as well as other assays known in the art.

LC-MS/MS-Based NSD2 Enzymatic Assay

This assay employed LC-MS/MS technology to monitor the SAH production from the NSD2 enzymatic reaction. The enzymatic reaction was performed in white proxiplate plus 384-well microplate (Perkin Elmer). The reaction mixture (10 µL) was composed of 8 nM NSD2 [1-1365], 1 M SAM (USB, 10601) and 400 nM nucleosome (purified from mouse liver) in reaction buffer (20 mM Tris-HCl, pH at 8.0, 0.01% Tween 20, 10 mM MgCl2, 50 mM NaCl, 1 mM DTT, 1 mM TCEP (pH7.5)). After 90 min incubation at room temperature, 3 µL quenching solution containing 2.5% TFA with 320 nM d4-SAH was added to stop the reaction.

For the inhibition assay, compound solutions were transferred into the wells by Mosquito™ (TTP LabTech). The inhibition assays were carried out by preincubating various concentrations of the inhibitor with 5 uL reaction mixture containing 16 nM NSD2 [1-1365] and 2 uM SAM (USB, 10601) in reaction buffer. After 20 min preincubation, 5 uL solution containing 800 nM nucleosome (purified from mouse liver) in reaction buffer was added to initiate the reaction. The reaction was stopped by 3 µL quenching solution containing 2.5% TFA with 320 nM d4-SAH after 90 min.

The SAH production from the enzymatic assays were monitored by LC-MS/MS on an API 4000 triple quadrupole mass spec with Turbolon Spray (Applied Biosystem) coupled with Prominenece UFLC(Shimazu). Liquid chromatography was performed on a Chromolith FastGradient HPLC column (RP-18e, 25-2 mm, from Merck) at a flow rate of 0.8 ml/min. The column was connected directly to the turbo ion electrospray operating in the positive-ion mode. Mobile phase A is 0.1% FA and 2% methanol in water and mobile phase B is 0.1% FA in ACN. Injection volume was 3 µl and the autosampler was kept at 4 degrees. SAH and d4-SAH were simultaneously monitored. Data were acquired and processed by Analyst software.

To quantify the formed SAH, d4-SAH was added as internal standard (IS). A series of SAH (Sigma, A9384) solution at varying concentration (1-500 nM in reaction buffer) was mixed with quenching solution mentioned above. Then LC-MS/MS was carried out on API 4000 LC/MS/MS system to detect both SAH and d4-SAH. The plot of SAH peak area/IS peak area vs SAH concentration was used to generate the normalization factor of SAH. The SAH production from real enzymatic reaction was derived from the standard curve of SAH. The down-limit of our system for the detection of SAH is around 1-2 nM, and the linear range can reach up to 500 nM.

In one embodiment, the compounds of the invention have an NSD2 IC$_{50}$<0.01 µM. In particular embodiments, the compounds of the invention have an NSD2 IC$_{50}$ between 0.001 µM and 0.01 µM, as exemplified in Table 2 ("+++"). In another embodiment, the compounds of the invention have an NSD2 IC$_{50}$<1 µM. In particular embodiments, the compounds of the invention have an NSD2 IC$_{50}$ between 0.01 and 1 µM., as exemplified in Table 2 ("++"). In yet another embodiment, the compounds of the invention have an NSD2 IC$_{50}$>1 µM, as exemplified in Table 2 ("+").

H3K36me2 cellular FRET assay in KMS11-Par line

Fluorescence Resonance Energy Transfer (FRET) assay was used to test the ability of candidate compound to reduce cellular H3K36me2 level in multiple myeloma cell line KMS11 (t(4;14)+) (Horizon Discovery Ltd.). Cells are maintained in RPM11640 media with 12.5% FBS and 50 U/ml Penicillin-Streptomycin. For assay compound treatment, single cell suspension was prepared in Opti-MEM supplemented with B-27 and N2 supplement (Invitrogen 11058-021, 17504-044, 17502-048). One day prior to cell treatment, 5,000 KMS11 cells were seeded into PDL coated TC plate (PerkinElmer #6007718) at the final volume of 30 µL/well.

Cells were treated with tested compounds at the desired concentration for 48 hours. Crude histone lysate was extracted by 0.4M HCl following neutralization by 0.5M Sodium phosphate, dibasic (Na2HPO4), pH ~12.5. Histone extract was incubated with Eu labeled anti-H3K36me2 antibody (abcam #ab ab9049) and d2 labeled anti-H3 antibody (abcam #ab1791) for 1 hour at room temperature. A Eu labeled anti-H3 antibody (CISBIO #64CUS000) was used for loading control. The abundancy of H3K36me2 or total H3 was measured by fluorescence signal on Perkin Elmer Envison machine.

H3K36Me2 Cellular ELISA Assay in CGTH-W-1 Line

An ELISA (enzyme-linked immunosorbent assay) based assay was used to test the ability of candidate compound to reduce cellular H3K36me2 level in thyroid carcinoma cell line CGTH-W-1, carrying NSD2 E1099K gain of function mutation. CGTH-W-1 (DSMZ) cells are maintained in RPM11640 media with 10% FBS and 50 U/ml Penicillin-Streptomycin. For assay compound treatment, single cell suspension was prepared in Opti-MEM supplemented with B-27 and N2 supplement (Invitrogen 11058-021, 17504-044, 17502-048) for ELISA and in maintenance media for cellTiter Glo (CTG) viability assay. One day prior to cell treatment, 500 CGTH-W-1 cells were seeded into 384-well Greiner CellStar TC plate (Greiner #781086) at the final volume of 30 µL/well.

Cells were treated with tested compounds at the desired concentration for 72 hours. Crude histone lysate was extracted by 0.4M HCl following neutralization by 0.5M Sodium phosphate, dibasic ($Na_2HPO_4$), pH ~12.5. Equal amount of histone lysate was loaded to Corning 384-well high biding plate (Corning #3577, black) for H3K36me2 and to Thermo 384-well high binding Nunc plate (Thermo #460372, white) for total H3 as loading control.

Histone bound plates were washed and blocked with 5% BSA. H3K36me2 and total H3 was detected by primary antibodies (H3K36me2 Abcam, #ab9049; total H3 Cell Signaling, #4499L) and further revealed by horseradish peroxidase (HRP) conjugated secondary antibody and ECL substrate. The abundance of H3K36me2 and total H3 was measured by Chemiluminesce on a plate reader. Cell viability was monitored on a parallel seeded plate with CellTiter-Glo reagent (Promega #G7573).

H3K36Me2 Cellular ELISA Assay in KMS11-Par Line

An ELISA (enzyme-linked immunosorbent assay) based assay was used to test the ability of candidate compound to reduce cellular H3K36me2 level in multiple myeloma cell line KMS11 (t(4;14)+). KMS11 (Horizon Discovery Ltd.) cells are maintained in RPM11640 media with 12.5% FBS and 50 U/ml Penicillin-Streptomycin. For assay compound treatment, single cell suspension was prepared in Opti-MEM supplemented with B-27 and N2 supplement (Invitrogen 11058-021, 17504-044, 17502-048) for ELISA and in maintenance media for cellTiter Glo (CTG) viability assay. One day prior to cell treatment, 1,250 KMS11 cells were seeded into 384-well Greiner CellStar TC plate (Greiner #781086) at the final volume of 30 µL/well.

Cells were treated with tested compounds at the desired concentration for 72 hours. Crude histone lysate was extracted by 0.4M HCl following neutralization by 0.5M Sodium phosphate, dibasic ($Na_2HPO_4$), pH ~12.5. Equal amount of histone lysate was loaded to Corning 384-well high biding plate (Corning #3577, black) for H3K36m2 and to Thermo 384-well high binding Nunc plate (Thermo #460372, white) for total H3.

Histone bound plates were washed and blocked with 5% BSA. H3K36me2 and total H3 was detected by primary antibodies (H3K36me2 Abcam, #ab9049; total H3 Cell Signaling, #4499L) and further revealed by horseradish peroxidase (HRP) conjugated secondary antibody and ECL substrate. The abundance of H3K36me2 and total H3 was measured by Chemiluminesce on a plate reader. Cell viability was monitored on a parallel seeded plate with CellTiter-Glo reagent (Promega #G7573).

The NSD2 biochemical activity and H3K36me2 cellular activity of the compounds of the present invention in different assay formats and cell lines are summarized in Table 2.

TABLE 2

| Ex No. | | H3K36me2 FRET in KMS11-Par (µM) | H3K36me2 ELISA in CGTH-W-1 (µM) | H3K36me2 ELISA in KMS11-Par (µM) | NSD2 $IC_{50}$ (µM) |
|---|---|---|---|---|---|
| 1 | (R)-9-((5-(3-aminopiperidin-1-yl)-2-(3-fluoro-4-methoxyphenyl)pyridin-4-yl)methyl)-9H-purin-6-amine | 3.03 | 0.75 | 4.09 | ++ |
| 2 | 9-((5-((3S,4R)-3-amino-4-fluoropiperidin-1-yl)-2-(2-fluorophenyl)pyridin-4-yl)methyl)-9H-purin-6-amine | 11.07 | n/a | n/a | ++ |
| 3 | (3S,4R)-3-amino-1-(4-((6-amino-9H-purin-9-yl)methyl)-6-(3,4-difluorophenyl)pyridin-3-yl)piperidin-4-ol | n/a | 8.25 | 33.3 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 4 | (R)-9-((5-(3-aminopiperidin-1-yl)-2-(3-fluorophenyl)pyridin-4-yl)methyl)-9H-purin-6-amine | 4.12 | n/a | n/a | ++ |
| 5 | 9-((5-((3S,4R)-3-amino-4-fluoropiperidin-1-yl)-2-(3-fluoro-4-methoxyphenyl)pyridin-4-yl)methyl)-9H-purin-6-amine | 6.46 | 1.77 | n/a | ++ |
| 6 | (R)-9-((5-(3-aminopiperidin-1-yl)-2-(2-fluoro-4-methoxyphenyl)pyridin-4-yl)methyl)-9H-purin-6-amine | 10.0 | n/a | n/a | ++ |
| 7 | (R)-4-(4-((6-amino-9H-purin-9-yl)methyl)-5-(3-aminopiperidin-1-yl)pyridin-2-yl)-2-chlorobenzonitrile | 15.1 | n/a | n/a | ++ |
| 8 | 9-((5-((3S,4R)-3-amino-4-fluoropiperidin-1-yl)-2-(3-fluorophenyl)pyridin-4-yl)methyl)-9H-purin-6-amine | 5.26 | n/a | n/a | ++ |
| 9 | 4-(5-((2S,3R)-3-amino-2-(methoxymethyl)piperidin-1-yl)-4-((6-amino-9H-purin-9-yl)methyl)pyridin-2-yl)-2-fluorobenzonitrile | 9.90 | n/a | n/a | ++ |
| 10 | 9-((5-((3S,4R)-3-amino-4-fluoropiperidin-1-yl)-2-(2-fluoro-4-methoxyphenyl)pyridin-4-yl)methyl)-9H-purin-6-amine | 7.63 | n/a | n/a | ++ |
| 11 | (R)-9-((5-(3-aminopiperidin-1-yl)-2-(4-methoxyphenyl)pyridin-4-yl)methyl)-9H-purin-6-amine | 11.2 | n/a | n/a | ++ |
| 12 | 9-((5-((3S,4R)-3-amino-4-fluoropiperidin-1-yl)-2-(3-chlorophenyl)pyridin-4-yl)methyl)-9H-purin-6-amine | 12.2 | n/a | n/a | ++ |
| 13 | 4-(5-((3S,4R)-3-amino-4-fluoropiperidin-1-yl)-4-((6-amino-9H-purin-9-yl)methyl)pyridin-2-yl)-2-fluorobenzonitrile | 20.7 | n/a | n/a | ++ |
| 14 | 9-((5-((3S,4R)-3-amino-4-fluoropiperidin-1-yl)-2-(2,3-dihydrobenzofuran-5-yl)pyridin-4-yl)methyl)-9H-purin-6-amine | n/a | n/a | n/a | ++ |
| 15 | 9-((5-(3-amino-4-methoxypiperidin-1-yl)-2-(3-fluoro-4-methoxyphenyl)pyridin-4-yl)methyl)-9H-purin-6-amine | 18.7 | n/a | n/a | ++ |
| 16 | (R)-9-((5-(5-amino-3,3-difluoropiperidin-1-yl)-2-(3-fluoro-4-methoxyphenyl)pyridin-4-yl)methyl)-9H-purin-6-amine | n/a | n/a | n/a | ++ |
| 17 | 9-((5-(3-amino-4,4-difluoropiperidin-1-yl)-2-(3-fluorophenyl)pyridin-4-yl)methyl)-9H-purin-6-amine | 154 | n/a | n/a | + |
| 18 | 3-amino-1-(4-((6-amino-9H-purin-9-yl)methyl)-6-(3,4-difluorophenyl)pyridin-3-yl)piperidine-4-carbonitrile | n/a | n/a | n/a | + |
| 19 | (R)-1-((5-(3-aminopiperidin-1-yl)-2-(3-fluoro-4-methoxyphenyl)pyridin-4-yl)methyl)-7-chloro-1H-imidazo[4,5-c]pyridin-4-amine | 3.90 | n/a | n/a | ++ |
| 20 | (R)-9-((5-(3-amino-3-methylpiperidin-1-yl)-2-(3-fluoro-4-methoxyphenyl)pyridin-4-yl)methyl)-9H-purin-6-amine | 2.95 | n/a | n/a | ++ |
| 21 | (R)-1-((5-(3-aminopiperidin-1-yl)-2-(3-fluoro-4-methoxyphenyl)pyridin-4-yl)methyl)-1H-imidazo[4,5-c]pyridin-4-amine | 20.8 | n/a | n/a | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 22 | (R)-9-((5-(3-amino-3-(cyclopropoxymethyl)piperidin-1-yl)-2-(3,4-difluorophenyl)pyridin-4-yl)methyl)-9H-purin-6-amine | 0.214 | n/a | n/a | +++ |
| 23 | (R)-9-((5-(3-amino-3-(methoxymethyl)piperidin-1-yl)-2-(3,4-difluorophenyl)pyridin-4-yl)methyl)-9H-purin-6-amine | 0.160 | n/a | n/a | +++ |
| 24 | (R)-9-((5-(3-amino-3-(methoxymethyl)piperidin-1-yl)-2-(3-fluorophenyl)pyridin-4-yl)methyl)-9H-purin-6-amine | 0.451 | n/a | n/a | +++ |
| 25 | (R)-9-((5-(3-amino-3-(isopropoxymethyl)piperidin-1-yl)-2-(3-fluoro-4-methoxyphenyl)pyridin-4-yl)methyl)-9H-purin-6-amine | 0.995 | n/a | n/a | +++ |
| 26 | (R)-9-((5-(3-amino-3-(methoxymethyl)piperidin-1-yl)-2-(5-chloro-2-fluorophenyl)pyridin-4-yl)methyl)-9H-purin-6-amine | 0.248 | n/a | 0.375 | +++ |
| 27 | (R)-9-((5-(3-amino-3-(methoxymethyl)piperidin-1-yl)-2-(3-chlorophenyl)pyridin-4-yl)methyl)-9H-purin-6-amine | 0.501 | n/a | n/a | +++ |
| 28 | (R)-9-((5-(3-amino-3-(methoxymethyl)piperidin-1-yl)-2-(3-chloro-4-fluorophenyl)pyridin-4-yl)methyl)-9H-purin-6-amine | n/a | n/a | n/a | +++ |
| 29 | (R)-9-((5-(3-amino-3-(methoxymethyl)piperidin-1-yl)-2-(2,4-difluorophenyl)pyridin-4-yl)methyl)-9H-purin-6-amine | 0.225 | n/a | n/a | +++ |
| 30 | (R)-9-((5-(3-amino-3-(cyclobutoxymethyl)piperidin-1-yl)-2-(3,4-difluorophenyl)pyridin-4-yl)methyl)-9H-purin-6-amine | 0.569 | 0.659 | 2.03 | +++ |
| 31 | (R)-9-((5-(3-amino-3-(cyclopropoxymethyl)piperidin-1-yl)-2-(3-fluoro-4-methoxyphenyl)pyridin-4-yl)methyl)-9H-purin-6-amine | n/a | n/a | n/a | +++ |
| 32 | (R)-9-((5-(3-amino-3-(cyclobutoxymethyl)piperidin-1-yl)-2-(3-fluoro-4-methoxyphenyl)pyridin-4-yl)methyl)-9H-purin-6-amine | 0.270 | 0.196 | 0.728 | +++ |
| 33 | (R)-9-((5-(3-amino-3-(methoxymethyl)piperidin-1-yl)-2-(2-fluoro-4-methoxyphenyl)pyridin-4-yl)methyl)-9H-purin-6-amine | 1.03 | n/a | n/a | +++ |
| 34 | (R)-9-((5-(3-amino-3-(isopropoxymethyl)piperidin-1-yl)-2-(3,4-difluorophenyl)pyridin-4-yl)methyl)-9H-purin-6-amine | 1.03 | n/a | n/a | +++ |
| 35 | (R)-9-((5-(3-amino-3-(cyclobutoxymethyl)piperidin-1-yl)-2-(3-fluorophenyl)pyridin-4-yl)methyl)-9H-purin-6-amine | 0.610 | n/a | n/a | +++ |
| 36 | (R)-9-((5-(3-amino-3-(cyclobutoxymethyl)piperidin-1-yl)-2-(4-fluorophenyl)pyridin-4-yl)methyl)-9H-purin-6-amine | 0.416 | n/a | n/a | ++ |
| 37 | (R)-9-((5-(3-amino-3-(isopropoxymethyl)piperidin-1-yl)-2-(4-fluorophenyl)pyridin-4-yl)methyl)-9H-purin-6-amine | 0.614 | n/a | 1.40 | ++ |
| 38 | (R)-9-((5-(3-amino-3-(methoxymethyl)piperidin-1-yl)-2-(3-fluoro-4-methoxyphenyl)pyridin-4-yl)methyl)-9H-purin-6-amine | 0.721 | n/a | n/a | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 39 | (R)-9-((5-(3-amino-3-((2,2,2-trifluoroethoxy)methyl)piperidin-1-yl)-2-(3-fluoro-4-methoxyphenyl)pyridin-4-yl)methyl)-9H-purin-6-amine | 2.56 | n/a | n/a | ++ |
| 40 | (R)-9-((5-(3-amino-3-((difluoromethoxy)methyl)piperidin-1-yl)-2-(3-fluorophenyl)pyridin-4-yl)methyl)-9H-purin-6-amine | 0.770 | n/a | n/a | ++ |
| 41 | (R)-9-((5-(3-amino-3-((difluoromethoxy)methyl)piperidin-1-yl)-2-(3,4-difluorophenyl)pyridin-4-yl)methyl)-9H-purin-6-amine | 1.09 | | 2.31 | ++ |
| 42 | (R)-9-((5-(3-amino-3-((difluoromethoxy)methyl)piperidin-1-yl)-2-(3-fluoro-4-methoxyphenyl)pyridin-4-yl)methyl)-9H-purin-6-amine | 1.23 | 0.789 | 10.7 | ++ |
| 43 | (R)-9-((5-(3-amino-3-((2,2,2-trifluoroethoxy)methyl)piperidin-1-yl)-2-(3,4-difluorophenyl)pyridin-4-yl)methyl)-9H-purin-6-amine | 1.24 | n/a | n/a | ++ |
| 44 | (R)-9-((5-(3-amino-3-((difluoromethoxy)methyl)piperidin-1-yl)-2-(4-fluorophenyl)pyridin-4-yl)methyl)-9H-purin-6-amine | 1.62 | n/a | n/a | ++ |
| 45 | (R)-9-((5-(3-amino-3-((2,2,2-trifluoroethoxy)methyl)piperidin-1-yl)-2-(4-fluorophenyl)pyridin-4-yl)methyl)-9H-purin-6-amine | 0.705 | n/a | n/a | ++ |
| 46 | (R)-1-((5-(3-amino-3-(methoxymethyl)piperidin-1-yl)-2-(3-fluoro-4-methoxyphenyl)pyridin-4-yl)methyl)-1H-imidazo[4,5-c]pyridin-4-amine | 0.315 | n/a | n/a | +++ |
| 47 | (S)-9-((5-(3-amino-3-(2,2-difluoroethyl)piperidin-1-yl)-2-(3,4-difluorophenyl)pyridin-4-yl)methyl)-9H-purin-6-amine | 1.18 | 0.377 | 1.54 | ++ |
| 48 | (S)-1-((5-(3-amino-3-(thiazol-2-ylmethyl)piperidin-1-yl)-2-(3,4-difluorophenyl)pyridin-4-yl)methyl)-1H-imidazo[4,5-c]pyridin-4-amine | n/a | n/a | 0.464 | +++ |
| 49 | (S)-1-((5-(3-amino-3-((1-methyl-1H-pyrazol-3-yl)methyl)piperidin-1-yl)-2-(4-fluorophenyl)pyridin-4-yl)methyl)-1H-imidazo[4,5-c]pyridin-4-amine | n/a | n/a | 12.7 | +++ |
| 50 | (S)-1-((5-(3-amino-3-(pyridin-2-ylmethyl)piperidin-1-yl)-2-(3-fluoro-4-methoxyphenyl)pyridin-4-yl)methyl)-1H-imidazo[4,5-c]pyridin-4-amine | n/a | n/a | 0.895 | +++ |
| 51 | (S)-1-((5-(3-amino-3-(pyridin-2-ylmethyl)piperidin-1-yl)-2-(3,4-difluorophenyl)pyridin-4-yl)methyl)-1H-imidazo[4,5-c]pyridin-4-amine | n/a | n/a | 1.53 | +++ |
| 52 | (S)-9-((5-(3-amino-3-(oxazol-2-ylmethyl)piperidin-1-yl)-2-(3,4-difluorophenyl)pyridin-4-yl)methyl)-9H-purin-6-amine | 1.20 | 0.541 | 1.32 | +++ |
| 53 | (S)-9-((5-(3-amino-3-(thiazol-2-ylmethyl)piperidin-1-yl)-2-(3,4-difluorophenyl)pyridin-4-yl)methyl)-9H-purin-6-amine | 0.327 | n/a | n/a | +++ |
| 54 | (S)-9-((5-(3-amino-3-(pyridin-2-ylmethyl)piperidin-1-yl)-2-(3,4-difluorophenyl)pyridin-4-yl)methyl)-9H-purin-6-amine | 0.450 | n/a | 0.780 | +++ |

TABLE 2-continued

| Ex No. | | H3K36me2 FRET in KMS11-Par (µM) | H3K36me2 ELISA in CGTH-W-1 (µM) | H3K36me2 ELISA in KMS11-Par (µM) | NSD2 IC$_{50}$ (µM) |
|---|---|---|---|---|---|
| 55 | (S)-9-((5-(3-amino-3-((6-methylpyridin-2-yl)methyl)piperidin-1-yl)-2-(3,4-difluorophenyl)pyridin-4-yl)methyl)-9H-purin-6-amine | n/a | n/a | 0.910 | +++ |
| 56 | (S)-9-((5-(3-amino-3-((1-methyl-1H-pyrazol-3-yl)methyl)piperidin-1-yl)-2-(3,4-difluorophenyl)pyridin-4-yl)methyl)-9H-purin-6-amine | n/a | 0.273 | 0.234 | +++ |
| 57 | (S)-1-((5-(3-amino-3-(thiazol-2-ylmethyl)piperidin-1-yl)-2-(3-fluoro-4-methoxyphenyl)pyridin-4-yl)methyl)-1H-imidazo[4,5-c]pyridin-4-amine | n/a | n/a | 0.610 | +++ |
| 58 | (S)-2-(3-amino-1-(4-((6-amino-9H-purin-9-yl)methyl)-6-(3-fluorophenyl)pyridin-3-yl)piperidin-3-yl)acetic acid | 2.64 | n/a | n/a | +++ |
| 59 | (S)-2-(3-amino-1-(4-((4-amino-1H-imidazo[4,5-c]pyridin-1-yl)methyl)-6-(3,4-difluorophenyl)pyridin-3-yl)piperidin-3-yl)-N,N-dimethylacetamide | 33.3 | n/a | n/a | +++ |
| 60 | 9-((5-(3-amino-3-(2-methoxyethyl)piperidin-1-yl)-2-(3,4-difluorophenyl)pyridin-4-yl)methyl)-9H-purin-6-amine | n/a | n/a | n/a | ++ |
| 61 | (S)-9-((5-(3-amino-3-(2,2-difluoroethyl)piperidin-1-yl)-2-(3-fluoro-4-methoxyphenyl)pyridin-4-yl)methyl)-9H-purin-6-amine | 1.42 | 0.643 | n/a | ++ |
| 62 | (S)-2-(3-amino-1-(4-((6-amino-9H-purin-9-yl)methyl)-6-(3,4-difluorophenyl)pyridin-3-yl)piperidin-3-yl)acetamide | n/a | n/a | n/a | ++ |
| 63 | (S)-1-((5-(3-amino-3-(oxazol-2-ylmethyl)piperidin-1-yl)-2-(3,4-difluorophenyl)pyridin-4-yl)methyl)-1H-imidazo[4,5-c]pyridin-4-amine | n/a | n/a | 7.91 | ++ |
| 64 | N-(4-(5-(3-amino-3-(2,2-difluoroethyl)piperidin-1-yl)-4-((6-amino-9H-purin-9-yl)methyl)pyridin-2-yl)phenyl)-3-bromopropanamide | n/a | n/a | 7.00 | ++ |
| 65 | 9-((5-((S)-3-amino-3-((R)-1-(pyridin-2-yl)ethyl)piperidin-1-yl)-2-(3,4-difluorophenyl)pyridin-4-yl)methyl)-9H-purin-6-amine | n/a | n/a | 1.13 | ++ |
| 66 | 2-(3-amino-1-(4-((6-amino-9H-purin-9-yl)methyl)-6-(3-fluorophenyl)pyridin-3-yl)piperidin-3-yl)-N-methylacetamide | 118 | n/a | n/a | ++ |
| 67 | 2-(3-amino-1-(4-((4-amino-7-chloro-1H-imidazo[4,5-c]pyridin-1-yl)methyl)-6-(3,4-difluorophenyl)pyridin-3-yl)piperidin-3-yl)-N-methylacetamide | 4.25 | n/a | n/a | ++ |
| 68 | 2-(3-amino-1-(4-((4-amino-7-chloro-1H-imidazo[4,5-c]pyridin-1-yl)methyl)-6-(3,4-difluorophenyl)pyridin-3-yl)piperidin-3-yl)-N,N-dimethylacetamide | n/a | n/a | n/a | ++ |
| 69 | 9-((5-(3-amino-3-((6-fluoropyridin-2-yl)methyl)piperidin-1-yl)-2-(3,4-difluorophenyl)pyridin-4-yl)methyl)-9H-purin-6-amine | n/a | n/a | 1.15 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 70 | (S)-2-(3-amino-1-(4-((6-amino-9H-purin-9-yl)methyl)-6-(3-fluorophenyl)pyridin-3-yl)piperidin-3-yl)-N,N-dimethylacetamide | 9.44 | n/a | n/a | ++ |
| 71 | (S)-9-((5-(3-amino-3-(2,2-difluoroethyl)piperidin-1-yl)-2-(4-fluorophenyl)pyridin-4-yl)methyl)-9H-purin-6-amine | 0.849 | n/a | n/a | ++ |
| 72 | 2-(3-amino-1-(4-((4-amino-1H-imidazo[4,5-c]pyridin-1-yl)methyl)-6-(3,4-difluorophenyl)pyridin-3-yl)piperidin-3-yl)-N-methylacetamide | 250 | n/a | n/a | ++ |
| 73 | methyl (S)-2-(3-amino-1-(4-((6-amino-9H-purin-9-yl)methyl)-6-(3-fluorophenyl)pyridin-3-yl)piperidin-3-yl)acetate | n/a | n/a | n/a | ++ |
| 74 | (S)-9-((5-(3-amino-3-(pyrazin-2-ylmethyl)piperidin-1-yl)-2-(3,4-difluorophenyl)pyridin-4-yl)methyl)-9H-purin-6-amine | n/a | n/a | 4.22 | ++ |
| 75 | N-(4-(5-(3-amino-3-(2,2-difluoroethyl)piperidin-1-yl)-4-((6-amino-9H-purin-9-yl)methyl)pyridin-2-yl)benzyl)-2-chloroacetamide | n/a | n/a | n/a | ++ |
| 76 | N-(4-(5-(3-amino-3-(2,2-difluoroethyl)piperidin-1-yl)-4-((6-amino-9H-purin-9-yl)methyl)pyridin-2-yl)phenyl)acrylamide | n/a | n/a | 2.12 | ++ |
| 77 | 2-(3-amino-1-(4-((6-amino-9H-purin-9-yl)methyl)-6-(3,4-difluorophenyl)pyridin-3-yl)piperidin-3-yl)acetonitrile | n/a | n/a | n/a | + |
| 78 | (R)-3-amino-1-(4-((6-amino-9H-purin-9-yl)methyl)-6-(3-fluorophenyl)pyridin-3-yl)-N-methylpiperidine-3-carboxamide | n/a | 0.012 | 0.078 | +++ |
| 79 | methyl (R)-3-amino-1-(4-((6-amino-9H-purin-9-yl)methyl)-6-(3-fluorophenyl)pyridin-3-yl)piperidine-3-carboxylate | 0.473 | n/a | n/a | +++ |
| 80 | (R)-3-amino-1-(4-((6-amino-9H-purin-9-yl)methyl)-6-(3-fluoro-4-methoxyphenyl)pyridin-3-yl)-N,N-dimethylpiperidine-3-carboxamide | 4.95 | n/a | n/a | +++ |
| 81 | isopropyl (R)-3-amino-1-(4-((6-amino-9H-purin-9-yl)methyl)-6-(3-fluoro-4-methoxyphenyl)pyridin-3-yl)piperidine-3-carboxylate | 0.115 | n/a | n/a | +++ |
| 82 | (R)-3-amino-1-(4-((6-amino-9H-purin-9-yl)methyl)-6-(3,4-difluorophenyl)pyridin-3-yl)-N-(tetrahydro-2H-pyran-4-yl)piperidine-3-carboxamide | n/a | n/a | n/a | ++ |
| 83 | tert-butyl (R)-3-amino-1-(4-((6-amino-9H-purin-9-yl)methyl)-6-(3-fluoro-4-methoxyphenyl)pyridin-3-yl)piperidine-3-carboxylate | 0.956 | n/a | n/a | ++ |
| 84 | (R)-(3-amino-1-(4-((6-amino-9H-purin-9-yl)methyl)-6-(3,4-difluorophenyl)pyridin-3-yl)piperidin-3-yl)(pyrrolidin-1-yl)methanone | n/a | n/a | n/a | ++ |
| 85 | 3-amino-1-(4-((6-amino-9H-purin-9-yl)methyl)-6-(3,4-difluorophenyl)pyridin-3-yl)-N-(tetrahydrofuran-3-yl)piperidine-3-carboxamide | n/a | 2.08 | 6.49 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 86 | (3-amino-1-(4-((6-amino-9H-purin-9-yl)methyl)-6-(3,4-difluorophenyl)pyridin-3-yl)piperidin-3-yl)(piperidin-1-yl)methanone | n/a | 8.69 | 33.3 | ++ |
| 87 | (3-amino-1-(4-((6-amino-9H-purin-9-yl)methyl)-6-(3,4-difluorophenyl)pyridin-3-yl)piperidin-3-yl)(2-methylpiperidin-1-yl)methanone | n/a | 1.60 | 6.42 | ++ |
| 88 | (3-amino-1-(4-((6-amino-9H-purin-9-yl)methyl)-6-(3,4-difluorophenyl)pyridin-3-yl)piperidin-3-yl)(2-methylpyrrolidin-1-yl)methanone | n/a | n/a | n/a | ++ |
| 89 | 1-(3-amino-1-(4-((6-amino-9H-purin-9-yl)methyl)-6-(3,4-difluorophenyl)pyridin-3-yl)piperidin-3-yl)-2,3-dimethylbutan-1-one | n/a | 0.245 | 0.684 | ++ |
| 90 | (R)-1-((R)-3-amino-1-(4-((6-amino-9H-purin-9-yl)methyl)-6-(3-fluoro-4-methoxyphenyl)pyridin-3-yl)piperidin-3-yl)ethan-1-ol | n/a | 0.239 | 0.432 | +++ |
| 91 | 9-((5-((R)-3-amino-3-((S)-fluoro(pyridin-2-yl)methyl)piperidin-1-yl)-2-(3,4-difluorophenyl)pyridin-4-yl)methyl)-9H-purin-6-amine | n/a | 0.121 | 0.890 | +++ |
| 92 | (S)-1-((R)-3-amino-1-(4-((6-amino-9H-purin-9-yl)methyl)-6-(3-fluoro-4-methoxyphenyl)pyridin-3-yl)piperidin-3-yl)ethan-1-ol | n/a | 2.11 | 4.89 | +++ |
| 93 | 9-((5-((R)-3-amino-3-((S)-1-methoxyethyl)piperidin-1-yl)-2-(3-fluoro-4-methoxyphenyl)pyridin-4-yl)methyl)-9H-purin-6-amine | 1.39 | 3.21 | 3.97 | ++ |
| 94 | 9-((5-((R)-3-amino-3-((R)-1-methoxyethyl)piperidin-1-yl)-2-(3-fluoro-4-methoxyphenyl)pyridin-4-yl)methyl)-9H-purin-6-amine | 3.04 | 1.09 | 1.20 | ++ |
| 95 | 9-((5-((R)-3-amino-3-((S)-1-methoxyethyl)piperidin-1-yl)-2-(3,4-difluorophenyl)pyridin-4-yl)methyl)-9H-purin-6-amine | 1.82 | 1.65 | 3.03 | ++ |
| 96 | (E)-1-(3-amino-1-(4-((6-amino-9H-purin-9-yl)methyl)-6-(3-fluoro-4-methoxyphenyl)pyridin-3-yl)piperidin-3-yl)ethan-1-one O-methyl oxime | 2.40 | n/a | n/a | ++ |
| 97 | 9-((5-((R)-3-amino-3-((R)-1-methoxyethyl)piperidin-1-yl)-2-(3,4-difluorophenyl)pyridin-4-yl)methyl)-9H-purin-6-amine | 1.50 | 1.16 | 1.24 | ++ |
| 98 | (S)-1-((R)-3-amino-1-(4-((6-amino-9H-purin-9-yl)methyl)-6-(3,4-difluorophenyl)pyridin-3-yl)piperidin-3-yl)-2-methylpropan-1-ol | n/a | 1.50 | 6.26 | ++ |
| 99 | 9-((5-(3-amino-3-((R)-1-ethoxyethyl)piperidin-1-yl)-2-(3,4-difluorophenyl)pyridin-4-yl)methyl)-9H-purin-6-amine | n/a | n/a | 21.0 | ++ |
| 100 | (3-amino-1-(4-((6-amino-9H-purin-9-yl)methyl)-6-(3,4-difluorophenyl)pyridin-3-yl)piperidin-3-yl)(cyclopentyl)methanone | n/a | n/a | n/a | +++ |
| 101 | (S)-1-((R)-3-amino-1-(4-((6-amino-9H-purin-9-yl)methyl)-6-(3,4-difluorophenyl)pyridin-3-yl)piperidin-3-yl)-2-methylbutan-1-one | n/a | 0.040 | 0.034 | +++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 102 | (R)-1-((R)-3-amino-1-(4-((6-amino-9H-purin-9-yl)methyl)-6-(3,4-difluorophenyl)pyridin-3-yl)piperidin-3-yl)-2-methylbutan-1-one | n/a | 0.060 | 0.252 | ++ |
| 103 | 1-(3-amino-1-(4-((6-amino-9H-purin-9-yl)methyl)-6-(3,4-difluorophenyl)pyridin-3-yl)piperidin-3-yl)-2-cyclopropylpropan-1-one | n/a | 0.138 | 0.379 | ++ |
| 104 | (R)-1-(3-amino-1-(4-((6-amino-9H-purin-9-yl)methyl)-6-(3,4-difluorophenyl)pyridin-3-yl)piperidin-3-yl)-2-methylpropan-1-one | n/a | 0.026 | 0.060 | ++ |
| 105 | (3-amino-1-(4-((6-amino-9H-purin-9-yl)methyl)-6-(3,4-difluorophenyl)pyridin-3-yl)piperidin-3-yl)(cyclobutyl)methanone | n/a | 0.067 | 0.140 | ++ |
| 106 | (3-amino-1-(4-((6-amino-9H-purin-9-yl)methyl)-6-(3,4-difluorophenyl)pyridin-3-yl)piperidin-3-yl)(3-methoxycyclopentyl)methanone | n/a | 0.501 | 1.43 | ++ |
| 107 | (3-amino-1-(4-((6-amino-9H-purin-9-yl)methyl)-6-(3,4-difluorophenyl)pyridin-3-yl)piperidin-3-yl)(1-methylcyclopropyl)methanone | n/a | 0.446 | 3.02 | ++ |
| 108 | (3-amino-1-(4-((6-amino-9H-purin-9-yl)methyl)-6-(3,4-difluorophenyl)pyridin-3-yl)piperidin-3-yl)(tetrahydro-2H-pyran-4-yl)methanone | n/a | 0.772 | 1.96 | ++ |
| 109 | (R)-1-(3-amino-1-(4-((6-amino-9H-purin-9-yl)methyl)-6-(3,4-difluorophenyl)pyridin-3-yl)piperidin-3-yl)-2,2-dimethylpropan-1-one | n/a | 2.092 | 2.729 | ++ |
| 110 | (3-amino-1-(4-((6-amino-9H-purin-9-yl)methyl)-6-(3,4-difluorophenyl)pyridin-3-yl)piperidin-3-yl)(1-methyl-1H-pyrazol-3-yl)methanone | n/a | 1.359 | 6.340 | ++ |
| 111 | (3-amino-1-(4-((6-amino-9H-purin-9-yl)methyl)-6-(3,4-difluorophenyl)pyridin-3-yl)piperidin-3-yl)(tetrahydrofuran-3-yl)methanone | n/a | n/a | n/a | + |
| 112 | (3-amino-1-(4-((6-amino-9H-purin-9-yl)methyl)-6-(3,4-difluorophenyl)pyridin-3-yl)piperidin-3-yl)(3-methyloxetan-3-yl)methanone | n/a | n/a | n/a | + |
| 113 | (R)-1-((R)-3-amino-1-(4-((6-amino-9H-purin-9-yl)methyl)-6-(3,4-difluorophenyl)pyridin-3-yl)piperidin-3-yl)-2,2-difluoroethan-1-ol; or (S)-1-((R)-3-amino-1-(4-((6-amino-9H-purin-9-yl)methyl)-6-(3,4-difluorophenyl)pyridin-3-yl)piperidin-3-yl)-2,2-difluoroethan-1-ol | n/a | 0.145 | 0.753 | ++ |
| 114 | | n/a | 0.443 | 1.94 | ++ |
| 115 | (R)-1-((R)-3-amino-1-(4-((6-amino-9H-purin-9-yl)methyl)-6-(4-(difluoromethyl)-2-methylphenyl)pyridin-3-yl)piperidin-3-yl)-2,2-difluoroethan-1-ol | n/a | 0.088 | 0.927 | +++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 116 | (S)-1-((R)-3-amino-1-(4-((6-amino-9H-purin-9-yl)methyl)-6-(4-(difluoromethoxy)-3-fluorophenyl)pyridin-3-yl)piperidin-3-yl)-2,2-difluoroethan-1-ol | n/a | 0.168 | 1.35 | +++ |
| 117 | (R)-1-((R)-3-amino-1-(4-((6-amino-9H-purin-9-yl)methyl)-6-(4,5-difluoro-2-methylphenyl)pyridin-3-yl)piperidin-3-yl)-2,2-difluoroethan-1-ol | n/a | 0.067 | 1.32 | +++ |
| 118 | (S)-1-((R)-3-amino-1-(4-((6-amino-9H-purin-9-yl)methyl)-6-(3,4-difluorophenyl)-5-methoxypyridin-3-yl)piperidin-3-yl)-2,2-difluoroethan-1-ol | n/a | n/a | n/a | +++ |
| 119 | (R)-1-((R)-3-amino-1-(4-((6-amino-9H-purin-9-yl)methyl)-6-(4-(difluoromethoxy)-3-fluorophenyl)pyridin-3-yl)piperidin-3-yl)-2,2-difluoroethan-1-ol | n/a | 0.228 | 1.49 | +++ |
| 120 | (S)-1-((R)-3-amino-1-(4-((6-amino-9H-purin-9-yl)methyl)-6-(4-(difluoromethyl)-2,5-difluorophenyl)pyridin-3-yl)piperidin-3-yl)-2,2-difluoroethan-1-ol | n/a | n/a | n/a | +++ |
| 121 | (R)-1-((R)-3-amino-1-(4-((6-amino-9H-purin-9-yl)methyl)-6-(3-chloro-4-methoxyphenyl)pyridin-3-yl)piperidin-3-yl)-2,2-difluoroethan-1-ol | n/a | 0.683 | 2.61 | +++ |
| 122 | (R)-1-((R)-3-amino-1-(4-((6-amino-9H-purin-9-yl)methyl)-6-(3-chloro-4-fluorophenyl)pyridin-3-yl)piperidin-3-yl)-2,2-difluoroethan-1-ol | n/a | 0.496 | 1.83 | +++ |
| 123 | (R)-1-((R)-3-amino-1-(4-((6-amino-9H-purin-9-yl)methyl)-6-(6-fluoro-1-methyl-1H-indazol-5-yl)pyridin-3-yl)piperidin-3-yl)-2,2-difluoroethan-1-ol | n/a | 1.49 | 7.85 | +++ |
| 124 | (R)-1-((R)-3-amino-1-(4-((6-amino-9H-purin-9-yl)methyl)-6-(4-chloro-3-fluorophenyl)pyridin-3-yl)piperidin-3-yl)-2,2-difluoroethan-1-ol | n/a | 0.159 | 0.848 | +++ |
| 125 | (S)-1-((R)-3-amino-1-(4-((6-amino-9H-purin-9-yl)methyl)-6-(3-chloro-4-methoxyphenyl)pyridin-3-yl)piperidin-3-yl)-2,2-difluoroethan-1-ol | n/a | 0.775 | 3.95 | +++ |
| 126 | (R)-1-((R)-3-amino-1-(4-((6-amino-9H-purin-9-yl)methyl)-6-(2,4-dimethylphenyl)pyridin-3-yl)piperidin-3-yl)-2,2-difluoroethan-1-ol | n/a | 0.469 | 1.11 | +++ |
| 127 | (S)-1-((R)-3-amino-1-(4-((6-amino-9H-purin-9-yl)methyl)-6-(3-fluoro-4-methoxyphenyl)pyridin-3-yl)piperidin-3-yl)-2,2-difluoroethan-1-ol | n/a | 0.262 | 0.901 | +++ |
| 128 | (S)-1-((R)-3-amino-1-(4-((6-amino-9H-purin-9-yl)methyl)-6-(4-(difluoromethoxy)-2,5-difluorophenyl)pyridin-3-yl)piperidin-3-yl)-2,2-difluoroethan-1-ol | n/a | 0.060 | 0.693 | +++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 129 | (R)-1-((R)-3-amino-1-(4-((6-amino-9H-purin-9-yl)methyl)-6-(4-(difluoromethyl)-5-fluoro-2-methylphenyl)pyridin-3-yl)piperidin-3-yl)-2,2-difluoroethan-1-ol | n/a | n/a | n/a | +++ |
| 130 | (R)-1-((R)-3-amino-1-(4-((6-amino-9H-purin-9-yl)methyl)-6-cyclohexylpyridin-3-yl)piperidin-3-yl)-2,2-difluoroethan-1-ol | n/a | 0.321 | 3.52 | +++ |
| 131 | (R)-1-((R)-3-amino-1-(4-((6-amino-9H-purin-9-yl)methyl)-6-(3-fluoro-4-methoxyphenyl)pyridin-3-yl)piperidin-3-yl)-2,2-difluoroethan-1-ol | n/a | 0.142 | 0.887 | +++ |
| 132 | (R)-1-((R)-3-amino-1-(4-((6-amino-9H-purin-9-yl)methyl)-6-(4-(difluoromethyl)-2-fluorophenyl)pyridin-3-yl)piperidin-3-yl)-2,2-difluoroethan-1-ol | n/a | 0.264 | 1.23 | +++ |
| 133 | (R)-1-((R)-3-amino-1-(4-((6-amino-9H-purin-9-yl)methyl)-6-(4-chloro-2-fluorophenyl)pyridin-3-yl)piperidin-3-yl)-2,2-difluoroethan-1-ol | n/a | 0.177 | 1.61 | ++ |
| 134 | (R)-1-((R)-3-amino-1-(4-((6-amino-9H-purin-9-yl)methyl)-6-(4-(difluoromethyl)-2,5-difluorophenyl)pyridin-3-yl)piperidin-3-yl)-2,2-difluoroethan-1-ol | n/a | 0.601 | 0.830 | ++ |
| 135 | (S)-1-((R)-3-amino-1-(4-((6-amino-9H-purin-9-yl)methyl)-5-fluoro-6-(2-fluoro-4-methoxyphenyl)pyridin-3-yl)piperidin-3-yl)-2,2-difluoroethan-1-ol | n/a | n/a | n/a | ++ |
| 136 | (R)-1-((R)-3-amino-1-(4-((6-amino-9H-purin-9-yl)methyl)-6-(1,6-dimethyl-1H-indazol-5-yl)pyridin-3-yl)piperidin-3-yl)-2,2-difluoroethan-1-ol | n/a | n/a | 8.80 | ++ |
| 137 | (S)-1-((R)-3-amino-1-(4-((6-amino-9H-purin-9-yl)methyl)-6-(4-(difluoromethyl)-2-fluorophenyl)pyridin-3-yl)piperidin-3-yl)-2,2-difluoroethan-1-ol | n/a | n/a | n/a | ++ |
| 138 | (R)-1-((R)-3-amino-1-(4-((6-amino-9H-purin-9-yl)methyl)-6-(4-(difluoromethoxy)-2-fluorophenyl)pyridin-3-yl)piperidin-3-yl)-2,2-difluoroethan-1-ol | n/a | 0.132 | 1.57 | ++ |
| 139 | (S)-1-((R)-3-amino-1-(4-((6-amino-9H-purin-9-yl)methyl)-6-(3-chloro-4-fluorophenyl)pyridin-3-yl)piperidin-3-yl)-2,2-difluoroethan-1-ol | n/a | 0.669 | 2.84 | ++ |
| 140 | (S)-1-((R)-3-amino-1-(4-((6-amino-9H-purin-9-yl)methyl)-6-(4-(difluoromethyl)-2-methylphenyl)pyridin-3-yl)piperidin-3-yl)-2,2-difluoroethan-1-ol | n/a | n/a | n/a | ++ |
| 141 | (R)-1-((R)-3-amino-1-(4-((6-amino-9H-purin-9-yl)methyl)-6-(2-fluoro-4-(trifluoromethyl)phenyl)pyridin-3-yl)piperidin-3-yl)-2,2-difluoroethan-1-ol | n/a | 1.15 | 7.70 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 142 | (S)-1-((R)-3-amino-1-(4-((6-amino-9H-purin-9-yl)methyl)-6-(2,4-difluorophenyl)-5-fluoropyridin-3-yl)piperidin-3-yl)-2,2-difluoroethan-1-ol | n/a | n/a | n/a | ++ |
| 143 | (S)-1-((R)-3-amino-1-(4-((6-amino-9H-purin-9-yl)methyl)-6-(6-fluoro-1-methyl-1H-indazol-5-yl)pyridin-3-yl)piperidin-3-yl)-2,2-difluoroethan-1-ol | n/a | n/a | n/a | ++ |
| 144 | 4-(5-((R)-3-amino-3-((S)-2,2-difluoro-1-hydroxyethyl)piperidin-1-yl)-4-((6-amino-9H-purin-9-yl)methyl)pyridin-2-yl)-2,5-difluorophenol | n/a | 2.58 | 10.4 | ++ |
| 145 | (S)-1-((R)-3-amino-1-(4-((6-amino-9H-purin-9-yl)methyl)-6-cyclohexylpyridin-3-yl)piperidin-3-yl)-2,2-difluoroethan-1-ol | n/a | 0.990 | 8.11 | ++ |
| 146 | (S)-1-((R)-3-amino-1-(4-((6-amino-9H-purin-9-yl)methyl)-6-(2-(difluoromethyl)-4,5-difluorophenyl)pyridin-3-yl)piperidin-3-yl)-2,2-difluoroethan-1-ol | n/a | 0.723 | 5.04 | ++ |
| 147 | (R)-1-((R)-3-amino-1-(4-((6-amino-9H-purin-9-yl)methyl)-6-(2,4-difluorophenyl)pyridin-3-yl)piperidin-3-yl)-2,2-difluoroethan-1-ol | n/a | 0.044 | 2.49 | ++ |
| 148 | (S)-1-((R)-3-amino-1-(4-((6-amino-9H-purin-9-yl)methyl)-6-(4-chloro-2-fluorophenyl)pyridin-3-yl)piperidin-3-yl)-2,2-difluoroethan-1-ol | n/a | 0.671 | 2.16 | ++ |
| 149 | (S)-1-((R)-3-amino-1-(4-((6-amino-9H-purin-9-yl)methyl)-6-(2,5-difluoro-4-methoxyphenyl)-5-fluoropyridin-3-yl)piperidin-3-yl)-2,2-difluoroethan-1-ol | n/a | n/a | n/a | ++ |
| 150 | (R)-1-((R)-3-amino-1-(4-((6-amino-9H-purin-9-yl)methyl)-6-(4-(difluoromethoxy)-2,5-difluorophenyl)pyridin-3-yl)piperidin-3-yl)-2,2-difluoroethan-1-ol | n/a | 0.307 | 1.67 | ++ |
| 151 | (S)-1-((R)-3-amino-1-(4-((6-amino-9H-purin-9-yl)methyl)-6-(2,4-difluorophenyl)pyridin-3-yl)piperidin-3-yl)-2,2-difluoroethan-1-ol | n/a | 0.8415 | 4.19 | ++ |
| 152 | (S)-1-((R)-3-amino-1-(4-((6-amino-9H-purin-9-yl)methyl)-6-(4-chloro-3-fluorophenyl)pyridin-3-yl)piperidin-3-yl)-2,2-difluoroethan-1-ol | n/a | 0.0687 | 1.77 | ++ |
| 153 | (S)-1-((R)-3-amino-1-(4-((6-amino-9H-purin-9-yl)methyl)-6-(4-(difluoromethoxy)-2-fluorophenyl)pyridin-3-yl)piperidin-3-yl)-2,2-difluoroethan-1-ol | n/a | 0.217 | 5.08 | ++ |
| 154 | (R)-1-((R)-3-amino-1-(4-((6-amino-9H-purin-9-yl)methyl)-6-(3-(difluoromethyl)-2,5-difluorophenyl)pyridin-3-yl)piperidin-3-yl)-2,2-difluoroethan-1-ol | n/a | 2.93 | 9.11 | ++ |
| 155 | (R)-1-((R)-3-amino-1-(4-((6-amino-9H-purin-9-yl)methyl)-5'-fluoro-[2,2'-bipyridin]-5-yl)piperidin-3-yl)-2,2-difluoroethan-1-ol | n/a | 1.17 | 16.4 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 156 | (R)-1-((R)-3-amino-1-(4-((6- | n/a | 0.041 | 0.574 | +++ |
| 157 | amino-9H-purin-9-yl)methyl)-6-(2,4,5-trifluorophenyl)pyridin-3-yl)piperidin-3-yl)-2,2-difluoroethan-1-ol; or (S)-1-((R)-3-amino-1-(4-((6-amino-9H-purin-9-yl)methyl)-6-(2,4,5-trifluorophenyl)pyridin-3-yl)piperidin-3-yl)-2,2-difluoroethan-1-ol | n/a | 0.385 | 1.31 | +++ |
| 158 | (R)-1-((R)-3-amino-1-(4-((6- | n/a | 0.100 | 0.802 | +++ |
| 159 | amino-9H-purin-9-yl)methyl)-6-(2-(difluoromethyl)-4-fluorophenyl)pyridin-3-yl)piperidin-3-yl)-2,2-difluoroethan-1-ol; or (S)-1-((R)-3-amino-1-(4-((6-amino-9H-purin-9-yl)methyl)-6-(2-(difluoromethyl)-4-fluorophenyl)pyridin-3-yl)piperidin-3-yl)-2,2-difluoroethan-1-ol | n/a | 0.140 | 1.13 | +++ |
| 160 | (R)-1-((R)-3-amino-1-(4-((6- | n/a | 0.035 | 0.434 | +++ |
| 161 | amino-9H-purin-9-yl)methyl)-6-(2,5-difluoro-4-methoxyphenyl)pyridin-3-yl)piperidin-3-yl)-2,2-difluoroethan-1-ol; or (S)-1-((R)-3-amino-1-(4-((6-amino-9H-purin-9-yl)methyl)-6-(2,5-difluoro-4-methoxyphenyl)pyridin-3-yl)piperidin-3-yl)-2,2-difluoroethan-1-ol | n/a | 0.073 | 0.502 | +++ |
| 162 | (R)-1-((R)-3-amino-1-(4-((6- | n/a | 0.086 | 0.440 | +++ |
| 163 | amino-9H-purin-9-yl)methyl)-6-(2-(difluoromethyl)-4-methoxyphenyl)pyridin-3-yl)piperidin-3-yl)-2,2-difluoroethan-1-ol; or (S)-1-((R)-3-amino-1-(4-((6-amino-9H-purin-9-yl)methyl)-6-(2-(difluoromethyl)-4-methoxyphenyl)pyridin-3-yl)piperidin-3-yl)-2,2-difluoroethan-1-ol | n/a | 0.204 | 1.85 | +++ |
| 164 | (R)-1-((R)-3-amino-1-(4-((6- | n/a | 0.130 | 1.06 | +++ |
| 165 | amino-9H-purin-9-yl)methyl)-6-(3,5-difluoro-4-methoxyphenyl)pyridin-3-yl)piperidin-3-yl)-2,2-difluoroethan-1-ol; or (S)-1-((R)-3-amino-1-(4-((6-amino-9H-purin-9-yl)methyl)-6-(3,5-difluoro-4-methoxyphenyl)pyridin-3-yl)piperidin-3-yl)-2,2-difluoroethan-1-ol | n/a | 0.218 | 1.08 | +++ |
| 166 | (S)-1-((R)-3-amino-1-(4-((6- | n/a | 0.432 | 8.51 | +++ |
| 167 | amino-9H-purin-9-yl)methyl)-6-(4-methoxy-2-(trifluoromethyl)phenyl)pyridin-3-yl)piperidin-3-yl)-2,2-difluoroethan-1-ol; or (R)-1-((R)-3-amino-1-(4-((6-amino-9H-purin-9-yl)methyl)-6-(4-methoxy-2-(trifluoromethyl)phenyl)pyridin-3-yl)piperidin-3-yl)-2,2-difluoroethan-1-ol | n/a | 0.559 | 6.12 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 168 | (S)-1-((R)-3-amino-1-(4-((6- | n/a | 0.997 | 4.78 | ++ |
| 169 | amino-9H-purin-9-yl)methyl)-6-(2-chloro-4-methoxyphenyl)pyridin-3-yl)piperidin-3-yl)-2,2-difluoroethan-1-ol; or (R)-1-((R)-3-amino-1-(4-((6-amino-9H-purin-9-yl)methyl)-6-(2-chloro-4-methoxyphenyl)pyridin-3-yl)piperidin-3-yl)-2,2-difluoroethan-1-ol | n/a | 0.426 | 2.99 | ++ |
| 170 | (R)-1-((R)-3-amino-1-(4-((6- | n/a | 0.161 | 1.47 | ++ |
| 171 | amino-9H-purin-9-yl)methyl)-6-(2-(difluoromethyl)-4,5-difluorophenyl)pyridin-3-yl)piperidin-3-yl)-2,2-difluoroethan-1-ol; or (S)-1-((R)-3-amino-1-(4-((6-amino-9H-purin-9-yl)methyl)-6-(2-(difluoromethyl)-4,5-difluorophenyl)pyridin-3-yl)piperidin-3-yl)-2,2-difluoroethan-1-ol | n/a | 0.886 | 5.52 | ++ |
| 172 | (R)-1-((R)-3-amino-1-(4-((6-amino-9H-purin-9-yl)methyl)-6-(2,3,4-trifluorophenyl)pyridin-3-yl)piperidin-3-yl)-2,2-difluoroethan-1-ol | n/a | 1.20 | 8.93 | ++ |
| 173 | (S)-1-((R)-3-amino-1-(4-((6- | n/a | 1.04 | 12.8 | ++ |
| 174 | amino-9H-purin-9-yl)methyl)-6-(4-fluoro-2-methoxyphenyl)pyridin-3-yl)piperidin-3-yl)-2,2-difluoroethan-1-ol; or (R)-1-((R)-3-amino-1-(4-((6-amino-9H-purin-9-yl)methyl)-6-(4-fluoro-2-methoxyphenyl)pyridin-3-yl)piperidin-3-yl)-2,2-difluoroethan-1-ol | n/a | 1.16 | 10.6 | ++ |
| 175 | (S)-1-((R)-3-amino-1-(4-((6- | n/a | 0.534 | 11.3 | ++ |
| 176 | amino-9H-purin-9-yl)methyl)-6'-chloro-5'-fluoro-[2,2'-bipyridin]-5-yl)piperidin-3-yl)-2,2-difluoroethan-1-ol; or (R)-1-((R)-3-amino-1-(4-((6-amino-9H-purin-9-yl)methyl)-6'-chloro-5'-fluoro-[2,2'-bipyridin]-5-yl)piperidin-3-yl)-2,2-difluoroethan-1-ol | n/a | 0.953 | 8.97 | ++ |
| 177 | 9-((5-(3-amino-(6-methylpyridin-2-yl)piperidin-1-yl)-2-(3,4-difluorophenyl)pyridin-4-yl)methyl)-9H-purin-6-amine | n/a | n/a | 0.407 | +++ |
| 178 | (R)-9-((5-(3-amino-3-(6-methoxypyridin-2-yl)piperidin-1-yl)-2-(3,4-difluorophenyl)pyridin-4-yl)methyl)-9H-purin-6-amine | n/a | 0.230 | n/a | +++ |
| 179 | 9-((5-(3-amino-3-(6-chloropyridin-2-yl)piperidin-1-yl)-2-(1,3-dihydroisobenzofuran-5-yl)pyridin-4-yl)methyl)-9H-purin-6-amine | n/a | 1.42 | n/a | ++ |
| 180 | (R)-9-((5-(3-amino-3-(6-chloropyridin-2-yl)piperidin-1-yl)-5'-chloro-6'-fluoro-[2,3'-bipyridin]-4-yl)methyl)-9H-purin-6-amine | n/a | 1.459 | 5.49 | ++ |
| 181 | (R)-9-((5-(3-amino-3-(6-chloropyridin-2-yl)piperidin-1-yl)-2-(2-fluoro-4-methoxyphenyl)pyridin-4-yl)methyl)-9H-purin-6-amine | n/a | 1.56 | 1.98 | ++ |
| 182 | (R)-9-((5-(3-amino-3-(6-cyclopropylpyridin-2-yl)piperidin-1-yl)-2-(4-fluorophenyl)pyridin-4-yl)methyl)-9H-purin-6-amine | n/a | 0.0975 | 0.142 | +++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 183 | 9-((5-((R)-3-amino-3-(6-((S)-1-fluoroethyl)pyridin-2-yl)piperidin-1-yl)-2-(4-fluorophenyl)pyridin-4-yl)methyl)-9H-purin-6-amine | n/a | 0.159 | 0.455 | ++ |
| 184 | 9-((5-(3-amino-3-(6-chloropyridin-2-yl)piperidin-1-yl)-2-(4-(difluoromethoxy)phenyl)pyridin-4-yl)methyl)-9H-purin-6-amine | n/a | 0.592 | n/a | ++ |
| 185 | (R)-9-((5-(3-amino-3-(6-chloropyridin-2-yl)piperidin-1-yl)-2-(2,3-dihydrobenzofuran-5-yl)pyridin-4-yl)methyl)-9H-purin-6-amine | n/a | n/a | n/a | ++ |
| 186 | 9-((5-(3-amino-3-(6-chloropyridin-2-yl)piperidin-1-yl)-2-(benzo[d][1,3]dioxol-5-yl)pyridin-4-yl)methyl)-9H-purin-6-amine | n/a | 0.967 | n/a | ++ |
| 187 | (R)-9-((5-(3-amino-3-(6-chloropyridin-2-yl)piperidin-1-yl)-2-(2,5-difluoro-4-methoxyphenyl)pyridin-4-yl)methyl)-9H-purin-6-amine | n/a | 0.383 | 0.815 | ++ |
| 188 | (R)-9-((5-(3-amino-3-(6-chloro-5-fluoropyridin-2-yl)piperidin-1-yl)-2-(3-fluoro-4-methoxyphenyl)pyridin-4-yl)methyl)-9H-purin-6-amine | n/a | 1.01 | 1.91 | +++ |
| 189 | 9-((5-(3-amino-3-(5-fluoropyridin-2-yl)piperidin-1-yl)-2-(4-fluorophenyl)pyridin-4-yl)methyl)-9H-purin-6-amine | n/a | n/a | n/a | ++ |
| 190 | (R)-9-((5-(3-amino-3-(5-fluoro-6-methylpyridin-2-yl)piperidin-1-yl)-2-(4-fluorophenyl)pyridin-4-yl)methyl)-9H-purin-6-amine | n/a | 0.258 | 0.687 | +++ |
| 191 | (R)-9-((5-(3-amino-3-(6-chloropyridin-2-yl)piperidin-1-yl)-6'-chloro-5'-fluoro-[2,2'-bipyridin]-4-yl)methyl)-9H-purin-6-amine | n/a | 1.38 | 4.56 | ++ |
| 192 | (R)-9-((5-(3-amino-3-(6-chloro-3-fluoropyridin-2-yl)piperidin-1-yl)-2-(3,4-difluorophenyl)pyridin-4-yl)methyl)-9H-purin-6-amine | n/a | 0.731 | 2.18 | ++ |
| 193 | 9-((5-(3-amino-3-(5-fluoro-6-(fluoromethyl)pyridin-2-yl)piperidin-1-yl)-2-(4-fluorophenyl)pyridin-4-yl)methyl)-9H-purin-6-amine | n/a | 0.876 | 1.85 | ++ |
| 194 | (R)-9-((5-(3-amino-3-(6-chloropyridin-2-yl)piperidin-1-yl)-6'-chloro-5'-methoxy-[2,2'-bipyridin]-4-yl)methyl)-9H-purin-6-amine | n/a | 0.805 | 3.28 | ++ |
| 195 | 6-(3-amino-1-(4-((6-amino-9H-purin-9-yl)methyl)-6-(3,4-difluorophenyl)pyridin-3-yl)piperidin-3-yl)picolinamide | n/a | 4.92 | n/a | ++ |
| 196 | (R)-9-((5-(3-amino-3-(6-chloropyridin-2-yl)piperidin-1-yl)-5'-fluoro-[2,2'-bipyridin]-4-yl)methyl)-9H-purin-6-amine | n/a | 0.637 | 2.69 | ++ |
| 197 | (R)-9-((5-(3-amino-3-(6-(1,1-difluoroethyl)pyridin-2-yl)piperidin-1-yl)-2-(4-fluorophenyl)pyridin-4-yl)methyl)-9H-purin-6-amine | n/a | n/a | n/a | ++ |
| 198 | (R)-9-((5-(3-amino-3-(pyridin-2-yl)piperidin-1-yl)-2-(3,4-difluorophenyl)pyridin-4-yl)methyl)-9H-purin-6-amine | n/a | 0.0177 | 0.041 | +++ |
| 199 | (R)-9-((5-(3-amino-3-(3-fluoropyridin-2-yl)piperidin-1-yl)-2-(3,4-difluorophenyl)pyridin-4-yl)methyl)-9H-purin-6-amine | n/a | n/a | 0.846 | +++ |

TABLE 2-continued

| Ex No. | | H3K36me2 FRET in KMS11-Par (µM) | H3K36me2 ELISA in CGTH-W-1 (µM) | H3K36me2 ELISA in KMS11-Par (µM) | NSD2 IC$_{50}$ (µM) |
|---|---|---|---|---|---|
| 200 | (R)-9-((5-(3-amino-3-(6-chloropyridin-2-yl)piperidin-1-yl)-2-(3,4-difluorophenyl)pyridin-4-yl)methyl)-9H-purin-6-amine | n/a | 0.18 | 0.33 | +++ |
| 201 | (R)-9-((5-(3-amino-3-(6-fluoropyridin-2-yl)piperidin-1-yl)-2-(3,4-difluorophenyl)pyridin-4-yl)methyl)-9H-purin-6-amine | n/a | 0.123 | 0.286 | +++ |
| 202 | (R)-9-((5-(3-amino-3-(6-ethylpyridin-2-yl)piperidin-1-yl)-2-(4-fluorophenyl)pyridin-4-yl)methyl)-9H-purin-6-amine | n/a | n/a | 0.264 | +++ |
| 203 | (R)-9-((5-(3-amino-3-(6-(difluoromethyl)pyridin-2-yl)piperidin-1-yl)-2-(4-fluorophenyl)pyridin-4-yl)methyl)-9H-purin-6-amine | n/a | n/a | 0.389 | +++ |
| 204 | (R)-9-((5-(3-amino-3-(6-chloropyridin-2-yl)piperidin-1-yl)-2-cyclopropylpyridin-4-yl)methyl)-9H-purin-6-amine | n/a | n/a | n/a | ++ |
| 205 | 9-((5-(3-amino-3-(6-chloropyridin-2-yl)piperidin-1-yl)-2-(4-fluorophenyl)pyridin-4-yl)methyl)-9H-purin-6-amine | n/a | n/a | 0.632 | +++ |
| 206 | (R)-2-(3-amino-1-(4-((6-amino-9H-purin-9-yl)methyl)-6-(3,4-difluorophenyl)pyridin-3-yl)piperidin-3-yl)-6-fluoropyridin-4-ol | n/a | 0.117 | 1.16 | +++ |
| 207 | (R)-9-((5-(3-amino-3-(5-fluoro-6-methylpyridin-2-yl)piperidin-1-yl)-2-(3-fluoro-4-methoxyphenyl)pyridin-4-yl)methyl)-9H-purin-6-amine | n/a | n/a | n/a | ++ |
| 208 | 6-(3-amino-1-(4-((6-amino-9H-purin-9-yl)methyl)-6-(3,4-difluorophenyl)pyridin-3-yl)piperidin-3-yl)picolinonitrile | n/a | 2.78 | n/a | ++ |
| 209 | (R)-9-((5-(3-amino-3-(5-(difluoromethoxy)pyridin-2-yl)piperidin-1-yl)-2-(3,4-difluorophenyl)pyridin-4-yl)methyl)-9H-purin-6-amine | n/a | 0.324 | n/a | +++ |
| 210 | 9-((5-(3-amino-3-(6-chloropyridin-2-yl)piperidin-1-yl)-2-(imidazo[1,2-a]pyridin-6-yl)pyridin-4-yl)methyl)-9H-purin-6-amine | n/a | n/a | n/a | ++ |
| 211 | (R)-9-((5-(3-amino-3-(6-chloropyridin-2-yl)piperidin-1-yl)-2-(4-methoxyphenyl)pyridin-4-yl)methyl)-9H-purin-6-amine | n/a | 0.387 | n/a | +++ |
| 212 | 9-((5-((R)-3-amino-3-(6-((R)-1-fluoroethyl)pyridin-2-yl)piperidin-1-yl)-2-(4-fluorophenyl)pyridin-4-yl)methyl)-9H-purin-6-amine | n/a | 0.132 | 0.289 | ++ |
| 213 | (R)-9-((5-(3-amino-3-(6-chloropyridin-2-yl)piperidin-1-yl)-2-(3-fluoro-4-methoxyphenyl)pyridin-4-yl)methyl)-9H-purin-6-amine | n/a | 0.258 | 0.387 | +++ |
| 214 | 6-(3-amino-1-(4-((6-amino-9H-purin-9-yl)methyl)-6-(3,4-difluorophenyl)pyridin-3-yl)piperidin-3-yl)-2-fluoropyridin-3-ol | n/a | 0.444 | 2.426 | ++ |
| 215 | 1-(6-((R)-3-amino-1-(4-((6-amino-9H-purin-9-yl)methyl)-6-(3,4-difluorophenyl)pyridin-3-yl)piperidin-3-yl)-2-fluoropyridin-3-yl)ethan-1-ol | n/a | n/a | n/a | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 216 | (R)-9-((5-(3-amino-3-(6-chloro-5-fluoropyridin-2-yl)piperidin-1-yl)-2-(4-methoxyphenyl)pyridin-4-yl)methyl)-9H-purin-6-amine | n/a | 1.88 | 2.57 | ++ |
| 217 | (R)-6-(3-amino-1-(4-((6-amino-9H-purin-9-yl)methyl)-6-(3,4-difluorophenyl)pyridin-3-yl)piperidin-3-yl)pyridin-2-ol | n/a | 2.241 | n/a | +++ |
| 218 | (R)-9-((5-(3-amino-3-(6-(difluoromethyl)-5-fluoropyridin-2-yl)piperidin-1-yl)-2-(4-fluorophenyl)pyridin-4-yl)methyl)-9H-purin-6-amine | n/a | 0.1011 | n/a | ++ |
| 219 | (R)-2-(3-amino-1-(4-((6-amino-9H-purin-9-yl)methyl)-6-(3,4-difluorophenyl)pyridin-3-yl)piperidin-3-yl)-6-chloropyridin-4-ol | n/a | 0.407 | 3.45 | +++ |
| 220 | 9-((5-(3-amino-3-(6-chloropyridin-2-yl)piperidin-1-yl)-2-(1-methyl-1H-benzo[d]imidazol-6-yl)pyridin-4-yl)methyl)-9H-purin-6-amine | n/a | n/a | n/a | ++ |
| 221 | (R)-9-((5-(3-amino-3-(6-chloro-5-fluoropyridin-2-yl)piperidin-1-yl)-2-(4-fluorophenyl)pyridin-4-yl)methyl)-9H-purin-6-amine | n/a | 0.269 | 1.29 | +++ |
| 222 | 9-((5-(3-amino-3-(6-chloropyridin-2-yl)piperidin-1-yl)-2-(pyrazolo[1,5-a]pyridin-6-yl)pyridin-4-yl)methyl)-9H-purin-6-amine | n/a | n/a | n/a | ++ |
| 223 | 9-((5-(3-amino-3-(6-chloropyridin-2-yl)piperidin-1-yl)-2-(pyrazolo[1,5-a]pyridin-6-yl)pyridin-4-yl)methyl)-9H-purin-6-amine | n/a | n/a | n/a | ++ |
| 224 | (R)-9-((5-(3-amino-3-(6-chloropyridin-2-yl)piperidin-1-yl)-6'-fluoro-5'-methoxy-[2,2'-bipyridin]-4-yl)methyl)-9H-purin-6-amine | n/a | 0.348 | 1.71 | +++ |
| 225 | 9-((5-(3-amino-3-(6-chloropyridin-2-yl)piperidin-1-yl)-2-(1-methyl-1H-indazol-5-yl)pyridin-4-yl)methyl)-9H-purin-6-amine | n/a | 1.96 | n/a | ++ |
| 226 | (R)-9-((5-(3-amino-3-(6-(fluoromethyl)pyridin-2-yl)piperidin-1-yl)-2-(3,4-difluorophenyl)pyridin-4-yl)methyl)-9H-purin-6-amine | n/a | 0.0668 | 0.169 | +++ |
| 227 | (R)-9-((5-(3-amino-3-(6-(difluoromethyl)pyridin-2-yl)piperidin-1-yl)-2-(3,4-difluorophenyl)pyridin-4-yl)methyl)-9H-purin-6-amine | n/a | 0.133 | 0.302 | ++ |
| 228 | 9-((5-(3-amino-3-(6-chloropyridin-2-yl)piperidin-1-yl)-2-(4-(difluoromethoxy)-3-fluorophenyl)pyridin-4-yl)methyl)-9H-purin-6-amine | n/a | 0.611 | n/a | ++ |
| 229 | 9-((5-(3-amino-3-(6-chloropyridin-2-yl)piperidin-1-yl)-6'-methyl-[2,3'-bipyridin]-4-yl)methyl)-9H-purin-6-amine | n/a | 1.97 | 7.49 | ++ |
| 230 | (R)-9-((5-(3-amino-3-(6-chloro-3-methoxypyridin-2-yl)piperidin-1-yl)-2-(3,4-difluorophenyl)pyridin-4-yl)methyl)-9H-purin-6-amine | n/a | 1.65 | 9.98 | ++ |
| 231 | (R)-9-((5-(3-amino-3-(6-chloropyridin-2-yl)piperidin-1-yl)-5'-fluoro-6'-methoxy-[2,3'-bipyridin]-4-yl)methyl)-9H-purin-6-amine | n/a | 2.15 | 7.44 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 232 | (R)-2-(3-amino-1-(4-((6-amino-9H-purin-9-yl)methyl)-6-(3,4-difluorophenyl)pyridin-3-yl)piperidin-3-yl)-6-methylpyridine 1-oxide | n/a | 1.47 | 7.65 | ++ |
| 233 | (R)-9-((5-(3-amino-3-(6-chloropyridin-2-yl)piperidin-1-yl)-2-(3,5-difluoro-4-methoxyphenyl)pyridin-4-yl)methyl)-9H-purin-6-amine | n/a | 0.341 | 1.1 | +++ |
| 234 | 1-(6-((R)-3-amino-1-(4-((6-amino-9H-purin-9-yl)methyl)-6-(3,4-difluorophenyl)pyridin-3-yl)piperidin-3-yl)-2-chloropyridin-3-yl)ethan-1-ol | n/a | 1.62 | 5.99 | ++ |
| 235 | (R)-9-((5-(3-amino-3-(6-fluoro-4-methoxypyridin-2-yl)piperidin-1-yl)-2-(3,4-difluorophenyl)pyridin-4-yl)methyl)-9H-purin-6-amine | n/a | 0.705 | 0.97 | +++ |
| 236 | (R)-9-((5-(3-amino-3-(6-chloropyridin-2-yl)piperidin-1-yl)-2-(2,6-difluoro-4-methoxyphenyl)pyridin-4-yl)methyl)-9H-purin-6-amine | n/a | 1.39 | 6.30 | ++ |
| 237 | (R)-9-((5-(3-amino-3-(6-chloropyridin-2-yl)piperidin-1-yl)-2-(2,6-difluoro-4-methoxyphenyl)pyridin-4-yl)methyl)-9H-purin-6-amine | n/a | 0.825 | 2.02 | ++ |
| 238 | (R)-9-((5-(3-amino-3-(6-chloropyridin-2-yl)piperidin-1-yl)-2-(2,4-difluorophenyl)pyridin-4-yl)methyl)-9H-purin-6-amine | n/a | 0.588 | 1.341 | +++ |
| 239 | (R)-2-(3-amino-1-(4-((6-amino-9H-purin-9-yl)methyl)-6-(3,4-difluorophenyl)pyridin-3-yl)piperidin-3-yl)-6-fluoropyridin-3-ol | n/a | 0.353 | 1.54 | +++ |
| 240 | 9-((5-(3-amino-3-(6-chloropyridin-2-yl)piperidin-1-yl)-5',6'-difluoro-[2,3'-bipyridin]-4-yl)methyl)-9H-purin-6-amine | n/a | 0.821 | 5.93 | ++ |
| 241 | (R)-9-((5-(3-amino-3-(5-fluoro-6-methylpyridin-2-yl)piperidin-1-yl)-2-(4-methoxyphenyl)pyridin-4-yl)methyl)-9H-purin-6-amine | n/a | 1.19 | 4.08 | ++ |
| 242 | (R)-9-((5-(3-amino-3-(6-chloropyridin-2-yl)piperidin-1-yl)-2-(2,3-difluoro-4-methoxyphenyl)pyridin-4-yl)methyl)-9H-purin-6-amine | n/a | 2.714 | 8.19 | ++ |
| 243 | (R)-9-((5-(3-amino-3-(6-chloropyridin-2-yl)piperidin-1-yl)-4'-fluoro-5'-methoxy-[2,2'-bipyridin]-4-yl)methyl)-9H-purin-6-amine | n/a | 0.541 | 2.44 | +++ |
| 244 | 5-(3-amino-3-(6-chloropyridin-2-yl)piperidin-1-yl)-4-((6-amino-9H-purin-9-yl)methyl)-5'-fluoro-[2,3'-bipyridin]-6'-ol | n/a | 12.5 | 33.3 | ++ |
| 245 | (S)-9-((5-(3-amino-3-(pyridin-4-yl)piperidin-1-yl)-2-(3,4-difluorophenyl)pyridin-4-yl)methyl)-9H-purin-6-amine | n/a | n/a | 2.15 | ++ |
| 246 | (S)-9-((5-(3-amino-3-(2-chloropyridin-4-yl)piperidin-1-yl)-2-(3,4-difluorophenyl)pyridin-4-yl)methyl)-9H-purin-6-amine | n/a | n/a | 16.7 | ++ |
| 247 | (S)-9-((5-(3-amino-3-(2-methylpyridin-4-yl)piperidin-1-yl)-2-(3,4-difluorophenyl)pyridin-4-yl)methyl)-9H-purin-6-amine | n/a | n/a | 33.3 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 248 | (S)-9-((5-(3-amino-3-(3-fluoropyridin-4-yl)piperidin-1-yl)-2-(3,4-difluorophenyl)pyridin-4-yl)methyl)-9H-purin-6-amine | n/a | n/a | 2.88 | ++ |
| 249 | 9-((5-(3-amino-3-(6-chloropyridazin-3-yl)piperidin-1-yl)-2-(3,4-difluorophenyl)pyridin-4-yl)methyl)-9H-purin-6-amine | n/a | n/a | n/a | +++ |
| 250 | (R)-9-((5-(3-amino-3-(6-ethylpyrazin-2-yl)piperidin-1-yl)-2-(4-fluorophenyl)pyridin-4-yl)methyl)-9H-purin-6-amine | n/a | n/a | n/a | ++ |
| 251 | (R)-9-((5-(3-amino-3-(2-ethylpyrimidin-4-yl)piperidin-1-yl)-2-(3,4-difluorophenyl)pyridin-4-yl)methyl)-9H-purin-6-amine | n/a | 0.440 | 1.52 | ++ |
| 252 | (R)-1-((5-(3-amino-3-(6-ethylpyridin-2-yl)piperidin-1-yl)-2-cyclopropylpyridin-4-yl)methyl)-1H-imidazo[4,5-c]pyridin-4-amine | n/a | n/a | 7.25 | ++ |
| 253 | 9-((5-(3-amino-3-(pyridazin-3-yl)piperidin-1-yl)-2-(3,4-difluorophenyl)pyridin-4-yl)methyl)-9H-purin-6-amine | n/a | 0.357 | n/a | ++ |
| 254 | 9-((5-(3-amino-3-(6-chloropyrazin-2-yl)piperidin-1-yl)-2-(3,4-difluorophenyl)pyridin-4-yl)methyl)-9H-purin-6-amine | n/a | n/a | 1.54 | ++ |
| 255 | 9-((5-(3-amino-3-(pyrimidin-4-yl)piperidin-1-yl)-2-(3,4-difluorophenyl)pyridin-4-yl)methyl)-9H-purin-6-amine | n/a | 0.232 | n/a | ++ |
| 256 | (R)-1-((5-(3-amino-3-(6-ethylpyrazin-2-yl)piperidin-1-yl)-2-(4-fluorophenyl)pyridin-4-yl)methyl)-1H-imidazo[4,5-c]pyridin-4-amine | n/a | n/a | n/a | ++ |
| 257 | (R)-9-((5-(3-amino-3-(2-methylpyrimidin-4-yl)piperidin-1-yl)-2-(3,4-difluorophenyl)pyridin-4-yl)methyl)-9H-purin-6-amine | n/a | 0.435 | 1.20 | ++ |
| 258 | (R)-9-((5-(3-amino-3-(6-methylpyrazin-2-yl)piperidin-1-yl)-2-(3,4-difluorophenyl)pyridin-4-yl)methyl)-9H-purin-6-amine | n/a | 0.434 | n/a | ++ |
| 259 | 9-((5-(3-amino-3-(pyrazin-2-yl)piperidin-1-yl)-2-(3,4-difluorophenyl)pyridin-4-yl)methyl)-9H-purin-6-amine | n/a | n/a | 3.54 | ++ |
| 260 | (R)-1-((5-(3-amino-3-(6-(difluoromethyl)pyridin-2-yl)piperidin-1-yl)-2-(3,4-difluorophenyl)pyridin-4-yl)methyl)-1H-imidazo[4,5-c]pyridin-4-amine | n/a | n/a | 1.52 | ++ |
| 261 | (R)-1-((5-(3-amino-3-(6-methylpyridin-2-yl)piperidin-1-yl)-2-(4-fluorophenyl)pyridin-4-yl)methyl)-1H-imidazo[4,5-c]pyridin-4-amine | n/a | n/a | 0.235 | +++ |
| 262 | 1-((5-(3-amino-3-(6-fluoropyridin-2-yl)piperidin-1-yl)-2-(3,4-difluorophenyl)pyridin-4-yl)methyl)-1H-imidazo[4,5-c]pyridin-4-amine | n/a | n/a | 1.33 | ++ |
| 263 | 1-((5-(3-amino-3-(6-methylpyridin-2-yl)piperidin-1-yl)-2-cyclopropylpyridin-4-yl)methyl)-1H-imidazo[4,5-c]pyridin-4-amine | n/a | n/a | 4.17 | ++ |
| 264 | (R)-1-((5-(3-amino-3-(6-(difluoromethyl)pyridin-2-yl)piperidin-1-yl)-2-cyclopropylpyridin-4-yl)methyl)-1H-imidazo[4,5-c]pyridin-4-amine | n/a | n/a | 9.63 | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 265 | 1-((5-(3-amino-3-(6-chloropyridin-2-yl)piperidin-1-yl)-2-(azetidin-1-yl)pyridin-4-yl)methyl)-1H-imidazo[4,5-c]pyridin-4-amine | n/a | n/a | n/a | + |
| 266 | 1-((5-(3-amino-3-(pyridin-2-yl)piperidin-1-yl)-2-(4-fluorophenyl)pyridin-4-yl)methyl)-1H-imidazo[4,5-c]pyridin-4-amine | n/a | n/a | 0.436 | +++ |
| 267 | 1-((5-(3-amino-3-(6-chloropyridin-2-yl)piperidin-1-yl)-2-cyclobutylpyridin-4-yl)methyl)-1H-imidazo[4,5-c]pyridin-4-amine | n/a | n/a | 1.91 | ++ |
| 268 | 1-((5-(3-amino-3-(6-chloropyridin-2-yl)piperidin-1-yl)-2-cyclobutylpyridin-4-yl)methyl)-1H-imidazo[4,5-c]pyridin-4-amine | n/a | n/a | n/a | ++ |
| 269 | (S)-9-((5-(3-amino-3-(1-methyl-1H-pyrazol-4-yl)piperidin-1-yl)-2-(3,4-difluorophenyl)pyridin-4-yl)methyl)-9H-purin-6-amine | n/a | n/a | 5.68 | +++ |
| 270 | 1-((5-(3-amino-3-(1-methyl-1H-pyrazol-4-yl)piperidin-1-yl)-2-(3,4-difluorophenyl)pyridin-4-yl)methyl)-1H-imidazo[4,5-c]pyridin-4-amine | n/a | n/a | 15.3 | ++ |
| 271 | 9-((5-(3-amino-3-(pyridin-3-yl)piperidin-1-yl)-2-(3,4-difluorophenyl)pyridin-4-yl)methyl)-9H-purin-6-amine | n/a | n/a | 33.3 | + |
| 272 | (S)-3-(3-amino-1-(4-((6-amino-9H-purin-9-yl)methyl)-6-(3,4-difluorophenyl)pyridin-3-yl)piperidin-3-yl)pyridin-2(1H)-one | n/a | 1.746 | 10.5 | +++ |
| 273 | (R)-9-((5-(3-amino-3-(1-(difluoromethyl)-1H-pyrazol-3-yl)piperidin-1-yl)-2-(4-fluorophenyl)pyridin-4-yl)methyl)-9H-purin-6-amine | n/a | n/a | n/a | +++ |
| 274 | (R)-9-((5-(3-amino-3-(1-isopropyl-1H-pyrazol-3-yl)piperidin-1-yl)-2-(4-fluorophenyl)pyridin-4-yl)methyl)-9H-purin-6-amine | n/a | n/a | 5.54 | +++ |
| 275 | (R)-9-((5-(3-amino-3-(1-methyl-1H-pyrazol-3-yl)piperidin-1-yl)-2-(3,4-difluorophenyl)pyridin-4-yl)methyl)-9H-purin-6-amine | n/a | n/a | n/a | +++ |
| 276 | (R)-1-((5-(3-amino-3-(1-ethyl-1H-pyrazol-3-yl)piperidin-1-yl)-2-cyclopropylpyridin-4-yl)methyl)-1H-imidazo[4,5-c]pyridin-4-amine | n/a | n/a | n/a | ++ |
| 277 | 1-((5-(3-amino-3-(1-ethyl-1H-pyrazol-3-yl)piperidin-1-yl)-2-(4-fluorophenyl)pyridin-4-yl)methyl)-1H-imidazo[4,5-c]pyridin-4-amine | n/a | n/a | 2.20 | ++ |
| 278 | 9-((5-(3-amino-3-(1-cyclopropyl-1H-pyrazol-3-yl)piperidin-1-yl)-2-(3,4-difluorophenyl)pyridin-4-yl)methyl)-9H-purin-6-amine | n/a | n/a | 0.475 | +++ |
| 279 | (R)-1-((5-(3-amino-3-(1-(difluoromethyl)-1H-pyrazol-3-yl)piperidin-1-yl)-2-(4-fluorophenyl)pyridin-4-yl)methyl)-1H-imidazo[4,5-c]pyridin-4-amine | n/a | n/a | n/a | +++ |
| 280 | 1-((5-(3-amino-3-(1-cyclopropyl-1H-pyrazol-3-yl)piperidin-1-yl)-2-(4-fluorophenyl)pyridin-4-yl)methyl)-1H-imidazo[4,5-c]pyridin-4-amine | n/a | n/a | 1.49 | +++ |
| 281 | 9-((5-(3-amino-3-(2-chlorothiazol-4-yl)piperidin-1-yl)-2-(4-fluorophenyl)pyridin-4-yl)methyl)-9H-purin-6-amine | n/a | 0.826 | n/a | ++ |

TABLE 2-continued

| Ex No. | | H3K36me2 FRET in KMS11-Par (μM) | H3K36me2 ELISA in CGTH-W-1 (μM) | H3K36me2 ELISA in KMS11-Par (μM) | NSD2 IC$_{50}$ (μM) |
|---|---|---|---|---|---|
| 282 | 9-((5-(3-amino-3-(1-methyl-1H-1,2,3-triazol-4-yl)piperidin-1-yl)-2-(3,4-difluorophenyl)pyridin-4-yl)methyl)-9H-purin-6-amine | n/a | 1.53 | n/a | ++ |
| 283 | (R)-9-((5-(3-amino-3-(2-methyl-2H-1,2,3-triazol-4-yl)piperidin-1-yl)-2-(3,4-difluorophenyl)pyridin-4-yl)methyl)-9H-purin-6-amine | n/a | 0.11 | 1.02 | +++ |
| 284 | (R)-9-((5-(3-amino-3-(5-methylisoxazol-3-yl)piperidin-1-yl)-2-(3,4-difluorophenyl)pyridin-4-yl)methyl)-9H-purin-6-amine | n/a | 0.1108 | 0.254 | +++ |
| 285 | (R)-2-((R)-3-amino-1-(4-((6-amino-9H-purin-9-yl)methyl)-6-(3,4-difluorophenyl)pyridin-3-yl)piperidin-3-yl)-2-fluoroethan-1-ol | n/a | 0.0437 | 0.885 | +++ |
| 286 | (R)-2-((R)-3-amino-1-(4-((6-amino-9H-purin-9-yl)methyl)-6-(2,4,5-trifluorophenyl)pyridin-3-yl)piperidin-3-yl)-2-fluoroethan-1-ol | n/a | 0.0059 | 0.655 | +++ |
| 287 | 9-((5-(3-amino-3-(1,2-difluoroethyl)piperidin-1-yl)-2-(3,4-difluorophenyl)pyridin-4-yl)methyl)-9H-purin-6-amine | n/a | n/a | n/a | ++ |
| 288 | 9-((5-((R)-3-amino-3-((2R,6S)-6-methyl-1,4-dioxan-2-yl)piperidin-1-yl)-2-(3,4-difluorophenyl)pyridin-4-yl)methyl)-9H-purin-6-amine | n/a | 2.39 | 5.72 | ++ |
| 289 | 9-((5-((R)-3-amino-3-((R)-1,4-dioxan-2-yl)piperidin-1-yl)-2-(3,4-difluorophenyl)pyridin-4-yl)methyl)-9H-purin-6-amine | n/a | 0.492 | 2.67 | +++ |
| 290 | 9-((5-((R)-3-amino-3-((R)-1,4-dioxan-2-yl)piperidin-1-yl)-2-(2,4,5-trifluorophenyl)pyridin-4-yl)methyl)-9H-purin-6-amine | n/a | 0.421 | 0.954 | ++ |
| 291 | 9-((5-((R)-3-amino-3-((R)-1,4-dioxan-2-yl)piperidin-1-yl)-2-(2-(difluoromethyl)-4,5-difluorophenyl)pyridin-4-yl)methyl)-9H-purin-6-amine | n/a | 0.812 | 1.69 | ++ |
| 292 | (R)-7-(4-((6-amino-9H-purin-9-yl)methyl)-6-(3,4-difluorophenyl)pyridin-3-yl)-3-oxa-1,7-diazaspiro[4.5]decan-2-one | n/a | n/a | n/a | ++ |
| 293 | (S)-9-((5-(3-amino-3-(1,1-difluoroprop-1-en-2-yl)piperidin-1-yl)-2-(3,4-difluorophenyl)pyridin-4-yl)methyl)-9H-purin-6-amine | n/a | 1.3 | 3.21 | ++ |
| 294 | 9-((5-(3-amino-3-(2,2-difluorovinyl)piperidin-1-yl)-2-(3,4-difluorophenyl)pyridin-4-yl)methyl)-9H-purin-6-amine | n/a | n/a | 9.44 | ++ |
| 295 | 9-((5-(3-amino-3-(1-fluoroethyl)piperidin-1-yl)-2-(3-fluoro-4-methoxyphenyl)pyridin-4-yl)methyl)-9H-purin-6-amine | 2.332 | n/a | 1.86 | ++ |
| 296 | (R)-9-((5-(3-((1H-pyrazol-1-yl)methyl)-3-aminopiperidin-1-yl)-2-(3,4-difluorophenyl)pyridin-4-yl)methyl)-9H-purin-6-amine | 0.336 | n/a | 1.41 | ++ |
| 297 | 9-((5-(3-amino-3-((methylthio)methyl)piperidin-1-yl)-2-(3,4-difluorophenyl)pyridin-4-yl)methyl)-9H-purin-6-amine | 2.354 | n/a | n/a | ++ |
| 298 | 9-((5-(3-amino-3-((methylsulfonyl)methyl)piperidin-1-yl)-2-(3,4-difluorophenyl)pyridin-4-yl)methyl)-9H-purin-6-amine | n/a | n/a | n/a | + |

TABLE 2-continued

| Ex No. | | H3K36me2 FRET in KMS11-Par (µM) | H3K36me2 ELISA in CGTH-W-1 (µM) | H3K36me2 ELISA in KMS11-Par (µM) | NSD2 IC$_{50}$ (µM) |
|---|---|---|---|---|---|
| 299 | (S)-1-((R)-3-amino-1-(4-((6-amino-9H-purin-9-yl)methyl)-6-(3,4-difluorophenyl)pyridin-3-yl)piperidin-3-yl)-2,2,2-trifluoroethan-1-ol | n/a | 1.155 | 9.83 | ++ |
| 300 | 9-((5-(3-amino-3-(1,2,2-trifluoroethyl)piperidin-1-yl)-2-(3,4-difluorophenyl)pyridin-4-yl)methyl)-9H-purin-6-amine | n/a | n/a | n/a | ++ |
| 301 | 3-amino-1-(4-((6-amino-9H-purin-9-yl)methyl)-6-(3,4-difluorophenyl)pyridin-3-yl)-3-(2,2-difluoroethyl)piperidin-4-ol | n/a | n/a | n/a | ++ |
| 302 | (3R,4R)-3-amino-1-(4-((6-amino-9H-purin-9-yl)methyl)-6-(3,4-difluorophenyl)pyridin-3-yl)-3-(6-chloropyridin-2-yl)piperidin-4-ol | n/a | n/a | 0.563 | ++ |
| 303 | (S)-9-((5-(3-amino-3-(2,2,2-trifluoroethyl)piperidin-1-yl)-2-(3-fluoro-4-methoxyphenyl)pyridin-4-yl)methyl)-9H-purin-6-amine | 5.37 | n/a | n/a | ++ |
| 304 | (S)-9-((5-(3-amino-3-ethynylpiperidin-1-yl)-2-(3,4-difluorophenyl)pyridin-4-yl)methyl)-9H-purin-6-amine | n/a | 0.101 | 0.592 | ++ |
| 305 | (R)-9-((5-(3-amino-3-(difluoromethyl)piperidin-1-yl)-2-(3-fluoro-4-methoxyphenyl)pyridin-4-yl)methyl)-9H-purin-6-amine | n/a | 3.40 | 4.80 | ++ |
| 306 | 9-((5-((3R,5R)-3-amino-5-(fluoromethyl)piperidin-1-yl)-2-(3-fluoro-4-methoxyphenyl)pyridin-4-yl)methyl)-9H-purin-6-amine | n/a | 6.46 | n/a | ++ |
| 307 | 9-((5-((3S,5S)-3-amino-3-(2,2-difluoroethyl)-5-methylpiperidin-1-yl)-2-(4-fluorophenyl)pyridin-4-yl)methyl)-9H-purin-6-amine | n/a | n/a | n/a | + |
| 308 | 9-((5-(3-amino-5-(methoxymethyl)piperidin-1-yl)-2-(3,4-difluorophenyl)pyridin-4-yl)methyl)-9H-purin-6-amine | n/a | n/a | 27.5 | ++ |
| 309 | 9-((5-((3R,5S)-3-amino-5-fluoropiperidin-1-yl)-2-(3,4-difluorophenyl)pyridin-4-yl)methyl)-9H-purin-6-amine | n/a | n/a | n/a | ++ |
| 310 | 9-((5-((2S,5R)-5-amino-2-methylpiperidin-1-yl)-2-(3,4-difluorophenyl)pyridin-4-yl)methyl)-9H-purin-6-amine | n/a | n/a | n/a | + |
| 311 | 9-((5-((2S,3R)-3-amino-2-((difluoromethoxy)methyl)piperidin-1-yl)-2-(3,4-difluorophenyl)pyridin-4-yl)methyl)-9H-purin-6-amine | n/a | n/a | n/a | ++ |
| 312 | ((2S,3R)-3-amino-1-(4-((6-amino-9H-purin-9-yl)methyl)-6-(3,4-difluorophenyl)pyridin-3-yl)piperidin-2-yl)methanol | n/a | n/a | n/a | ++ |
| 313 | 9-((5-((2S,3R)-3-amino-2-((2,2-difluoroethoxy)methyl)piperidin-1-yl)-2-(3,4-difluorophenyl)pyridin-4-yl)methyl)-9H-purin-6-amine | n/a | n/a | n/a | ++ |
| 314 | 2-((2R,3R)-3-amino-1-(4-((6-amino-9H-purin-9-yl)methyl)-6-(3,4-difluorophenyl)pyridin-3-yl)piperidin-2-yl)ethan-1-ol | n/a | n/a | n/a | ++ |
| 315 | (2S,3R)-3-amino-1-(4-((6-amino-9H-purin-9-yl)methyl)-6-(3,4-difluorophenyl)pyridin-3-yl)-N-methylpiperidine-2-carboxamide | n/a | n/a | n/a | + |
| 316 | (R)-1-((2S,3R)-3-amino-1-(4-((6-amino-9H-purin-9-yl)methyl)-6-(3,4-difluorophenyl)pyridin-3- | n/a | n/a | n/a | + |

TABLE 2-continued

| Ex No. | | H3K36me2 FRET in KMS11-Par (µM) | H3K36me2 ELISA in CGTH-W-1 (µM) | H3K36me2 ELISA in KMS11-Par (µM) | NSD2 IC$_{50}$ (µM) |
|---|---|---|---|---|---|
| | yl)piperidin-2-yl)-2,2,2-trifluoroethan-1-ol | | | | |
| 317 | (2S,3R)-3-amino-1-(4-((6-amino-9H-purin-9-yl)methyl)-6-(3,4-difluorophenyl)pyridin-3-yl)-N,N-dimethylpiperidine-2-carboxamide | n/a | n/a | n/a | + |
| 318 | (2S,3R)-3-amino-1-(4-((6-amino-9H-purin-9-yl)methyl)-6-(3,4-difluorophenyl)pyridin-3-yl)piperidine-2-carboxamide | n/a | n/a | n/a | + |
| 319 | (2S,3R)-3-amino-1-(4-((6-amino-9H-purin-9-yl)methyl)-6-(3,4-difluorophenyl)pyridin-3-yl)piperidine-2-carboxamide | n/a | n/a | n/a | + |
| 320 | 2-((2R,3R)-3-amino-1-(4-((6-amino-9H-purin-9-yl)methyl)-6-(3,4-difluorophenyl)pyridin-3-yl)piperidin-2-yl)acetamide | n/a | n/a | n/a | + |
| 321 | 9-((2-(3,4-difluorophenyl)-5-(4-oxa-1,8-diazaspiro[5.5]undecan-8-yl)pyridin-4-yl)methyl)-9H-purin-6-amine | n/a | n/a | n/a | + |
| 322 | (S)-3-(3-amino-1-(4-((6-amino-9H-purin-9-yl)methyl)-6-(3,4-difluorophenyl)pyridin-3-yl)piperidin-3-yl)-N,N-dimethylpropanamide | n/a | n/a | >33.70 | ++ |
| 323 | 9-((5-((2R,3R)-3-amino-2-phenylpiperidin-1-yl)-2-(3,4-difluorophenyl)pyridin-4-yl)methyl)-9H-purin-6-amine | n/a | n/a | n/a | + |
| 324 | 3-amino-1-(4-((6-amino-9H-purin-9-yl)methyl)-6-(3,4-difluorophenyl)pyridin-3-yl)piperidin-2-one | n/a | n/a | n/a | + |
| 325 | (R)-5-amino-1-(4-((6-amino-9H-purin-9-yl)methyl)-6-(3,4-difluorophenyl)pyridin-3-yl)piperidin-2-one | n/a | n/a | n/a | + |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A method for treating multiple myeloma, comprising administering to a subject in need of such treatment a therapeutically effective amount of a compound of Formula (I):

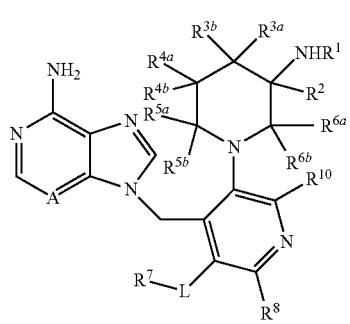

or an enantiomer, an enantiomeric mixture, or a pharmaceutically acceptable salt thereof;
wherein:
A is N or CR$^9$ wherein R$^9$ is hydrogen or halo;
L is a bond;
R$^1$ is H; or
R$^1$ and R$^2$ together with NH forms a 5-8 membered heterocyclyl containing 1-2 heteroatoms selected from N, O and S as ring members; wherein said 5-8 membered heterocyclyl is unsubstituted or substituted by an oxo substituent;
R$^2$ is selected from the group consisting of:
(i) hydrogen, —C$_{1-6}$ alkyl, -haloC$_{1-6}$ alkyl, -hydroxyC$_{1-6}$ alkylene, -hydroxyhaloC$_{1-6}$ alkylene, —C$_{1-6}$ alkoxyC$_{1-6}$alkylene, -haloC$_{1-6}$ alkoxyC$_{1-6}$ alkylene, difluoromethoxyl, 2,2,2-trifluoroethoxyl, or —C$_{3-8}$ cycloalkoxy(C$_{1-6}$ alkyl);
(ii) cyano; -cyanoC$_{1-6}$ alkylene; —C$_{1-6}$ alkylthioC$_{1-6}$alkyl; —C$_{2-6}$ alkenyl; -haloC$_{2-6}$ alkenyl; —C$_{2-6}$ alkynyl; —C$_{1-4}$ alkylSOC$_{1-4}$alkyl; —C$_{1-4}$ alkylSO$_2$C$_{1-4}$alkyl; —SO$_2$R$^8$ or —C(C$_{1-4}$ alkyl)=N—O(C$_{1-4}$ alkyl);
(iii) —C$_{1-4}$alkylcarbonyl; —(CR$^a$R$^b$)$_p$—C(=O)—OR$^{10}$; or —C(=O)—(CR$^a$R$^b$)$_q$R$^{11}$; wherein R$^{11}$ is C$_{3-7}$ cycloalkyl, 5-6 membered heterocyclyl or 5-6 membered heteroaryl, each of which is independently unsubstituted or substituted with C$_{1-6}$ alkyl or C$_{1-6}$ alkoxy;

(iv) —(CR$^a$R$^b$)$_r$—C(=O)—NR$^{12}$R$^{13}$ wherein R$^{12}$ is hydrogen or C$_{1-6}$ alkyl; R$^{13}$ is hydrogen, —C$_{1-6}$ alkyl or a 5-6 membered heterocyclic ring; or R$^{12}$ and R$^{13}$ together form a 5-6 membered heterocyclic ring; wherein said 5-6 membered heterocyclic ring is unsubstituted or substituted with C$_{1-4}$ alkyl;

(v) 5-6 membered heterocyclylC$_{0-6}$alkyl or 5-6 membered heterocyclyl(haloC$_{1-4}$ alkyl) wherein each said heterocyclyl radical is unsubstituted or substituted by oxo; and (vi) 5-9 membered heteroarylC$_{0-6}$alkyl or 5-9 membered heteroaryl(haloC$_{1-4}$alkyl), wherein each said heteroaryl radical is unsubstituted or substituted by —C$_{1-4}$ alkyl, -haloC$_{1-4}$ alkyl, -hydroxyC$_{1-4}$ alkylene, —C$_{1-4}$ alkoxy, -haloC$_{1-4}$ alkoxy, halo, hydroxy, cyano, oxido, -aminocarbonylC$_{0-6}$alkyl, —C$_{1-4}$alkylaminocarbonylC$_{0-6}$ alkyl, -diC$_{1-4}$alkylaminocarbonylC$_{0-6}$alkyl or —C$_{3-7}$ cycloalkyl;

R$^{3a}$, R$^{3b}$, R$^{4a}$, and R$^{4b}$ are independently hydrogen, halo, cyano, hydroxyl, —C$_{1-6}$ alkyl, -haloC$_{1-6}$ alkyl, -hydroxyC$_{1-6}$ alkylene, —C$_{1-6}$ alkoxy, or —C$_{1-6}$ alkoxyC$_{1-6}$alkylene;

R$^{5a}$ and R$^{5b}$ are independently hydrogen or —C$_{1-6}$ alkyl;

R$^{6a}$ and R$^{6b}$ are independently hydrogen, —C$_{1-6}$ alkyl, -hydroxyC$_{1-6}$ alkylene, —C$_{1-6}$alkoxyC$_{1-6}$alkylene, -haloC$_{1-6}$ alkoxyC$_{1-6}$ alkylene, -hydroxyhaloC$_{1-6}$ alkylene, aryl, —C(=O)—OR$^{14}$, or —(CR$^a$R$^b$)$_s$—C(=O)—NR$^{15}$R$^{16}$; or R$^{3a}$ and R$^{3b}$, R$^{4a}$ and R$^{4b}$, R$^{5a}$ and R$^{5b}$ or R$^{6a}$ and R$^{6b}$ forms an oxo substituent;

R$^7$ is H, —C$_{1-4}$ alkoxy, halo or C$_{1-4}$ alkyl;

R$^8$ is C$_{3-8}$ cycloalkyl(C$_{0-6}$ alkyl); 4-6 membered heterocyclylC$_{0-6}$alkyl comprising 1-3 heteroatoms selected from N, O and S; aryl or 5-9 membered heteroarylC$_{0-6}$ alkyl comprising 1-3 heteroatoms selected from N, O and S; wherein R$^8$ is unsubstituted or substituted by 1-3 R$^{17}$;

R$^{17}$ is halo, hydroxy, cyano, —C$_{1-6}$ alkyl, -haloC$_{1-6}$ alkyl, —C$_{1-6}$ alkoxy, -haloC$_{1-6}$ alkoxy, —NR$^a$C(=O)CR$^c$=C(R$^c$)$_2$ or —(CR$^a$R$^b$)$_t$—NR$^a$—C(=O)—R$^{18}$;

R$^a$, R$^b$, R$^c$, R$^{10}$, R$^{14}$, R$^{15}$ and R$^{16}$ are independently hydrogen or —C$_{1-4}$ alkyl;

R$^{18}$ is —C$_{1-4}$ alkyl or —C$_{1-4}$ haloalkyl; and p, q, r, s and t are independently 0-4.

2. The method of claim 1, wherein A is N.

3. The method of claim 2, wherein:

R$^{3a}$ is hydrogen or halo; and R$^{3b}$ is hydrogen, halo, -hydroxyl, —C$_{1-6}$ alkoxy or cyano; or R$^{4a}$ is hydrogen or halo; and R$^{4b}$ is hydrogen, halo, —C$_{1-6}$alkoxyC$_{1-6}$alkylene, —C$_{1-6}$ alkyl or -haloC$_{1-6}$ alkyl; or R$^{5a}$ is hydrogen and R$^{5b}$ is hydrogen or —C$_{1-6}$ alkyl; or R$^{5a}$ and R$^{5b}$ together form an oxo substituent.

4. The method of claim 2, wherein:

R$^{6a}$ is hydrogen;

R$^{6b}$ is hydrogen, -haloC$_{1-6}$ alkoxyC$_{1-6}$ alkylene, -hydroxyC$_{1-6}$ alkylene, -hydroxyhaloC$_{1-6}$ alkylene, carboxyl, phenyl or —(CR$^a$R$^b$)$_t$—C(O)—NR$^{15}$R$^{16}$;

R$^a$, R$^b$, R$^{15}$ and R$^{16}$ are independently hydrogen or —C$_{1-4}$ alkyl; and t is 0-1; or R$^{6a}$ and R$^{6b}$ together form an oxo substituent.

5. The method of claim 3, wherein R$^7$ is H, —C$_{1-4}$ alkoxy or halo.

6. The method of claim 2, wherein R$^1$, R$^{3a}$, R$^{3b}$, R$^{4a}$, R$^{4b}$, R$^{5a}$, R$^{5b}$, R$^{6a}$, R$^{6b}$ and R$^7$ are hydrogen.

7. The method of claim 1, wherein said compound is a compound of Formula (II):

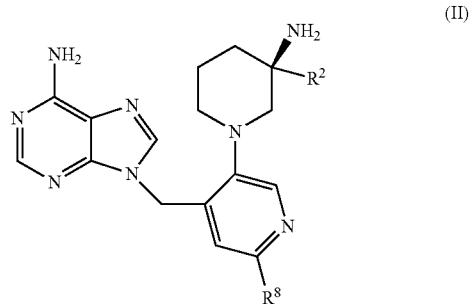

(II)

or an enantiomer, an enantiomeric mixture, or a pharmaceutically acceptable salt thereof.

8. The method of claim 7, wherein R$^2$ is —C$_{1-6}$ alkyl, -haloC$_{1-6}$ alkyl, -hydroxyC$_{1-6}$ alkylene, -hydroxyhaloC$_{1-6}$ alkylene, —C$_{1-6}$alkoxyC$_{1-6}$alkylene, -haloC$_{1-6}$ alkoxyC$_{1-6}$ alkylene or —C$_{3-8}$ cycloalkoxy(C$_{1-6}$ alkyl).

9. The method of claim 7, wherein R$^2$ is 2,2-difluoroethyl; 2-methyl-propan-1-olyl; ethan-1-olyl; 2,2-difluoroethan-1-olyl; 2-fluoroethan-1-olyl; 2,2,2-trifluoroethan-1-olyl; difluoromethoxyl; or 2,2,2-trifluoroethoxyl.

10. The method of claim 2, wherein R$^2$ is 2,2-difluoroethyl; 2-methyl-propan-1-olyl; ethan-1-olyl; 2,2-difluoroethan-1-olyl; 2-fluoroethan-1-olyl; 2,2,2-trifluoroethan-1-olyl; difluoromethoxyl; or 2,2,2-trifluoroethoxyl.

11. The method of claim 7, wherein R$^2$ is

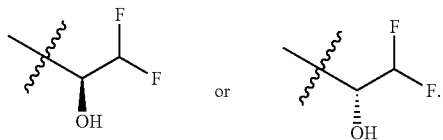 [SMILES: *[C@H](O)C(F)F ; *[C@@H](O)C(F)F]

12. The method of claim 7, wherein R$^8$ is phenyl substituted with 1-3 R$^{17}$;

R$^{17}$ is halo, hydroxy, cyano, —C$_{1-6}$ alkyl, -haloC$_{1-6}$ alkyl, —C$_{1-6}$ alkoxy, -haloC$_{1-6}$ alkoxy, —NR$^d$C(O)CR$^d$=C(R$^d$)$_2$ or —(CR$^a$R$^b$)—NR$^d$—C(O)—R$^{18}$;

R$^a$, R$^b$ and R$^d$ are independently hydrogen or —C$_{1-4}$ alkyl;

R$^{18}$ is C$_{1-4}$ haloalkyl; and t is 0-1.

13. The method of claim 9, wherein R$^8$ is phenyl substituted with 1-3 R$^{17}$; and R$^{17}$ is halo, hydroxy, —C$_{1-6}$ alkyl, -haloC$_{1-6}$ alkyl, —C$_{1-6}$ alkoxy or -haloC$_{1-6}$ alkoxy.

14. The method of claim 2, wherein R$^8$ is phenyl substituted with 1-3 R$^{17}$; and R$^{17}$ is halo, hydroxy, —C$_{1-6}$ alkyl, -haloC$_{1-6}$ alkyl, —C$_{1-6}$ alkoxy or -haloC$_{1-6}$ alkoxy.

15. The method of claim 1, wherein said compound has the following formula or a pharmaceutically acceptable salt thereof:

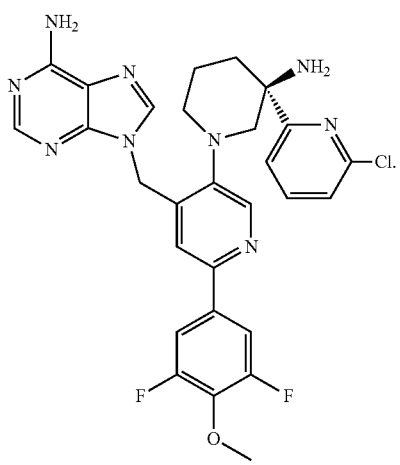 [SMILES: COc1c(F)cc(-c2cc(Cn3cnc4c(N)ncnc43)c(N3CCC[C@](N)(c4cccc(Cl)n4)C3)cn2)cc1F]

16. The method of claim 1, wherein said compound has the following formula or a pharmaceutically acceptable salt thereof:

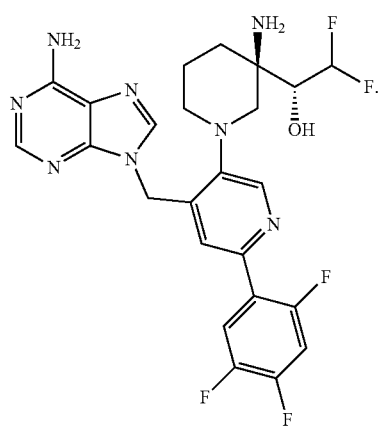 [SMILES: Nc1ncnc2c1ncn2Cc1cc(-c2cc(F)c(F)cc2F)ncc1N1CCC[C@](N)([C@@H](O)C(F)F)C1]

17. A method for treating multiple myeloma, comprising administering to a subject in need of such treatment a therapeutically effective amount of a compound having the following formula or a pharmaceutically acceptable salt thereof:

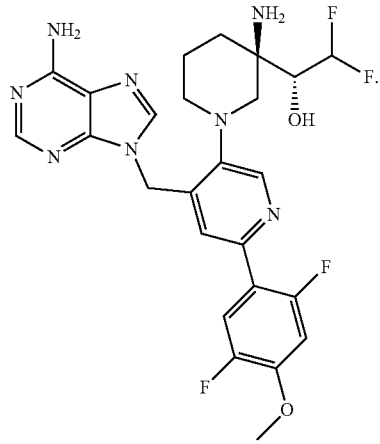 [SMILES: COc1cc(F)c(-c2cc(Cn3cnc4c(N)ncnc43)c(N3CCC[C@](N)([C@@H](O)C(F)F)C3)cn2)cc1F]

18. The method of claim 17, wherein the compound has the formula:

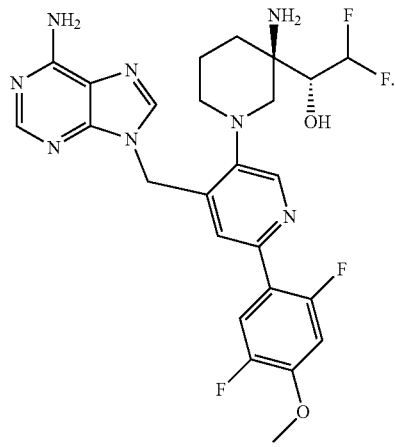 [SMILES: COc1cc(F)c(-c2cc(Cn3cnc4c(N)ncnc43)c(N3CCC[C@](N)([C@@H](O)C(F)F)C3)cn2)cc1F]

19. A method for treating multiple myeloma, comprising administering to a subject in need of such treatment a therapeutically effective amount of a compound having the following formula or a pharmaceutically acceptable salt thereof:

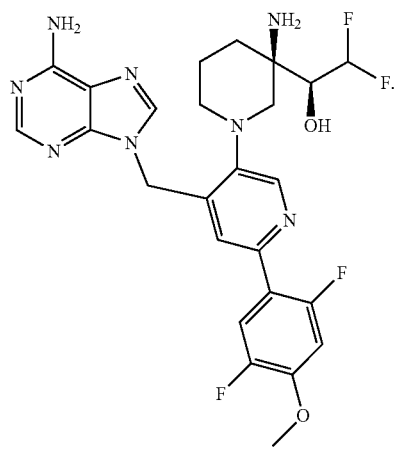 [SMILES: COc1cc(F)c(-c2cc(Cn3cnc4c(N)ncnc43)c(N3CCC[C@](N)([C@H](O)C(F)F)C3)cn2)cc1F]

20. The method of claim 19, wherein the compound has the formula:

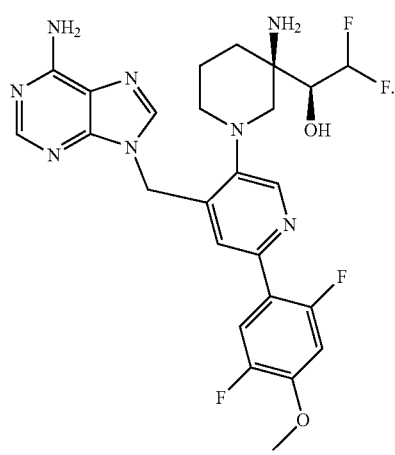 [SMILES: COc1cc(F)c(-c2cc(Cn3cnc4c(N)ncnc43)c(N3CCC[C@](N)([C@H](O)C(F)F)C3)cn2)cc1F]

* * * * *